(12) United States Patent
Cigan et al.

(10) Patent No.: US 11,773,400 B2
(45) Date of Patent: Oct. 3, 2023

(54) METHODS FOR PRODUCING GENETIC MODIFICATIONS IN A PLANT GENOME WITHOUT INCORPORATING A SELECTABLE TRANSGENE MARKER, AND COMPOSITIONS THEREOF

(71) Applicants: CORTEVA AGRISCIENCE LLC, Indianapolis, IN (US); PIONEER HI-BRED INTERNATIONAL, INC., Johnston, IA (US)

(72) Inventors: Andrew Mark Cigan, Johnston, IA (US); Saverio Carl Falco, Wilmington, DE (US); Michael Lassner, Urbandale, IA (US); Zhan-Bin Liu, West Chester, PA (US); Sergei Svitashev, Johnston, IA (US)

(73) Assignees: E.I. DU PONT DE NEMOURS AND COMPANY; PIONEER HI-BRED INTERNATIONAL, INC.

( * ) Notice: Subject to any disclaimer, the term of this patent is extended or adjusted under 35 U.S.C. 154(b) by 0 days.

(21) Appl. No.: 14/913,607

(22) PCT Filed: Aug. 20, 2014

(86) PCT No.: PCT/US2014/051781
§ 371 (c)(1),
(2) Date: Feb. 22, 2016

(87) PCT Pub. No.: WO2015/026886
PCT Pub. Date: Feb. 26, 2015

(65) Prior Publication Data
US 2016/0208271 A1  Jul. 21, 2016

Related U.S. Application Data

(60) Provisional application No. 62/023,239, filed on Jul. 11, 2014, provisional application No. 61/953,090, filed on Mar. 14, 2014, provisional application No. 61/937,045, filed on Feb. 7, 2014, provisional application No. 61/882,532, filed on Sep. 25, 2013, provisional application No. 61/868,706, filed on Aug. 22, 2013.

(51) Int. Cl.
*C12N 15/82* (2006.01)
*C12N 15/63* (2006.01)
*C12N 15/00* (2006.01)
*A01H 1/00* (2006.01)

(52) U.S. Cl.
CPC ......... *C12N 15/8216* (2013.01); *C12N 15/00* (2013.01); *C12N 15/63* (2013.01); *C12N 15/8213* (2013.01); *C12N 15/8247* (2013.01); *C12N 15/8274* (2013.01); *A01H 1/00* (2013.01)

(58) Field of Classification Search
None
See application file for complete search history.

(56) References Cited

U.S. PATENT DOCUMENTS

| | | | |
|---|---|---|---|
| 5,036,006 A | 7/1991 | Sanford et al. | |
| 5,959,177 A | 9/1999 | Hein et al. | |
| 6,603,061 B1 * | 8/2003 | Armstrong | A01H 4/001 435/419 |
| 7,292,055 B2 | 8/2007 | Choo et al. | |
| 7,868,149 B2 * | 1/2011 | Boukharov | C07K 14/415 536/23.1 |
| 8,586,361 B2 | 11/2013 | Tao et al. | |
| 8,697,359 B1 | 4/2014 | Zhang | |
| 8,771,945 B1 | 7/2014 | Zhang | |
| 8,795,965 B2 | 8/2014 | Zhang | |
| 8,865,406 B2 | 10/2014 | Zhang | |
| 8,871,445 B2 | 10/2014 | Cong et al. | |
| 8,889,356 B2 | 11/2014 | Zhang | |
| 8,889,418 B2 | 11/2014 | Zhang et al. | |

(Continued)

FOREIGN PATENT DOCUMENTS

| | | |
|---|---|---|
| DE | 102015006335 | 11/2016 |
| WO | 2005/049842 A2 | 6/2005 |

(Continued)

OTHER PUBLICATIONS

Shan et al. Targeted genome modification of crop plants using a CRISPR-Cas system. Nature Biotechnology, vol. 31 No. 8, 686-688 (2013) Published online Aug. 8, 2013.*

(Continued)

*Primary Examiner* — Cynthia E Collins

(57) ABSTRACT

Compositions and methods are provided for genome modification of a target sequence in the genome of a plant or plant cell, without incorporating a selectable transgene marker. The methods and compositions employ a guide polynucleotide/Cas endonuclease system to provide an effective system for modifying or altering target sites within the genome of a plant, plant cell or seed, without incorporating a selectable transgene marker. Once a genomic target site is identified, a variety of methods can be employed to further modify the target sites such that they contain a variety of polynucleotides of interest. Breeding methods and methods for selecting plants utilizing a guide polynucleotide/Cas endonuclease system are also disclosed. Compositions and methods are also provided for editing a nucleotide sequence in the genome of a cell, without incorporating a selectable transgene marker.

Figure 1:
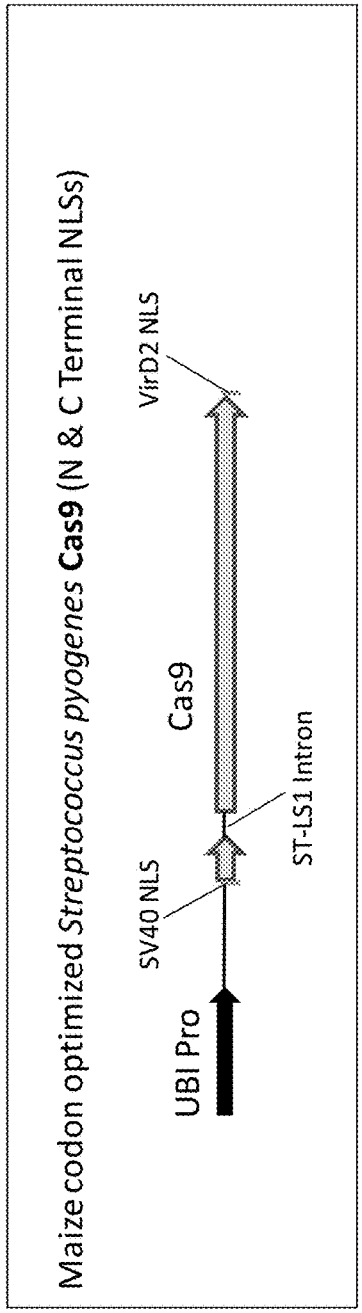
Figure 1:
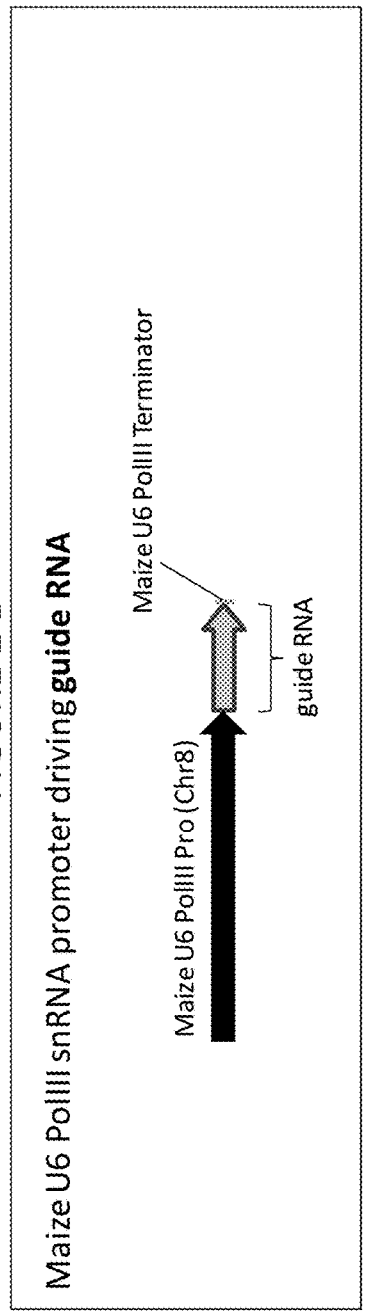
Figure 1:
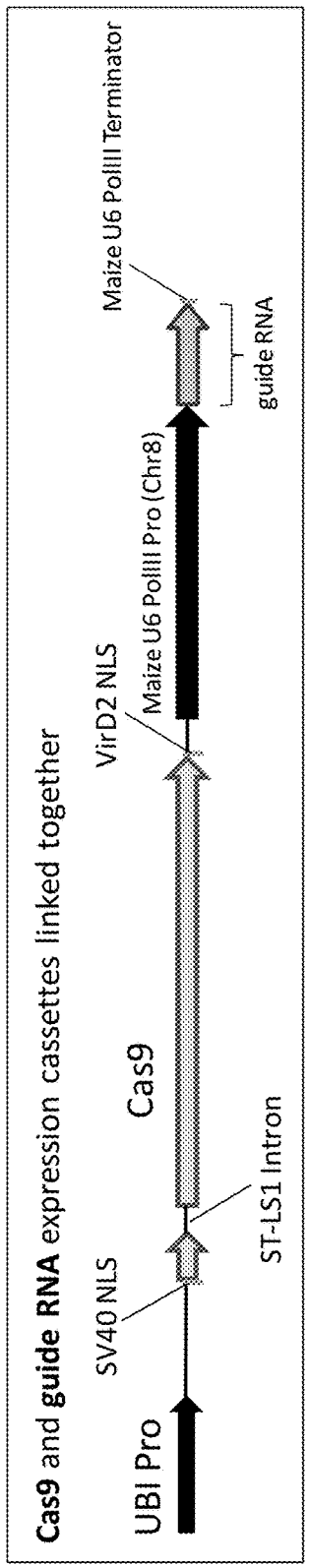

6 Claims, 46 Drawing Sheets
Specification includes a Sequence Listing.

(56) References Cited

U.S. PATENT DOCUMENTS

| | | |
|---|---|---|
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,163,284 B2 | 10/2015 | Liu et al. |
| 9,493,782 B2 | 11/2016 | Cigan et al. |
| 9,840,713 B2* | 12/2017 | Zhang ............... C12N 9/22 |
| 9,885,033 B2 | 2/2018 | Joung |
| 10,113,162 B2* | 10/2018 | Mathis ............... C12P 7/6445 |
| 2004/0231016 A1 | 11/2004 | Wang |
| 2007/0083945 A1 | 4/2007 | Byrum |
| 2007/0178593 A1 | 8/2007 | Miller |
| 2007/0199095 A1 | 8/2007 | Allen |
| 2009/0100536 A1* | 4/2009 | Adams ............... A01D 45/00 800/260 |
| 2009/0104700 A1 | 4/2009 | Samuel et al. |
| 2009/0133152 A1 | 5/2009 | Lyznik |
| 2010/0076057 A1 | 3/2010 | Sontheimer et al. |
| 2010/0159598 A1 | 6/2010 | Jayakumar et al. |
| 2010/0311168 A1 | 12/2010 | Samuel et al. |
| 2010/0313293 A1 | 12/2010 | Albertsen |
| 2011/0035836 A1 | 2/2011 | Eudes et al. |
| 2011/0165679 A1 | 7/2011 | Gordon-Kamm et al. |
| 2011/0247100 A1 | 10/2011 | Samboju et al. |
| 2012/0023619 A1 | 1/2012 | Samboju et al. |
| 2012/0023620 A1 | 1/2012 | Yau et al. |
| 2012/0244569 A1 | 9/2012 | Samuel et al. |
| 2013/0198888 A1 | 8/2013 | Falco et al. |
| 2013/0263324 A1 | 10/2013 | Lassner et al. |
| 2014/0020131 A1 | 1/2014 | Bidney et al. |
| 2014/0068797 A1 | 3/2014 | Doudna et al. |
| 2014/0096284 A1 | 4/2014 | Martin-Ortigosa et al. |
| 2014/0179006 A1 | 6/2014 | Zhang |
| 2014/0179770 A1 | 6/2014 | Zhang |
| 2014/0182012 A1 | 6/2014 | Eudes et al. |
| 2014/0186843 A1 | 7/2014 | Zhang |
| 2014/0186919 A1* | 7/2014 | Zhang ............... C12N 15/63 435/196 |
| 2014/0186958 A1 | 7/2014 | Zhang |
| 2014/0189896 A1 | 7/2014 | Zhang |
| 2014/0227787 A1 | 8/2014 | Zhang |
| 2014/0234972 A1 | 8/2014 | Zhang |
| 2014/0242664 A1 | 8/2014 | Zhang |
| 2014/0242699 A1 | 8/2014 | Zhang |
| 2014/0242700 A1 | 8/2014 | Zhang |
| 2014/0242702 A1 | 8/2014 | Chen et al. |
| 2014/0242703 A1 | 8/2014 | Samuel et al. |
| 2014/0248702 A1 | 9/2014 | Zhang |
| 2014/0256046 A1 | 9/2014 | Zhang |
| 2014/0273231 A1 | 9/2014 | Zhang et al. |
| 2014/0273232 A1 | 9/2014 | Zhang et al. |
| 2014/0273234 A1 | 9/2014 | Zhang |
| 2014/0273235 A1 | 9/2014 | Voytas |
| 2014/0310830 A1 | 10/2014 | Zhang |
| 2014/0335620 A1 | 11/2014 | Zhang |
| 2014/0342456 A1 | 11/2014 | Mali et al. |
| 2014/0357530 A1 | 12/2014 | Zhang |
| 2014/0370558 A1* | 12/2014 | Mathis ............... C12P 7/6445 435/134 |
| 2015/0044191 A1 | 2/2015 | Liu |
| 2015/0044772 A1 | 2/2015 | Zhao |
| 2015/0059010 A1 | 2/2015 | Cigan |
| 2015/0067922 A1* | 3/2015 | Yang ............... C12N 15/8245 800/298 |
| 2015/0079681 A1 | 3/2015 | Zhang |
| 2015/0082478 A1 | 3/2015 | Cigan et al. |
| 2015/0167000 A1 | 6/2015 | Voytas et al. |
| 2015/0167009 A1 | 6/2015 | D'Halluin |
| 2015/0284727 A1 | 10/2015 | Kim et al. |
| 2015/0291967 A1* | 10/2015 | Mathis ............... C12N 15/8209 800/300.1 |
| 2016/0024524 A1 | 1/2016 | Joung |
| 2016/0201072 A1 | 7/2016 | Cigan et al. |
| 2016/0208272 A1 | 7/2016 | Cigan et al. |
| 2016/0251667 A1 | 9/2016 | Cigan et al. |
| 2017/0022521 A1 | 1/2017 | Samuel et al. |
| 2017/0166912 A1 | 6/2017 | Brower-Toland |
| 2017/0183677 A1 | 6/2017 | Gao et al. |
| 2018/0002715 A1 | 1/2018 | Cigan et al. |
| 2018/0057832 A1 | 3/2018 | Li |
| 2018/0142263 A1 | 5/2018 | May et al. |
| 2018/0163203 A1 | 6/2018 | Bennett et al. |
| 2018/0230476 A1 | 8/2018 | Cigan et al. |
| 2018/0258417 A1 | 9/2018 | Cigan et al. |
| 2018/0273960 A1 | 9/2018 | Cigan et al. |
| 2018/0282763 A1 | 10/2018 | Cigan et al. |
| 2018/0327785 A1 | 11/2018 | Cigan et al. |
| 2018/0346895 A1 | 12/2018 | Cigan et al. |
| 2018/0371479 A1 | 12/2018 | Cigan et al. |
| 2019/0040405 A1 | 2/2019 | Cigan et al. |
| 2019/0100745 A1 | 4/2019 | Cigan et al. |
| 2019/0100762 A1 | 4/2019 | Cigan et al. |
| 2019/0136248 A1 | 5/2019 | Cigan et al. |

FOREIGN PATENT DOCUMENTS

| | | |
|---|---|---|
| WO | 2007/025097 A2 | 3/2007 |
| WO | 2009/042164 A1 | 4/2009 |
| WO | 2010/011961 A3 | 1/2010 |
| WO | 2010077319 | 7/2010 |
| WO | 2011143124 | 11/2011 |
| WO | 2012/129373 A2 | 9/2012 |
| WO | 2012164565 | 12/2012 |
| WO | 2013066423 | 5/2013 |
| WO | 2013068845 | 5/2013 |
| WO | 2013/098244 A1 | 7/2013 |
| WO | 2013112686 | 8/2013 |
| WO | 2013/142578 A1 | 9/2013 |
| WO | 2013141680 | 9/2013 |
| WO | 2013173535 | 11/2013 |
| WO | 2013176772 | 11/2013 |
| WO | 2014018423 | 1/2014 |
| WO | 2014/065596 A1 | 5/2014 |
| WO | 2014071006 | 5/2014 |
| WO | 2014/093479 A1 | 6/2014 |
| WO | 2014089290 | 6/2014 |
| WO | 2014093635 | 6/2014 |
| WO | 2014093694 | 6/2014 |
| WO | 2014093712 | 6/2014 |
| WO | 2014093768 | 6/2014 |
| WO | 2014/144155 A1 | 9/2014 |
| WO | 2014144761 | 9/2014 |
| WO | 2014150624 | 9/2014 |
| WO | 2014165825 | 10/2014 |
| WO | 2014/186686 A2 | 11/2014 |
| WO | 2014194190 | 12/2014 |
| WO | 2015006294 | 1/2015 |
| WO | 2015026883 | 2/2015 |
| WO | 2015026885 | 2/2015 |
| WO | 2015026886 | 2/2015 |
| WO | 2015026887 | 2/2015 |
| WO | 2015071474 | 5/2015 |
| WO | 2015112896 | 7/2015 |
| WO | 2015131101 | 9/2015 |
| WO | 2015189693 | 12/2015 |
| WO | 2016007347 | 1/2016 |
| WO | 2016033298 | 3/2016 |
| WO | 2016149352 | 9/2016 |
| WO | 2016186946 | 11/2016 |
| WO | 2017034971 | 3/2017 |
| WO | 2017062855 | 4/2017 |
| WO | 2017066497 | 4/2017 |
| WO | 2017155714 | 9/2017 |
| WO | 2017155715 | 9/2017 |
| WO | 2017218185 | 12/2017 |

OTHER PUBLICATIONS

Li et al. Multiplex and homologous recombination-mediated genome editing in *Arabidopsis* and Nicotiana benthamiana using guide RNA

(56) References Cited

OTHER PUBLICATIONS and Cas9. Nature Biotechnology, vol. 31 No. 8, 688-691 (2013) Published online Aug. 8, 2013.*
Li et al. Cas9-Guide RNA Directed Genome Editing in Soybean. Plant Physiology Oct. 2015, 169 (2) 960-970; DOI: 10.1104/pp.15.00783. (Year: 2015).*
Cong et al. Multiplex genome engineering using CRISPR/Cas systems. Science. Feb. 15, 2013;339(6121):819-23. Epub Jan. 3, 2013. (Year: 2013).*
Mali et al. RNA-guided human genome engineering via Cas9. Science. Feb. 15, 2013;339(6121):823-6. Epub Jan. 3, 2013. (Year: 2013).*
Li et al. Multiplex and homologous recombination-mediated genome editing in Arabidopsis and Nicotiana benthamiana using guide RNA and Cas9. Nat. Biotechnol. Aug. 2013;31(8):688-91; published Aug. 8, 2013. (Year: 2013).*
Deyle et al. Adeno-associated virus vector integration. Curr. Opin. Mol. Ther. Aug. 2009;11(4):442-7. (Year: 2009).*
Rodolphe Barrangou et al., CRISPR PRovides Acquired Resistance Against Viruses in Prokaryotes, Science, 2007, pp. 1709-1712, vol. 315.
Rodolphe Barrangou et al., RNA-mediated programmable DNA cleavage, Nature Biotechnology, Sep. 2012, pp. 836-838, vol. 30, No. 9.
Rodolphe Barrangou et al., CRISPR-Cas sytems and RNA-guided interference, Wires RNA, 2013, pp. 267-278, vol. 4.
Khaoula Belhaj et al., Plant genome editing made easy: targeted mutagenesis in model and crop plants using the CRISPR/Cas system, Plant Methods, 2013, pp. 39-48, vol. 9.
Nannan Chang et al., Genome editing with RNA-guided Cas9 nuclease in Zebrafish embryos, Cell Research, 2013, pp. 465-472, vol. 23.
Seung Woo Cho et al., Targeted genome engineering in human cells with the Cas9 RNA-guided endonuclease, Nature Biotechnology, Mar. 2013, pp. 230-232, vol. 31, No. 3.
Krzysztof Chylinski et al., The tracrRNA and Cas9 families of type II CRISPR-Cas immunity systems, RNA Biology, May 2013, pp. 726-737, vol. 10, No. 10.
Le Cong et al., Multiplex Genome Engineering Using CRISPR/Cas Systems, Sciencexpress Reports, Jan. 3, 2013, pp. 1-7, vol. 1.
Elitza Deltcheva et al., Crispr RNA maturation by trans-encoded small RNA and host factor RNase III, Nature, Mar. 31, 2011, pp. 602-607, vol. 471.
Kathleen D'Halluin et al., Targeted molecular trait stacking in cotton through targeted double-strand break induction, Plant Biotechnology Journal, pp. 933-941, vol. 11.
James E. DiCarlo et al., Genome engineering in Saccharomyces cerevisiae using CRISPR-Cas systems, Nucleic Acids Research, Mar. 4, 2013, pp. 4336-4343, vol. 41, No. 7.
Zhengyan Feng et al., Efficient genome editing in plants using a CRISPR/Cas system, Cell Research, 2013, pp. 1229-1232, vol. 23.
Yanfang Fu et al., Improving CRISPR-Cas nuclease specificity using truncated guide RNAs, Nature Biotechnology, Mar. 2014, vol. 32, No. 3.
Todd Funke et al., Structural Basis of Glyphosate Resistance Resulting from the Double Mutation $Thr^{97}$ Ile and $Pro^{101}$ Ser in 5-Enolpyruvylshikimate-e-phosphate Synthase from Escherichia coli, Journal of Biological Chemistry, Apr. 10, 2009, pp. 9864-9860, vol. 284, No. 15.
Thomas Gaj et al., ZFN, Talen and CRISPR/Cas-based methods for genome engineering, Trends Biotechnology, Jul. 2013, pp. 397-405, vol. 31(7).
Josiane E. Garneau et al., The CRISPR/Cas bacterial immune system cleaves bacteriophase and plasmid DNA, Nature, 2010, pp. 67-71, vol. 468.
Giedrius Gasiunas et al., Cas9-crRNA ribonucleoprotein complex mediates specific DNA cleavage for adaptive immunity in bacteria, PNAS, Sep. 4, 2012, e2579-2586.

Luke A Gilbert et al., CRISPR-Mediated Modular RNA-Guided Regulation of Transcription in Eukaryotes, Cell, Jul. 18, 2013, pp. 442-451, vol. 154(2).
Scott J. Gratz et al., Genome Engineering of Drosophila with the CRISPR RNA-Guided Cas9 Nuclease, Aug. 2013, Genetics, pp. 1029-1035, vol. 194.
Daniel H. Haft et al., A Guild of 45 CRISPR-Associated (Cas) Protein Families and Multiple CRISPR/Cas Subtypes Exist in Prokaryotic Genomes, PLoS Computational Biology, Nov. 2005, pp. 474-483, vol. 1, Issue 6.
Caryn R. Hale et al. , RNA-Guided RNA Cleavage by a CRISPR RNA-Cas Protein Complex, Cell, Nov. 25, 2009, pp. 945-956, vol. 139.
Rachel E. Haurwitz et al., Sequence- and Structure-Specific RNA Processing by a CRISPR Endonuclease, Science, Sep. 10, 2010, pp. 1355-1358, vol. 329.
Philippe Horvath et al., Diversity, Activity, and Evolution of CRISPR Loci in Streptococcus thermophilus, Journal of Bacteriology, Feb. 2008, pp. 1401-1412, vol. 190, No. 4.
Philippe Horvath et al., CRISPR/Cas, the Immune System of Bacteria and Archaea, Science, Jan. 8, 2010, pp. 167-170, vol. 327.
Zhonggang Hou et al., Efficient genome engineering in human pluripotent stem cells using Cas9 from Neisseria meningitides, PNAS, Sep. 24, 2013, pp. 15644-15649, vol. 110, No. 39.
Patrick D. Hsu et al., DNA targeting specificity of RNA-guided Cas9 nucleases, Nature Biotechnology, Sep. 2013, pp. 827-834, vol. 31, No. 9.
Woong Y. Hwang et al., Efficient In Vivo Genome Editing Using RNA-Guided Nucleases, Nature Biotech, Mar. 2013, pp. 227-229, vol. 31, No. 3.
Kyle Jacoby et al., Expanding LAGLIDADG endonuclease scaffold diversity by rapidly surveying evolutionary sequence space, Nucleic Acids Research, Feb. 2012, pp. 4954-4964, vol. 40, No. 11.
Wenyan Jiang et al., RNA-guided editing of bacterial genomes using CRISPR-Cas systems, Nature Biotechnology, Mar. 2013, pp. 233, vol. 31, No. 3.
Martin Jinek et al., A Programmable Dual-RNA-Guided DNA Endonuclease in Adaptive Bacterial Immunity, Science, Aug. 17, 2012, pp. 816-821, vol. 337.
Martin Jinek et al., RNA-programmed genome editing in human cells, eLife, 2013, e00471, pp. 1-9.
Ross A. Johnson et al., A rapid assay to quantify the cleavage efficiency of custom-designed nucleases in planta, Plant Mol Biol, 2013, pp. 207-221, vol. 82.
Eugene V. Koonin et al., CRISPR-CAS Evolution of an RNA-based adaptive immunity system in prokaryotes, RNA Biology, May 2013, pp. 679-686, vol. 10:5.
Jian-Feng Li et al., Multiplex and homologous recombination-mediated genome editing in Arabidopsis and Nicotiana benthamiana using guide RNA and Cas9, Nature Biotechnology, Aug. 2013, pp. 688-691, vol. 31, No. 8.
Michael R. Lieber et al., The Mechanism of Double-Strand DNA Break Repair by the Nonhomologous DNA End Joining Pathway, Annu Rev Biochem, 2010, pp. 181-211, vol. 79.
Ming Ma et al., A Guide RNA Sequence Design Platform for the CRISPR/Cas9 System for Model Organism Genomes, BioMed Research International, 2013, 4 pages, Article ID 270805.
Morgan L. Maeder et al., CRISPR RNA-guided activation of endogenous human genes, Nature Methods, Oct. 2013, pp. 977-979, vol. 10, No. 10.
Kira S. Makarova et al., Evolution and classification of the CRISPR-Cas systems, Nat Rev Microbiol, Jun. 2011, pp. 467-477, vol. 9(6).
Prashant Mali et al., RNA-Guided Human Genome Engineering via Cas9, Sciencexpress, Feb. 15, 2013, pp. 823-826, vol. 15, 339(6121).
Yanfei Mao et al., Application of the CRISPR-Cas System for Efficient Genome Engineering in Plants, Molecular Plant, Nov. 2013, pp. 2008-2011, vol. 6, No. 6.
Luciano A. Marraffini et al., CRISPR Interference Limits Horizontal Gene Transfer in Staphylococci by Targeting DNA, Science, Dec. 19, 2008, pp. 1843-1845, vol. 322(5909).
Luciano A. Marraffini et al., CRISPR interference: RNA-directed adaptive immunity in bacteria and archaea, Nat Rev Genet, Mar. 2010, pp. 181-190, vol. 11(3).

(56) References Cited

OTHER PUBLICATIONS

Jin Miao et al., Targeted mutagenesis in rice using CRISPR-Cas System, Cell Research, 2013, pp. 1233-1236, vol. 23.
Jeffrey C. Miller et al., A Tale nuclease architecture for efficient genome editing, Nature Biotechnology, Feb. 2011, pp. 143-148, vol. 29.
F. J. Mojica et al., Biological significance of a family of regularly spaced repeats in the genomes of Archaea, Bacteria and mitochondria, Molecular Microbiology, May 2000, pp. 244-246, vol. 36.
Vladimir Nekrasov et al., Targeted mutagenesis in the model plant *Nicotiana benthamiana* using Cas9 RNA-guided endonuclease, Nature Biotechnology, pp. 691-693, vol. 31, No. 8.
Nancy Podevin et al., Site-directed nucleases: a paradigm shift in predictable, knowledge-based plant breeding, Trends in Biotechnology, Jun. 2013, pp. 375-383, vol. 31, No. 6.
Lei S. Qi et al., Repurposing CRISPR as an RNA-Guided Platform for Sequence-Specific Control of Gene Expression, Cell, Feb. 28, 2013, pp. 1173-1183, vol. 152(5).
Sivaprakash Ramalingam et al., A CRISPR way to engineer the human genome, Genome Biology, 2013, 4 pages, vol. 14:107.
Paul D. Sadowski, Site-specific genetic recombination: hops, flips, and flops, FASEB, 1993, pp. 760-767, vol. 7.
Neville E. Sanjana et al., A Transcription Activator-Like Effector (TALE) Toolbox for Genome Engineering, Nat. Protoc, 2012, pp. 171-192, vol. 7(1).
Rimantas Sapranauskas et al., The *Streptococcus thermophilus* CRISPR/Cas system provides immunity in *Escherichia coli* Nucleic Acids Research, Aug. 2011, pp. 9275-9282, vol. 39, No. 21.
Brian Sauer, Site-specific recombination: developments and applications, Current Opinion in Biotechnology, 1994, pp. 521-527, vol. 5.
Qiwei Shan et al., Targeted genome modification of crop plants using a CRISPR-Cas system, Nature Biotechnology, Aug. 2013, pp. 686-688, vol. 31, No. 8.
Bin Shen et al., Generation of gene-modified mice via Cas9/RNA-mediated gene targeting, Cell Research, May 2013, pp. 720-723, vol. 23, No. 5.
Bruno Tinland et al., The T-DNA-linked VirD2 protein contains two distinct functional nuclear localization signals, Proc. Natl. Acad. Sci, Aug. 1992, pp. 7442-7446, vol. 89.
John Van Der Oost, New Tool for Genome Surgery, Science, Feb. 15, 2013, pp. 768-770, vol. 339.
Daniel F. Voytas, Plant Genome Engineering with Sequence-Specific Nucleases, Annual Review of Plant Biology, pp. 327-350, vol. 64.
Jianbin Wang et al., Targeted gene addition to a predetermined site in the human genome using a ZFN-based nicking enzyme, Genome Research, 2012, pp. 1316-1326.
Haoyi Wang et al., One-Step Generation of Mice Carrying Mutations in Multiple Genes by CRISPR/Cas-Mediated Genome Engineering, Cell, May 9, 2013, pp. 910-918, vol. 153(4).
Blake Wiedenheft et al., RNA-guided genetic silencing systems in bacteria and archaea, Nature, Feb. 16, 2012, pp. 331-338, vol. 482.
Kabin Xie et al., RNA-Guided Genome Editing in Plants Using a CRISPR-Cas System, Nov. 2013, Molecular Plant, pp. 1975-1983, vol. 6, No. 6.
International Search Report and Written Opinion—PCT/US2014/051781 —dated Dec. 3, 2014.
Ainley et al: "Trait stacking via targeted genome editing", Plant Biotechnology Journal, Aug. 19, 2013, pp. 1126-1134, vol. 11, No. 9.
Beurdeley et al: "Compact designer TALENs for efficient genome engineering", Nat Commun, Apr. 23, 2013, pp. 1-8, vol. 4, No. 1762.
Bolotin et al: "Clustered regularly interspaced short palindrome repeats (CRISPRs) have spacers of extrachromosomal origin", Microbiology, 2005, vol. 151, pp. 2551-2561.
Bolotin et al: "Complete sequence and comparative genome analysis of the dairy bacterium *Streptococcus thermophilus*", Nature Biotechnology, 2004, vol. 22 No. 12, pp. 1554-1558.
Carte et al: "Cas6 is an endoribonuclease that generates guide RNAs for invader defense in prokaryotes", Genes and Development, 2008, vol. 22, pp. 3489-3496.
Cheng et al: "Multiplexed activation of endogenous genes by CRISPR-on, an RNA-guided transcriptional activator system", Cell Research, 2013, pp. 1163-1171, vol. 23.
Claesson M J et al: "Multireplicon genome architecture of Lactobaciilus salivarius", PNAS, Apr. 1, 2006, pp. 6718-6723, vol. 103 No. 17.
Database: "cas9-CRISPR-associated endonuclease CAs9—Bacillus cereus VD131—cas9 gene & protein", UniProt database entry: R8LDU5.
Database: "CRISPR-associated endonuclease Cas9, Lactobacillus salivarius (strain UCC118): Q1WVK1_LACS1", UniProt.
Database: hypothetical protein [*Lactobacillus reuteri*]: NCBI Reference Sequence WP_019251774.1.
Djukanovic et al: "Male-sterile maize plants produced by targeted mutagenesis of the cytochrome P450-like gene (MS26) using a re-designed I-CreI homing endonuclease", The Plant Journal, Nov. 5, 2013, pp. 888-899, vol. 76, No. 5.
Esvelt et al: "Orthogonal Cas9 proteins for RNA-guided gene regulation and editing", Nature Methods, Sep. 29, 2013, pp. 1116-1121, vol. 10 No. 11.
Fujita et al.,"The point mutation in the promoter region and the single nucleotide polymorphism in exon 1 of the cytokeratin 19 gene in human lung cancer cell lines" Lung Cancer, Dec. 2001, vol. 34 No. 3 pp. 387-394.
Ganal et al: "A large maize (*Zea mays* L.) SNP genotyping array: development and germplasm genotyping, and genetic mapping to compare with B73 reference genome", PLOS One, vol. 6, No. 12, Dec. 8, 2011, p. e28334.
Gardlik et al., "Vectors and delivery systems in gene therapy", Med Sci Monit, 2005, RA110-121, vol. 11 No. 14.
Garside et al: "Cas5d processes pre-crRNA and is a member of a larger family of CRISPR RNA endonucleases", RNA, 2012, vol. 18 pp. 2020-2028.
Grissa I et al: "CRISPRFinder: a web tool to identify clustered regularly interspaced short palindromic repeats", Nucleic Acids Research, Information Retrieval Ltd, GB, May 31, 2007, pp. W52-W57, vol. 35.
Houdebine, "The methods to generate transgenic animals and to control transgene expression", J Biotech, 2002,145-160, vol. 98.
Jiang et al., "Demonstration of CRISPR/Cas9/sgRNA-mediated targeted gene modificaiton in *Arabidopsis*, tobacco, sorghum and rice", Nucleic Acids Research, Sep. 2, 2013, pp. e188-e188, XP055219328, vol. 41 No. 20.
Jore et al: "Structural basis for CRISPR RNA-guided DNA recognition by Cascade", Nature Structural & Mol Biol, 2011, vol. 18 No. 5, pp. 529-537 (and Supplemental).
Li et al. High-efficiency TALEN-based gene editing produces disease-resistant rice. Nat Biotechnol. May 7, 2012, pp. 390-392, vol. 30 No. 5.
Li et al., "In vivo genome editing restores hemostasis in a mouse model of hemophilia", Nature, 2011, pp. 217-221, vol. 475 No. 7355.
Li et al: "Varied transcriptional efficiencies of multiple *Arabidopsis* U6 small nuclear RNA genes", Journal of Integrative Plant Biology,Feb. 2007, pp. 222-229, vol. 49 No. 2.
Liang et al: "Targeted mutagenesis in *Zea mays* using TALENs and the CRISPR/Cas system", Journal of Genetics and Genomics, Dec. 14, 2013, pp. 63-68, vol. 41, No. 2.
Makarova et al:"The basic building blocks and evolution of CRISPR-Cas systems", Biochem Soc Trans, 2013, vol. 41 Part 6, pp. 1392-1400 (and Supplemental).
Mali et al., CAS9 transcriptional activators for target specificity screening and paired nickases for cooperative genome engineering, Nat. Biotechnol., Sep. 2013, pp. 833-838, vol. 31(9).
Ming-Bo Wang et al., Hairpin RNAs derived from RNA polymerase II and polymerase III promoter-directed transgenes are processed differently in plants, RNA, May 2008, pp. 903-913, vol. 14 No. 5.
Nam et al: "Cas5d Protein Processes Pre-crRNA and Assembles into a Cascade-like Interference Complex in Subtype I-C/Dvulg CRISPR-Cas System", Structure, 2012, vol. 20 pp. 1574-1584.

(56) References Cited

OTHER PUBLICATIONS

Peng et al, "A Synthetic arabinose-inducible promoter confers high levels of recombinant protein expression in hyperthermophilic Archaeon sulfolobus islandicus", Appl Environ Microbiol, Aug. 2012,pp. 5630-5637, vol. 78 No. 16.

Peter R. Beetham, A tool for functional plant genomics: Chimeric RNA/DNA oligonucleotides cause in vivo gene-specific mutations, Proc. Natl., Acad. Sci USA, Plant Biology, Jul. 1999, pp. 8774-8778, vol. 96.

Phillips, "The challenge of gene therapy and DNA delivery", Pharm Pharmacology, 2001, 1169-1174 vol. 53.

Puchta et al: "Gene replacement by homologous recombination in plants", Plant Mol Biol, 2002, vol. 48 pp. 173-182.

Reeks et al., "CRISPR interference: a structural perspective.", 2013, Biochem J, pp. 155-166, vol. 453.

Relic et al., Interaction of the DNA modifying proteins VirD1 and VirD2 of Agrobacterium tumefaciens: Analysis by subcellular localization in mammalian cells, Proc Natl Acad Sci, 2008, 95:9105-9110.

Retallack et al, "A single base pair mutation changes the specificities of both a transcription activation protein and its binding site", PNAS,Oct. 1993, pp. 9562-9565, vol. 90.

Shah et al: "Protospacer recognition motifs", RNA Biology, May 1, 2013, pp. 1547-6286, vol. 10 No. 5.

Shukla et al: Precise genome modificaiton in the crop species *Zea mays* using zinc-finger nucleases, Nature, Apr. 29, 2009, p. 437, vol. 459, No. 7245.

Sinkunas et al: "Cas3 is a single-stranded DNA nuclease and ATP-dependent helicase in the CRISPR/Cas immune system", EMBO, vol. 30 No. 7, Apr. 2011, pp. 1335-1342.

Strauss, "Zinc Fingers, TAL Effectors, or Cas9-Based DNA Binding Proteins: What's Best for Targeting Desired Genome Loci?", MolecularPlant, Sep. 2013, vol. 6 No. 5 pp. 1384-1387.

Ui-Tei et al, "Functional dissection of siRNA sequence by systematic DNA substitution: modified siRNA with a DNA seed arm is a powerful tool for mammalian gene silencing with significantly reduced off-target effect" Nucleic Acid Res. 2008, pp. 2146-2151, vol. 36 No. 7.

Westra et al: "CRISPR immunity relies on the consecutive binding and degradation of negatively supercoiled invader DNA by Cascade and Cas3", Mol Cell, Apr. 19, 2012,pp. 595-605, vol. 46 No 5.

Wierzbicki et al: "Noncoding Transcription by RNA Polymerase Pol IVb/Pol V Mediates Transcriptional Silencing of Overlapping and Adjacent Genes", Cell, 2008, vol. 135, pp. 635-648.

Zhang, "Transcription Activator-Like Effector Nucleases Enable Efficient Plant Genome Engineering",Plant Physiology, 2013, vol. 161, pp. 20-27.

Mao et al., Comparison of nonhomologous end joining and homologous recombination in human cells, DNA Repair, 2008, 7:1765-1771.

Ziemienowicz, Import of Agrobacterium T-DNA into plant nuclei: two distinct functions of VirD2 and VirE2 proteins, The Plant Cell, 2001, 13:369-383.

Communication of a Notice of European Opposition & Opponents Submissions: dated Oct. 24, 2022: Ref No. N417331 EPAXB/CX: European Application No. 14761478.8.

\* cited by examiner

FIGURE 3A

LIGCas-1

Expected Site of Cleavage → PAM

| | | Count | SEQ ID NO: |
|---|---|---|---|
| Reference | CTGTAACGATTTACGCACCTGCTGGGAATTGTACCGTACGTGCCCGGCGAGATATATATACCTCACACGTACGCGTATATATAC | | 55 |
| Mutation 1 | AGGACTGTAACGATTTACGCACCTGCTGGGAATTGTACCGTACGTGCCCGGTCGGAGGATATATATACCTCACACGTACGCGTATATATAC | 14488 | 56 |
| Mutation 2 | AGGACTGTAACGATTTACGCACCTGCTGGGAATTGTACCGTACGTGCCCGGACGGAGGATATATATACCTCACACGTACGCGTATATATAC | 7746 | 57 |
| Mutation 3 | AGGACTGTAACGATTTA-GCACCTGCTGGGAATTGTACCGTACGTGCCCGGTGCCGGAGGATATATATACCTCACACGTACGCGTATATATAC | 5028 | 58 |
| Mutation 4 | AGGACTGTAACGATTTACGCACCTGCTGGGAATTGTACCGTACGTGC--GGTCGGAGGATATATATACCTCACACGTACGCGTATATATAC | 1425 | 59 |
| Mutation 5 | AGGACTGTAACGATTTACGCACCTGCTGGGAATTGTACCGTACGTGCCCCGGCCGGAGGATATATATACCTCACACGTACGCGTATATATAC | 1056 | 60 |
| Mutation 6 | AGGACTGTAACGATTTACGCACCTGCTGGGAATTGTACCGTACGTGCCCCGG-CGGAGGATATATATACCTCACACGTACGCGTATATATAC | 963 | 61 |
| Mutation 7 | AGGACTGTAACGATTTACGCACCTGCTGGGAATTGTACCGTACGTGCCCCGG-GGAGGATATATATACCTCACACGTACGGTATATATAC | 732 | 62 |
| Mutation 8 | AGGACTGTAACGATTTACGCACCTGCTGGGAATTGTACCGTACGTGCCCCGG---AGGATATATATACCTCACACGTACGCGTATATATAC | 730 | 63 |
| Mutation 9 | AGGACTGTAACGATTTACGCACCTGCTGGGAATTGTACCGTACGTGC---GTCGGAGGATATATATACCTCACACGTACGCGTATATATAC | 492 | 64 |
| Mutation 10 | AGGACTGTAACGATTTACGCACCTGCTGGGAATTGTACCGTACCG--------------------------------------TAC | 390 | 65 |

LIGCas-2

Expected Site of Cleavage → PAM

| | | Count | SEQ ID NO: |
|---|---|---|---|
| Reference | CTGTAACGATTTACGCACCTGCTGGGAATTGTACCGTACGTGCCCGGCGGAGAGGATATATATACCTCACACGTACGCGTATATATAC | | 55 |
| Mutation 1 | TCCTCTGTAACGATTTACGCACCTGCTGGGAATTGTACCGTACGTGCCCGGCCGGAGGATATATATACCTCACACGTACGCGTATATATAC | 4221 | 66 |
| Mutation 2 | TCCTCTGTAACGATTTACGCACCTGCTGGGAATTGTACCGTACGTGACCCGGCGGAGGATATATATACCTCACACGTACGCGTATATATAC | 3452 | 67 |
| Mutation 3 | TCCTCTGTAACGATTTACGCACCTGCTGGGAATTGTACCGTACGTACGT-CCCGGGCGGAGGATATATATACCTCACACGTACGCGTATATATAC | 3395 | 68 |
| Mutation 4 | TCCTCTGTAACGATTTACGCACCTGCTGGGAATTGTACCGTACGTGCCCGGTCCCCGGCGGAGGATATATATACCTCACACGTACGCGTATATATAC | 1870 | 69 |
| Mutation 5 | TCCTCTGTAACGATTTACGCACCTGCTGGGAATTGTACCGTACGTAC---CCCGGCGGAGGATATATATACCTCACACGTACGCGTATATATAC | 1344 | 70 |
| Mutation 6 | TCCTCTGTAACGATTTACGCACCTGCTGGGAATTGTACCGTACGTA----CCCGGCGGAGGATATATATACCTCACACGTACGCGTATATATAC | 876 | 71 |
| Mutation 7 | TCCTCTGTAACGATTTACGCACCTGCTGGGAATTGTACCGTACGTA-----CCCGGCGGAGGATATATATACCTCACACGTACGCGTATATATAC | 507 | 72 |
| Mutation 8 | TCCTCTGTAACGATTTACGCACCTGCTGGGAATTGTACCGTACGTGAACCCGGAGGATATATATACCTCACACGTACGCGTATATATAC | 364 | 73 |
| Mutation 9 | TCCTCTGTAACGATTTACGCACCTGCTGGGAATTGTACCGTACGTG-----------------TACGCGTATATATAC | 331 | 74 |
| Mutation 10 | TCCTCTGTAACGATTTACGCACCTGCTGGGAATTGTACCGTACGTACG--CCCCGCGGAGGATATATATACCTCACACGTACGCGTATATATAC | 315 | 75 |

FIGURE 3 B

Expected Site of Cleavage → PAM

| | LIGCas-3 | Count | SEQ ID NO: |
|---|---|---|---|
| Reference | CGCAAATGAGTAGCAGCCACGTATATATACGCGTACGGCGTG[AG]TATATATATATCCTCCGCCGGGCCACGTACGGTACAATTCCCAG | | 76 |
| Mutation 1 | AAGGCGCAAATGAGTAGCAGCCACGCGTACGCGTACGCGTACGTTGTGAGGTATATATATCCTCCGCCGGGCCACGTACGGTACAATTCCCAG | 16861 | 77 |
| Mutation 2 | AAGGCGCAAATGAGTAGCAGCCACGCGTACGCGTACGCGTACGTACG-GTGAGGTATATATATCCTCCGCCGGGCCACGTACGGTACAATTCCCAG | 3648 | 78 |
| Mutation 3 | AAGGCGCAAATGAGTAGCAGCCACGCGTACGCGTACGCGTACGCGTAC-TGTGAGGTATATATATCCTCCGCCGGGCCACGTACGGTACAATTCCCAG | 2263 | 79 |
| Mutation 4 | AAGGCGCAAATGAGTAGCAGCCACGCGTACGCGTACGCGTACGCGTACG--TGAGGTATATATATCCTCCGCCGGGCCACGTACGGTACAATTCCCAG | 2132 | 80 |
| Mutation 5 | AAGGCGCAAATGAGTAGCAGCCACGCGTACGCGTACGCGTACGCGTATATA---TCCTCCGCCGGGCCACGTACGGTACAATTCCCAG | 1181 | 81 |
| Mutation 6 | AAGGCGCAAATGAGTAGCAGCCACGCGTACGCGTACGCGTATATATACG-------CGTACGGTACGGTACAATTCCCAG | 848 | 82 |
| Mutation 7 | AAGGCGCAAATGAGTAGCAGCCACGCGTACGCGTACGCGTATATATACGCGT--GTGAGGTATATATATCCTCCGCCGGGCCACGTACGGTACAATTCCCAG | 327 | 83 |
| Mutation 8 | AAGGCGCAAATGAGTAGCAGCCACGCGTACGCGTACGCGTATATATACGC------CCTCCGCCGGGCCACGTACGGTACAATTCCCAG | 263 | 84 |
| Mutation 9 | AAGGCGCAAATGAGTAGCAGCCACGCGTACGCGTACGCGTATATAT-------CGGGGCCACGTACGGTACAATTCCCAG | 227 | 85 |
| Mutation 10 | AAGGCGCAAATGAGTAGCAGCCACGCGTACGCGTACGCGTATATATACGCGTA--TGTGAGGTATATATATCCTCCGCCGGGCCACGTACGGTACAATTCCCAG | 209 | 86 |

Expected Site of Cleavage →

| | LIG3-4 HOMING ENDONUCLEASE | Count | SEQ ID NO: |
|---|---|---|---|
| Reference | CGCAAATGAGTAGCAGCCACGTATATATACGCGTACGGCGTACGTGTGAGGTATATATATCCTCCGCCGGGCCACGTACGGTACAATTCCCAG | | 76 |
| Mutation 1 | CCTTCGCAAATGAGTAGCAGCCACGCGTACGCGTACGCGTACGCGTACGTG--AGGTATATATATCCTCCGCCGGGCCACGTACGGTACAATTCCCAG | 358 | 87 |
| Mutation 2 | CCTTCGCAAATGAGTAGCAGCCACGCGTACGCGTACGCGTACGCGTATATA------TCCTCCGCCGGGCCACGTACGGTACAATTCCCAG | 241 | 88 |
| Mutation 3 | CCTTCGCAAATGAGTAGCAGCCACGCGCAGCGTACGCGTACGCGTATATATACGCGCGT-----ACGTACGGTACAATTCCCAG | 150 | 89 |
| Mutation 4 | CCTTCGCAAATGAGTAGCAGCCACGCGTACGCGTACGCGTATATATATACG-----CGTACGGTACAATTCCCAG | 143 | 90 |
| Mutation 5 | CCTTCGCAAATGAGTAGCAGCCACGCGTACGCGTACGCGTA---------CGCCGGGCCACGTACGGTACAATTCCCAG | 97 | 91 |
| Mutation 6 | CCTTCGCAAATGAGTAGCAGCCACGCGTACGCGTACGCGTATATATACGTGT------GAGGTATATATATCCTCCGCCGGGCCACGTACGGTACAATTCCCAG | 52 | 92 |
| Mutation 7 | CCTTCGCAAATGAGTAGCAGCCACGCGTACGCGTACGCGTACGCGT-----GTGAGGTATATATATCCTCCGCCGGGCCACGTACGGTACAATTCCCAG | 50 | 93 |
| Mutation 8 | CCTTCGCAAATGAGTAGCAGCCACGCGTACGCGTACGCGTATATAT------CCTCCGCCGGGCCACGTACGGTACAATTCCCAG | 46 | 94 |
| Mutation 9 | CCTTCGCAAATGAGTAGCAGCCACGCGTACGCGTACGCGTACGTGT--GGTATATATATCCTCCGCCGGGCCACGTACGGTACAATTCCCAG | 42 | 95 |
| Mutation 10 | CCTTCGCAAATGAGTAGCAGCCACGCGTACGCGTACGCGTACG-----GTATATATACGTGTGAGGTATATATATCCTCCGCCGGGCACGTACGGTACA | 32 | 96 |

FIGURE 6

|  | 55CasRNA-1 | SEQ ID NO: |
|---|---|---|
| Reference | CCGGTTTCGCGTGCTCTGGCTTTACATTACATGGGCAGGTCTTCACGACGGTTGGCTGGAGAGAGCCGGCTGGTAGGGGAGGACCTCAACGGC | 104 |
| Mutation 1 | CCGGTTTCGCGTGCTCTGGCTTTACATTACATGGGCAGGTCTCACGA-GGTTGGGCTGGAGAGAGCCGGCTGGTAGGGGAGGACCTCAACGGC | 105 |
| Mutation 2 | CCGGTTTCGCGTGCTCTGGCTTTACATTACATGGGCAGGTCTCAC-ACGGGCTGGAGAGAGCCGGCTGGTAGGGGAGGACCTCAACGGC | 106 |
| Mutation 3 | CGGGTTTCGCGTGCTGCTGGCTTTACATTACATGGGCAGGTCTCACGACGGTTTGGGCTGGAGAGAGCCGGCTGGTAGGGGAGGACCTCAACGGC | 107 |
| Mutation 4 | CCGGTTTCGCGTGCTGCTGCTTTACATTGCATGAGCAGGT*CGT*--GACGGTTGGGCTGGAGAGAGCCGGCTGGTAGGGGAGGACCTCAACGGC | 108 |
| Mutation 5 | GGGCAGGTCT--CGACGGTTGGGCTGGAGAGAGCCGGCTGGTAGGGGAGGACCTCAACGGC | 109 |
| Mutation 6 | CCGGTTTCGCGTGCTC-------------------------------TTGGGCTGGAGAGAGCCGGCTGGTAGGGGAGGACCTCAACGGC | 110 |

Expected Site of Cleavage → PAM

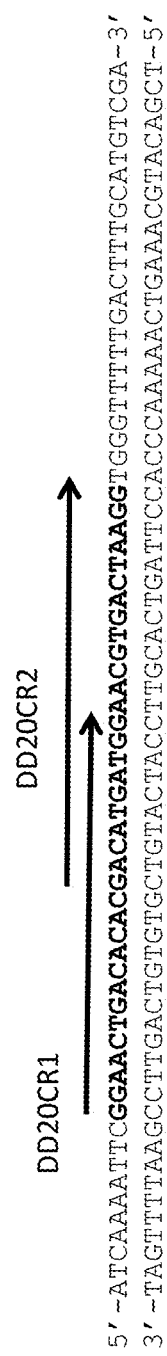
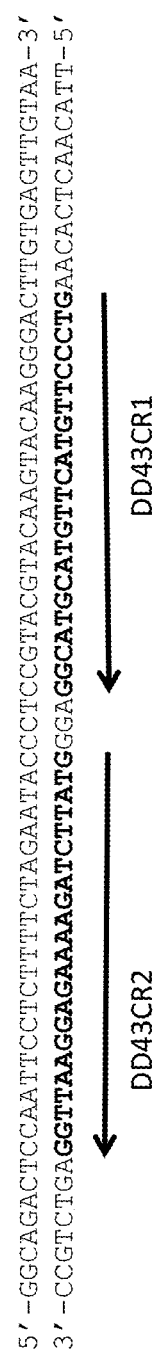
FIGURE 10 A
FIGURE 10 B

FIGURE 12
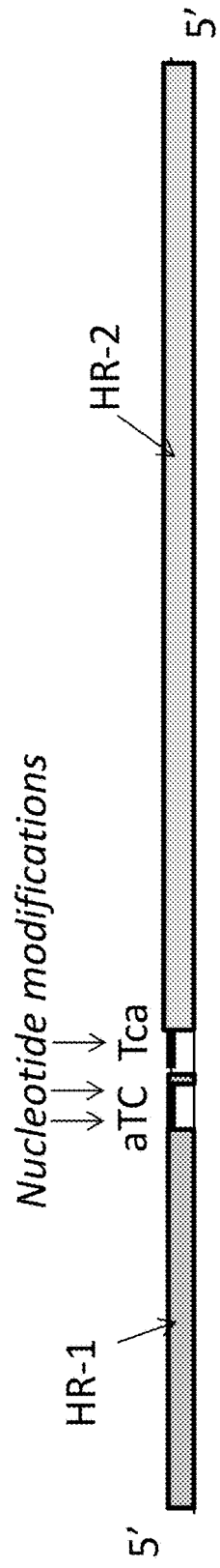
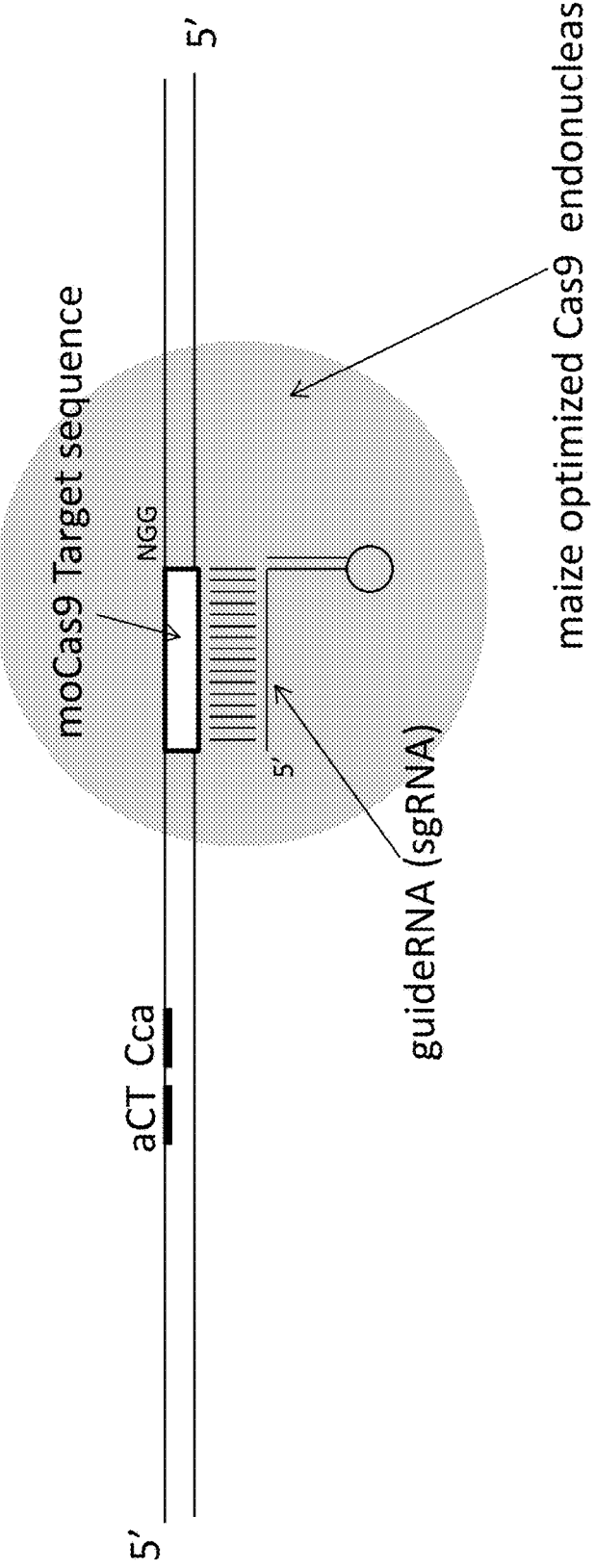

FIGURE 14

*Events with intact moCas target sequence (underlined)*
SEQ ID NO: 205  GGGGAATGCTGGAACTGCAATGCGGGCCATTGACAGCAGCTGTTACTGCTGGTGGAAATGC

*Events with mutagenized moCas target sequences (underlined)*
SEQ ID NO: 206  GGGGAATGCTGGAACTGCAATGCGGGCCATTG---GCAGCTGTTACTGCTGCTGGTGGAAATGC
SEQ ID NO: 207  GGGGAATGCTGGAACTGCA------------CAGCAGCTGTTACTGCTGCTGGTGGAAATGC
SEQ ID NO: 208  GGGGAATGCTG-----------------------TTACTGCTGCTGGTGGAAATGC FIGURE 16
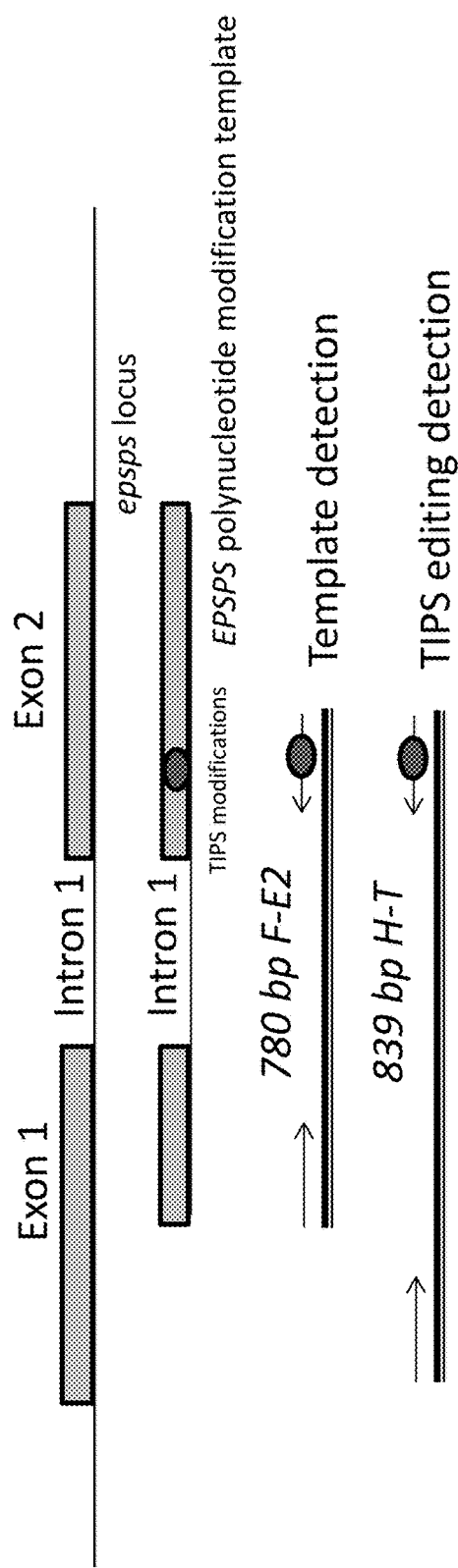
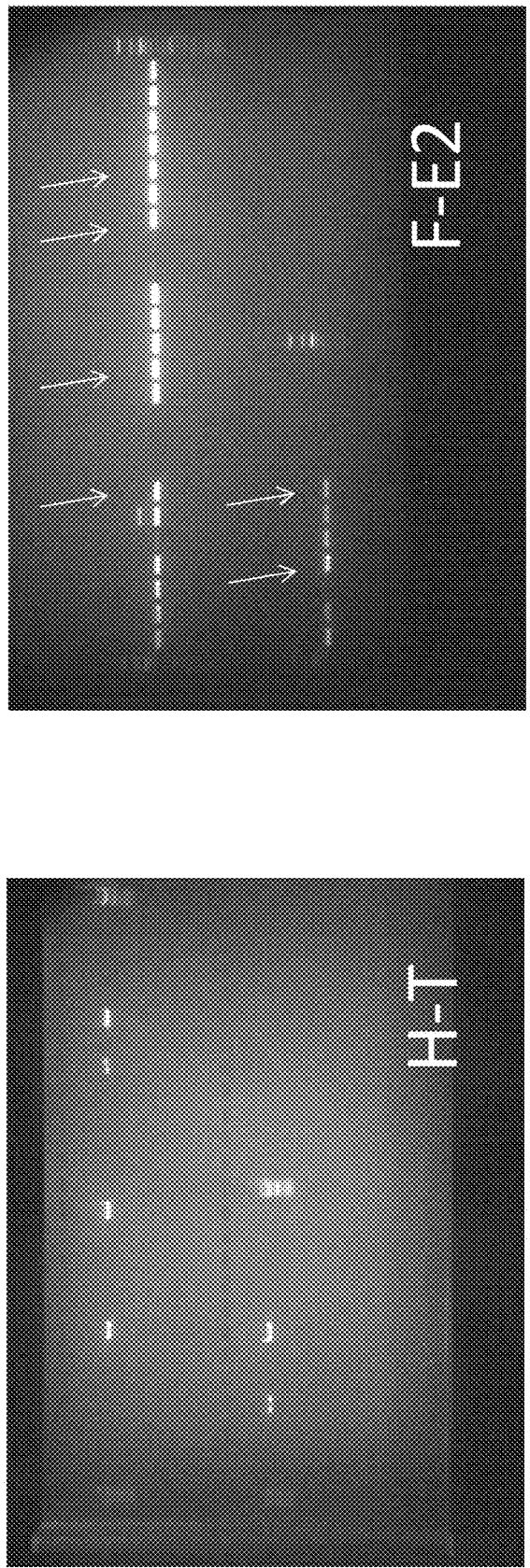

FIGURE 23
A. Linked gRNA and Cas9 gene expression cassettes
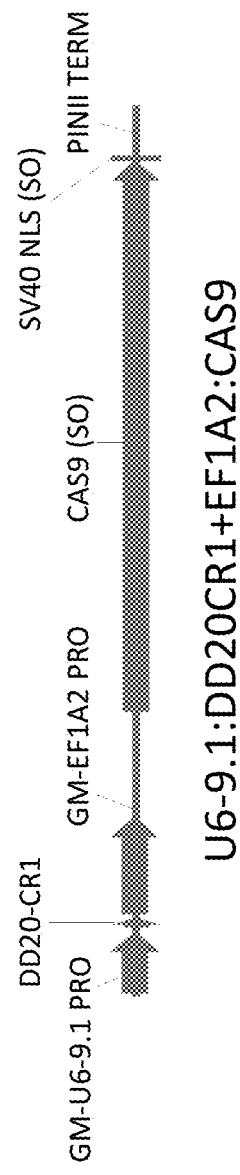
U6-9.1:DD20CR1+EF1A2:CAS9
B. Repair DNA cassette with homologous regions.
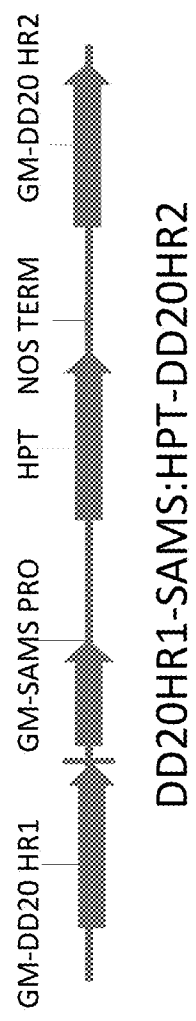
DD20HR1-SAMS:HPT-DD20HR2

A. Diagram of Glycine max chromosome 04 indicating relative positions of DD20 and DD43 target sites.

B. DD20 qPCR amplicon, 45936307-45936370

C. DD43 qPCR amplicon, 45731879-45731993

A. Transiently expressed gRNA and Cas9 assembled in vivo capable to cleave genomic DNA at target DD20.

B. DNA break repaired by NHEJ.

C. DNA break repaired by HR.

FIGURE 26-A

DD20CR1 target site

| | |
|---|---|
| SEQ ID NO:335 | ACTTGTACTTATCAAAATTCGGAACTGACACGACATGATGGAACGTGACTAAGGTGGG |
| SEQ ID NO:336 | ACTTGTACTTATCAAAATTCGGAACTGACACGACACGAC-TGATGGAACGTGACTAAGGTGGG |
| SEQ ID NO:337 | ACTTGTACTTATCAAAATTCGGAACTGACACGACACGA-ATGATGGAACGTGACTAAGGTGGG |
| SEQ ID NO:338 | ACTTGTACTTATCAAAATTCGGAACTGACACGACACGA--TGATGGAACGTGACTAAGGTGGG |
| SEQ ID NO:339 | ACTTGTACTTATCAAAATTCGGAACTGACACGACACGAC--GATGGAACGTGACTAAGGTGGG |
| SEQ ID NO:340 | ACTTGTACTTATCAAAATTCGGAACTGACACGACACACGG--TGATGGAACGTGACTAAGGTGGG |
| SEQ ID NO:341 | ACTTGTACTTATCAAAATTCGGAACTGACACGACACAC---ATGATGGAACGTGACTAAGGTGGG |
| SEQ ID NO:342 | ACTTGTACTTATCAAAATTCGGAACTGACACGACACACG---TGATGGAACGTGACTAAGGTGGG |
| SEQ ID NO:343 | ACTTGTACTTATCAAAATTCGGAACTGACACGACACAC----TGATGGAACGTGACTAAGGTGGG |
| SEQ ID NO:344 | ACTTGTACTTATCAAAATTCGGAACTGACACGACACACG----GATGGAACGTGACTAAGGTGGG |
| SEQ ID NO:345 | ACTTGTACTTATCAAAATTCGGAACTGACACGACACAC-----GATGGAACGTGACTAAGGTGGG |
| SEQ ID NO:346 | ACTTGTACTTATCAAAATTCGGAACTGACACGACACA------TGATGGAACGTGACTAAGGTGGG |
| SEQ ID NO:347 | ACTTGTACTTATCAAAATTCGGAACTGACACGACACAC------ATGATGGAACGTGACTAAGGTGGG |
| SEQ ID NO:348 | ACTTGTACTTATCAAAATTCGGAACTGACACGACACAC------TGATGGAACGTGACTAAGGTGGG |
| SEQ ID NO:349 | ACTTGTACTTATCAAAATTCGGAACTGACACGACACAC------GATGGAACGTGACTAAGGTGGG |
| SEQ ID NO:350 | ACTTGTACTTATCAAAATTCGGAACTGACACGACACTGA------TGATGGAACGTGACTAAGGTGGG |
| SEQ ID NO:351 | ACTTGTACTTATCAAAATTCGGAACTGACACGACACTGA-------TGGAACGTGACTAAGGTGGG |
| SEQ ID NO:352 | ACTTGTACTTATCAAAATTCGGAACTGACACGACACTGA--------TGATGGAACGTGACTAAGGTGGG |
| SEQ ID NO:353 | ACTTGTACTTATCAAAATTCGGAACTGACACGACACTG--------GAACGTGACTAAGGTGGG |
| SEQ ID NO:354 | ACTTGTACCTATCAAAATTCGGAACTGACACGACACTGA--------GGAACGTGACTAAGGTGGG |
| SEQ ID NO:355 | ACTTGTACTTATCAAAATTCGGAACTGACACGACACTGA---------ATGGAACGTGACTAAGGTGGG |
| SEQ ID NO:356 | ACTTGTACTTATCAAAATTCGGAACTGACACGACACTGA---------TGGAACGTGACTAAGGTGGG |
| SEQ ID NO:357 | ACTTGTACTTATCAAAATTCGGAACTGACACGACACTGA---------GAACGTGACTAAGGTGGG |
| SEQ ID NO:358 | ACTTGTACTTATCAAAATTCGGAACTGACACGACACGACAT^TC----------GG |
| SEQ ID NO:359 | ACTTGTACTTATCAAAATTCGGAACTGACACGACACA-------------AAGGTGGG |
| SEQ ID NO:360 | ACTTGTACTTATCAAAATTCGGAAC----------------GTGACTAAGGTGGG |
| SEQ ID NO:361 | ACT--------------------------------------ATGGAACGTGACTAAGGTGGG |

Insertion starts at ^ with the insert size indicated.

| | |
|---|---|
| SEQ ID NO:362 | ACTTGTACTTATCAAAATTCGGAACTGACACACG^155-GATGGAACGTGACTAAGGTGGG |
| SEQ ID NO:363 | ACTTGTACTTATCAAAA^50---------TGATGGAACGTGACTAAGGTGGG |

FIGURE 26-B

```
                   DD20CR2 target site
                   ┌─────────────────────┐
                   ↓                     ↓
SEQID NO:364  GACACACGACATGATGATGGAACGTGACTA|GGTGGGTTTTTTGACTTTTGCATGTCGAAGTGAG
SEQID NO:365  GACACACGACATGATGATGGAACGTGACTAAGGTGGGTTTTTTGACTTTTGCATGTCGAAGTGAG
SEQID NO:366  GACACACGACATGATGATGGAACGTA-CTAAGGTGGGTTTTTTGACTTTTGCATGTCGAAGTGAG
SEQID NO:367  GACACACGACATGATGATGGAACGT---CTAAGGTGGGTTTTTTGACTTTTGCATGTCGAAGTGAG
SEQID NO:368  GACACACGACATGATGATGGAACGTGA---AAGGTGGGTTTTTTGACTTTTGCATGTCGAAGTGAG
SEQID NO:369  GACACACGACATGATGATGGAACG----CTAAGGTGGGTTTTTTGACTTTTGCATGTCGAAGTGAG
SEQID NO:370  GACACACGACATGATGATGGAACGTG-----AAGGTGGGTTTTTTGACTTTTGCATGTCGAAGTGAG
SEQID NO:371  GACACACGACATGATGATGGAACGTG-------AGGTGGGTTTTTTGACTTTTGCATGTCGAAGTGAG
SEQID NO:372  GACACACGACATGATGATGGAACG------TAAGGTGGGTTTTTTGACTTTTGCATGTCGAAGTGAG
SEQID NO:373  GACACACGACATGATGATGGAAC-----CTAAGGTGGGTTTTTTGACTTTTGCATGTCGAAGTGAG
SEQID NO:374  GACACACGACATGATGATGGAACGTG-------AGGTGGGTTTTTTGACTTTTGCATGTCGAAGTGAG
SEQID NO:375  GACACACGACATGATGATGGAA------CTAAGGTGGGTTTTTTGACTTTTGCATGTCGAAGTGAG
SEQID NO:376  GACACACGACATGATGATGGAA---------TAAGGTGGGTTTTTTGACTTTTGCATGTCGAAGTGAG
SEQID NO:377  GACACACGACATGATGATGG---------CTAAGGTGGGTTTTTTGACTTTTGCATGTCGAAGTGAG
SEQID NO:378  GACACACGACATGATGATGGA----------TAAGGTGGGTTTTTTGACTTTTGCATGTCGAAGTGAG
SEQID NO:379  GACACACGACATGATGATGGA------------AGGTGGGTTTTTTGACTTTTGCATGTCGAAGTGAG
SEQID NO:380  GACACACGACATGATGATGGA------------AGGTGGGTTTTTTGACTTTTGCATGTCGAAGTGAG
SEQID NO:381  GACACACGACATGATGATGG-------------GTTTTTGGGTTTTTTGACTTTTGCATGTCGAAGTGAG
SEQID NO:382  GACACACGAC--------------------AGGTGGGTTTTTTGACTTTTGCATGTCGAAGTGAG
SEQID NO:383  GACAC------------------------TAAGGTGGGTTTTTTGACTTTTGCATGTCGAAGTGAG
SEQID NO:384  GACACACGACATGATGATGGAAC---------------------------------------GTGAG
SEQID NO:385  GACACACGACATGATGATGG--------------------133bp deletion----------------
```

FIGURE 26-C

DD43CR1 target site

| SEQID NO:386 | AGCCTTACAAACTCACAAGTCCCTTGTACTTGTACGTA CGGAGGGTATTCTAGAAAAGAGG |
| SEQID NO:387 | AGCCTTACAAACTCACAAGTCCCTTGTACTTGTACGTA-CGGAGGGTATTCTAGAAAAGAGG |
| SEQID NO:388 | AGCCTTACAAACTCACAAGTCCCTTGTACTTGTACGTA--GGAGGGTATTCTAGAAAAGAGG |
| SEQID NO:389 | AGCCTTACAAACTCACAAGTCCCTTGTACTTGTACGTA---GAGGGTATTCTAGAAAAGAGG |
| SEQID NO:390 | AGCCTTACAAACTCACAAGTCCCTTGTACTTGTACGTA----AGGGTATTCTAGAAAAGAGG |
| SEQID NO:391 | AGCCTTACAAACTCACAAGTCCCTTGTACTTGTACGTA-----GGGTATTCTAGAAAAGAGG |
| SEQID NO:392 | AGCCTTACAAACTCACAAGTCCCTTGTACTTGTACGTA------GGTATTCTAGAAAAGAGG |
| SEQID NO:393 | AGCCTTACAAACTCACAAGTCCCTTGTACTTGTACTT------GGTATTCTAGAAAAGAGG |
| SEQID NO:394 | AGCCTTACAAACTCACAAGTCCCTTGTACTTGTACTT-------GTATTCTAGAAAAGAGG |
| SEQID NO:395 | AGCCTTACAAACTCACAAGTCCCTTGTACTTGTACT--------GTATTCTAGAAAAGAGG |
| SEQID NO:396 | AGCCTTACAAACTCACAAGCCCCTTGTACTTGTACT---------TATTCTAGAAAAGAGG |
| SEQID NO:397 | AGCCTTACAAACTCACAAGTCCCTTGTACTTGTA----------TATTCTAGAAAAGAGG |
| SEQID NO:398 | AGCCTTACAAACTCACAAGTCCCTTGTACTTGT-----------TATTCTAGAAAAGAGG |
| SEQID NO:399 | AGCCTTACAAACTCACAAGTCCCTTGTACTTGTACTTG------------TATTCTAGAAAAGAGG |
| SEQID NO:400 | AGCCTTACAAACTCACAAGTCCCTTGTACTTGTACTCCCTT---------TATTCTAGAAAAGAGG |
| SEQID NO:401 | AGCCTTACAAACTCACAAGTCCCTTGTACTTGTACTCCCT----------TATTCTAGAAAAGAGG |
| SEQID NO:402 | AGCCTTACAAACTCACAAGTCCCTTGTACTTGTACTCCC-----------TATTCTAGAAAAGAGG |
| SEQID NO:403 | AGCCTTACAAACTCACAAGTCCCTTGTACTTGTACTTGTA-----------AGAAAAGAGG |
| SEQID NO:404 | AGCCTTACAAACTCACAAGTCC--------TAAATTAA^AGGTTATTCTAGAAAAGAGG |

Insertion starts at ^ with the insert size indicated.

| SEQID NO:405 | AGCCTTACAAACTCACAAGTCCCTTGTACTTGTAC^167GTACGGAGGGTATTCTAGAAAAGAGG |
| SEQID NO:406 | AGCCTTACAAACTCACAAGTCCCTTGTACTTGTAC^38--GTACGGAGGGTATTCTAGAAAAGAGG |
| SEQID NO:407 | AGCCTTACAAACTCACAAGTCCCTTGTACTTGTA^130-----GTACGGAGGGTATTCTAGAAAAGAGG |
| SEQID NO:408 | AGCCTTACAAACTCACAAGTCCCTTGTACTTGTAC^171GTACGGAGGGTATTCTAGAAAAGAGG |
| SEQID NO:409 | AGCCTTACAAACTCACAAGTCCCTTGTACTTGTAC^220GTACGGAGGGTATTCTAGAAAAGAGG |
| SEQID NO:410 | AGCCTTACAAACTCACAAGTCCCTTGTACTTGTAC^190GTACGGAGGGTATTCTAGAAAAGAGG |
| SEQID NO:411 | AGCCTTACAAACTCACAAGTCCCTT^110-------GTACGGAGGGTATTCTAGAAAAGAGG |
| SEQID NO:412 | AGCCTTACAAACTCACAAGTCCCTTGTACTTGTAC^125GTACGGAGGGTATTCTAGAAAAGAGG |
| SEQID NO:413 | AGCCTTACAAACTCACAAGTCCCTTGTACTTGTAC^154GTACGGAGGGTATTCTAGAAAAGAGG |
| SEQID NO:414 | AGCCTTACAAACTCACAAGTCCCTTGTACTTGTA^177------GAGGGTATTCTAGAAAAGAGG |

FIGURE 27 A

Expected Site of Cleavage ↓   PAM

| Sequence | Count | SEQ ID NO: |
|---|---|---|
| LIGCas-1 CTGTAACGATTTACGCACCTGCTGGGAATTGTACCGTACGTGCCCCGGCGAG|ATATATATACCTCACACGTACGCGTATATATAC | | 55 |
| TCCTCTGTAACGATTACGCACCTGCTGGGAATTGTACCGTACGTGCCCCGGT|CGGAGGATATATATACCTCACACGTACGCGTATATATAC | 2116 | 415 |
| TCCTCTGTAACGATTACGCACCTGCTGGGAATTGTACCGTACGTGCCCCGGA|CGGAGGATATATATACCTCACACGTACGCGTATATATAC | 1156 | 416 |
| TCCTCTGTAACGATTACGCACCTGCTGGGAATTGTACCGTACGTGCCCCGGG|CGGAGGATATATATACCTCACACGTACGCGTATATATAC | 473 | 417 |
| TCCTCTGTAACGATTACGCACCTGCTGGGAATTGTACCGTACGTGCCCCGGC|CGGAGGATATATATACCTCACACGTACGCGTATATATAC | 161 | 418 |
| TCCTCTGTAACGATTACGCACCTGCTGGGAATTGTACCGTACGTGCCCCGGA|TCGGAGGATATATATACCTCACACGTACGCGTATATATAC | 133 | 419 |
| TCCTCTGTAACGATTACGCACCTGCTGGGAATTGTACCGTACGTGCCCCGG----AGGATATATATACCTCACACGTACGCGTATATATAC | 82 | 420 |
| TCCTCTGTAACGATTACGCACCTGCTGGGAATTGTACCGTACGTGCCCCGG--------TTCACACGTACGCGTATATATAC | 77 | 421 |
| TCCTCTGTAACGATTACGCACCTGCTGGGAATTGTACCGTACGT--------ACGCGTACGCGTATATATAC | 55 | 422 |
| TCCTCTGTAACGATTACGCACCTGCTGGGAATTGTACCGTACGTGCCCCGGTTCGGAGGATATATATACCTCACACGTACGCGTATATATAC | 39 | 423 |
| TCCTCTGTAACGATTACGCACCTGCTGGGAATTGTACCGTACGTGCCCC---CGGAGGATATATATACCTCACACGTACGCGTATATATAC | 39 | 424 |

FIGURE 27-B

FIGURE 27C

| | | Count | SEQ ID NO: |
|---|---|---|---|
| LIGCas-3 | CGCAAATGAGTAGCAGCGCACGTATATACGCGTACGCGTACGTGT[AGG]ATATATATATCCTCCGCCGGGCACGTACGGTACAATTCCCAG | | 76 |
| | AAGGCGCAAATGAGTAGCAGCGCACGTATATACGCGTACGCGTACGTGTATATATATATATATCCTCCGCCGGGCACGTACGGTACAATTCCCAG | 1208 | 435 |
| | AAGGCGCAAATGAGTAGCAGCGCACGTATATACGCGTACGCGTACG-GTGAGGTATATATATATCCTCCGCCGGGCACGTACGGTACAATTCCCAG | 453 | 436 |
| | AAGGCGCAAATGAGTAGCAGCGCACGTATATACGCGTACGCGTACGT--GAGGTATATATATATCCTCCGCCGGGCACGTACGGTACAATTCCCAG | 338 | 437 |
| | AAGGCGCAAATGAGTAGCAGCGCACGTATATACGCGTACGCGTAC-TGTGAGGTATATATATATCCTCCGCCGGGCACGTACGGTACAATTCCCAG | 145 | 438 |
| | AAGGCGCAAATGAGTAGCAGCGCACGTATATACGCGCACGTATATA------TCCTCCGCCGGGCACGTACGGTACAATTCCCAG | 94 | 439 |
| | AAGGCGCAAATGAGTAGCAGCGCACGTATATACGCGTACGCGT-----GTGAGGTATATATATCCTCCGCCGGGCACGTACGGTACAATTCCCAG | 53 | 440 |
| | AAGGCGCAAATGAGTAGCAGCGCACGTATATACGCGTACGCGTACG------TGAGGTATATATATCCTCCGCCGGGCACGTACGGTACAATTCCCAG | 42 | 441 |
| | AAGGCGCAAATGAGTAGCAGCGCACGTATATACGCGTACGCGTAC-------TATATATATATATATCCTCCGCCGGGCACGTACGGTACAATTCCCAG | 37 | 442 |
| | AAGGCGCAAATGAGTAGCAGCGCACGTATATACGCGTACGCGTACG---GAGGTATATATATATCCTCCGCCGGGCACGTACGGTACAATTCCCAG | 20 | 443 |
| | AAGGCGCAAATGAGTAGCAGCGCACGTATATACGCGTATATACGCGTACG-ATGAGGTATATATATCCTCCGCCGGGCACGTACGGTACAATTCCCAG | 19 | 444 |

Expected Site of Cleavage / PAM

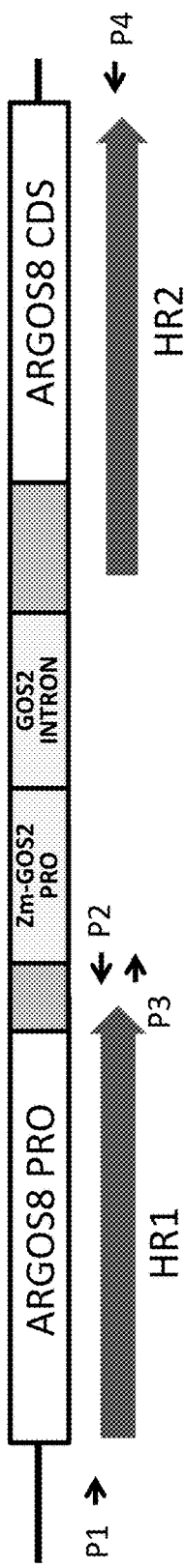
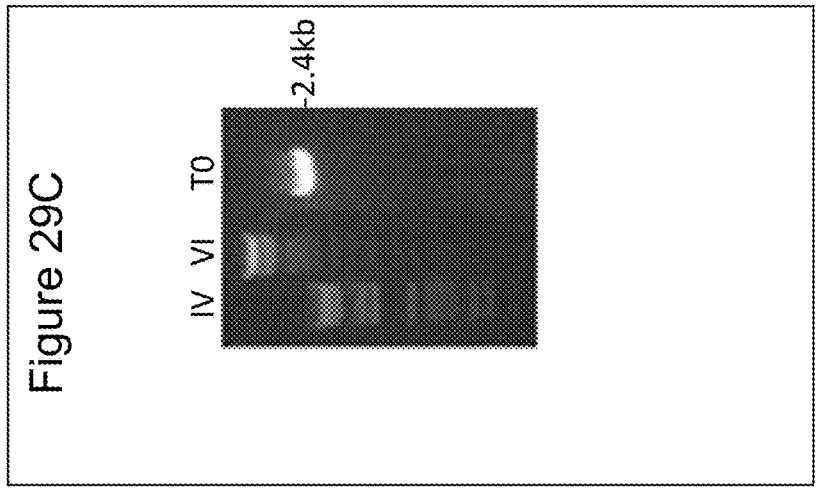
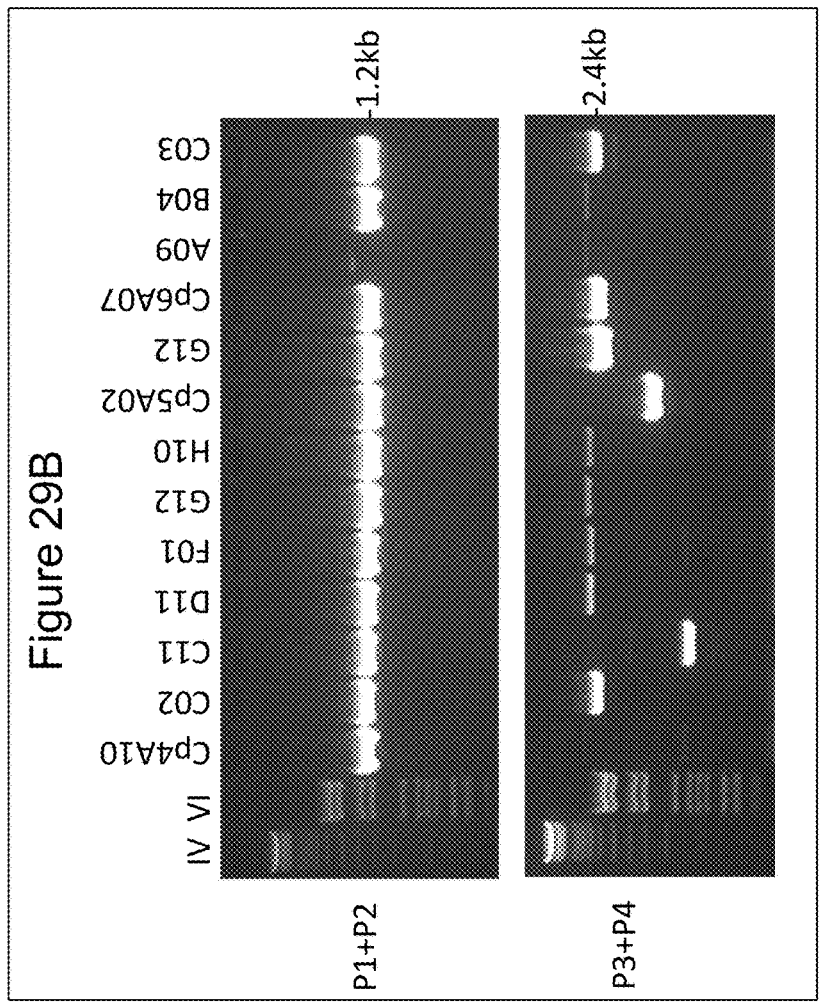
Figure 29A
Figure 29C
Figure 29B

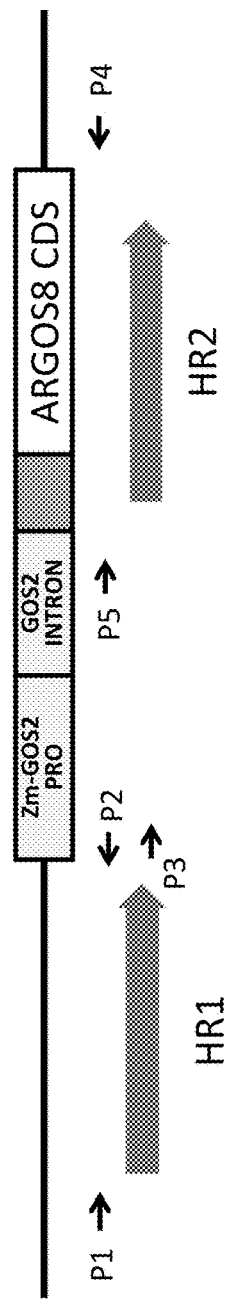
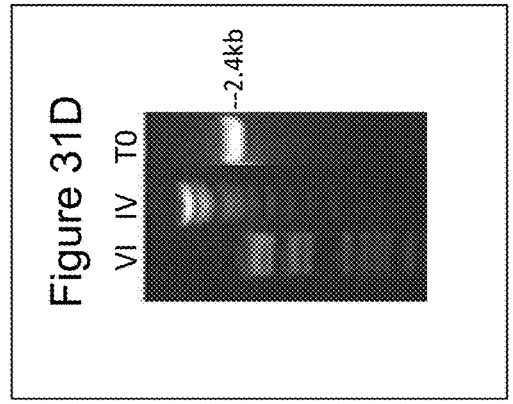
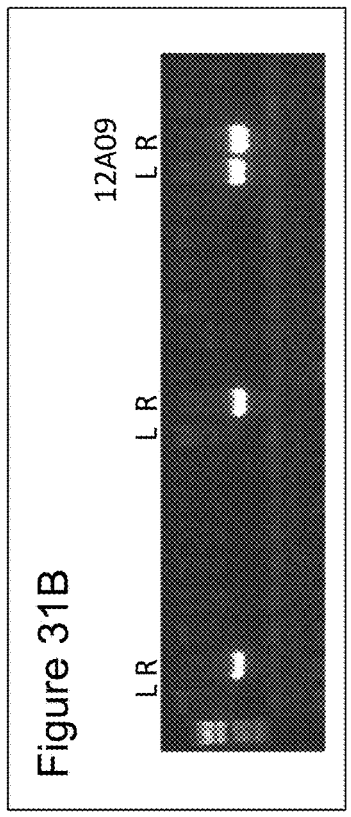
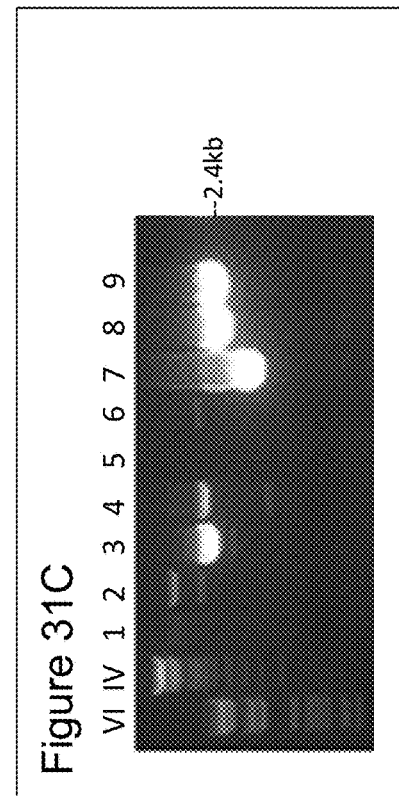
Figure 31A
Figure 31B
Figure 31C
Figure 31D

Figure 34 A

| | |
|---|---|
| VEDAKEEV | Maize |
| GKESKEEI | Petunia |
| GKKSEEEI | Tomato |
| EKDAKEEV | Sorghum |
| VEDSKEEV | Rice |
| GKDGKEEI | Amarathus |

Figure 34 B

```
            T              P    moCas9 target sequence
K  GCTAAAGAGGAAGTGCAGCTCTTCTTGGGAATGCTGGAACTGCAATGCGGCCATTGACAGCAGCTGTACTGCTGG
```

Figure 34 C

```
            I              S    moCas9 target sequence
R  GCTAGAGAGGAAGTGCAGCTCTTCTTGGGAATGCTGGAATGCGCAATCGCAATGCGGTCATTGACAGCAGCTGTTACTGCTGG
```

Figure 35 A

CATATCTG

Figure 35 B

CATCTC...ACGATCAGAT..GCACCGCATGTCGCATGCCTA

Figure 35 C

CATATCTGCACGATCAGATATGCACCGCATGTCGCATATCTG

SEQUENCE LISTING

<160> NUMBER OF SEQ ID NOS: 571

<210> SEQ ID NO 1
<211> LENGTH: 4107
<212> TYPE: DNA
<213> ORGANISM: Streptococcus pyogenes

<400> SEQUENCE: 1

```
atggataaga aatactcaat aggcttagat atcggcacaa atagcgtcgg atgggcggtg      60
atcactgatg aatataaggt tccgtctaaa aagttcaagg ttctgggaaa tacagaccgc     120
cacagtatca aaaaaatct tataggggct cttttatttg acagtggaga gacagcggaa     180
gcgactcgtc tcaaacggac agctcgtaga aggtatacac gtcggaagaa tcgtatttgt     240
tatctacagg agatttttc aaatgagatg gcgaaagtag atgatagttt ctttcatcga     300
cttgaagagt cttttttggt ggaagaagac aagaagcatg aacgtcatcc tattttttgga    360 aatatagtag atgaagttgc ttatcatgag aaatatccaa ctatctatca tctgcgaaaa     420
aaattggtag attctactga taaagcggat ttgcgcttaa tctatttggc cttagcgcat     480
atgattaagt ttcgtggtca ttttttgatt gagggagatt taaatcctga taatagtgat     540
gtggacaaac tatttatcca gttggtacaa acctacaatc aattatttga agaaaaccct    600
attaacgcaa gtggagtaga tgctaaagcg attctttctg cacgattgag taaatcaaga     660
cgattagaaa atctcattgc tcagctcccc ggtgagaaga aaaatggctt atttgggaat     720
ctcattgctt tgtcattggg tttgaccct aattttaaat caaattttga tttggcagaa      780
gatgctaaat tacagctttc aaaagatact tacgatgatg atttagataa tttattggcg     840
caaattggag atcaatatgc tgatttgttt ttggcagcta agaatttatc agatgctatt     900
ttactttcag atatcctaag agtaaatact gaaataacta aggctcccct atcagcttca     960
atgattaaac gctacgatga acatcatcaa gacttgactc ttttaaaagc tttagttcga    1020
caacaacttc cagaaaagta taaagaaatc ttttttgatc aatcaaaaaa cggatatgca    1080
ggttatattg atggggagc tagccaagaa gaattttata aatttatcaa accaatttta    1140
gaaaaaatgg atggtactga ggaattattg gtgaaactaa atcgtgaaga tttgctgcgc    1200
aagcaacgga cctttgacaa cggctctatt ccccatcaaa ttcacttggg tgagctgcat    1260
gctattttga agacaagaga gacttttat ccattttaa aagacaatcg tgagaagatt    1320
gaaaaaatct tgactttcg aattccttat tatgttggtc cattggcgcg tggcaatagt    1380
cgttttgcat ggatgactcg gaagtctgaa gaaacaatta ccccatggaa ttttgaagaa    1440
gttgtcgata aaggtgcttc agctcaatca tttattgaac gcatgacaaa ctttgataaa    1500
aatcttccaa atgaaaaagt actaccaaaa catagtttgc tttatgagta ttttacggtt    1560
tataacgaat tgacaaaggt caaatatgtt actgaaggaa tgcgaaaacc agcatttctt    1620
tcaggtgaac agaagaaagc cattgttgat ttactcttca aaacaaatcg aaaagtaacc    1680
```

```
gttaagcaat taaaagaaga ttatttcaaa aaaatagaat gttttgatag tgttgaaatt    1740
tcaggagttg aagatagatt taatgcttca ttaggtacct accatgattt gctaaaaatt    1800
attaaagata aagattttt ggataatgaa gaaaatgaag atatcttaga ggatattgtt    1860
ttaacattga ccttatttga agatagggag atgattgagg aaagacttaa acatatgct    1920 cacctctttg atgataaggt gatgaaacag cttaaacgtc gccgttatac tggttgggga    1980
cgtttgtctc gaaaattgat taatggtatt agggataagc aatctggcaa aacaatatta    2040
gattttttga aatcagatgg ttttgccaat cgcaattta tgcagctgat ccatgatgat    2100
agtttgacat ttaaagaaga cattcaaaaa gcacaagtgt ctggacaagg cgatagttta    2160
catgaacata ttgcaaattt agctggtagc cctgctatta aaaaggtat tttacagact    2220 gtaaagttg ttgatgaatt ggtcaaagta atggggcggc ataagccaga aaatatcgtt    2280
attgaaatgg cacgtgaaaa tcagacaact caaaagggcc agaaaaattc gcgagagcgt    2340
atgaaacgaa tcgaagaagg tatcaaagaa ttaggaagtc agattcttaa agagcatcct    2400
gttgaaaata ctcaattgca aaatgaaaag ctctatctct attatctcca aatggaaga    2460 gacatgtatg tggaccaaga attagatatt aatcgtttaa gtgattatga tgtcgatcac    2520
attgttccac aaagtttcct taaagacgat tcaatagaca ataaggtctt aacgcgttct    2580
gataaaaatc gtggtaaatc ggataacgtt ccaagtgaag aagtagtcaa aaagatgaaa    2640
aactattgga gacaacttct aaacgccaag ttaatcactc aacgtaagtt tgataattta    2700
acgaaagctg aacgtggagg tttgagtgaa cttgataaag ctggttttat caaacgccaa    2760
ttggttgaaa ctcgccaaat cactaagcat gtggcacaaa ttttggatag tcgcatgaat    2820
actaaatacg atgaaaatga taaacttatt cgagaggtta aagtgattac cttaaaatct    2880
aaattagttt ctgacttccg aaaagatttc caattctata agtacgtga gattaacaat    2940 taccatcatg cccatgatgc gtatctaaat gccgtcgttg gaactgcttt gattaagaaa    3000
tatccaaaac ttgaatcgga gtttgtctat ggtgattata agtttatga tgttcgtaaa    3060 atgattgcta agtctgagca agaaataggc aaagcaaccg caaaatattt cttttactct    3120
aatatcatga acttcttcaa aacagaaatt acacttgcaa atggagagat tcgcaaacgc    3180
cctctaatcg aaactaatgg ggaaactgga gaaattgtct gggataaagg gcgagatttt    3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt ttgatagtcc aacggtagct    3420
tattcagtcc tagtggttgc taaggtggaa aagggaaat cgaagaagtt aaaatccgtt    3480
aaagagttac tagggatcac aattatggaa agaagttcct ttgaaaaaaa tccgattgac    3540 ttttttagaag ctaaaggata taaggaagtt aaaaaagact taatcattaa actacctaaa    3600
tatagtcttt ttgagttaga aaacggtcgt aaacggatgc tggctagtgc cggagaatta    3660
caaaaaggaa atgagctggc tctgccaagc aaatatgtga atttttata tttagctagt    3720 cattatgaaa agttgaaggg tagtccagaa gataacgaac aaaaacaatt gtttgtggag    3780
cagcataagc attatttaga tgagattatt gagcaaatca gtgaatttc taagcgtgtt    3840 attttagcag atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatatt tgatacaaca attgatcgta aacgatatac gtctacaaaa    4020
```

```
gaagttttag atgccactct tatccatcaa tccatcactg gtctttatga aacacgcatt    4080
gatttgagtc agctaggagg tgactga                                       4107

<210> SEQ ID NO 2
<211> LENGTH: 189
<212> TYPE: DNA
<213> ORGANISM: Solanum tuberosum

<400> SEQUENCE: 2
gtaagtttct gcttctacct ttgatatata tataataatt atcattaatt agtagtaata     60
taatatttca aatattttt tcaaaataaa agaatgtagt atatagcaat tgcttttctg    120
tagtttataa gtgtgtatat tttaatttat aacttttcta atatatgacc aaaacatggt    180
gatgtgcag                                                           189

<210> SEQ ID NO 3
<211> LENGTH: 9
<212> TYPE: PRT
<213> ORGANISM: Simian virus 40

<400> SEQUENCE: 3

Met Ala Pro Lys Lys Lys Arg Lys Val
1               5

<210> SEQ ID NO 4
<211> LENGTH: 18
<212> TYPE: PRT
<213> ORGANISM: Agrobacterium tumefaciens

<400> SEQUENCE: 4

Lys Arg Pro Arg Asp Arg His Asp Gly Glu Leu Gly Gly Arg Lys Arg
1               5                   10                  15

Ala Arg

<210> SEQ ID NO 5
<211> LENGTH: 6717
<212> TYPE: DNA
<213> ORGANISM: Artificial Sequence
<220> FEATURE:
<223> OTHER INFORMATION: synthesized sequence-Maize optimized Cas9
      expression cassette

<400> SEQUENCE: 5
gtgcagcgtg acccggtcgt gcccctctct agagataatg agcattgcat gtctaagtta     60
taaaaaatta ccacatattt tttttgtcac acttgtttga agtgcagttt atctatcttt    120
atacatatat ttaaacttta ctctacgaat aatataatct atagtactac aataatatca    180
gtgttttaga gaatcatata aatgaacagt tagacatggt ctaaggaca attgagtatt    240 ttgacaacag gactctacag ttttatcttt ttagtgtgca tgtgttctcc tttttttttg    300
caaatagctt cacctatata atacttcatc cattttatta gtacatccat ttagggttta    360
gggttaatgg ttttttataga ctaattttt tagtacatct attttattct attttagcct    420
ctaaattaag aaaactaaaa ctctatttta gttttttat ttaataattt agatatataaaa    480 tagaataaaa taaagtgact aaaaattaaa caaataccct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggaccccc tcgagagtt ccgctccacc gttggacttg    720
```

```
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840
ttcgctttcc cttcctcgcc cgccgtaata aatagacacc ccctccacac cctctttccc    900
caacctcgtg ttgttcggag cgcacacaca cacaaccaga tctcccccaa atccacccgt    960
cggcacctcc gcttcaaggt acgccgctcg tcctccccccc cccccctctc taccttctct   1020
agatcggcgt tccggtccat gcatggttag ggcccggtag ttctacttct gttcatgttt   1080
gtgttagatc cgtgtttgtg ttagatccgt gctgctagcg ttcgtacacg gatgcgacct   1140
gtacgtcaga cacgttctga ttgctaactt gccagtgttt ctctttgggg aatcctggga   1200
tggctctagc cgttccgcag acgggatcga tttcatgatt ttttttgttt cgttgcatag   1260
ggtttggttt gccctttttcc tttatttcaa tatatgccgt gcacttgttt gtcgggtcat   1320
cttttcatgc ttttttttgt cttggttgtg atgatgtggt ctggttgggc ggtcgttcta   1380
gatcggagta gaattctgtt tcaaactacc tggtggattt attaattttg gatctgtatg   1440
tgtgtgccat acatattcat agttacgaat tgaagatgat ggatgaaat atcgatctag    1500
gataggtata catgttgatg cgggttttac tgatgcatat acagagatgc ttttgttcg   1560
cttggttgtg atgatgtggt gtggttgggc ggtcgttcat tcgttctaga tcggagtaga   1620
atactgtttc aaactacctg gtgtatttat taattttgga actgtatgtg tgtgtcatac   1680
atcttcatag ttacgagttt aagatggatg gaaatatcga tctaggatag gtatacatgt   1740
tgatgtgggt tttactgatg catatacatg atggcatatg cagcatctat tcatatgctc   1800
taaccttgag tacctatcta ttataataaa caagtatgtt ttataattat tttgatcttg   1860
atatacttgg atgatggcat atgcagcagc tatatgtgga tttttttagc cctgccttca   1920
tacgctatttt atttgcttgg tactgtttct tttgtcgatg ctcaccctgt tgtttggtgt   1980
tacttctgca ggtcgactct agaggatcca tggcaccgaa gaagaagcgc aaggtgatgg   2040
acaagaagta cagcatcggc ctcgacatcg gcaccaactc ggtgggctgg gccgtcatca   2100
cggacgaata aaggtcccg tcgaagaagt tcaaggtcct cggcaataca gaccgccaca   2160
gcatcaagaa aaacttgatc ggcgcccctcc tgttcgatag cggcgagacc gcggaggcga   2220
ccaggctcaa gaggaccgcc aggagacggt acactaggcg caagaacagg atctgctacc   2280
tgcaggagat cttcagcaac gagatggcga aggtggacga ctccttcttc caccgcctgg   2340
aggaatcatt cctggtggag gaggacaaga agcatgagcg gcacccaatc ttcggcaaca   2400
tcgtcgacga ggtaagtttc tgcttctacc tttgatatat atataataat tatcattaat   2460
tagtagtaat ataatatttc aaatattttt ttcaaaataa agaatgtag tatatagcaa    2520
ttgcttttct gtagtttata agtgtgtata ttttaattta taacttttct aatatatgac   2580
caaaacatgg tgatgtgcag gtggcctacc acgagaagta cccgacaatc taccacctcc   2640
ggaagaaact ggtggacagc acagacaagg cggacctccg gctcatctac cttgccctcg   2700
cgcatatgat caagttccgc ggccacttcc tcatcgaggg cgacctgaac ccggacaact   2760
ccgacgtgga caagctgttc atccagctcg tgcagacgta caatcaactg ttcgaggaga   2820
acccataaa cgctagcggc gtggacgcca aggccatcct ctcggccagg ctctcgaaat   2880
caagaaggct ggagaacctt atcgcgcagt tgccaggcga aaagaagaac ggcctcttcg   2940
gcaaccttat tgcgctcagc ctcggcctga cgccgaactt caaatcaaac ttcgacctcg   3000
cggaggacgc caagctccag ctctcaaagg acacctacga cgacgacctc gacaacctcc   3060
tggcccagat aggagaccag tacgcggacc tcttcctcgc cgccaagaac ctctccgacg   3120
```

```
ctatcctgct cagcgacatc cttcgggtca acaccgaaat taccaaggca ccgctgtccg    3180
ccagcatgat taaacgctac gacgagcacc atcaggacct cacgctgctc aaggcactcg    3240
tccgccagca gctccccgag aagtacaagg agatcttctt cgaccaatca aaaaacggct    3300
acgcgggata tatcgacggc ggtgccagcc aggaagagtt ctacaagttc atcaaaccaa    3360
tcctggagaa gatggacggc accgaggagt tgctggtcaa gctcaacagg gaggacctcc    3420
tcaggaagca gaggaccttc gacaacggct ccatcccgca tcagatccac ctgggcgaac    3480
tgcatgccat cctgcggcgc caggaggact tctacccgtt cctgaaggat aaccgggaga    3540
agatcgagaa gatcttgacg ttccgcatcc catactacgt gggcccgctg gctcgcggca    3600
actcccggtt cgcctggatg acccggaagt cggaggagac catcacaccc tggaactttg    3660
aggaggtggt cgataagggc gctagcgctc agagcttcat cgagcgcatg accaacttcg    3720
ataaaaacct gcccaatgaa aaagtcctcc ccaagcactc gctgctctac gagtacttca    3780
ccgtgtacaa cgagctcacc aaggtcaaat acgtcaccga gggcatgcgg aagccggcgt    3840
tcctgagcgg cgagcagaag aaggcgatag tggacctcct cttcaagacc aacaggaagg    3900
tgaccgtgaa gcaattaaaa gaggactact tcaagaaaat agagtgcttc gactccgtgg    3960
agatctcggg cgtggaggat cggttcaacg cctcactcgg cacgtatcac gacctcctca    4020
agatcattaa agacaaggac ttcctcgaca acgaggagaa cgaggacatc ctcgaggaca    4080
tcgtcctcac cctgaccctg ttcgaggacc gcgaaatgat cgaggagagg ctgaagacct    4140
acgcgcacct gttcgacgac aaggtcatga acagctcaa gaggcgccgc tacactggtt    4200
ggggaaggct gtcccgcaag ctcattaatg gcatcaggga caagcagagc ggcaagacca    4260
tcctggactt cctcaagtcc gacgggttcg ccaaccgcaa cttcatgcag ctcattcacg    4320
acgactcgct cacgttcaag gaagacatcc agaaggcaca ggtgagcggg cagggtgact    4380
ccctccacga acacatcgcc aacctggccg gctcgccggc cattaaaaag gcatcctgc     4440 agacggtcaa ggtcgtcgac gagctcgtga aggtgatggg ccggcacaag cccgaaaata    4500
tcgtcataga gatggccagg gagaaccaga ccacccaaaa agggcagaag aactcgcgcg    4560
agcggatgaa acgatcgag gagggcatta aagagctcgg gtcccagatc ctgaaggagc    4620
accccgtgga aaatacccag ctccagaatg aaaagctcta cctctactac ctgcagaacg    4680
gccgcgacat gtacgtggac caggagctgg acattaatcg gctatcggac tacgacgtcg    4740
accacatcgt gccgcagtcg ttcctcaagg acgatagcat cgacaacaag gtgctcaccc    4800
ggtcggataa aaatcggggc aagagcgaca acgtgcccag cgaggaggtc gtgaagaaga    4860
tgaaaaacta ctggcgccag ctcctcaacg cgaaactgat cacccagcgc aagttcgaca    4920
acctgacgaa ggcggaacgc ggtggcttga gcgaactcga taaggcgggc ttcataaaaa    4980
ggcagctggt cgagacgcgc cagatcacga agcatgtcgc ccagatcctg gacagccgca    5040
tgaatactaa gtacgatgaa aacgacaagc tgatccggga ggtgaaggtg atcacgctga    5100
agtccaagct cgtgtcggac ttccgcaagg acttccagtt ctacaaggtc cgcgagatca    5160
acaactacca ccacgcccac gacgcctacc tgaatgcggt ggtcgggacc gccctgatca    5220
agaagtaccc gaagctggag tcggagttcg tgtacgcgca ctacaaggtc tacgacgtgc    5280
gcaaaatgat cgccaagtcc gagcaggaga tcggcaaggc cacggcaaaa tacttcttct    5340
actcgaacat catgaacttc ttcaagaccg agatcaccct cgcgaacggc gagatccgca    5400
agcgcccgct catcgaaacc aacggcgaga cgggcgagat cgtctgggat aagggccggg    5460
```

```
atttcgcgac ggtccgcaag gtgctctcca tgccgcaagt caatatcgtg aaaaagacgg    5520
aggtccagac gggcgggttc agcaaggagt ccatcctccc gaagcgcaac tccgacaagc    5580
tcatcgcgag gaagaaggat tgggacccga aaaaatatgg cggcttcgac agcccgaccg    5640
tcgcatacag cgtcctcgtc gtggcgaagg tggagaaggg caagtcaaag aagctcaagt    5700
ccgtgaagga gctgctcggg atcacgatta tggagcggtc ctccttcgag aagaacccga    5760
tcgacttcct agaggccaag ggatataagg aggtcaagaa ggacctgatt attaaactgc    5820
cgaagtactc gctcttcgag ctggaaaacg gccgcaagag gatgctcgcc tccgcaggcg    5880
agttgcagaa gggcaacgag ctcgccctcc cgagcaaata cgtcaatttc ctgtacctcg    5940
ctagccacta tgaaaagctc aagggcagcc ggaggacaa cgagcagaag cagctcttcg    6000
tggagcagca caagcattac ctggacgaga tcatcgagca gatcagcgag ttctcgaagc    6060
gggtgatcct cgccgacgcg aacctggaca aggtgctgtc ggcatataac aagcaccgcg    6120
acaaaccaat acgcgagcag gccgaaaata tcatccacct cttcaccctc accaacctcg    6180
gcgctccggc agccttcaag tacttcgaca ccacgattga ccggaagcgg tacacgagca    6240
cgaaggaggt gctcgatgcg acgctgatcc accagagcat cacagggctc tatgaaacac    6300
gcatcgacct gagccagctg gcggagaca agagaccacg ggaccgccac gatggcgagc    6360
tgggaggccg caagcgggca aggtaggtac cgttaaccta gacttgtcca tcttctggat    6420
tggccaactt aattaatgta tgaaataaaa ggatgcacac atagtgacat gctaatcact    6480
ataatgtggg catcaaagtt gtgtgttatg tgtaattact agttatctga ataaaagaga    6540
aagagatcat ccatatttct tatcctaaat gaatgtcacg tgtctttata attctttgat    6600
gaaccagatg catttcatta accaaatcca tatacatata aatattaatc atatataatt    6660
aatatcaatt gggttagcaa aacaaatcta gtctaggtgt gttttgcgaa tgcggcc      6717
```

```
<210> SEQ ID NO 6
<211> LENGTH: 39
<212> TYPE: RNA
<213> ORGANISM: Artificial Sequence
<220> FEATURE:
<223> OTHER INFORMATION: synthesized sequence-crRNA containing the
      LIGCas-3 target sequence in the variable targeting domain

<400> SEQUENCE: 6
gcguacgcgu acgugugguu uuagagcuau gcuguuuug                            39

<210> SEQ ID NO 7
<211> LENGTH: 86
<212> TYPE: RNA
<213> ORGANISM: Streptococcus pyogenes
<220> FEATURE:
<221> NAME/KEY: misc_feature
<222> LOCATION: (1)..(86)
<223> OTHER INFORMATION: tracrRNA

<400> SEQUENCE: 7
ggaaccauuc aaaacagcau agcaaguuaa aauaaggcua guccguuauc aacuugaaaa    60
aguggcaccg agucggugcu uuuuuu                                         86

<210> SEQ ID NO 8
<211> LENGTH: 94
<212> TYPE: RNA
<213> ORGANISM: Artificial Sequence
<220> FEATURE:
<223> OTHER INFORMATION: synthesized sequence- Long guide RNA containing
      the LIGCas-3 target sequence in the variable targeting domain
```

<400> SEQUENCE: 8

```
gcguacgcgu acgugugguu uuagagcuag aaauagcaag uuaaaauaag gcuaguccgu    60
uaucaacuug aaaaaguggc accgagucgg ugcu                                94
```

<210> SEQ ID NO 9
<211> LENGTH: 1000
<212> TYPE: DNA
<213> ORGANISM: Zea mays

<400> SEQUENCE: 9

```
tgagagtaca atgatgaacc tagattaatc aatgccaaag tctgaaaaat gcaccctcag    60
tctatgatcc agaaaatcaa gattgcttga ggccctgttc ggttgttccg gattagagcc   120
ccggattaat tcctagccgg attacttctc taatttatat agattttgat gagctggaat   180
gaatcctggc ttattccggt acaaccgaac aggccctgaa ggataccagt aatcgctgag   240
ctaaattggc atgctgtcag agtgtcagta ttgcagcaag gtagtgagat aaccggcatc   300
atggtgccag tttgatggca ccattagggt tagagatggt ggccatgggc gcatgtcctg   360
gccaactttg tatgatatat ggcagggtga ataggaaagt aaaattgtat tgtaaaaagg   420
gatttcttct gtttgttagc gcatgtacaa ggaatgcaag ttttgagcga gggggcatca   480
aagatctggc tgtgtttcca gctgtttttg ttagccccat cgaatccttg acataatgat   540
cccgcttaaa taagcaacct cgcttgtata gttccttgtg ctctaacaca cgatgatgat   600
aagtcgtaaa atagtggtgt ccaaagaatt tccaggccca gttgtaaaag ctaaaatgct   660
attcgaattt ctactagcag taagtcgtgt ttagaaatta ttttttttata tacctttttt   720
ccttctatgt acagtaggac acagtgtcag cgccgcgttg acggagaata tttgcaaaaa   780
agtaaaagag aaagtcatag cggcgtatgt gccaaaaact tcgtcacaga gagggccata   840
agaaacatgg cccacggccc aatacgaagc accgcgacga agcccaaaca gcagtccgta   900
ggtggagcaa agcgctgggt aatacgcaaa cgttttgtcc caccttgact aatcacaaga   960
gtggagcgta ccttataaac cgagccgcaa gcaccgaatt                        1000
```

<210> SEQ ID NO 10
<211> LENGTH: 16
<212> TYPE: DNA
<213> ORGANISM: Zea mays

<400> SEQUENCE: 10

```
tttttttttt tttttt                                                    16
```

<210> SEQ ID NO 11
<211> LENGTH: 59
<212> TYPE: RNA
<213> ORGANISM: Artificial Sequence
<220> FEATURE:
<223> OTHER INFORMATION: synthesized sequence- Short guide RNA
      containing the LIGCas-3 variable targeting domain

<400> SEQUENCE: 11

```
gcguacgcgu acgugugguu uuagagcuag aaauagcaag uuaaaauaag gcuaguccg     59
```

<210> SEQ ID NO 12
<211> LENGTH: 1102
<212> TYPE: DNA
<213> ORGANISM: Artificial Sequence
<220> FEATURE:
<223> OTHER INFORMATION: synthesized sequence- Maize optimized long guide RNA expression cassette containing the LIGCas-3 variable
targeting domain

<400> SEQUENCE: 12
tgagagtaca atgatgaacc tagattaatc aatgccaaag tctgaaaaat gcaccctcag      60
tctatgatcc agaaaatcaa gattgcttga ggccctgttc ggttgttccg gattagagcc     120
ccggattaat tcctagccgg attacttctc taatttatat agattttgat gagctggaat     180
gaatcctggc ttattccggt acaaccgaac aggccctgaa ggataccagt aatcgctgag     240
ctaaattggc atgctgtcag agtgtcagta ttgcagcaag gtagtgagat aaccggcatc     300
atggtgccag tttgatggca ccattagggt tagagatggt ggccatgggc gcatgtcctg     360
gccaactttg tatgatatat ggcagggtga ataggaaagt aaaattgtat tgtaaaaagg     420
gatttcttct gtttgttagc gcatgtacaa ggaatgcaag ttttgagcga gggggcatca     480
aagatctggc tgtgtttcca gctgtttttg ttagccccat cgaatccttg acataatgat     540
cccgcttaaa taagcaacct cgcttgtata gttccttgtg ctctaacaca cgatgatgat     600
aagtcgtaaa atagtggtgt ccaaagaatt tccaggccca gttgtaaaag ctaaaatgct     660
attcgaattt ctactagcag taagtcgtgt ttagaaatta ttttttttata tacctttttt     720 ccttctatgt acagtaggac acagtgtcag cgccgcgttg acggagaata tttgcaaaaa     780
agtaaaagag aaagtcatag cggcgtatgt gccaaaaact tcgtcacaga gagggccata     840
agaaacatgg cccacggccc aatacgaagc accgcgacga agcccaaaca gcagtccgta     900
ggtggagcaa agcgctgggt aatacgcaaa cgttttgtcc caccttgact aatcacaaga     960
gtggagcgta ccttataaac cgagccgcaa gcaccgaatt gcgtacgcgt acgtgtggtt    1020
ttagagctag aaatagcaag ttaaaataag gctagtccgt tatcaacttg aaaaagtggc    1080
accgagtcgg tgcttttttt tt                                             1102

<210> SEQ ID NO 13
<211> LENGTH: 27
<212> TYPE: DNA
<213> ORGANISM: Zea mays

<400> SEQUENCE: 13
gtactccatc cgccccatcg agtaggg                                         27

<210> SEQ ID NO 14
<211> LENGTH: 24
<212> TYPE: DNA
<213> ORGANISM: Zea mays

<400> SEQUENCE: 14
gcacgtacgt caccatcccg ccgg                                            24

<210> SEQ ID NO 15
<211> LENGTH: 24
<212> TYPE: DNA
<213> ORGANISM: Zea mays

<400> SEQUENCE: 15
gacgtacgtg ccctactcga tggg                                            24

<210> SEQ ID NO 16
<211> LENGTH: 24
<212> TYPE: DNA
<213> ORGANISM: Zea mays

```
<400> SEQUENCE: 16
gtaccgtacg tgccccggcg gagg                                              24

<210> SEQ ID NO 17
<211> LENGTH: 24
<212> TYPE: DNA
<213> ORGANISM: Zea mays

<400> SEQUENCE: 17
ggaattgtac cgtacgtgcc ccgg                                              24

<210> SEQ ID NO 18
<211> LENGTH: 20
<212> TYPE: DNA
<213> ORGANISM: Zea mays

<400> SEQUENCE: 18
gcgtacgcgt acgtgtgagg                                                   20

<210> SEQ ID NO 19
<211> LENGTH: 22
<212> TYPE: DNA
<213> ORGANISM: Zea mays

<400> SEQUENCE: 19
gctggccgag gtcgactacc gg                                                22

<210> SEQ ID NO 20
<211> LENGTH: 23
<212> TYPE: DNA
<213> ORGANISM: Zea mays

<400> SEQUENCE: 20
ggccgaggtc gactaccggc cgg                                               23

<210> SEQ ID NO 21
<211> LENGTH: 23
<212> TYPE: DNA
<213> ORGANISM: Zea mays

<400> SEQUENCE: 21
ggcgcgagct cgtgcttcac cgg                                               23

<210> SEQ ID NO 22
<211> LENGTH: 21
<212> TYPE: DNA
<213> ORGANISM: Zea mays

<400> SEQUENCE: 22
ggtgccaatc atgcgtcgcg g                                                 21

<210> SEQ ID NO 23
<211> LENGTH: 20
<212> TYPE: DNA
<213> ORGANISM: Zea mays

<400> SEQUENCE: 23
ggtcgccatc acgggacagg                                                   20

<210> SEQ ID NO 24
<211> LENGTH: 24
<212> TYPE: DNA
<213> ORGANISM: Zea mays
```

```
<400> SEQUENCE: 24
gtcgcggcac ctgtcccgtg atgg                                          24

<210> SEQ ID NO 25
<211> LENGTH: 23
<212> TYPE: DNA
<213> ORGANISM: Zea mays

<400> SEQUENCE: 25
ggaatgctgg aactgcaatg cgg                                           23

<210> SEQ ID NO 26
<211> LENGTH: 24
<212> TYPE: DNA
<213> ORGANISM: Zea mays

<400> SEQUENCE: 26
gcagctcttc ttggggaatg ctgg                                          24

<210> SEQ ID NO 27
<211> LENGTH: 23
<212> TYPE: DNA
<213> ORGANISM: Zea mays

<400> SEQUENCE: 27
gcagtaacag ctgctgtcaa tgg                                           23

<210> SEQ ID NO 28
<211> LENGTH: 56
<212> TYPE: DNA
<213> ORGANISM: Artificial Sequence
<220> FEATURE:
<223> OTHER INFORMATION: synthesized sequence- MS26Cas-1 forward primer

<400> SEQUENCE: 28
ctacactctt tccctacacg acgctcttcc gatctaggac cggaagctcg ccgcgt       56

<210> SEQ ID NO 29
<211> LENGTH: 54
<212> TYPE: DNA
<213> ORGANISM: Artificial Sequence
<220> FEATURE:
<223> OTHER INFORMATION: synthesized sequence- MS26Cas-1 and MS26Cas-3
      reverse primer

<400> SEQUENCE: 29
caagcagaag acggcatacg agctcttccg atcttcctgg aggacgacgt gctg         54

<210> SEQ ID NO 30
<211> LENGTH: 59
<212> TYPE: DNA
<213> ORGANISM: Artificial Sequence
<220> FEATURE:
<223> OTHER INFORMATION: synthesized sequence- MS26Cas-2 forward primer

<400> SEQUENCE: 30
ctacactctt tccctacacg acgctcttcc gatctaaggt cctggaggac gacgtgctg    59

<210> SEQ ID NO 31
<211> LENGTH: 51
<212> TYPE: DNA
<213> ORGANISM: Artificial Sequence
<220> FEATURE:
<223> OTHER INFORMATION: synthesized sequence- MS26Cas-2 and MS26
``` meganuclease reverse primer

<400> SEQUENCE: 31
caagcagaag acggcatacg agctcttccg atctccggaa gctcgccgcg t          51

<210> SEQ ID NO 32
<211> LENGTH: 56
<212> TYPE: DNA
<213> ORGANISM: Artificial Sequence
<220> FEATURE:
<223> OTHER INFORMATION: synthesized sequence- MS26Cas-3 forward primer

<400> SEQUENCE: 32
ctacactctt tccctacacg acgctcttcc gatcttcctc cggaagctcg ccgcgt       56

<210> SEQ ID NO 33
<211> LENGTH: 59
<212> TYPE: DNA
<213> ORGANISM: Artificial Sequence
<220> FEATURE:
<223> OTHER INFORMATION: synthesized sequence- MS26 Meganuclease forward
      primer

<400> SEQUENCE: 33
ctacactctt tccctacacg acgctcttcc gatctttcct cctggaggac gacgtgctg    59

<210> SEQ ID NO 34
<211> LENGTH: 63
<212> TYPE: DNA
<213> ORGANISM: Artificial Sequence
<220> FEATURE:
<223> OTHER INFORMATION: synthesized sequence- LIGCas-1 forward primer

<400> SEQUENCE: 34
ctacactctt tccctacacg acgctcttcc gatctaggac tgtaacgatt tacgcacctg   60
ctg                                                                63

<210> SEQ ID NO 35
<211> LENGTH: 58
<212> TYPE: DNA
<213> ORGANISM: Artificial Sequence
<220> FEATURE:
<223> OTHER INFORMATION: synthesized sequence- LIGCas-1 and LIGCas-2
      reverse primer

<400> SEQUENCE: 35
caagcagaag acggcatacg agctcttccg atctgcaaat gagtagcagc gcacgtat     58

<210> SEQ ID NO 36
<211> LENGTH: 63
<212> TYPE: DNA
<213> ORGANISM: Artificial Sequence
<220> FEATURE:
<223> OTHER INFORMATION: synthesized sequence- LIGCas-2 forward primer

<400> SEQUENCE: 36
ctacactctt tccctacacg acgctcttcc gatcttcctc tgtaacgatt tacgcacctg   60
ctg                                                                63

<210> SEQ ID NO 37
<211> LENGTH: 60
<212> TYPE: DNA
<213> ORGANISM: Artificial Sequence
<220> FEATURE:
<223> OTHER INFORMATION: synthesized sequence- LIGCas-3 forward primer

<400> SEQUENCE: 37
ctacactctt tccctacacg acgtcttcc gatctaaggc gcaaatgagt agcagcgcac    60

<210> SEQ ID NO 38
<211> LENGTH: 57
<212> TYPE: DNA
<213> ORGANISM: Artificial Sequence
<220> FEATURE:
<223> OTHER INFORMATION: synthesized sequence- LIGCas-3 and LIG3-4
      meganuclease reverse primer

<400> SEQUENCE: 38
caagcagaag acggcatacg agctcttccg atctcacctg ctgggaattg taccgta    57

<210> SEQ ID NO 39
<211> LENGTH: 60
<212> TYPE: DNA
<213> ORGANISM: Artificial Sequence
<220> FEATURE:
<223> OTHER INFORMATION: synthesized sequence- LIG3-4 meganuclease
      forward primer

<400> SEQUENCE: 39
ctacactctt tccctacacg acgctcttcc gatctccttc gcaaatgagt agcagcgcac    60

<210> SEQ ID NO 40
<211> LENGTH: 58
<212> TYPE: DNA
<213> ORGANISM: Artificial Sequence
<220> FEATURE:
<223> OTHER INFORMATION: synthesized sequence- MS45Cas-1 forward primer

<400> SEQUENCE: 40
ctacactctt tccctacacg acgctcttcc gatctaggag gacccgttcg gcctcagt    58

<210> SEQ ID NO 41
<211> LENGTH: 54
<212> TYPE: DNA
<213> ORGANISM: Artificial Sequence
<220> FEATURE:
<223> OTHER INFORMATION: synthesized sequence- MS45Cas-1, MS45Cas-2 and
      MS45Cas-3 reverse primer

<400> SEQUENCE: 41
caagcagaag acggcatacg agctcttccg atctgccggc tggcattgtc tctg    54

<210> SEQ ID NO 42
<211> LENGTH: 58
<212> TYPE: DNA
<213> ORGANISM: Artificial Sequence
<220> FEATURE:
<223> OTHER INFORMATION: synthesized sequence- MS45Cas-2 forward primer

<400> SEQUENCE: 42
ctacactctt tccctacacg acgctcttcc gatcttcctg gacccgttcg gcctcagt    58

<210> SEQ ID NO 43
<211> LENGTH: 58
<212> TYPE: DNA
<213> ORGANISM: Artificial Sequence
<220> FEATURE:
<223> OTHER INFORMATION: synthesized sequence- MS45Cas-3 forward primer

<400> SEQUENCE: 43
ctacactctt tccctacacg acgctcttcc gatctgaagg gacccgttcg gcctcagt    58

<210> SEQ ID NO 44
<211> LENGTH: 58
<212> TYPE: DNA
<213> ORGANISM: Artificial Sequence
<220> FEATURE:
<223> OTHER INFORMATION: synthesized sequence- ALSCas-1 forward primer

<400> SEQUENCE: 44
ctacactctt tccctacacg acgctcttcc gatctaaggc gacgatgggc gtctcctg    58

<210> SEQ ID NO 45
<211> LENGTH: 53
<212> TYPE: DNA
<213> ORGANISM: Artificial Sequence
<220> FEATURE:
<223> OTHER INFORMATION: synthesized sequence- ALSCas-1, ALSCas-2 and
      ALSCas-3 reverse primer

<400> SEQUENCE: 45
caagcagaag acggcatacg agctcttccg atctgcgtct gcatcgccac ctc    53

<210> SEQ ID NO 46
<211> LENGTH: 58
<212> TYPE: DNA
<213> ORGANISM: Artificial Sequence
<220> FEATURE:
<223> OTHER INFORMATION: synthesized sequence- ALSCas-2 forward primer

<400> SEQUENCE: 46
ctacactctt tccctacacg acgctcttcc gatctttccc gacgatgggc gtctcctg    58

<210> SEQ ID NO 47
<211> LENGTH: 58
<212> TYPE: DNA
<213> ORGANISM: Artificial Sequence
<220> FEATURE:
<223> OTHER INFORMATION: synthesized sequence- ALSCas-3 forward primer

<400> SEQUENCE: 47
ctacactctt tccctacacg acgctcttcc gatctggaac gacgatgggc gtctcctg    58

<210> SEQ ID NO 48
<211> LENGTH: 63
<212> TYPE: DNA
<213> ORGANISM: Artificial Sequence
<220> FEATURE:
<223> OTHER INFORMATION: synthesized sequence- EPSPSCas-1 forward primer

<400> SEQUENCE: 48
ctacactctt tccctacacg acgctcttcc gatctggaag aggaaacata cgttgcattt    60
cca    63

<210> SEQ ID NO 49
<211> LENGTH: 57
<212> TYPE: DNA
<213> ORGANISM: Artificial Sequence
<220> FEATURE:
<223> OTHER INFORMATION: synthesized sequence- PSPSCas-1 and EPSPSCas-3
      reverse primer

<400> SEQUENCE: 49
caagcagaag acggcatacg agctcttccg atctggtgga aagttcccag ttgagga    57

<210> SEQ ID NO 50

```
<211> LENGTH: 62
<212> TYPE: DNA
<213> ORGANISM: Artificial Sequence
<220> FEATURE:
<223> OTHER INFORMATION: synthesized sequence- PSPSCas-2 forward primer

<400> SEQUENCE: 50
ctacactctt tccctacacg acgctcttcc gatctaagcg gtggaaagtt cccagttgag    60
ga                                                                  62

<210> SEQ ID NO 51
<211> LENGTH: 58
<212> TYPE: DNA
<213> ORGANISM: Artificial Sequence
<220> FEATURE:
<223> OTHER INFORMATION: synthesized sequence- EPSPSCas-2 reverse primer

<400> SEQUENCE: 51
caagcagaag acggcatacg agctcttccg atctgaggaa acatacgttg catttcca      58

<210> SEQ ID NO 52
<211> LENGTH: 63
<212> TYPE: DNA
<213> ORGANISM: Artificial Sequence
<220> FEATURE:
<223> OTHER INFORMATION: synthesized sequence- EPSPSCas-3 forward primer

<400> SEQUENCE: 52
ctacactctt tccctacacg acgctcttcc gatctccttg aggaaacata cgttgcattt    60
cca                                                                 63

<210> SEQ ID NO 53
<211> LENGTH: 43
<212> TYPE: DNA
<213> ORGANISM: Artificial Sequence
<220> FEATURE:
<223> OTHER INFORMATION: synthesized sequence- Forward primer for
      secondary PCR

<400> SEQUENCE: 53
aatgatacgg cgaccaccga gatctacact ctttccctac acg                     43

<210> SEQ ID NO 54
<211> LENGTH: 18
<212> TYPE: DNA
<213> ORGANISM: Artificial Sequence
<220> FEATURE:
<223> OTHER INFORMATION: synthesized sequence- Reverse primer for
      secondary PCR

<400> SEQUENCE: 54
caagcagaag acggcata                                                 18

<210> SEQ ID NO 55
<211> LENGTH: 93
<212> TYPE: DNA
<213> ORGANISM: Zea mays

<400> SEQUENCE: 55
ctgtaacgat ttacgcacct gctgggaatt gtaccgtacg tgccccggcg gaggatatat    60
atacctcaca cgtacgcgta cgcgtatata tac                                93

<210> SEQ ID NO 56
<211> LENGTH: 98
```

```
<212> TYPE: DNA
<213> ORGANISM: Zea mays

<400> SEQUENCE: 56
aggactgtaa cgatttacgc acctgctggg aattgtaccg tacgtgcccc ggtcggagga    60
tatatatacc tcacacgtac gcgtacgcgt atatatac                           98

<210> SEQ ID NO 57
<211> LENGTH: 98
<212> TYPE: DNA
<213> ORGANISM: Zea mays

<400> SEQUENCE: 57
aggactgtaa cgatttacgc acctgctggg aattgtaccg tacgtgcccc ggacggagga    60
tatatatacc tcacacgtac gcgtacgcgt atatatac                           98

<210> SEQ ID NO 58
<211> LENGTH: 98
<212> TYPE: DNA
<213> ORGANISM: Zea mays

<400> SEQUENCE: 58
aggactgtaa cgatttacgc acctgctggg aattgtaccg tacgtgcccc gggcggagga    60
tatatatacc tcacacgtac gcgtacgcgt atatatac                           98

<210> SEQ ID NO 59
<211> LENGTH: 95
<212> TYPE: DNA
<213> ORGANISM: Zea mays

<400> SEQUENCE: 59
aggactgtaa cgatttacgc acctgctggg aattgtaccg tacgtgcggt cggaggatat    60 atataccctca cacgtacgcg tacgcgtata tatac                             95

<210> SEQ ID NO 60
<211> LENGTH: 98
<212> TYPE: DNA
<213> ORGANISM: Zea mays

<400> SEQUENCE: 60
aggactgtaa cgatttacgc acctgctggg aattgtaccg tacgtgcccc ggccggagga    60
tatatatacc tcacacgtac gcgtacgcgt atatatac                           98

<210> SEQ ID NO 61
<211> LENGTH: 96
<212> TYPE: DNA
<213> ORGANISM: Zea mays

<400> SEQUENCE: 61
aggactgtaa cgatttacgc acctgctggg aattgtaccg tacgtgcccc gcggaggata    60 tatataccctc acacgtacgc gtacgcgtat atatac                            96

<210> SEQ ID NO 62
<211> LENGTH: 96
<212> TYPE: DNA
<213> ORGANISM: Zea mays

<400> SEQUENCE: 62
aggactgtaa cgatttacgc acctgctggg aattgtaccg tacgtgcccc ggggaggata    60
```

```
tatataccte acacgtacgc gtacgcgtat atatac                              96
```

<210> SEQ ID NO 63
<211> LENGTH: 94
<212> TYPE: DNA
<213> ORGANISM: Zea mays

<400> SEQUENCE: 63

```
aggactgtaa cgatttacgc acctgctggg aattgtaccg tacgtgcccc ggaggatata    60
tatacctcac acgtacgcgt acgcgtatat atac                                94
```

<210> SEQ ID NO 64
<211> LENGTH: 94
<212> TYPE: DNA
<213> ORGANISM: Zea mays

<400> SEQUENCE: 64

```
aggactgtaa cgatttacgc acctgctggg aattgtaccg tacgtgcgtc ggaggatata    60
tatacctcac acgtacgcgt acgcgtatat atac                                94
```

<210> SEQ ID NO 65
<211> LENGTH: 43
<212> TYPE: DNA
<213> ORGANISM: Zea mays

<400> SEQUENCE: 65

```
aggactgtaa cgatttacgc acctgctggg aattgtaccg tac                      43
```

<210> SEQ ID NO 66
<211> LENGTH: 98
<212> TYPE: DNA
<213> ORGANISM: Zea mays

<400> SEQUENCE: 66

```
tcctctgtaa cgatttacgc acctgctggg aattgtaccg tacgtgaccc cggcggagga    60
tatatatacc tcacacgtac gcgtacgcgt atatatac                            98
```

<210> SEQ ID NO 67
<211> LENGTH: 96
<212> TYPE: DNA
<213> ORGANISM: Zea mays

<400> SEQUENCE: 67

```
tcctctgtaa cgatttacgc acctgctggg aattgtaccg tacgtccccg gcggaggata    60 tatataccte acacgtacgc gtacgcgtat atatac                              96
```

<210> SEQ ID NO 68
<211> LENGTH: 98
<212> TYPE: DNA
<213> ORGANISM: Zea mays

<400> SEQUENCE: 68

```
tcctctgtaa cgatttacgc acctgctggg aattgtaccg tacgtgtccc cggcggagga    60
tatatatacc tcacacgtac gcgtacgcgt atatatac                            98
```

<210> SEQ ID NO 69
<211> LENGTH: 94
<212> TYPE: DNA
<213> ORGANISM: Zea mays

<400> SEQUENCE: 69

```
tcctctgtaa cgatttacgc acctgctggg aattgtaccg tacccccggc ggaggatata    60
tatacctcac acgtacgcgt acgcgtatat atac                               94

<210> SEQ ID NO 70
<211> LENGTH: 93
<212> TYPE: DNA
<213> ORGANISM: Zea mays

<400> SEQUENCE: 70
tcctctgtaa cgatttacgc acctgctggg aattgtaccg tacccggcg gaggatatat    60 atacctcaca cgtacgcgta cgcgtatata tac                                93

<210> SEQ ID NO 71
<211> LENGTH: 98
<212> TYPE: DNA
<213> ORGANISM: Zea mays

<400> SEQUENCE: 71
tcctctgtaa cgatttacgc acctgctggg aattgtaccg tacgtggccc cggcggagga    60
tatatatacc tcacacgtac gcgtacgcgt atatatac                           98

<210> SEQ ID NO 72
<211> LENGTH: 92
<212> TYPE: DNA
<213> ORGANISM: Zea mays

<400> SEQUENCE: 72
tcctctgtaa cgatttacgc acctgctggg aattgtaccg tacccggcgg aggatatata    60
tacctcacac gtacgcgtac gcgtatatat ac                                 92

<210> SEQ ID NO 73
<211> LENGTH: 99
<212> TYPE: DNA
<213> ORGANISM: Zea mays

<400> SEQUENCE: 73
tcctctgtaa cgatttacgc acctgctggg aattgtaccg tacgtgaacc ccggcggagg    60
atatatatac ctcacacgta cgcgtacgcg tatatatac                          99

<210> SEQ ID NO 74
<211> LENGTH: 61
<212> TYPE: DNA
<213> ORGANISM: Zea mays

<400> SEQUENCE: 74
tcctctgtaa cgatttacgc acctgctggg aattgtaccg tacgtgtacg cgtatatata    60
c                                                                   61

<210> SEQ ID NO 75
<211> LENGTH: 95
<212> TYPE: DNA
<213> ORGANISM: Zea mays

<400> SEQUENCE: 75
tcctctgtaa cgatttacgc acctgctggg aattgtaccg tacgccccgg cggaggatat    60 atataccctca cacgtacgcg tacgcgtata tatac                             95

<210> SEQ ID NO 76
```

```
<211> LENGTH: 93
<212> TYPE: DNA
<213> ORGANISM: Zea mays

<400> SEQUENCE: 76
cgcaaatgag tagcagcgca cgtatatata cgcgtacgcg tacgtgtgag gtatatatat    60
cctccgccgg ggcacgtacg gtacaattcc cag                                 93

<210> SEQ ID NO 77
<211> LENGTH: 98
<212> TYPE: DNA
<213> ORGANISM: Zea mays

<400> SEQUENCE: 77
aaggcgcaaa tgagtagcag cgcacgtata tatacgcgta cgcgtacgtt gtgaggtata    60
tatatcctcc gccggggcac gtacggtaca attcccag                            98

<210> SEQ ID NO 78
<211> LENGTH: 96
<212> TYPE: DNA
<213> ORGANISM: Zea mays

<400> SEQUENCE: 78
aaggcgcaaa tgagtagcag cgcacgtata tatacgcgta cgcgtacggt gaggtatata    60
tatcctccgc cggggcacgt acggtacaat tcccag                              96

<210> SEQ ID NO 79
<211> LENGTH: 96
<212> TYPE: DNA
<213> ORGANISM: Zea mays

<400> SEQUENCE: 79
aaggcgcaaa tgagtagcag cgcacgtata tatacgcgta cgcgtactgt gaggtatata    60
tatcctccgc cggggcacgt acggtacaat tcccag                              96

<210> SEQ ID NO 80
<211> LENGTH: 95
<212> TYPE: DNA
<213> ORGANISM: Zea mays

<400> SEQUENCE: 80
aaggcgcaaa tgagtagcag cgcacgtata tatacgcgta cgcgtacgtg aggtatatat    60
atcctccgcc ggggcacgta cggtacaatt cccag                               95

<210> SEQ ID NO 81
<211> LENGTH: 68
<212> TYPE: DNA
<213> ORGANISM: Zea mays

<400> SEQUENCE: 81
aaggcgcaaa tgagtagcag cgcacgtata tatatcctcc gccggggcac gtacggtaca    60
attcccag                                                             68

<210> SEQ ID NO 82
<211> LENGTH: 55
<212> TYPE: DNA
<213> ORGANISM: Zea mays

<400> SEQUENCE: 82
aaggcgcaaa tgagtagcag cgcacgtata tatacgcgta cggtacaatt cccag         55
```

<210> SEQ ID NO 83
<211> LENGTH: 93
<212> TYPE: DNA
<213> ORGANISM: Zea mays

<400> SEQUENCE: 83
aaggcgcaaa tgagtagcag cgcacgtata tatacgcgta cgcgtgtgag gtatatatat      60
cctccgccgg ggcacgtacg gtacaattcc cag                                  93

<210> SEQ ID NO 84
<211> LENGTH: 69
<212> TYPE: DNA
<213> ORGANISM: Zea mays

<400> SEQUENCE: 84
aaggcgcaaa tgagtagcag cgcacgtata tatacgcgta cgccggggca cgtacggtac      60
aattcccag                                                             69

<210> SEQ ID NO 85
<211> LENGTH: 66
<212> TYPE: DNA
<213> ORGANISM: Zea mays

<400> SEQUENCE: 85
aaggcgcaaa tgagtagcag cgcacgtata tatcctccgc cggggcacgt acggtacaat      60
tcccag                                                                66

<210> SEQ ID NO 86
<211> LENGTH: 95
<212> TYPE: DNA
<213> ORGANISM: Zea mays

<400> SEQUENCE: 86
aaggcgcaaa tgagtagcag cgcacgtata tatacgcgta cgcgtatgtg aggtatatat      60
atcctccgcc ggggcacgta cggtacaatt cccag                                95

<210> SEQ ID NO 87
<211> LENGTH: 95
<212> TYPE: DNA
<213> ORGANISM: Zea mays

<400> SEQUENCE: 87
ccttcgcaaa tgagtagcag cgcacgtata tatacgcgta cgcgtacgtg aggtatatat      60
atcctccgcc ggggcacgta cggtacaatt cccag                                95

<210> SEQ ID NO 88
<211> LENGTH: 68
<212> TYPE: DNA
<213> ORGANISM: Zea mays

<400> SEQUENCE: 88
ccttcgcaaa tgagtagcag cgcacgtata tatcctcc gccggggcac gtacggtaca       60
attcccag                                                              68

<210> SEQ ID NO 89
<211> LENGTH: 65
<212> TYPE: DNA
<213> ORGANISM: Zea mays

```
<400> SEQUENCE: 89
ccttcgcaaa tgagtagcag cgcacgtata tatacgcgta cgcgtacgta cggtacaatt      60
cccag                                                                 65

<210> SEQ ID NO 90
<211> LENGTH: 55
<212> TYPE: DNA
<213> ORGANISM: Zea mays

<400> SEQUENCE: 90
ccttcgcaaa tgagtagcag cgcacgtata tatacgcgta cggtacaatt cccag          55

<210> SEQ ID NO 91
<211> LENGTH: 69
<212> TYPE: DNA
<213> ORGANISM: Zea mays

<400> SEQUENCE: 91
ccttcgcaaa tgagtagcag cgcacgtata tatacgcgta cgccggggca cgtacggtac     60
aattcccag                                                             69

<210> SEQ ID NO 92
<211> LENGTH: 85
<212> TYPE: DNA
<213> ORGANISM: Zea mays

<400> SEQUENCE: 92
ccttcgcaaa tgagtagcag cgcacgtata tatacgtgtg aggtatatat atcctccgcc     60
ggggcacgta cggtacaatt cccag                                           85

<210> SEQ ID NO 93
<211> LENGTH: 93
<212> TYPE: DNA
<213> ORGANISM: Zea mays

<400> SEQUENCE: 93
ccttcgcaaa tgagtagcag cgcacgtata tatacgcgta cgcgtgtgag gtatatatat     60
cctccgccgg ggcacgtacg gtacaattcc cag                                  93

<210> SEQ ID NO 94
<211> LENGTH: 66
<212> TYPE: DNA
<213> ORGANISM: Zea mays

<400> SEQUENCE: 94
ccttcgcaaa tgagtagcag cgcacgtata tatcctccgc cggggcacgt acggtacaat     60
tcccag                                                                66

<210> SEQ ID NO 95
<211> LENGTH: 95
<212> TYPE: DNA
<213> ORGANISM: Zea mays

<400> SEQUENCE: 95
ccttcgcaaa tgagtagcag cgcacgtata tatacgcgta cgcgtacgtg tggtatatat     60
atcctccgcc ggggcacgta cggtacaatt cccag                                95

<210> SEQ ID NO 96
<211> LENGTH: 102
```

```
<212> TYPE: DNA
<213> ORGANISM: Zea mays

<400> SEQUENCE: 96
ccttcgcaaa tgagtagcag cgcacgtata tatacgcgta cggtatatat acgtgtgagg      60
tatatatatc ctccgccggg gcacgtacgg tacaattccc ag                        102

<210> SEQ ID NO 97
<211> LENGTH: 5424
<212> TYPE: DNA
<213> ORGANISM: Artificial Sequence
<220> FEATURE:
<223> OTHER INFORMATION: synthesized sequence- donor DNA -HR Repair DNA

<400> SEQUENCE: 97
cccatagaaa actgtgtgct ataatacacc aaaaggaaag caaagtgaaa aggaaacttt      60
gaatagccaa gaagactcgg agtgcttcac gccttcacct atcccacata ggtgatgagc    120
taagagtaaa atgtagattc tctcgagtac tgaatattgc ctgcactttt ccttgcagta    180
aatacacctt taatccatga cgagagtcca ctctttgagt ccgtcttgag attcttccat    240
tgatcataca acatgacctc gaagtcctga tggagaacaa cttatataat taaaactaca    300
atacagaaag ttcctgacaa ttaaaacctt tggtggtggc atgccgtagg ttaaaaaaaa    360
tagataatga caacaaact ggagacacgc tctttgccga gtgctcacac gtttgctgag    420
agcgagcact cggcaaatat atgatttgcc gaataccacc ctcctcggca aaacaataca    480
ctaggcaaaa aggtagtttc ccatcaccat gatgcccgcc gttaatgtac cttctatgcc    540
gagtatgttg gcgctcagca aagagatcgt taccggcgtt tgtttcacca agagctcttt    600
gacgagtgtg gcacacgaca aaacctttg ccgagtgtaa ttagtcgttt gccaagtgac    660
tggtgcagtt ggcaaaggag tcgttttatta tgtgtgggca aaatgatata tggtgccagt    720
tagggctagc aaattaaagg ggggggggg ggggttaggt tgaagaaggt gacgagtaat    780
aaggtctcgg acggccgcgc gcatatatat cagatccgat ccaatggcac acggtgcaaa    840
cgaaaagcac gaaatttcca ccagcttaat taggagagaga aaaatagagc accagctgat    900
gagtgaatga atgagataga cgggacacag agggtccagc aggctagcct actctggccg    960
ccctaaatag aagtcagtgc cgtgacgacg cgcaaacttc ttttgatcgg ctgcggaaat   1020
aatatactgt aacgatttac gcacctgctg ggaattgtac cgtacgtgcc ccggcggagg   1080
atatatatac ctcacacaag ggcgaattgt actagttagt tagctagtcg gtcctagatg   1140
ccgtaatcat tagctaatcg taagtgacgc ttggacacga gcggcttgag ctaggaacct   1200
acgaagtcat cggaatcagc tcaggtgtac agaagttcct atactttctg gagaatagga   1260
acttcggaat aggaacttcg tatacgctag ggccgcattc gcaaaacaca cctagactag   1320
atttgttttg ctaacccaat tgatattaat tatatatgat taatatttat atgtatatgg   1380
atttggttaa tgaaatgcat ctggttcatc aaagaattat aaagacacgt gacattcatt   1440
taggataaga aatatggatg atctctttct cttttattca gataactagt aattacacat   1500
aacacacaac tttgatgccc acattatagt gattagcatg tcactatgtg tgcatccttt   1560
tatttcatac attaattaag ttggccaatc cagaagatgg acaagtctag gtttcgactc   1620
agatctgcgt caccgggcgc accgggcgcg gcggggccgg cagctcgaag tcgcgctgcc   1680
agaagccgac gtcgtgccag ccgccgtgct tgtagccggc ggcgcggagg gtgccgcggg   1740
cggtgtagcc gagggcctcg tggaggcgca cggacgggtc gttcgggagg ccgatcacgg   1800
```

```
ccaccacgga cttgaagccc tgggcctcca tgctcttgag gaggtgggtg tagagggtgg    1860
agccgaggcc gaggcgctgg tggcggtggg acacgtacac ggtggactcc acggtccagt    1920
cgtaggcgtt gcgggccttc cacgggccgg cgtaggcgat gccggccacc acgccctcca    1980
cctcggccac gagccacggg tagcggtcct ggaggcgctc caggtcgtcg atccactcct    2040
gcggggtctg cggctcggtg cggaagttca cggtggaggt ctcgatgtag tggttcacga    2100
tgtcgcacac ggcggccatg tcggcggcgg tggccgggcg gatctcgacg gggcggcgct    2160
cgggggacat ggtgtcgtgt ggatcccggt ggatctgaag ttcctatact ttctagagaa    2220
taggaacttc ggaataggaa cttcgctagc gaattgatcc tctagagtcg acctgcagaa    2280
gtaacaccaa acaacagggt gagcatcgac aaaagaaaca gtaccaagca aataaatagc    2340
gtatgaaggc agggctaaaa aaatccacat atagctgctg catatgccat catccaagta    2400
tatcaagatc aaaataatta taaaacatac ttgtttatta taatagatag gtactcaagg    2460
ttagagcata tgaatagatg ctgcatatgc catcatgtat atgcatcagt aaaacccaca    2520
tcaacatgta tacctatcct agatcgatat ttccatccat cttaaactcg taactatgaa    2580
gatgtatgac acacatatac agttccaaaa ttaataaata caccaggtag tttgaaacag    2640
tattctactc cgatctagaa cgaatgaacg accgcccaac cacaccacat catcacaacc    2700
aagcgaacaa aaagcatctc tgtatatgca tcagtaaaac ccgcatcaac atgtatacct    2760
atcctagatc gatatttcca tccatcatct tcaattcgta actatgaata tgtatggcac    2820
acacatacag atccaaaatt aataaatcca ccaggtagtt tgaaacagaa ttctactccg    2880
atctagaacg accgcccaac cagaccacat catcacaacc aagacaaaaa aaagcatgaa    2940
aagatgaccc gacaaacaag tgcacggcat atattgaaat aaaggaaaag ggcaaaccaa    3000
accctatgca acgaaacaaa aaaaatcatg aaatcgatcc cgtctgcgga acggctagag    3060
ccatcccagg attccccaaa gagaaacact ggcaagttag caatcagaac gtgtctgacg    3120
tacaggtcgc atccgtgtac gaacgctagc agcacggatc taacacaaac acggatctaa    3180
cacaaacatg aacagaagta gaactaccgg gccctaacca tgcatggacc ggaacgccga    3240
tctagagaag gtagagaggg ggggggggga ggacagcgg cgtaccttga agcggaggtg    3300
ccgacgggtg gatttggggg agatctggtt gtgtgtgtgt gcgctccgaa caacacgagg    3360
ttggggaaag agggtgtgga gggggtgtct atttattacg gcgggcgagg aagggaaagc    3420
gaaggagcgg tgggaaagga atcccccgta gctgccggtg ccgtgagagg aggaggaggc    3480
cgcctgccgt gccggctcac gtctgccgct ccgccacgca atttctggat gccgacagcg    3540
gagcaagtcc aacggtggag cggaactctc gagagggtc cagaggcagc gacagagatg    3600
ccgtgccgtc tgcttcgctt ggcccgacgc gacgctgctg gttcgctggt tggtgtccgt    3660
tagactcgtc gacggcgttt aacaggctgg cattatctac tcgaaacaag aaaaatgttt    3720
ccttagtttt tttaatttct aaagggtat ttgtttaatt tttagtcact ttattttatt    3780
ctattttata tctaaattat taaataaaaa aactaaaata gagttttagt tttcttaatt    3840
tagaggctaa aatagaataa aatagatgta ctaaaaaaat tagtctataa aaaccattaa    3900
ccctaaaccc taaatggatg tactaataaa atggatgaag tattatatag gtgaagctat    3960
ttgcaaaaaa aaaggagaac acatgcacac taaaaagata aaactgtaga gtcctgttgt    4020
caaaatactc aattgtcctt tagaccatgt ctaactgttc atttatatga ttctctaaaa    4080
cactgatatt attgtagtac tatagattat attattcgta gagtaaagtt taaatatatg    4140
tataaagata gataaactgc acttcaaaca agtgtgacaa aaaaaatatg tggtaatttt    4200
```

```
ttataactta gacatgcaat gctcattatc tctagagagg ggcacgaccg ggtcacgctg    4260
cactgcaggc tagcggcgaa ttcgcccttg tacgcgtacg cgtatatata cgtgcgctgc    4320
tactcatttg cgcgggaata cagctcagtc tgctgtgcgc tgcaggatgt acatacatac    4380
atgcgcaggt gcaaagtcta cgcgcgcggg caatgcaagc ccctggcgta gttgggccat    4440
gactgagatc acgcctcatg gtcatggaac gaaacaccgc gtccggccgg gctgcccctg    4500
gcgtcacgcg ggaggcagct gctagcgtta gcgtacgtac ccaccgtctc gtacacacca    4560
ccgcagggag agagaagagc gatgcaatgc acatgtacag catccgcatc atgcatagat    4620
actcatatct tcaaggccac acatgcagca gtgtcgtacg ctacgttgtt tcaacggagg    4680
aggaggatac atacatagac acccacagcc agcctagcat atagcagata gcatacggac    4740
tcccgggtga ggaaaaatgg agggcgaacc aaaccaacca caaagaagca gcagcagcag    4800
cagcagcagc tgcggctgct atcaccactc accaactcca attaaagatc tctctctctc    4860
tctctactgg ccggccctgt cagtgccagc gcccggtttg ttgctagctg agctgcgggc    4920
gtcgctctta gatatagccc aaaactcact ccaccaccac tcgttccatg gaaccctaga    4980
ccaaaagtac tcgcgctctc ggccctcgct ctcgccctct ccctctccgc agcaaaagag    5040
atccggccgg ccgagaaggg cgcgcgctag ctgcccggct actagctggc gcccgcccgc    5100
gcatatatct gtgtcatcgc catcacccac accatggccc ggccggccaa caccgccgta    5160
ttagctctgt ctgtcgctcg tccacctgcg accgactgag cgatcgatct ccaccgagct    5220
ctccgctaag cgctgtcctt gccgcgtcc tcccctccgt ccctacgca tccatttccg    5280 tgtgctcgtg tgtgcgcgcg cgggcactcc tgctcctgct ccctccggcc cctcctcccc    5340
tcccaggctc ccagctagcc gcgcccgccc gcgcgacctg cacctgcaca gatcgggcgg    5400
ccgggccgac cgatcgatcg agat                                          5424
```

<210> SEQ ID NO 98  
<211> LENGTH: 24  
<212> TYPE: DNA  
<213> ORGANISM: Artificial Sequence  
<220> FEATURE:  
<223> OTHER INFORMATION: synthesized sequence- Forward PCR primer

<400> SEQUENCE: 98
cccgttattg tatgaggtaa tgac                                            24

<210> SEQ ID NO 99  
<211> LENGTH: 31  
<212> TYPE: DNA  
<213> ORGANISM: Artificial Sequence  
<220> FEATURE:  
<223> OTHER INFORMATION: synthesized sequence- Reverse PCR primer for  
      site-specific transgene insertion at junction 1

<400> SEQUENCE: 99
gctcgtgtcc aagcgtcact tacgattagc t                                    31

<210> SEQ ID NO 100  
<211> LENGTH: 32  
<212> TYPE: DNA  
<213> ORGANISM: Artificial Sequence  
<220> FEATURE:  
<223> OTHER INFORMATION: synthesized sequence- Forward PCR primer for  
      site-specific transgene insertion at junction 2

<400> SEQUENCE: 100

```
ccatgtctaa ctgttcattt atatgattct ct                              32
```

```
<210> SEQ ID NO 101
<211> LENGTH: 24
<212> TYPE: DNA
<213> ORGANISM: Artificial Sequence
<220> FEATURE:
<223> OTHER INFORMATION: synthesized sequence- Reverse PCR primer for
      site-specific transgene insertion at junction 2

<400> SEQUENCE: 101
gcagccgata ggttcatcat cttc                                       24

<210> SEQ ID NO 102
<211> LENGTH: 7850
<212> TYPE: DNA
<213> ORGANISM: Artificial Sequence
<220> FEATURE:
<223> OTHER INFORMATION: synthesized sequence- Linked Cas9 and LIGCas-3
      long guide RNA expression cassettes

<400> SEQUENCE: 102
gtgcagcgtg acccggtcgt gccccctctct agagataatg agcattgcat gtctaagtta   60
taaaaaatta ccacatattt tttttgtcac acttgtttga agtgcagttt atctatcttc  120
atacatatat ttaaacttta ctctacgaat aatataatct atagtactac aataatatca  180
gtgttttaga gaatcatata aatgaacagt tagacatggt ctaaaggaca attgagtatt  240
ttgacaacag gactctacag ttttatcttt ttagtgtgca tgtgttctcc tttttttttg  300
caaatagctt cacctatata atacttcatc cattttatta gtacatccat ttagggttta  360
gggttaatgg tttttataga ctaatttttt tagtacatct atttttattct atttttagcct  420 ctaaattaag aaaactaaaa ctctatttta gtttttttat ttaataattt agatataaaa  480
tagaataaaa taaagtgact aaaaattaaa caaatacctt taagaaatt aaaaaaacta   540 aggaaacatt tttcttgttt cgagtagata atgccagcct gttaaacgcc gtcgacgagt  600
ctaacggaca ccaaccagcg aaccagcagc gtcgcgtcgg gccaagcgaa gcagacggca  660
cggcatctct gtcgctgcct ctggaccccct tcgagagtt ccgctccacc gttggacttg  720
ctccgctgtc ggcatccaga aattgcgtgg cggagcggca gacgtgagcc ggcacggcag  780
gcggcctcct cctcctctca cggcaccggc agctacgggg gattcctttc ccaccgctcc  840
ttcgctttcc cttcctcgcc cgccgtaata aatagacacc ccctccacac cctctttccc  900
caacctcgtg ttgttcggag cgcacacaca caaccagaa tctccccaa atccaccccgt   960 cggcacctcc gcttcaaggt acgccgctcg tcctcccccc ccccctctc taccttctct 1020 agatcggcgt tccggtccat gcatggttag ggcccggtag ttctacttct gttcatgttt 1080
gtgttagatc cgtgtttgtg ttagatccgt gctgctagcg ttcgtacacg gatgcgacct 1140
gtacgtcaga cacgttctga ttgctaactt gccagtgttt ctctttgggg aatcctggga 1200
tggctctagc cgttccgcag acgggatcga tttcatgatt ttttttgttt cgttgcatag 1260
ggtttggttt gccctttttcc tttatttcaa tatatgccgt gcacttgttt gtcgggtcat 1320
cttttcatgc ttttttttgt cttggttgtg atgatgtggt ctggttgggc ggtcgttcta 1380
gatcggagta gaattctgtt tcaaactacc tggtggattt attaattttg gatctgtatg 1440
tgtgtgccat acatattcat agttacgaat tgaagatgat ggatggaaat atcgatctag 1500
gataggtata catgttgatg cgggttttac tgatgcatat acagagatgc ttttgttcg  1560 cttggttgtg atgatgtggt gtggttgggc ggtcgttcat tcgttctaga tcggagtaga 1620
```

-continued

```
atactgtttc aaactacctg gtgtatttat taattttgga actgtatgtg tgtgtcatac    1680
atcttcatag ttacgagttt aagatggatg gaaatatcga tctaggatag gtatacatgt    1740
tgatgtgggt tttactgatg catatacatg atggcatatg cagcatctat tcatatgctc    1800
taaccttgag tacctatcta ttataataaa caagtatgtt ttataattat tttgatcttg    1860
atatacttgg atgatggcat atgcagcagc tatatgtgga ttttttttagc cctgccttca    1920
tacgctattt atttgcttgg tactgtttct tttgtcgatg ctcaccctgt tgtttggtgt    1980
tacttctgca ggtcgactct agaggatcca tggcaccgaa gaagaagcgc aaggtgatgg    2040
acaagaagta cagcatcggc ctcgacatcg gcaccaactc ggtgggctgg gccgtcatca    2100
cggacgaata aaggtcccg tcgaagaagt tcaaggtcct cggcaataca gaccgccaca    2160
gcatcaagaa aaacttgatc ggcgccctcc tgttcgatag cggcgagacc gcggaggcga    2220
ccaggctcaa gaggaccgcc aggagacggt acactaggcg caagaacagg atctgctacc    2280
tgcaggagat cttcagcaac gagatggcga aggtggacga ctccttcttc caccgcctgg    2340
aggaatcatt cctggtggag gaggacaaga agcatgagcg gcacccaatc ttcggcaaca    2400
tcgtcgacga ggtaagtttc tgcttctacc tttgatatat atataataat tatcattaat    2460
tagtagtaat ataatatttc aaatatttt ttcaaaataa aagaatgtag tatatagcaa    2520
ttgcttttct gtagtttata agtgtgtata ttttaattta taacttttct aatatatgac    2580
caaaacatgg tgatgtgcag gtggcctacc acgagaagta cccgacaatc taccacctcc    2640
ggaagaaact ggtggacagc acagacaagg cggacctccg gctcatctac cttgccctcg    2700
cgcatatgat caagttccgc ggccacttcc tcatcgaggg cgacctgaac ccggacaact    2760
ccgacgtgga caagctgttc atccagctcg tgcagacgta caatcaactg ttcgaggaga    2820
accccataaa cgctagcggc gtggacgcca aggccatcct ctcggccagg ctctcgaaat    2880
caagaaggct ggagaacctt atcgcgcagt gccaggcga aaagaagaac ggcctcttcg    2940
gcaaccttat tgcgctcagc ctcggcctga cgccgaactt caaatcaaac ttcgacctcg    3000
cggaggacgc caagctccag ctctcaaagg acacctacga cgacgacctc gacaacctcc    3060
tggcccagat aggagaccag tacgcggacc tcttcctcgc cgccaagaac ctctccgacg    3120
ctatcctgct cagcgacatc cttcgggtca acaccgaaat taccaaggca ccgctgtccg    3180
ccagcatgat taaacgctac gacgagcacc atcaggacct cacgctgctc aaggcactcg    3240
tccgccagca gctccccgag aagtacaagg agatcttctt cgaccaatca aaaaacggct    3300
acgcgggata tatcgacggc ggtgccagcc aggaagagtt ctacaagttc atcaaaccaa    3360
tcctggagaa gatggacggc accgaggagt tgctggtcaa gctcaacagg gaggacctcc    3420
tcaggaagca gaggaccttc gacaacggct ccatcccgca tcagatccac ctgggcgaac    3480
tgcatgccat cctgcggcgc caggaggact tctacccgtt cctgaaggat aaccgggaga    3540
agatcgagaa gatcttgacg ttccgcatcc catactacgt gggcccgctg gctcgcggca    3600
actcccggtt cgcctggatg acccggaagt cggaggagac catcacaccc tggaactttg    3660
aggaggtggt cgataagggc gctagcgctc agagcttcat cgagcgcatg accaacttcg    3720
ataaaaacct gcccaatgaa aaagtcctcc ccaagcactc gctgctctac gagtacttca    3780
ccgtgtacaa cgagctcacc aaggtcaaat acgtcaccga gggcatgcgg aagccggcgt    3840
tcctgagcgg cgagcagaag aaggcgatag tggacctcct cttcaagacc aacaggaagg    3900
tgaccgtgaa gcaattaaaa gaggactact tcaagaaaat agagtgcttc gactccgtgg    3960
```

| | |
|---|---|
| agatctcggg cgtggaggat cggttcaacg cctcactcgg cacgtatcac gacctcctca | 4020 |
| agatcattaa agacaaggac ttcctcgaca acgaggagaa cgaggacatc ctcgaggaca | 4080 |
| tcgtcctcac cctgaccctg ttcgaggacc gcgaaatgat cgaggagagg ctgaagacct | 4140 |
| acgcgcacct gttcgacgac aaggtcatga acagctcaa gaggcgccgc tacactggtt | 4200 |
| ggggaaggct gtcccgcaag ctcattaatg gcatcaggga caagcagagc ggcaagacca | 4260 |
| tcctggactt cctcaagtcc gacgggttcg ccaaccgcaa cttcatgcag ctcattcacg | 4320 |
| acgactcgct cacgttcaag gaagacatcc agaaggcaca ggtgagcggg cagggtgact | 4380 |
| ccctccacga acacatcgcc aacctggccg gctcgccggc cattaaaaag gcatcctgc | 4440 |
| agacggtcaa ggtcgtcgac gagctcgtga aggtgatggg ccggcacaag cccgaaaata | 4500 |
| tcgtcataga gatggccagg gagaaccaga ccacccaaaa agggcagaag aactcgcgcg | 4560 |
| agcggatgaa acggatcgag gagggcatta aagagctcgg gtcccagatc ctgaaggagc | 4620 |
| accccgtgga aaatacccag ctccagaatg aaaagctcta cctctactac ctgcagaacg | 4680 |
| gccgcgacat gtacgtggac caggagctgg acattaatcg gctatcggac tacgacgtcg | 4740 |
| accacatcgt gccgcagtcg ttcctcaagg acgatagcat cgacaacaag gtgctcaccc | 4800 |
| ggtcggataa aaatcggggc aagagcgaca acgtgcccag cgaggaggtc gtgaagaaga | 4860 |
| tgaaaaacta ctggcgccag ctcctcaacg cgaaactgat cacccagcgc aagttcgaca | 4920 |
| acctgacgaa ggcggaacgc ggtggcttga gcgaactcga taaggcgggc ttcataaaaa | 4980 |
| ggcagctggt cgagacgcgc cagatcacga agcatgtcgc ccagatcctg acagccgca | 5040 |
| tgaatactaa gtacgatgaa aacgacaagc tgatccggga ggtgaaggtg atcacgctga | 5100 |
| agtccaagct cgtgtcggac ttccgcaagg acttccagtt ctacaaggtc cgcgagatca | 5160 |
| acaactacca ccacgcccac gacgcctacc tgaatgcggt ggtcgggacc gccctgatca | 5220 |
| agaagtaccc gaagctggag tcggagttcg tgtacggcga ctacaaggtc tacgacgtgc | 5280 |
| gcaaaatgat cgccaagtcc gagcaggaga tcggcaaggc cacggcaaaa tacttcttct | 5340 |
| actcgaacat catgaacttc ttcaagaccg agatcaccct cgcgaacggc gagatccgca | 5400 |
| agcgcccgct catcgaaacc aacgcgaga cgggcgagat cgtctgggat aagggccggg | 5460 |
| atttcgcgac ggtccgcaag gtgctctcca tgccgcaagt caatatcgtg aaaaagacgg | 5520 |
| aggtccagac gggcgggttc agcaaggagt ccatcctccc gaagcgcaac tccgacaagc | 5580 |
| tcatcgcgag gaagaaggat tgggacccga aaaaatatgg cggcttcgac agcccgaccg | 5640 |
| tcgcatacag cgtcctcgtc gtggcgaagg tggagaaggg caagtcaaag aagctcaagt | 5700 |
| ccgtgaagga gctgctcggg atcacgatta tggagcggtc ctccttcgag aagaacccga | 5760 |
| tcgacttcct agaggccaag ggatataagg aggtcaagaa ggacctgatt attaaactgc | 5820 |
| cgaagtactc gctcttcgag ctggaaaacg gccgcaagag gatgctcgcc tccgcaggcg | 5880 |
| agttgcagaa gggcaacgag ctcgcccctcc cgagcaaata cgtcaatttc ctgtacctcg | 5940 |
| ctagccacta tgaaaagctc aagggcagcc ggaggacaa cgagcagaag cagctcttcg | 6000 |
| tggagcagca caagcattac ctggacgaga tcatcgagca gatcagcgag ttctcgaagc | 6060 |
| gggtgatcct cgccgacgcg aacctggaca aggtgctgtc ggcatataac aagcaccgcg | 6120 |
| acaaaccaat acgcgagcag gccgaaaata tcatccacct cttcacccctc accaacctcg | 6180 |
| gcgctccggc agccttcaag tacttcgaca ccacgattga ccggaagcgg tacacgagca | 6240 |
| cgaaggaggt gctcgatgcg acgctgatcc accagagcat cacagggctc tatgaaacac | 6300 |
| gcatcgacct gagccagctg ggcggagaca agagaccacg ggaccgccac gatggcgagc | 6360 |

```
tgggaggccg caagcgggca aggtaggtac cgttaaccta gacttgtcca tcttctggat   6420
tggccaactt aattaatgta tgaaataaaa ggatgcacac atagtgacat gctaatcact   6480
ataatgtggg catcaaagtt gtgtgttatg tgtaattact agttatctga ataaaagaga   6540
aagagatcat ccatatttct tatcctaaat gaatgtcacg tgtctttata attctttgat   6600
gaaccagatg catttcatta accaaatcca tatacatata aatattaatc atatataatt   6660
aatatcaatt gggttagcaa acaaatctag tctaggtgt gttttgcgaa tgcggccccc    6720
cctcgaggtc gacggtatcg ataagctttg agagtacaat gatgaaccta gattaatcaa   6780
tgccaaagtc tgaaaaatgc accctcagtc tatgatccag aaaatcaaga ttgcttgagg   6840
ccctgttcgg ttgttccgga ttagagcccc ggattaattc ctagccggat tacttctcta   6900
atttatatag attttgatga gctggaatga atcctggctt attccggtac aaccgaacag   6960
gccctgaagg ataccagtaa tcgctgagct aaattggcat gctgtcagag tgtcagtatt   7020
gcagcaaggt agtgagataa ccggcatcat ggtgccagtt tgatggcacc attagggtta   7080
gagatggtgg ccatgggcgc atgtcctggc caactttgta tgatatatgg cagggtgaat   7140
aggaaagtaa aattgtattg taaaaaggga tttcttctgt ttgttagcgc atgtacaagg   7200
aatgcaagtt ttgagcgagg gggcatcaaa gatctggctg tgtttccagc tgttttttgtt  7260 agccccatcg aatccttgac ataatgatcc cgcttaaata agcaacctcg cttgtatagt   7320
tccttgtgct ctaacacacg atgatgataa gtcgtaaaat agtggtgtcc aaagaatttc   7380
caggcccagt tgtaaaagct aaatgctat tcgaatttct actagcagta agtcgtgttt     7440
agaaattatt tttttatata cctttttttcc ttctatgtac agtaggacac agtgtcagcg   7500
ccgcgttgac ggagaatatt tgcaaaaaag taaagagaa agtcatagcg gcgtatgtgc    7560
caaaaacttc gtcacagaga gggccataag aaacatggcc cacggcccaa tacgaagcac   7620
cgcgacgaag cccaaacagc agtccgtagg tggagcaaag cgctgggtaa tacgcaaacg   7680
ttttgtccca ccttgactaa tcacaagagt ggagcgtacc ttataaaccg agccgcaagc   7740
accgaattgc gtacgcgtac gtgtggtttt agagctagaa atagcaagtt aaaataaggc   7800
tagtccgtta tcaacttgaa aaagtggcac cgagtcggtg cttttttttt               7850
```

```
<210> SEQ ID NO 103
<211> LENGTH: 23
<212> TYPE: DNA
<213> ORGANISM: Zea mays

<400> SEQUENCE: 103
tgggcaggtc tcacgacggt tgg                                              23

<210> SEQ ID NO 104
<211> LENGTH: 91
<212> TYPE: DNA
<213> ORGANISM: Zea mays

<400> SEQUENCE: 104
ccggtttcgc gtgctctggc tttacattac atgggcaggt ctcacgacgg ttgggctgga     60
gagccggctg gtaggggagg acctcaacgg c                                     91

<210> SEQ ID NO 105
<211> LENGTH: 90
<212> TYPE: DNA
<213> ORGANISM: Zea mays
```

<400> SEQUENCE: 105
ccggtttcgc gtgctctggc tttacattac atgggcaggt ctcacgaggt tgggctggag    60
agccggctgg tagggagga cctcaacggc                                      90

<210> SEQ ID NO 106
<211> LENGTH: 90
<212> TYPE: DNA
<213> ORGANISM: Zea mays

<400> SEQUENCE: 106
ccggtttcgc gtgctctggc tttacattac atgggcaggt ctcacacggt tgggctggag    60
agccggctgg tagggagga cctcaacggc                                      90

<210> SEQ ID NO 107
<211> LENGTH: 92
<212> TYPE: DNA
<213> ORGANISM: Zea mays

<400> SEQUENCE: 107
ccggtttcgc gtgctctggc tttacattac atgggcaggt ctcacgacgg tttgggctgg    60
agagccggct ggtagggag gacctcaacg gc                                   92

<210> SEQ ID NO 108
<211> LENGTH: 89
<212> TYPE: DNA
<213> ORGANISM: Zea mays

<400> SEQUENCE: 108
ccggtttcgc gtgctctggc tttacattgc atgagcaggt cgtgacggtt gggctggaga    60
gccggctggt aggggaggac ctcaacggc                                      89

<210> SEQ ID NO 109
<211> LENGTH: 57
<212> TYPE: DNA
<213> ORGANISM: Zea mays

<400> SEQUENCE: 109
gggcaggtct cgacggttgg gctggagagc cggctggtag gggaggacct caacggc       57

<210> SEQ ID NO 110
<211> LENGTH: 57
<212> TYPE: DNA
<213> ORGANISM: Zea mays

<400> SEQUENCE: 110
ccggtttcgc gtgctcttgg gctggagagc cggctggtag gggaggacct caacggc       57

<210> SEQ ID NO 111
<211> LENGTH: 22
<212> TYPE: DNA
<213> ORGANISM: Zea mays

<400> SEQUENCE: 111
atatacctca cacgtacgcg ta                                             22

<210> SEQ ID NO 112
<211> LENGTH: 1053
<212> TYPE: DNA
<213> ORGANISM: Zea mays

<400> SEQUENCE: 112

```
atgaacacca agtacaacaa ggagttcctg ctctacctgg ccggcttcgt ggacggcgac    60
ggctccatca aggcgcagat caagccgaac cagtcctgca agttcaagca ccagctctcc   120
ctgaccttcc aggtgaccca gaagacgcag aggcgctggt tcctcgacaa gctggtcgac   180
gagatcgggg tgggctacgt ctacgaccgc gggtcggtgt ccgactacga gctctcccag   240
atcaagcccc tgcacaactt cctcacccag ctccagccgt tcctcaagct gaagcagaag   300
caggcgaacc tcgtcctgaa gatcatcgag cagctcccct cggccaagga gtccccggac   360
aagttcctgg aggtgtgcac gtgggtcgac cagatcgcgg ccctcaacga cagcaagacc   420
cgcaagacga cctcggagac ggtgcgggcg gtcctggact ccctcccagg atccgtggga   480
ggtctatcgc catctcaggc atccagcgcc gcatcctcgg cttcctcaag cccgggttca   540
gggatctccg aagcactcag agctggagca actaagtcca aggaattcct gctctacctg   600
gccggcttcg tggacggcga cggctccatc atcgcgtcca tcaagccgcg ccagtgctac   660
aagttcaagc acgagctccg cctggagttc accgtgaccc agaagacgca gaggcgctgg   720
ttcctcgaca agctggtcga cgagatcggg gtgggctacg tctacgaccg cgggtcggtg   780
tccgactacc gcctctccca gatcaagccc ctgcacaact tcctcaccca gctccagccg   840
ttcctcaagc tgaagcagaa gcaggcgaac ctcgtcctga gatcatcga gcagctcccc   900
tcggccaagg agtccccgga caagttcctg gaggtgtgca cgtgggtcga ccagatcgcg   960
gccctcaacg acagcaagac cgcaagacg acctcggaga cggtgcgggc ggtcctggac  1020
tccctcagcg agaagaagaa gtcgtccccc tga                              1053
```

<210> SEQ ID NO 113
<211> LENGTH: 22
<212> TYPE: DNA
<213> ORGANISM: Zea mays

<400> SEQUENCE: 113

```
gatggtgacg tacgtgccct ac                                            22
```

<210> SEQ ID NO 114
<211> LENGTH: 1053
<212> TYPE: DNA
<213> ORGANISM: Zea mays

<400> SEQUENCE: 114

```
atgaacacca agtacaacaa ggagttcctc ctctacctgg caggtttcgt ggacggcgat    60
gggtctatca tcgcccagat taccccgcaa cagtcctaca agttcaagca cgccctgcgg   120
ctgaggttca cggtcactca gaagacgcag cgcaggtggt tcctcgataa gctggtcgac   180
gaaatcggag tcgcaaggt gcgggacagg ggctctgtca gcgactacat cctctcccag   240
aagaagccgc tccacaactt cctgacccag ctgcagccct tcctcaagct caagcagaag   300
caggccaacc tggtgctcaa gatcatcgag cagctgccat ctgccaagga gtcaccagac   360
aagttccttg aggtctgcac ctgggtcgat cagatcgctg ccctgaacga ctccaagacg   420
aggaagacca cctccgagac cgtcagggct gtgctggact cactcccagg atccgttggc   480
ggtctcagcc cttctcaggc tagctcggct gcttcctcag ccagcagctc acctggctcc   540
ggtatcagcg aggctctcag agcaggtgcc accaagtcca aggagttcct cctgtacctg   600
gcaggcttcg ttgacggcga cggctcgatc atggcgtcca ttaccccgaa ccagtcgtgt   660
aagttcaagc atcagctgcg cctgcgcttt accgtcacgc agaagaccca gaggcgctgg   720
```

| | |
|---|---|
| ttcctggaca aactggtgga cgagatcggg gtcgggaagg tgtacgacag agggagcgtt | 780 |
| agcgactacc ggctgtccca gaagaagccg ctccacaact tcctgacgca gctccaaccc | 840 |
| ttcctgaagc tgaagcagaa gcaggcgaac cttgtgctga agatcattga gcagctgccg | 900 |
| agcgccaagg agagccctga caagttcctg gaggtctgca cctgggtcga ccagatcgct | 960 |
| gccctcaacg actccaagac caggaagacc acgagcgaga ccgttcgggc tgtcctggac | 1020 |
| agcctctccg agaagaagaa gtcgagcccg tag | 1053 |

<210> SEQ ID NO 115
<211> LENGTH: 4104
<212> TYPE: DNA
<213> ORGANISM: Artificial sequence
<220> FEATURE:
<223> OTHER INFORMATION: synthesized sequence- soybean codon optimized Cas9

<400> SEQUENCE: 115

| | |
|---|---|
| atggacaaaa agtactcaat agggctcgac ataggggacta actccgttgg atgggccgtc | 60 |
| atcaccgacg agtacaaggt gcccctccaag aagttcaagg tgttgggaaa caccgacagg | 120 |
| cacagcataa agaagaattt gatcggtgcc ctcctcttcg actccggaga gaccgctgag | 180 |
| gctaccaggc tcaagaggac cgctagaagg cgctacacca aaggaaggaa cagaatctgc | 240 |
| tacctgcagg agatcttctc caacgagatg gccaaggtgg acgactcctt cttccaccgc | 300 |
| cttgaggaat cattcctggt ggaggaggat aaaaagcacg agagacaccc aatcttcggg | 360 |
| aacatcgtcg acgaggtggc ctaccatgaa aagtacccta ccatctacca cctgaggaag | 420 |
| aagctggtcg actctaccga caaggctgac ttgcgcttga tttacctggc tctcgctcac | 480 |
| atgataaagt ccgcggaca cttcctcatt gagggagacc tgaacccaga caactccgac | 540 |
| gtggacaagc tcttcatcca gctcgttcag acctacaacc agcttttcga ggagaaccca | 600 |
| atcaacgcca gtggagttga cgccaaggct atcctctctg ctcgtctgtc aaagtccagg | 660 |
| aggcttgaga acttgattgc ccagctgcct ggcgaaaaga gaacggact gttcggaaac | 720 |
| ttgatcgctc tctccctggg attgactccc aacttcaagt ccaacttcga cctcgccgag | 780 |
| gacgctaagt tgcagttgtc taaagacacc tacgacgatg acctcgacaa cttgctggcc | 840 |
| cagataggcg accaatacgc cgatctcttc ctcgccgcta agaacttgtc cgacgcaatc | 900 |
| ctgctgtccg acatcctgag agtcaacact gagattacca agctcctct gtctgcttcc | 960 |
| atgattaagc gctacgacga gcaccaccaa gatctgaccc tgctcaaggc cctggtgaga | 1020 |
| cagcagctgc ccgagaagta caaggagatc ttttcgacc agtccaagaa cggctacgcc | 1080 |
| ggatacattg acggaggcgc ctcccaggaa gagttctaca gttcatcaa gcccatcctt | 1140 |
| gagaagatgg acggtaccga ggagctgttg gtgaagttga acagagagga cctgttgagg | 1200 |
| aagcagagaa ccttcgacaa cggaagcatc cctcaccaaa tccacctggg agagctccac | 1260 |
| gccatcttga ggaggcagga ggatttctat cccttcctga aggacaaccg cgagaagatt | 1320 |
| gagaagatct tgaccttcag aattccttac tacgtcgggc cactcgccag aggaaactct | 1380 |
| aggttcgcct ggatgacccg caaatctgaa gagaccatta ctcccctggaa cttcgaggaa | 1440 |
| gtcgtggaca gggcgcttc cgctcagtct ttcatcgaga ggatgaccaa cttcgataaa | 1500 |
| aatctgccca acgagaaggt gctgcccaag cactccctgt tgtacgagta tttcacagtg | 1560 |
| tacaacgagc tcaccaaggt gaagtacgtc acagagggaa tgaggaagcc tgccttcttg | 1620 |
| tccggagagc agaagaaggc catcgtcgac ctgctcttca gaccaacag gaaggtgact | 1680 |

-continued

| | |
|---|---|
| gtcaagcagc tgaaggagga ctacttcaag aagatcgagt gcttcgactc cgtcgagatc | 1740 |
| tctggtgtcg aggacaggtt caacgcctcc cttgggactt accacgatct gctcaagatt | 1800 |
| attaaagaca aggacttcct ggacaacgag gagaacgagg acatccttga ggacatcgtg | 1860 |
| ctcaccctga ccttgttcga agacaggaa atgatcgaag agaggctcaa gacctacgcc | 1920 |
| cacctcttcg acgacaaggt gatgaaacag ctgaagagac gcagatatac cggctgggga | 1980 |
| aggctctccc gcaaattgat caacgggatc agggacaagc agtcaggaa gactatactc | 2040 |
| gacttcctga agtccgacgg attcgccaac aggaacttca tgcagctcat tcacgacgac | 2100 |
| tccttgacct tcaaggagga catccagaag gctcaggtgt ctggacaggg tgactccttg | 2160 |
| catgagcaca ttgctaactt ggccggctct cccgctatta agaagggcat tttgcagacc | 2220 |
| gtgaaggtcg ttgacgagct cgtgaaggtg atgggacgcc acaagccaga gaacatcgtt | 2280 |
| attgagatgg ctcgcgagaa ccaaactacc cagaaagggc agaagaattc ccgcgagagg | 2340 |
| atgaagcgca ttgaggaggg cataaaagag cttggctctc agatcctcaa ggagcacccc | 2400 |
| gtcgagaaca ctcagctgca gaacgagaag ctgtacctgt actacctcca aaacggaagg | 2460 |
| gacatgtacg tggaccagga gctggacatc aacaggttgt ccgactacga cgtcgaccac | 2520 |
| atcgtgcctc agtccttcct gaaggatgac tccatcgaca ataaagtgct gacacgctcc | 2580 |
| gataaaaata gaggcaagtc cgacaacgtc ccctccgagg aggtcgtgaa gaagatgaaa | 2640 |
| aactactgga gacagctctt gaacgccaag ctcatcaccc agcgtaagtt cgacaacctg | 2700 |
| actaaggctg agagaggagg attgtccgag ctcgataagg ccggattcat caagagacag | 2760 |
| ctcgtcgaaa cccgccaaat taccaagcac gtggcccaaa ttctggattc ccgcatgaac | 2820 |
| accaagtacg atgaaaatga caagctgatc cgcgaggtca aggtgatcac cttgaagtcc | 2880 |
| aagctggtct ccgacttccg caaggacttc cagttctaca aggtgaggga gatcaacaac | 2940 |
| taccaccacg cacacgacgc ctacctcaac gctgtcgttg gaaccgccct catcaaaaaa | 3000 |
| tatcctaagc tggagtctga gttcgtctac ggcgactaca aggtgtacga cgtgaggaag | 3060 |
| atgatcgcta agtctgagca ggagatcggc aaggccaccg ccaagtactt cttctactcc | 3120 |
| aacatcatga acttcttcaa gaccgagatc actctcgcca acggtgagat caggaagcgc | 3180 |
| ccactgatcg agaccaacgg tgagactgga gagatcgtgt gggacaaagg gagggatttc | 3240 |
| gctactgtga ggaaggtgct ctccatgcct caggtgaaca tcgtcaagaa gaccgaagtt | 3300 |
| cagaccggag gattctccaa ggagtccatc ctccccaaga gaaactccga caagctgatc | 3360 |
| gctagaaaga aagactggga ccctaagaag tacggaggct tcgattctcc taccgtggcc | 3420 |
| tactctgtgc tggtcgtggc caaggtggag aagggcaagt ccaagaagct gaaatccgtc | 3480 |
| aaggagctcc tcgggattac catcatggag aggagttcct tcgagaagaa ccctatcgac | 3540 |
| ttcctggagg ccaagggata taaagaggtg aagaaggacc tcatcatcaa gctgcccaag | 3600 |
| tactccctct tcgagttgga gaacggaagg aagaggatgc tggcttctgc cggagagttg | 3660 |
| cagaagggaa atgagctcgc ccttccctcc aagtacgtga acttcctgta cctcgcctct | 3720 |
| cactatgaaa agttgaaggg ctctcctgag gacaacgagc agaagcagct cttcgtggag | 3780 |
| cagcacaagc actacctgga cgaaattatc gagcagatct ctgagttctc caagcgcgtg | 3840 |
| atattggccg acgccaacct cgacaaggtg ctgtccgcct acaacaagca gggataag | 3900 |
| cccattcgcg agcaggctga aaacattatc caccgtgttta ccctcacaaa cttgggagcc | 3960 |
| cctgctgcct tcaagtactt cgacaccacc attgacagga gagatacac ctccaccaag | 4020 |
| gaggtgctcg acgcaacact catccaccaa tccatcaccg gcctctatga aacaaggatt | 4080 | gacttgtccc agctgggagg cgac                                           4104

<210> SEQ ID NO 116
<211> LENGTH: 1503
<212> TYPE: DNA
<213> ORGANISM: Glycine max

<400> SEQUENCE: 116
ccgggtttac ttattttgtg ggtatctata cttttattag attttaatc aggctcctga      60
tttcttttta tttcgattga attcctgaac ttgtattatt cagtagatcg aataaattat    120
aaaaagataa atcataaaaa taatatttta tcctatcaat catattaaag caatgaatat    180
gtaaaattaa tcttatcttt attttaaaaa atcatatagg tttagtattt ttttaaaaat    240
aaagatagga ttagttttac tattcactgc ttattacttt taaaaaaatc ataaaggttt    300
agtattttt taaaataaat ataggaatag ttttactatt cactgcttta atagaaaaat    360
agtttaaaat ttaagatagt tttaatccca gcatttgcca cgtttgaacg tgagccgaaa    420
cgatgtcgtt acattatctt aacctagctg aaacgatgtc gtcataatat cgccaaatgc    480
caactggact acgtcgaacc cacaaatccc acaaagcgcg tgaaatcaaa tcgctcaaac    540
cacaaaaaag aacaacgcgt tgttacacg ctcaatccca cgcgagtaga gcacagtaac     600
cttcaaataa gcgaatgggg cataatcaga aatccgaaat aaacctaggg gcattatcgg    660
aaatgaaaag tagctcactc aatataaaaa tctaggaacc ctagttttcg ttatcactct    720
gtgctccctc gctctatttc tcagtctctg tgtttgcggc tgaggattcc gaacgagtga    780
ccttcttcgt ttctcgcaaa ggtaacagcc tctgctcttg tctcttcgat tcgatctatg    840
cctgtctctt atttacgatg atgtttcttc ggttatgttt ttttattat gctttatgct      900
gttgatgttc ggttgtttgt ttcgctttgt ttttgtggtt cagtttttta ggattctttt    960
ggttttgaa tcgattaatc ggaagagatt ttcgagttat tggtgtgtt ggaggtgaat     1020
ctttttttg aggtcataga tctgttgtat ttgtgttata acatgcgac tttgtatgat     1080
ttttacgag gttatgatgt tctggttgtt ttattatgaa tctgttgaga cagaaccatg    1140
atttttgttg atgttcgttt acactattaa aggtttgttt taacaggatt aaaagttttt    1200
taagcatgtt gaaggagtct tgtagatatg taaccgtcga tagttttttt gtgggtttgt    1260
tcacatgtta tcaagcttaa tcttttacta tgtatgcgac catatctgga tccagcaaag    1320
gcgatttttt aattccttgt gaaacttttg taatatgaag ttgaaatttt gttattggta    1380
aactataaat gtgtgaagtt ggagtatacc tttaccttct tatttggctt tgtgatagtt    1440
taatttatat gtattttgag ttctgacttg tatttctttg aattgattct agtttaagta    1500
atc                                                                 1503

<210> SEQ ID NO 117
<211> LENGTH: 33
<212> TYPE: DNA
<213> ORGANISM: Artificial sequence
<220> FEATURE:
<223> OTHER INFORMATION: synthesized sequence- inker SV40 NLS

<400> SEQUENCE: 117
tctagagccg atcccaagaa gaagagaaag gtg                                  33

<210> SEQ ID NO 118
<211> LENGTH: 1379
<212> TYPE: PRT

<213> ORGANISM: Artificial sequence
<220> FEATURE:
<223> OTHER INFORMATION: synthesized sequence- Cas9 with a SV40 NLS

<400> SEQUENCE: 118

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
```

```
              385                 390                 395                 400
Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
                450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
                610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
                770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815
```

-continued

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

Ser Arg Ala Asp Pro Lys Lys Lys Arg Lys Val
1370                1375

<210> SEQ ID NO 119
<211> LENGTH: 8519
<212> TYPE: DNA
<213> ORGANISM: Artificial sequence
<220> FEATURE:
<223> OTHER INFORMATION: synthesized sequence- QC782

<400> SEQUENCE: 119
ccgggtttac ttattttgtg ggtatctata cttttattag atttttaatc aggctcctga      60
tttcttttta tttcgattga attcctgaac ttgtattatt cagtagatcg aataaattat     120
aaaaagataa aatcataaaa taatatttta tcctatcaat catattaaag caatgaatat     180
gtaaaattaa tcttatcttt attttaaaaa atcatatagg tttagtattt ttttaaaaat     240
aaagatagga ttagttttac tattcactgc ttattacttt taaaaaaatc ataaaggttt     300
agtatttttt taaaataaat ataggaatag ttttactatt cactgcttta atagaaaaat     360
agtttaaaat ttaagatagt tttaatccca gcatttgcca cgtttgaacg tgagccgaaa     420
cgatgtcgtt acattatctt aacctagctg aaacgatgtc gtcataatat cgccaaatgc     480
caactggact acgtcgaacc cacaaatccc acaaagcgcg tgaaatcaaa tcgctcaaac     540
cacaaaaaag aacaacgcgt tgttacacgc tcaatcccca gcgagtaga gcacagtaac     600
cttcaaataa gcgaatgggg cataatcaga atccgaaat aaacctaggg gcattatcgg     660
aaatgaaaag tagctcactc aatataaaaa tctaggaacc ctagttttcg ttatcactct     720
gtgctccctc gctctatttc tcagtctctg tgtttgcggc tgaggattcc gaacgagtga     780
ccttcttcgt ttctcgcaaa ggtaacagcc tctgctcttg tctcttcgat tcgatctatg     840
cctgtctctt atttacgatg atgtttcttc ggttatgttt ttttatttat gctttatgct     900
gttgatgttc ggttgtttgt ttcgctttgt ttttgtggtt cagtttttta ggattctttt     960
ggttttttgaa tcgattaatc ggaagagatt ttcgagttat ttggtgtgtt ggaggtgaat    1020
ctttttttttg aggtcataga tctgttgtat ttgtgttata acatgcgac tttgtatgat    1080

```
ttttttacgag gttatgatgt tctggttgtt ttattatgaa tctgttgaga cagaaccatg    1140
atttttgttg atgttcgttt acactattaa aggtttgttt taacaggatt aaaagttttt    1200
taagcatgtt gaaggagtct tgtagatatg taaccgtcga tagttttttt gtgggtttgt    1260
tcacatgtta tcaagcttaa tcttttacta tgtatgcgac catatctgga tccagcaaag    1320 gcgattttt aattccttgt gaaacttttg taatatgaag ttgaaatttt gttattggta    1380
aactataaat gtgtgaagtt ggagtatacc tttaccttct tatttggctt tgtgatagtt    1440
taatttatat gtatttgag ttctgacttg tatttctttg aattgattct agtttaagta    1500
atccatggac aaaaagtact caatagggct cgacataggg actaactccg ttggatgggc    1560
cgtcatcacc gacgagtaca aggtgccctc caagaagttc aaggtgttgg aaacaccga    1620 caggcacagc ataaagaaga atttgatcgg tgccctcctc ttcgactccg agagaccgc    1680 tgaggctacc aggctcaaga ggaccgctag aaggcgctac accagaagga agaacagaat    1740
ctgctacctg caggagatct tctccaacga gatggccaag gtggacgact ccttcttcca    1800
ccgccttgag gaatcattcc tggtggagga ggataaaaag cacgagagac acccaatctt    1860
cgggaacatc gtcgacgagg tggcctacca tgaaaagtac cctaccatct accacctgag    1920
gaagaagctg gtcgactcta ccgacaaggc tgacttgcgc ttgattacc tggctctcgc    1980 tcacatgata aagttccgcg gacacttcct cattgaggga gacctgaacc cagacaactc    2040
cgacgtggac aagctcttca tccagctcgt tcagacctac aaccagcttt cgaggagaa    2100 cccaatcaac gccagtggag ttgacgccaa ggctatcctc tctgctcgtc tgtcaaagtc    2160
caggaggctt gagaacttga ttgcccagct gcctggcgaa aagaagaacg gactgttcgg    2220
aaacttgatc gctctctccc tgggattgac tcccaacttc aagtccaact tcgacctcgc    2280
cgaggacgct aagttgcagt tgtctaaaga cacctacgac gatgacctcg acaacttgct    2340
ggcccagata ggcgaccaat acgccgatct cttcctcgcc gctaagaact tgtccgacgc    2400
aatcctgctg tccgacatcc tgagagtcaa cactgagatt accaaagctc tctgtctgc    2460 ttccatgatt aagcgctacg acgagcacca ccaagatctg accctgctca aggccctggt    2520
gagacagcag ctgcccgaga gtacaagga gatctttttc gaccagtcca agaacggcta    2580
cgccggatac attgacggag gcgcctccca ggaagagttc tacaagttca tcaagcccat    2640
ccttgagaag atggacggta ccgaggagct gttggtgaag ttgaacagag aggacctgtt    2700
gaggaagcag agaaccttcg acaacggaag catccctcac caaatccacc tgggagagct    2760
ccacgccatc ttgaggaggc aggaggattt ctatcccttc ctgaaggaca accgcgagaa    2820
gattgagaag atcttgacct tcagaattcc ttactacgtc gggccactcg ccagaggaaa    2880
ctctaggttc gcctggatga cccgcaaatc tgaagagacc attactccct ggaacttcga    2940
ggaagtcgtg gacaagggcg cttccgctca gtctttcatc gagaggatga ccaacttcga    3000
taaaaatctg cccaacgaga aggtgctgcc caagcactcc ctgttgtacg agtatttcac    3060
agtgtacaac gagctcacca aggtgaagta cgtcacagag ggaatgagga agcctgcctt    3120
cttgtccgga gagcagaaga aggccatcgt cgacctgctc ttcaagacca acaggaaggt    3180
gactgtcaag cagctgaagg aggactactt caagaagatc gagtgcttcg actccgtcga    3240
gatctctggt gtcgaggaca ggttcaacgc ctcccttggg acttaccacg atctgctcaa    3300
gattattaaa gacaaggact cctggacaa cgaggagaac gaggacatcc ttgaggacat    3360
cgtgctcacc ctgaccttgt tcgaagacag ggaaatgatc gaagagaggc tcaagaccta    3420
cgcccacctc ttcgacgaca aggtgatgaa acagctgaag agacgcagat ataccggctg    3480
```

```
gggaaggctc tcccgcaaat tgatcaacgg gatcagggac aagcagtcag ggaagactat    3540
actcgacttc ctgaagtccg acggattcgc caacaggaac ttcatgcagc tcattcacga    3600
cgactccttg accttcaagg aggacatcca gaaggctcag gtgtctggac agggtgactc    3660
cttgcatgag cacattgcta acttggccgg ctctcccgct attaagaagg cattttgca    3720 gaccgtgaag gtcgttgacg agctcgtgaa ggtgatggga cgccacaagc cagagaacat    3780
cgttattgag atggctcgcg agaaccaaac tacccagaaa gggcagaaga attcccgcga    3840
gaggatgaag cgcattgagg agggcataaa agagcttggc tctcagatcc tcaaggagca    3900
ccccgtcgag aacactcagc tgcagaacga gaagctgtac ctgtactacc tccaaaacgg    3960
aagggacatg tacgtggacc aggagctgga catcaacagg ttgtccgact acgacgtcga    4020
ccacatcgtg cctcagtcct tcctgaagga tgactccatc gacaataaag tgctgacacg    4080
ctccgataaa aatagaggca agtccgacaa cgtccctcc gaggaggtcg tgaagaagat     4140
gaaaaactac tggagacagc tcttgaacgc caagctcatc acccagcgta agttcgacaa    4200
cctgactaag gctgagagag gaggattgtc cgagctcgat aaggccggat tcatcaagag    4260
acagctcgtc gaaacccgcc aaattaccaa gcacgtggcc caaattctgg attcccgcat    4320
gaacaccaag tacgatgaaa atgacaagct gatccgcgag gtcaaggtga tcaccttgaa    4380
gtccaagctg gtctccgact tccgcaagga cttccagttc tacaaggtga gggagatcaa    4440
caactaccac cacgcacacg acgcctacct caacgctgtc gttggaaccg ccctcatcaa    4500
aaaatatcct aagctggagt ctgagttcgt ctacggcgac tacaaggtgt acgacgtgag    4560
gaagatgatc gctaagtctg agcaggagat cggcaaggcc accgccaagt acttcttcta    4620
ctccaacatc atgaacttct tcaagaccga gatcactctc gccaacggtg agatcaggaa    4680
gcgcccactg atcgagacca acggtgagac tggagagatc gtgtgggaca agggagggga    4740
tttcgctact gtgaggaagg tgctctccat gcctcaggtg aacatcgtca agaagaccga    4800
agttcagacc ggaggattct ccaaggagtc catcctcccc aagagaaact ccgacaagct    4860
gatcgctaga aagaaagact gggaccctaa gaagtacgga ggcttcgatt ctcctaccgt    4920
ggcctactct gtgctggtcg tggccaaggt ggagaagggc aagtccaaga agctgaaatc    4980
cgtcaaggag ctcctcggga ttaccatcat ggagaggagt tccttcgaga gaaaccctat    5040
cgacttcctg gaggccaagg gatataaaga ggtgaagaag gacctcatca tcaagctgcc    5100
caagtactcc ctcttcgagt tggagaacgg aaggaagagg atgctggctt ctgccggaga    5160
gttgcagaag ggaaatgagc tcgcccttcc ctccaagtac gtgaacttcc tgtacctcgc    5220
ctctcactat gaaagttga agggctctcc tgaggacaac gagcagaagc agctcttcgt     5280
ggagcagcac aagcactacc tggacgaaat tatcgagcag atctctgagt ctccaagcg    5340 cgtgatattg gccgacgcca acctcgacaa ggtgctgtcc gcctacaaca gcacaggga    5400 taagcccatt cgcgagcagg ctgaaaacat tatcacctg tttacccctca caaacttggg   5460 agcccctgct gccttcaagt acttcgacac caccattgac aggaagagat acacctccac   5520
caaggaggtg ctcgacgcaa cactcatcca ccaatccatc accggcctct atgaaacaag   5580
gattgacttg tcccagctgg gaggcgactc tagagccgat cccaagaaga gagaaaggt   5640 gtaggttaac ctagacttgt ccatcttctg gattggccaa cttaattaat gtatgaaata    5700
aaaggatgca cacatagtga catgctaatc actataatgt gggcatcaaa gttgtgtgtt    5760
atgtgtaatt actagttatc tgaataaaag agaaagagat catccatatt tcttatccta    5820
```

-continued

```
aatgaatgtc acgtgtctttt ataattctttt gatgaaccag atgcatttca ttaaccaaat    5880
ccatatacat ataaatatta atcatatata attaatatca attgggttag caaaacaaat    5940
ctagtctagg tgtgttttgc gaatgcggcc gctcgagggg gggcccggta ccggcgcgcc    6000
gttctatagt gtcacctaaa tcgtatgtgt atgatacata aggttatgta ttaattgtag    6060
ccgcgttcta acgacaatat gtccatatgg tgcactctca gtacaatctg ctctgatgcc    6120
gcatagttaa gccagcccgc acacccgcca cacccgctg acgcgccctg acgggcttgt    6180
ctgctcccgg catccgctta cagacaagct gtgaccgtct ccgggagctg catgtgtcag    6240
aggttttcac cgtcatcacc gaaacgcgcg agacgaaagg gcctcgtgat acgcctattt    6300
ttataggtta atgtcatgac caaaatccct taacgtgagt tttcgttcca ctgagcgtca    6360
gaccccgtag aaaagatcaa aggatcttct tgagatcctt ttttttctgcg cgtaatctgc    6420 tgcttgcaaa caaaaaaacc accgctacca gcggtggttt gtttgccgga tcaagagcta    6480 ccaactctttt ttccgaaggt aactggcttc agcagagcgc agataccaaa tactgtcctt    6540
ctagtgtagc cgtagttagg ccaccacttc aagaactctg tagcaccgcc tacatacctc    6600
gctctgctaa tcctgttacc agtggctgct gccagtggcg ataagtcgtg tcttaccggg    6660
ttggactcaa gacgatagtt accggataag gcgcagcggt cgggctgaac gggggggttcg    6720 tgcacacagc ccagcttgga gcgaacgacc tacaccgaac tgagatacct acagcgtgag    6780
cattgagaaa gcgccacgct tcccgaaggg agaaaggcgg acaggtatcc ggtaagcggc    6840
agggtcggaa caggagagcg cacgagggag cttccagggg gaaacgcctg gtatctttat    6900
agtcctgtcg ggtttcgcca cctctgactt gagcgtcgat ttttgtgatg ctcgtcaggg    6960
gggcggagcc tatggaaaaa cgccagcaac gcggcctttt tacggttcct ggccttttgc    7020
tggccttttg ctcacatgtt ctttcctgcg ttatccctg attctgtgga taaccgtatt    7080
accgcctttg agtgagctga taccgctcgc cgcagccgaa cgaccgagcg cagcgagtca    7140
gtgagcgagg aagcggaaga gcgcccaata cgcaaaccgc ctctccccgc gcgttggccg    7200
attcattaat gcaggttgat cagatctcga tcccgcgaaa ttaatacgac tcactatagg    7260
gagaccacaa cggtttccct ctagaaataa ttttgtttaa cttaagaag gagatatacc    7320 catggaaaag cctgaactca ccgcgacgtc tgtcgagaag tttctgatcg aaaagttcga    7380
cagcgtctcc gacctgatgc agctctcgga gggcgaagaa tctcgtgctt tcagcttcga    7440
tgtaggaggg cgtggatatg tcctgcgggt aaatagctgc gccgatggtt tctacaaaga    7500
tcgttatgtt tatcggcact ttgcatcggc cgcgctcccg attccggaag tgcttgacat    7560
tggggaattc agcgagagcc tgacctattg catctcccgc cgtgcacagg gtgtcacgtt    7620
gcaagacctg cctgaaaccg aactgcccgc tgttctgcag ccggtcgcgg aggctatgga    7680
tgcgatcgct gcggccgatc ttagccagac gagcgggttc ggcccattcg gaccgcaagg    7740
aatcggtcaa tacactacat ggcgtgattt catatgcgcg attgctgatc cccatgtgta    7800
tcactggcaa actgtgatgg acgacaccgt cagtgcgtcc gtcgcgcagg ctctcgatga    7860
gctgatgctt tgggccgagg actgccccga agtccggcac ctcgtgcacg cggatttcgg    7920
ctccaacaat gtcctgacgg acaatggccg cataacagcg gtcattgact ggagcgaggc    7980
gatgttcggg gattcccaat acgaggtcgc caacatcttc ttctggaggc cgtggttggc    8040
ttgtatggag cagcagacgc gctacttcga gcggaggcat ccggagcttg caggatcgcc    8100
gcggctccgg gcgtatatgc tccgcattgg tcttgaccaa ctctatcaga gcttggttga    8160
cggcaatttc gatgatgcag cttgggcgca gggtcgatgc gacgcaatcg tccgatccgg    8220
```

```
agccgggact gtcgggcgta cacaaatcgc ccgcagaagc gcggccgtct ggaccgatgg    8280
ctgtgtagaa gtactcgccg atagtggaaa ccgacgcccc agcactcgtc cgagggcaaa    8340
ggaatagtga ggtacagctt ggatcgatcc ggctgctaac aaagcccgaa aggaagctga    8400
gttggctgct gccaccgctg agcaataact agcataaccc cttggggcct ctaaacgggt    8460
cttgaggggt tttttgctga aaggaggaac tatatccgga tgatcgggcg cgccggtac     8519

<210> SEQ ID NO 120
<211> LENGTH: 434
<212> TYPE: DNA
<213> ORGANISM: Glycine max

<400> SEQUENCE: 120
ccgggtgtga tttagtataa agtgaagtaa tggtcaaaag aaaaagtgta aaacgaagta      60
cctagtaata agtaatattg aacaaaataa atggtaaagt gtcagatata taaataggc     120 tttaataaaa ggaagaaaaa aaacaaacaa aaaataggtt gcaatggggc agagcagagt     180
catcatgaag ctagaaaggc taccgataga taaactatag ttaattaaat acattaaaaa     240
atacttggat ctttctctta ccctgtttat attgagacct gaaacttgag agagatacac     300
taatcttgcc ttgttgtttc attccctaac ttacaggact cagcgcatgt catgtggtct     360
cgttccccat ttaagtccca caccgtctaa acttattaaa ttattaatgt ttataactag     420
atgcacaaca acaa                                                       434

<210> SEQ ID NO 121
<211> LENGTH: 104
<212> TYPE: DNA
<213> ORGANISM: Artificial sequence
<220> FEATURE:
<223> OTHER INFORMATION: synthesized sequence- Guide RNA for DD43CR1

<400> SEQUENCE: 121
gtcccttgta cttgtacgta gttttagagc tagaaatagc aagttaaaat aaggctagtc      60
cgttatcaac ttgaaaaagt ggcaccgagt cggtgctttt tttt                      104

<210> SEQ ID NO 122
<211> LENGTH: 3098
<212> TYPE: DNA
<213> ORGANISM: Artificial sequence
<220> FEATURE:
<223> OTHER INFORMATION: synthesized sequence- QC783

<400> SEQUENCE: 122
ccgggtgtga tttagtataa agtgaagtaa tggtcaaaag aaaaagtgta aaacgaagta      60
cctagtaata agtaatattg aacaaaataa atggtaaagt gtcagatata taaataggc     120 tttaataaaa ggaagaaaaa aaacaaacaa aaaataggtt gcaatggggc agagcagagt     180
catcatgaag ctagaaaggc taccgataga taaactatag ttaattaaat acattaaaaa     240
atacttggat ctttctctta ccctgtttat attgagacct gaaacttgag agagatacac     300
taatcttgcc ttgttgtttc attccctaac ttacaggact cagcgcatgt catgtggtct     360
cgttccccat ttaagtccca caccgtctaa acttattaaa ttattaatgt ttataactag     420
atgcacaaca acaaagcttg tcccttgtac ttgtacgtag ttttagagct agaaatagca     480
agttaaaata aggctagtcc gttatcaact tgaaaaagtg gcaccgagtc ggtgcttttt     540
tttgcggccg ctcgaggggg ggcccggtac cggcgcgccg ttctatagtg tcacctaaat     600
```

| | |
|---|---|
| cgtatgtgta tgatacataa ggttatgtat taattgtagc cgcgttctaa cgacaatatg | 660 |
| tccatatggt gcactctcag tacaatctgc tctgatgccg catagttaag ccagccccga | 720 |
| cacccgccaa cacccgctga cgcgccctga cgggcttgtc tgctcccggc atccgcttac | 780 |
| agacaagctg tgaccgtctc cgggagctgc atgtgtcaga ggttttcacc gtcatcaccg | 840 |
| aaacgcgcga gacgaaaggg cctcgtgata cgcctatttt tataggttaa tgtcatgacc | 900 |
| aaaatccctt aacgtgagtt ttcgttccac tgagcgtcag accccgtaga aaagatcaaa | 960 |
| ggatcttctt gagatccttt ttttctgcgc gtaatctgct gcttgcaaac aaaaaaacca | 1020 |
| ccgctaccag cggtggtttg tttgccggat caagagctac caactctttt tccgaaggta | 1080 |
| actggcttca gcagagcgca gataccaaat actgtccttc tagtgtagcc gtagttaggc | 1140 |
| caccacttca agaactctgt agcaccgcct acatacctcg ctctgctaat cctgttacca | 1200 |
| gtggctgctg ccagtggcga taagtcgtgt cttaccgggt tggactcaag acgatagtta | 1260 |
| ccggataagg cgcagcggtc gggctgaacg gggggttcgt gcacacagcc cagcttggag | 1320 |
| cgaacgacct acaccgaact gagatacccta cagcgtgagc attgagaaag cgccacgctt | 1380 |
| cccgaaggga gaaaggcgga caggtatccg gtaagcggca gggtcggaac aggagagcgc | 1440 |
| acgagggagc ttccagggggg aaacgcctgg tatctttata gtcctgtcgg gtttcgccac | 1500 |
| ctctgacttg agcgtcgatt tttgtgatgc tcgtcagggg ggcggagcct atggaaaaac | 1560 |
| gccagcaacg cggcctttttt acggttcctg gccttttgct ggccttttgc tcacatgttc | 1620 |
| tttcctgcgt tatcccctga ttctgtggat aaccgtatta ccgcctttga gtgagctgat | 1680 |
| accgctcgcc gcagccgaac gaccgagcgc agcgagtcag tgagcgagga agcggaagag | 1740 |
| cgcccaatac gcaaaccgcc tctccccgcg cgttggccga ttcattaatg caggttgatc | 1800 |
| agatctcgat cccgcgaaat taatacgact cactataggg agaccacaac ggtttccctc | 1860 |
| tagaaataat tttgtttaac tttaagaagg agatataccc atggaaaagc ctgaactcac | 1920 |
| cgcgacgtct gtcgagaagt ttctgatcga aaagttcgac agcgtctccg acctgatgca | 1980 |
| gctctcggag ggcgaagaat ctcgtgcttt cagcttcgat gtaggagggc gtggatatgt | 2040 |
| cctgcgggta aatagctgcg ccgatggttt ctacaaagat cgttatgttt atcggcactt | 2100 |
| tgcatcggcc gcgctcccga ttccggaagt gcttgacatt ggggaattca gcgagagcct | 2160 |
| gacctattgc atctcccgcc gtgcacaggg tgtcacgttg caagacctgc ctgaaaccga | 2220 |
| actgcccgct gttctgcagc cggtcgcgga ggctatggat gcgatcgctg cggccgatct | 2280 |
| tagccagacg agcgggttcg gcccattcgg accgcaagga atcggtcaat acactacatg | 2340 |
| gcgtgatttc atatgcgcga ttgctgatcc ccatgtgtat cactggcaaa ctgtgatgga | 2400 |
| cgacaccgtc agtgcgtccg tcgcgcaggc tctcgatgag ctgatgcttt gggccgagga | 2460 |
| ctgccccgaa gtccggcacc tcgtgcacgc ggatttcggc tccaacaatg tcctgacgga | 2520 |
| caatggccgc ataacagcgg tcattgactg gagcgaggcg atgttcgggg attcccaata | 2580 |
| cgaggtcgcc aacatcttct tctggaggcc gtggttggct tgtatggagc agcagacgcg | 2640 |
| ctacttcgag cggaggcatc cggagcttgc aggatcgccg cggctccggg cgtatatgct | 2700 |
| ccgcattggt cttgaccaac tctatcagag cttggttgac ggcaatttcg atgatgcagc | 2760 |
| ttgggcgcag ggtcgatgcg acgcaatcgt ccgatccgga gccgggactg tcgggcgtac | 2820 |
| acaaatcgcc cgcagaagcg cggccgtctg gaccgatggc tgtgtagaag tactcgccga | 2880 |
| tagtggaaac cgacgcccca gcactcgtcc gagggcaaag gaatagtgag gtacagcttg | 2940 |
| gatcgatccg gctgctaaca aagcccgaaa ggaagctgag ttggctgctg ccaccgctga | 3000 |

```
gcaataacta gcataacccc ttggggcctc taaacgggtc ttgaggggtt ttttgctgaa    3060
aggaggaact atatccggat gatcgggcgc gccggtac                           3098

<210> SEQ ID NO 123
<211> LENGTH: 9093
<212> TYPE: DNA
<213> ORGANISM: Artificial sequence
<220> FEATURE:
<223> OTHER INFORMATION: synthesized sequence- QC815

<400> SEQUENCE: 123
ccgggtgtga tttagtataa agtgaagtaa tggtcaaaag aaaaagtgta aaacgaagta      60
cctagtaata agtaatattg aacaaaataa atggtaaagt gtcagatata taaataggc     120 tttaataaaa ggaagaaaaa aaacaaacaa aaaataggtt gcaatggggc agagcagagt     180
catcatgaag ctagaaaggc taccgataga taaactatag ttaattaaat acattaaaaa     240
atacttggat ctttctctta ccctgtttat attgagacct gaaacttgag agagatacac     300
taatcttgcc ttgttgtttc attccctaac ttacaggact cagcgcatgt catgtggtct     360
cgttccccat ttaagtccca caccgtctaa acttattaaa ttattaatgt ttataactag     420
atgcacaaca acaaagcttg tcccttgtac ttgtacgtag ttttagagct agaaatagca     480
agttaaaata aggctagtcc gttatcaact tgaaaaagtg gcaccgagtc ggtgcttttt     540
tttgcggccg caattggatc gggtttactt attttgtggg tatctatact tttattagat     600
ttttaatcag gctcctgatt tcttttttatt tcgattgaat tcctgaactt gtattattca     660
gtagatcgaa taaattataa aaagataaaa tcataaaata atattttatc ctatcaatca     720
tattaaagca atgaatatgt aaaattaatc ttatctttat tttaaaaaat catataggtt     780
tagtattttt ttaaaaataa agataggatt agttttacta ttcactgctt attactttta     840
aaaaaatcat aaaggtttag tattttttta aaataaatat aggaatagtt ttactattca     900
ctgctttaat agaaaaatag tttaaaattt aagatagttt taatcccagc atttgccacg     960
tttgaacgtg agccgaaacg atgtcgttac attatcttaa cctagctgaa acgatgtcgt    1020
cataatatcg ccaaatgcca actggactac gtcgaaccca caaatcccac aaagcgcgtg    1080
aaatcaaatc gctcaaacca caaaaaagaa caacgcgttt gttacacgct caatcccacg    1140
cgagtagagc acagtaacct tcaaataagc gaatggggca taatcagaaa tccgaaataa    1200
acctaggggc attatcggaa atgaaaagta gctcactcaa tataaaaatc taggaaccct    1260
agttttcgtt atcactctgt gctccctcgc tctatttctc agtctctgtg tttgcggctg    1320
aggattccga acgagtgacc ttcttcgttt ctcgcaaagg taacagcctc tgctcttgtc    1380
tcttcgattc gatctatgcc tgtctcttat ttacgatgat gtttcttcgg ttatgttttt    1440
ttatttatgc tttatgctgt tgatgttcgg ttgtttgttt cgctttgttt ttgtggttca    1500
gttttttagg attcttttgg tttttgaatc gattaatcgg aagagatttt cgagttattt    1560
ggtgtgttgg aggtgaatct ttttttttgag gtcatagatc tgttgtattt gtgttataaa    1620
catgcgactt tgtatgattt tttacgaggt tatgatgttc tggttgtttt attatgaatc    1680
tgttgagaca gaaccatgat ttttgttgat gttcgtttac actattaaag gtttgtttta    1740
acaggattaa aagttttta agcatgttga aggagtcttg tagatatgta accgtcgata    1800 gttttttgt gggtttgttc acatgttatc aagcttaatc ttttactatg tatgcgacca    1860
tatctggatc cagcaaaggc gatttttaa ttccttgtga aacttttgta atatgaagtt    1920
```

```
gaaattttgt tattggtaaa ctataaatgt gtgaagttgg agtatacctt taccttctta    1980
tttggctttg tgatagttta atttatatgt attttgagtt ctgacttgta tttctttgaa    2040
ttgattctag tttaagtaat ccatggacaa aaagtactca atagggctcg acatagggac    2100
taactccgtt ggatgggccg tcatcaccga cgagtacaag gtgccctcca agaagttcaa    2160
ggtgttggga acaccgaca ggcacagcat aaagaagaat ttgatcggtg ccctcctctt    2220
cgactccgga gagaccgctg aggctaccag gctcaagagg accgctagaa ggcgctacac    2280
cagaaggaag aacagaatct gctacctgca ggagatcttc tccaacgaga tggccaaggt    2340
ggacgactcc ttcttccacc gccttgagga atcattcctg gtggaggagg ataaaaagca    2400
cgagagacac ccaatcttcg gaacatcgt cgacgaggtg gcctaccatg aaaagtaccc    2460
taccatctac cacctgagga gaagctggt cgactctacc gacaaggctg acttgcgctt    2520
gatttacctg gctctcgctc acatgataaa gttccgcgga cacttcctca ttgagggaga    2580
cctgaaccca gacaactccg acgtggacaa gctcttcatc cagctcgttc agacctacaa    2640
ccagcttttc gaggagaacc caatcaacgc cagtggagtt gacgccaagg ctatcctctc    2700
tgctcgtctg tcaaagtcca ggaggcttga aacttgatt gcccagctgc ctggcgaaaa    2760
gaagaacgga ctgttcggaa acttgatcgc tctctccctg ggattgactc ccaacttcaa    2820
gtccaacttc gacctcgccg aggacgctaa gttgcagttg tctaaagaca cctacgacga    2880
tgacctcgac aacttgctgg cccagatagg cgaccaatac gccgatctct cctcgccgc    2940 taagaacttg tccgacgcaa tcctgctgtc cgacatcctg agagtcaaca ctgagattac    3000
caaagctcct ctgtctgctt ccatgattaa gcgctacgac gagcaccacc aagatctgac    3060
cctgctcaag gccctggtga cagcagct gcccgagaag tacaaggaga tcttttttcga    3120 ccagtccaag aacggctacg ccggatacat tgacggaggc gcctcccagg aagagttcta    3180
caagttcatc aagcccatcc ttgagaagat ggacggtacc gaggagctgt tggtgaagtt    3240
gaacagagag gacctgttga ggaagcagag aaccttcgac aacggaagca tccctcacca    3300
aatccacctg ggagagctcc acgccatctt gaggaggcag gaggatttct atcccttcct    3360
gaaggacaac cgcgagaaga ttgagaagat cttgaccttc agaattcctt actacgtcgg    3420
gccactcgcc agaggaaact ctaggttcgc ctggatgacc cgcaaatctg aagagaccat    3480
tactccctgg aacttcgagg aagtcgtgga caagggcgct tccgctcagt ctttcatcga    3540
gaggatgacc aacttcgata aaaatctgcc caacgagaag gtgctgccca gcactccct    3600 gttgtacgag tatttcacag tgtacaacga gctcaccaag gtgaagtacg tcacagaggg    3660
aatgaggaag cctgccttct tgtccggaga gcagaagaag gccatcgtcg acctgctctt    3720
caagaccaac aggaaggtga ctgtcaagca gctgaaggag gactacttca gaagatcga    3780 gtgcttcgac tccgtcgaga tctctggtgt cgaggacagg ttcaacgcct cccttgggac    3840
ttaccacgat ctgctcaaga ttattaaaga caaggacttc ctggacaacg aggagaacga    3900
ggacatcctt gaggacatcg tgctcacccct gaccttgttc gaagacaggg aaatgatcga    3960
agagaggctc aagacctacg cccacctctt cgacgacaag gtgatgaaac agctgaagag    4020
acgcagatat accggctggg gaaggctctc ccgcaaattg atcaacggga tcaggacaa    4080 gcagtcaggg aagactatac tcgacttcct gaagtccgac ggattcgcca acaggaactt    4140
catgcagctc attcacgacg actccttgac cttcaaggag gacatccaga aggctcaggt    4200
gtctggacag ggtgactcct tgcatgagca cattgctaac ttggccggct ctcccgctat    4260
taagaagggc attttgcaga ccgtgaaggt cgttgacgag ctcgtgaagg tgatgggacg    4320
```

```
ccacaagcca gagaacatcg ttattgagat ggctcgcgag aaccaaacta cccagaaagg    4380
gcagaagaat tcccgcgaga ggatgaagcg cattgaggag ggcataaaag agcttggctc    4440
tcagatcctc aaggagcacc ccgtcgagaa cactcagctg cagaacgaga agctgtacct    4500
gtactacctc caaaacggaa gggacatgta cgtggaccag gagctggaca tcaacaggtt    4560
gtccgactac gacgtcgacc acatcgtgcc tcagtccttc ctgaaggatg actccatcga    4620
caataaagtg ctgacacgct ccgataaaaa tagaggcaag tccgacaacg tccctccga    4680 ggaggtcgtg aagaagatga aaaactactg gagacagctc ttgaacgcca agctcatcac    4740
ccagcgtaag ttcgacaacc tgactaaggc tgagagagga ggattgtccg agctcgataa    4800
ggccggattc atcaagagac agctcgtcga aacccgccaa attaccaagc acgtggccca    4860
aattctggat tcccgcatga acaccaagta cgatgaaaat gacaagctga tccgcgaggt    4920
caaggtgatc accttgaagt ccaagctggt ctccgacttc cgcaaggact tccagttcta    4980
caaggtgagg gagatcaaca actaccacca cgcacacgac gcctacctca cgctgtcgt    5040 tggaaccgcc ctcatcaaaa aatatcctaa gctggagtct gagttcgtct acggcgacta    5100
caaggtgtac gacgtgagga agatgatcgc taagtctgag caggagatcg gcaaggccac    5160
cgccaagtac ttcttctact ccaacatcat gaacttcttc aagaccgaga tcactctcgc    5220
caacggtgag atcaggaagc gcccactgat cgagaccaac ggtgagactg agagatcgt    5280 gtgggacaaa gggagggatt cgctactgt gaggaaggtg ctctccatgc ctcaggtgaa    5340
catcgtcaag aagaccgaag ttcagaccgg aggattctcc aaggagtcca tcctccccaa    5400
gagaaactcc gacaagctga tcgctagaaa gaaagactgg gaccctaaga agtacggagg    5460
cttcgattct cctaccgtgg cctactctgt gctggtcgtg gccaaggtgg agaagggcaa    5520
gtccaagaag ctgaaatccg tcaaggagct cctcgggatt accatcatgg agaggagttc    5580
cttcgagaag aaccctatcg acttcctgga ggccaaggga tataaagagg tgaagaagga    5640
cctcatcatc aagctgccca gtactcccct cttcgagttg gagaacggaa ggaagaggat    5700
gctggcttct gccggagagt tgcagaaggg aaatgagctc gcccttccct ccaagtacgt    5760
gaacttcctg tacctcgcct ctcactatga aaagttgaag ggctctcctg aggacaacga    5820
gcagaagcag ctcttcgtgg agcagcacaa gcactacctg gacgaaatta tcgagcagat    5880
ctctgagttc tccaagcgcg tgatattggc cgacgccaac ctcgacaagg tgctgtccgc    5940
ctacaacaag cacagggata agcccattcg cgagcaggct gaaaacatta tccacctgtt    6000
taccctcaca aacttgggag cccctgctgc cttcaagtac ttcgacacca ccattgacag    6060
gaagagatac acctccacca aggaggtgct cgacgcaaca ctcatccacc aatccatcac    6120
cggcctctat gaaacaagga ttgacttgtc ccagctggga ggcgactcta gagccgatcc    6180
caagaagaag agaaaggtgt aggttaacct agacttgtcc atcttctgga ttggccaact    6240
taattaatgt atgaaataaa aggatgcaca catagtgaca tgctaatcac tataatgtgg    6300
gcatcaaagt tgtgtgttat gtgtaattac tagttatctg aataaaagag aaagagatca    6360
tccatatttc ttatcctaaa tgaatgtcac gtgtctttat aattctttga tgaaccagat    6420
gcatttcatt aaccaaatcc atatacatat aaatattaat catatataat taatatcaat    6480
tgggttagca aaacaaatct agtctaggtg tgttttgcga attcgatatc aagcttatcg    6540
ataccgtcga ggggggccc ggtaccgcg cgccgttcta tagtgtcacc taaatcgtat    6600
gtgtatgata cataaggtta tgtattaatt gtagccgcgt tctaacgaca atatgtccat    6660
```

```
atggtgcact ctcagtacaa tctgctctga tgccgcatag ttaagccagc cccgacaccc   6720
gccaacaccc gctgacgcgc cctgacgggc ttgtctgctc ccggcatccg cttacagaca   6780
agctgtgacc gtctccggga gctgcatgtg tcagaggttt tcaccgtcat caccgaaacg   6840
cgcgagacga aagggcctcg tgatacgcct attttatag gttaatgtca tgaccaaaat   6900
cccttaacgt gagttttcgt tccactgagc gtcagacccc gtagaaaaga tcaaaggatc   6960
ttcttgagat cctttttttc tgcgcgtaat ctgctgcttg caaacaaaaa aaccaccgct   7020
accagcggtg gtttgtttgc cggatcaaga gctaccaact cttttccga aggtaactgg   7080 cttcagcaga gcgcagatac caaatactgt ccttctagtg tagccgtagt taggccacca   7140
cttcaagaac tctgtagcac cgcctacata cctcgctctg ctaatcctgt taccagtggc   7200
tgctgccagt ggcgataagt cgtgtcttac cgggttggac tcaagacgat agttaccgga   7260
taaggcgcag cggtcgggct gaacggggg ttcgtgcaca cagcccagct tggagcgaac   7320
gacctacacc gaactgagat acctacagcg tgagcattga gaaagcgcca cgcttcccga   7380
agggagaaag gcggacaggt atccggtaag cggcagggtc ggaacaggag agcgcacgag   7440
ggagcttcca gggggaaacg cctggtatct ttatagtcct gtcgggtttc gccacctctg   7500
acttgagcgt cgatttttgt gatgctcgtc agggggggcgg agcctatgga aaacgccag   7560 caacgcggcc ttttacggt tcctggcctt ttgctggcct tttgctcaca tgttctttcc   7620
tgcgttatcc cctgattctg tggataaccg tattaccgcc tttgagtgag ctgataccgc   7680
tcgccgcagc cgaacgaccg agcgcagcga gtcagtgagc gaggaagcgg aagagcgccc   7740
aatacgcaaa ccgcctctcc ccgcgcgttg gccgattcat taatgcaggt tgatcagatc   7800
tcgatcccgc gaaattaata cgactcacta tagggagacc acaacggttt ccctctagaa   7860
ataattttgt ttaactttaa gaaggagata tacccatgga aaagcctgaa ctcaccgcga   7920
cgtctgtcga agtttctg atcgaaaagt tcgacagcgt ctccgacctg atgcagctct   7980
cggagggcga agaatctcgt gctttcagct tcgatgtagg agggcgtgga tatgtcctgc   8040
gggtaaatag ctgcgccgat ggtttctaca agatcgtta tgtttatcgg cactttgcat   8100
cggccgcgct cccgattccg gaagtgcttg acattgggga attcagcgag agcctgacct   8160
attgcatctc ccgccgtgca cagggtgtca cgttgcaaga cctgcctgaa accgaactgc   8220
ccgctgttct gcagccggtc gcggaggcta tggatgcgat cgctgcggcc gatcttagcc   8280
agacgagcgg gttcggccca ttcggaccgc aaggaatcgg tcaatacact acatggcgtg   8340
atttcatatg cgcgattgct gatcccatg tgtatcactg gcaaactgtg atggacgaca   8400
ccgtcagtgc gtccgtcgcg caggctctcg atgagctgat gctttgggcc gaggactgcc   8460
ccgaagtccg gcacctcgtg cacgcggatt tcggctccaa caatgtcctg acggacaatg   8520
gccgcataac agcggtcatt gactggagcg aggcgatgtt cggggattcc caatacgagg   8580
tcgccaacat cttcttctgg aggccgtggt tggcttgtat ggagcagcag acgcgctact   8640
tcgagcggag gcatccggag cttgcaggat cgccgcggct ccgggcgtat atgctccgca   8700
ttggtcttga ccaactctat cagagcttgg ttgacggcaa tttcgatgat gcagcttggg   8760
cgcagggtcg atgcgacgca atcgtccgat ccggagccgg gactgtcggg cgtacacaaa   8820
tcgcccgcag aagcgcggcc gtctggaccg atggctgtgt agaagtactc gccgatagtg   8880
gaaaccgacg ccccagcact cgtccgaggg caaggaata gtgaggtaca gcttggatcg   8940
atccggctgc taacaaagcc cgaaaggaag ctgagttggc tgctgccacc gctgagcaat   9000
aactagcata accccttggg gcctctaaac gggtcttgag gggttttttg ctgaaaggag   9060
```

-continued

| | |
|---|---|
| gaactatatc cggatgatcg ggcgcgccgg tac | 9093 |

<210> SEQ ID NO 124
<211> LENGTH: 4107
<212> TYPE: DNA
<213> ORGANISM: Steptococcus pyogenes

<400> SEQUENCE: 124

| | |
|---|---|
| atggataaga aatactcaat aggcttagat atcggcacaa atagcgtcgg atgggcggtg | 60 |
| atcactgatg attataaggt tccgtctaaa aagctcaagg gtctgggaaa tacagaccgc | 120 |
| cacggtatca aaaaaaatct tatagggggct cttttatttg acagtggaga gacagcggaa | 180 |
| gcgactcgtc tcaaacggac agctcgtaga aggtatacac gtcggaagaa tcgtatttgt | 240 |
| tatctacagg agattttttc aaatgagatg gcgaaagtag atgatagttt ctttcatcga | 300 |
| cttgaagagt cttttttggt ggaagaagac aagaagcatg aacgtcatcc tattttttgga | 360 |
| aatatagtag atgaagttgc ttatcatgag aaatatccaa ctatctatca tctgcgaaaa | 420 |
| aaattggcag attctactga taaagtggat ttgcgcttaa tctatttggc cttagcgcat | 480 |
| atgattaagt tcgtggtca tttttttgatt gagggagatt taaatcctga ataatagtgat | 540 |
| gtggacaaac tatttatcca gttggtacaa acctacaatc aattatttga agaaaaccct | 600 |
| attaacgcaa gtagagtaga tgctaaagcg attctttctg cacgattgag taaatcaaga | 660 |
| cgattagaaa atctcattgc tcagctcccc ggtgagaaga aaaatggatt gtttgggaat | 720 |
| ctcattgctt tgtcattggg attgaccccct aatttttaaat caaattttga tttggcagaa | 780 |
| gatgctaaat tacagctttc aaaagatact tacgatgatg atttagataa tttattggcg | 840 |
| caaattggag atcaatatgc tgatttgttt ttggcagcta agaatttatc agatgctact | 900 |
| ttacttttcag atatcctaag agtaaatagt gaaataacta aggctcccct atcagcttca | 960 |
| atgattaagc gctacgatga acatcatcaa gacttgactc ttttaaaagc tttagttcga | 1020 |
| caacaacttc cagaaaagta taaagaaatc tttttttgatc aatcaaaaaa cggatatgca | 1080 |
| ggttatattg atgggggagc tagccaagaa gaatttttata aatttatcaa accaatttta | 1140 |
| gaaaaaatgg atggtactga ggaattattg gcgaaactaa atcgtgaaga tttgctgcgc | 1200 |
| aagcaacgga cctttgacaa cggctctatt ccctatcaaa ttcacttggg tgagctgcat | 1260 |
| gctattttga gaagacaaga agactttat ccattttaa aagacaatcg tgagaagatt | 1320 |
| gaaaaaatct tgacttttcg aattccttat tatgttggtc cattggcgcg tggcaatagt | 1380 |
| cgttttgcat ggatgactcg gaagtctgaa gaaacaatta ccccatggaa ttttgaagaa | 1440 |
| gttgtcgata aggtgcttc agctcaatca tttattgaac gcatgacaaa ctttgataaa | 1500 |
| aatcttccaa atgaaaaagt actaccaaaa catagtttgc tttatgagta ttttacggtt | 1560 |
| tataacgaat tgacaaaagt caaatatgtt actgagggaa tgcgaaaacc agcatttctt | 1620 |
| tcaggtgaac agaagaaagc cattgttgat ttactcttca aaacaaatcg aaaagtaacc | 1680 |
| gttaagcaat taaagaaga ttatttcaaa aaaatagaat gttttgatag tgttgaaatt | 1740 |
| tcaggagttg aagatagatt taatgcttca ttaggtacct accatgattt gctaaaaatt | 1800 |
| attaaagata aagattttt ggataatgaa gaaacgaag atatcttaga ggatattgtt | 1860 |
| ttaacattga ccttatttga agatagggag atgattgagg aaagacttaa aacatatgct | 1920 |
| cacctctttg atgataaggt gatgaaacag cttaaacgtc gccgttatac tggttgggga | 1980 |
| cgtttgtctc gaaaattgat taatggtatt agggataagc aatctggcaa aacaatatta | 2040 |

```
gattttttga aatcagatgg ttttgccaat cgcaatttta tgcagctgat ccatgatgat    2100
agtttgacat ttaaagaaga cattcaaaaa gcacaagtgt ctggacaagg cgatagttta    2160
catgaacata ttgcaaattt agctggtagc cctgctatta aaaaggtat tttacagact     2220
gtaaagttg ttgatgaatt ggtcaaagta atggggcggc ataagccaga aaatatcgtt     2280
attgaaatgg cacgtgaaaa tcagacaact caaaagggcc agaaaaattc gcgtgagcgt    2340
atgaaacgta ttgaagaagg aataaaagaa ctaggaagtg atattctaaa ggagtatcct    2400
gttgaaaaca ctcaattaca aaatgaaaag ctctatctct attatctcca aaatggaaga    2460
gacatgtatg tggaccaaga attagatatt aatcgtttaa gtgattatga tgtcgatcac    2520
attgttccac aaagtttcct taaagacgat tcaatagaca ataaggtctt aacgcgttct    2580
gataaaaatc gtggtaaatc ggataacgtt ccaagtgaag aagtagtcaa aaagatgaaa    2640
aactattgga gacaacttct aaacgccaag ttaatcactc aacgtaagtt tgataattta    2700
acaaaagctg aacgtggagg tttgagtgaa cttgataaag ttggttttat caaacgccaa    2760
ttggttgaaa ctcgccaaat cactaagcat gtggcacaaa ttttggatag tcgcatgaat    2820
actaaatacg atgaaaatga taaacttatt cgagaggtta gagtgattac cttaaaatct    2880
aaattagttt ctgacttccg aaaagatttc caattctata agtacgtga gattaacaat     2940
taccatcatg cccatgatgc gtatcttaat gccgtcgttg aactgctttt gattaagaaa    3000
tatccaaaac ttgaatcgga gtttgtctat ggtgattata agtttatga tgttcgtaaa     3060
atgattgcta agtctgagca ggaaataggc aaagcaaccg caaatatttt cttttactct    3120
aatatcatga acttcttcaa aacagaaatt acacttgcaa atggagagat tcgcaaacgc    3180
cctctaatcg aaactaatgg ggaaactgga gaaattgtct gggataaagg gcgagatttt    3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt ttgatagtcc aacggtagct    3420
tattcagtcc tagtggttgc taaggtggaa aaagggaaat cgaagaagtt aaaatccgtt    3480
aaagagttac tagggatcac aataatgaaa agaagctctt ttgaaaaaga tccgattgac    3540
tttttagaag ctaaaggata taaggaagtt agaaaagact taatcattaa actacctaaa    3600
tatagtcttt ttgagttaga aaacggtcgt aaacggatgc tggctagtgc cggagaattg    3660
caaaaaggaa atgagctagc tctgccaagc aaatatgtga atttttata tttagctagt    3720
cattatgaaa agttgaaggg tagtccagaa gataacgaac aaaaacaatt gtttgtggag    3780
cagcataagc attatttaga tgagattatt gagcaaatca gtgaattttc taagcgtgtt    3840
attttagcag atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatattt tgatacaaca attgatcgta aacgatatac gtctacaaaa    4020
gaagttttag atgccactct tatccatcaa tccatcactg gtctttatga aacacgcatt    4080
gatttgagtc agctaggagg tgactga                                        4107
```

<210> SEQ ID NO 125
<211> LENGTH: 20
<212> TYPE: DNA
<213> ORGANISM: Glycine max

<400> SEQUENCE: 125

```
ggaactgaca cacgacatga                                                  20
```

<210> SEQ ID NO 126
<211> LENGTH: 20
<212> TYPE: DNA
<213> ORGANISM: Glycine max

<400> SEQUENCE: 126
gacatgatgg aacgtgacta                                                   20

<210> SEQ ID NO 127
<211> LENGTH: 20
<212> TYPE: DNA
<213> ORGANISM: Glycine max

<400> SEQUENCE: 127
gtcccttgta cttgtacgta                                                   20

<210> SEQ ID NO 128
<211> LENGTH: 20
<212> TYPE: DNA
<213> ORGANISM: Glycine max

<400> SEQUENCE: 128
gtattctaga aaagaggaat                                                   20

<210> SEQ ID NO 129
<211> LENGTH: 70
<212> TYPE: DNA
<213> ORGANISM: Glycine max

<400> SEQUENCE: 129
atcaaaattc ggaactgaca cacgacatga tggaacgtga ctaaggtggg tttttgactt       60
tgcatgtcga                                                              70

<210> SEQ ID NO 130
<211> LENGTH: 70
<212> TYPE: DNA
<213> ORGANISM: Glycine max

<400> SEQUENCE: 130
tcgacatgca aagtcaaaaa cccaccttag tcacgttcca tcatgtcgtg tgtcagttcc       60
gaattttgat                                                              70

<210> SEQ ID NO 131
<211> LENGTH: 70
<212> TYPE: DNA
<213> ORGANISM: Glycine max

<400> SEQUENCE: 131
ggcagactcc aattcctctt ttctagaata ccctccgtac gtacaagtac aagggacttg       60
tgagttgtaa                                                              70

<210> SEQ ID NO 132
<211> LENGTH: 70
<212> TYPE: DNA
<213> ORGANISM: Glycine max

<400> SEQUENCE: 132
ttacaactca caagtccctt gtacttgtac gtacggaggg tattctagaa aagaggaatt      60
ggagtctgcc                                                              70

<210> SEQ ID NO 133
<211> LENGTH: 71
<212> TYPE: DNA
<213> ORGANISM: Artificial sequence
<220> FEATURE:
<223> OTHER INFORMATION: synthesized sequence-primer DD20-S3

<400> SEQUENCE: 133
ctacactctt tccctacacg acgctcttcc gatctggaat ttacagcaca agtagatcac    60
ttgtacttat c                                                         71

<210> SEQ ID NO 134
<211> LENGTH: 59
<212> TYPE: DNA
<213> ORGANISM: Artificial sequence
<220> FEATURE:
<223> OTHER INFORMATION: synthesized sequence-primer DD20-A

<400> SEQUENCE: 134
caagcagaag acggcatacg agctcttccg atctaaatca ctctcacttc gacatgcaa     59

<210> SEQ ID NO 135
<211> LENGTH: 71
<212> TYPE: DNA
<213> ORGANISM: Artificial sequence
<220> FEATURE:
<223> OTHER INFORMATION: synthesized sequence-primer DD20-S4

<400> SEQUENCE: 135
ctacactctt tccctacacg acgctcttcc gatctttcct ttacagcaca agtagatcac    60
ttgtacttat c                                                         71

<210> SEQ ID NO 136
<211> LENGTH: 68
<212> TYPE: DNA
<213> ORGANISM: Artificial sequence
<220> FEATURE:
<223> OTHER INFORMATION: synthesized sequence-primer DD43-S3

<400> SEQUENCE: 136
ctacactctt tccctacacg acgctcttcc gatctagctg taaatacagc cttacaactc    60
acaagtcc                                                             68

<210> SEQ ID NO 137
<211> LENGTH: 63
<212> TYPE: DNA
<213> ORGANISM: Artificial sequence
<220> FEATURE:
<223> OTHER INFORMATION: synthesized sequence-Primer, DD43-A

<400> SEQUENCE: 137
caagcagaag acggcatacg agctcttccg atctttaatt taggactaaa agaagaggca    60
gac                                                                  63

<210> SEQ ID NO 138
<211> LENGTH: 68
<212> TYPE: DNA
<213> ORGANISM: Artificial sequence
<220> FEATURE:
<223> OTHER INFORMATION: synthesized sequence- Primer, DD43-S4

<400> SEQUENCE: 138
ctacactctt tccctacacg acgctcttcc gatctctagg taaatacagc cttacaactc    60

```
acaagtcc                                                             68

<210> SEQ ID NO 139
<211> LENGTH: 68
<212> TYPE: DNA
<213> ORGANISM: Artificial sequence
<220> FEATURE:
<223> OTHER INFORMATION: synthesized sequence- Primer, DD43-S5

<400> SEQUENCE: 139
ctacactctt tccctacacg acgctcttcc gatctgatcg taaatacagc cttacaactc    60
acaagtcc                                                             68

<210> SEQ ID NO 140
<211> LENGTH: 43
<212> TYPE: DNA
<213> ORGANISM: Artificial sequence
<220> FEATURE:
<223> OTHER INFORMATION: synthesized sequence- Primer, JKY557

<400> SEQUENCE: 140
aatgatacgg cgaccaccga gatctacact ctttccctac acg                      43

<210> SEQ ID NO 141
<211> LENGTH: 18
<212> TYPE: DNA
<213> ORGANISM: Artificial sequence
<220> FEATURE:
<223> OTHER INFORMATION: synthesized sequence- primer, JKY558

<400> SEQUENCE: 141
caagcagaag acggcata                                                  18

<210> SEQ ID NO 142
<211> LENGTH: 117
<212> TYPE: DNA
<213> ORGANISM: Artificial sequence
<220> FEATURE:
<223> OTHER INFORMATION: synthesized sequence- DD20CR1 PCR amplicon

<400> SEQUENCE: 142
ggaatttaca gcacaagtag atcacttgta cttatcaaaa ttcggaactg acacacgaca    60
tgatggaacg tgactaaggt gggttttttga ctttgcatgt cgaagtgaga gtgattt     117

<210> SEQ ID NO 143
<211> LENGTH: 117
<212> TYPE: DNA
<213> ORGANISM: Artificial sequence
<220> FEATURE:
<223> OTHER INFORMATION: synthesized sequence- DD20CR2 PCR amplicon

<400> SEQUENCE: 143
ttcctttaca gcacaagtag atcacttgta cttatcaaaa ttcggaactg acacacgaca    60
tgatggaacg tgactaaggt gggttttttga ctttgcatgt cgaagtgaga gtgattt     117

<210> SEQ ID NO 144
<211> LENGTH: 108
<212> TYPE: DNA
<213> ORGANISM: Artificial sequence
<220> FEATURE:
<223> OTHER INFORMATION: synthesized sequence- DD43CR1 PCR amplicon

<400> SEQUENCE: 144
```
agctgtaaat acagccttac aactcacaag tcccttgtac ttgtacgtac ggagggtatt    60
ctagaaaaga ggaattggag tctgcctctt cttttagtcc taaattaa                108

<210> SEQ ID NO 145
<211> LENGTH: 108
<212> TYPE: DNA
<213> ORGANISM: Artificial sequence
<220> FEATURE:
<223> OTHER INFORMATION: synthesized sequence- DD43CR2 PCR amplicon

<400> SEQUENCE: 145
ctaggtaaat acagccttac aactcacaag tcccttgtac ttgtacgtac ggagggtatt    60
ctagaaaaga ggaattggag tctgcctctt cttttagtcc taaattaa                108

<210> SEQ ID NO 146
<211> LENGTH: 108
<212> TYPE: DNA
<213> ORGANISM: artificial sequence
<220> FEATURE:
<223> OTHER INFORMATION: synthesized sequence- amplicon

<400> SEQUENCE: 146
ctaggtaaat acagccttac aactcacaag tcccttgtac ttgtacgtac ggagggtatt    60
ctagaaaaga ggaattggag tctgcctctt cttttagtcc taaattaa                108

<210> SEQ ID NO 147
<211> LENGTH: 101
<212> TYPE: DNA
<213> ORGANISM: Glycine max

<400> SEQUENCE: 147
ggaatttaca gcacaagtag atcacttgta cttatcaaaa ttcggaactg acacacgatg    60
atggaacgtg actaaggtgg gttttgact ttgcatgtcg a                        101

<210> SEQ ID NO 148
<211> LENGTH: 101
<212> TYPE: DNA
<213> ORGANISM: Glycine max

<400> SEQUENCE: 148
ggaatttaca gcacaagtag atcacttgta cttatcaaaa ttcggaactg acacacgatg    60
gaacgtgact aaggtgggtt tttgactttg catgtcgaag t                       101

<210> SEQ ID NO 149
<211> LENGTH: 101
<212> TYPE: DNA
<213> ORGANISM: Glycine max

<400> SEQUENCE: 149
ggaatttaca gcacaagtag atcacttgta cttatcaaaa ttcggaactg acacacgact    60
gatggaacgt gactaaggtg ggttttgac tttgcatgtc g                        101

<210> SEQ ID NO 150
<211> LENGTH: 101
<212> TYPE: DNA
<213> ORGANISM: Glycine max

<400> SEQUENCE: 150
ggaatttaca gcacaagtag atcacttgta cttatcaaaa ttcggaactg acacacatgg    60
aacgtgacta aggtgggttt ttgactttgc atgtcgaagt g                       101

<210> SEQ ID NO 151
<211> LENGTH: 101
<212> TYPE: DNA
<213> ORGANISM: Glycine max

<400> SEQUENCE: 151
ggaatttaca gcacaagtag atcacttgta cttatcaaaa ttcggaactg acacatgatg    60
gaacgtgact aaggtgggtt tttgactttg catgtcgaag t                       101

<210> SEQ ID NO 152
<211> LENGTH: 101
<212> TYPE: DNA
<213> ORGANISM: Glycine max

<400> SEQUENCE: 152
ggaatttaca gcacaagtag atcacttgta cttatcaaaa ttcggaactg acacagacat    60
gatggaacgt gactaaggtg ggttttgac tttgcatgtc g                        101

<210> SEQ ID NO 153
<211> LENGTH: 101
<212> TYPE: DNA
<213> ORGANISM: Glycine max

<400> SEQUENCE: 153
ggaatttaca gcacaagtag atcacttgta cttatcaaaa ttcggaactg acacgacatg    60
atggaacgtg actaaggtgg gttttgact tgcatgtcg a                         101

<210> SEQ ID NO 154
<211> LENGTH: 101
<212> TYPE: DNA
<213> ORGANISM: Glycine max

<400> SEQUENCE: 154
ggaatttaca gcacaagtag atcacttgta cttatcaaaa ttcggaactg acacaagaaa    60
tgatggaacg tgactaaggt gggttttga ctttgcatgt c                        101

<210> SEQ ID NO 155
<211> LENGTH: 101
<212> TYPE: DNA
<213> ORGANISM: Glycine max

<400> SEQUENCE: 155
ggaatttaca gcacaagtag atcacttgta cttatcaaaa ttcggaactg acacacgatt    60
gaacgtgact aaggtgggtt tttgactttg catgtcgaag t                       101

<210> SEQ ID NO 156
<211> LENGTH: 101
<212> TYPE: DNA
<213> ORGANISM: Glycine max

<400> SEQUENCE: 156
ggaatttaca gcacaagtag atcacttgta cttatcaaaa ttcggaactg acacacattg    60
aacgtgacta aggtgggttt ttgactttgc atgtcgaagt g                       101

<210> SEQ ID NO 157
<211> LENGTH: 101
<212> TYPE: DNA
<213> ORGANISM: Glycine max

<400> SEQUENCE: 157
ttcctttaca gcacaagtag atcacttgta cttatcaaaa ttcggaactg acacacgaca    60
tgatggaacg tctaaggtgg gttttttgact ttgcatgtcg a                        101

<210> SEQ ID NO 158
<211> LENGTH: 101
<212> TYPE: DNA
<213> ORGANISM: Glycine max

<400> SEQUENCE: 158
ttcctttaca gcacaagtag atcacttgta cttatcaaaa ttcggaactg acacacgaca    60
tgatggaacc taaggtgggt ttttgacttt gcatgtcgaa g                         101

<210> SEQ ID NO 159
<211> LENGTH: 101
<212> TYPE: DNA
<213> ORGANISM: Glycine max

<400> SEQUENCE: 159
ttcctttaca gcacaagtag atcacttgta cttatcaaaa ttcggaactg acacacgaca    60
tgatggaacg tgactaggtg ggttttttgac tttgcatgtc g                        101

<210> SEQ ID NO 160
<211> LENGTH: 101
<212> TYPE: DNA
<213> ORGANISM: Glycine max

<400> SEQUENCE: 160
ttcctttaca gcacaagtag atcacttgta cttatcaaaa ttcggaactg acacacgaca    60
tgatggaact aaggtgggtt tttgactttg catgtcgaag t                         101

<210> SEQ ID NO 161
<211> LENGTH: 101
<212> TYPE: DNA
<213> ORGANISM: Glycine max

<400> SEQUENCE: 161
ttcctttaca gcacaagtag atcacttgta cttatcaaaa ttcggaactg acacacgaca    60
tgatggaacg aaggtgggtt tttgactttg catgtcgaag t                         101

<210> SEQ ID NO 162
<211> LENGTH: 101
<212> TYPE: DNA
<213> ORGANISM: Glycine max

<400> SEQUENCE: 162
ttcctttaca gcacaagtag atcacttgta cttatcaaaa ttcggaactg acacacgaca    60
tgatggaagg tgggtttttg actttgcatg tcgaagtgag a                         101

<210> SEQ ID NO 163
<211> LENGTH: 101
<212> TYPE: DNA
<213> ORGANISM: Glycine max

<400> SEQUENCE: 163
ttcctttaca gcacaagtag atcacttgta cttatcaaaa ttcggaactg acacacgaca    60
tgatggacgt gactaaggtg ggttttttgac tttgcatgtc g                        101

<210> SEQ ID NO 164
<211> LENGTH: 101
<212> TYPE: DNA
<213> ORGANISM: Glycine max

<400> SEQUENCE: 164
ttcctttaca gcacaagtag atcacttgta cttatcaaaa ttcggaactg acacacgaca    60
tgatggaact ttactaaggt gggttttga ctttgcatgt c    101

<210> SEQ ID NO 165
<211> LENGTH: 101
<212> TYPE: DNA
<213> ORGANISM: Glycine max

<400> SEQUENCE: 165
ttcctttaca gcacaagtag atcacttgta cttatcaaaa ttcggaactg acacacgaca    60
tgatggaacg tgacaaggtg ggttttgac tttgcatgtc g    101

<210> SEQ ID NO 166
<211> LENGTH: 101
<212> TYPE: DNA
<213> ORGANISM: Glycine max

<400> SEQUENCE: 166
ttcctttaca gcacaagtag atcacttgta cttatcaaaa ttcggaactg acacactaca    60
ttatttaact ttactaaggt gggttttga ctttgcatgt c    101

<210> SEQ ID NO 167
<211> LENGTH: 108
<212> TYPE: DNA
<213> ORGANISM: Glycine max

<400> SEQUENCE: 167
agctgtaaat acagccttac aactcacaag tcccttgtac ttgtacgtac ggagggtatt    60
ctagaaaaga ggaattggag tctgcctctt cttttagtcc taaattaa    108

<210> SEQ ID NO 168
<211> LENGTH: 101
<212> TYPE: DNA
<213> ORGANISM: Glycine max

<400> SEQUENCE: 168
agctgtaaat acagccttac aactcacaag tcccttgtac ggagggtatt ctagaaaaga    60
ggaattggag tctgcctctt cttttagtcc taaattaaag a    101

<210> SEQ ID NO 169
<211> LENGTH: 101
<212> TYPE: DNA
<213> ORGANISM: Glycine max

<400> SEQUENCE: 169
agctgtaaat acagccttac aactcacaag tcccttgtac ttgtacggag ggtattctag    60
aaaagaggaa ttggagtctg cctcttcttt tagtcctaaa t    101

<210> SEQ ID NO 170
<211> LENGTH: 101
<212> TYPE: DNA
<213> ORGANISM: Glycine max

<400> SEQUENCE: 170

```
agctgtaaat acagccttac aactcacaag tcccttacgg agggtattct agaaaagagg    60
aattggagtc tgcctcttct tttagtccta aattaaagat c                      101

<210> SEQ ID NO 171
<211> LENGTH: 101
<212> TYPE: DNA
<213> ORGANISM: Glycine max

<400> SEQUENCE: 171
agctgtaaat acagccttac aactcacaag tcccttgtac ttgtaccgta cggagggtat    60
tctagaaaag aggaattgga gtctgcctct tcttttagtc c                      101

<210> SEQ ID NO 172
<211> LENGTH: 101
<212> TYPE: DNA
<213> ORGANISM: Glycine max

<400> SEQUENCE: 172
agctgtaaat acagccttac aactcacaag tcccttgtac tgtacggagg gtattctaga    60
aaagaggaat tggagtctgc ctcttctttt agtcctaaat t                      101

<210> SEQ ID NO 173
<211> LENGTH: 101
<212> TYPE: DNA
<213> ORGANISM: Glycine max

<400> SEQUENCE: 173
agctgtaaat acagccttac aactcacaag tcccttgtag tacggagggt attctagaaa    60
agaggaattg gagtctgcct cttcttttag tcctaaatta a                      101

<210> SEQ ID NO 174
<211> LENGTH: 101
<212> TYPE: DNA
<213> ORGANISM: Glycine max

<400> SEQUENCE: 174
agctgtaaat acagccttac aactcacaag tcccttgtac ttgtacgtag ggtattctag    60
aaaagaggaa ttggagtctg cctcttcttt tagtcctaaa t                      101

<210> SEQ ID NO 175
<211> LENGTH: 100
<212> TYPE: DNA
<213> ORGANISM: Glycine max

<400> SEQUENCE: 175
agctgtaaat acagccttac aactcacaag tcctacactc tttccctaca cgacgctctt    60
cttttagtcc taaattaaag atcggaagat ctcgtatgcc                        100

<210> SEQ ID NO 176
<211> LENGTH: 101
<212> TYPE: DNA
<213> ORGANISM: Glycine max

<400> SEQUENCE: 176
agctgtaaat acagccttac aactcacaag tcccttgtac ttgtacctta cggagggtat    60
tctagaaaag aggaattgga gtctgcctct tcttttagtc c                      101

<210> SEQ ID NO 177
<211> LENGTH: 101
```

```
<212> TYPE: DNA
<213> ORGANISM: Glycine max

<400> SEQUENCE: 177
ctaggtaaat acagccttac aactcacaag tcccttgtac ttgtacgtac ggagggtatt        60
ctagaaaatt ggagtctgcc tcttcttta gtcctaaatt a                            101

<210> SEQ ID NO 178
<211> LENGTH: 101
<212> TYPE: DNA
<213> ORGANISM: Glycine max

<400> SEQUENCE: 178
ctaggtaaat acagccttac aactcacaag tcccttgtac ttgtacgtac ggagggtatt        60
ctagaaaaga attggagtct gcctcttctt ttagtcctaa a                           101

<210> SEQ ID NO 179
<211> LENGTH: 101
<212> TYPE: DNA
<213> ORGANISM: Glycine max

<400> SEQUENCE: 179
ctaggtaaat acagccttac aactcacaag tcccttgtac ttgtacgtac ggagggtatt        60
ctagaattgg agtctgcctc ttcttttagt cctaaattaa a                           101

<210> SEQ ID NO 180
<211> LENGTH: 101
<212> TYPE: DNA
<213> ORGANISM: Glycine max

<400> SEQUENCE: 180
ctaggtaaat acagccttac aactcacaag tcccttgtac ttgtacgtac ggagggtatt        60
ctagaaaaga aattggagtc tgcctcttct tttagtccta a                           101

<210> SEQ ID NO 181
<211> LENGTH: 101
<212> TYPE: DNA
<213> ORGANISM: Glycine max

<400> SEQUENCE: 181
ctaggtaaat acagccttac aactcacaag tcccttgtac ttgtacgtac ggagggtatt        60
ctagaaaaat tggagtctgc ctcttctttt agtcctaaat t                           101

<210> SEQ ID NO 182
<211> LENGTH: 101
<212> TYPE: DNA
<213> ORGANISM: Glycine max

<400> SEQUENCE: 182
ctaggtaaat acagccttac aactcacaag tcccttgtac ttgtacgtac ggagggtatt        60
ctagaaaaga ggattggagt ctgcctcttc ttttagtcct a                           101

<210> SEQ ID NO 183
<211> LENGTH: 101
<212> TYPE: DNA
<213> ORGANISM: Glycine max

<400> SEQUENCE: 183
ctaggtaaat acagccttac aactcacaag tcccttgtac ttgtacgtac ggagggtatt        60
```
ctagaaattg gagtctgcct cttcttttag tcctaaatta a                               101

<210> SEQ ID NO 184
<211> LENGTH: 101
<212> TYPE: DNA
<213> ORGANISM: Glycine max

<400> SEQUENCE: 184
ctaggtaaat acagccttac aactcacaag tcccttgtac ttgtacgtac ggagggtatt          60
ctattggagt ctgcctcttc ttttagtcct aaattaaaga t                             101

<210> SEQ ID NO 185
<211> LENGTH: 101
<212> TYPE: DNA
<213> ORGANISM: Glycine max

<400> SEQUENCE: 185
ctaggtaaat acagccttac aactcacaag tcccttgtac ttgtacgtac ggagggtatt          60
ctagtctgcc tcttctttta gtcctaaatt aaagatcgga a                             101

<210> SEQ ID NO 186
<211> LENGTH: 101
<212> TYPE: DNA
<213> ORGANISM: Glycine max

<400> SEQUENCE: 186
ctaggtaaat acagccttac aactcacaag tcccttgtac ttgtacgtac ggagggtatt          60
ctagaaaagt ctgcctcttc ttttagtcct aaattaaaga t                             101

<210> SEQ ID NO 187
<211> LENGTH: 101
<212> TYPE: DNA
<213> ORGANISM: Glycine max

<400> SEQUENCE: 187
ctaggtaaat acagccttac aactcacaag tcccttgtac ttgtacgtac ggagggtatt          60
ctagaaaaga gaattggagt ctgcctcttc ttttagtcct a                             101

<210> SEQ ID NO 188
<211> LENGTH: 101
<212> TYPE: DNA
<213> ORGANISM: Glycine max

<400> SEQUENCE: 188
ctaggtaaat acagccttac aactcacaag tcccttgtac ttgtacgtac ggagggtatt          60
ctagaaaaga ggagtctgcc tcttctttta gtcctaaatt a                             101

<210> SEQ ID NO 189
<211> LENGTH: 101
<212> TYPE: DNA
<213> ORGANISM: Glycine max

<400> SEQUENCE: 189
ctaggtaaat acagccttac aactcacaag tcccttgtac ttgtacgtac ggagggtatt          60
ctaattggag tctgcctctt cttttagtcc taaattaaag a                             101

<210> SEQ ID NO 190
<211> LENGTH: 101
<212> TYPE: DNA
<213> ORGANISM: Glycine max

<400> SEQUENCE: 190
ctaggtaaat acagccttac aactcacaag tcccttgtac ttgtacgtac ggagggtatt    60
ctagaaaaga ggaaattgga gtctgcctct tcttttagtc c                      101

<210> SEQ ID NO 191
<211> LENGTH: 101
<212> TYPE: DNA
<213> ORGANISM: Glycine max

<400> SEQUENCE: 191
ctaggtaaat acagccttac aactcacaag tcccttgtac ttgtacgtac ggagggtatt    60
ctagaaagag gaattggagt ctgcctcttc ttttagtcct a                      101

<210> SEQ ID NO 192
<211> LENGTH: 1377
<212> TYPE: PRT
<213> ORGANISM: Artificial sequence
<220> FEATURE:
<223> OTHER INFORMATION: synthesized sequence- maize optimized moCAS9
      endonuclease

<400> SEQUENCE: 192

Met Ala Pro Lys Lys Arg Lys Val Met Asp Lys Lys Tyr Ser Ile
1               5                   10                  15

Gly Leu Asp Ile Gly Thr Asn Ser Val Gly Trp Ala Val Ile Thr Asp
                20                  25                  30

Glu Tyr Lys Val Pro Ser Lys Lys Phe Lys Val Leu Gly Asn Thr Asp
            35                  40                  45

Arg His Ser Ile Lys Lys Asn Leu Ile Gly Ala Leu Leu Phe Asp Ser
        50                  55                  60

Gly Glu Thr Ala Glu Ala Thr Arg Leu Lys Arg Thr Ala Arg Arg Arg
65                  70                  75                  80

Tyr Thr Arg Arg Lys Asn Arg Ile Cys Tyr Leu Gln Glu Ile Phe Ser
                85                  90                  95

Asn Glu Met Ala Lys Val Asp Asp Ser Phe Phe His Arg Leu Glu Glu
            100                 105                 110

Ser Phe Leu Val Glu Glu Asp Lys Lys His Glu Arg His Pro Ile Phe
        115                 120                 125

Gly Asn Ile Val Asp Glu Val Ala Tyr His Glu Lys Tyr Pro Thr Ile
    130                 135                 140

Tyr His Leu Arg Lys Lys Leu Val Asp Ser Thr Asp Lys Ala Asp Leu
145                 150                 155                 160

Arg Leu Ile Tyr Leu Ala Leu Ala His Met Ile Lys Phe Arg Gly His
                165                 170                 175

Phe Leu Ile Glu Gly Asp Leu Asn Pro Asp Asn Ser Asp Val Asp Lys
            180                 185                 190

Leu Phe Ile Gln Leu Val Gln Thr Tyr Asn Gln Leu Phe Glu Glu Asn
        195                 200                 205

Pro Ile Asn Ala Ser Gly Val Asp Ala Lys Ala Ile Leu Ser Ala Arg
    210                 215                 220

Leu Ser Lys Ser Arg Arg Leu Glu Asn Leu Ile Ala Gln Leu Pro Gly
225                 230                 235                 240

Glu Lys Lys Asn Gly Leu Phe Gly Asn Leu Ile Ala Leu Ser Leu Gly
                245                 250                 255

Leu Thr Pro Asn Phe Lys Ser Asn Phe Asp Leu Ala Glu Asp Ala Lys

```
            260                 265                 270
Leu Gln Leu Ser Lys Asp Thr Tyr Asp Asp Leu Asp Asn Leu Leu
        275                 280                 285

Ala Gln Ile Gly Asp Gln Tyr Ala Asp Leu Phe Leu Ala Ala Lys Asn
    290                 295                 300

Leu Ser Asp Ala Ile Leu Leu Ser Asp Ile Leu Arg Val Asn Thr Glu
305                 310                 315                 320

Ile Thr Lys Ala Pro Leu Ser Ala Ser Met Ile Lys Arg Tyr Asp Glu
                325                 330                 335

His His Gln Asp Leu Thr Leu Leu Lys Ala Leu Val Arg Gln Gln Leu
            340                 345                 350

Pro Glu Lys Tyr Lys Glu Ile Phe Phe Asp Gln Ser Lys Asn Gly Tyr
        355                 360                 365

Ala Gly Tyr Ile Asp Gly Gly Ala Ser Gln Glu Glu Phe Tyr Lys Phe
    370                 375                 380

Ile Lys Pro Ile Leu Glu Lys Met Asp Gly Thr Glu Glu Leu Leu Val
385                 390                 395                 400

Lys Leu Asn Arg Glu Asp Leu Leu Arg Lys Gln Arg Thr Phe Asp Asn
                405                 410                 415

Gly Ser Ile Pro His Gln Ile His Leu Gly Glu Leu His Ala Ile Leu
            420                 425                 430

Arg Arg Gln Glu Asp Phe Tyr Pro Phe Leu Lys Asp Asn Arg Glu Lys
        435                 440                 445

Ile Glu Lys Ile Leu Thr Phe Arg Ile Pro Tyr Tyr Val Gly Pro Leu
    450                 455                 460

Ala Arg Gly Asn Ser Arg Phe Ala Trp Met Thr Arg Lys Ser Glu Glu
465                 470                 475                 480

Thr Ile Thr Pro Trp Asn Phe Glu Glu Val Val Asp Lys Gly Ala Ser
                485                 490                 495

Ala Gln Ser Phe Ile Glu Arg Met Thr Asn Phe Asp Lys Asn Leu Pro
            500                 505                 510

Asn Glu Lys Val Leu Pro Lys His Ser Leu Leu Tyr Glu Tyr Phe Thr
        515                 520                 525

Val Tyr Asn Glu Leu Thr Lys Val Lys Tyr Val Thr Glu Gly Met Arg
    530                 535                 540

Lys Pro Ala Phe Leu Ser Gly Glu Gln Lys Lys Ala Ile Val Asp Leu
545                 550                 555                 560

Leu Phe Lys Thr Asn Arg Lys Val Thr Val Lys Gln Leu Lys Glu Asp
                565                 570                 575

Tyr Phe Lys Lys Ile Glu Cys Phe Asp Ser Val Glu Ile Ser Gly Val
            580                 585                 590

Glu Asp Arg Phe Asn Ala Ser Leu Gly Thr Tyr His Asp Leu Leu Lys
        595                 600                 605

Ile Ile Lys Asp Lys Asp Phe Leu Asp Asn Glu Glu Asn Glu Asp Ile
    610                 615                 620

Leu Glu Asp Ile Val Leu Thr Leu Thr Leu Phe Glu Asp Arg Glu Met
625                 630                 635                 640

Ile Glu Glu Arg Leu Lys Thr Tyr Ala His Leu Phe Asp Asp Lys Val
                645                 650                 655

Met Lys Gln Leu Lys Arg Arg Arg Tyr Thr Gly Trp Gly Arg Leu Ser
            660                 665                 670

Arg Lys Leu Ile Asn Gly Ile Arg Asp Lys Gln Ser Gly Lys Thr Ile
        675                 680                 685
```

Leu Asp Phe Leu Lys Ser Asp Gly Phe Ala Asn Arg Asn Phe Met Gln
690                 695                 700

Leu Ile His Asp Asp Ser Leu Thr Phe Lys Glu Asp Ile Gln Lys Ala
705                 710                 715                 720

Gln Val Ser Gly Gln Gly Asp Ser Leu His Glu His Ile Ala Asn Leu
            725                 730                 735

Ala Gly Ser Pro Ala Ile Lys Lys Gly Ile Leu Gln Thr Val Lys Val
            740                 745                 750

Val Asp Glu Leu Val Lys Val Met Gly Arg His Lys Pro Glu Asn Ile
            755                 760                 765

Val Ile Glu Met Ala Arg Glu Asn Gln Thr Thr Gln Lys Gly Gln Lys
770                 775                 780

Asn Ser Arg Glu Arg Met Lys Arg Ile Glu Glu Gly Ile Lys Glu Leu
785                 790                 795                 800

Gly Ser Gln Ile Leu Lys Glu His Pro Val Glu Asn Thr Gln Leu Gln
            805                 810                 815

Asn Glu Lys Leu Tyr Leu Tyr Tyr Leu Gln Asn Gly Arg Asp Met Tyr
            820                 825                 830

Val Asp Gln Glu Leu Asp Ile Asn Arg Leu Ser Asp Tyr Asp Val Asp
            835                 840                 845

His Ile Val Pro Gln Ser Phe Leu Lys Asp Asp Ser Ile Asp Asn Lys
850                 855                 860

Val Leu Thr Arg Ser Asp Lys Asn Arg Gly Lys Ser Asp Asn Val Pro
865                 870                 875                 880

Ser Glu Glu Val Val Lys Lys Met Lys Asn Tyr Trp Arg Gln Leu Leu
            885                 890                 895

Asn Ala Lys Leu Ile Thr Gln Arg Lys Phe Asp Asn Leu Thr Lys Ala
            900                 905                 910

Glu Arg Gly Gly Leu Ser Glu Leu Asp Lys Ala Gly Phe Ile Lys Arg
            915                 920                 925

Gln Leu Val Glu Thr Arg Gln Ile Thr Lys His Val Ala Gln Ile Leu
930                 935                 940

Asp Ser Arg Met Asn Thr Lys Tyr Asp Glu Asn Asp Lys Leu Ile Arg
945                 950                 955                 960

Glu Val Lys Val Ile Thr Leu Lys Ser Lys Leu Val Ser Asp Phe Arg
            965                 970                 975

Lys Asp Phe Gln Phe Tyr Lys Val Arg Glu Ile Asn Asn Tyr His His
            980                 985                 990

Ala His Asp Ala Tyr Leu Asn Ala Val Val Gly Thr Ala Leu Ile Lys
            995                 1000                1005

Lys Tyr Pro Lys Leu Glu Ser Glu Phe Val Tyr Gly Asp Tyr Lys
    1010                1015                1020

Val Tyr Asp Val Arg Lys Met Ile Ala Lys Ser Glu Gln Glu Ile
    1025                1030                1035

Gly Lys Ala Thr Ala Lys Tyr Phe Phe Tyr Ser Asn Ile Met Asn
    1040                1045                1050

Phe Phe Lys Thr Glu Ile Thr Leu Ala Asn Gly Glu Ile Arg Lys
    1055                1060                1065

Arg Pro Leu Ile Glu Thr Asn Gly Glu Thr Gly Glu Ile Val Trp
    1070                1075                1080

Asp Lys Gly Arg Asp Phe Ala Thr Val Arg Lys Val Leu Ser Met
    1085                1090                1095

```
Pro Gln Val Asn Ile Val Lys Lys Thr Glu Val Gln Thr Gly Gly
    1100                1105                1110

Phe Ser Lys Glu Ser Ile Leu Pro Lys Arg Asn Ser Asp Lys Leu
    1115                1120                1125

Ile Ala Arg Lys Lys Asp Trp Asp Pro Lys Lys Tyr Gly Gly Phe
    1130                1135                1140

Asp Ser Pro Thr Val Ala Tyr Ser Val Leu Val Val Ala Lys Val
    1145                1150                1155

Glu Lys Gly Lys Ser Lys Lys Leu Lys Ser Val Lys Glu Leu Leu
    1160                1165                1170

Gly Ile Thr Ile Met Glu Arg Ser Ser Phe Glu Lys Asn Pro Ile
    1175                1180                1185

Asp Phe Leu Glu Ala Lys Gly Tyr Lys Glu Val Lys Lys Asp Leu
    1190                1195                1200

Ile Ile Lys Leu Pro Lys Tyr Ser Leu Phe Glu Leu Glu Asn Gly
    1205                1210                1215

Arg Lys Arg Met Leu Ala Ser Ala Gly Glu Leu Gln Lys Gly Asn
    1220                1225                1230

Glu Leu Ala Leu Pro Ser Lys Tyr Val Asn Phe Leu Tyr Leu Ala
    1235                1240                1245

Ser His Tyr Glu Lys Leu Lys Gly Ser Pro Glu Asp Asn Glu Gln
    1250                1255                1260

Lys Gln Leu Phe Val Glu Gln His Lys His Tyr Leu Asp Glu Ile
    1265                1270                1275

Ile Glu Gln Ile Ser Glu Phe Ser Lys Arg Val Ile Leu Ala Asp
    1280                1285                1290

Ala Asn Leu Asp Lys Val Leu Ser Ala Tyr Asn Lys His Arg Asp
    1295                1300                1305

Lys Pro Ile Arg Glu Gln Ala Glu Asn Ile Ile His Leu Phe Thr
    1310                1315                1320

Leu Thr Asn Leu Gly Ala Pro Ala Ala Phe Lys Tyr Phe Asp Thr
    1325                1330                1335

Thr Ile Asp Arg Lys Arg Tyr Thr Ser Thr Lys Glu Val Leu Asp
    1340                1345                1350

Ala Thr Leu Ile His Gln Ser Ile Thr Gly Leu Tyr Glu Thr Arg
    1355                1360                1365

Ile Asp Leu Ser Gln Leu Gly Gly Asp
    1370                1375

<210> SEQ ID NO 193
<211> LENGTH: 6677
<212> TYPE: DNA
<213> ORGANISM: Artificial sequence
<220> FEATURE:
<223> OTHER INFORMATION: synthesized sequence- maize optimized moCAS9
      endonuclease

<400> SEQUENCE: 193
ctgcagtgca gcgtgacccg gtcgtgcccc tctctagaga taatgagcat tgcatgtcta     60
agttataaaa aattaccaca tatttttttt gtcacacttg tttgaagtgc agtttatcta    120
tctttataca tatatttaaa ctttactcta cgaataatat aatctatagt actacaataa    180
tatcagtgtt ttagagaatc atataaatga acagttagac atggtctaaa ggacaattga    240 gtatttgac aacaggactc tacagttta tcttttagt gtgcatgtgt tctccttttt    300
ttttgcaaat agcttcacct atataatact tcatccattt tattagtaca tccatttagg    360
```

```
gtttagggtt aatggttttt atagactaat ttttttagta catctatttt attctatttt      420
agcctctaaa ttaagaaaac taaaactcta ttttagtttt tttatttaat aatttagata      480
taaaatagaa taaaataaag tgactaaaaa ttaaacaaat accctttaag aaattaaaaa      540
aactaaggaa acattttttct tgtttcgagt agataatgcc agcctgttaa acgccgtcga     600
cgagtctaac ggacaccaac cagcgaacca gcagcgtcgc gtcgggccaa gcgaagcaga      660
cggcacggca tctctgtcgc tgcctctgga cccctctcga gagttccgct ccaccgttgg      720
acttgctccg ctgtcggcat ccagaaattg cgtggcggag cggcagacgt gagccggcac      780
ggcaggcggc ctcctcctcc tctcacggca cggcagctac gggggattcc tttcccaccg     840
ctccttcgct ttcccttcct cgcccgccgt aataaataga caccccctcc acaccctctt      900
tccccaacct cgtgttgttc ggagcgcaca cacacacaac cagatctccc ccaaatccac      960
ccgtcggcac ctccgcttca aggtacgccg ctcgtcctcc ccccccccc tctctacctt      1020 ctctagatcg gcgttccggt ccatgcatgg ttagggcccg gtagttctac ttctgttcat      1080
gtttgtgtta gatccgtgtt tgtgttagat ccgtgctgct agcgttcgta cacggatgcg     1140
acctgtacgt cagacacgtt ctgattgcta acttgccagt gtttctcttt ggggaatcct     1200
gggatggctc tagccgttcc gcagacggga tcgatttcat gattttttt gtttcgttgc      1260 atagggtttg gtttgcccttt tcctttatt tcaatatatg ccgtgcactt gtttgtcggg    1320
tcatcttttc atgcttttt ttgtcttggt tgtgatgatg tggtctggtt gggcggtcgt      1380
tctagatcgg agtagaattc tgtttcaaac tacctggtgg atttattaat tttggatctg     1440
tatgtgtgtg ccatacatat tcatagttac gaattgaaga tgatggatgg aaatatcgat     1500
ctaggatagg tatacatgtt gatgcgggtt ttactgatgc atatacagag atgcttttttg    1560 ttcgcttggt tgtgatgatg tggtgtggtt gggcggtcgt tcattcgttc tagatcggag     1620
tagaatactg tttcaaacta cctggtgtat ttattaattt tggaactgta tgtgtgtgtc     1680
atacatcttc atagttacga gtttaagatg gatggaaata tcgatctagg ataggtatac     1740
atgttgatgt gggttttact gatgcatata catgatggca tatgcagcat ctattcatat     1800
gctctaacct tgagtaccta tctattataa taaacaagta tgttttataa ttattttgat     1860
cttgatatac ttggatgatg gcatatgcag cagctatatg tggatttttt tagccctgcc     1920
ttcatacgct atttatttgc ttggtactgt ttcttttgtc gatgctcacc ctgttgtttg     1980
gtgttacttc tgcaggtcga ctctagagga tccccatggc cccgaagaag aagaggaagg     2040
tgcacatgga taagaagtac agcatcggcc tcgacatcgg gaccaacagc gtcggctggg     2100
ccgtcatcac cgacgaatat aaggtgccca gcaagaagtt caaggtgctc gggaatacag     2160
accgccacag catcaagaag aacctgatcg gcgccctcct gttcgactcg ggcgagaccg     2220
ctgaggccac cagactaaag aggaccgctc gccgccgcta cacccgccgc aagaaccgca     2280
tatgctacct ccaggagatc ttcagcaacg agatggccaa ggtggacgac agcttcttcc     2340
accgccttga ggagtcgttc ctcgtggagg aggacaagaa gcatgagagg caccccgatct    2400 tcgggaacat cgtggacgag gtaagttttct gcttctacct ttgatatata tataataatt    2460
atcattaatt agtagtaata taatatttca aatattttt tcaaaataaa agaatgtagt      2520
atatagcaat tgctttttctg tagtttataa gtgtgtatat tttaatttat aacttttcta    2580
atatatgacc aaaacatggt gatgtgcagg tggcgtacca cgagaagtac ccgacgatct     2640
accacctccg caagaagctg gtcgactcca cagacaaggc cgacctcaga ctgatctacc     2700
```

```
tggccctcgc gcacatgatc aagttccgcg ggcacttcct catcgagggc gacctgaacc    2760
cggacaactc cgacgtcgac aagctcttca tccagctggt ccagacctac aatcaactgt    2820
tcgaggagaa cccgatcaac gcgtccggcg tggacgcgaa ggccatcctc agcgcgaggc    2880
tcagcaaatc aagacggctg gagaacctga tcgcccagct cccaggcgag aagaaaaacg    2940
gcttgttcgg caacctgatc gcgctctcgc tcggcctcac gcccaacttc aaatcaaact    3000
tcgacctggc cgaggacgcg aaactgcagc tgtccaagga cacttacgac gacgacctcg    3060
acaacctgct ggcgcaaatc ggtgaccagt acgcagacct cttcctggcc gccaagaacc    3120
tctcggacgc catcctgctg tccgatatcc tgagagtgaa tacggagatc accaaggcgc    3180
cgctcagcgc ctccatgatt aaaaggtacg acgagcacca ccaggacctg acgctgctca    3240
aggccctggt gcgccagcag ctcccccgaga agtacaagga gatcttcttc gaccaatcaa    3300
aaaacggcta cgccggctac atcgacgggg gcgcctccca ggaggagttc tacaagttca    3360
tcaaaccaat tctcgagaag atggacggca cggaggagct tctcgtgaag ctcaaccggg    3420
aggacctcct gaggaagcag aggacgttcg acaacggctc gataccgcat cagatccacc    3480
tgggcgagct ccacgccatc ctgcgccggc aggaggattt ctatccgttc ctcaaggaca    3540
acagggagaa gatcgagaaa attctgacgt tccgcatccc gtactacgtg ggccctctcg    3600
cgcgcgggaa cagccggttc gcctggatga ctcggaagtc ggaggagacg atcacgccgt    3660
ggaacttcga ggaggtggtg acaagggcg cctccgccca gtcgttcatc gagcgcatga    3720
cgaacttcga taaaaatctg cccaatgaaa aagtgctccc gaagcacagc ctcctctacg    3780
agtacttcac ggtgtacaac gagctcacga aggtgaagta cgtgaccgag ggtatgcgga    3840
agccggcgtt cctgagcggc gagcagaaga aggccatcgt ggacctcctc ttcaagacga    3900
accggaaagt caccgtgaag caattaaagg aggactactt caagaaaata gagtgcttcg    3960
acagcgtcga gatctcgggc gtcgaggaca ggttcaacgc gtcgctgggc acataccacg    4020
acctcctcaa gatcattaaa gacaaggact tcctggacaa cgaggagaac gaggacatcc    4080
tcgaggacat cgtgctgacc ctcaccctgt ttgaggaccg ggagatgatc gaggagcgcc    4140
tcaagacgta cgctcacctt ttcgacgaca aggtgatgaa acagctgaag cggcgccgct    4200
acaccggatg gggccggctc tcccgcaagc tcattaatgg gatcagggac aagcagtccg    4260
gcaagaccat actcgatttc ctgaagagcg acggcttcgc caaccggaac ttcatgcagc    4320
tcatccacga cgactccctc actttcaagg aggacatcca gaaggcccag gtcagcggac    4380
agggcgactc gctccacgaa cacatcgcca acctggccgg gtcgcctgcg attaaaaagg    4440
gaatccttca gaccgtcaag gtcgtggacg agctggtgaa ggtgatgggc aggcacaagc    4500
ccgaaaatat cgtcattgag atggcccggg agaaccagac cacgcagaaa ggccagaaga    4560
acagccggga gcgcatgaaa cggatcgagg agggtatcaa ggagctgggc tcgcagatcc    4620
tcaaggagca ccctgtggaa atacccagc tgcagaatga aaagctctac ctctactacc    4680
tccagaacgg ccgcgacatg tacgtggacc aggagctgga cattaatcgc ctctcggact    4740
acgacgtcga ccacatcgtc ccgcagtcct tcctgaagga cgacagcatc gacaacaagg    4800
tcttgacccg ctccgataaa aatcgcggga agtccgacaa cgtgccgtcg gaggaggtgg    4860
tcaagaagat gaaaaactac tggcgccagc tgctcaacgc caagctaatc acgcagcgca    4920
agttcgacaa cctcaccaag gccgaacgcg gcggtctctc cgagcttgat aaggctgggt    4980
tcatcaagag acagctggtg gagacccggc agatcaccaa gcatgtcgcc cagatcctgg    5040
actcgcgcat gaatactaag tacgatgaaa acgacaagct catccgcgag gtgaaggtga    5100
```

```
tcaccctgaa gagcaagctg gtctcggact tccggaagga cttccagttc tacaaggtcc      5160
gggagatcaa caactaccac cacgcgcacg acgcctacct gaacgcggtg gtgggcacag      5220
cccttataaa gaagtaccct aagctcgagt ccgagttcgt gtacggcgac tacaaggtgt      5280
acgacgtccg caagatgatc gcgaagagcg agcaggagat cgggaaggcc accgcaaaat      5340
acttcttcta ctccaacatc atgaacttct tcaagaccga gatcaccctg gccaacgggg      5400
agatccgcaa gcgcccgctg attgagacga acggagagac aggcgagata gtctgggaca      5460
agggcaggga cttcgccacc gtgcgcaagg ttctgtccat gccgcaggtg aacatcgtga      5520
agaagactga ggtgcagaca gcggcttct cgaaggagtc catcctgccc aagcggaaca      5580
gcgacaagct catcgcgcgg aagaaggact gggaccctaa aaatatggc gggttcgact       5640 cgcccaccgt ggcttactcg gtcctcgtgg tggccaaggt cgagaagggc aaaagcaaga      5700
agctgaagag cgtcaaggag ctcctcggca tcaccatcat ggagcggtcc agcttcgaga      5760
agaacccgat cgacttcctc gaggcgaagg gatataagga ggtgaagaag gacctcatca      5820
ttaaactgcc gaagtactcg ctattcgaac tggagaatgg tcgcaagagg atgctcgcga      5880
gcgctggcga gctgcagaaa gggaacgagc tggctctccc gagcaagtac gtcaacttcc      5940
tctacctggc ctcccactat gaaaagctca agggctcgcc ggaggacaac gagcagaagc      6000
agctgttcgt cgagcagcac aagcattacc tcgacgagat catcgagcag atctcggagt      6060
tcagcaagcg cgtgatcctg gccgacgcca acctcgacaa ggtgctgtcc gcatataaca      6120
agcaccgcga caaccaata cgggagcagg ccgaaaatat catccacctg ttcaccctca       6180
cgaacctggg cgcccccgcc gcgttcaagt acttcgacac aaccatcgac cgcaagcggt      6240
acacgagcac gaaggaggtg ctggacgcca cgttgattca ccagtccatc acgggcctgt      6300
atgaaacaag gatcgatctc agccagctcg gcggcgacta ggtaccacat ggttaaccta      6360
gacttgtcca tcttctggat tggccaactt aattaatgta tgaaataaaa ggatgcacac      6420
atagtgacat gctaatcact ataatgtggg catcaaagtt gtgtgttatg tgtaattact      6480
agttatctga ataaaagaga aagagatcat ccatatttct tatcctaaat gaatgtcacg      6540
tgtctttata attctttgat gaaccagatg catttcatta accaaatcca tatacatata      6600
aatattaatc atatataatt aatatcaatt gggttagcaa aacaaatcta gtctaggtgt      6660
gttttgcgaa ttgcggc                                                    6677
```

<210> SEQ ID NO 194
<211> LENGTH: 100
<212> TYPE: DNA
<213> ORGANISM: Artificial sequence
<220> FEATURE:
<223> OTHER INFORMATION: synthesized sequence- DNA version of guide RNA
      (EPSPS sgRNA)

<400> SEQUENCE: 194

```
gcagtaacag ctgctgtcaa gttttagagc tagaaatagc aagttaaaat aaggctagtc       60
cgttatcaac ttgaaaaagt ggcaccgagt cggtgctttt                            100
```

<210> SEQ ID NO 195
<211> LENGTH: 3708
<212> TYPE: DNA
<213> ORGANISM: Artificial sequence
<220> FEATURE:
<223> OTHER INFORMATION: synthesized sequence- EPSPS polynucleotide
      template

<400> SEQUENCE: 195

```
ctgcagccca tcaaggagat ctccggcacc gtcaagctgc cggggtccaa gtcgctttcc      60
aacaggatcc tcctgctcgc cgccctgtcc gaggtgagcg attttggtgc ttgctgcgct     120
gccctgtctc actgctacct aaatgttttg cctgtcgaat accatggatt ctcggtgtaa     180
tccatctcac gatcagatgc accgcatgtc gcatgcctag ctctctctaa tttgtctagt     240
agtttgtata cggattaaga ttgataaatc ggtaccgcaa aagctaggtg taaataaaca     300
ctacaaaatt ggatgttccc ctatcggcct gtactcggct actcgttctt gtgatggcat     360
gttatttctt cttggtgttt ggtgaactcc cttatgaaat ttgggcgcaa agaaatcgcc     420
ctcaagggtt gatcttatgc catcgtcatg ataaacagtg aagcacggat gatcctttac     480
gttgttttta acaaactttg tcagaaaact agcaatgtta acttcttaat gatgatttca     540
caacaaaaaa ggtaaccttg ctactaacat aacaaagac ttgttgctta ttaattatat      600
gttttttttaa tctttgatca ggggacaaca gtggttgata acctgttgaa cagtgaggat    660
gtccactaca tgctcggggc cttgaggact cttggtctct ctgtcgaagc ggacaaagct    720
gccaaaagag ctgtagttgt tggctgtggt ggaaagttcc cagttgagga tgctaaagag    780
gaagtgcagc tcttcttggg gaatgctgga atcgcaatgc ggtcattgac agcagctgtt    840
actgctgctg gtggaaatgc aacgtatgtt tcctctctct ctctacaata cttgttggag    900
ttagtatgaa acccatgtgt atgtctagtg gcttatggtg tattggtttt tgaacttcag    960
ttacgtgctt gatggagtac caagaatgag ggagagaccc attggcgact tggttgtcgg  1020
attgaagcag cttggtgcag atgttgattg tttccttggc actgactgcc cacctgttcg  1080
tgtcaatgga atcggagggc tacctggtgg caaggttagt tactaagggc cacatgttac  1140
attcttctgt aaatggtaca actattgtcg agcttttgca tttgtaagga aaacattgat  1200
tgatctgaat ttgatgctac accacaaaat atctacaaat ggtcatccct aactagcaaa  1260
ccatgtctcc attaagctca atgaagtaat acttggcatg tgtttatcaa cttaatttcc  1320
atcttctggg gtattgcctg ttttctagtc taatagcatt tgttttttaga attagctctt  1380
acaactgtta tgttctacag gtcaagctgt ctggctccat cagcagtcag tacttgagtg  1440
ccttgctgat ggctgctcct ttggctcttg gggatgtgga gattgaaatc attgataaat  1500
taatctccat tccctacgtc gaaatgacat tgagattgat ggagcgtttt ggtgtgaaag  1560
cagagcattc tgatagctgg gacagattct acattaaggg aggtcaaaaa tacaagtaag  1620
ctctgtaatg tatttcacta ctttgatgcc aatgtttcag ttttcagttt tccaaacagt  1680
cgcatcaata tttgaataga tgcactgtag aaaaaaatca ttgcagggaa aaactagtac  1740
tgagtatttt gactgtaaat tatttaacca gtcggaatat agtcagtcta ttggagtcaa  1800
gagcgtgaac cgaaatagcc agttaattat cccattatac agaggacaac catgtatact  1860
attgaaactt ggtttaagag aatctaggta gctggactcg tagctgcttg gcatggatac  1920
cttcttatct ttaggaaaag acacttgatt ttttttctgt ggccctctat gatgtgtgaa  1980
cctgcttctc tattgctttta gaaggatata tctatgtcgt tatgcaacat gcttcccttta  2040
gtcatttgta ctgaaatcag tttcataagt tcgttagtgg ttccctaaac gaaaccttgt  2100
ttttctttgc aatcaacagg tcccctaaaa atgcctatgt tgaaggtgat gcctcaagcg  2160
caagctattt cttggctggt gctgcaatta ctggagggac tgtgactgtg gaaggttgtg  2220
gcaccaccag tttgcaggta aagatttctt ggctggtgct acgataactg cttttgtctt  2280
tttggtttca gcattgttct cagagtcact aaataacatt atcatctgca aacgtcaaat  2340
```

```
agacatactt aggtgaatgg atattcatgt aaccgtttcc ttacaaattt gctgaaacct    2400
cagggtgatg tgaagtttgc tgaggtactg gagatgatgg gagcgaaggt tacatggacc    2460
gagactagcg taactgttac tggcccaccg cgggagccat ttgggaggaa cacctcaag     2520 gcgattgatg tcaacatgaa caagatgcct gatgtcgcca tgactcttgc tgtggttgcc    2580
ctctttgccg atggcccgac agccatcaga gacggtaaaa cattctcagc cctacaacca    2640
tgcctcttct acatcactac ttgacaagac taaaaactat tggctcgttg gcagtggctt    2700
cctggagagt aaaggagacc gagaggatgg ttgcgatccg gacggagcta accaaggtaa    2760
ggctacatac ttcacatgtc tcacgtcgtc tttccatagc tcgctgcctc ttagcggctt    2820
gcctgcggtc gctccatcct cggttgctgt ctgtgtttc cacagctggg agcatctgtt    2880
gaggaagggc cggactactg catcatcacg ccgccggaga agctgaacgt gacggcgatc    2940
gacacgtacg acgaccacag gatggccatg gccttctccc ttgccgcctg tgccgaggtc    3000
cccgtgacca tccgggaccc tgggtgcacc cggaagacct tccccgacta cttcgatgtg    3060
ctgagcactt tcgtcaagaa ttaataaagc gtgcgatact accacgcagc ttgattgaag    3120
tgataggctt gtgctgagga aatacatttc ttttgttctg ttttttctct ttcacgggat    3180
taagttttga gtctgtaacg ttagttgttt gtagcaagtt tctatttcgg atcttaagtt    3240
tgtgcactgt aagccaaatt tcatttcaag agtggtcgt tggaataata agaataataa     3300
attacgtttc agtggctgtc aagcctgctg ctacgtttta ggagatggca ttagacattc    3360
atcatcaaca acaataaaac cttttagcct caaacaataa tagtgaagtt attttttagt    3420
cctaaacaag ttgcattagg atatagttaa aacacaaaag aagctaaagt tagggtttag    3480
acatgtggat attgttttcc atgtatagta tgttctttct ttgagtctca tttaactacc    3540
tctacacata ccaactttag tttttttct acctcttcat gttactatgg tgccttctta    3600
tcccactgag cattggtata tttagaggtt tttgttgaac atgcctaaat catctcaatc    3660
aacgatggac aatcttttct tcgattgagc tgaggtacgt catctaga                3708
```

<210> SEQ ID NO 196
<211> LENGTH: 15
<212> TYPE: DNA
<213> ORGANISM: Artificial sequence
<220> FEATURE:
<223> OTHER INFORMATION: synthesized sequence- TIPS nucleotide
      modifications

<400> SEQUENCE: 196
atcgcaatgc ggtca                                                     15

<210> SEQ ID NO 197
<211> LENGTH: 19
<212> TYPE: DNA
<213> ORGANISM: Artificial sequence
<220> FEATURE:
<223> OTHER INFORMATION: synthesized sequence- Primer Seqeunce-1 F-E2

<400> SEQUENCE: 197
ccgaggagat cgtgctgca                                                 19

<210> SEQ ID NO 198
<211> LENGTH: 20
<212> TYPE: DNA
<213> ORGANISM: Artificial sequence
<220> FEATURE:
<223> OTHER INFORMATION: synthesized sequence- Primer Seqeunce-2 F-E2

<400> SEQUENCE: 198
caatggccgc attgcagttc                                          20

<210> SEQ ID NO 199
<211> LENGTH: 19
<212> TYPE: DNA
<213> ORGANISM: Artificial sequence
<220> FEATURE:
<223> OTHER INFORMATION: synthesized sequence- Primer Seqeunce-1 F-T

<400> SEQUENCE: 199
ccgaggagat cgtgctgca                                           19

<210> SEQ ID NO 200
<211> LENGTH: 20
<212> TYPE: DNA
<213> ORGANISM: Artificial sequence
<220> FEATURE:
<223> OTHER INFORMATION: synthesized sequence- Primer Seqeunce-2 F-T

<400> SEQUENCE: 200
tgaccgcatt gcgattccag                                          20

<210> SEQ ID NO 201
<211> LENGTH: 24
<212> TYPE: DNA
<213> ORGANISM: Artificial sequence
<220> FEATURE:
<223> OTHER INFORMATION: synthesized sequence- Primer Seqeunce-1 H-T

<400> SEQUENCE: 201
tccaagtcgc tttccaacag gatc                                     24

<210> SEQ ID NO 202
<211> LENGTH: 20
<212> TYPE: DNA
<213> ORGANISM: Artificial sequence
<220> FEATURE:
<223> OTHER INFORMATION: synthesized sequence- Primer Seqeunce-2 H-T

<400> SEQUENCE: 202
tgaccgcatt gcgattccag                                          20

<210> SEQ ID NO 203
<211> LENGTH: 19
<212> TYPE: DNA
<213> ORGANISM: Artificial sequence
<220> FEATURE:
<223> OTHER INFORMATION: synthesized sequence- Primer Seqeunce-1 F-E3

<400> SEQUENCE: 203
ccgaggagat cgtgctgca                                           19

<210> SEQ ID NO 204
<211> LENGTH: 24
<212> TYPE: DNA
<213> ORGANISM: Artificial sequence
<220> FEATURE:
<223> OTHER INFORMATION: synthesized sequence- Primer Seqeunce-2 F-E3

<400> SEQUENCE: 204
accaagctgc ttcaatccga caac                                     24

<210> SEQ ID NO 205

```
<211> LENGTH: 63
<212> TYPE: DNA
<213> ORGANISM: Zea mays

<400> SEQUENCE: 205
ggggaatgct ggaactgcaa tgcggccatt gacagcagct gttactgctg ctggtggaaa    60
tgc                                                                  63

<210> SEQ ID NO 206
<211> LENGTH: 60
<212> TYPE: DNA
<213> ORGANISM: Zea mays

<400> SEQUENCE: 206
ggggaatgct ggaactgcaa tgcggccatt ggcagctgtt actgctgctg gtggaaatgc    60

<210> SEQ ID NO 207
<211> LENGTH: 50
<212> TYPE: DNA
<213> ORGANISM: Zea mays

<400> SEQUENCE: 207
ggggaatgct ggaactgcac agcagctgtt actgctgctg gtggaaatgc                50

<210> SEQ ID NO 208
<211> LENGTH: 33
<212> TYPE: DNA
<213> ORGANISM: Zea mays

<400> SEQUENCE: 208
ggggaatgct gttactgctg ctggtggaaa tgc                                  33

<210> SEQ ID NO 209
<211> LENGTH: 51
<212> TYPE: DNA
<213> ORGANISM: Zea mays

<400> SEQUENCE: 209
aatgctggaa tcgcaatgcg gtcattgaca gcagctgtta ctgctgctgg t              51

<210> SEQ ID NO 210
<211> LENGTH: 51
<212> TYPE: DNA
<213> ORGANISM: Zea mays

<400> SEQUENCE: 210
aatgctggaa ctgcaatgcg gccattgaca gcagctgtta ctgctgctgg t              51

<210> SEQ ID NO 211
<211> LENGTH: 5124
<212> TYPE: DNA
<213> ORGANISM: Zea mays

<400> SEQUENCE: 211
atggcggcca tggcgaccaa ggccgccgcg ggcaccgtgt cgctggacct cgccgcgccg    60
ccggcggcgg cagcggcggc ggcggtgcag gcgggtgccg aggagatcgt gctgcagccc   120
atcaaggaga tctccggcac cgtcaagctg ccggggtcca agtcgctttc caacaggatc   180
ctcctgctcg ccgccctgtc cgaggtgagc gattttggtg cttgctgcgc tgccctgtct   240
cactgctacc taaatgtttt gcctgtcgaa taccatggat tctcggtgta atccatctca   300
cgatcagatg caccgcatgt cgcatgccta gctctctcta atttgtctag tagtttgtat   360
```

```
acggattaag attgataaat cggtaccgca aaagctaggt gtaaataaac actacaaaat     420
tggatgttcc cctatcggcc tgtactcggc tactcgttct tgtgatggca tgttatttct     480
tcttggtgtt tggtgaactc ccttatgaaa tttgggcgca agaaatcgc cctcaagggt      540
tgatcttatg ccatcgtcat gataaacagt gaagcacgga tgatccttta cgttgttttt     600
aacaaacttt gtcagaaaac tagcaatgtt aacttcttaa tgatgatttc acaacaaaaa     660
aggtaaccttt gctactaaca taacaaaaga cttgttgctt attaattata tgttttttta    720
atctttgatc aggggacaac agtggttgat aacctgttga acagtgagga tgtccactac     780
atgctcgggg ccttgaggac tcttggtctc tctgtcgaag cggacaaagc tgccaaaaga     840
gctgtagttg ttggctgtgg tggaaagttc ccagttgagg atgctaaaga ggaagtgcag     900
ctcttcttgg ggaatgctgg aactgcaatg cggccattga cagcagctgt tactgctgct     960
ggtggaaatg caacgtatgt ttcctctctc tctctacaat acttgttgga gttagtatga    1020
aacccatgtg tatgtctagt ggcttatggt gtattggttt ttgaacttca gttacgtgct    1080
tgatggagta ccaagaatga gggagagacc cattggcgac ttggttgtcg gattgaagca    1140
gcttggtgca gatgttgatt gtttccttgg cactgactgc ccacctgttc gtgtcaatgg    1200
aatcggaggg ctacctggtg gcaaggttag ttactaaggg ccacatgtta cattcttctg    1260
taaatggtac aactattgtc gagcttttgc atttgtaagg aaaacattga ttgatctgaa    1320
tttgatgcta caccacaaaa tatctacaaa tggtcatccc taactagcaa accatgtctc    1380
cattaagctc aatgaagtaa tacttggcat gtgtttatca acttaatttc catcttctgg    1440
ggtattgcct gttttctagt ctaatagcat tgttttttag aattagctct tacaactgtt    1500
atgttctaca ggtcaagctg tctggctcca tcagcagtca gtacttgagt gccttgctga    1560
tggctgctcc tttggctctt ggggatgtgg agattgaaat cattgataaa ttaatctcca    1620
ttccctacgt cgaaatgaca ttgagattga tggagcgttt tggtgtgaaa gcagagcatt    1680
ctgatagctg ggacagattc tacattaagg gaggtcaaaa atacaagtaa gctctgtaat    1740
gtatttcact actttgatgc caatgtttca gttttcagtt ttccaaacag tcgcatcaat    1800
atttgaatag atgcactgta gaaaaaaatc attgcaggga aaaactagta ctgagtattt    1860
tgactgtaaa ttatttaacc agtcggaata tagtcagtct attggagtca agagcgtgaa    1920
ccgaaatagc cagttaatta tcccattata cagaggacaa ccatgtatac tattgaaact    1980
tggtttaaga gaatctaggt agctggactc gtagctgctt ggcatggata ccttcttatc    2040
tttaggaaaa gacacttgat ttttttttctg tggccctcta tgatgtgtga acctgcttct    2100
ctattgcttt agaaggatat atctatgtcg ttatgcaaca tgcttcccctt agtcatttgt    2160
actgaaatca gtttcataag ttcgttagtg gttccctaaa cgaaaccttg tttttctttg    2220
caatcaacag gtcccctaaa aatgcctatg ttgaaggtga tgcctcaagc gcaagctatt    2280
tcttggctgg tgctgcaatt actggaggga ctgtgactgt ggaaggttgt ggcaccacca    2340
gtttgcaggt aaagatttct tggctggtgc tacgataact gcttttgtct ttttggtttc    2400
agcattgttc tcagagtcac taaataacat tatcatctgc aaacgtcaaa tagacatact    2460
taggtgaatg gatattcatg taaccgtttc cttacaaatt tgctgaaacc tcagggtgat    2520
gtgaagtttg ctgaggtact ggagatgatg ggagcgaagg ttacatggac cgagactagc    2580
gtaactgtta ctgcccacc gcgggagcca tttgggagga aacacctcaa ggcgattgat     2640
gtcaacatga acaagatgcc tgatgtcgcc atgactcttg ctgtggttgc cctctttgcc    2700
```

| | |
|---|---|
| gatggcccga cagccatcag agacggtaaa acattctcag ccctacaacc atgcctcttc | 2760 |
| tacatcacta cttgacaaga ctaaaaacta ttggctcgtt ggcagtggct tcctggagag | 2820 |
| taaaggagac cgagaggatg gttgcgatcc ggacggagct aaccaaggta aggctacata | 2880 |
| cttcacatgt ctcacgtcgt cttccatag ctcgctgcct cttagcggct tgcctgcggt | 2940 |
| cgctccatcc tcggttgctg tctgtgtttt ccacagctgg gagcatctgt tgaggaaggg | 3000 |
| ccggactact gcatcatcac gccgccggag aagctgaacg tgacggcgat cgacacgtac | 3060 |
| gacgaccaca ggatggccat ggccttctcc cttgccgcct gtgccgaggt ccccgtgacc | 3120 |
| atccgggacc ctgggtgcac ccggaagacc ttcccccgact acttcgatgt gctgagcact | 3180 |
| ttcgtcaaga attaataaag cgtgcgatac taccacgcag cttgattgaa gtgataggct | 3240 |
| tgtgctgagg aaatacattt cttttgttct gttttttctc tttcacggga ttaagttttg | 3300 |
| agtctgtaac gttagttgtt tgtagcaagt ttctatttcg gatcttaagt ttgtgcactg | 3360 |
| taagccaaat ttcatttcaa gagtggttcg ttggaataat aagaataata aattacgttt | 3420 |
| cagtggctgt caagcctgct gctacgtttt aggagatggc attagacatt catcatcaac | 3480 |
| aacaataaaa ccttttagcc tcaaacaata atagtgaagt tatttttttag tcctaaacaa | 3540 |
| gttgcattag gatatagtta aaacacaaaa gaagctaaag ttagggttta gacatgtgga | 3600 |
| tattgttttc catgtatagt atgttctttc tttgagtctc atttaactac ctctacacat | 3660 |
| accaactttta gtttttttttc tacctcttca tgttactatg gtgccttctt atcccactga | 3720 |
| gcattggtat atttagaggt ttttgttgaa catgcctaaa tcatctcaat caacgatgga | 3780 |
| caatcttttc ttcgattgag ctgaggtacg tcatctagag gataggacct tgagaatatg | 3840 |
| tgtccgtcaa tagctaaccc tctactaatt ttttcaatca agcaacctat tggcttgact | 3900 |
| ttaattcgta ccggcttcta ctacttctac agtatttttgt ctctataaat tgcagctaca | 3960 |
| acagtcagaa cggctggctt taaaatcaaa tggcctaagg atcattgaaa ggcatcttag | 4020 |
| caatgtctaa aattattacc ttctctagac gttgatatct ttgctccgga ttcgatccct | 4080 |
| tgttgtatga ccacaaatcc aacaccaaat acgcatttct gcaacacacc caaacaccc | 4140 |
| ttccaaataa gtggaatggt tgagaaattt gctattttga ttaaatattg gtgaaggggc | 4200 |
| aaggctgagg aaacgagacg aaggttcctt gacagctgaa aaatggaaca ctctagaggc | 4260 |
| ggagggagcg aggcgagctg tgtgaattgc cacccattga ttaagaatcc aacaacttga | 4320 |
| ctagcaaatg ccgacatggg tagcctacaa aggcgagttt tggagctggt ttcgtaataa | 4380 |
| ggaaatttct caaccaacta cttttccttag aaaagagttg cttgaccgga tcaacatctc | 4440 |
| cccctaaacc ccttggaggg ggagggggct aagatttaa tctacaagtt agatctaact | 4500 |
| gtccacctca atcccctca aggaggtttt tgtattattt gttagtgtag aatgataaag | 4560 |
| tggatgtatt gataggagat ggggtacaca tatttatagg gactcaaccc taaccctaat | 4620 |
| gggtcggcag cccaacagtg gtgtccggcc cacacacaca ctcacacaca cagtctaaca | 4680 |
| tccccgcag tcgcaacggg gacaccacac acgatgagac tggagtagag gccgaaggta | 4740 |
| ggagccgacg ggttgaaatc cccctagtc gcagcgtcgt gatagtacga atgttgcggc | 4800 |
| tggagtagag accggtgtgt gctccaagaa gacgatagcc cctagatgcc gaggtagccg | 4860 |
| aagtcgaggt ggtcgcggtc ggaagacgcg cagcaaaagc ctgatcttcg ggatggtcga | 4920 |
| cgttcgagcg tcaacgatcg gtagggcgac acaataaaag ggcaccagca ggtcgacctt | 4980 |
| cctgcttctt cgatcgtcca gacgtcaagg agcctcgcta gggaggccga cggcagcgca | 5040 |
| cgcggctacg ccggtcatgg tgtcctcacc cgcggcagaa aagaagggga atgtcggatc | 5100 | cgaccgagaa ggccacggca gcga                                               5124

<210> SEQ ID NO 212
<211> LENGTH: 3387
<212> TYPE: DNA
<213> ORGANISM: Streptococcus thermophilus

<400> SEQUENCE: 212

| | | | | | |
|---|---|---|---|---|---|
| atgagtgact | tagttttagg | acttgatatc | ggtataggtt | ctgttggtgt | aggtatcctt    60 |
| aacaaagtga | caggagaaat | tatccataaa | aactcacgca | tcttcccagc | agctcaagca   120 |
| gaaaataacc | tagtacgtag | aacgaatcgt | caaggaagac | gcttgacacg | acgtaaaaaa   180 |
| catcgtatag | ttcgtttaaa | tcgtctattt | gaggaaagtg | gattaatcac | cgattttacg   240 |
| aagatttcaa | ttaatcttaa | cccatatcaa | ttacgagtta | agggcttgac | cgatgaattg   300 |
| tctaatgaag | aactgtttat | cgctcttaaa | aatatggtga | acaccgtgg  | gattagttac   360 |
| ctcgatgatg | ctagtgatga | cggaaattca | tcagtaggag | actatgcaca | aattgttaag   420 |
| gaaaatagta | acaattaga  | aactaagaca | ccgggacaga | tacagttgga | acgctaccaa   480 |
| acatatggtc | aattacgtgg | tgattttact | gttgagaaag | atggcaaaaa | acatcgcttg   540 |
| attaatgtct | ttccaacatc | agcttatcgt | tcagaagcct | taaggatact | gcaaactcaa   600 |
| caagaattta | atccacagat | tacagatgaa | tttattaatc | gttatctcga | aattttaact   660 |
| ggaaaacgga | atattatca  | tggacccgga | aatgaaaagt | cacggactga | ttatggtcgt   720 |
| tacagaacga | gtggagaaac | tttagacaat | atttttggaa | ttctaattgg | gaaatgtaca   780 |
| ttttatccag | aagagtttag | agcagcaaaa | gcttcctaca | cggctcaaga | attcaatttg   840 |
| ctaaatgatt | tgaacaatct | aacagttcct | actgaaacca | aaagttgag  | caaagaacag   900 |
| aagaatcaaa | tcattaatta | tgtcaaaaat | gaaaaggcaa | tggggccagc | gaaacttttt   960 |
| aaatatatcg | ctaagttact | ttcttgtgat | gttgcagata | tcaagggata | ccgtatcgac  1020 |
| aaatcaggta | aggctgagat | tcatactttc | gaagcctatc | gaaaaatgaa | aacgcttgaa  1080 |
| accttagata | ttgaacaaat | ggatagaaa  | acgcttgata | aattagccta | tgtcttaaca  1140 |
| ttaaacactg | agagggaagg | tattcaagaa | gcctagaac  | atgaatttgc | tgatggtagc  1200 |
| tttagccaga | agcaagttga | cgaattggtt | caattccgca | aagcaaatag | ttccattttt  1260 |
| ggaaaaggat | ggcataattt | ttctgtcaaa | ctgatgatgg | agttaattcc | agaattgtat  1320 |
| gagacgtcag | aagagcaaat | gactatcctg | acacgacttg | gaaaacaaaa | acgacttcgt  1380 |
| cttcaaataa | aacaaaatat | ttcaaataaa | acaaaatata | tagatgagaa | actattaact  1440 |
| gaagaaatct | ataatcctgt | tgttgctaag | tctgttcgcc | aggctataaa | aatcgtaaat  1500 |
| gcggcgatta | agaatacgg  | agactttgac | aatattgtca | tcgaaatggc | tcgtgaaaca  1560 |
| aatgaagatg | atgaaagaa  | agctattcaa | aagattcaaa | aagccaacaa | agatgaaaaa  1620 |
| gatgcagcaa | tgcttaaggc | tgctaaccaa | tataatggaa | aggctgaatt | accacatagt  1680 |
| gttttccacg | gtcataagca | attagcgact | aaaatccgcc | tttggcatca | gcaaggagaa  1740 |
| cgttgccttt | atactggtaa | gacaatctca | atccatgatt | tgataaataa | tcctaatcag  1800 |
| tttgaagtag | atcatatttt | acctctttct | atcacattcg | atgatagcct | tgcaaataag  1860 |
| gttttggttt | atgcaactgc | taaccaagaa | aaaggacaac | gaacaccttta | tcaggcttta  1920 |
| gatagtatgg | atgatgcgtg | gtcttttccgt | gaattaaaag | cttttgtacg | tgagtcaaaa  1980 |
| acactttcaa | acaagaaaaa | agaataccctc | cttacagaag | aagatatttc | aaagtttgat  2040 |

| | | | | |
|---|---|---|---|---|
| gttcgaaaga | aatttattga | acgaaatctt | gtagatacaa | gatacgcttc aagagttgtc | 2100 |
| ctcaatgccc | ttcaagaaca | ctttagagct | cacaagattg | atacaaaagt ttccgtggtt | 2160 |
| cgtggccaat | ttacatctca | attgagacgc | cattggggaa | ttgagaagac tcgtgatact | 2220 |
| tatcatcacc | atgctgtcga | tgcattgatt | attgccgcct | caagtcagtt gaatttgtgg | 2280 |
| aaaaaacaaa | agaataccct | tgtaagttat | tcagaagaac | aactccttga tattgaaaca | 2340 |
| ggtgaactta | ttagtgatga | tgagtacaag | gaatctgtgt | tcaaagcccc ttatcaacat | 2400 |
| tttgttgata | cattgaagag | taaagaattt | gaagacagta | tcttattctc atatcaagtg | 2460 |
| gattctaagt | ttaatcgtaa | aatatcagat | gccactattt | atgcgacaag acaggctaaa | 2520 |
| gtgggaaaag | ataagaagga | tgaaacttat | gtcttaggga | aaatcaaaga tatctatact | 2580 |
| caggatggtt | atgatgcctt | tatgaagatt | tataagaagg | ataagtcaaa attcctcatg | 2640 |
| tatcgtcacg | acccacaaac | ctttgagaaa | gttatcgagc | caattttaga gaactatcct | 2700 |
| aataagcaaa | tgaatgaaaa | aggaaaagag | gtaccatgta | atcctttcct aaaatataaa | 2760 |
| gaagaacatg | gctatattcg | taaatatagt | aaaaaaggca | atggtcctga aatcaagagt | 2820 |
| cttaaatact | atgatagtaa | gcttttaggt | aatcctattg | atattactcc agagaatagt | 2880 |
| aaaaataaag | ttgtcttaca | gtcattaaaa | ccttggagaa | cagatgtcta tttcaataag | 2940 |
| gctactggaa | aatacgaaat | ccttggatta | aaatatgctg | atctacaatt tgagaaaggg | 3000 |
| acaggaacat | ataagatttc | ccaggaaaaa | tacaatgaca | ttaagaaaaa agagggtgta | 3060 |
| gattctgatt | cagaattcaa | gtttacactt | tataaaaatg | atttgttact cgttaaagat | 3120 |
| acagaaacaa | agaacaaca | gcttttccgt | tttctttctc | gaactttacc taaacaaaag | 3180 |
| cattatgttg | aattaaaacc | ttatgataaa | cagaaatttg | aaggaggtga ggcgttaatt | 3240 |
| aaagtgttgg | gtaacgttgc | taatggtggt | caatgcataa | aaggactagc aaaatcaaat | 3300 |
| atttctattt | ataaagtaag | aacagatgtc | ctaggaaatc | agcatatcat caaaaatgag | 3360 |
| ggtgataagc | ctaagctaga | tttttaa | | | 3387 |

<210> SEQ ID NO 213
<211> LENGTH: 3369
<212> TYPE: DNA
<213> ORGANISM: Streptococcus thermophilus

<400> SEQUENCE: 213

| | | | | |
|---|---|---|---|---|
| atgagtgact | tagttttagg | acttgatatc | ggtataggtt | ctgttggtgt aggtatcctt | 60 |
| aacaaagtga | caggagaaat | tatccataaa | aactcacgca | tcttcccagc agctcaagca | 120 |
| gaaaataacc | tagtacgtag | aacgaatcgt | caaggaagac | gcttgacacg acgtaaaaaa | 180 |
| catcgtatag | ttcgttaaa | tcgtctattt | gaggaaagtg | gattaatcac cgattttacg | 240 |
| aagatttcaa | ttaatcttaa | cccatatcaa | ttacgagtta | agggcttgac cgatgaattg | 300 |
| tctaatgaag | aactgtttat | cgctcttaaa | aatatggtga | acaccgtggg gattagttac | 360 |
| ctcgatgatg | ctagtgatga | cggaaattca | tcagtaggag | actatgcaca aattgttaag | 420 |
| gaaatagta | acaattaga | aactaagaca | ccgggacaga | tacagttgga acgctaccaa | 480 |
| acatatggtc | aattacgtgg | tgattttact | gttgagaaag | atggcaaaaa acatcgcttg | 540 |
| attaatgtct | ttccaacatc | agcttatcgt | tcagaagcct | taaggatact gcaaactcaa | 600 |
| caagaattta | attcacagat | tacagatgaa | tttattaatc | gttatctcga aattttaact | 660 |
| ggaaaacgga | aatattatca | tggacccgga | atgaaaagt | cacggactga ttatggtcgt | 720 |
| tacagaacga | atggagaaac | tttagacaat | attttttggaa | ttctaattgg gaaatgtaca | 780 |

```
ttttatccag acgagtttag agcagcaaaa gcttcctaca cggctcaaga attcaatttg    840
ctaaatgatt tgaacaatct aacagttcct actgaaacca aaaagttgag caaagaacag    900
aagaatcaaa tcattaatta tgtcaaaaat gaaaaggtaa tggggccagc gaaacttttt    960
aaatatatcg ctaaattact ttcttgtgat gttgcagata tcaagggaca ccgtatcgac   1020
aaatcaggta aggctgagat tcatactttc gaagcctatc gaaaaatgaa acgcttgaa    1080 accttagata ttgagcaaat ggatagagaa acgcttgata aattagccta tgtcttaaca   1140
ttaaacactg agagggaagg tattcaagaa gctttagaac atgaatttgc tgatggtagc   1200
tttagccaga agcaagttga cgaattggtt caattccgca aagcaaatag ttccattttt   1260
ggaaaaggat ggcataattt ttctgtcaaa ctgatgatgg agttaattcc agaattgtat   1320
gagacgtcag aagagcaaat gactatcctg acacgacttg aaaacaaaa aacaacttcg   1380 tcttcaaata aacaaaata tatagatgag aaactattaa ctgaagaaat ctataatcct   1440
gttgttgcta agtctgttcg ccaggctata aaaatcgtaa atgcggcgat taaagaatac   1500
ggagactttg acaatattgt catcgaaatg gctcgtgaaa caaatgaaga tgatgaaaag   1560
aaagctattc aaaagattca aaagccaac aaagatgaaa aagatgcagc aatgcttaag   1620
gctgctaacc aatataatgg aaaggctgaa ttaccacata gtgttttcca cggtcataag   1680
caattagcga ctaaaatccg cctttggcat cagcaaggag aacgttgcct ttatactggt   1740
aagacaatct caatccatga tttgataaat aatcctaatc agtttgaagt agatcatatt   1800
ttacctcttt ctatcacatt cgatgatagc cttgcaaata aggttttggt ttatgcaact   1860
gctaaccaag aaaaaggaca acgaacacct tatcaggctt tagatagtat ggatgatgcg   1920
tggtctttcc gtgaattaaa agcttttgta cgtgagtcaa aaacactttc aaacaagaaa   1980
aaagaatacc tccttacaga agaagatatt tcaaagtttg atgttcgaaa gaaatttatt   2040
gaacgaaatc ttgtagatac aagatacgct tcaagagttg tcctcaatgc ccttcaagaa   2100
cactttagag ctcacaagat tgatacaaaa gtttccgtgg ttcgtggcca atttacatct   2160
caattgagac gccattgggg aattgagaag actcgtgata cttatcatca ccatgctgtc   2220
gatgcattga ttattgccgc ctcaagtcag ttgaatttgt ggaaaaaaca aaagaatacc   2280
cttgtaagtt attcagaaga acaactcctt gatattgaaa caggtgaact tattagtgat   2340
gatgagtaca aggaatctgt gttcaaagcc ccttatcaac attttgttga tacattgaag   2400
agtaaagaat ttgaagacag tatcttattc tcatatcaag tggattctaa gtttaatcgt   2460
aaaatatcag atgccactat ttatgcgaca agacaggcta agtgggaaa agataagaag   2520 gatgaaactt atgtcttagg gaaaatcaaa gatatctata ctcaggatgg ttatgatgcc   2580
tttatgaaga tttataagaa ggataagtca aaattcctca tgtatcgtca cgacccacaa   2640
acctttgaga aagttatcga gccaatttta gagaactatc ctaataagga aatgaatgaa   2700
aaagggaaag aagtaccatg taatcctttc ctaaaatata agaagaaca tggctatatt   2760 cgtaaatata gtaaaaaagg caatggtcct gaaatcaaga gtcttaaata ctatgatagt   2820
aagcttttag gtaatcctat tgatattact ccagagaata gtaaaaataa agttgtctta   2880
cagtcattaa aaccttggag aacagatgtc tatttcaata aaaatactgg taaatatgaa   2940 atttaggac tgaaatatgc tgatttacaa tttgaaaaga agacaggaac atataagatt   3000
tcccaggaaa aatacaatgg cattatgaaa gaagagggtg tagattctga ttcagaattc   3060
aagtttacac tttataaaaa tgatttgtta ctcgttaaag atacagaaac aaaagaacaa   3120
```

| | |
|---|---:|
| cagcttttcc gttttctttc tcgaactatg cctaatgtga aatattatgt agagttaaag | 3180 |
| ccttattcaa aagataaatt tgagaagaat gagtcactta ttgaaatttt aggttctgca | 3240 |
| gataagtcag gacgatgtat aaaagggcta ggaaaatcaa atatttctat ttataaggta | 3300 |
| agaacagatg tcctaggaaa tcagcatatc atcaaaaatg agggtgataa gcctaagcta | 3360 |
| gattttttaa | 3369 |

<210> SEQ ID NO 214
<211> LENGTH: 4113
<212> TYPE: DNA
<213> ORGANISM: Streptococcus agalactiae

<400> SEQUENCE: 214

| | |
|---|---:|
| atgaataagc catattcaat aggccttgac atcggtacta attccgtcgg atggagcatt | 60 |
| attacagatg attataaagt acctgctaag aagatgagag ttttagggaa cactgataaa | 120 |
| gaatatatta agaagaatct cataggtgct ctgctttttg atggcgggaa tactgctgca | 180 |
| gatagacgct tgaagcgaac tgctcgtcgt cgttatacac gtcgtagaaa tcgtattcta | 240 |
| tatttacaag aaattttttgc agaggaaatg agtaaagttg atgatagttt ctttcatcga | 300 |
| ttagaggatt cttttctagt tgaggaagat aagagaggga gcaagtatcc tatctttgca | 360 |
| acattgcagg aagagaaaga ttatcatgaa aaattttcga caatctatca tttgagaaaa | 420 |
| gaattagcta caagaaaga aaaagcagac cttcgtctta tttatattgc tctagctcat | 480 |
| atcattaaat ttagagggca tttcctaatt gaggatgata gctttgatgt caggaataca | 540 |
| gacatttcaa acaatatca agatttttta gaaatcttta atacaacttt tgaaaataat | 600 |
| gatttgttat ctcaaaacgt tgacgtagag gcaatactaa cagataagat tagcaagtct | 660 |
| gcgaagaaaa tcgtatttt agcgcagtat cctaaccaaa aatctactgg catttttgca | 720 |
| gaattttttga aattgattgt cggaaatcaa gctgacttca agaaatattt caatttggag | 780 |
| gataaaacgc cgcttcaatt cgctaaggat agctacgatg aagatttaga aaatcttctt | 840 |
| ggacagattg gtgatgaatt tgcagactta ttctcagcag cgaaaaagtt atatgatagt | 900 |
| gtcctttttgt ctggcattct tacagtaatc gacctcagta ccaaggcgcc actttcagct | 960 |
| tctatgattc agcgttatga tgaacataga gaggacttga acagttaaa acaattcgta | 1020 |
| aaagcttcat tgccggaaaa atatcaagaa atatttgctg attcatcaaa agatggctac | 1080 |
| gctggttata ttgaaggtaa aactaatcaa gaagcttttt ataaatacct gtcaaaattg | 1140 |
| ttgaccaagc aagaagatag cgagaatttt cttgaaaaaa tcaagaatga agatttcttg | 1200 |
| agaaaacaaa ggacctttga taatggctca attccacacc aagtccattt gacagagctg | 1260 |
| aaagctatta tccgccgtca atcagaatac tatcccttct tgaaagagaa tcaagatagg | 1320 |
| attgaaaaaa tccttacctt tagaattcct tattatatcg ggccactagc acgtgagaag | 1380 |
| agtgattttg catggatgac tcgcaaaaca gatgacagta ttcgaccttg gaattttgaa | 1440 |
| gacttggttg ataaagaaaa atctgcggaa gcttttatcc atcgtatgac caacaatgat | 1500 |
| ttttatcttc ctgaagaaaa agttttacca agcatagtc ttatttatga aaaatttacg | 1560 |
| gtctataatg agttgactaa ggttagatat aaaaatgagc aaggtgagac ttattttttt | 1620 |
| gatagcaata ttaaacaaga atctttgat ggagtattca aggaacatcg taaggtatcc | 1680 |
| aagaagaagt tgctagattt tctggctaaa gaatatgagg agtttaggat agtagatgtt | 1740 |
| attggtctag ataagaaaa taagctttc aacgcctcat tggaactta ccacgatctc | 1800 |
| gaaaaaatac tagacaaaga ttttctagat aatccagata atgagtctat tctggaagat | 1860 |

-continued

```
atcgtccaaa ctctaacatt atttgaagac agagaaatga ttaagaagcg tcttgaaaac    1920
tataaagatc ttttacaga gtcacaacta aaaaaactct atcgtcgtca ctatactggc    1980
tggggacgat tgtctgctaa gttaatcaat ggtattcgag ataaagagag tcaaaaaaca    2040
atcttggact atcttattga tgatggtaga tctaatcgca actttatgca gttgataaat    2100
gatgatggtc tatcttttcaa atcaattatc agtaaggcac aggctggtag tcattcagat    2160
aatctaaaag aagttgtagg tgagcttgca ggtagccctg ctattaaaaa gggaattcta    2220
caaagtttga aaattgttga tgagcttgtt aaagtcatgg gatacgaacc tgaacaaatt    2280
gtggttgaga tggcgcgtga gaatcaaaca acaaatcaag gtcgtcgtaa ctctcgacaa    2340
cgctataaac ttcttgatga tggcgttaag aatctagcta gtgacttgaa tggcaatatt    2400
ttgaaagaat atcctacgga taatcaagcg ttgcaaaatg aaagactttt cctttactac    2460
ttacaaaacg gaagagatat gtatacaggg gaagctctag atattgacaa tttaagtcaa    2520
tatgatattg accacattat tcctcaagct ttcataaaag atgattctat tgataatcgt    2580
gttttggtat catctgctaa aaatcgtgga agtcagatg atgttcctag ccttgaaatt    2640
gtaaaagatt gtaagttttt ctggaaaaaa ttacttgatg ctaagttaat gagtcagcgt    2700
aagtatgata atttgactaa ggcagagcgc ggaggcctaa cttccgatga taaggcaaga    2760
tttatccaac gtcagttggt tgagacacga caaattacca agcatgttgc ccgtatcttg    2820
gatgaacgct ttaataatga gcttgatagt aaaggtagaa ggatccgcaa agttaaaatt    2880
gtaaccttga agtcaaattt ggtttcaaat ttccgaaaag aatttggatt ctataaaatt    2940
cgtgaagtta acaattatca ccatgcacat gatgcctatc ttaatgcagt agttgctaaa    3000
gctattctaa ccaaatatcc tcagttagag ccagaatttg tctacggcga ctatccaaaa    3060
tataatagtt acaaaacgcg taaatccgct acagaaaagc tattttttcta ttcaaatatt    3120 atgaacttct ttaaaactaa ggtaaccttta gcggatggaa ccgttgttgt aaaagatgat    3180
attgaagtta ataatgatac gggtgaaatt gtttgggata aaaagaaaca ctttgcgaca    3240
gttagaaaag tcttgtcata ccctcagaac aatatcgtga agaagacaga gattcagaca    3300 ggtggttct ctaaggaatc aatcttggcg catggtaact cagataagtt gattccaaga    3360
aaaacgaagg atatttattt agatcctaag aaatatggag gttttgatag tccgatagta    3420
gcttactctg ttttagttgt agctgatatc aaaaagggta agcacaaaa actaaaaaca    3480 gttacggaac ttttaggaat taccatcatg gagaggtcca gatttgagaa aaatccatca    3540
gctttccttg aatcaaaagg ctatttaaat attagggctg ataaactaat tatttttgccc    3600 aagtatagtc tgttcgaatt agaaaatggg cgtcgtcgat tacttgctag tgctggtgaa    3660
ttacaaaaag gtaatgagct agccttacca acacaattta tgaagttctt ataccttgca    3720
agtcgttata atgagtcaaa aggtaaacca gaggagattg agaagaaaca agaatttgta    3780
aatcaacatg tctcttattt tgatgacatc cttcaattaa ttaatgattt ttcaaaacga    3840
gttattctag cagatgctaa tttagagaaa atcaataagc tttaccaaga taataaggaa    3900
aatatatcag tagatgaact tgctaataat attatcaatc tatttacttt taccagtcta    3960
ggagctccag cagcttttaa attttttgat aaaaatagttg atagaaaacg ctatacatca    4020
actaaagaag tacttaattc taccctaatt catcaatcta ttactggact ttatgaaaca    4080
cgtattgatt tgggtaagtt aggagaagat tga                                 4113
```

<210> SEQ ID NO 215

<211> LENGTH: 4134
<212> TYPE: DNA
<213> ORGANISM: Streptococcus agalactiae

<400> SEQUENCE: 215

```
atgaataagc catattcaat aggccttgac atcggtacta attccgtcgg atggagcatt      60
attacagatg attataaagt acctgctaag aagatgagag ttttagggaa cactgataaa     120
gaatatatta agaagaatct cataggtgct ctgcttttg atggcgggaa tactgctgca      180
gatagacgct tgaagcgaac tgctcgtcgt cgttatacac gtcgtagaaa tcgtattcta     240
tatttacaag aaattttgc agaggaaatg agtaaagttg atgatagttt ctttcatcga      300
ttagaggatt ctttttctagt tgaggaagat aagagaggta gcaagtatcc tatctttgca    360
acaatgcagg aggagaaaata ttatcatgaa aaatttccga caatctatca tttgagaaaa   420
gaattggctg acaagaaaga aaaagcagac cttcgtcttg tttatctggc tctagctcat    480
atcattaaat tcagagggca tttcctaatt gaggatgata gatttgatgt gaggaatacc    540
gatattcaaa acaatatca agccttttta gaaattttg atactacctt tgaaaataat      600
catttgttat ctcaaaatgt agatgtagaa gcaattctaa cagataagat tagcaagtct    660
gcgaagaagg atcgcatctt agcgcagtat cctaaccaaa aatctactgg tattttttgca  720
gaattttga aattgattgt cggaaatcaa gctgacttca agaaacatttt caatttggag   780
gataaaacac cgcttcaatt cgctaaggat agctacgatg aagatttaga aaatcttctt    840
ggacagattg gtgatgaatt tgcagactta ttctcagtag cgaaaaagct atatgatagt    900
gttcttttat ctggcattct tacagtaact gatctcagta ccaaggcgcc actttctgcc    960
tctatgattc agcgttatga tgaacatcat gaggacttaa agcatctaaa acaattcgta   1020
aaagcttcat tacctgaaaa ttatcggaa gtatttgctg attcatcaaa agatggctac   1080
gctggctata ttgaaggcaa aactaatcaa gaagcttttt ataaatatct gttaaaattg   1140
ttgaccaaac aagaaggtag cgagtatttt cttgagaaaa ttaagaatga agattttttg  1200
agaaaacaga gaacctttga taatggctca atcccgcatc aagtccattt gacagaattg   1260
agggctatta ttcgacgtca atcagaatac tatccattct tgaaagagaa tcaagatagg   1320
attgaaaaaa tccttacctt tagaattcct tattatgtcg ggccactagc acgtgagaag   1380
agtgattttg catggatgac tcgcaaaaca gatgacagta ttcgaccttg gaattttgaa   1440
gacttggttg ataaagaaaa atctgcggaa gcttttatcc atcgcatgac caacaatgac   1500
ctctatcttc cagaagaaaa agttttacca aagcatagtc ttatttatga aaaatttact   1560
gtttacaatg aattaacgaa ggttagattt ttggcagaag gctttaaaga ttttcaatttt   1620
ttaaatagga agcaaaaaga aactatcttt aacagcttgt ttaaggaaaa acgtaaagta   1680
actgaaaagg atattattag ttttttgaat aaagttgatg gatatgaagg aattgcaatc   1740
aaaggaattg agaaacagtt taacgctagc ctttcaaccct atcatgatct taaaaaata   1800
cttggcaagg atttccttga taatacagat aacgagctta ttttggaaga tatcgtccaa   1860
actctaaccct tatttgaaga tagagaaatg attaagaagt gtcttgacat ctataaagat   1920
ttttttacag agtcacagct taaaaagctc tatcgccgtc actatactgg ctggggacga   1980
ttgtctgcta agctaataaa tggcatccga aataaagaga tcaaaaaac aatcttggac   2040
tatcttattg atgatggaag tgcaaaccga aacttcatgc agttgataaa tgatgatgat   2100
ctatcattta aaccaattat tgacaaggca cgaactggta gtcattcgga taatctgaaa   2160
gaagttgtag gtgaacttgc tggtagccct gctattaaaa aagggattct acaaagtttg   2220
```

```
aaaatagttg atgagctggt taaagtcatg ggctatgaac ctgaacaaat cgtggttgaa    2280
atggcacgtg agaaccaaac gacagcaaaa ggattaagtc gttcacgaca acgcttgaca    2340
accttgagag aatctcttgc taatttgaag agtaatattt tggaagagaa aaagcctaag    2400
tatgtgaaag atcaagttga aaatcatcat ttatctgatg accgtctttt cctttactac    2460
ttacaaaacg gaagagatat gtatacaaaa aaggctctgg atattgataa tttaagtcaa    2520
tatgatattg accacattat tcctcaagct ttcataaaag atgattctat tgataatcgt    2580
gttttggtat catctgctaa aaatcgtgga aaatcagatg atgttcctag cattgaaatt    2640
gtaaaagctc gcaaaatgtt ctggaaaaat ttactggatg ctaagttaat gagtcagcgt    2700
aagtatgata atttgactaa ggcagagcgc ggaggcctaa cttccgatga taaggcaaga    2760
tttatccaac gtcagttggt tgagactcga caaattacca agcatgtagc tcgtatcttg    2820
gatgaacgct tcaataatga agttgataat ggtaaaaaga tttgcaaggt taaaattgta    2880
accttgaagt caaatttggt ttcaaatttc cgaaaagaat ttggattcta taaaattcgt    2940
gaagttaatg attatcacca tgcacacgat gcttatctta atgcagtagt tgccaaagct    3000
attctaacca aatatccaca gttagagcca gagtttgtct acggaatgta tagacagaaa    3060
aaactttcga aaatcgttca tgaggataag gaagaaaaat atagtgaagc aaccaggaaa    3120
atgtttttct actccaactt gatgaatatg ttcaaaagag ttgtgaggtt agcagatggt    3180
tctattgttg taagaccagt aatagaaact ggtagatata tgagaaaaac tgcatgggat    3240
aaaaagaaac actttgcgac agttagaaaa gtcttgtcat accctcagaa caatatcgtg    3300
aagaagacag agattcagac aggtggtttc tctaaggaat caatcttggc gcatggtaac    3360
tcagataagt tgattccaag aaaaacgaag gatatttatt tagatcctaa gaaatatgga    3420
ggttttgata gtccgatagt agcttactct gttttagttg tagctgatat caaaaaaggt    3480
aaagcacaaa aactaaaaac agttacggaa cttttaggaa ttaccatcat ggagaggtcc    3540
agatttgaga aaaatccatc agctttcctt gaatcaaaag gttatttaaa tattagggac    3600
gataaattaa tgattttacc gaagtatagt ctgttcgaat tagaaaatgg gcgtcgtcga    3660
ttacttgcta gtgctggtga attacaaaaa ggtaacgagc tagccttacc aacacaattt    3720
atgaagttct tataccttgc aagtcgttat aatgagtcaa aaggtaaacc agaggagatt    3780
gagaagaaac aagaatttgt aaatcaacat gtctcttatt ttgatgacat ccttcaatta    3840
attaatgatt tttcaaaacg agttattcta gcagatgcta atttagagaa atcaataaag    3900
ctttaccagg ataataagga aaatatacca gtagatgaac ttgctaataa tattatcaat    3960
ctatttactt ttaccagtct aggagctcca gcagctttta aattttttga taaaatagtt    4020
gatagaaaac gctatacatc aactaaagaa gtacttaatt ctactctaat ccatcaatct    4080
attactggac tttatgaaac acgtattgat ttgggtaaat taggagaaga ttga          4134
```

<210> SEQ ID NO 216
<211> LENGTH: 4038
<212> TYPE: DNA
<213> ORGANISM: Streptococcus mutans

<400> SEQUENCE: 216

```
atgaaaaaac ttactctat tggacttgat attggaacca attctgttgg ttgggctgtt    60 gtgcagatg actacaaagt tcctgctaag aagatgaagg ttctgggaaa tacagataaa    120
agtcatatcg agaaaaattt gcttggcgct ttattatttg atagcgggaa tactgcagaa    180
```

```
gacagacggt taaagagaac tgctcgccgt cgttacacac gtcgcagaaa tcgtatttta        240
tatttgcaag agattttttc agaagaaatg ggcaaggtag atgatagttt ctttcatcgt        300
ttagaggatt cttttcttgt tactgaggat aaacgaggag agcgccatcc cattttgggg       360
aatcttgaag aagaagttaa gtatcatgaa aattttccaa ccatttatca tttgcggcaa        420
tatcttgcgg ataatccaga aaaagttgat ttgcgtttag tttatttggc tttggcacat        480
ataattaagt ttagaggtca tttttttaatt gaaggaaagt ttgatacacg caataatgat       540
gtacaaagac tgtttcaaga attttttagca gtctatgata atacttttga gaatagttcg      600
cttcaggagc aaaatgttca agttgaagaa attctgactg ataaaatcag taaatctgct       660
aagaaagata gagttttgaa acttttttcct aatgaaaagt ctaatggccg ctttgcagaa      720
tttctaaaac taattgttgg taatcaagct gattttaaaa agcattttga attagaagag       780
aaagcaccat tgcaatttttc taaagatact tatgaagaag agttagaagt actattagct      840
caaattggag ataattacgc agagctcttt ttatcagcaa agaaactgta tgatagtatc       900
cttttatcag ggatttttaac agttactgat gttggtacca aagcgccttt atctgcttcg      960
atgattcagc gatataatga acatcagatg gatttagctc agcttaaaca attcattcgt      1020
cagaaattat cagataaata aacgaagtt ttttctgatg tttcaaaaga cggctatgcg       1080
ggttatattg atgggaaaac aaatcaagaa gcttttttata aataccttaa aggtctatta     1140
aataagattg agggaagtgg ctatttcctt gataaaattg agcgtgaaga ttttctaaga      1200
aagcaacgta cctttgacaa tggctctatt ccacatcaga ttcatcttca agaaatgcgt      1260
gctatcattc gtagacaggc tgaattttat ccgttttttag cagacaatca agataggatt    1320
gagaaattat tgactttccg tattccctac tatgttggtc cattagcgcg cggaaaaagt     1380
gattttgctt ggttaagtcg gaaatcggct gataaaatta ccatggaa ttttgatgaa       1440 atcgttgata aagaatcctc tgcagaagct tttatcaatc gtatgacaaa ttatgatttg    1500
tacttgccaa atcaaaaagt tcttcctaaa catagtttat tatacgaaaa atttactgtt    1560
tacaatgaat taacaaaggt taaatataaa acagagcaag gaaaaacagc attttttttgat  1620 gccaatatga agcaagaaat ctttgatggc gtatttaagg tttatcgaaa agtaactaaa   1680
gataaattaa tggatttcct tgaaaaagaa tttgatgaat ttcgtattgt tgatttaaca     1740
ggtctggata aagaaaataa agtatttaac gcttcttatg gaacttatca tgatttgtgt    1800 aaaatttttag ataaagattt tctcgataat tcaaagaatg aaaagatttt agaagatatt   1860
gtgttgacct taacgttatt tgaagataga gaaatgatta gaaaacgtct agaaaattac    1920 agtgattttat tgaccaaaga acaagtgaaa aagctggaaa gacgtcatta tactggttgg   1980
ggaagattat cagctgagtt aattcatggt attcgcaata agaaagcag aaaaacaatt    2040 cttgattatc tcattgatga tggcaatagc aatcggaact ttatgcaact gattaacgat   2100
gatgctcttt ctttcaaaga agagattgct aaggcacaag ttattggaga acagacaat    2160 ctaaatcaag ttgttagtga tattgctggc agccctgcta ttaaaaaagg aatttttacaa  2220 agcttgaaga ttgttgatga gcttgtcaaa attatgggac atcaacctga aatatcgtc    2280 gtggagatgc gcgtgaaaa ccagtttacc aatcagggac gacgaaattc acagcaacgt   2340
ttgaaaggtt tgacagattc tattaaagaa tttggaagtc aaattcttaa agaacatccg   2400
gttgagaatt cacagttaca aaatgataga ttgtttctat attatttaca aaacggcaga   2460
gatatgtata ctgagaagaa attggatatt gattatctaa gccagtatga tatagaccat   2520
attatcccgc aagcttttat aaaggataat tctattgata atagagtatt gactagctca    2580
```

```
aaggaaaatc gtggaaaatc ggatgatgta ccaagtaaag atgttgttcg taaaatgaaa    2640
tcctattgga gtaagctact ttcggcaaag cttattacaa acgtaaaatt tgataaatttg   2700 acaaaagctg aacgaggtgg attgaccgac gatgataaag ctggattcat caagcgtcaa   2760
ttagtagaaa cacgacaaat taccaaacat gtagcacgta ttctggacga acgatttaat   2820
acagaaacag atgaaaacaa caagaaaatt cgtcaagtaa aaattgtgac cttgaaatca   2880
aatcttgttt ccaatttccg taaagagttt gaactctaca aagtgcgtga attaatgac   2940 tatcatcatg cacatgatgc ctatctcaat gctgtaattg gaaaggcttt actaggtgtt   3000
tacccacaat tggaacctga atttgtttat ggtgattatc ctcattttca tggacataaa   3060
gaaaataaag caactgctaa gaaatttttc tattcaaata ttatgaactt ctttaaaaaa   3120
gatgatgtcc gtactgataa aaatggtgaa attatctgga aaaaagatga gcatatttct   3180
aatattaaaa aagtgctttc ttatccacaa gttaatattg ttaagaaagt agaggagcaa   3240
acgggaggat tttctaaaga atctatcttg ccgaaaggta attctgacaa gcttattcct   3300
cgaaaaacga agaaatttta ttgggatacc aagaaatatg gaggatttga tagcccgatt   3360
gttgcttatt ctatttttagt tattgctgat attgaaaaag gtaaatctaa aaaattgaaa   3420
acagtcaaag ccttagttgg tgtcactatt atggaaaaga tgacttttga aagggatcca   3480
gttgcttttc ttgagcgaaa aggctatcga aatgttcaag aagaaaatat tataaagtta   3540
ccaaaatata gtttatttaa actagaaaac ggacgaaaaa ggctattggc aagtgctagg   3600
gaacttcaaa agggaaatga aatcgttttg ccaaatcatt taggaaccct gctttatcac   3660
gctaaaaata ttcataaagt tgatgaacca aagcatttgg actatgttga taaacataaa   3720
gatgaattta aggagttgct agatgttgtg tcaaactttt ctaaaaaata tactttagca   3780
gaaggaaatt tagaaaaaat caagaaatta tatgcacaaa ataatggtga agatcttaaa   3840
gaattagcaa gttcatttat caacttatta acatttactg ctataggagc accggctact   3900
tttaaattct ttgataaaaa tattgatcga aaacgatata cttcaactac tgaaattctc   3960
aacgctaccc tcatccacca atccatcacc ggtctttatg aaacgcggat tgatctcaat   4020
aagttaggag gagactaa                                                  4038
```

<210> SEQ ID NO 217
<211> LENGTH: 20
<212> TYPE: DNA
<213> ORGANISM: Artificial Sequence
<220> FEATURE:
<223> OTHER INFORMATION: synthesized sequence- Mprimer qADH-F

<400> SEQUENCE: 217
caagtcgcgg ttttcaatca                                                20

<210> SEQ ID NO 218
<211> LENGTH: 21
<212> TYPE: DNA
<213> ORGANISM: Artificial Sequence
<220> FEATURE:
<223> OTHER INFORMATION: synthesized sequence- Primer qADH-R

<400> SEQUENCE: 218
tgaaggtgga agtcccaaca a                                              21

<210> SEQ ID NO 219
<211> LENGTH: 19
<212> TYPE: DNA

```
<213> ORGANISM: Artificial Sequence
<220> FEATURE:
<223> OTHER INFORMATION: synthesized sequence- probe ADH-VIC

<400> SEQUENCE: 219
tgggaagcct atctaccac                                                    19

<210> SEQ ID NO 220
<211> LENGTH: 15
<212> TYPE: DNA
<213> ORGANISM: Artificial Sequence
<220> FEATURE:
<223> OTHER INFORMATION: synthesized sequence- Probe wtEPSPS

<400> SEQUENCE: 220
cggccattga cagca                                                        15

<210> SEQ ID NO 221
<211> LENGTH: 20
<212> TYPE: DNA
<213> ORGANISM: Artificial Sequence
<220> FEATURE:
<223> OTHER INFORMATION: synthesized sequence- Forward primer qEPSPS-F

<400> SEQUENCE: 221
tcttggggaa tgctggaact                                                   20

<210> SEQ ID NO 222
<211> LENGTH: 21
<212> TYPE: DNA
<213> ORGANISM: Artificial Sequence
<220> FEATURE:
<223> OTHER INFORMATION: synthesized sequence- reverse primer qEPSPSR

<400> SEQUENCE: 222
caccagcagc agtaacagct g                                                 21

<210> SEQ ID NO 223
<211> LENGTH: 17
<212> TYPE: DNA
<213> ORGANISM: Artificial Sequence
<220> FEATURE:
<223> OTHER INFORMATION: synthesized sequence- FAM-wtEPSPS R probe

<400> SEQUENCE: 223
tgctgtcaat ggccgca                                                      17

<210> SEQ ID NO 224
<211> LENGTH: 20
<212> TYPE: DNA
<213> ORGANISM: Artificial Sequence
<220> FEATURE:
<223> OTHER INFORMATION: synthesized sequence- forward primer qEPSPS-F

<400> SEQUENCE: 224
tcttggggaa tgctggaact                                                   20

<210> SEQ ID NO 225
<211> LENGTH: 20
<212> TYPE: DNA
<213> ORGANISM: Artificial Sequence
<220> FEATURE:
<223> OTHER INFORMATION: synthesized sequence- reverse primer q wtEPSPS
      RA

<400> SEQUENCE: 225
```

```
ccaccagcag cagtaacagc                                                20

<210> SEQ ID NO 226
<211> LENGTH: 21
<212> TYPE: DNA
<213> ORGANISM: Artificial Sequence
<220> FEATURE:
<223> OTHER INFORMATION: synthesized sequence- forward primer q epTIPS F

<400> SEQUENCE: 226
ggaagtgcag ctcttcttgg g                                              21

<210> SEQ ID NO 227
<211> LENGTH: 19
<212> TYPE: DNA
<213> ORGANISM: Artificial Sequence
<220> FEATURE:
<223> OTHER INFORMATION: synthesized sequence- reverse primer q epTIPS R

<400> SEQUENCE: 227
agctgctgtc aatgaccgc                                                 19

<210> SEQ ID NO 228
<211> LENGTH: 15
<212> TYPE: DNA
<213> ORGANISM: Artificial Sequence
<220> FEATURE:
<223> OTHER INFORMATION: synthesized sequence- TIPS probe

<400> SEQUENCE: 228
aatgctggaa tcgca                                                     15

<210> SEQ ID NO 229
<211> LENGTH: 23
<212> TYPE: DNA
<213> ORGANISM: Zea mays
<220> FEATURE:
<221> NAME/KEY: misc_feature
<222> LOCATION: (1)..(23)
<223> OTHER INFORMATION: MHP14Cas1 target site

<400> SEQUENCE: 229
gttaaatctg acgtgaatct gtt                                            23

<210> SEQ ID NO 230
<211> LENGTH: 21
<212> TYPE: DNA
<213> ORGANISM: Zea mays
<220> FEATURE:
<221> NAME/KEY: misc_feature
<222> LOCATION: (1)..(21)
<223> OTHER INFORMATION: MHP14Cas3 target site

<400> SEQUENCE: 230
acaaacattg aagcgacata g                                              21

<210> SEQ ID NO 231
<211> LENGTH: 18
<212> TYPE: DNA
<213> ORGANISM: Zea mays
<220> FEATURE:
<221> NAME/KEY: misc_feature
<222> LOCATION: (1)..(18)
<223> OTHER INFORMATION: TS8Cas1 target site

<400> SEQUENCE: 231
gtacgtaacg tgcagtac                                                  18
```

```
<210> SEQ ID NO 232
<211> LENGTH: 20
<212> TYPE: DNA
<213> ORGANISM: Zea mays
<220> FEATURE:
<221> NAME/KEY: misc_feature
<222> LOCATION: (1)..(20)
<223> OTHER INFORMATION: TS8Cas2 target site

<400> SEQUENCE: 232
gctcatcagt gatcagctgg                                              20

<210> SEQ ID NO 233
<211> LENGTH: 17
<212> TYPE: DNA
<213> ORGANISM: Zea mays
<220> FEATURE:
<221> NAME/KEY: misc_feature
<222> LOCATION: (1)..(17)
<223> OTHER INFORMATION: TS9Cas2 target site

<400> SEQUENCE: 233
ggctgtttgc ggcctcg                                                 17

<210> SEQ ID NO 234
<211> LENGTH: 21
<212> TYPE: DNA
<213> ORGANISM: Zea mays
<220> FEATURE:
<221> NAME/KEY: misc_feature
<222> LOCATION: (1)..(21)
<223> OTHER INFORMATION: TS9Cas3 target site

<400> SEQUENCE: 234
gcctcgaggt tgcacgcacg t                                            21

<210> SEQ ID NO 235
<211> LENGTH: 20
<212> TYPE: DNA
<213> ORGANISM: Zea mays
<220> FEATURE:
<221> NAME/KEY: misc_feature
<222> LOCATION: (1)..(20)
<223> OTHER INFORMATION: TS10Cas1 target site

<400> SEQUENCE: 235
gcctcgcctt cgctagttaa                                              20

<210> SEQ ID NO 236
<211> LENGTH: 18
<212> TYPE: DNA
<213> ORGANISM: Zea mays
<220> FEATURE:
<221> NAME/KEY: misc_feature
<222> LOCATION: (1)..(18)
<223> OTHER INFORMATION: TS10Cas3 target site

<400> SEQUENCE: 236
gctcgtgttg gagataca                                                18

<210> SEQ ID NO 237
<211> LENGTH: 80
<212> TYPE: DNA
<213> ORGANISM: Zea mays

<400> SEQUENCE: 237
```

```
gttaaatctg acgtgaatct gtttggaatt gaaaaacaag tgcttccttt catacaccac    60
tatgtcgctt caatgtttgt                                                80

<210> SEQ ID NO 238
<211> LENGTH: 80
<212> TYPE: DNA
<213> ORGANISM: Zea mays

<400> SEQUENCE: 238
acaaacattg aagcgacata gtggtgtatg aaaggaagca cttgtttttc aattccaaac    60
agattcacgt cagatttaac                                                80

<210> SEQ ID NO 239
<211> LENGTH: 66
<212> TYPE: DNA
<213> ORGANISM: Zea mays

<400> SEQUENCE: 239
ccagtactgc acgttacgta cgtacgaact aatatactcc accagctgat cactgatgag    60
ccgagc                                                               66

<210> SEQ ID NO 240
<211> LENGTH: 66
<212> TYPE: DNA
<213> ORGANISM: Zea mays

<400> SEQUENCE: 240
gctcggctca tcagtgatca gctggtggag tatattagtt cgtacgtacg taacgtgcag    60
tactgg                                                               66

<210> SEQ ID NO 241
<211> LENGTH: 35
<212> TYPE: DNA
<213> ORGANISM: Zea mays

<400> SEQUENCE: 241
ccgacgtgcg tgcaacctcg aggccgcaaa cagcc                               35

<210> SEQ ID NO 242
<211> LENGTH: 35
<212> TYPE: DNA
<213> ORGANISM: Zea mays

<400> SEQUENCE: 242
ggctgtttgc ggcctcgagg ttgcacgcac gtcgg                               35

<210> SEQ ID NO 243
<211> LENGTH: 68
<212> TYPE: DNA
<213> ORGANISM: Zea mays

<400> SEQUENCE: 243
gctcgtgttg gagatacagg gacagcaagt acttggccct taactagcga aggcgaggcg    60
gccatgga                                                             68

<210> SEQ ID NO 244
<211> LENGTH: 68
<212> TYPE: DNA
<213> ORGANISM: Zea mays

<400> SEQUENCE: 244
```
tccatggccg cctcgccttc gctagttaag ggccaagtac ttgctgtccc tgtatctcca        60
acacgagc                                                                68

<210> SEQ ID NO 245
<211> LENGTH: 1108
<212> TYPE: DNA
<213> ORGANISM: Artificial Sequence
<220> FEATURE:
<223> OTHER INFORMATION: synthesized sequence- MHP14Cas-1 guideRNA
      cassette

<400> SEQUENCE: 245
tgagagtaca atgatgaacc tagattaatc aatgccaaag tctgaaaaat gcaccctcag        60
tctatgatcc agaaaatcaa gattgcttga ggccctgttc ggttgttccg gattagagcc       120
ccggattaat tcctagccgg attacttctc taatttatat agattttgat gagctggaat       180
gaatcctggc ttattccggt acaaccgaac aggccctgaa ggataccagt aatcgctgag       240
ctaaattggc atgctgtcag agtgtcagta ttgcagcaag gtagtgagat aaccggcatc       300
atggtgccag tttgatggca ccattagggt tagagatggt ggccatgggc gcatgtcctg       360
gccaactttg tatgatatat ggcagggtga ataggaaagt aaaattgtat tgtaaaaagg       420
gatttcttct gtttgttagc gcatgtacaa ggaatgcaag ttttgagcga gggggcatca       480
aagatctggc tgtgtttcca gctgtttttg ttagccccat cgaatccttg acataatgat       540
cccgcttaaa taagcaacct cgcttgtata gttccttgtg ctctaacaca cgatgatgat       600
aagtcgtaaa atagtggtgt ccaaagaatt tccaggccca gttgtaaaag ctaaaatgct       660
attcgaattt ctactagcag taagtcgtgt ttagaaatta ttttttttata taccttttt       720 ccttctatgt acagtaggac acagtgtcag cgccgcgttg acggagaata tttgcaaaaa       780
agtaaaagag aaagtcatag cggcgtatgt gccaaaaact tcgtcacaga gagggccata       840
agaaacatgg cccacggccc aatacgaagc accgcgacga agcccaaaca gcagtccgta       900
ggtggagcaa agcgctgggt aatacgcaaa cgttttgtcc caccttgact aatcacaaga       960
gtggagcgta ccttataaac cgagccgcaa gcaccgaatt gttaaatctg acgtgaatct      1020
gttgttttag agctagaaat agcaagttaa ataaggcta gtccgttatc aacttgaaaa      1080
agtggcaccg agtcggtgct tttttttt                                        1108

<210> SEQ ID NO 246
<211> LENGTH: 1106
<212> TYPE: DNA
<213> ORGANISM: Artificial Sequence
<220> FEATURE:
<223> OTHER INFORMATION: synthesized sequence- MHP14Cas-3 gRNA cassette

<400> SEQUENCE: 246
tgagagtaca atgatgaacc tagattaatc aatgccaaag tctgaaaaat gcaccctcag        60
tctatgatcc agaaaatcaa gattgcttga ggccctgttc ggttgttccg gattagagcc       120
ccggattaat tcctagccgg attacttctc taatttatat agattttgat gagctggaat       180
gaatcctggc ttattccggt acaaccgaac aggccctgaa ggataccagt aatcgctgag       240
ctaaattggc atgctgtcag agtgtcagta ttgcagcaag gtagtgagat aaccggcatc       300
atggtgccag tttgatggca ccattagggt tagagatggt ggccatgggc gcatgtcctg       360
gccaactttg tatgatatat ggcagggtga ataggaaagt aaaattgtat tgtaaaaagg       420
gatttcttct gtttgttagc gcatgtacaa ggaatgcaag ttttgagcga gggggcatca       480

```
aagatctggc tgtgtttcca gctgttttg  ttagccccat cgaatccttg acataatgat      540
cccgcttaaa taagcaacct cgcttgtata gttccttgtg ctctaacaca cgatgatgat      600
aagtcgtaaa atagtggtgt ccaaagaatt ccaggccca  gttgtaaaag ctaaatgct       660 attcgaattt ctactagcag taagtcgtgt ttagaaatta ttttttttata tacctttttt      720 ccttctatgt acagtaggac acagtgtcag cgccgcgttg acggagaata tttgcaaaaa      780
agtaaaagag aaagtcatag cggcgtatgt gccaaaaact tcgtcacaga gagggccata      840
agaaacatgg cccacggccc aatacgaagc accgcgacga agcccaaaca gcagtccgta      900
ggtggagcaa agcgctgggt aatacgcaaa cgttttgtcc caccttgact aatcacaaga      960
gtggagcgta ccttataaac cgagccgcaa gcaccgaatt gcaaacattg aagcgacata     1020
ggttttagag ctagaaatag caagttaaaa taaggctagt ccgttatcaa cttgaaaaag     1080
tggcaccgag tcggtgcttt tttttt                                          1106

<210> SEQ ID NO 247
<211> LENGTH: 1103
<212> TYPE: DNA
<213> ORGANISM: Artificial Sequence
<220> FEATURE:
<223> OTHER INFORMATION: synthesized sequence- TS8Cas-1 guideRNA
      cassette

<400> SEQUENCE: 247
tgagagtaca atgatgaacc tagattaatc aatgccaaag tctgaaaaat gcaccctcag       60
tctatgatcc agaaaatcaa gattgcttga ggccctgttc ggttgttccg gattagagcc      120
ccggattaat tcctagccgg attacttctc taatttatat agattttgat gagctggaat      180
gaatcctggc ttattccggt acaaccgaac aggccctgaa ggataccagt aatcgctgag      240
ctaaattggc atgctgtcag agtgtcagta ttgcagcaag gtagtgagat aaccggcatc      300
atggtgccag tttgatggca ccattagggt tagagatggt ggccatgggc gcatgtcctg      360
gccaactttg tatgatatat ggcagggtga ataggaaagt aaaattgtat tgtaaaaagg      420
gatttcttct gtttgttagc gcatgtacaa ggaatgcaag ttttgagcga gggggcatca      480
aagatctggc tgtgtttcca gctgttttg  ttagccccat cgaatccttg acataatgat      540
cccgcttaaa taagcaacct cgcttgtata gttccttgtg ctctaacaca cgatgatgat      600
aagtcgtaaa atagtggtgt ccaaagaatt ccaggccca  gttgtaaaag ctaaatgct       660 attcgaattt ctactagcag taagtcgtgt ttagaaatta ttttttttata tacctttttt      720 ccttctatgt acagtaggac acagtgtcag cgccgcgttg acggagaata tttgcaaaaa      780
agtaaaagag aaagtcatag cggcgtatgt gccaaaaact tcgtcacaga gagggccata      840
agaaacatgg cccacggccc aatacgaagc accgcgacga agcccaaaca gcagtccgta      900
ggtggagcaa agcgctgggt aatacgcaaa cgttttgtcc caccttgact aatcacaaga      960
gtggagcgta ccttataaac cgagccgcaa gcaccgaatt gtacgtaacg tgcagtacgt     1020
tttagagcta gaaatagcaa gttaaaataa ggctagtccg ttatcaactt gaaaaagtgg     1080
caccgagtcg gtgctttttt ttt                                             1103

<210> SEQ ID NO 248
<211> LENGTH: 1105
<212> TYPE: DNA
<213> ORGANISM: Artificial Sequence
<220> FEATURE:
<223> OTHER INFORMATION: synthesized sequence- TS8Cas-2 guideRNA
``` cassette

<400> SEQUENCE: 248

```
tgagagtaca atgatgaacc tagattaatc aatgccaaag tctgaaaaat gcaccctcag      60
tctatgatcc agaaaatcaa gattgcttga ggccctgttc ggttgttccg gattagagcc     120
ccggattaat tcctagccgg attacttctc taatttatat agattttgat gagctggaat    180
gaatcctggc ttattccggt acaaccgaac aggccctgaa ggataccagt aatcgctgag    240
ctaaattggc atgctgtcag agtgtcagta ttgcagcaag gtagtgagat aaccggcatc    300
atggtgccag tttgatggca ccattagggt tagagatggt ggccatgggc gcatgtcctg    360
gccaactttg tatgatatat ggcagggtga ataggaaagt aaaattgtat tgtaaaaagg    420
gatttcttct gtttgttagc gcatgtacaa ggaatgcaag ttttgagcga ggggcatca     480
aagatctggc tgtgtttcca gctgttttg ttagccccat cgaatccttg acataatgat    540
cccgcttaaa taagcaacct cgcttgtata gttccttgtg ctctaacaca cgatgatgat   600
aagtcgtaaa atagtggtgt ccaaagaatt tccaggccca gttgtaaaag ctaaaatgct    660
attcgaattt ctactagcag taagtcgtgt ttagaaatta tttttttata tacctttttt   720
ccttctatgt acagtaggac acagtgtcag cgccgcgttg acggagaata tttgcaaaaa    780
agtaaaagag aaagtcatag cggcgtatgt gccaaaaact tcgtcacaga gagggccata    840
agaaacatgg cccacggccc aatacgaagc accgcgacga gcccaaaca gcagtccgta   900
ggtggagcaa agcgctgggt aatacgcaaa cgttttgtcc caccttgact aatcacaaga    960
gtggagcgta cctataaaac cgagccgcaa gcaccgaatt gctcatcagt gatcagctgg    1020
gttttagagc tagaaatagc aagttaaaat aaggctagtc cgttatcaac ttgaaaaagt    1080
ggcaccgagt cggtgctttt ttttt                                            1105
```

<210> SEQ ID NO 249
<211> LENGTH: 1102
<212> TYPE: DNA
<213> ORGANISM: Artificial Sequence
<220> FEATURE:
<223> OTHER INFORMATION: synthesized sequence- TS9Cas-2 guideRNA
      cassette

<400> SEQUENCE: 249

```
tgagagtaca atgatgaacc tagattaatc aatgccaaag tctgaaaaat gcaccctcag      60
tctatgatcc agaaaatcaa gattgcttga ggccctgttc ggttgttccg gattagagcc     120
ccggattaat tcctagccgg attacttctc taatttatat agattttgat gagctggaat    180
gaatcctggc ttattccggt acaaccgaac aggccctgaa ggataccagt aatcgctgag    240
ctaaattggc atgctgtcag agtgtcagta ttgcagcaag gtagtgagat aaccggcatc    300
atggtgccag tttgatggca ccattagggt tagagatggt ggccatgggc gcatgtcctg    360
gccaactttg tatgatatat ggcagggtga ataggaaagt aaaattgtat tgtaaaaagg    420
gatttcttct gtttgttagc gcatgtacaa ggaatgcaag ttttgagcga ggggcatca     480
aagatctggc tgtgtttcca gctgttttg ttagccccat cgaatccttg acataatgat    540
cccgcttaaa taagcaacct cgcttgtata gttccttgtg ctctaacaca cgatgatgat   600
aagtcgtaaa atagtggtgt ccaaagaatt tccaggccca gttgtaaaag ctaaaatgct    660
attcgaattt ctactagcag taagtcgtgt ttagaaatta tttttttata tacctttttt   720
ccttctatgt acagtaggac acagtgtcag cgccgcgttg acggagaata tttgcaaaaa    780
```

```
agtaaaagag aaagtcatag cggcgtatgt gccaaaaact tcgtcacaga gagggccata    840
agaaacatgg cccacggccc aatacgaagc accgcgacga agcccaaaca gcagtccgta    900
ggtggagcaa agcgctgggt aatacgcaaa cgttttgtcc caccttgact aatcacaaga    960
gtggagcgta ccttataaac cgagccgcaa gcaccgaatt ggctgtttgc ggcctcggtt   1020
ttagagctag aaatagcaag ttaaaataag gctagtccgt tatcaacttg aaaaagtggc   1080
accgagtcgg tgcttttttt tt                                             1102
```

<210> SEQ ID NO 250
<211> LENGTH: 1106
<212> TYPE: DNA
<213> ORGANISM: Artificial Sequence
<220> FEATURE:
<223> OTHER INFORMATION: synthesized sequence- TS9Cas-3 guideRNA cassette

<400> SEQUENCE: 250

```
tgagagtaca atgatgaacc tagattaatc aatgccaaag tctgaaaaat gcaccctcag     60
tctatgatcc agaaaatcaa gattgcttga ggccctgttc ggttgttccg gattagagcc    120
ccggattaat tcctagccgg attacttctc taatttatat agattttgat gagctggaat    180
gaatcctggc ttattccggt acaaccgaac aggccctgaa ggataccagt aatcgctgag    240
ctaaattggc atgctgtcag agtgtcagta ttgcagcaag gtagtgagat aaccggcatc    300
atggtgccag tttgatggca ccattagggt tagagatggt ggccatgggc gcatgtcctg    360
gccaactttg tatgatatat ggcagggtga ataggaaagt aaaattgtat tgtaaaaagg    420
gatttcttct gtttgttagc gcatgtacaa ggaatgcaag ttttgagcga gggggcatca    480
aagatctggc tgtgtttcca gctgtttttg ttagccccat cgaatccttg acataatgat    540
cccgcttaaa taagcaacct cgcttgtata gttccttgtg ctctaacaca cgatgatgat    600
aagtcgtaaa atagtggtgt ccaaagaatt tccaggccca gttgtaaaag ctaaaatgct    660
attcgaattt ctactagcag taagtcgtgt ttagaaatta ttttttttata tacctttttt    720 ccttctatgt acagtaggac acagtgtcag cgccgcgttg acggagaata tttgcaaaaa    780
agtaaaagag aaagtcatag cggcgtatgt gccaaaaact tcgtcacaga gagggccata    840
agaaacatgg cccacggccc aatacgaagc accgcgacga agcccaaaca gcagtccgta    900
ggtggagcaa agcgctgggt aatacgcaaa cgttttgtcc caccttgact aatcacaaga    960
gtggagcgta ccttataaac cgagccgcaa gcaccgaatt ggctcgaggt tgcacgcacg   1020
tgttttagag ctagaaatag caagttaaaa taaggctagt ccgttatcaa cttgaaaaag   1080
tggcaccgag tcggtgcttt tttttt                                         1106
```

<210> SEQ ID NO 251
<211> LENGTH: 1105
<212> TYPE: DNA
<213> ORGANISM: Artificial Sequence
<220> FEATURE:
<223> OTHER INFORMATION: synthesized sequence- TS10Cas-1 guideRNA cassette

<400> SEQUENCE: 251

```
tgagagtaca atgatgaacc tagattaatc aatgccaaag tctgaaaaat gcaccctcag     60
tctatgatcc agaaaatcaa gattgcttga ggccctgttc ggttgttccg gattagagcc    120
ccggattaat tcctagccgg attacttctc taatttatat agattttgat gagctggaat    180
gaatcctggc ttattccggt acaaccgaac aggccctgaa ggataccagt aatcgctgag    240
```

```
ctaaattggc atgctgtcag agtgtcagta ttgcagcaag gtagtgagat aaccggcatc    300
atggtgccag tttgatggca ccattagggt tagagatggt ggccatgggc gcatgtcctg    360
gccaactttg tatgatatat ggcagggtga ataggaaagt aaaattgtat tgtaaaaagg    420
gatttcttct gtttgttagc gcatgtacaa ggaatgcaag ttttgagcga gggggcatca    480
aagatctggc tgtgtttcca gctgttttgt ttagccccat cgaatccttg acataatgat    540
cccgcttaaa taagcaacct cgcttgtata gttccttgtg ctctaacaca cgatgatgat    600
aagtcgtaaa atagtggtgt ccaaagaatt ccaggccca gttgtaaaag ctaaatgct     660 attcgaattt ctactagcag taagtcgtgt ttagaaatta ttttttttata tacctttttt    720 ccttctatgt acagtaggac acagtgtcag cgccgcgttg acggagaata tttgcaaaaa    780
agtaaaagag aaagtcatag cggcgtatgt gccaaaaact tcgtcacaga gagggccata    840
agaaacatgg cccacggccc aatacgaagc accgcgacga agcccaaaca gcagtccgta    900
ggtggagcaa agcgctgggt aatacgcaaa cgttttgtcc caccttgact aatcacaaga    960
gtggagcgta ccttataaac cgagccgcaa gcaccgaatt gcctcgcctt cgctagttaa   1020
gttttagagc tagaaatagc aagttaaaat aaggctagtc cgttatcaac ttgaaaaagt   1080
ggcaccgagt cggtgctttt ttttt                                          1105

<210> SEQ ID NO 252
<211> LENGTH: 1103
<212> TYPE: DNA
<213> ORGANISM: Artificial Sequence
<220> FEATURE:
<223> OTHER INFORMATION: synthesized sequence- TSCas-3 guideRNA cassette

<400> SEQUENCE: 252
tgagagtaca atgatgaacc tagattaatc aatgccaaag tctgaaaaat gcaccctcag     60
tctatgatcc agaaaatcaa gattgcttga ggccctgttc ggttgttccg gattagagcc    120
ccggattaat tcctagccgg attacttctc taatttatat agattttgat gagctggaat    180
gaatcctggc ttattccggt acaaccgaac aggccctgaa ggataccagt aatcgctgag    240
ctaaattggc atgctgtcag agtgtcagta ttgcagcaag gtagtgagat aaccggcatc    300
atggtgccag tttgatggca ccattagggt tagagatggt ggccatgggc gcatgtcctg    360
gccaactttg tatgatatat ggcagggtga ataggaaagt aaaattgtat tgtaaaaagg    420
gatttcttct gtttgttagc gcatgtacaa ggaatgcaag ttttgagcga gggggcatca    480
aagatctggc tgtgtttcca gctgttttgt ttagccccat cgaatccttg acataatgat    540
cccgcttaaa taagcaacct cgcttgtata gttccttgtg ctctaacaca cgatgatgat    600
aagtcgtaaa atagtggtgt ccaaagaatt ccaggccca gttgtaaaag ctaaatgct     660 attcgaattt ctactagcag taagtcgtgt ttagaaatta ttttttttata tacctttttt    720 ccttctatgt acagtaggac acagtgtcag cgccgcgttg acggagaata tttgcaaaaa    780
agtaaaagag aaagtcatag cggcgtatgt gccaaaaact tcgtcacaga gagggccata    840
agaaacatgg cccacggccc aatacgaagc accgcgacga agcccaaaca gcagtccgta    900
ggtggagcaa agcgctgggt aatacgcaaa cgttttgtcc caccttgact aatcacaaga    960
gtggagcgta ccttataaac cgagccgcaa gcaccgaatt gctcgtgttg agatacagt    1020 tttagagcta gaaatagcaa gttaaaataa ggctagtccg ttatcaactt gaaaagtgg    1080 caccgagtcg gtgcttttt ttt                                            1103
```

<210> SEQ ID NO 253
<211> LENGTH: 4928
<212> TYPE: DNA
<213> ORGANISM: Artificial Sequence
<220> FEATURE:
<223> OTHER INFORMATION: synthesized sequence- MHP14Cas1 donor

<400> SEQUENCE: 253

| | | | | | |
|---|---|---|---|---|---|
| gccatgtcat | cttgtagtta | gggcttggag | ctagtcgacc | gttggaggct | ttgtcctcat | 60 |
| gcggcaccgg | acagtctggt | gctacaccgg | acagtccggt | gccctctga | ccatctgctc | 120 |
| tgacatctga | attgcactgt | tcactttgca | gagtcgacca | ttgcgtgcag | gtagccattg | 180 |
| ctccgctggt | gcaccggaca | gtccagtggc | acaccggaca | gtccgatgaa | ttatagcgga | 240 |
| gctgcgcctg | ggaaacccga | agctgaggag | tttgagctga | ttcaccctgg | tgcaccggac | 300 |
| actgtccggt | ggcacactgg | acagtccggt | gcgccggacc | agggcacact | tcggtttcct | 360 |
| ttttgctcct | ttcttttgaa | gcctaacttg | ttcttttgat | tggtttgtgt | tgaacccttta | 420 |
| gcacctgtag | aatgtatgat | ctagagcaaa | ctagttagtc | caattatttg | tgttgggcaa | 480 |
| ttcaaccacc | aaaaacattt | aggaaaatgt | ttgatcttat | ttccctttca | tattctctta | 540 |
| ttgctagttg | tcggggtgaa | gttgagctct | tgcttaggtt | ttaattagtg | ttgatttta | 600 |
| gaaaaaccca | attcaccccc | ctcttgggca | tcgtgatcct | tttagcaaca | aaatgtgcac | 660 |
| acatcaaaac | aagcgcttct | accatatgta | gttgttgcac | aataatggtc | ctccttagga | 720 |
| tttgcaaccg | tttaacaata | gctatgtgac | cacagattta | tgtcggatgc | acgaaaattg | 780 |
| taggatttta | catttctttta | ccttggttca | caaacattga | agcgacatag | tggtgtatga | 840 |
| aaggaagcac | ttgttttttca | attccaaacc | gcggtaccat | ttaaatctta | agcctaggat | 900 |
| aacttcgtat | agcatacatt | atacgaagtt | atggcgccgc | tagcctgcag | tgcagcgtga | 960 |
| cccggtcgtg | ccctctcta | gagataatga | gcattgcatg | tctaagttat | aaaaaattac | 1020 |
| cacatatttt | ttttgtcaca | cttgtttgaa | gtgcagttta | tctatctta | tacatatatt | 1080 |
| taaactttac | tctacgaata | atataatcta | tagtactaca | ataatatcag | tgttttagag | 1140 |
| aatcatataa | atgaacagtt | agacatggtc | taaaggacaa | ttgagtattt | tgacaacagg | 1200 |
| actctacagt | tttatctttt | tagtgtgcat | gtgttctcct | tttttttttgc | aaatagcttc | 1260 |
| acctatataa | tacttcatcc | attttattag | tacatccatt | tagggtttag | ggttaatggt | 1320 |
| ttttatagac | taatttttttt | agtacatcta | ttttattcta | ttttagcctc | taaattaaga | 1380 |
| aaactaaaac | tctattttag | ttttttttatt | taataattta | gatataaaat | agaataaaat | 1440 |
| aaagtgacta | aaaattaaac | aaataccctt | taagaaatta | aaaaaactaa | ggaaacattt | 1500 |
| ttcttgtttc | gagtagataa | tgccagcctg | ttaaacgccg | tcgacgagtc | taacggacac | 1560 |
| caaccagcga | accagcagcg | tcgcgtcggg | ccaagcgaag | cagacggcac | ggcatctctg | 1620 |
| tcgctgcctc | tggaccccctc | tcgagagttc | cgctccaccg | ttggacttgc | tccgctgtcg | 1680 |
| gcatccagaa | attgcgtggc | ggagcggcag | acgtgagccg | gcacggcagg | cggcctcctc | 1740 |
| ctcctctcac | ggcaccggca | gctacggggg | attccttttcc | caccgctcct | tcgctttccc | 1800 |
| ttcctcgccc | gccgtaataa | atagacaccc | cctccacacc | ctctttcccc | aacctcgtgt | 1860 |
| tgttcggagc | gcacacacac | acaaccagat | ctcccccaaa | tccaccccgtc | ggcacctccg | 1920 |
| cttcaaggta | cgccgctcgt | cctccccccc | cccctctct | accttctcta | gatcggcgtt | 1980 |
| ccggtccatg | catggttagg | gcccggtagt | tctacttctg | ttcatgtttg | tgttagatcc | 2040 |
| gtgtttgtgt | tagatccgtg | ctgctagcgt | tcgtacacgg | atgcgacctg | tacgtcagac | 2100 |

-continued

```
acgttctgat tgctaacttg ccagtgtttc tctttgggga atcctgggat ggctctagcc   2160
gttccgcaga cgggatcgat ttcatgattt tttttgtttc gttgcatagg gtttggtttg   2220 ccctttcct ttatttcaat atatgccgtg cacttgtttg tcgggtcatc ttttcatgct    2280 ttttttgtc ttggttgtga tgatgtggtc tggttgggcg gtcgttctag atcggagtag    2340
aattctgttt caaactacct ggtggattta ttaattttgg atctgtatgt gtgtgccata   2400
catattcata gttacgaatt gaagatgatg gatggaaata tcgatctagg ataggtatac   2460
atgttgatgc gggttttact gatgcatata cagagatgct ttttgttcgc ttggttgtga   2520
tgatgtggtg tggttgggcg gtcgttcatt cgttctagat cggagtagaa tactgtttca   2580
aactacctgg tgtatttatt aattttggaa ctgtatgtgt gtgtcataca tcttcatagt   2640
tacgagttta agatggatgg aaatatcgat ctaggatagg tatacatgtt gatgtgggtt   2700
ttactgatgc atatacatga tggcatatgc agcatctatt catatgctct aaccttgagt   2760
acctatctat tataataaac aagtatgttt tataattatt ttgatcttga tatacttgga   2820
tgatggcata tgcagcagct atatgtggat ttttttagcc ctgccttcat acgctattta   2880
tttgcttggt actgtttctt ttgtcgatgc tcaccctgtt gtttggtgtt acttctgcag   2940
gtcgactcta gaggatcaat tcgctagcga agttcctatt ccgaagttcc tattctctag   3000
aaagtatagg aacttcagat ccaccgggat ccccgatcat gcaaaaactc attaactcag   3060
tgcaaaacta tgcctggggc agcaaaacgg cgttgactga actttatggt atggaaaatc   3120
cgtccagcca gccgatggcc gagctgtgga tgggcgcaca tccgaaaagc agttcacgag   3180
tgcagaatgc cgccggagat atcgtttcac tgcgtgatgt gattgagagt gataaatcga   3240
ctctgctcgg agaggccgtt gccaaacgct tggcgaact gcctttcctg ttcaaagtat    3300
tatgcgcagc acagccactc tccattcagg ttcatccaaa caaacacaat tctgaaatcg   3360
gttttgccaa agaaaatgcc gcaggtatcc cgatggatgc cgccgagcgt aactataaag   3420
atcctaacca caagccggag ctggtttttg cgctgacgcc tttccttgcg atgaacgcgt   3480
ttcgtgaatt ttccgagatt gtctccctac tccagccggt cgcaggtgca catccggcga   3540
ttgctcactt tttacaacag cctgatgccg aacgtttaag cgaactgttc gccagcctgt   3600
tgaatatgca gggtgaagaa aaatcccgcg cgctggcgat tttaaaatcg gccctcgata   3660
gccagcaggg tgaaccgtgg caaacgattc gtttaatttc tgaattttac ccggaagaca   3720
gcggtctgtt ctccccgcta ttgctgaatg tggtgaaatt gaaccctggc gaagcgatgt   3780
tcctgttcgc tgaaacaccg cacgcttacc tgcaaggcgt ggcgctggaa gtgatggcaa   3840
actccgataa cgtgctgcgt gcgggtctga cgcctaaata cattgatatt ccggaactgg   3900
ttgccaatgt gaaattcgaa gccaaacagg ctaaccagtt gttgacccag ccggtgaaac   3960
aaggtgcaga actggacttc ccgattccag tggatgattt tgccttctcg ctgcatgacc   4020
ttagtgataa agaaaccacc attagccagc agagtgccgc catttgttc tgcgtcgaag    4080 gcgatgcaac gttgtggaaa ggttctcagc agttacagct taaaccgggt gaatcagcgt   4140
ttattgccgc caacgaatca ccggtgactg tcaaaggcca cggccgttta gcgcgtgttt   4200
acaacaagct gtaagagctt actgaaaaaa ttaacatctc ttgctaagct gggggtggaa   4260
cctagacttg tccatcttct ggattggcca acttaattaa tgtatgaaat aaaaggatgc   4320
acacatagtg acatgctaat cactataatg tgggcatcaa agttgtgtgt tatgtgtaat   4380
tactagttat ctgaataaaa gagaaagaga tcatccatat ttcttatcct aaatgaatgt   4440
```

```
cacgtgtctt tataattctt tgatgaacca gatgcatttc attaaccaaa tccatataca    4500
tataaatatt aatcatatat aattaatatc aattgggtta gcaaaacaaa tctagtctag    4560
gtgtgttttg cgaatgcggc cctagcgtat acgaagttcc tattccgaag ttcctattct    4620
ccagaaagta taggaacttc tgtacacctg agctgattcc gatgacttcg taggttccta    4680
gctcaagccg ctcgtgtcca agcgtcactt acgattagct aatgattacg gcatctagga    4740
ccgactagct aactaactag taccgaggcc ggccccgcgg gagctcggcg cgccagattc    4800
acgtcagatt taaccaaaac tatattatga ggtacacata ttacaatcca aaatgaatta    4860
tctagttctc gagttgtaca cagtttatca cgtgttttac acattccaac cctaaactcc    4920
aaccgtgg                                                             4928

<210> SEQ ID NO 254
<211> LENGTH: 4570
<212> TYPE: DNA
<213> ORGANISM: Artificial Sequence
<220> FEATURE:
<223> OTHER INFORMATION: synthesized sequence- MHP14Cas3 donor

<400> SEQUENCE: 254
acacttcggt ttccttttg ctcctttctt ttgaagccta acttgttctt ttgattggtt       60
tgtgttgaac ctttagcacc tgtagaatgt atgatctaga gcaaactagt tagtccaatt      120
atttgtgttg ggcaattcaa ccaccaaaaa catttaggaa aatgtttgat cttatttccc      180
tttcatattc tcttattgct agttgtcggg gtgaagttga gctcttgctt aggttttaat      240
tagtgttgat tttagaaaaa acccaattca cccccctctt gggcatcgtg atccttttag      300
caacaaaatg tgcacacatc aaaacaagcg cttctaccat atgtagttgt tgcacaataa      360
tggtcctcct taggatttgc aaccgtttaa caatagctat gtgaccacag atttatgtcg      420
gatgcacgaa aattgtagga ttttacattt ctttaccttg gttcacaaac attgaagcga      480
caggtaccat ttaaatctta agcctaggat aacttcgtat agcatacatt atacgaagtt      540
atggcgccgc tagcctgcag tgcagcgtga cccggtcgtg cccctctcta gagataatga      600
gcattgcatg tctaagttat aaaaaattac cacatatttt ttttgtcaca cttgtttgaa      660
gtgcagttta tctatcttta tacatatatt taaactttac tctacgaata atataatcta      720
tagtactaca ataatatcag tgttttagag aatcatataa atgaacagtt agacatggtc      780
taaaggacaa ttgagtattt tgacaacagg actctacagt tttatctttt tagtgtgcat      840
gtgttctcct tttttttgc aaatagcttc acctatataa tacttcatcc attttattag       900
tacatccatt tagggtttag ggttaatggt tttatagac taatttttt agtacatcta         960 ttttattcta tttagcctc taaattaaga aaactaaaac tctattttag ttttttatt        1020 taataattta gatataaaat agaataaaat aaagtgacta aaaattaaac aaatacccctt     1080 taagaaatta aaaaaactaa ggaaacattt ttcttgtttc gagtagataa tgccagcctg      1140
ttaaacgccg tcgacgagtc taacggacac caaccagcga accagcagcg tcgcgtcggg      1200
ccaagcgaag cagacggcac ggcatctctg tcgctgcctc tggacccctc tcgagagttc      1260
cgctccaccg ttggacttgc tccgctgtcg gcatccagaa attgcgtggc ggagcggcag      1320
acgtgagccg gcacggcagg cggcctcctc ctcctctcac ggcaccggca gctacggggg      1380
attcctttcc caccgctcct tcgctttccc ttcctcgccc gccgtaataa atagacaccc      1440
cctccacacc ctctttcccc aacctcgtgt tgttcggagc gcacacacac acaaccgat      1500 ctcccccaaa tccacccgtc ggcacctccg cttcaaggta cgccgctcgt cctccccccc     1560
```

```
ccccctctct accttctcta gatcggcgtt ccggtccatg catggttagg gcccggtagt    1620
tctacttctg ttcatgtttg tgttagatcc gtgtttgtgt tagatccgtg ctgctagcgt    1680
tcgtacacgg atgcgacctg tacgtcagac acgttctgat tgctaacttg ccagtgtttc    1740
tctttgggga atcctgggat ggctctagcc gttccgcaga cgggatcgat ttcatgattt    1800
tttttgtttc gttgcatagg gtttggtttg ccctttcct ttatttcaat atatgccgtg     1860
cacttgtttg tcgggtcatc ttttcatgct ttttttgtc ttggttgtga tgatgtggtc     1920
tggttgggcg gtcgttctag atcggagtag aattctgttt caaactacct ggtggattta    1980
ttaattttgg atctgtatgt gtgtgccata catattcata gttacgaatt gaagatgatg    2040
gatggaaata tcgatctagg ataggtatac atgttgatgc gggttttact gatgcatata    2100
cagagatgct ttttgttcgc ttggttgtga tgatgtggtg tggttgggcg gtcgttcatt    2160
cgttctagat cggagtagaa tactgtttca aactacctgg tgtatttatt aattttggaa    2220
ctgtatgtgt gtgtcataca tcttcatagt tacgagttta agatggatgg aaatatcgat    2280
ctaggatagg tatacatgtt gatgtgggtt ttactgatgc atatacatga tggcatatgc    2340
agcatctatt catatgctct aaccttgagt acctatctat tataataaac aagtatgttt    2400
tataattatt ttgatcttga tatacttgga tgatggcata tgcagcagct atatgtggat    2460
ttttttagcc ctgccttcat acgctattta tttgcttggt actgtttctt ttgtcgatgc    2520
tcaccctgtt gtttggtgtt acttctgcag gtcgactcta gaggatcaat tcgctagcga    2580
agttcctatt ccgaagttcc tattctctag aaagtatagg aacttcagat ccaccgggat    2640
ccccgatcat gcaaaaactc attaactcag tgcaaaacta tgcctggggc agcaaaacgg    2700
cgttgactga actttatggt atggaaaatc cgtccagcca gccgatggcc gagctgtgga    2760
tgggcgcaca tccgaaaagc agttcacgag tgcagaatgc cgccggagat atcgtttcac    2820
tgcgtgatgt gattgagagt gataaatcga ctctgctcgg agaggccgtt gccaaacgct    2880
ttggcgaact gccttttcctg ttcaaagtat tatgcgcagc acagccactc tccattcagg    2940
ttcatccaaa caaacacaat tctgaaatcg gttttgccaa agaaaatgcc gcaggtatcc    3000
cgatggatgc cgccgagcgt aactataaag atcctaacca aagccggag ctggtttttg     3060 cgctgacgcc tttccttgcg atgaacgcgt tcgtgaatt ttccgagatt gtctccctac      3120
tccagccggt cgcaggtgca catccggcga ttgctcactt tttacaacag cctgatgccg    3180
aacgtttaag cgaactgttc gccagcctgt tgaatatgca gggtgaagaa aaatcccgcg    3240
cgctggcgat tttaaaatcg gccctcgata gccagcaggg tgaaccgtgg caaacgattc    3300
gtttaatttc tgaattttac ccggaagaca gcggtctgtt ctccccgcta ttgctgaatg    3360
tggtgaaatt gaaccctggc gaagcgatgt tcctgttcgc tgaaacaccg cacgcttacc    3420
tgcaaggcgt ggcgctggaa gtgatggcaa actccgataa cgtgctgcgt gcgggtctga    3480
cgcctaaata cattgatatt ccggaactgg ttgccaatgt gaaattcgaa gccaaaccgg    3540
ctaaccagtt gttgacccag ccggtgaaac aaggtgcaga actggacttc ccgattccag    3600
tggatgattt tgccttctcg ctgcatgacc ttagtgataa agaaaccacc attagccagc    3660
agagtgccgc cattttgttc tgcgtcgaag gcgatgcaac gttgtggaaa ggttctcagc    3720
agttacagct taaaccgggt gaatcagcgt ttattgccgc caacgaatca ccggtgactg    3780
tcaaaggcca cggccgttta gcgcgtgttt acaacaagct gtaagagctt actgaaaaaa    3840
ttaacatctc ttgctaagct gggggtggaa cctagacttg tccatcttct ggattggcca    3900
```

```
acttaattaa tgtatgaaat aaaaggatgc acacatagtg acatgctaat cactataatg     3960
tgggcatcaa agttgtgtgt tatgtgtaat tactagttat ctgaataaaa gagaaagaga     4020
tcatccatat ttcttatcct aaatgaatgt cacgtgtctt tataattctt tgatgaacca     4080
gatgcatttc attaaccaaa tccatataca tataaatatt aatcatatat aattaatatc     4140
aattgggtta gcaaaacaaa tctagtctag gtgtgttttg cgaatgcggc cctagcgtat     4200
acgaagttcc tattccgaag ttcctattct ccagaaagta taggaacttc tgtacacctg     4260
agctgattcc gatgacttcg taggttccta gctcaagccg ctcgtgtcca agcgtcactt     4320
acgattagct aatgattacg gcatctagga ccgactagct aactaactag taccgaggcc     4380
ggccccgcgg gagctcggcg cgcctagtgg tgtatgaaag gaagcacttg ttttcaatt      4440 ccaaacagat tcacgtcaga tttaaccaaa actatattat gaggtacaca tattacaatc     4500
caaaatgaat tatctagttc tcgagttgta cacagtttat cacgtgtttt acacattcca     4560
accctaaact                                                            4570
```

<210> SEQ ID NO 255
<211> LENGTH: 5091
<212> TYPE: DNA
<213> ORGANISM: Artificial Sequence
<220> FEATURE:
<223> OTHER INFORMATION: synthesized sequence- TS8Cas-1 donor

<400> SEQUENCE: 255

```
cacacatgac tgcctgagaa tctgctgccg ttgcctctca tattatattc gatcccctga       60
ctaaaaaaac tcggggccgg ctaatacgta ctgtacgtac gcagaattta cggtccagca      120
cgggcatgcc gcgcgggctg actttgctcc actgactcga tcatgtgcgg attccatcgc      180
ggcgtagcgt agccaaccgc aacgcaaacc gacttcatct ttttttttta ttatgaacaa      240
aaggagatcg agagaaacgt gaacggtaaa taatatatct gatcccatgc atgcacgctg      300
cctgggtcga tctcgctctc gctccgccca gacgaacatg catgctggtc aggctcaacg      360
ctcaggcggg caagctgtgg gaggacatgg gatgggagag gaggacacat gcatgctggc      420
cagtcaggca ctgtgctggc acatgaggta gggatagggg ggccctcggc cagtgtccag      480
gccgcatgca tgcatgcccc ccctgctgct cgaccgaaca acgttggatg cctggattga      540
tgcaacagtt tggacggacg gaccatacgt tatgtaccag taggtaccat ttaaatctta      600
agcctaggat aacttcgtat agcatacatt atacgaagtt atggcgccgc tagcctgcag      660
tgcagcgtga cccggtcgtg cccctctcta gagataatga gcattgcatg tctaagttat      720
aaaaaattac cacatatttt ttttgtcaca cttgtttgaa gtgcagttta tctatcttta      780
tacatatatt taaactttac tctacgaata atataatcta tagtactaca ataatatcag      840
tgttttagag aatcatataa atgaacagtt agacatggtc taaaggacaa ttgagtatt       900 tgacaacagg actctacagt tttatctttt tagtgtgcat gtgttctcct ttttttttgc      960
aaatagcttc acctatataa tacttcatcc atttattag tacatccatt tagggtttag      1020
ggttaatggt ttttatagac taatttttt agtacatcta ttttattcta ttttagcctc      1080
taaattaaga aaactaaaac tctatttag tttttttatt taataattta gatataaaat      1140
agaataaaat aaagtgacta aaattaaac aaatacccct taagaaatta aaaaaactaa      1200
ggaaacattt tccttgtttc gagtagataa tgccagcctg ttaaacgccg tcgacgagtc      1260
taacggacac caaccagcga accagcagcg tcgcgtcggg ccaagcgaag cagacggcac      1320
ggcatctctg tcgctgcctc tggaccccctc tcgagagttc cgctccaccg ttggacttgc      1380
```

-continued

```
tccgctgtcg gcatccagaa attgcgtggc ggagcggcag acgtgagccg gcacggcagg    1440
cggcctcctc ctcctctcac ggcaccggca gctacggggg attcctttcc caccgctcct    1500
tcgctttccc ttcctcgccc gccgtaataa atagacaccc cctccacacc ctctttcccc    1560
aacctcgtgt tgttcggagc gcacacacac acaaccagat ctcccccaaa tccaccggtc    1620
ggcacctccg cttcaaggta cgccgctcgt cctccccccc ccccctctct accttctcta    1680
gatcggcgtt ccggtccatg catggttagg gcccggtagt tctacttctg ttcatgtttg    1740
tgttagatcc gtgtttgtgt tagatccgtg ctgctagcgt tcgtacacgg atgcgacctg    1800
tacgtcagac acgttctgat tgctaacttg ccagtgtttc tctttgggga atcctgggat    1860
ggctctagcc gttccgcaga cgggatcgat ttcatgattt tttttgtttc gttgcatagg    1920
gtttggtttg cccttttcct ttatttcaat atatgccgtg cacttgtttg tcgggtcatc    1980
ttttcatgct ttttttttgtc ttggttgtga tgatgtggtc tggttgggcg gtcgttctag    2040
atcggagtag aattcgtttt caaactacct ggtggattta ttaattttgg atctgtatgt    2100
gtgtgccata catattcata gttacgaatt gaagatgatg gatggaaata tcgatctagg    2160
ataggtatac atgttgatgc gggttttact gatgcatata cagagatgct tttttgttcgc   2220
ttggttgtga tgatgtggtg tggttgggcg gtcgttcatt cgttctagat cggagtagaa    2280
tactgtttca aactacctgg tgtatttatt aattttggaa ctgtatgtgt gtgtcataca    2340
tcttcatagt tacgagttta agatggatgg aaatatcgat ctaggatagg tatacatgtt    2400
gatgtgggtt ttactgatgc atatacatga tggcatatgc agcatctatt catatgctct    2460
aaccttgagt acctatctat tataataaac aagtatgttt tataattatt ttgatcttga    2520
tatacttgga tgatggcata tgcagcagct atatgtggat ttttttagcc ctgccttcat    2580
acgctattta tttgcttggt actgtttctt ttgtcgatgc tcaccctgtt gtttggtgtt    2640
acttctgcag gtcgactcta gaggatcaat tcgctagcga agttcctatt ccgaagttcc    2700
tattctctag aaagtatagg aacttcagat ccaccgggat ccccgatcat gcaaaaactc    2760
attaactcag tgcaaaacta tgcctggggc agcaaaacgg cgttgactga actttatggt    2820
atggaaaatc cgtccagcca gccgatggcc gagctgtgga tgggcgcaca tccgaaaagc    2880
agttcacgag tgcagaatgc cgccggagat atcgtttcac tgcgtgatgt gattgagagt    2940
gataaatcga ctctgctcgg agaggccgtt gccaaacgct ttggcgaact gccttttcctg   3000
ttcaaagtat tatgcgcagc acagccactc tccattcagg ttcatccaaa caaacacaat    3060
tctgaaatcg gttttgccaa agaaaatgcc gcaggtatcc cgatggatgc cgccgagcgt    3120
aactataaag atcctaacca caagccggag ctggttttttg cgctgacgcc tttccttgcg    3180
atgaacgcgt tcgtgaatt ttccgagatt gtctccctac tccagccggt cgcaggtgca    3240
catccggcga ttgctcactt tttacaacag cctgatgccg aacgtttaag cgaactgttc    3300
gccagcctgt tgaatatgca gggtgaagaa aaatcccgcg cgctggcgat tttaaaatcg    3360
gccctcgata gccagcaggg tgaaccgtgg caaacgattc gtttaatttc tgaattttac    3420
ccggaagaca cgcgtctgtt ctccccgcta ttgctgaatg tggtgaaatt gaaccctggc    3480
gaagcgatgt tcctgttcgc tgaaacaccg cacgcttacc tgcaaggcgt ggcgctggaa    3540
gtgatggcaa actccgataa cgtgctgcgt gcgggtctga cgcctaaata cattgatatt    3600
ccggaactgg ttgccaatgt gaaattcgaa gccaaccggg ctaaccagtt gttgacccag    3660
ccggtgaaac aaggtgcaga actggacttc ccgattccag tggatgattt tgccttctcg    3720
```

```
ctgcatgacc ttagtgataa agaaaccacc attagccagc agagtgccgc catttttgttc    3780
tgcgtcgaag gcgatgcaac gttgtggaaa ggttctcagc agttacagct taaaccgggt    3840
gaatcagcgt ttattgccgc caacgaatca ccggtgactg tcaaaggcca cggccgttta    3900
gcgcgtgttt acaacaagct gtaagagctt actgaaaaaa ttaacatctc ttgctaagct    3960
gggggtggaa cctagacttg tccatcttct ggattggcca acttaattaa tgtatgaaat    4020
aaaaggatgc acacatagtg acatgctaat cactataatg tgggcatcaa agttgtgtgt    4080
tatgtgtaat tactagttat ctgaataaaa gagaaagaga tcatccatat ttcttatcct    4140
aaatgaatgt cacgtgtctt tataattctt tgatgaacca gatgcatttc attaaccaaa    4200
tccatataca tataaatatt aatcatatat aattaatatc aattgggtta gcaaaacaaa    4260
tctagtctag gtgtgttttg cgaatgcggc cctagcgtat acgaagttcc tattccgaag    4320
ttcctattct ccagaaagta taggaacttc tgtacacctg agctgattcc gatgacttcg    4380
taggttccta gctcaagccg ctcgtgtcca agcgtcactt acgattagct aatgattacg    4440
gcatctagga ccgactagct aactaactag taccgaggcc ggccccgcgg actgcacgtt    4500
acgtacgtac gaactaatat actccaccag ctgatcactg atgagccgag ccgccatgca    4560
ttgtaattta taacatgtgc ggctgtacgc ttccatctca ataccttttt tatatatata    4620
ttgtacttta tagtctacga cataatctgc catggtaatt tataagatgt gctttattgc    4680
tcgttgttct gttctcatct gtgtccatgg catggcatgg atacaaaatg tatgtatggc    4740
cacgcatcca atctgtgacg ttgtcaaggc agaggtccaa ccgtccaaga ccctcttgtg    4800
ccgccctgta cttgcagtca gtgacgttgt gagaaaaagc tgtgggtggt ctccgcagag    4860
cgcgcgggcc acgagaggga gccccatctc tcggccgagg ggtacggggg ctccagacac    4920
ggtcctttgg tttcttctgc ctgtagcgag cggccccgcc ccccaccgcg ctgctagcct    4980
agccgatgct gatccatcca ccacccacaa gggattgttc cacgacttgt ggacctgacc    5040
atgacgtgac ttcacgccat gtacgctcag ccgctcacta gctttttttt c             5091
```

<210> SEQ ID NO 256
<211> LENGTH: 5237
<212> TYPE: DNA
<213> ORGANISM: Artificial Sequence
<220> FEATURE:
<223> OTHER INFORMATION: synthesized sequence- TS8Cas-2 donor

<400> SEQUENCE: 256

```
tctctttcag ggcttgttcg tttacgttgg attgcacccg gaatcgttac agctaatcaa      60
agtttatata aattagagaa gcaaccggat aggaatcgtt ccgacccacc aattcgacac     120
aaacgaacaa ggcctcaatc cttctcaatc cacctccaac ccaataagct cttggaggcg     180
gcggcgggag agcagccaca cacatgactg cctgagaatc tgctgccgtt gcctctcata     240
ttatattcga tcccctgact aaaaaaaactc ggggccggct aatacgtact gtacgtacgc     300
agaatttacg gtccagcacg ggcatgccgc gcgggctgac tttgctccac tgactcgatc     360
atgtgcggat tccatcgcgg cgtagcgtag ccaaccgcaa cgcaaaccga cttcatcttt     420
tttttttatt atgaacaaaa ggagatcgag agaaacgtga acggtaaata atatatctga     480
tcccatgcat gcacgctgcc tgggtcgatc tcgctctcgc tccgcccaga cgaacatgca     540
tgctggtcag gctcaacgct caggcgggca agctgtggga ggacatggga tgggagagga     600
ggacacatgc atgctggcca gtcaggcact gtgctggcac atgaggtagg ataggggggg     660
ccctcggcca gtgtccaggc cgcatgcatg catgcccccc ctgctgctcg accgaacaac     720
```

```
gttggatgcc tggattgatg caacagtttg gacggacgga ccatacgtta tgtaccagta    780
ctgcacgtta cgtacgtacg aactaatata ctccaccagg taccatttaa atcttaagcc    840
taggataact tcgtatagca tacattatac gaagttatgg cgccgctagc ctgcagtgca    900
gcgtgacccg gtcgtgcccc tctctagaga taatgagcat tgcatgtcta agttataaaa    960
aattaccaca tatttttttt gtcacacttg tttgaagtgc agtttatcta tctttataca   1020
tatatttaaa ctttactcta cgaataatat aatctatagt actacaataa tatcagtgtt   1080
ttagagaatc atataaatga acagttagac atggtctaaa ggacaattga gtattttgac   1140
aacaggactc tacagtttta tcttttttagt gtgcatgtgt tctccttttt ttttgcaaat   1200
agcttcacct atataatact tcatccattt tattagtaca tccatttagg gtttagggtt   1260
aatggttttt atagactaat ttttttagta catctatttt attctatttt agcctctaaa   1320
ttaagaaaac taaaactcta ttttagttttt tttatttaat aatttagata taaaatagaa   1380
taaaataaag tgactaaaaa ttaaacaaat acccttttaag aaattaaaaa aactaaggaa   1440
acattttttct tgtttcgagt agataatgcc agcctgttaa acgccgtcga cgagtctaac   1500
ggacaccaac cagcgaacca gcagcgtcgc gtcgggccaa gcgaagcaga cggcacggca   1560
tctctgtcgc tgcctctgga cccctctcga gagttccgct ccaccgttgg acttgctccg   1620
ctgtcggcat ccagaaattg cgtggcggag cggcagacgt gagccggcac ggcaggcggc   1680
ctcctcctcc tctcacggca ccggcagcta cgggggattc ctttcccacc gctccttcgc   1740
tttcccttcc tcgcccgccg taataaatag acacccctc cacaccctct ttccccaacc   1800
tcgtgttgtt cggagcgcac acacacacaa ccagatctcc cccaaatcca cccgtcggca   1860
cctccgcttc aaggtacgcc gctcgtcctc cccccccccc ctctctacct tctctagatc   1920
ggcgttccgg tccatgcatg gttagggccc ggtagttcta cttctgttca tgtttgtgtt   1980
agatccgtgt ttgtgttaga tccgtgctgc tagcgttcgt acacggatgc gacctgtacg   2040
tcagacacgt tctgattgct aacttgccag tgtttctctt tggggaatcc tgggatggct   2100
ctagccgttc cgcagacggg atcgatttca tgattttttt tgtttcgttg catagggttt   2160
ggtttgccct tttcctttat ttcaatatat gccgtgcact tgtttgtcgg tcatcttttt   2220
catgcttttt tttgtcttgg ttgtgatgat gtggtctggt tgggcggtcg ttctagatcg   2280
gagtagaatt ctgtttcaaa ctacctggtg gatttattaa ttttggatct gtatgtgtgt   2340
gccatacata ttcatagtta cgaattgaag atgatggatg gaaatatcga tctaggatag   2400
gtatacatgt tgatgcgggt tttactgatg catatacaga gatgctttttt gttcgcttgg   2460
ttgtgatgat gtggtgtggt tgggcggtcg ttcattcgtt ctagatcgga gtagaatact   2520
gtttcaaact acctggtgta tttattaatt ttggaactgt atgtgtgtgt catacatctt   2580
catagttacg agtttaagat ggatggaaat atcgatctag ataggtata catgttgatg   2640
tgggttttac tgatgcatat acatgatggc atatgcagca tctattcata tgctctaacc   2700
ttgagtacct atctattata ataaacaagt atgttttata attattttga tcttgatata   2760
cttggatgat ggcatatgca gcagctatat gtggattttt ttagccctgc cttcatacgc   2820
tatttatttg cttggtactg tttcttttgt cgatgctcac cctgttgttt ggtgttactt   2880
ctgcaggtcg actctagagg atcaattcgc tagcgaagtt cctattccga agttcctatt   2940
ctctagaaag tataggaact tcagatccac cgggatcccc gatcatgcaa aaactcatta   3000
actcagtgca aaactatgcc tggggcagca aaacggcgtt gactgaactt tatggtatgg   3060
```

```
aaaatccgtc cagccagccg atggccgagc tgtggatggg cgcacatccg aaaagcagtt    3120
cacgagtgca gaatgccgcc ggagatatcg tttcactgcg tgatgtgatt gagagtgata    3180
aatcgactct gctcggagag gccgttgcca aacgctttgg cgaactgcct ttcctgttca    3240
aagtattatg cgcagcacag ccactctcca ttcaggttca tccaaacaaa cacaattctg    3300
aaatcggttt tgccaaagaa aatgccgcag gtatcccgat ggatgccgcc gagcgtaact    3360
ataaagatcc taaccacaag ccggagctgg tttttgcgct gacgcctttc cttgcgatga    3420
acgcgtttcg tgaattttcc gagattgtct ccctactcca gccggtcgca ggtgcacatc    3480
cggcgattgc tcacttttta caacagcctg atgccgaacg tttaagcgaa ctgttcgcca    3540
gcctgttgaa tatgcagggt gaagaaaaat cccgcgcgct ggcgatttta aaatcggccc    3600
tcgatagcca gcagggtgaa ccgtggcaaa cgattcgttt aatttctgaa ttttacccgg    3660
aagacagcgg tctgttctcc ccgctattgc tgaatgtggt gaaattgaac cctggcgaag    3720
cgatgttcct gttcgctgaa acaccgcacg cttacctgca aggcgtggcg ctggaagtga    3780
tggcaaactc cgataacgtg ctgcgtgcgg gtctgacgcc taaatacatt gatattccgg    3840
aactggttgc caatgtgaaa ttcgaagcca aaccggctaa ccagttgttg acccagccgg    3900
tgaaacaagg tgcagaactg gacttcccga ttccagtgga tgattttgcc ttctcgctgc    3960
atgaccttag tgataaagaa accaccatta gccagcagag tgccgccatt ttgttctgcg    4020
tcgaaggcga tgcaacgttg tggaaaggtt ctcagcagtt acagcttaaa ccgggtgaat    4080
cagcgtttat tgccgccaac gaatcaccgg tgactgtcaa aggccacggc cgtttagcgc    4140
gtgtttacaa caagctgtaa gagcttactg aaaaaattaa catctcttgc taagctgggg    4200
gtggaaccta gacttgtcca tcttctggat tggccaactt aattaatgta tgaaataaaa    4260
ggatgcacac atagtgacat gctaatcact ataatgtggg catcaaagtt gtgtgttatg    4320
tgtaattact agttatctga ataaaagaga aagagatcat ccatatttct tatcctaaat    4380
gaatgtcacg tgtctttata attctttgat gaaccagatg catttcatta accaaatcca    4440
tatacatata aatattaatc atatataatt aatatcaatt gggttagcaa aacaaatcta    4500
gtctaggtgt gttttgcgaa tgcggcccta gcgtatacga agttcctatt ccgaagttcc    4560
tattctccag aaagtatagg aacttctgta cacctgagct gattccgatg acttcgtagg    4620
ttcctagctc aagccgctcg tgtccaagcg tcacttacga ttagctaatg attacggcat    4680
ctaggaccga ctagctaact aactagtacc gaggccggcc ccgcgggagc tcgctgatca    4740
ctgatgagcc gagccgccat gcattgtaat ttataacatg tgcggctgta cgcttccatc    4800
tcaaatacct ttttatatat atattgtact ttatagtcta cgacataatc tgccatggta    4860
atttataaga tgtgctttat tgctcgttgt tctgttctca tctgtgtcca tggcatggca    4920
tggatacaaa atgtatgtat ggccacgcat ccaatctgtg acgttgtcaa ggcagaggtc    4980
caaccgtcca agaccctctt gtgccgcccct gtacttgcag tcagtgacgt tgtgagaaaa    5040
agctgtgggt ggtctccgca gagcgcgcgg gccacgagag ggagcccccat ctctcggccg    5100 aggggtacgg gggctccaga cacggtcctt tggtttcttc tgcctgtagc gagcggcccc    5160
gccccccacc gcgctgctag cctagccgat gctgatccat ccaccaccca caagggattg    5220
ttccacgact tgtggac                                                  5237
```

<210> SEQ ID NO 257
<211> LENGTH: 5427
<212> TYPE: DNA
<213> ORGANISM: Artificial Sequence
<220> FEATURE:
<223> OTHER INFORMATION: synthesized sequence- TS9Cas-2 donor

<400> SEQUENCE: 257

```
agcaaggaac taaactgtta ttggacgcta agtttagta ctttatcttt aacatctttc      60
agcatttcta tgtagatatt taagggctaa attttagcaa gtgtgctgat aaattttagc     120
ctaaatgttt ctgttgggct aaattttagc aagtgtactg ttaaatttta gcatattcct    180
tttagagtgg tatgggtgtg catagactaa atgtttccgt tgggccctaa tttaacgatg    240
tgtacgcagg cctgtttaga tgacttggta ccggcatatg gcctcgtact gtttcatttg    300
atgacgcgag cgtgcggccc atgcagcagc agcacgccgg gaaggcagcg gattttgaag    360
tactattgga cagcgcggcg cggggaccgg gtcgttggcg cgcggtggag tgggggtggg    420
tggtcctggc gtcctgccct gcgcgatggt cgatggatgc cccatgcgcg tgtaaccgcc    480
cagccgtcgc catccgacca ggtgggcaga cgtacgtacg gtggcacgcc cacggcccat    540
cggccatcgc gatcgcgttc gtatcgtgtc ctcaataacg aaagcgccaa cggaaggcgc    600
tgtcgtcgtc agttcaccgc gcgccggcgc cctgtgtcct cgtccctctc gacttctcga    660
ccagtaagaa ctctcgcgag ctgcggagct gctggcgatg gccggccggt gggatccgac    720
gtgcgtgcaa cctcgaattt aaatcttaag cctaggataa cttcgtatag catacattat    780
acgaagttat ggcgccgcta gcctgcagtg cagcgtgacc cggtcgtgcc cctctctaga    840
gataatgagc attgcatgtc taagttataa aaaattacca catattttttt ttgtcacact    900
tgtttgaagt gcagtttatc tatctttata catatattta aactttactc tacgaataat    960
ataatctata gtactacaat aatatcagtg ttttagagaa tcatataaat gaacagttag   1020
acatggtcta aaggacaatt gagtattttg acaacaggac tctacagttt tatctttta    1080
gtgtgcatgt gttctccttt tttttgcaa atagcttcac ctatataata cttcatccat    1140
tttattagta catccattta gggtttaggg ttaatggttt ttatagacta attttttag   1200
tacatctatt ttattctatt ttagcctcta aattaagaaa actaaaactc tatttttagtt    1260
tttttattta ataatttaga tataaaatag aataaaataa agtgactaaa aattaaacaa    1320
ataccctta agaaattaaa aaaactaagg aaacatttt cttgtttcga gtagataatg     1380
ccagcctgtt aaacgccgtc gacgagtcta acggacacca accagcgaac cagcagcgtc   1440
gcgtcgggcc aagcgaagca gacggcacgg catctctgtc gctgcctctg gacccctctc   1500
gagagttccg ctccaccgtt ggacttgctc cgctgtcggc atccagaaat tgcgtggcgg    1560
agcggcagac gtgagccggc acggcaggcg gcctcctcct cctctcacgg caccggcagc    1620
tacgggggat tcctttccca ccgctccttc gctttccctt cctcgcccgc cgtaataaat    1680
agacaccccc tccacaccct ctttcccaa cctcgtgttg ttcggagcgc acacacacac    1740
aaccagatct cccccaaatc caccgtcgg cacctccgct tcaaggtacg ccgctcgtcc     1800
tccccccccc ccctctctac cttctctaga tcggcgttcc ggtccatgca tggttagggc    1860
ccggtagttc tacttctgtt catgtttgtg ttagatccgt gtttgtgtta gatccgtgct    1920
gctagcgttc gtacacggat gcgacctgta cgtcagacac gttctgattg ctaacttgcc    1980
agtgtttctc tttggggaat cctgggatgg ctctagccgt tccgcagacg ggatcgattt    2040
catgattttt tttgtttcgt tgcatagggt ttggtttgcc ctttccttt atttcaatat    2100
atgccgtgca cttgtttgtc gggtcatctt ttcatgcttt ttttgtctt ggttgtgatg    2160
atgtggtctg gttgggcggt cgttctagat cggagtagaa ttctgtttca aactacctgg    2220
```

```
tggatttatt aattttggat ctgtatgtgt gtgccataca tattcatagt tacgaattga    2280
agatgatgga tggaaatatc gatctaggat aggtatacat gttgatgcgg gttttactga    2340
tgcatataca gagatgcttt ttgttcgctt ggttgtgatg atgtggtgtg gttgggcggt    2400
cgttcattcg ttctagatcg gagtagaata ctgtttcaaa ctacctggtg tatttattaa    2460
ttttggaact gtatgtgtgt gtcatacatc ttcatagtta cgagtttaag atggatggaa    2520
atatcgatct aggataggta tacatgttga tgtgggtttt actgatgcat atacatgatg    2580
gcatatgcag catctattca tatgctctaa ccttgagtac ctatctatta aataaacaa     2640 gtatgtttta taattatttt gatcttgata tacttggatg atggcatatg cagcagctat    2700
atgtggattt ttttagccct gccttcatac gctatttatt tgcttggtac tgtttctttt    2760
gtcgatgctc accctgttgt ttggtgttac ttctgcaggt cgactctaga ggatcaattc    2820
gctagcgaag ttcctattcc gaagttccta ttctctagaa agtataggaa cttcagatcc    2880
accgggatcc ccgatcatgc aaaaactcat taactcagtg caaaactatg cctggggcag    2940
caaaacggcg ttgactgaac tttatggtat ggaaaatccg tccagccagc cgatggccga    3000
gctgtggatg ggcgcacatc cgaaaagcag ttcacgagtg cagaatgccg ccggagatat    3060
cgtttcactc gtgatgtga ttgagagtga taaatcgact ctgctcggag aggccgttgc     3120
caaacgcttt ggcgaactgc ctttcctgtt caaagtatta tgcgcagcac agccactctc    3180
cattcaggtt catccaaaca aacacaattc tgaaatcggt tttgccaaag aaaatgccgc    3240
aggtatcccg atggatgccg ccgagcgtaa ctataaagat cctaaccaca gccggagct     3300 ggttttgcg ctgacgcctt tccttgcgat gaacgcgttt cgtgaatttt ccagagattgt    3360 ctccctactc cagccggtcg caggtgcaca tccggcgatt gctcacttt tacaacagcc     3420 tgatgccgaa cgtttaagcg aactgttcgc cagcctgttg aatatgcagg gtgaagaaaa    3480
atcccgcgcg ctggcgattt taaaatcggc cctcgatagc cagcagggtg aaccgtggca    3540
aacgattcgt ttaatttctg aattttaccc ggaagacagc ggtctgttct ccccgctatt    3600
gctgaatgtg gtgaaattga accctggcga agcgatgttc ctgttcgctg aaacaccgca    3660
cgcttacctg caaggcgtgg cgctggaagt gatggcaaac tccgataacg tgctgcgtgc    3720
gggtctgacg cctaaataca ttgatattcc ggaactggtt gccaatgtga aattcgaagc    3780
caaaccggct aaccagttgt tgacccagcc ggtgaaacaa ggtgcagaac tggacttccc    3840
gattccagtg atgattttg ccttctcgct gcatgacctt agtgataaag aaaccaccat     3900
tagccagcag agtgccgcca ttttgttctg cgtcgaaggc gatgcaacgt gtgtgaaagg    3960
ttctcagcag ttacagctta aaccgggtga atcagcgttt attgccgcca acgaatcacc    4020
ggtgactgtc aaaggccacg gccgtttagc gcgtgtttac aacaagctgt aagagcttac    4080
tgaaaaaatt aacatctctt gctaagctgg gggtggaacc tagacttgtc catcttctgg    4140
attggccaac ttaattaatg tatgaaataa aaggatgcac acatagtgac atgctaatca    4200
ctataatgtg ggcatcaaag ttgtgtgtta tgtgtaatta ctagttatct gaataaaaga    4260
gaaagagatc atccatattt cttatcctaa atgaatgtca cgtgtcttta taattctttg    4320
atgaaccaga tgcatttcat taaccaaatc catatacata taaatattaa tcatatataa    4380
ttaatatcaa ttgggttagc aaaacaaatc tagtctaggt gtgttttgcg aatgcggccc    4440
tagcgtatac gaagttccta ttccgaagtt cctattctcc agaaagtata ggaacttctg    4500
tacacctgag ctgattccga tgcttcgta ggttcctagc tcaagccgct cgtgtccaag     4560
cgtcacttac gattagctaa tgattacggc atctaggacc gactagctaa ctaactagta    4620
```

```
ccgaggccgg ccccgcggga gctcggccgc aaacagcctg gtgacagacg aagccagcaa    4680
gcacgtacgt acgcacgtct ctgctggtct ggatgtgtat ggatatggac gtctcacgtc    4740
tggacgtcgt cgtcgccgtt gtattgtatc atgccaacca cttccgtacc gtacccctc     4800 gcgtgccaac atgaccaccg ccggtacgtc tccatcgtcg gccgtcggcg tctcaggcag    4860
ctctcaatta agcggacgtg ttttggtaat ctggtggaac gccgcgcgca ctgagggttt    4920
gggggccccg gcggacgagc gagcgagaga cggtgcatgc atgccaaatg caacgaggg    4980 cccgcccgcc catccaataa ccaacccaga cgtagcgcaa ccaacgtacg agtcctgtgc    5040
tggcgcgtac gactaccacg ctagctgccg cgacatgcga actacggtcc accaggcacc    5100
agccatgaca atatatactg tatatatatt tttcttcttc tttttgtttc cgctctctca    5160
agttcctgct ctgctcctgc ctgtccgcgg tgccgatcgg cgagagagca tgcatggaca    5220
tggaccacgc gagatccagg aaccggcacg ggcccatgcg tggcaggcgg ccgtttcgtc    5280
aggttccccg aaatgcccca actgcgcggc tgcaggatgg ctcatggctg ctgcctagc    5340 tggcccgtga caccgatcga tcggtaacga cgacgcacgc acctgaagca caggaaggag    5400
cctccctctc gcatgcacgt tagtact                                         5427

<210> SEQ ID NO 258
<211> LENGTH: 5426
<212> TYPE: DNA
<213> ORGANISM: Artificial Sequence
<220> FEATURE:
<223> OTHER INFORMATION: synthesized sequence- TS9Cas-3 donor

<400> SEQUENCE: 258
agcaaggaac taaactgtta ttggacgcaa agtttagtac tttatcttta acatctttca      60
gcatttctat gtagatattt aagggctaaa ttttagcaag tgtgctgata aattttagcc     120
taaatgtttc tgttgggcta aattttagca agtgtactgt taaattttag catattcctt     180
ttagagtggt atgggtgtgc atagactaaa tgtttccgtt gggccctaat ttaacgatgt     240
gtacgcaggc ctgtttagat gacttggtac cggcatatgg cctcgtactg tttcatttga     300
tgacgcgagc gtgcggccca tgcagcagca gcacgccggg aaggcagcgg attttgaagt     360
actattggac agcgcggcgc ggggaccggg tcgttggcgc gcggtggagt gggggtgggt    420
ggtcctggcg tcctgccctg cgcgatggtc gatggatgcc ccatgcgcgt gtaaccgccc    480
agccgtcgcc atccgaccag gtgggcagac gtacgtacgg tggcacgccc acggcccatc    540
ggccatcgcg atcgcgttcg tatcgtgtcc tcaataacga aagcgccaac ggaaggcgct    600
gtcgtcgtca gttcaccgcg cgccggcgcc ctgtgtcctc gtccctctcg acttctcgac    660
cagtaagaac tctcgcgagc tgcggagctg ctggcgatgg ccggccggtg ggatccgacg    720
atttaaatct taagcctagg ataacttcgt atagcataca ttatacgaag ttatggcgcc    780
gctagcctgc agtgcagcgt gacccggtcg tgccctctc tagagataat gagcattgca    840
tgtctaagtt ataaaaaatt accacatatt ttttttgtca cacttgttg aagtgcagtt      900 tatctatctt tatacatata tttaaactt actctacgaa taatataatc tatagtacta    960
caataatatc agtgttttag agaatcatat aaatgaacag ttagacatgg tctaaaggac   1020
aattgagtat tttgacaaca ggactctaca gttttatctt tttagtgtgc atgtgttctc    1080
cttttttttt gcaaatagct tcacctatat aatacttcat ccatttatt agtcatcca     1140 tttagggttt agggttaatg gttttatag actaattttt ttagtacatc tattttattc    1200
```

```
tattttagcc tctaaattaa gaaaactaaa actctatttt agttttttta tttaataatt      1260
tagatataaa atagaataaa ataaagtgac taaaaattaa acaaataccc tttaagaaat      1320
taaaaaaact aaggaaacat ttttcttgtt tcgagtagat aatgccagcc tgttaaacgc      1380
cgtcgacgag tctaacggac accaaccagc gaaccagcag cgtcgcgtcg ggccaagcga      1440
agcagacggc acggcatctc tgtcgctgcc tctggacccc tctcgagagt tccgctccac      1500
cgttggactt gctccgctgt cggcatccag aaattgcgtg gcggagcggc agacgtgagc      1560
cggcacggca ggcggcctcc tcctcctctc acggcaccgg cagctacggg ggattccttt      1620
cccaccgctc cttcgctttc ccttcctcgc ccgccgtaat aaatagacac ccctccaca      1680 ccctctttcc ccaacctcgt gttgttcgga gcgcacacac acacaaccag atctccccca      1740
aatccacccg tcggcacctc cgcttcaagg tacgccgctc gtcctccccc cccccctct      1800 ctaccttctc tagatcggcg ttccggtcca tgcatggtta gggcccggta gttctacttc      1860
tgttcatgtt tgtgttagat ccgtgtttgt gttagatccg tgctgctagc gttcgtacac      1920
ggatgcgacc tgtacgtcag acacgttctg attgctaact tgccagtgtt tctctttggg      1980
gaatcctggg atggctctag ccgttccgca gacgggatcg atttcatgat ttttttttgtt     2040 tcgttgcata gggtttggtt tgcccttttc ctttatttca atatatgccg tgcacttgtt      2100
tgtcgggtca tcttttcatg cttttttttg tcttggttgt gatgatgtgg tctggttggg      2160
cggtcgttct agatcggagt agaattctgt ttcaaactac ctggtggatt tattaattt      2220 ggatctgtat gtgtgtgcca tacatattca tagttacgaa ttgaagatga tggatggaaa      2280
tatcgatcta ggataggtat acatgttgat gcgggtttta ctgatgcata tacagagatg      2340 cttttttgttc gcttggttgt gatgatgtgg tgtggttggg cggtcgttca ttcgttctag      2400
atcggagtag aatactgttt caaactacct ggtgtattta ttaattttgg aactgtatgt      2460
gtgtgtcata catcttcata gttacgagtt taagatggat ggaaatatcg atctaggata      2520
ggtatacatg ttgatgtggg ttttactgat gcatatacat gatggcatat gcagcatcta      2580
ttcatatgct ctaaccttga gtacctatct attataataa acaagtatgt tttataatta      2640
ttttgatctt gatatacttg gatgatggca tatgcagcag ctatatgtgg attttttag      2700 ccctgccttc atacgctatt tatttgcttg gtactgtttc ttttgtcgat gctcaccctg      2760
ttgtttggtg ttacttctgc aggtcgactc tagaggatca attcgctagc gaagttccta      2820
ttccgaagtt cctattctct agaaagtata ggaacttcag atccaccggg atccccgatc      2880
atgcaaaaac tcattaactc agtgcaaaac tatgcctggg gcagcaaaac ggcgttgact      2940
gaactttatg gtatggaaaa tccgtccagc cagccgatgg ccgagctgtg gatgggcgca      3000
catccgaaaa gcagttcacg agtgcagaat gccgccggag atatcgtttc actgcgtgat      3060
gtgattgaga gtgataaatc gactctgctc ggagaggccg ttgccaaacg ctttggcgaa      3120
ctgcctttcc tgttcaaagt attatgcgca gcacagccac tctccattca ggttcatcca      3180
aacaaacaca attctgaaat cggttttgcc aaagaaaatg ccgcaggtat cccgatggat      3240
gccgccgagc gtaactataa agatcctaac cacaagccgg agctggtttt tgcgctgacg      3300
cctttccttg cgatgaacgc gtttcgtgaa ttttccgaga ttgtctccct actccagccg      3360
gtcgcaggtg cacatccggc gattgctcac ttttacaac agcctgatgc cgaacgttta      3420
agcgaactgt tcgccagcct gttgaatatg cagggtgaag aaaaatcccg cgcgctggcg      3480
attttaaaat cggccctcga tagccagcag ggtgaaccgt ggcaaacgat tcgtttaatt      3540
tctgaatttt acccggaaga cagcggtctg ttctccccgc tattgctgaa tgtggtgaaa      3600
```

```
ttgaaccctg gcgaagcgat gttcctgttc gctgaaacac cgcacgctta cctgcaaggc    3660
gtggcgctgg aagtgatggc aaactccgat aacgtgctgc gtgcgggtct gacgcctaaa    3720
tacattgata ttccggaact ggttgccaat gtgaaattcg aagccaaacc ggctaaccag    3780
ttgttgaccc agccggtgaa acaaggtgca gaactggact tcccgattcc agtggatgat    3840
tttgccttct cgctgcatga ccttagtgat aaagaaacca ccattagcca gcagagtgcc    3900
gccattttgt tctgcgtcga aggcgatgca acgttgtgga aggttctca gcagttacag     3960 cttaaaccgg gtgaatcagc gtttattgcc gccaacgaat caccggtgac tgtcaaaggc    4020
cacggccgtt tagcgcgtgt ttacaacaag ctgtaagagc ttactgaaaa aattaacatc    4080
tcttgctaag ctgggggtgg aacctagact tgtccatctt ctggattggc aacttaatt    4140 aatgtatgaa ataaaaggat gcacacatag tgacatgcta atcactataa tgtgggcatc    4200
aaagttgtgt gttatgtgta attactagtt atctgaataa aagagaaaga gatcatccat    4260
atttcttatc ctaaatgaat gtcacgtgtc tttataattc tttgatgaac cagatgcatt    4320
tcattaacca aatccatata catataaata ttaatcatat ataattaata tcaattgggt    4380
tagcaaaaca aatctagtct aggtgtgttt tgcgaatgcg gccctagcgt atacgaagtt    4440
cctattccga agttcctatt ctccagaaag tataggaact tctgtacacc tgagctgatt    4500
ccgatgactt cgtaggttcc tagctcaagc cgctcgtgtc caagcgtcac ttacgattag    4560
ctaatgatta cggcatctag gaccgactag ctaactaact agtaccgagg ccggccccgc    4620
gggagctctg cgtgcaacct cgaggccgca aacagcctgg tgacagacga agccagcaag    4680
cacgtacgta cgcacgtctc tgctggtctg gatgtgtatg gatatggacg tctcacgtct    4740
ggacgtcgtc gtcgccgttg tattgtatca tgccaaccac ttccgtaccg taccccctcg    4800
cgtgccaaca tgaccaccgc cggtacgtct ccatcgtcgg ccgtcggcgt ctcaggcagc    4860
tctcaattaa gcggacgtgt tttggtaatc tggtggaacg ccgcgcgcac tgagggtttg    4920
ggggccccgg cggacgagcg agcgagagac ggtgcatgca tgccaaatgg caacgagggc    4980
ccgcccgccc atccaataac caacccagac gtagcgcaac caacgtacga gtcctgtgct    5040
ggcgcgtacg actaccacgc tagctgccgc gacatgcgaa ctacggtcca ccaggcacca    5100
gccatgacaa tatatactgt atatatattt ttcttcttct ttttgtttcc gctctctcaa    5160
gttcctgctc tgctcctgcc tgtccgcggt gccgatcggc gagagagcat gcatggacat    5220
ggaccacgcg agatccagga accggcacgg gcccatgcgt ggcaggcggc cgtttcgtca    5280
ggttccccga aatgccccaa ctgcgcggct gcaggatggc tcatggctgg ctgcctagct    5340
ggcccgtgac accgatcgat cggtaacgac gacgcacgca cctgaagcac aggaaggagc    5400
ctccctctcg catgcacgtt agtact                                          5426
```

<210> SEQ ID NO 259
<211> LENGTH: 5152
<212> TYPE: DNA
<213> ORGANISM: Artificial Sequence
<220> FEATURE:
<223> OTHER INFORMATION: synthesized sequence- TS10Cas-1 donor

<400> SEQUENCE: 259

```
ggtaccaaat agtaaacggg aggggaggtc gctagtagta aacgctaggt agctaggata      60
atccgtctcg tgttggacgg aaggttttgg acgcatctgc gtgcacagcc cgctgataca     120
gatctgatcg actagctagc tagatgccga ggccccagag caaggcccgg atactcctgc     180
```

```
acagtccctg agatttcagc acagcaggtg ctgttgcatc aatatataaa tccctgcttt    240
attaatttaa tctctgtgca tgtatccata catcgtcagc ggctcagcgc tatcacactg    300
cagtgcacgc agctagttga gcgcctgggt cagtatatat atagctagta gggacaaagg    360
ggggcactgt acgttggttt ggtttggcac gcacgcgatc gagagtggtg gaatggactg    420
cagatcatcg atcgctgcac tgtacgcacg cgcaccggac tgcatttgca tgcccctgaa    480
ggaggaaagg ggaaggaaag aaaagaaata ggagaaagaa gaagaagcag agaaatacgt    540
cacagtccaa gaagagtgag ccgccctagc tagcttcaac cctgacgaac ccggcagcca    600
cacttccggc catgtatgca tgcatgcatg gcttagcttc agatgtccaa tcgaatccat    660
caagacctgg ccggttttcc atggccgcct cgccttcgct agtggtacca tttaaatctt    720
aagcctagga taacttcgta tagcatacat tatacgaagt tatggcgccg ctagcctgca    780
gtgcagcgtg acccggtcgt gcccctctct agagataatg agcattgcat gtctaagtta    840
taaaaaatta ccacatattt tttttgtcac acttgtttga agtgcagttt atctatcttt    900
atacatatat ttaaacttta ctctacgaat aatataatct atagtactac aataatatca    960
gtgtttagaa gaatcatata aatgaacagt tagacatggt ctaaaggaca attgagtatt   1020
ttgacaacag gactctacag ttttatcttt ttagtgtgca tgtgttctcc tttttttttg   1080
caaatagctt cacctatata atacttcatc cattttatta gtacatccat ttagggttta   1140
gggttaatgg ttttttataga ctaatttttt tagtacatct attttattct attttagcct   1200
ctaaattaag aaaactaaaa ctctatttta gttttttttat ttaataattt agatataaaa   1260
tagaataaaa taaagtgact aaaaattaaa caaataccct ttaagaaatt aaaaaaacta   1320
aggaaacatt tttcttgttt cgagtagata atgccagcct gttaaacgcc gtcgacgagt   1380
ctaacggaca ccaaccagcg aaccagcagc gtcgcgtcgg gccaagcgaa gcagacggca   1440
cggcatctct gtcgctgcct ctggacccct ctcgagagtt ccgctccacc gttggacttg   1500
ctccgctgtc ggcatccaga aattgcgtgg cggagcggca gacgtgagcc ggcacggcag   1560
gcggcctcct cctcctctca cggcaccggc agctacgggg gattcctttc ccaccgctcc   1620
ttcgcttttcc cttcctcgcc cgccgtaata aatagacacc cctccacac cctctttccc   1680
caacctcgtg ttgttcggag cgcacacaca cacaaccaga tctcccccaa atccacccgt   1740
cggcacctcc gcttcaaggt acgccgctcg tcctccccc ccccctctc taccttctct   1800
agatcggcgt tccggtccat gcatggttag ggcccggtag ttctacttct gttcatgttt   1860
gtgttagatc cgtgtttgtg ttagatccgt gctgctagcg ttcgtacacg gatgcgacct   1920
gtacgtcaga cacgttctga ttgctaactt gccagtgttt ctctttgggg aatcctggga   1980
tggctctagc cgttccgcag acgggatcga tttcatgatt ttttttgttt cgttgcatag   2040
ggtttggttt gcccttttcc tttatttcaa tatatgccgt gcacttgttt gtcgggtcat   2100
cttttcatgc tttttttttgt cttggttgtg atgatgtggt ctggttgggc ggtcgttcta   2160
gatcggagta gaattctgtt tcaaactacc tggtggattt attaattttg gatctgtatg   2220
tgtgtgccat acatattcat agttacgaat tgaagatgat ggatggaaat atcgatctag   2280
gataggtata catgttgatg cgggttttac tgatgcatat acagagatgc ttttttgttcg   2340
cttggttgtg atgatgtggt gtggttgggc ggtcgttcat tcgttctaga tcggagtaga   2400
atactgtttc aaactacctg gtgtatttat taatttggaa actgtatgtg tgtgtcatac   2460
atcttcatag ttacgagttt aagatggatg gaaatatcga tctaggatag gtatacatgt   2520
tgatgtgggt tttactgatg catatacatg atggcatatg cagcatctat tcatatgctc   2580
```

```
taaccttgag tacctatcta ttataataaa caagtatgtt ttataattat tttgatcttg    2640
atatacttgg atgatggcat atgcagcagc tatatgtgga ttttttttagc cctgccttca    2700 tacgctattt attgcttgg tactgtttct tttgtcgatg ctcaccctgt tgtttggtgt    2760
tacttctgca ggtcgactct agaggatcaa ttcgctagcg aagttcctat tccgaagttc    2820
ctattctcta gaaagtatag gaacttcaga tccaccggga tccccgatca tgcaaaaact    2880
cattaactca gtgcaaaact atgcctgggg cagcaaaacg gcgttgactg aactttatgg    2940
tatggaaaat ccgtccagcc agccgatggc cgagctgtgg atgggcgcac atccgaaaag    3000
cagttcacga gtgcagaatg ccgccggaga tatcgtttca ctgcgtgatg tgattgagag    3060
tgataaatcg actctgctcg agaggccgt tgccaaacgc tttggcgaac tgcctttcct    3120
gttcaaagta ttatgcgcag cacagccact ctccattcag gttcatccaa acaaacacaa    3180
ttctgaaatc ggttttgcca agaaaatgc cgcaggtatc ccgatggatg ccgccgagcg    3240
taactataaa gatcctaacc acaagccgga gctggttttt gcgctgacgc ctttccttgc    3300
gatgaacgcg tttcgtgaat tttccgagat tgtctcccta ctccagccgg tcgcaggtgc    3360
acatccggcg attgctcact ttttacaaca gcctgatgcc gaacgtttaa gcgaactgtt    3420
cgccagcctg ttgaatatgc agggtgaaga aaaatcccgc gcgctggcga ttttaaaatc    3480
ggccctcgat agccagcagg gtgaaccgtg gcaaacgatt cgtttaattt ctgaattta    3540 cccggaagac agcggtctgt tctccccgct attgctgaat gtggtgaaat tgaaccctgg    3600
cgaagcgatg ttcctgttcg ctgaaacacc gcacgcttac ctgcaaggcg tggcgctgga    3660
agtgatggca aactccgata cgtgctgcg tgcgggtctg acgcctaaat acattgatat    3720
tccggaactg gttgccaatg tgaaattcga agccaaaccg gctaaccagt tgttgaccca    3780
gccggtgaaa caaggtgcag aactggactt cccgattcca gtggatgatt ttgccttctc    3840
gctgcatgac cttagtgata agaaaaccac cattagccag cagagtgccg ccatttgtt    3900 ctgcgtcgaa ggcgatgcaa cgttgtggaa aggttctcag cagttacagc ttaaaccggg    3960
tgaatcagcg tttattgccg ccaacgaatc accggtgact gtcaaaggcc acggccgttt    4020
agcgcgtgtt tacaacaagc tgtaagagct tactgaaaaa attaacatct cttgctaagc    4080
tgggggtgga acctagactt gtccatcttc tggattggcc aacttaatta atgtatgaaa    4140
taaaaggatg cacacatagt gacatgctaa tcactataat gtgggcatca agttgtgtg    4200 ttatgtgtaa ttactagtta tctgaataaa agagaaagag atcatccata tttcttatcc    4260
taaatgaatg tcacgtgtct ttataattct ttgatgaacc agatgcattt cattaaccaa    4320
atccatatac atataaatat taatcatata taattaatat caattgggtt agcaaaacaa    4380
atctagtcta ggtgtgtttt gcgaatgcgg ccctagcgta tacgaagttc ctattccgaa    4440
gttcctattc tccagaaagt ataggaactt ctgtacacct gagctgattc cgatgacttc    4500
gtaggttcct agctcaagcc gctcgtgtcc aagcgtcact tacgattagc taatgattac    4560
ggcatctagg accgactagc taactaacta gtaccgaggc cggccccgcg ggagctcggc    4620
gcgcctaagg gccaagtact tgctgtccct gtatctccaa cacgagcctt gattcctgcc    4680
ggccggtgat ggcaatggcc gctagtagtc tccgctagct agggagcggc gatccgacgc    4740
gacgccacca tgtgtctaga aaagaagttt cttgctttgc atgcagactt attagcgcgg    4800
tcgacacctg tggggacccc gtgtcttgag acaatgagac tgcctgtccg cccaagacac    4860
tacttgtagc catgaagcca tcgactcctc tccttgctct ccagtaatcc agtggatgga    4920
```

```
tccatcatcg atagtttagt ttatcagtct tcttgaggcc ggtgtccccc atgcataatg    4980
atgacagaaa gcctgggcca ggtaaaagcc aaaaagtttg accctctagg tactggggcc    5040
agccctggcg tttgaacaaa aaaaaaatct gagcgtgtcg ccccggcctg ttttcgaact    5100
cctaaacgac gtcgcaactt tttttataca cacactaccg gtacatggct tt            5152
```

<210> SEQ ID NO 260
<211> LENGTH: 5146
<212> TYPE: DNA
<213> ORGANISM: Artificial Sequence
<220> FEATURE:
<223> OTHER INFORMATION: synthesized sequence- TS10Cas-3 donor

<400> SEQUENCE: 260

```
aaatagtaaa cgggagggga ggtcgctagt agtaaacgct aggtagctag gataatccgt      60
ctcgtgttgg acggaaggtt ttggacgcat ctgcgtgcac agcccgctga tacagatctg     120
atcgactagc tagctagatg ccgaggcccc agagcaaggc ccggatactc ctgcacagtc     180
cctgagattt cagcacagca ggtgctgttg catcaatata taaatccctg ctttattaat     240
ttaatctctg tgcatgtatc catacatcgt cagcggctca gcgctatcac actgcagtgc     300
acgcagctag ttgagcgcct gggtcagtat atatatagct agtagggaca aaggggggca     360
ctgtacgttg gtttggtttg gcacgcacgc gatcgagagt ggtggaatgg actgcagatc     420
atcgatcgct gcactgtacg cacgcgcacc ggactgcatt tgcatgcccc tgaaggagga     480
aaggggaagg aaagaaaaga aataggagaa agaagaagaa gcagagaaat acgtcacagt     540
ccaagaagag tgagccgccc tagctagctt caaccctgac gaacccggca gccacacttc     600
cggccatgta tgcatgcatg catggcttag cttcagatgt ccaatcgaat ccatcaagac     660
ctggccggtt ttccatggcc gcctcgcctt cgctagttaa gggccaagta cttgctgtcc     720
ctgtggtacc atttaaatct taagcctagg ataacttcgt atagcataca ttatacgaag     780
ttatggcgcc gctagcctgc agtgcagcgt gacccgtcg tgcccctctc tagagataat     840
gagcattgca tgtctaagtt ataaaaaatt accacatatt ttttttgtca cacttgtttg     900
aagtgcagtt tatctatctt tatacatata tttaaacttt actctacgaa taatataatc     960
tatagtacta caataatatc agtgttttag agaatcatat aaatgaacag ttagacatgg    1020
tctaaaggac aattgagtat tttgacaaca ggactctaca gttttatctt tttagtgtgc    1080
atgtgttctc cttttttttt gcaaatagct tcacctatat aatacttcat ccatttttatt   1140 agtacatcca tttagggttt agggttaatg gtttttatag actaattttt ttagtacatc    1200
tattttattc tattttagcc tctaaattaa gaaaactaaa actctatttt agtttttta     1260 tttaataatt tagatataaa atagaataaa ataagtgac taaaaattaa acaaataccc     1320
tttaagaaat taaaaaaact aaggaaacat ttttcttgtt tcgagtagat aatgccagcc    1380
tgttaaacgc cgtcgacgag tctaacggac accaaccagc gaaccagcag cgtcgcgtcg    1440
ggccaagcga agcagacggc acggcatctc tgtcgctgcc tctggacccc tctcgagagt    1500
tccgctccac cgttggactt gctccgctgt cggcatccag aaattgcgtg gcggagcggc    1560
agacgtgagc cggcacggca ggcggcctcc tcctcctctc acggcaccgg cagctacggg    1620
ggattccttt cccaccgctc cttcgctttc ccttcctcgc ccgccgtaat aaatagacac    1680
cccctccaca ccctctttcc ccaacctcgt gttgttcgga gcgcacacac acacaaccag    1740
atctccccca aatccaccc tcggcacctc cgcttcaagg tacgccgctc gtcctccccc     1800
ccccccctct ctaccttctc tagatcggcg ttccggtcca tgcatggtta gggcccggta    1860
```

```
gttctacttc tgttcatgtt tgtgttagat ccgtgtttgt gttagatccg tgctgctagc    1920
gttcgtacac ggatgcgacc tgtacgtcag acacgttctg attgctaact tgccagtgtt    1980
tctctttggg gaatcctggg atggctctag ccgttccgca gacgggatcg atttcatgat    2040 ttttttttgtt tcgttgcata gggtttggtt tgccctttc ctttatttca atatatgccg    2100
tgcacttgtt tgtcgggtca tcttttcatg ctttttttg tcttggttgt gatgatgtgg    2160
tctggttggg cggtcgttct agatcggagt agaattctgt ttcaaactac ctggtggatt    2220
tattaatttt ggatctgtat gtgtgtgcca tacatattca tagttacgaa ttgaagatga    2280
tggatggaaa tatcgatcta ggataggtat acatgttgat gcggttttta ctgatgcata    2340
tacagagatg cttttgttc gcttggttgt gatgatgtgg tgtggttggg cggtcgttca    2400
ttcgttctag atcggagtag aatactgttt caaactacct ggtgtattta ttaattttgg    2460
aactgtatgt gtgtgtcata catcttcata gttacgagtt taagatggat ggaaatatcg    2520
atctaggata ggtatacatg ttgatgtggg ttttactgat gcatatacat gatggcatat    2580
gcagcatcta ttcatatgct ctaaccttga gtacctatct attataataa acaagtatgt    2640
tttataatta ttttgatctt gatatacttg gatgatggca tatgcagcag ctatatgtgg    2700 attttttttag ccctgccttc atacgctatt tatttgcttg gtactgtttc ttttgtcgat    2760
gctcaccctg ttgtttggtg ttacttctgc aggtcgactc tagaggatca attcgctagc    2820
gaagttccta ttccgaagtt cctattctct agaaagtata ggaacttcag atccaccggg    2880
atccccgatc atgcaaaaac tcattaactc agtgcaaaac tatgcctggg gcagcaaaac    2940
ggcgttgact gaactttatg gtatggaaaa tccgtccagc cagccgatgg ccgagctgtg    3000
gatgggcgca catccgaaaa gcagttcacg agtgcagaat gccgccggag atatcgtttc    3060
actgcgtgat gtgattgaga gtgataaatc gactctgctc ggagaggccg ttgccaaacg    3120
ctttggcgaa ctgcctttcc tgttcaaagt attatgcgca gcacagccac tctccattca    3180
ggttcatcca aacaaacaca attctgaaat cggttttgcc aaagaaaatg ccgcaggtat    3240
cccgatggat gccgccgagc gtaactataa agatcctaac cacaagccgg agctggtttt    3300
tgcgctgacg cctttccttg cgatgaacgc gtttcgtgaa ttttccgaga ttgtctccct    3360
actccagccg gtcgcaggtg cacatccggc gattgctcac tttttacaac agcctgatgc    3420
cgaacgttta agcgaactgt tcgccagcct gttgaatatg cagggtgaag aaaaatcccg    3480
cgcgctggcg atttttaaaat cggccctcga tagccagcag ggtgaaccgt ggcaaacgat    3540
tcgtttaatt tctgaatttt acccggaaga cagcggtctg ttctcccgc tattgctgaa    3600 tgtggtgaaa ttgaaccctg gcgaagcgat gttcctgttc gctgaaacac cgcacgctta    3660
cctgcaaggc gtgcgctgg aagtgatggc aaactccgat aacgtgctgc gtgcgggtct    3720
gacgcctaaa tacattgata ttccggaact ggttgccaat gtgaaattcg aagccaaacc    3780
ggctaaccag ttgttgaccc agccggtgaa acaaggtgca gaactggact ccccgattcc    3840
agtggatgat tttgccttct cgctgcatga ccttagtgat aaagaaacca ccattagcca    3900
gcagagtgcc gccattttgt tctgcgtcga aggcgatgca acgttgtgga aaggttctca    3960
gcagttacag cttaaaccgg gtgaatcagc gtttattgcc gcaacgaat caccggtgac    4020 tgtcaaaggc cacggccgtt tagcgcgtgt ttacaacaag ctgtaagagc ttactgaaaa    4080
aattaacatc tcttgctaag ctgggggtgg aacctagact tgtccatctt ctggattggc    4140
caacttaatt aatgtatgaa ataaaaggat gcacacatag tgacatgcta atcactataa    4200
```

```
tgtgggcatc aaagttgtgt gttatgtgta attactagtt atctgaataa aagagaaaga    4260
gatcatccat atttcttatc ctaaatgaat gtcacgtgtc tttataattc tttgatgaac    4320
cagatgcatt tcattaacca aatccatata catataaata ttaatcatat ataattaata    4380
tcaattgggt tagcaaaaca aatctagtct aggtgtgttt tgcgaatgcg gccctagcgt    4440
atacgaagtt cctattccga agttcctatt ctccagaaag tataggaact tctgtacacc    4500
tgagctgatt ccgatgactt cgtaggttcc tagctcaagc cgctcgtgtc caagcgtcac    4560
ttacgattag ctaatgatta cggcatctag gaccgactag ctaactaact agtaccgagg    4620
ccggccccgc gggagctcgg cgcgccatct ccaacacgag ccttgattcc tgccggccgg    4680
tgatggcaat ggccgctagt agtctccgct agctagggag cggcgatccg acgcgacgcc    4740
accatgtgtc tagaaaagaa gtttcttgct ttgcatgcag acttattagc gcggtcgaca    4800
cctgtgggga ccccgtgtct tgagacaatg agactgcctg tccgcccaag acactacttg    4860
tagccatgaa gccatcgact cctctccttg ctctccagta atccagtgga tggatccatc    4920
atcgatagtt tagtttatca gtcttcttga ggccggtgtc ccccatgcat aatgatgaca    4980
gaaagcctgg gccaggtaaa agccaaaaag tttgaccctc taggtactgg ggccagccct    5040
ggcgtttgaa caaaaaaaaa atctgagcgt gtcgccccgg cctgtttcg aactcctaaa     5100 cgacgtcgca acttttttta tacacacact accggtacat ggcttt                   5146
```

<210> SEQ ID NO 261
<211> LENGTH: 32
<212> TYPE: DNA
<213> ORGANISM: Artificial Sequence
<220> FEATURE:
<223> OTHER INFORMATION: synthesized sequence- ubir primer from donor

<400> SEQUENCE: 261
ccatgtctaa ctgttcattt atatgattct ct                                  32

<210> SEQ ID NO 262
<211> LENGTH: 31
<212> TYPE: DNA
<213> ORGANISM: Artificial Sequence
<220> FEATURE:
<223> OTHER INFORMATION: synthesized sequence- psbf primer from dono

<400> SEQUENCE: 262
gctcgtgtcc aagcgtcact tacgattagc t                                   31

<210> SEQ ID NO 263
<211> LENGTH: 27
<212> TYPE: DNA
<213> ORGANISM: Artificial Sequence
<220> FEATURE:
<223> OTHER INFORMATION: synthesized sequence- MHP14 14-1HR1f primer

<400> SEQUENCE: 263
ctcacatgag gctcttcttt gcttgct                                        27

<210> SEQ ID NO 264
<211> LENGTH: 26
<212> TYPE: DNA
<213> ORGANISM: Artificial Sequence
<220> FEATURE:
<223> OTHER INFORMATION: synthesized sequence- MHP14 14-1HR2r primer

<400> SEQUENCE: 264
aggatcctat tccccaattt gtagat                                         26

<210> SEQ ID NO 265
<211> LENGTH: 21
<212> TYPE: DNA
<213> ORGANISM: Artificial Sequence
<220> FEATURE:
<223> OTHER INFORMATION: synthesized sequence- CHR1-8 8HR1f primer

<400> SEQUENCE: 265
cagtccgtgg attgaagcca t                                          21

<210> SEQ ID NO 266
<211> LENGTH: 22
<212> TYPE: DNA
<213> ORGANISM: Artificial Sequence
<220> FEATURE:
<223> OTHER INFORMATION: synthesized sequence- CHR1-8 8HR2r primer

<400> SEQUENCE: 266
ctctgtctcc gagacgtgct ta                                         22

<210> SEQ ID NO 267
<211> LENGTH: 26
<212> TYPE: DNA
<213> ORGANISM: Artificial Sequence
<220> FEATURE:
<223> OTHER INFORMATION: synthesized sequence- CHR1-9 9HR1f primer

<400> SEQUENCE: 267
ggagcaaatg ttttaggtat gaaatg                                     26

<210> SEQ ID NO 268
<211> LENGTH: 28
<212> TYPE: DNA
<213> ORGANISM: Artificial Sequence
<220> FEATURE:
<223> OTHER INFORMATION: synthesized sequence- CHR1-9  9HR2r primer

<400> SEQUENCE: 268
cggattctaa agatcatacg taaatgaa                                   28

<210> SEQ ID NO 269
<211> LENGTH: 21
<212> TYPE: DNA
<213> ORGANISM: Artificial Sequence
<220> FEATURE:
<223> OTHER INFORMATION: synthesized sequence- CHR1-10  10HR1f primer

<400> SEQUENCE: 269
tggcttgtct atgcgcatct c                                          21

<210> SEQ ID NO 270
<211> LENGTH: 20
<212> TYPE: DNA
<213> ORGANISM: Artificial Sequence
<220> FEATURE:
<223> OTHER INFORMATION: synthesized sequence- CHR1-10  10HR2r primer

<400> SEQUENCE: 270
ccagacccaa acagcaggtt                                            20

<210> SEQ ID NO 271
<211> LENGTH: 18
<212> TYPE: DNA
<213> ORGANISM: Artificial Sequence
<220> FEATURE:

```
<223> OTHER INFORMATION: synthesized sequence- MHP14Cas-1 probe

<400> SEQUENCE: 271
cagattcacg tcagattt                                                 18

<210> SEQ ID NO 272
<211> LENGTH: 27
<212> TYPE: DNA
<213> ORGANISM: Artificial Sequence
<220> FEATURE:
<223> OTHER INFORMATION: synthesized sequence- MHP14cas-1 forward primer

<400> SEQUENCE: 272
catagtggtg tatgaaagga agcactt                                       27

<210> SEQ ID NO 273
<211> LENGTH: 30
<212> TYPE: DNA
<213> ORGANISM: Artificial Sequence
<220> FEATURE:
<223> OTHER INFORMATION: synthesized sequence- MHP14cas-1 reverse primer

<400> SEQUENCE: 273
cattttggat tgtaatatgt gtacctcata                                    30

<210> SEQ ID NO 274
<211> LENGTH: 17
<212> TYPE: DNA
<213> ORGANISM: Artificial Sequence
<220> FEATURE:
<223> OTHER INFORMATION: synthesized sequence- MHP14Cas-3 probe

<400> SEQUENCE: 274
caccactatg tcgcttc                                                  17

<210> SEQ ID NO 275
<211> LENGTH: 22
<212> TYPE: DNA
<213> ORGANISM: Artificial Sequence
<220> FEATURE:
<223> OTHER INFORMATION: synthesized sequence- MHP14Cas-3 forward primer

<400> SEQUENCE: 275
cggatgcacg aaaattgtag ga                                            22

<210> SEQ ID NO 276
<211> LENGTH: 24
<212> TYPE: DNA
<213> ORGANISM: Artificial Sequence
<220> FEATURE:
<223> OTHER INFORMATION: synthesized sequence- MHP14Cas-3 reverse primer

<400> SEQUENCE: 276
ctgacgtgaa tctgtttgga attg                                          24

<210> SEQ ID NO 277
<211> LENGTH: 18
<212> TYPE: DNA
<213> ORGANISM: Artificial Sequence
<220> FEATURE:
<223> OTHER INFORMATION: synthesized sequence- TS8Cas-1 probe

<400> SEQUENCE: 277
tacgtaacgt gcagtact                                                 18
```

```
<210> SEQ ID NO 278
<211> LENGTH: 21
<212> TYPE: DNA
<213> ORGANISM: Artificial Sequence
<220> FEATURE:
<223> OTHER INFORMATION: synthesized sequence- TS8Cas-1 forward primer

<400> SEQUENCE: 278
acggacggac catacgttat g                                              21

<210> SEQ ID NO 279
<211> LENGTH: 26
<212> TYPE: DNA
<213> ORGANISM: Artificial Sequence
<220> FEATURE:
<223> OTHER INFORMATION: synthesized sequence- TS8Cas-1 reverse primer

<400> SEQUENCE: 279
tcagctggtg gagtatatta gttcgt                                         26

<210> SEQ ID NO 280
<211> LENGTH: 18
<212> TYPE: DNA
<213> ORGANISM: Artificial Sequence
<220> FEATURE:
<223> OTHER INFORMATION: synthesized sequence- TS8Cas-2 probe

<400> SEQUENCE: 280
ccagctgatc actgatga                                                  18

<210> SEQ ID NO 281
<211> LENGTH: 21
<212> TYPE: DNA
<213> ORGANISM: Artificial Sequence
<220> FEATURE:
<223> OTHER INFORMATION: synthesized sequence- TS8Cas-2 forward primer

<400> SEQUENCE: 281
acggacggac catacgttat g                                              21

<210> SEQ ID NO 282
<211> LENGTH: 26
<212> TYPE: DNA
<213> ORGANISM: Artificial Sequence
<220> FEATURE:
<223> OTHER INFORMATION: synthesized sequence- TS8Cas-2 reverse primer

<400> SEQUENCE: 282
cgcacatgtt ataaattaca atgcat                                         26

<210> SEQ ID NO 283
<211> LENGTH: 14
<212> TYPE: DNA
<213> ORGANISM: Artificial Sequence
<220> FEATURE:
<223> OTHER INFORMATION: synthesized sequence- TS9Cas-2 probe

<400> SEQUENCE: 283
ctgtttgcgg cctc                                                      14

<210> SEQ ID NO 284
<211> LENGTH: 19
<212> TYPE: DNA
<213> ORGANISM: Artificial Sequence
<220> FEATURE:
<223> OTHER INFORMATION: synthesized sequence- TS9Cas-2 forward primer
```

<400> SEQUENCE: 284
ctgcggagct gctggcgat                                                19

<210> SEQ ID NO 285
<211> LENGTH: 20
<212> TYPE: DNA
<213> ORGANISM: Artificial Sequence
<220> FEATURE:
<223> OTHER INFORMATION: synthesized sequence- TS9Cas-2 reverse primer

<400> SEQUENCE: 285
cttgctggct tcgtctgtca                                               20

<210> SEQ ID NO 286
<211> LENGTH: 15
<212> TYPE: DNA
<213> ORGANISM: Artificial Sequence
<220> FEATURE:
<223> OTHER INFORMATION: synthesized sequence- TS9Cas-3 probe

<400> SEQUENCE: 286
ccgacgtgcg tgcaa                                                    15

<210> SEQ ID NO 287
<211> LENGTH: 19
<212> TYPE: DNA
<213> ORGANISM: Artificial Sequence
<220> FEATURE:
<223> OTHER INFORMATION: synthesized sequence- TS9Cas-3 forward primer

<400> SEQUENCE: 287
ctgcggagct gctggcgat                                                19

<210> SEQ ID NO 288
<211> LENGTH: 20
<212> TYPE: DNA
<213> ORGANISM: Artificial Sequence
<220> FEATURE:
<223> OTHER INFORMATION: synthesized sequence- TS9Cas-3 reverse primer

<400> SEQUENCE: 288
cttgctggct tcgtctgtca                                               20

<210> SEQ ID NO 289
<211> LENGTH: 17
<212> TYPE: DNA
<213> ORGANISM: Artificial Sequence
<220> FEATURE:
<223> OTHER INFORMATION: synthesized sequence- TS10Cas-1 probe

<400> SEQUENCE: 289
tcgccttcgc tagttaa                                                  17

<210> SEQ ID NO 290
<211> LENGTH: 20
<212> TYPE: DNA
<213> ORGANISM: Artificial Sequence
<220> FEATURE:
<223> OTHER INFORMATION: synthesized sequence- TS10Cas-1 forward primer

<400> SEQUENCE: 290
aagacctggc cggttttcca                                               20

<210> SEQ ID NO 291
<211> LENGTH: 18

-continued

```
<212> TYPE: DNA
<213> ORGANISM: Artificial Sequence
<220> FEATURE:
<223> OTHER INFORMATION: synthesized sequence- TS10Cas-1 reverse primer

<400> SEQUENCE: 291
tagcggccat tgccatca                                                   18

<210> SEQ ID NO 292
<211> LENGTH: 19
<212> TYPE: DNA
<213> ORGANISM: Artificial Sequence
<220> FEATURE:
<223> OTHER INFORMATION: synthesized sequence- TS10Cas-3 probe

<400> SEQUENCE: 292
ctgtatctcc aacacgagc                                                  19

<210> SEQ ID NO 293
<211> LENGTH: 20
<212> TYPE: DNA
<213> ORGANISM: Artificial Sequence
<220> FEATURE:
<223> OTHER INFORMATION: synthesized sequence- TS10Cas-3 forward primer

<400> SEQUENCE: 293
aagacctggc cggttttcca                                                 20

<210> SEQ ID NO 294
<211> LENGTH: 18
<212> TYPE: DNA
<213> ORGANISM: Artificial Sequence
<220> FEATURE:
<223> OTHER INFORMATION: synthesized sequence- TS10Cas-3 reverse primer

<400> SEQUENCE: 294
tagcggccat tgccatca                                                   18

<210> SEQ ID NO 295
<211> LENGTH: 472
<212> TYPE: DNA
<213> ORGANISM: Glycine max
<220> FEATURE:
<221> NAME/KEY: misc_feature
<222> LOCATION: (1)..(472)
<223> OTHER INFORMATION: GM-U6-9.1 promoter

<400> SEQUENCE: 295
cccgggttaa gagaattgta agtgtgcttt tatatattta aaattaatat attttgaaat     60
gttaaaatat aaaagaaaat tcaatgtaaa ttaaaaataa ataaatgttt aataaagata    120
aattttaaaa cataaaagaa aatgtctaac aagaggatta agatcctgtg ctcttaaatt    180
tttaggtgtt gaaatcttag ccatacaaaa tatatttat taaaaccaag catgaaaaaa    240
gtcactaaag agctatataa ctcatgcagc tagaaatgaa gtgaagggaa tccagtttgt    300
tctcagtcga aagagtgtct atctttgttc ttttctgcaa ccgagttaag caaaatggga    360
atgcgaggta tcttcctttc gttaggggag caccagatgc atagttagtc ccacattgat    420
gaatataaca agagcttcac agaatatata gcccaggcca cagtaaaagc tt            472

<210> SEQ ID NO 296
<211> LENGTH: 5958
<212> TYPE: DNA
<213> ORGANISM: Artificial sequence
<220> FEATURE:
```

<223> OTHER INFORMATION: synthesized sequence- EF1A2-CAS9

<400> SEQUENCE: 296

```
gggtttactt attttgtggg tatctatact tttattagat ttttaatcag gctcctgatt      60
tcttttatt tcgattgaat tcctgaactt gtattattca gtagatcgaa taaattataa     120
aaagataaaa tcataaaata atattttatc ctatcaatca tattaaagca atgaatatgt    180
aaaattaatc ttatctttat tttaaaaaat catataggtt tagtattttt ttaaaaataa    240
agataggatt agttttacta ttcactgctt attacttttta aaaaaatcat aaaggtttag   300
tatttttta aaataaatat aggaatagtt ttactattca ctgctttaat agaaaaatag    360
tttaaattt aagatagttt taatcccagc atttgccacg tttgaacgtg agccgaaacg    420
atgtcgttac attatcttaa cctagctgaa acgatgtcgt cataatatcg ccaaatgcca    480
actggactac gtcgaaccca caaatcccac aaagcgcgtg aaatcaaatc gctcaaacca    540
caaaaagaa caacgcgttt gttacacgct caatcccacg cgagtagagc acagtaacct     600
tcaaataagc gaatggggca taatcagaaa tccgaaataa acctagggc attatcggaa    660
atgaaagta gctcactcaa tataaaaatc taggaaccct agttttcgtt atcactctgt    720
gctccctcgc tctatttctc agtctctgtg tttgcggctg aggattccga acgagtgacc    780
ttcttcgttt ctcgcaaagg taacagcctc tgctcttgtc tcttcgattc gatctatgcc    840
tgtctcttat ttacgatgat gtttcttcgg ttatgttttt ttatttatgc tttatgctgt    900
tgatgttcgg ttgtttgttt cgctttgttt ttgtggttca gttttttagg attcttttgg    960
tttttgaatc gattaatcgg aagagatttt cgagttattt ggtgtgttgg aggtgaatct   1020
ttttttgag gtcatagatc tgttgtattt gtgttataaa catgcgactt tgtatgattt   1080
tttacgaggt tatgatgttc tggttgtttt attatgaatc tgttgagaca gaaccatgat   1140
ttttgttgat gttcgtttac actattaaag gtttgttta acaggattaa aagttttta   1200
agcatgttga aggagtcttg tagatatgta accgtcgata gttttttttgt gggtttgttc   1260
acatgttatc aagcttaatc ttttactatg tatgcgacca tatctggatc cagcaaaggc   1320
gatttttaa ttccttgtga aactttgtta atatgaagtt gaaattttgt tattggtaaa   1380
ctataaatgt gtgaagttgg agtataccct taccttctta tttggctttg tgatagttta   1440
atttatatgt atttttgagtt ctgacttgta tttctttgaa ttgattctag tttaagtaat   1500
ccatggacaa aaagtactca atagggctcg acatagggac taactccgtt ggatgggccg   1560
tcatcaccga cgagtacaag gtgccctcca agaagttcaa ggtgttggga aacaccgaca   1620
ggcacagcat aaagaagaat tgatcggtg ccctcctctt cgactccgga gagaccgctg    1680
aggctaccag gctcaagagg accgctagaa ggcgctacac cagaaggaag aacagaatct   1740
gctacctgca ggagatcttc tccaacgaga tggccaaggt ggacgactcc ttcttccacc    1800
gccttgagga atcattcctg gtggaggagg ataaaaagca cgagagacac ccaatcttcg   1860
ggaacatcgt cgacgaggtg gcctaccatg aaaagtaccc taccatctac cacctgagga    1920
agaagctggt cgactctacc gacaaggctg acttgcgctt gatttacctg gctctcgctc   1980
acatgataaa gttccgcgga cacttcctca ttgagggaga cctgaaccca gacaactccg   2040
acgtggacaa gctcttcatc cagctcgttc agacctacaa ccagctttc gaggagaacc   2100
caatcaacgc cagtggagtt gacgccaagg ctatcctctc tgctcgtctg tcaaagtcca   2160
ggaggcttga gaacttgatt gcccagctgc ctggcgaaaa gaagaacgga ctgttcggaa    2220
acttgatcgc tctctcctg ggattgactc ccaacttcaa gtccaacttc gacctcgccg    2280
```

```
aggacgctaa gttgcagttg tctaaagaca cctacgacga tgacctcgac aacttgctgg    2340
cccagatagg cgaccaatac gccgatctct tcctcgccgc taagaacttg tccgacgcaa    2400
tcctgctgtc cgacatcctg agagtcaaca ctgagattac caaagctcct ctgtctgctt    2460
ccatgattaa cgctacgac gagcaccacc aagatctgac cctgctcaag gccctggtga    2520
gacagcagct gcccgagaag tacaaggaga tctttttcga ccagtccaag aacggctacg    2580
ccggatacat tgacggaggc gcctcccagg aagagttcta caagttcatc aagcccatcc    2640
ttgagaagat ggacggtacc gaggagctgt tggtgaagtt gaacagagag gacctgttga    2700
ggaagcagag aaccttcgac aacggaagca tccctcacca aatccacctg ggagagctcc    2760
acgccatctt gaggaggcag gaggatttct atcccttcct gaaggacaac cgcgagaaga    2820
ttgagaagat cttgaccttc agaattcctt actacgtcgg ccactcgcc agaggaaact    2880 ctaggttcgc ctggatgacc cgcaaatctg aagagaccat tactccctgg aacttcgagg    2940
aagtcgtgga caagggcgct tccgctcagt ctttcatcga gaggatgacc aacttcgata    3000
aaaatctgcc caacgagaag gtgctgccca gcactccct gttgtacgag tatttcacag    3060
tgtacaacga gctcaccaag gtgaagtacg tcacagaggg aatgaggaag cctgccttct    3120
tgtccggaga gcagaagaag gccatcgtcg acctgctctt caagaccaac aggaaggtga    3180
ctgtcaagca gctgaaggag gactacttca gaagatcga gtgcttcgac tccgtcgaga    3240
tctctggtgt cgaggacagg ttcaacgcct cccttgggac ttaccacgat ctgctcaaga    3300
ttattaaaga caaggacttc ctggacaacg aggagaacga ggacatcctt gaggacatcg    3360
tgctcaccct gaccttgttc gaagacaggg aaatgatcga agagaggctc aagacctacg    3420
cccacctctt cgacgacaag gtgatgaaac agctgaagag acgcagatat accggctggg    3480
gaaggctctc ccgcaaattg atcaacggga tcagggacaa gcagtcaggg aagactatac    3540
tcgacttcct gaagtccgac ggattcgcca caggaactt catgcagctc attcacgacg    3600
actccttgac cttcaaggag gacatccaga aggctcaggt gtctggacag ggtgactcct    3660
tgcatgagca cattgctaac ttggccggct ctcccgctat taagaagggc attttgcaga    3720
ccgtgaaggt cgttgacgag ctcgtgaagg tgatgggacg ccacaagcca gagaacatcg    3780
ttattgagat ggctcgcgag aaccaaacta cccagaaagg gcagaagaat tcccgcgaga    3840
ggatgaagcg cattgaggag ggcataaaag agcttggctc tcagatcctc aaggagcacc    3900
ccgtcgagaa cactcagctg cagaacgaga agctgtacct gtactacctc caaaacggaa    3960
gggacatgta cgtggaccag gagctggaca tcaacaggtt gtccgactac gacgtcgacc    4020
acatcgtgcc tcagtccttc ctgaaggatg actccatcga caataaagtg ctgacacgct    4080
ccgataaaaa tagaggcaag tccgacaacg tcccctccga ggaggtcgtg aagaagatga    4140
aaaactactg gagacagctc ttgaacgcca agctcatcac ccagcgtaag ttcgacaacc    4200
tgactaaggc tgagagagga ggattgtccg agctcgataa ggccggattc atcaagagac    4260
agctcgtcga aacccgccaa attaccaagc acgtggccca aattctggat tcccgcatga    4320
acaccaagta cgatgaaaat gacaagctga tccgcgaggt caaggtgatc accttgaagt    4380
ccaagctggt ctccgacttc cgcaaggact tccagttcta caaggtgagg gagatcaaca    4440
actaccacca cgcacacgac gcctacctca acgctgtcgt tggaaccgcc ctcatcaaaa    4500
aatatcctaa gctggagtct gagttcgtct acggcgacta caaggtgtac gacgtgagga    4560
agatgatcgc taagtctgag caggagatcg gcaaggccac cgccaagtac ttcttctact    4620
```

| | |
|---|---|
| ccaacatcat gaacttcttc aagaccgaga tcactctcgc caacggtgag atcaggaagc | 4680 |
| gcccactgat cgagaccaac ggtgagactg gagagatcgt gtgggacaaa gggagggatt | 4740 |
| tcgctactgt gaggaaggtg ctctccatgc ctcaggtgaa catcgtcaag aagaccgaag | 4800 |
| ttcagaccgg aggattctcc aaggagtcca tcctccccaa gagaaactcc gacaagctga | 4860 |
| tcgctagaaa gaaagactgg gaccctaaga agtacggagg cttcgattct cctaccgtgg | 4920 |
| cctactctgt gctggtcgtg gccaaggtgg agaagggcaa gtccaagaag ctgaaatccg | 4980 |
| tcaaggagct cctcgggatt accatcatgg agaggagttc cttcgagaag aaccctatcg | 5040 |
| acttcctgga ggccaaggga tataaagagg tgaagaagga cctcatcatc aagctgccca | 5100 |
| agtactccct cttcgagttg gagaacggaa ggaagaggat gctggcttct gccggagagt | 5160 |
| tgcagaaggg aaatgagctc gcccttccct ccaagtacgt gaacttcctg tacctcgcct | 5220 |
| ctcactatga aaagttgaag ggctctcctg aggacaacga gcagaagcag ctcttcgtgg | 5280 |
| agcagcacaa gcactacctg gacgaaatta tcgagcagat ctctgagttc tccaagcgcg | 5340 |
| tgatattggc cgacgccaac ctcgacaagg tgctgtccgc ctacaacaag cacagggata | 5400 |
| agcccattcg cgagcaggct gaaaacatta tccacctgtt taccctcaca aacttgggag | 5460 |
| cccctgctgc cttcaagtac ttcgacacca ccattgacag gaagagatac acctccacca | 5520 |
| aggaggtgct cgacgcaaca ctcatccacc aatccatcac cggcctctat gaaacaagga | 5580 |
| ttgacttgtc ccagctggga ggcgactcta gagccgatcc aagaagaag agaaaggtgt | 5640 |
| aggttaacct agacttgtcc atcttctgga ttggccaact taattaatgt atgaaataaa | 5700 |
| aggatgcaca catagtgaca tgctaatcac tataatgtgg gcatcaaagt tgtgtgttat | 5760 |
| gtgtaattac tagttatctg aataaaagag aaagagatca tccatatttc ttatcctaaa | 5820 |
| tgaatgtcac gtgtctttat aattctttga tgaaccagat gcatttcatt aaccaaatcc | 5880 |
| atatacatat aaatattaat catatataat taatatcaat tgggttagca aaacaaatct | 5940 |
| agtctaggtg tgttttgc | 5958 |

<210> SEQ ID NO 297
<211> LENGTH: 573
<212> TYPE: DNA
<213> ORGANISM: Artificial sequence
<220> FEATURE:
<223> OTHER INFORMATION: synthesized sequence- U6-9.1-DD20CR1

<400> SEQUENCE: 297

| | |
|---|---|
| ccgggttaag agaattgtaa gtgtgctttt atatatttaa aattaatata ttttgaaatg | 60 |
| ttaaaatata aagaaaatt caatgtaaat taaaaataaa taaatgttta ataaagataa | 120 |
| attttaaaac ataaaagaaa atgtctaaca agaggattaa gatcctgtgc tcttaaattt | 180 |
| ttaggtgttg aaatcttagc catacaaaat atattttatt aaaccaagc atgaaaaag | 240 |
| tcactaaaga gctatataac tcatgcagct agaaatgaag tgaagggaat ccagtttgtt | 300 |
| ctcagtcgaa agagtgtcta tctttgttct tttctgcaac cgagttaagc aaaatgggaa | 360 |
| tgcgaggtat cttcctttcg ttaggggagc accagatgca tagttagtcc cacattgatg | 420 |
| aatataacaa gagcttcaca gaatatatag cccaggccac agtaaaagct tggaactgac | 480 |
| acacgacatg agttttagag ctagaaatag caagttaaaa taaggctagt ccgttatcaa | 540 |
| cttgaaaaag tggcaccgag tcggtgcttt ttt | 573 |

<210> SEQ ID NO 298
<211> LENGTH: 6611

<212> TYPE: DNA
<213> ORGANISM: Artificial sequence
<220> FEATURE:
<223> OTHER INFORMATION: synthesized sequence- U6-9.1-DD20CR1+EF1A2-CAS9

<400> SEQUENCE: 298

```
cgcgccggta cccgggttaa gagaattgta agtgtgcttt tatatattta aaattaatat     60
attttgaaat gttaaaatat aaaagaaaat tcaatgtaaa ttaaaaataa ataaatgttt    120
aataagata aattttaaaa cataaaagaa aatgtctaac aagaggatta agatcctgtg    180
ctcttaaatt tttaggtgtt gaaatcttag ccatacaaaa tatattttat taaaaccaag    240
catgaaaaaa gtcactaaag agctatataa ctcatgcagc tagaaatgaa gtgaagggaa    300
tccagtttgt tctcagtcga aagagtgtct atctttgttc ttttctgcaa ccgagttaag    360
caaaatggga atgcgaggta tcttcctttc gttaggggag caccagatgc atagttagtc    420
ccacattgat gaatataaca agagcttcac agaatatata gcccaggcca cagtaaaagc    480
ttggaactga cacgacat gagttttaga gctagaaata gcaagttaaa ataaggctag    540
tccgttatca acttgaaaaa gtggcaccga gtcggtgctt ttttttgcgg ccgcaattgg    600
atcgggttta cttattttgt gggtatctat acttttatta gatttttaat caggctcctg    660
attctttttt atttcgattg aattcctgaa cttgtattat tcagtagatc gaataaatta    720
taaaagata aaatcataaa ataatatttt atcctatcaa tcatattaaa gcaatgaata    780
tgtaaaatta atcttatctt tattttaaaa aatcatatag gtttagtatt ttttaaaaa    840
taaagatagg attagttta ctattcactg cttattactt ttaaaaaat cataaaggtt    900
tagtattttt ttaaaataaa tataggaata gttttactat tcactgcttt aatagaaaaa    960
tagtttaaaa tttaagatag ttttaatccc agcatttgcc acgtttgaac gtgagccgaa   1020
acgatgtcgt tacattatct taacctagct gaaacgatgt cgtcataata tcgccaaatg   1080
ccaactggac tacgtcgaac ccacaaatcc cacaaagcgc gtgaaatcaa atcgctcaaa   1140
ccacaaaaaa gaacaacgcg tttgttacac gctcaatccc acgcgagtag agcacagtaa   1200
ccttcaaata agcgaatggg gcataatcag aaatccgaaa taaacctagg ggcattatcg   1260
gaaatgaaaa gtagctcact caatataaaa atctaggaac cctagttttc gttatcactc   1320
tgtgctccct cgctctattt ctcagtctct gtgtttgcgg ctgaggattc cgaacgagtg   1380
accttcttcg tttctcgcaa aggtaacagc ctctgctctt gtctcttcga ttcgatctat   1440
gcctgtctct tatttacgat gatgtttctt cggttatgtt tttttattta tgctttatgc   1500
tgttgatgtt cggttgtttg tttcgctttg tttttgtggt tcagtttttt aggattcttt   1560
tggttttttga atcgattaat cggaagagat tttcgagtta tttggtgtgt tggaggtgaa   1620
tctttttttt gaggtcatag atctgttgta tttgtgttat aaacatgcga ctttgtatga   1680
tttttttacga ggttatgatg ttctggttgt tttattatga atctgttgag acagaaccat   1740
gattttgtt gatgttcgtt tacactatta aaggtttgtt ttaacaggat taaaagtttt   1800
ttaagcatgt tgaaggagtc ttgtagatat gtaaccgtcg atagttttt tgtgggtttg   1860
ttcacatgtt atcaagctta atcttttact atgtatgcga ccatatctgg atccagcaaa   1920
ggcgatttt taattccttg tgaaactttt gtaatatgaa gttgaaattt tgttattggt   1980
aaactataaa tgtgtgaagt tggagtatac ctttaccttc ttatttggct ttgtgatagt   2040
ttaatttata tgtattttga gttctgactt gtatttcttt gaattgattc tagttttaagt   2100
aatccatgga caaaaagtac tcaatagggc tcgacatagg gactaactcc gttggatggg   2160
```

-continued

```
ccgtcatcac cgacgagtac aaggtgccct ccaagaagtt caaggtgttg ggaaacaccg    2220
acaggcacag cataaagaag aatttgatcg gtgccctcct cttcgactcc ggagagaccg    2280
ctgaggctac caggctcaag aggaccgcta gaaggcgcta caccagaagg aagaacagaa    2340
tctgctacct gcaggagatc ttctccaacg agatggccaa ggtggacgac tccttcttcc    2400
accgccttga ggaatcattc ctggtggagg aggataaaaa gcacgagaga cacccaatct    2460
tcgggaacat cgtcgacgag gtggcctacc atgaaaagta ccctaccatc taccacctga    2520
ggaagaagct ggtcgactct accgacaagg ctgacttgcg cttgatttac ctggctctcg    2580
ctcacatgat aaagttccgc ggacacttcc tcattgaggg agacctgaac ccagacaact    2640
ccgacgtgga caagctcttc atccagctcg ttcagaccta caaccagctt ttcgaggaga    2700
acccaatcaa cgccagtgga gttgacgcca aggctatcct ctctgctcgt ctgtcaaagt    2760
ccaggaggct tgagaacttg attgcccagc tgcctggcga aaagaagaac ggactgttcg    2820
gaaacttgat cgctctctcc ctgggattga ctcccaactt caagtccaac ttcgacctcg    2880
ccgaggacgc taagttgcag ttgtctaaag acacctacga cgatgacctc gacaacttgc    2940
tggcccagat aggcgaccaa tacgccgatc tcttcctcgc cgctaagaac ttgtccgacg    3000
caatcctgct gtccgacatc ctgagagtca acactgagat taccaaagct cctctgtctg    3060
cttccatgat taagcgctac gacgagcacc accaagatct gaccctgctc aaggccctgg    3120
tgagacagca gctgcccgag aagtacaagg agatcttttt cgaccagtcc aagaacggct    3180
acgccggata cattgacgga ggcgcctccc aggaagagtt ctacaagttc atcaagccca    3240
tccttgagaa gatggacggt accgaggagc tgttggtgaa gttgaacaga gaggacctgt    3300
tgaggaagca gagaaccttc gacaacggaa gcatccctca ccaaatccac ctgggagagc    3360
tccacgccat cttgaggagg caggaggatt tctatccctt cctgaaggac aaccgcgaga    3420
agattgagaa gatcttgacc ttcagaattc cttactacgt cgggccactc gccagaggaa    3480
actctaggtt cgcctggatg acccgcaaat ctgaagagac cattactccc tggaacttcg    3540
aggaagtcgt ggacaagggc gcttccgctc agtctttcat cgagaggatg accaacttcg    3600
ataaaaatct gcccaacgag aaggtgctgc caagcactc cctgttgtac gagtatttca    3660
cagtgtacaa cgagctcacc aaggtgaagt acgtcacaga gggaatgagg aagcctgcct    3720
tcttgtccgg agagcagaag aaggccatcg tcgacctgct cttcaagacc aacaggaagg    3780
tgactgtcaa gcagctgaag gaggactact tcaagaagat cgagtgcttc gactccgtcg    3840
agatctctgg tgtcgaggac aggttcaacg cctcccttgg gacttaccac gatctgctca    3900
agattattaa agacaaggac ttcctggaca acgaggagaa cgaggacatc cttgaggaca    3960
tcgtgctcac cctgaccttg ttcgaagaca gggaaatgat cgaagagagg ctcaagacct    4020
acgcccacct cttcgacgac aaggtgatga aacagctgaa gagacgcaga tataccggct    4080
ggggaaggct ctcccgcaaa ttgatcaacg ggatcaggga caagcagtca gggaagacta    4140
tactcgactt cctgaagtcc gacggattcg ccaacaggaa cttcatgcag ctcattcacg    4200
acgactcctt gaccttcaag gaggacatcc agaaggctca ggtgtctgga cagggtgact    4260
ccttgcatga gcacattgct aacttggccg gctctcccgc tattaagaag gcattttgc    4320 agaccgtgaa ggtcgttgac gagctcgtga aggtgatggg acgccacaag ccagagaaca    4380
tcgttattga gatggctcgc gagaaccaaa ctacccagaa agggcagaag aattcccgcg    4440
agaggatgaa gcgcattgag gagggcataa agagcttggg ctctcagatc ctcaaggagc    4500
accccgtcga gaacactcag ctgcagaacg agaagctgta cctgtactac ctccaaaacg    4560
```

```
gaagggacat gtacgtggac caggagctgg acatcaacag gttgtccgac tacgacgtcg    4620
accacatcgt gcctcagtcc ttcctgaagg atgactccat cgacaataaa gtgctgacac    4680
gctccgataa aaatagaggc aagtccgaca acgtcccctc cgaggaggtc gtgaagaaga    4740
tgaaaaacta ctggagacag ctcttgaacg ccaagctcat cacccagcgt aagttcgaca    4800
acctgactaa ggctgagaga ggaggattgt ccgagctcga taaggccgga ttcatcaaga    4860
gacagctcgt cgaaacccgc caaattacca agcacgtggc ccaaattctg gattcccgca    4920
tgaacaccaa gtacgatgaa atgacaagc tgatccgcga ggtcaaggtg atcaccttga     4980
agtccaagct ggtctccgac ttccgcaagg acttccagtt ctacaaggtg agggagatca    5040
acaactacca ccacgcacac gacgcctacc tcaacgctgt cgttggaacc gccctcatca    5100
aaaaatatcc taagctggag tctgagttcg tctacggcga ctacaaggtg tacgacgtga    5160
ggaagatgat cgctaagtct gagcaggaga tcggcaaggc caccgccaag tacttcttct    5220
actccaacat catgaacttc ttcaagaccg agatcactct cgccaacggt gagatcagga    5280
agcgcccact gatcgagacc aacggtgaga ctggagagat cgtgtgggac aaagggaggg    5340
atttcgctac tgtgaggaag gtgctctcca tgcctcaggt gaacatcgtc aagaagaccg    5400
aagttcagac cggaggattc tccaaggagt ccatcctccc caagagaaac tccgacaagc    5460
tgatcgctag aaagaaagac tgggacccta agaagtacgg aggcttcgat tctcctaccg    5520
tggcctactc tgtgctggtc gtggccaagg tggagaaggg caagtccaag aagctgaaat    5580
ccgtcaagga gctcctcggg attaccatca tggagaggag ttccttcgag aagaacccta    5640
tcgacttcct ggaggccaag ggatataaag aggtgaagaa ggacctcatc atcaagctgc    5700
ccaagtactc cctcttcgag ttggagaacg gaaggaagag gatgctggct tctgccggag    5760
agttgcagaa gggaaatgag ctcgcccttc cctccaagta cgtgaacttc ctgtacctcg    5820
cctctcacta tgaaaagttg aagggctctc ctgaggacaa cgagcagaag cagctcttcg    5880
tggagcagca caagcactac ctggacgaaa ttatcgagca gatctctgag ttctccaagc    5940
gcgtgatatt ggccgacgcc aacctcgaca aggtgctgtc cgcctacaac aagcacaggg    6000
ataagcccat tcgcgagcag gctgaaaaca ttatccacct gtttaccctc acaaacttgg    6060
gagcccctgc tgccttcaag tacttcgaca ccaccattga caggaagaga tacacctcca    6120
ccaaggaggt gctcgacgca acactcatcc accaatccat caccggcctc tatgaaacaa    6180
ggattgactt gtcccagctg ggaggcgact ctagagccga tcccaagaag aagagaaagg    6240
tgtaggttaa cctagacttg tccatcttct ggattggcca acttaattaa tgtatgaaat    6300
aaaaggatgc acacatagtg acatgctaat cactataatg tgggcatcaa agttgtgtgt    6360
tatgtgtaat tactagttat ctgaataaaa gagaaagaga tcatccatat ttcttatcct    6420
aaatgaatgt cacgtgtctt tataattctt tgatgaacca gatgcatttc attaaccaaa    6480
tccatataca tataaatatt aatcatatat aattaatatc aattgggtta gcaaaacaaa    6540
tctagtctag gtgtgttttg cgaattcgat atcaagctta tcgataccgt cgagggggggg    6600
cccggtaccg g                                                         6611
```

<210> SEQ ID NO 299  
<211> LENGTH: 5686  
<212> TYPE: DNA  
<213> ORGANISM: Artificial sequence  
<220> FEATURE:  
<223> OTHER INFORMATION: synthesized sequence- DD20HR1-SAMS:HPT-DD20HR2

<400> SEQUENCE: 299

```
cgcgcctcta gttgaagaca cgttcatgtc ttcatcgtaa gaagacactc agtagtcttc      60
ggccagaatg gccatctgga ttcagcaggc ctagaaggcc atttaaatcc tgaggatctg     120
gtcttcctaa ggacccggga tatcgctatc aactttgtat agaaaagttg ggccgaattc     180
gagctcggta cggccagaat ccggtaagtg actagggtca cgtgacccta gtcacttaaa     240
ttcggccaga atggccatct ggattcagca ggcctagaag gcccggaccg attaaacttt     300
aattcggtcc gggttacctc gagcctagta ataattacac atctaagata tcccttctt     360
tttcaagtaa aataatatca tatgatctca ttttagtgaa acaatactat ttccctgata     420
actctcttca acattaggga cttcatctaa tcatctactt tcaaggtata actagacgta     480
tttgttcttt taaaaaaaac actagatgta ctcgtcaact caaaattcat cgttcatgca     540
ttttaattaa actttaatta gctaatgagt agaaaaagat catacgagta aaatagaaga     600
atcttcctag attttggaag aatggattgg agtgtaagtg aattgatcca ttagtggaag     660
atgctcttta caatggccaa actgttctaa ttgttagagc acatttgaga tgaaacactt     720
cagtagtgga ggtaacctac aatcctagga tctgtatcct ctatcactaa tggagcaatg     780
ggtttgagat tgacttactc cttccttgt ctctcgtagt gcatatgcgc actttcaaag     840
gctacacaaa agccgttaac tttttgttta tttaagttac gaaagatagt tgaattagag     900
taaatggtga tattgaatta ggattttaaa taattttaaa agaattttt taataaaaaa     960
aatattgtgt tgttggatca aaattttta ataacatgaa taaggaaatg gattgcaatg    1020
aggttttaaa caattatttt aacatatagg attttagaaa gacttttata atattttgtt    1080
gaagtttaga ttttaatata tttatgtttt aaaattttaa aaaaaacttc atgaatttat    1140
aatatttgaa aaagacacgt gaatatttag aaaacattta aaattacaat aataaatcat    1200
aatgagatag ggtgtattca tgtgtagacg agacaccaag tatatggttc acaagtgaat    1260
catctttttt ttttacagca caagtagatc acttgtactt atcaaaattc ggaactgaca    1320
cacactagtg gtcacctaag tgactagggt cacgtgaccc tagtcactta ttcccaaaca    1380
ctagtaacgg ccgccagtgt gctggaattc gcccttccca agctttgctc tagatcaaac    1440
tcacatccaa acataacatg gatatcttcc ttaccaatca tactaattat tttgggttaa    1500
atattaatca ttattttaa gatattaatt aagaaattaa aagatttttt aaaaaaatgt    1560
ataaaattat attattcatg attttcata catttgattt tgataataaa tatattttt    1620
ttaatttctt aaaaaatgtt gcaagacact tattagacat agtcttgttc tgtttacaaa    1680
agcattcatc atttaataca ttaaaaaata tttaatacta acagtagaat cttcttgtga    1740
gtggtgtggg agtaggcaac ctggcattga aacgagagaa agagagtcag aaccagaaga    1800
caaataaaaa gtatgcaaca aacaaatcaa aatcaaaggg caaggctgg ggttggctca    1860
attggttgct acattcaatt ttcaactcag tcaacggttg agattcactc tgacttcccc    1920
aatctaagcc gcggatgcaa acggttgaat ctaacccaca atccaatctc gttacttagg    1980
ggcttttccg tcattaactc accctgcca cccggtttcc ctataaattg gaactcaatg    2040
ctcccctcta aactcgtatc gcttcagagt tgagaccaag acacactcgt tcatatatct    2100
ctctgctctt ctcttctctt ctacctctca aggtactttt cttctccctc taccaaatcc    2160
tagattccgt ggttcaattt cggatcttgc acttctggtt tgctttgcct tgcttttcc    2220
tcaactgggt ccatctagga tccatgtgaa actctactct ttcttaaata tctgcggaat    2280
acgcgtttga ctttcagatc tagtcgaaat catttcataa ttgcctttct ttctttagc    2340
```

```
ttatgagaaa taaaatcact ttttttttat ttcaaaataa accttgggcc ttgtgctgac    2400
tgagatgggg tttggtgatt acagaatttt agcgaatttt gtaattgtac ttgtttgtct    2460
gtagttttgt tttgttttct tgtttctcat acattcctta ggcttcaatt ttattcgagt    2520
ataggtcaca ataggaattc aaactttgag caggggaatt aatcccttcc ttcaaatcca    2580
gtttgtttgt atatatgttt aaaaaatgaa acttttgctt taaattctat tataactttt    2640
tttatggctg aaattttgtc atgtgtcttt gctctctgtt gtaaattttac tgtttaggta    2700 ctaactctag gcttgttgtg cagttttga agtataacaa cagaagttcc tattccgaag    2760
ttcctattct ctagaaagta taggaacttc cactagtcca tgaaaaagcc tgaactcacc    2820
gcgacgtctg tcgagaagtt tctgatcgaa aagttcgaca gcgtctccga cctgatgcag    2880
ctctcggagg gcgaagaatc tcgtgctttc agcttcgatg taggagggcg tggatatgtc    2940
ctgcgggtaa atagctgcgc cgatggtttc tacaaagatc gttatgttta tcggcacttt    3000
gcatcggccg cgctcccgat tccggaagtg cttgacattg gggaattcag cgagagcctg    3060
acctattgca tctcccgccg tgcacagggt gtcacgttgc aagacctgcc tgaaaccgaa    3120
ctgcccgctg ttctgcagcc ggtcgcgag gccatggatg cgatcgctgc ggccgatctt    3180
agccagacga gcgggttcgg cccattcgga ccgcaaggaa tcggtcaata cactacatgg    3240
cgtgatttca tatgcgcgat tgctgatccc catgtgtatc actggcaaac tgtgatggac    3300
gacaccgtca gtgcgtccgt cgcgcaggct ctcgatgagc tgatgctttg ggccgaggac    3360
tgccccgaag tccggcacct cgtgcacgcg gatttcggct ccaacaatgt cctgacggac    3420
aatggccgca taacagcggt cattgactgg agcgaggcga tgttcgggga ttcccaatac    3480
gaggtcgcca acatcttctt ctggaggccg tggttggctt gtatggagca gcagacgcgc    3540
tacttcgagc ggaggcatcc ggagcttgca ggatcgccgc ggctccgggc gtatatgctc    3600
cgcattggtc ttgaccaact ctatcagagc ttggttgacg gcaatttcga tgatgcagct    3660
tgggcgcagg gtcgatgcga cgcaatcgtc cgatccggag ccgggactgt cgggcgtaca    3720
caaatcgccc gcagaagcgc ggccgtctgg accgatggct gtgtagaagt actcgccgat    3780
agtggaaacc gacgcccag cactcgtccg agggcaaagg aatagtgagg tacctaaaga    3840
aggagtgcgt cgaagcagat cgttcaaaca tttggcaata agtttctta agattgaatc    3900 ctgttgccgg tcttgcgatg attatcatat aatttctgtt gaattacgtt aagcatgtaa    3960
taattaacat gtaatgcatg acgttattta tgagatgggt ttttatgatt agagtcccgc    4020
aattatacat ttaatacgcg atagaaaaca aaatatagcg cgcaaactag gataaattat    4080
cgcgcgcggt gtcatctatg ttactagatc gatgtcgacc cgggcccag gaggccggcc    4140 cagctgatga tccggtgaa gttcctattc cgaagttcct attctccaga agtatagga    4200 acttcactag agcttgcggc cgcgcatgct gacttaatca gctaacgcca ctcgacctgc    4260
aggcatgccc gcggatatcg atgggccccg gccgaagctt caagtttgta caaaaaagca    4320
ggctggcgcc ggaaccaatt cagtcgactg gatccggtac cgaattcgcg ccgcactcg    4380 agatatctag acccagcttt cttgtacaaa gtggccgtta acggatcggc cagaatccgg    4440
taagtgacta gggtcacgtg accctagtca cttaaattcg gccagaatgg ccatctggat    4500
tcagcaggcc tagaaggccc ggaccgatta aactttaatt cggtccgggt tacctctaga    4560
aagcttgtcg acctgcagac acgacatgat ggaacgtgac taaggtgggt ttttgacttt    4620
gcatgtcgaa gtgagagtga ttttattgag agaataatag aagacctaca aaacaaatga    4680
```

| | |
|---|---|
| tcccgacgct aaagtaagta cgagagttaa gagaataaat gggaaaatat gcatacatga | 4740 |
| ttaggtgtgt gttcgtctca agaaagtacg aatgaatatg gtgtgtttgt agtacatgaa | 4800 |
| tgatgtgttt tgagggttca agggaaattg atatttatag agtgaaatgg aaccagaggt | 4860 |
| ctttgttgac aagggttgtt atgactcttg caaataatta atagcttata aataatagcc | 4920 |
| aataacttat tatagataga gttagagata atatatagct aaatttgaac aaggcataca | 4980 |
| aaacaaaaat gctaaatatg aataagacaa tcaaaattgt agtcgatgtt caactctttg | 5040 |
| tcgttgaaga acttgtttgc agtggtatag taaatgggtg tgagtgcagt gtctcaccca | 5100 |
| tctcacacca cacaaccaac ttcatatcta aagatattgt cgctgaatac aaaattgagt | 5160 |
| tatggaatat acaattcata atatagatac gaaaaatcat ttcttacaaa acattcaatc | 5220 |
| aaaaattatt caaacataat tctagattaa gtaatccgaa gtacaagtta gtatcctaga | 5280 |
| tccgttaatt taaaattatg tttgcataat tttggatttg gtgttctata agggcacaat | 5340 |
| tttgttcatt cttacaagtt tgtcaattct aaaatatatg caaatttgaa gaaaaaaaat | 5400 |
| ttacgaatgt gtctcaaaca ataacttaat gggaggagaa tgagggatga agaagctcaa | 5460 |
| aattaccaac gccttctacc tcaagaagct acttcacaca aaatatgact ggcggaagga | 5520 |
| taggggacaa ccgataacga aaggagata cataaggtaa tgtacgttgt tgtgtgaggg | 5580 |
| atccggtcac ctaagtgact agggtcacgt gaccctagtc acttattccc gggcaacttt | 5640 |
| attatacaaa gttgatagat ctcgaattca ttccgattaa tcgtgg | 5686 |

<210> SEQ ID NO 300
<211> LENGTH: 6611
<212> TYPE: DNA
<213> ORGANISM: Artificial sequence
<220> FEATURE:
<223> OTHER INFORMATION: synthesized sequence- U6-9.1-DD20CR2+EF1A2-CAS9

<400> SEQUENCE: 300

| | |
|---|---|
| cgcgccggta cccgggttaa gagaattgta agtgtgcttt tatatattta aaattaatat | 60 |
| attttgaaat gttaaaatat aaagaaaat tcaatgtaaa ttaaaaataa ataaatgttt | 120 |
| aataaagata aattttaaaa cataaaagaa aatgtctaac aagaggatta agatcctgtg | 180 |
| ctcttaaatt tttaggtgtt gaaatcttag ccatacaaaa tatattttat taaaaccaag | 240 |
| catgaaaaaa gtcactaaag agctatataa ctcatgcagc tagaaatgaa gtgaagggaa | 300 |
| tccagtttgt tctcagtcga aagagtgtct atctttgttc ttttctgcaa ccgagttaag | 360 |
| caaaatggga atgcgaggta tcttcctttc gttaggggag caccagatgc atagttagtc | 420 |
| ccacattgat gaatataaca agagcttcac agaatatata gcccaggcca cagtaaaagc | 480 |
| ttgacatgat ggaacgtgac tagttttaga gctagaaata gcaagttaaa ataaggctag | 540 |
| tccgttatca acttgaaaaa gtggcaccga gtcggtgctt ttttttgcgg ccgcaattgg | 600 |
| atcgggttta cttattttgt gggtatctat acttttatta gatttttaat caggctcctg | 660 |
| atttcttttt atttcgattg aattcctgaa cttgtattat tcagtagatc gaataaatta | 720 |
| taaaaagata aaatcataaa ataatatttt atcctatcaa tcatattaaa gcaatgaata | 780 |
| tgtaaaatta atcttatctt tattttaaaa aatcatatag gtttagtatt ttttaaaaa | 840 |
| taaagatagg attagtttta ctattcactg cttattactt ttaaaaaaat cataaaggtt | 900 |
| tagtattttt ttaaaataaa ataggaata gttttactat tcactgcttt aatagaaaaa | 960 |
| tagtttaaaa tttaagatag ttttaatccc agcatttgcc acgttgaac gtgagccgaa | 1020 |
| acgatgtcgt tacattatct taacctagct gaaacgatgt cgtcataata tcgccaaatg | 1080 |

```
ccaactggac tacgtcgaac ccacaaatcc cacaaagcgc gtgaaatcaa atcgctcaaa    1140
ccacaaaaaa gaacaacgcg tttgttacac gctcaatccc acgcgagtag agcacagtaa    1200
ccttcaaata agcgaatggg gcataatcag aaatccgaaa taaacctagg ggcattatcg    1260
gaaatgaaaa gtagctcact caatataaaa atctaggaac cctagttttc gttatcactc    1320
tgtgctccct cgctctattt ctcagtctct gtgtttgcgg ctgaggattc cgaacgagtg    1380
accttcttcg tttctcgcaa aggtaacagc ctctgctctt gtctcttcga ttcgatctat    1440
gcctgtctct tatttacgat gatgtttctt cggttatgtt tttttattta tgctttatgc    1500
tgttgatgtt cggttgtttg tttcgctttg tttttgtggt tcagttttt aggattcttt    1560 tggttttga atcgattaat cggaagagat tttcgagtta tttggtgtgt tggaggtgaa    1620 tcttttttt gaggtcatag atctgttgta tttgtgttat aaacatgcga ctttgtatga    1680 tttttacga ggttatgatg ttctggttgt tttattatga atctgttgag acagaaccat    1740 gattttgtt gatgttcgtt tacactatta aaggtttgtt ttaacaggat taaaagtttt    1800
ttaagcatgt tgaaggagtc ttgtagatat gtaaccgtcg atagttttt tgtgggtttg    1860 ttcacatgtt atcaagctta atctttact atgtatgcga ccatatctgg atccagcaaa    1920
ggcgattttt taattccttg tgaaactttt gtaatatgaa gttgaaattt tgttattggt    1980
aaactataaa tgtgtgaagt tggagtatac ctttaccttc ttatttggct ttgtgatagt    2040
ttaatttata tgtattttga gttctgactt gtatttcttt gaattgattc tagtttaagt    2100
aatccatgga caaaaagtac tcaataggge tcgacatagg gactaactcc gttggatggg    2160
ccgtcatcac cgacgagtac aaggtgccct ccaagaagtt caaggtgttg ggaaacaccg    2220
acaggcacag cataaagaag aatttgatcg gtgccctcct cttcgactcc ggagagaccg    2280
ctgaggctac caggctcaag aggaccgcta gaaggcgcta caccagaagg aagaacagaa    2340
tctgctacct gcaggagatc ttctccaacg agatggccaa ggtggacgac tccttcttcc    2400
accgccttga ggaatcattc ctggtggagg aggataaaaa gcacgagaga cacccaatct    2460
tcgggaacat cgtcgacgag gtggcctacc atgaaaagta ccctaccatc taccacctga    2520
ggaagaagct ggtcgactct accgacaagg ctgacttgcg cttgatttac ctggctctcg    2580
ctcacatgat aaagttccgc ggacacttcc tcattgaggg agacctgaac ccagacaact    2640
ccgacgtgga caagctcttc atccagctcg ttcagaccta caaccagctt ttcgaggaga    2700
acccaatcaa cgccagtgga gttgacgcca aggctatcct ctctgctcgt ctgtcaaagt    2760
ccaggaggct tgagaacttg attgcccagc tgcctggcga aaagaagaac ggactgttcg    2820
gaaacttgat cgctctctcc ctgggattga ctcccaactt caagtccaac ttcgacctcg    2880
ccgaggacgc taagttgcag ttgtctaaag acacctacga cgatgacctc gacaacttgc    2940
tggcccagat aggcgaccaa tacgccgatc tcttcctcgc cgctaagaac ttgtccgacg    3000
caatcctgct gtccgacatc ctgagagtca acactgagat taccaaagct cctctgtctg    3060
cttccatgat taagcgctac gacgagcacc accaagatct gaccctgctc aaggccctgg    3120
tgagacagca gctgcccgag aagtacaagg agatcttttt cgaccagtcc aagaacggct    3180
acgccggata cattgacgga ggcgcctccc aggaagagtt ctacaagttc atcaagccca    3240
tccttgagaa gatggacggt accgaggagc tgttggtgaa gttgaacaga gaggacctgt    3300
tgaggaagca gagaaccttc gacaacggaa gcatccctca ccaaatccac ctgggagagc    3360
tccacgccat cttgaggagg caggaggatt tctatccctt cctgaaggac aaccgcgaga    3420
```

```
agattgagaa gatcttgacc ttcagaattc cttactacgt cgggccactc gccagaggaa    3480
actctaggtt cgcctggatg acccgcaaat ctgaagagac cattactccc tggaacttcg    3540
aggaagtcgt ggacaagggc gcttccgctc agtctttcat cgagaggatg accaacttcg    3600
ataaaaatct gcccaacgag aaggtgctgc ccaagcactc cctgttgtac gagtatttca    3660
cagtgtacaa cgagctcacc aaggtgaagt acgtcacaga gggaatgagg aagcctgcct    3720
tcttgtccgg agagcagaag aaggccatcg tcgacctgct cttcaagacc aacaggaagg    3780
tgactgtcaa gcagctgaag gaggactact tcaagaagat cgagtgcttc gactccgtcg    3840
agatctctgg tgtcgaggac aggttcaacg cctcccttgg gacttaccac gatctgctca    3900
agattattaa agacaaggac ttcctggaca acgaggagaa cgaggacatc cttgaggaca    3960
tcgtgctcac cctgaccttg ttcgaagaca gggaaatgat cgaagagagg ctcaagacct    4020
acgcccacct cttcgacgac aaggtgatga acagctgaa gagacgcaga tataccggct    4080
ggggaaggct ctcccgcaaa ttgatcaacg ggatcaggga caagcagtca ggaagacta    4140 tactcgactt cctgaagtcc gacggattcg ccaacaggaa cttcatgcag ctcattcacg    4200
acgactcctt gaccttcaag gaggacatcc agaaggctca ggtgtctgga cagggtgact    4260
ccttgcatga gcacattgct aacttggccg gctctcccgc tattaagaag gcatttttgc    4320
agaccgtgaa ggtcgttgac gagctcgtga aggtgatggg acgccacaag ccagagaaca    4380
tcgttattga gatggctcgc gagaaccaaa ctacccagaa agggcagaag aattcccgcg    4440
agaggatgaa gcgcattgag gagggcataa aagagcttgg ctctcagatc ctcaaggagc    4500
accccgtcga gaacactcag ctgcagaacg agaagctgta cctgtactac ctccaaaacg    4560
gaagggacat gtacgtggac caggagctgg acatcaacag gttgtccgac tacgacgtcg    4620
accacatcgt gcctcagtcc ttcctgaagg atgactccat cgacaataaa gtgctgacac    4680
gctccgataa aaatagaggc aagtccgaca acgtcccctc cgaggaggtc gtgaagaaga    4740
tgaaaaacta ctggagacag ctcttgaacg ccaagctcat cacccagcgt aagttcgaca    4800
acctgactaa ggctgagaga ggaggattgt ccgagctcga taaggccgga ttcatcaaga    4860
gacagctcgt cgaaacccgc caaattacca agcacgtggc ccaaattctg gattcccgca    4920
tgaacaccaa gtacgatgaa atgacaagc tgatccgcga ggtcaaggtg atcaccttga    4980
agtccaagct ggtctccgac ttccgcaagg acttccagtt ctacaaggtg agggagatca    5040
acaactacca ccacgcacac gacgcctacc tcaacgctgt cgttggaacc gccctcatca    5100
aaaaatatcc taagctggag tctgagttcg tctacgccga ctacaaggtg tacgacgtga    5160
ggaagatgat cgctaagtct gagcaggaga tcggcaaggc caccgccaag tacttcttct    5220
actccaacat catgaacttc ttcaagaccg agatcactct cgccaacggt gagatcagga    5280
agcgcccact gatcgagacc aacggtgaga ctggagagat cgtgtgggac aaagggaggg    5340
atttcgctac tgtgaggaag gtgctctcca tgcctcaggt gaacatcgtc aagaagaccg    5400
aagttcagac cggaggattc tccaaggagt ccatcctccc caagagaaac tccgacaagc    5460
tgatcgctag aaagaaagac tgggacccta gaagtacgg aggcttcgat tctcctaccg    5520
tggcctactc tgtgctggtc gtgggccaag tggagaaggg caagtccaag aagctgaaat    5580
ccgtcaagga gctcctcggg attaccatca tggagaggag ttccttcgag aagaacccta    5640
tcgacttcct ggaggccaag ggatataaag aggtgaagaa ggacctcatc atcaagctgc    5700
ccaagtactc cctcttcgag ttggagaacg gaaggaagg gatgctggct ctgccggag    5760 agttgcagaa gggaaatgag ctcgccctc cctccaagta cgtgaacttc ctgtacctcg    5820
```

```
cctctcacta tgaaaagttg aagggctctc ctgaggacaa cgagcagaag cagctcttcg    5880
tggagcagca caagcactac ctggacgaaa ttatcgagca gatctctgag ttctccaagc    5940
gcgtgatatt ggccgacgcc aacctcgaca aggtgctgtc cgcctacaac aagcacaggg    6000
ataagcccat tcgcgagcag gctgaaaaca ttatccacct gtttaccctc acaaacttgg    6060
gagcccctgc tgccttcaag tacttcgaca ccaccattga caggaagaga tacacctcca    6120
ccaaggaggt gctcgacgca acactcatcc accaatccat caccggcctc tatgaaacaa    6180
ggattgactt gtcccagctg ggaggcgact ctagagccga tcccaagaag aagagaaagg    6240
tgtaggttaa cctagacttg tccatcttct ggattggcca acttaattaa tgtatgaaat    6300
aaaaggatgc acacatagtg acatgctaat cactataatg tgggcatcaa agttgtgtgt    6360
tatgtgtaat tactagttat ctgaataaaa gagaaagaga tcatccatat ttcttatcct    6420
aaatgaatgt cacgtgtctt tataattctt tgatgaacca gatgcatttc attaaccaaa    6480
tccatataca tataaatatt aatcatatat aattaatatc aattgggtta gcaaaacaaa    6540
tctagtctag gtgtgttttg cgaattcgat atcaagctta tcgataccgt cgaggggggg    6600
cccggtaccg g                                                         6611

<210> SEQ ID NO 301
<211> LENGTH: 6611
<212> TYPE: DNA
<213> ORGANISM: Artificial sequence
<220> FEATURE:
<223> OTHER INFORMATION: synthesized sequence- U6-9.1:DD43CR1+EF1A2:CAS9

<400> SEQUENCE: 301
cgcgccggta cccgggttaa gagaattgta agtgtgcttt tatatattta aaattaatat      60
attttgaaat gttaaaatat aaaagaaaat tcaatgtaaa ttaaaaataa ataaatgttt     120
aataaagata aattttaaaa cataaaagaa aatgtctaac aagaggatta agatcctgtg     180
ctcttaaatt tttaggtgtt gaaatcttag ccatacaaaa tatattttat aaaaccaag     240 catgaaaaaa gtcactaaag agctatataa ctcatgcagc tagaaatgaa gtgaagggaa     300
tccagtttgt tctcagtcga aagagtgtct atctttgttc ttttctgcaa ccagagttaag   360 caaaatggga atgcgaggta tcttcctttc gttaggggag caccagatgc atagttagtc     420
ccacattgat gaatataaca agagcttcac agaatatata gcccaggcca cagtaaaagc     480
ttgtcccttg tacttgtacg tagtttttaga gctagaaata gcaagttaaa ataaggctag     540
tccgttatca acttgaaaaa gtggaccga gtcggtgctt ttttttgcgg ccgcaattgg      600
atcgggttta cttattttgt gggtatctat acttttatta gattttttaat caggctcctg     660 atttctttt atttcgattg aattcctgaa cttgtattat tcagtagatc gaataaatta     720 taaaagata aaatcataaa ataatatttt atcctatcaa tcatattaaa gcaatgaata     780
tgtaaaatta atcttatctt tattttaaaa aatcatatag gtttagtatt tttttaaaaa     840
taaagatagg attagtttta ctattcactg cttattactt ttaaaaaaat cataaaggtt     900
tagtattttt ttaaaataaa tataggaata gttttactat tcactgcttt aatagaaaaa     960
tagtttaaaa tttaagatag ttttaatccc agcatttgcc acgttgaac gtgagccgaa     1020 acgatgtcgt tacattatct taacctagct gaaacgatgt cgtcataata tcgccaaatg    1080
ccaactggac tacgtcgaac ccacaaatcc cacaaagcgc gtgaaatcaa atcgctcaaa    1140
ccacaaaaaa gaacaacgcg tttgttacac gctcaatccc acgcgagtag agcacagtaa    1200
```

```
ccttcaaata agcgaatggg gcataatcag aaatccgaaa taaacctagg ggcattatcg    1260
gaaatgaaaa gtagctcact caatatataaaa atctaggaac cctagttttc gttatcactc    1320
tgtgctccct cgctctattt ctcagtctct gtgtttgcgg ctgaggattc cgaacgagtg    1380
accttcttcg tttctcgcaa aggtaacagc ctctgctctt gtctcttcga ttcgatctat    1440
gcctgtctct tatttacgat gatgtttctt cggttatgtt tttttattta tgctttatgc    1500
tgttgatgtt cggttgtttg tttcgctttg tttttgtggt tcagtttttt aggattcttt    1560
tggttttga atcgattaat cggaagagat tttcgagtta tttggtgtgt tggaggtgaa    1620
tcttttttt gaggtcatag atctgttgta tttgtgttat aaacatgcga ctttgtatga    1680
tttttacga ggttatgatg ttctggttgt tttattatga atctgttgag acagaaccat    1740
gattttgtt gatgttcgtt tacactatta aaggtttgtt ttaacaggat taaaagttt    1800
ttaagcatgt tgaaggagtc ttgtagatat gtaaccgtcg atagttttt tgtgggttg    1860
ttcacatgtt atcaagctta atcttttact atgtatgcga ccatatctgg atccagcaaa    1920
ggcgattttt taattccttg tgaaactttt gtaatatgaa gttgaaattt tgttattggt    1980
aaactataaa tgtgtgaagt tggagtatac ctttaccttc ttatttggct ttgtgatagt    2040
ttaatttata tgtattttga gttctgactt gtatttcttt gaattgattc tagttttaagt    2100
aatccatgga caaaagtac tcaatagggc tcgacatagg gactaactcc gttggatggg    2160
ccgtcatcac cgacgagtac aaggtgccct ccaagaagtt caaggtgttg ggaaacaccg    2220
acaggcacag cataaagaag aatttgatcg gtgccctcct cttcgactcc ggagagaccg    2280
ctgaggctac caggctcaag aggaccgcta gaagcgcta caccagaagg aagaacagaa    2340
tctgctacct gcaggagatc ttctccaacg agatggccaa ggtggacgac tccttcttcc    2400
accgccttga ggaatcattc ctggtggagg aggataaaaa gcacgagaga cacccaatct    2460
tcgggaacat cgtcgacgag gtggcctacc atgaaaagta ccctaccatc taccacctga    2520
ggaagaagct ggtcgactct accgacaagg ctgacttgcg cttgatttac ctggctctcg    2580
ctcacatgat aaagttccgc ggacacttcc tcattgaggg agacctgaac ccagacaact    2640
ccgacgtgga caagctcttc atccagctcg ttcagaccta caaccagctt tcgaggaga    2700
acccaatcaa cgccagtgga gttgacgcca aggctatcct ctctgctcgt ctgtcaaagt    2760
ccaggaggct tgagaacttg attgcccagc tgcctggcga aaagaagaac ggactgttcg    2820
gaaacttgat cgctctctcc ctgggattga ctcccaactt caagtccaac ttcgacctcg    2880
ccgaggacgc taagttgcag ttgtctaaag acacctacga cgatgacctc gacaacttgc    2940
tggcccagat aggcgaccaa tacgccgatc tcttcctcgc cgctaagaac ttgtccgacg    3000
caatcctgct gtccgacatc ctgagagtca acactgagat taccaaagct cctctgtctg    3060
cttccatgat taagcgctac gacgagcacc accaagatct gaccctgctc aaggccctgg    3120
tgagacagca gctgcccgag aagtacaagg agatcttttt cgaccagtcc aagaacggct    3180
acgccggata cattgacgga ggcgcctccc aggaagagt ctacaagttc atcaagccca    3240
tccttgagaa gatggacggt accgaggagc tgttggtgaa gttgaacaga gaggacctgt    3300
tgaggaagca gagaaccttc gacaacggaa gcatccctca ccaaatccac ctgggagagc    3360
tccacgccat cttgaggagg caggaggatt tctatccctt cctgaaggac aaccgcgaga    3420
agattgagaa gatcttgacc ttcagaattc cttactacgt cgggccactc gccgaggaa    3480
actctaggtt cgcctggatg acccgcaaat ctgaagagac cattactccc tggaacttcg    3540
aggaagtcgt ggacaagggc gcttccgctc agtctttcat cgagaggatg accaacttcg    3600
```

-continued

| | |
|---|---|
| ataaaaatct gcccaacgag aaggtgctgc ccaagcactc cctgttgtac gagtatttca | 3660 |
| cagtgtacaa cgagctcacc aaggtgaagt acgtcacaga gggaatgagg aagcctgcct | 3720 |
| tcttgtccgg agagcagaag aaggccatcg tcgacctgct cttcaagacc aacaggaagg | 3780 |
| tgactgtcaa gcagctgaag gaggactact tcaagaagat cgagtgcttc gactccgtcg | 3840 |
| agatctctgg tgtcgaggac aggttcaacg cctcccttgg gacttaccac gatctgctca | 3900 |
| agattattaa agacaaggac ttcctggaca acgaggagaa cgaggacatc cttgaggaca | 3960 |
| tcgtgctcac cctgaccttg ttcgaagaca gggaaatgat cgaagagagg ctcaagacct | 4020 |
| acgcccacct cttcgacgac aaggtgatga acagctgaa gagacgcaga tataccggct | 4080 |
| ggggaaggct ctcccgcaaa ttgatcaacg ggatcaggga caagcagtca gggaagacta | 4140 |
| tactcgactt cctgaagtcc gacggattcg ccaacaggaa cttcatgcag ctcattcacg | 4200 |
| acgactcctt gaccttcaag gaggacatcc agaaggctca ggtgtctgga cagggtgact | 4260 |
| ccttgcatga gcacattgct aacttggccg gctctcccgc tattaagaag gcattttgc | 4320 |
| agaccgtgaa ggtcgttgac gagctcgtga aggtgatggg acgccacaag ccagagaaca | 4380 |
| tcgttattga gatggctcgc gagaaccaaa ctacccagaa agggcagaag aattcccgcg | 4440 |
| agaggatgaa gcgcattgag gagggcataa aagagcttgg ctctcagatc ctcaaggagc | 4500 |
| accccgtcga gaacactcag ctgcagaacg agaagctgta cctgtactac ctccaaaacg | 4560 |
| gaagggacat gtacgtggac caggagctgg acatcaacag gttgtccgac tacgacgtcg | 4620 |
| accacatcgt gcctcagtcc ttcctgaagg atgactccat cgacaataaa gtgctgacac | 4680 |
| gctccgataa aaatagaggc aagtccgaca acgtcccctc cgaggaggtc gtgaagaaga | 4740 |
| tgaaaaacta ctggagacag ctcttgaacg ccaagctcat cacccagcgt aagttcgaca | 4800 |
| acctgactaa ggctgagaga ggaggattgt ccgagctcga taaggccgga ttcatcaaga | 4860 |
| gacagctcgt cgaaacccgc caaattacca agcacgtggc ccaaattctg gattcccgca | 4920 |
| tgaacaccaa gtacgatgaa aatgacaagc tgatccgcga ggtcaaggtg atcaccttga | 4980 |
| agtccaagct ggtctccgac ttccgcaagg acttccagtt ctacaaggtg agggagatca | 5040 |
| acaactacca ccacgcacac gacgcctacc tcaacgctgt cgttggaacc gccctcatca | 5100 |
| aaaaatatcc taagctggag tctgagttcg tctacggcga ctacaaggtg tacgacgtga | 5160 |
| ggaagatgat cgctaagtct gagcaggaga tcggcaaggc caccgccaag tacttcttct | 5220 |
| actccaacat catgaacttc ttcaagaccg agatcactct cgccaacggt gagatcagga | 5280 |
| agcgcccact gatcgagacc aacggtgaga ctggagagat cgtgtgggac aaagggaggg | 5340 |
| atttcgctac tgtgaggaag gtgctctcca tgcctcaggt gaacatcgtc aagaagaccg | 5400 |
| aagttcagac cggaggattc tccaaggagt ccatcctccc caagagaaac tccgacaagc | 5460 |
| tgatcgctag aaagaaagac tgggacccta gaagtacgg aggcttcgat tctcctaccg | 5520 |
| tggcctactc tgtgctggtc gtggccaagg tggagaaggg caagtccaag aagctgaaat | 5580 |
| ccgtcaagga gctcctcggg attaccatca tggagaggag ttccttcgag aagaacccta | 5640 |
| tcgacttcct ggaggccaag ggatataaag aggtgaagaa ggacctcatc atcaagctgc | 5700 |
| ccaagtactc cctcttcgag ttggagaacg gaaggagag gatgctggct ctgccggag | 5760 |
| agttgcagaa gggaaatgag ctcgcccttc cctccaagta cgtgaacttc ctgtacctcg | 5820 |
| cctctcacta tgaaaagttg aagggctctc tgaggacaa cgagcagaag cagctcttcg | 5880 |
| tggagcagca caagcactac ctggacgaaa ttatcgagca gatctctgag ttctccaagc | 5940 |

```
gcgtgatatt ggccgacgcc aacctcgaca aggtgctgtc cgcctacaac aagcacaggg      6000
ataagcccat tcgcgagcag gctgaaaaca ttatccacct gtttaccctc acaaacttgg      6060
gagcccctgc tgccttcaag tacttcgaca ccaccattga caggaagaga tacacctcca      6120
ccaaggaggt gctcgacgca acactcatcc accaatccat caccggcctc tatgaaacaa      6180
ggattgactt gtcccagctg ggaggcgact ctagagccga tcccaagaag aagagaaagg      6240
tgtaggttaa cctagacttg tccatcttct ggattggcca acttaattaa tgtatgaaat      6300
aaaaggatgc acacatagtg acatgctaat cactataatg tgggcatcaa agttgtgtgt      6360
tatgtgtaat tactagttat ctgaataaaa gagaaagaga tcatccatat ttcttatcct      6420
aaatgaatgt cacgtgtctt tataattctt tgatgaacca gatgcatttc attaaccaaa      6480
tccatataca tataaatatt aatcatatat aattaatatc aattgggtta gcaaaacaaa      6540
tctagtctag gtgtgttttg cgaattcgat atcaagctta tcgataccgt cgaggggggg      6600
cccggtaccg g                                                          6611

<210> SEQ ID NO 302
<211> LENGTH: 5719
<212> TYPE: DNA
<213> ORGANISM: Artificial sequence
<220> FEATURE:
<223> OTHER INFORMATION: synthesized sequence- DD43HR1-SAMS:HPT-DD43HR2

<400> SEQUENCE: 302
cgcgcctcta gttgaagaca cgttcatgtc ttcatcgtaa aagacactc agtagtcttc        60 ggccagaatg gccatctgga ttcagcaggc ctagaaggcc atttaaatcc tgaggatctg       120
gtcttcctaa ggacccggga tatcgctatc aactttgtat agaaaagttg ggccgaattc       180
gagctcggta cggccagaat ccggtaagtg actagggtca cgtgacccta gtcacttaaa       240
ttcggccaga atggccatct ggattcagca ggcctagaag gcccggaccg attaaacttt       300
aattcggtcc gggttacctc gagatcttgt tcccctcctt ggtttggcat aaattgattt       360
tcatggctct ctcggtcga aactggagct aattcaccct tagtctctct taaaattctg       420
gctgtaagaa acaccacaga acacataaat tataaactaa ttataatttg aagagtaaaa       480
tatgttttta ctcttatgat ttaattagtg tagttttaat tttctccttt ttttaaaaaa       540
ttttggtatt cataaatttc aatttttaa aaataattgt tgttacccgt taatgataac       600
gggatatgtt atgttaccac taaatcggac aaaaaaaatt caaaacttt ataaggatta       660 aaattaacaa aaatatttta aaaaatctaa acctcaataa agttaaattt ataagcacaa       720
aataatactt ttaagcctaa tttggcaaga cacaagcaag ctcacctgta gcattaatag       780
aaaggaagca agcaagaga aaagcaacca gaaggaagcg tttgcttggt gacacagcca       840
tcttacttga atttatggta ttactgagaa accttgatct tgcttcaaaa tcttctagtt       900
accctctttt tataggcaga aagagaacta gctagttgcc aataggatat gaggacatgt       960
ggtgcaatgc actcactctt caaggacaag aaaacaatg gctacaattg tggttcaaat      1020
caatgtctcc tgctctgtcc tgcctgaaaa tgacacccct tgcttggaa agaggatca       1080 aagctaagaa caggagtggc ttcattccct tcatgtaacc aaaacttttc gcattctgtc      1140
attcgtgaat cagcaaaatc tgcaaccaaa aatatatggt gcctaaataa agaaataaa       1200 ataatttaga gttgcggact aaaataataa acaaaagaaa tatattataa tctagaatta      1260
atttaggact aaaagaagag gcagactcca attcctcttt tctagaatac cctccgtacg      1320
tacactagtg gtcacctaag tgactagggt cacgtgaccc tagtcactta ttcccaaaca      1380
```

```
ctagtaacgg ccgccagtgt gctggaattc gcccttccca agctttgctc tagatcaaac      1440
tcacatccaa acataacatg gatatcttcc ttaccaatca tactaattat tttgggttaa      1500
atattaatca ttattttaa gatattaatt aagaaattaa aagattttt aaaaaaatgt        1560 ataaaattat attattcatg attttcata catttgattt tgataataaa tatatttttt       1620
ttaatttctt aaaaaatgtt gcaagacact tattagacat agtcttgttc tgtttacaaa      1680
agcattcatc atttaataca ttaaaaaata tttaatacta acagtagaat cttcttgtga      1740
gtggtgtggg agtaggcaac ctggcattga aacgagagaa agagagtcag aaccagaaga      1800
caaataaaaa gtatgcaaca aacaaatcaa atcaaaggg caaaggctgg ggttggctca       1860
attggttgct acattcaatt ttcaactcag tcaacggttg agattcactc tgacttcccc      1920
aatctaagcc gcggatgcaa acggttgaat ctaacccaca atccaatctc gttacttagg      1980
ggcttttccg tcattaactc accctgcca cccggtttcc ctataaattg gaactcaatg       2040
ctcccctcta aactcgtatc gcttcagagt tgagaccaag acacactcgt tcatatatct      2100
ctctgctctt ctcttctctt ctacctctca aggtactttt cttctccctc taccaaatcc      2160
tagattccgt ggttcaattt cggatcttgc acttctggtt tgctttgcct tgcttttcc      2220 tcaactgggt ccatctagga tccatgtgaa actctactct ttctttaata tctgcggaat      2280
acgcgtttga ctttcagatc tagtcgaaat catttcataa ttgcctttct ttcttttagc      2340
ttatgagaaa taaatcact ttttttttat ttcaaaataa accttgggcc ttgtgctgac       2400
tgagatgggg tttggtgatt acagaatttt agcgaatttt gtaattgtac ttgtttgtct      2460
gtagttttgt tttgttttct tgtttctcat acattcctta ggcttcaatt ttattcgagt      2520
ataggtcaca ataggaattc aaactttgag caggggaatt aatcccttcc ttcaaatcca      2580
gtttgtttgt atatatgttt aaaaaatgaa acttttgctt taaattctat tataactttt      2640
tttatggctg aaattttgc atgtgtcttt gctctctgtt gtaaatttac tgtttaggta      2700
ctaactctag gcttgttgtg cagttttga agtataacaa cagaagttcc tattccgaag      2760
ttcctattct ctagaaagta taggaacttc cactagtcca tgaaaaagcc tgaactcacc      2820
gcgacgtctg tcgagaagtt tctgatcgaa aagttcgaca gcgtctccga cctgatgcag      2880
ctctcggagg gcgaagaatc tcgtgctttc agcttcgatg taggagggcg tggatatgtc      2940
ctgcgggtaa atagctgcgc cgatggtttc tacaaagatc gttatgttta tcggcacttt      3000
gcatcggccg cgctcccgat tccggaagtg cttgacattg ggaattcag cgagagcctg       3060 acctattgca tctcccgccg tgcacagggt gtcacgttgc aagacctgcc tgaaaccgaa      3120
ctgcccgctg ttctgcagcc ggtcgcggag gccatggatg cgatcgctgc ggccgatctt      3180
agccagacga gcgggttcgg cccattcgga ccgcaaggaa tcggtcaata cactacatgg      3240
cgtgatttca tatgcgcgat tgctgatccc catgtgtatc actggcaaac tgtgatggac      3300
gacaccgtca gtgcgtccgt cgcgcaggct ctcgatgagc tgatgcttg ggccgaggac       3360 tgccccgaag tccggcacct cgtgcacgcg gatttcggct ccaacaatgt cctgacggac      3420
aatggccgca taacagcggt cattgactgg agcgaggcga tgttcgggga ttcccaatac      3480
gaggtcgcca acatcttctt ctggaggccg tggttggctt gtatgagca gcagacgcgc      3540 tacttcgagc ggaggcatcc ggagcttgca ggatcgccgc ggctccgggc gtatatgctc      3600
cgcattggtc ttgaccaact ctatcagagc ttggttgacg gcaatttcga tgatgcagct      3660
tgggcgcagg gtcgatgcga cgcaatcgtc cgatccggag ccgggactgt cgggcgtaca      3720
```

```
caaatcgccc gcagaagcgc ggccgtctgg accgatggct gtgtagaagt actcgccgat    3780
agtggaaacc gacgccccag cactcgtccg agggcaaagg aatagtgagg tacctaaaga    3840
aggagtgcgt cgaagcagat cgttcaaaca tttggcaata aagtttctta agattgaatc    3900
ctgttgccgg tcttgcgatg attatcatat aatttctgtt gaattacgtt aagcatgtaa    3960
taattaacat gtaatgcatg acgttattta tgagatgggt ttttatgatt agagtcccgc    4020
aattatacat ttaatacgcg atagaaaaca aaatatagcg cgcaaactag gataaattat    4080
cgcgcgcggt gtcatctatg ttactagatc gatgtcgacc cgggccctag gaggccggcc    4140
cagctgatga tcccggtgaa gttcctattc cgaagttcct attctccaga agtatagga    4200 acttcactag agcttgcggc cgcgcatgct gacttaatca gctaacgcca ctcgacctgc    4260
aggcatgccc gcggatatcg atgggccccg gccgaagctt caagtttgta caaaaaagca    4320
ggctggcgcc ggaaccaatt cagtcgactg gatccggtac cgaattcgcg gccgcactcg    4380
agatatctag acccagcttt cttgtacaaa gtggccgtta acggatcggc cagaatccgg    4440
taagtgacta gggtcacgtg accctagtca cttaaattcg gccagaatgg ccatctggat    4500
tcagcaggcc tagaaggccc ggaccgatta aactttaatt cggtccgggt tacctctaga    4560
aagcttgtcg acctgcaggt acaagtacaa gggacttgtg agttgtaagg ctgtatttac    4620
aatagtgaaa agagaatcat ctgggtgatt gggttttag tccccagtga cgaattaaag    4680
gtttgaattc ttagtatgtt tgggaatcaa ttaggaattt cgtttggac tttcaaagc    4740 aattattcac ttttcattc attaaatgtg actaaaaaat tgttattct ccattggcca    4800 ggatgcatcg tttatataaa cataaccta gtgaaagcag tgttttcatg tgacagcggc    4860
agactatatc ttaaacaaaa ttacttgtaa agaaagatac cgttaggaaa aaaatgaaaa    4920
gaaaattgaa gctatcactt gtttactttc ctaatatctt tcaagaatac aatgtggtga    4980
atttcaattt tccctacata tgtataccgt cagcctgacg caacttatga aacttctctt    5040
tctttcattt gatgtatata taaagacaca ttatatataa agaaacttta tatatatctc    5100
catcatattt tagtacttgc tactatgtaa aattagctgt tggaagtatc tcaagaaaca    5160 tttaattat tgaaccaagc attaaccatt catctacatt tgagttctaa aataaatctt    5220
aaatgatgtg gaggaaggga aattgttaat tatttccctc ttctcctaca tggatatacc    5280
tgaaacatgc aatggatgga ttagatttta acatttgcag cctgagaagt tcactgactt    5340
tcctccagct atttatgtg tgcccgccac catttatagc tcatgattgt agctgaactg    5400
caaaaactgc atcgattgca aactgaaatt gagaatctct tttcaacttt atatgctgat    5460
tgatgcatgc tgagcatgct atactagtac tcgaagttcc tatatgtaga ctttgttact    5520
gcctaatata ctttgtgttt gttctcaagt tcttatttta tttcatattt tttcctataa    5580
aaggttaatg gctctataaa ggttgagtga cggatccggt cacctaagtg actagggtca    5640
cgtgacccta gtcacttatt cccgggcaac tttattatac aaagttgata gatctcgaat    5700
tcattccgat taatcgtgg                                                 5719
```

<210> SEQ ID NO 303
<211> LENGTH: 6611
<212> TYPE: DNA
<213> ORGANISM: Artificial sequence
<220> FEATURE:
<223> OTHER INFORMATION: synthesized sequence- U6-9.1:DD43CR2+EF1A2:CAS9

<400> SEQUENCE: 303

```
cgcgccggta cccgggttaa gagaattgta agtgtgcttt tatatattta aaattaatat     60
```

```
attttgaaat gttaaaatat aaaagaaaat tcaatgtaaa ttaaaaataa ataaatgttt      120
aataaagata aattttaaaa cataaaagaa aatgtctaac aagaggatta agatcctgtg      180
ctcttaaatt tttaggtgtt gaaatcttag ccatacaaaa tatattttat taaaaccaag      240
catgaaaaaa gtcactaaag agctatataa ctcatgcagc tagaaatgaa gtgaagggaa      300
tccagtttgt tctcagtcga aagagtgtct atctttgttc ttttctgcaa ccgagttaag      360
caaaatggga atgcgaggta tcttcctttc gttaggggag caccagatgc atagttagtc      420
ccacattgat gaatataaca agagcttcac agaatatata gcccaggcca cagtaaaagc      480
ttgtattcta gaaagaggga atgttttaga gctagaaata gcaagttaaa ataaggctag      540
tccgttatca acttgaaaaa gtggcaccga gtcggtgctt tttttgcgg ccgcaattgg       600 atcgggttta cttattttgt gggtatctat acttttatta gatttttaat caggctcctg      660
atttcttttt atttcgattg aattcctgaa cttgtattat tcagtagatc gaataaatta      720 taaaagata aaatcataaa ataatatttt atcctatcaa tcatattaaa gcaatgaata       780
tgtaaaatta atcttatctt tattttaaaa aatcatatag gtttagtatt ttttaaaaa      840 taaagatagg attagtttta ctattcactg cttattactt ttaaaaaat cataaaggtt       900 tagtattttt ttaaaataaa tataggaata gttttactat tcactgcttt aatagaaaaa      960
tagtttaaaa tttaagatag ttttaatccc agcatttgcc acgttgaac gtgagccgaa      1020 acgatgtcgt tacattatct taacctagct gaaacgatgt cgtcataata tcgccaaatg     1080
ccaactggac tacgtcgaac ccacaaatcc cacaaagcgc gtgaaatcaa atcgctcaaa     1140 ccacaaaaa gaacaacgcg tttgttacac gctcaatccc acgcgagtag agcacagtaa      1200
ccttcaaata agcgaatggg gcataatcag aaatccgaaa taaacctagg ggcattatcg     1260
gaaatgaaaa gtagctcact caatataaaa atctaggaac cctagttttc gttatcactc     1320
tgtgctccct cgctctattt ctcagtctct gtgtttgcgg ctgaggattc cgaacgagtg     1380
accttcttcg tttctcgcaa aggtaacagc ctctgctctt gtctcttcga ttcgatctat     1440
gcctgtctct tatttacgat gatgtttctt cggttatgtt tttttattta tgctttatgc     1500
tgttgatgtt cggttgtttg tttcgctttg ttttttgtggt tcagtttttt aggattcttt    1560 tggttttttga atcgattaat cggaagagat tttcgagtta tttggtgtgt tggaggtgaa    1620 tcttttttttt gaggtcatag atctgttgta tttgtgttat aaacatgcga ctttgtatga   1680 tttttttacga ggttatgatg ttctggttgt tttattatga atctgttgag acagaaccat   1740 gattttttgtt gatgttcgtt tacactatta aaggtttgtt ttaacaggat taaaagtttt   1800
ttaagcatgt tgaaggagtc ttgtagatat gtaaccgtcg atagttttt tgtgggtttg    1860 ttcacatgtt atcaagctta atcttttact atgtatgcga ccatatctgg atccagcaaa    1920
ggcgattttt taattccttg tgaaactttt gtaatatgaa gttgaaattt tgttattggt    1980
aaactataaa tgtgtgaagt tggagtatac ctttaccttc ttatttggct ttgtgatagt    2040
ttaatttata tgtattttga gttctgactt gtatttcttt gaattgattc tagtttaagt    2100
aatccatgga caaaaagtac tcaatagggc tcgacatagg gactaactcc gttggatggg    2160
ccgtcatcac cgacgagtac aaggtgccct ccaagaagtt caaggtgttg ggaaacaccg    2220
acaggcacag cataaagaag aatttgatcg gtgccctcct cttcgactcc ggagagaccg    2280
ctgaggctac caggctcaag aggaccgcta aaggcgcta caccgaagg aagaacagaa     2340 tctgctacct gcaggagatc ttctccaacg agatggccaa ggtggacgac tccttcttcc    2400
```

```
accgccttga ggaatcattc ctggtggagg aggataaaaa gcacgagaga cacccaatct    2460
tcgggaacat cgtcgacgag gtggcctacc atgaaaagta ccctaccatc taccacctga    2520
ggaagaagct ggtcgactct accgacaagg ctgacttgcg cttgatttac ctggctctcg    2580
ctcacatgat aaagttccgc ggacacttcc tcattgaggg agacctgaac ccagacaact    2640
ccgacgtgga caagctcttc atccagctcg ttcagaccta caaccagctt ttcgaggaga    2700
acccaatcaa cgccagtgga gttgacgcca aggctatcct ctctgctcgt ctgtcaaagt    2760
ccaggaggct tgagaacttg attgcccagc tgcctggcga aaagaagaac ggactgttcg    2820
gaaacttgat cgctctctcc ctgggattga ctcccaactt caagtccaac ttcgacctcg    2880
ccgaggacgc taagttgcag ttgtctaaag acacctacga cgatgacctc gacaacttgc    2940
tggcccagat aggcgaccaa tacgccgatc tcttcctcgc cgctaagaac ttgtccgacg    3000
caatcctgct gtccgacatc ctgagagtca acactgagat taccaaagct cctctgtctg    3060
cttccatgat taagcgctac gacgagcacc accaagatct gaccctgctc aaggccctgg    3120
tgagacagca gctgcccgag aagtacaagg agatcttttt cgaccagtcc aagaacggct    3180
acgccggata cattgacgga ggcgcctccc aggaagagtt ctacaagttc atcaagccca    3240
tccttgagaa gatggacggt accgaggagc tgttggtgaa gttgaacaga gaggacctgt    3300
tgaggaagca gagaaccttc gacaacggaa gcatccctca ccaaatccac ctgggagagc    3360
tccacgccat cttgaggagg caggaggatt tctatccctt cctgaaggac aaccgcgaga    3420
agattgagaa gatcttgacc ttcagaattc cttactacgt cgggccactc gccagaggaa    3480
actctaggtt cgcctggatg acccgcaaat ctgaagagac cattactccc tggaacttcg    3540
aggaagtcgt ggacaagggc gcttccgctc agtctttcat cgagaggatg accaacttcg    3600
ataaaaatct gcccaacgag aaggtgctgc ccaagcactc cctgttgtac gagtatttca    3660
cagtgtacaa cgagctcacc aaggtgaagt acgtcacaga gggaatgagg aagcctgcct    3720
tcttgtccgg agagcagaag aaggccatcg tcgacctgct cttcaagacc aacaggaagg    3780
tgactgtcaa gcagctgaag gaggactact tcaagaagat cgagtgcttc gactccgtcg    3840
agatctctgg tgtcgaggac aggttcaacg cctcccttgg gacttaccac gatctgctca    3900
agattattaa agacaaggac ttcctggaca acgaggagaa cgaggacatc cttgaggaca    3960
tcgtgctcac cctgaccttg ttcgaagaca gggaaatgat cgaagagagg ctcaagacct    4020
acgcccacct cttcgacgac aaggtgatga acagctgaa gagacgcaga tataccggct    4080
ggggaaggct ctcccgcaaa ttgatcaacg ggatcaggga caagcagtca gggaagacta    4140
tactcgactt cctgaagtcc gacggattcg ccaacaggaa cttcatgcag ctcattcacg    4200
acgactcctt gaccttcaag gaggacatcc agaaggctca ggtgtctgga cagggtgact    4260
ccttgcatga gcacattgct aacttggccg gctctcccgc tattaagaag gcatttgc    4320 agaccgtgaa ggtcgttgac gagctcgtga aggtgatggg acgccacaag ccagagaaca    4380
tcgttattga gatggctcgc gagaaccaaa ctacccagaa agggcagaag aattcccgcg    4440
agaggatgaa gcgcattgag gagggcataa agagcttgg ctctcagatc ctcaaggagc    4500
accccgtcga gaacactcag ctgcagaacg agaagctgta cctgtactac ctccaaaacg    4560
gaagggacat gtacgtggac caggagctgg acatcaacag gttgtccgac tacgacgtcg    4620
accacatcgt gcctcagtcc ttcctgaagg atgactccat cgacaataaa gtgctgacac    4680
gctccgataa aaatagaggc aagtccgaca acgtcccctc cgaggaggtc gtgaagaaga    4740
tgaaaaacta ctggagacag ctccttgaacg ccaagctcat cacccagcgt aagttcgaca    4800
```

```
acctgactaa ggctgagaga ggaggattgt ccgagctcga taaggccgga ttcatcaaga    4860
gacagctcgt cgaaacccgc caaattacca agcacgtggc ccaaattctg gattcccgca    4920
tgaacaccaa gtacgatgaa aatgacaagc tgatccgcga ggtcaaggtg atcaccttga    4980
agtccaagct ggtctccgac ttccgcaagg acttccagtt ctacaaggtg agggagatca    5040
acaactacca ccacgcacac gacgcctacc tcaacgctgt cgttggaacc gccctcatca    5100
aaaaatatcc taagctggag tctgagttcg tctacggcga ctacaaggtg tacgacgtga    5160
ggaagatgat cgctaagtct gagcaggaga tcggcaaggc caccgccaag tacttcttct    5220
actccaacat catgaacttc ttcaagaccg agatcactct cgccaacggt gagatcagga    5280
agcgcccact gatcgagacc aacggtgaga ctggagagat cgtgtgggac aaagggaggg    5340
atttcgctac tgtgaggaag gtgctctcca tgcctcaggt gaacatcgtc aagaagaccg    5400
aagttcagac cggaggattc tccaaggagt ccatcctccc caagagaaac tccgacaagc    5460
tgatcgctag aaagaaagac tgggacccta gaagtacgg aggcttcgat tctcctaccg    5520
tggcctactc tgtgctggtc gtggccaagg tggagaaggg caagtccaag aagctgaaat    5580
ccgtcaagga gctcctcggg attaccatca tggagaggga ttccttcgag aagaacccta    5640
tcgacttcct ggaggccaag ggatataaag aggtgaagaa ggacctcatc atcaagctgc    5700
ccaagtactc cctcttcgag ttggagaacg gaaggaagag gatgctggct tctgccggag    5760
agttgcagaa gggaaatgag ctcgcccttc cctccaagta cgtgaacttc ctgtacctcg    5820
cctctcacta tgaaaagttg aagggctctc ctgaggacaa cgagcagaag cagctcttcg    5880
tggagcagca caagcactac ctggacgaaa ttatcgagca gatctctgag ttctccaagc    5940
gcgtgatatt ggccgacgcc aacctcgaca aggtgctgtc cgcctacaac aagcacaggg    6000
ataagcccat cgcgagcag gctgaaaaca ttatccacct gtttaccctc acaaacttgg    6060
gagcccctgc tgccttcaag tacttcgaca ccaccattga caggaagaga tacacctcca    6120
ccaaggaggt gctcgacgca acactcatcc accaatccat caccggcctc tatgaaacaa    6180
ggattgactt gtcccagctg ggaggcgact ctagagccga tcccaagaag aagagaaagg    6240
tgtaggttaa cctagacttg tccatcttct ggattggcca acttaattaa tgtatgaaat    6300
aaaaggatgc acacatagtg acatgctaat cactataatg tgggcatcaa agttgtgtgt    6360
tatgtgtaat tactagttat ctgaataaaa gagaaagaga tcatccatat ttcttatcct    6420
aaatgaatgt cacgtgtctt tataattctt tgatgaacca gatgcatttc attaaccaaa    6480
tccatataca tataaatatt aatcatatat aattaatatc aattgggtta gcaaaacaaa    6540
tctagtctag gtgtgttttg cgaattcgat atcaagctta tcgataccgt cgaggggggg    6600
cccggtaccg g                                                        6611
```

<210> SEQ ID NO 304  
<211> LENGTH: 64  
<212> TYPE: DNA  
<213> ORGANISM: Artificial sequence  
<220> FEATURE:  
<223> OTHER INFORMATION: synthesized sequence- DD20 qPCR amplicon

<400> SEQUENCE: 304

```
attcggaact gacacacgac atgatggaac gtgactaagg tgggttttg actttgcatg    60 tcga                                                                64
```

<210> SEQ ID NO 305

```
<211> LENGTH: 115
<212> TYPE: DNA
<213> ORGANISM: Artificial sequence
<220> FEATURE:
<223> OTHER INFORMATION: synthesized sequence- DD43 qPCR amplicon

<400> SEQUENCE: 305
aaagaagagg cagactccaa ttcctctttt ctagaatacc ctccgtacgt acaagtacaa    60
gggacttgtg agttgtaagg ctgtatttac aatagtgaaa agagaatcat ctggg        115

<210> SEQ ID NO 306
<211> LENGTH: 20
<212> TYPE: DNA
<213> ORGANISM: Artificial sequence
<220> FEATURE:
<223> OTHER INFORMATION: synthesized sequence- primer, DD20-CR1

<400> SEQUENCE: 306
ggaactgaca cacgacatga                                                20

<210> SEQ ID NO 307
<211> LENGTH: 20
<212> TYPE: DNA
<213> ORGANISM: Artificial sequence
<220> FEATURE:
<223> OTHER INFORMATION: synthesized sequence- primer, DD20-CR2

<400> SEQUENCE: 307
gacatgatgg aacgtgacta                                                20

<210> SEQ ID NO 308
<211> LENGTH: 22
<212> TYPE: DNA
<213> ORGANISM: Artificial sequence
<220> FEATURE:
<223> OTHER INFORMATION: synthesized sequence- primer, DD20-F

<400> SEQUENCE: 308
attcggaact gacacacgac at                                             22

<210> SEQ ID NO 309
<211> LENGTH: 17
<212> TYPE: DNA
<213> ORGANISM: Artificial sequence
<220> FEATURE:
<223> OTHER INFORMATION: synthesized sequence- FAM-MGB probe, DD20-T

<400> SEQUENCE: 309
atggaacgtg actaagg                                                   17

<210> SEQ ID NO 310
<211> LENGTH: 22
<212> TYPE: DNA
<213> ORGANISM: Artificial sequence
<220> FEATURE:
<223> OTHER INFORMATION: synthesized sequence- primer, DD20-R

<400> SEQUENCE: 310
tcgacatgca aagtcaaaaa cc                                             22

<210> SEQ ID NO 311
<211> LENGTH: 20
<212> TYPE: DNA
<213> ORGANISM: Artificial sequence
<220> FEATURE:
<223> OTHER INFORMATION: synthesized sequence- primer, DD43CR1
```

<400> SEQUENCE: 311
gtcccttgta cttgtacgta                                           20

<210> SEQ ID NO 312
<211> LENGTH: 20
<212> TYPE: DNA
<213> ORGANISM: Artificial sequence
<220> FEATURE:
<223> OTHER INFORMATION: synthesized sequence- primer, DD43CR2

<400> SEQUENCE: 312
gtattctaga aaagaggaat                                           20

<210> SEQ ID NO 313
<211> LENGTH: 26
<212> TYPE: DNA
<213> ORGANISM: Artificial sequence
<220> FEATURE:
<223> OTHER INFORMATION: synthesized sequence- primer, DD43-F

<400> SEQUENCE: 313
ttctagaata ccctccgtac gtacaa                                    26

<210> SEQ ID NO 314
<211> LENGTH: 26
<212> TYPE: DNA
<213> ORGANISM: Artificial sequence
<220> FEATURE:
<223> OTHER INFORMATION: synthesized sequence- primer, DD43-F2

<400> SEQUENCE: 314
aaagaagagg cagactccaa ttcctc                                    26

<210> SEQ ID NO 315
<211> LENGTH: 19
<212> TYPE: DNA
<213> ORGANISM: Artificial sequence
<220> FEATURE:
<223> OTHER INFORMATION: synthesized sequence- FAM-MGB probe, DD43-T

<400> SEQUENCE: 315
caagggactt gtgagttgt                                            19

<210> SEQ ID NO 316
<211> LENGTH: 26
<212> TYPE: DNA
<213> ORGANISM: Artificial sequence
<220> FEATURE:
<223> OTHER INFORMATION: synthesized sequence- primer, DD43-R

<400> SEQUENCE: 316
cccagatgat tctcttttca ctattg                                    26

<210> SEQ ID NO 317
<211> LENGTH: 19
<212> TYPE: DNA
<213> ORGANISM: Artificial sequence
<220> FEATURE:
<223> OTHER INFORMATION: synthesized sequence- primer, Cas9-F

<400> SEQUENCE: 317
ccttcttcca ccgccttga                                            19

<210> SEQ ID NO 318

```
<211> LENGTH: 19
<212> TYPE: DNA
<213> ORGANISM: Artificial sequence
<220> FEATURE:
<223> OTHER INFORMATION: synthesized sequence- FAM-MGB probe, Cas9-T

<400> SEQUENCE: 318
aatcattcct ggtggagga                                                   19

<210> SEQ ID NO 319
<211> LENGTH: 21
<212> TYPE: DNA
<213> ORGANISM: Artificial sequence
<220> FEATURE:
<223> OTHER INFORMATION: synthesized sequence- primer, Cas9-R

<400> SEQUENCE: 319
tgggtgtctc tcgtgctttt t                                                21

<210> SEQ ID NO 320
<211> LENGTH: 22
<212> TYPE: DNA
<213> ORGANISM: Artificial sequence
<220> FEATURE:
<223> OTHER INFORMATION: synthesized sequence- primer, Sams-76F

<400> SEQUENCE: 320
aggcttgttg tgcagttttt ga                                               22

<210> SEQ ID NO 321
<211> LENGTH: 22
<212> TYPE: DNA
<213> ORGANISM: Artificial sequence
<220> FEATURE:
<223> OTHER INFORMATION: synthesized sequence- FAM-MGB probe, FRT1I-63T

<400> SEQUENCE: 321
tggactagtg gaagttccta ta                                               22

<210> SEQ ID NO 322
<211> LENGTH: 21
<212> TYPE: DNA
<213> ORGANISM: Artificial sequence
<220> FEATURE:
<223> OTHER INFORMATION: synthesized sequence- primer, FRT1I-41F

<400> SEQUENCE: 322
gcggtgagtt caggcttttt c                                                21

<210> SEQ ID NO 323
<211> LENGTH: 31
<212> TYPE: DNA
<213> ORGANISM: Artificial sequence
<220> FEATURE:
<223> OTHER INFORMATION: synthesized sequence- primer, DD20-LB

<400> SEQUENCE: 323
ggttataccT tcttcttagt gtggtctatc c                                     31

<210> SEQ ID NO 324
<211> LENGTH: 31
<212> TYPE: DNA
<213> ORGANISM: Artificial sequence
<220> FEATURE:
<223> OTHER INFORMATION: synthesized sequence- primer, Sams-A1

<400> SEQUENCE: 324
```
cccaaaataa ttagtatgat tggtaaggaa g                                   31

<210> SEQ ID NO 325
<211> LENGTH: 23
<212> TYPE: DNA
<213> ORGANISM: Artificial sequence
<220> FEATURE:
<223> OTHER INFORMATION: synthesized sequence- primer, QC498A-S1

<400> SEQUENCE: 325
ggaacttcac tagagcttgc ggc                                            23

<210> SEQ ID NO 326
<211> LENGTH: 28
<212> TYPE: DNA
<213> ORGANISM: Artificial sequence
<220> FEATURE:
<223> OTHER INFORMATION: synthesized sequence- primer, DD20-RB

<400> SEQUENCE: 326
gccattacat tcttcataag ttcctctc                                       28

<210> SEQ ID NO 327
<211> LENGTH: 26
<212> TYPE: DNA
<213> ORGANISM: Artificial sequence
<220> FEATURE:
<223> OTHER INFORMATION: synthesized sequence- primer, DD43-LB

<400> SEQUENCE: 327
gtgtagtcca ttgtagccaa gtcacc                                         26

<210> SEQ ID NO 328
<211> LENGTH: 24
<212> TYPE: DNA
<213> ORGANISM: Artificial sequence
<220> FEATURE:
<223> OTHER INFORMATION: synthesized sequence- primer, DD43-RB

<400> SEQUENCE: 328
caaaccggag agagaggaag aacc                                           24

<210> SEQ ID NO 329
<211> LENGTH: 2105
<212> TYPE: DNA
<213> ORGANISM: Artificial Sequence
<220> FEATURE:
<223> OTHER INFORMATION: synthesized sequence- DD20 HR1-HR2 PCR amplicon

<400> SEQUENCE: 329
ggttatacct tcttcttagt gtggtctatc ccctagtaat aattacacat ctaagatatc     60
cccttctttt tcaagtaaaa taatatcata tgatctcatt ttagtgaaac aatactattt    120
ccctgataac tctcttcaac attagggact tcatctaatc atctactttc aaggtataac    180
tagacgtatt tgttctttta aaaaaaacac tagatgtact cgtcaactca aaattcatcg    240
ttcatgcatt ttaattaaac tttaattagc taatgagtag aaaagatca tacgagtaaa    300 atagaagaat cttcctagat tttggaagaa tggattggag tgtaagtgaa ttgatccatt    360
agtggaagat gctctttaca atggccaaac tgttctaatt gttagagcac atttgagatg    420
aaacacttca gtagtggagg taacctacaa tcctaggatc tgtatcctct atcactaatg    480
gagcaatggg tttgagattg acttactcct ttccttgtct ctcgtagtgc atatgcgcac    540

```
tttcaaaggc tacacaaaag ccgttaactt tttgtttatt taagttacga aagatagttg      600
aattagagta aatggtgata ttgaattagg attttaaata attttaaaag aattttttta      660
ataaaaaaaa tattgtgttg ttggatcaaa attttaaat aacatgaata aggaaatgga       720
ttgcaatgag gttttaaaca attattttaa catataggat tttagaaaga cttttataat      780
attttgttga agtttagatt ttaatatatt tatgttttaa aattttaaaa aaaacttcat      840
gaatttataa tatttgaaaa agacacgtga atatttagaa acatttaaa attacaataa       900 taaatcataa tgagataggg tgtattcatg tgtagacgag acaccaagta tatggttcac      960
aagtgaatca tcttttttt ttacagcaca agtagatcac ttgtacttat caaaattcgg      1020
aactgacaca cgacatgatg gaacgtgact aaggtgggtt tttgactttg catgtcgaag     1080
tgagagtgat tttattgaga gaataataga agacctacaa aacaaatgat cccgacgcta     1140
aagtaagtac gagagttaag agaataaatg ggaaaatatg catacatgat taggtgtgtg     1200
ttcgtctcaa gaaagtacga atgaatatgg tgtgtttgta gtacatgaat gatgtgtttt     1260
gagggttcaa gggaaattga tatttataga gtgaaatgga accagaggtc tttgttgaca     1320
agggttgtta tgactcttgc aaataattaa tagcttataa ataatagcca ataacttatt     1380
atagatagag ttagagataa tatatagcta aatttgaaca aggcatacaa aacaaaaatg     1440
ctaaatatga ataagacaat caaaattgta gtcgatgttc aactctttgt cgttgaagaa     1500
cttgtttgca gtggtatagt aaatgggtgt gagtgcagtg tctcacccat ctcacaccac     1560
acaaccaact tcatatctaa agatattgtc gctgaataca aaattgagtt atggaatata     1620
caattcataa tatagatacg aaaaatcatt tcttacaaaa cattcaatca aaaattattc     1680
aaacataatt ctagattaag taatccgaag tacaagttag tatcctagat ccgttaattt     1740
aaaattatgt ttgcataatt ttggatttgg tgttctataa gggcacaatt ttgttcattc     1800
ttacaagttt gtcaattcta aaatatatgc aaatttgaag aaaaaaaatt tacgaatgtg     1860
tctcaaacaa taacttaatg ggaggagaat gagggatgaa gaagctcaaa attaccaacg     1920
ccttctacct caagaagcta cttcacacaa aatatgactg gcggaaggat aggggacaac     1980
cgataacgag aaggagatac ataaggtaat gtacgttgtt gtgtgaggta cacaattatg     2040
gggatgaaga agttcaactt tagtcgaaaa aatgtttgag aggaacttat gaagaatgta     2100
atggc                                                                 2105
```

<210> SEQ ID NO 330
<211> LENGTH: 1204
<212> TYPE: DNA
<213> ORGANISM: Artificial Sequence
<220> FEATURE:
<223> OTHER INFORMATION: synthesized sequence- DD20 HR1-SAMS PCR
      amplicon

<400> SEQUENCE: 330

```
ggttatacct tcttcttagt gtggtctatc ccctagtaat aattacacat ctaagatatc       60
cccttctttt tcaagtaaaa taatatcata tgatctcatt ttagtgaaac aatactattt      120
ccctgataac tctcttcaac attagggact tcatctaatc atctactttc aaggtataac      180
tagacgtatt tgttctttta aaaaaaacac tagatgtact cgtcaactca aaattcatcg      240
ttcatgcatt ttaattaaac tttaattagc taatgagtag aaaaagatca tacgagtaaa      300
atagaagaat cttcctagat tttggaagaa tggattggag tgtaagtgaa ttgatccatt      360
agtggaagat gctctttaca atggccaaac tgttctaatt gttagagcac atttgagatg      420
```

| | | |
|---|---|---|
| aaacacttca gtagtggagg taacctacaa tcctaggatc tgtatcctct atcactaatg | 480 | |
| gagcaatggg tttgagattg acttactcct ttccttgtct ctcgtagtgc atatgcgcac | 540 | |
| tttcaaaggc tacacaaaag ccgttaactt tttgtttatt taagttacga aagatagttg | 600 | |
| aattagagta aatggtgata ttgaattagg attttaaata atttttaaaag aattttttta | 660 | |
| ataaaaaaaa tattgtgttg ttggatcaaa attttttaaat aacatgaata aggaaatgga | 720 | |
| ttgcaatgag gttttaaaca attatttttaa catataggat tttagaaaga cttttataat | 780 | |
| attttgttga agtttagatt ttaatatatt tatgtttttaa aattttaaaa aaaacttcat | 840 | |
| gaatttataa tatttgaaaa agacacgtga atatttagaa acatttaaa attacaataa | 900 | |
| taaatcataa tgagataggg tgtattcatg tgtagacgag acaccaagta tatggttcac | 960 | |
| aagtgaatca tctttttttt ttacagcaca agtagatcac ttgtacttat caaaattcgg | 1020 | |
| aactgacaca cactagtggt cacctaagtg actagggtca cgtgaccta gtcacttatt | 1080 | |
| cccaaacact agtaacggcc gccagtgtgc tggaattcgc ccttcccaag ctttgctcta | 1140 | |
| gatcaaactc acatccaaac ataacatgga tatcttcctt accaatcata ctaattattt | 1200 | |
| tggg | 1204 | |

<210> SEQ ID NO 331
<211> LENGTH: 1459
<212> TYPE: DNA
<213> ORGANISM: Artificial Sequence
<220> FEATURE:
<223> OTHER INFORMATION: synthesized sequence- DD20 NOS-HR2 PCR amplicon

<400> SEQUENCE: 331

| | | |
|---|---|---|
| ggaacttcac tagagcttgc ggccgcgcat gctgacttaa tcagctaacg ccactcgacc | 60 | |
| tgcaggcatg cccgcggata tcgatgggcc ccggccgaag cttcaagttt gtacaaaaaa | 120 | |
| gcaggctggc gccggaacca attcagtcga ctggatccgg taccgaattc gcggccgcac | 180 | |
| tcgagatatc tagacccagc tttcttgtac aaagtggccg ttaacggatc ggccagaatc | 240 | |
| cggtaagtga ctagggtcac gtgaccctag tcacttaaat tcggccagaa tggccatctg | 300 | |
| gattcagcag gcctagaagg cccggaccga ttaaacttta attcggtccg ggttacctct | 360 | |
| agaaagcttg tcgacctgca gacacgacat gatggaacgt gactaaggtg ggttttgac | 420 | |
| tttgcatgtc gaagtgagag tgattttatt gagagaataa tagaagacct acaaaacaaa | 480 | |
| tgatcccgac gctaaagtaa gtacgagagt taagagaata aatgggaaaa tatgcataca | 540 | |
| tgattaggtg tgtgttcgtc tcaagaaagt acgaatgaat atggtgtgtt tgtagtacat | 600 | |
| gaatgatgtg ttttgagggt tcaagggaaa ttgatattta tagagtgaaa tggaaccaga | 660 | |
| ggtctttgtt gacaagggtt gttatgactc ttgcaaataa ttaatagctt ataaataata | 720 | |
| gccaataact tattatagat agagttagag ataatatata gctaaatttg aacaaggcat | 780 | |
| acaaaacaaa aatgctaaat atgaataaga caatcaaaat tgtagtcgat gttcaactct | 840 | |
| ttgtcgttga agaacttgtt tgcagtggta tagtaaatgg gtgtgagtgc agtgtctcac | 900 | |
| ccatctcaca ccacacaacc aacttcatat ctaaagatat tgtcgctgaa tacaaaattg | 960 | |
| agttatggaa tatacaattc ataatataga tacgaaaaat catttcttac aaaacattca | 1020 | |
| atcaaaaatt attcaaacat aattctagat taagtaatcc gaagtacaag ttagtatcct | 1080 | |
| agatccgtta atttaaaatt atgtttgcat aattttggat ttggtgttct ataagggcac | 1140 | |
| aattttgttc attcttacaa gtttgtcaat tctaaaatat atgcaaattt gaagaaaaaa | 1200 | |
| aatttacgaa tgtgtctcaa acaataactt aatgggagga gaatgaggga tgaagaagct | 1260 | |

```
caaaattacc aacgccttct acctcaagaa gctacttcac acaaaatatg actggcggaa    1320
ggatagggga caaccgataa cgagaaggag atacataagg taatgtacgt tgttgtgtga    1380
ggtacacaat tatggggatg aagaagttca actttagtcg aaaaaatgtt tgagaggaac    1440
ttatgaagaa tgtaatggc                                                 1459

<210> SEQ ID NO 332
<211> LENGTH: 2098
<212> TYPE: DNA
<213> ORGANISM: Artificial Sequence
<220> FEATURE:
<223> OTHER INFORMATION: synthesized sequence- DD43 HR1-HR2 PCR amplicon

<400> SEQUENCE: 332
gtgtagtcca ttgtagccaa gtcaccaata tcttgttccc ctccttggtt tggcataaat      60
tgattttcat ggctcttctc ggtcgaaact ggagctaatt cacccttagt ctctcttaaa     120
attctggctg taagaaacac cacagaacac ataaattata aactaattat aatttgaaga     180
gtaaaatatg ttttactctt tatgatttaa ttagtgtagt tttaattttc tccttttttt     240
aaaaaatttt ggtattcata aatttcaatt ttttaaaaat aattgttgtt acccgttaat     300
gataacggga tatgttatgt taccactaaa tcggacaaaa aaaattcaaa acttttataa     360
ggattaaaat taacaaaaat attttaaaaa aatctaacct caataaagtt aaatttataa     420
gcacaaaata atacttttaa gcctaatttg gcaagacaca agcaagctca cctgtagcat     480
taatagaaag gaagcaaagc aagagaaaag caaccagaag gaagcgtttg cttggtgaca     540
cagccatctt acttgaattt atggtattac tgagaaacct tgatcttgct tcaaaatctt     600
ctagttaccc tcttttttata ggcagaaaga gaactagcta gttgccaata ggatatgagg     660
acatgtggtg caatgcactc actcttcaag gacaagaaaa acaatggcta caattgtggt     720
tcaaatcaat gtctcctgct ctgtcctgcc tgaaaatgac acccttttgc ttggaaaaga     780
ggatcaaagc taagaacagg agtggcttca ttcccttcat gtaaccaaac actttcgcat     840
tctgtcattc gtgaatcagc aaaatctgca accaaaaata tatggtgcct aaataaaaga     900
aataaaataa tttagagttg cggactaaaa taataaacaa agaaatata ttataatcta     960 gaattaattt aggactaaaa gaagaggcag actccaattc ctcttttcta gaatacctc    1020 cgtacgtaca agtacaaggg acttgtgagt tgtaaggctg tatttacaat agtgaaaaga    1080
gaatcatctg ggtgattggg ttttagtcc ccagtgacga attaaaggtt tgaattctta    1140
gtatgtttgg gaatcaatta ggaatttcgt tttggacttt ccaaagcaat tattcacttt    1200
ttcattcatt aaatgtgact aaaaaattgt tatttctcca ttggccagga tgcatcgttt    1260
atataaacat aaccttagtg aaagcagtgt tttcatgtga cagcggcaga ctatatctta    1320
aacaaaatta cttgtaaaga aagataccgt taggaaaaaa atgaaaagaa aattgaagct    1380
atcacttgtt tactttccta atatctttca agaatacaat gtggtgaatt tcaatttttcc   1440 ctacatatgt ataccgtcag cctgacgcaa cttatgaaac ttctctttct ttcatttgat    1500
gtatatataa agacacatta tatataaaga aactttatat atatctccat catatttag    1560 tacttgctac tatgtaaaat tagctgttgg aagtatctca agaaacattt aatttattga    1620
accaagcatt aaccattcat ctacatttga gttctaaaat aaatcttaaa tgatgtggag    1680
gaagggaaat tgttaattat ttccctcttc tcctacatgg atataccctga acatgcaat   1740 ggatggatta gattttaaca tttgcagcct gagaagttca ctgactttcc tccagctatt    1800
```

| | |
|---|---:|
| ttatgtgtgc cgccaccat ttatagctca tgattgtagc tgaactgcaa aaactgcatc | 1860 |
| gattgcaaac tgaaattgag aatctctttt caactttata tgctgattga tgcatgctga | 1920 |
| gcatgctata ctagtactcg aagttcctat atgtagactt tgttactgcc taatatactt | 1980 |
| tgtgtttgtt ctcaagttct tatttattt catattttt cctataaaag gttaatggct | 2040 |
| ctataaaggt tgagtgacat atatatacta taaaggttct tcctctctct ccggtttg | 2098 |

<210> SEQ ID NO 333
<211> LENGTH: 1202
<212> TYPE: DNA
<213> ORGANISM: Artificial Sequence
<220> FEATURE:
<223> OTHER INFORMATION: synthesized sequence- DD43 HR1-SAMS PCR PCR
       amplicon

<400> SEQUENCE: 333

| | |
|---|---:|
| gtgtagtcca ttgtagccaa gtcaccaata tcttgttccc ctccttggtt tggcataaat | 60 |
| tgattttcat ggctcttctc ggtcgaaact ggagctaatt cacccttagt ctctcttaaa | 120 |
| attctggctg taagaaacac cacagaacac ataaattata aactaattat aatttgaaga | 180 |
| gtaaaatatg tttttactct tatgatttaa ttagtgtagt tttaattttc tccttttttt | 240 |
| aaaaaatttt ggtattcata aatttcaatt ttttaaaaat aattgttgtt acccgttaat | 300 |
| gataacggga tatgttatgt taccactaaa tcggacaaaa aaaattcaaa acttttataa | 360 |
| ggattaaaat taacaaaaat atttaaaaa aatctaacct caataaagtt aaatttataa | 420 |
| gcacaaaata atactttaa gcctaatttg gcaagacaca agcaagctca cctgtagcat | 480 |
| taatagaaag gaagcaaagc aagagaaaag caaccagaag gaagcgtttg cttggtgaca | 540 |
| cagccatctt acttgaattt atggtattac tgagaaacct tgatcttgct tcaaaatctt | 600 |
| ctagttaccc tcttttata ggcagaaaga gaactagcta gttgccaata ggatatgagg | 660 |
| acatgtggtg caatgcactc actcttcaag gacaagaaaa acaatggcta caattgtggt | 720 |
| tcaaatcaat gtctcctgct ctgtcctgcc tgaaaatgac acccttttgc ttggaaaga | 780 |
| ggatcaaagc taagaacagg agtggcttca ttcccttcat gtaaccaaac actttcgcat | 840 |
| tctgtcattc gtgaatcagc aaaatctgca accaaaaata tatggtgcct aaataaaga | 900 |
| aataaaataa tttagagttg cggactaaaa taataaacaa agaaatata ttataatcta | 960 |
| gaattaattt aggactaaaa gaagaggcag actccaattc ctcttttcta gaatacctc | 1020 |
| cgtacgtaca ctagtggtca cctaagtgac tagggtcacg tgaccctagt cacttattcc | 1080 |
| caaacactag taacggccgc cagtgtgctg gaattcgccc ttcccaagct tgctctaga | 1140 |
| tcaaactcac atccaaacat aacatggata tcttccttac caatcatact aattattttg | 1200 |
| gg | 1202 |

<210> SEQ ID NO 334
<211> LENGTH: 1454
<212> TYPE: DNA
<213> ORGANISM: Artificial Sequence
<220> FEATURE:
<223> OTHER INFORMATION: synthesized sequence- DD43 NOS-HR2 PCR PCR
       amplicon

<400> SEQUENCE: 334

| | |
|---|---:|
| ggaacttcac tagagcttgc ggccgcgcat gctgacttaa tcagctaacg ccactcgacc | 60 |
| tgcaggcatg cccgcggata tcgatgggcc ccggccgaag cttcaagttt gtacaaaaaa | 120 |
| gcaggctggc gccggaacca attcagtcga ctggatccgg taccgaattc gcggccgcac | 180 |

```
tcgagatatc tagacccagc tttcttgtac aaagtggccg ttaacggatc ggccagaatc    240
cggtaagtga ctagggtcac gtgaccctag tcacttaaat tcggccagaa tggccatctg    300
gattcagcag gcctagaagg cccggaccga ttaaacttta attcggtccg ggttacctct    360
agaaagcttg tcgacctgca ggtacaagta caagggactt gtgagttgta aggctgtatt    420
tacaatagtg aaaagagaat catctgggtg attgggtttt tagtccccag tgacgaatta    480
aaggtttgaa ttcttagtat gtttgggaat caattaggaa tttcgttttg gacttttcca    540
agcaattatt cactttttca ttcattaaat gtgactaaaa aattgttatt tctccattgg    600
ccaggatgca tcgtttatat aaacataacc ttagtgaaag cagtgttttc atgtgacagc    660
ggcagactat atcttaaaca aaattacttg taaagaaaga taccgttagg aaaaaaatga    720
aaagaaaatt gaagctatca cttgtttact ttcctaatat ctttcaagaa tacaatgtgg    780
tgaatttcaa ttttccctac atatgtatac cgtcagcctg acgcaactta tgaaacttct    840 cttttctttca tttgatgtat atataaagac acattatata taaagaaact ttatatatat    900
ctccatcata ttttagtact tgctactatg taaaattagc tgttggaagt atctcaagaa    960
acatttaatt tattgaacca agcattaacc attcatctac atttgagttc taaaataaat   1020
cttaaatgat gtggaggaag ggaaattgtt aattatttcc ctcttctcct acatggatat   1080
acctgaaaca tgcaatggat ggattagatt ttaacatttg cagcctgaga agttcactga   1140
ctttcctcca gctatttat gtgtgcccgc caccatttat agctcatgat tgtagctgaa   1200
ctgcaaaaac tgcatcgatt gcaaactgaa attgagaatc tcttttcaac tttatatgct   1260
gattgatgca tgctgagcat gctatactag tactcgaagt tcctatatgt agactttgtt   1320
actgcctaat atactttgtg tttgttctca agttcttatt ttatttcata tttttttccta   1380 taaaaggtta atggctctat aaaggttgag tgacatatat atactataaa ggttcttcct   1440
ctctctccgg tttg                                                    1454
```

<210> SEQ ID NO 335
<211> LENGTH: 60
<212> TYPE: DNA
<213> ORGANISM: Glycine max
<220> FEATURE:
<221> NAME/KEY: misc_feature
<222> LOCATION: (1)..(60)
<223> OTHER INFORMATION: soybean genomic DD20CR1 target region

<400> SEQUENCE: 335

```
acttgtactt atcaaaattc ggaactgaca cacgacatga tggaacgtga ctaaggtggg    60
```

<210> SEQ ID NO 336
<211> LENGTH: 59
<212> TYPE: DNA
<213> ORGANISM: Glycine max

<400> SEQUENCE: 336

```
acttgtactt atcaaaattc ggaactgaca cacgactgat ggaacgtgac taaggtggg    59
```

<210> SEQ ID NO 337
<211> LENGTH: 59
<212> TYPE: DNA
<213> ORGANISM: Glycine max

<400> SEQUENCE: 337

```
acttgtactt atcaaaattc ggaactgaca cacgaatgat ggaacgtgac taaggtggg    59
```

```
<210> SEQ ID NO 338
<211> LENGTH: 58
<212> TYPE: DNA
<213> ORGANISM: Glycine max

<400> SEQUENCE: 338
acttgtactt atcaaaattc ggaactgaca cacgatgatg gaacgtgact aaggtggg        58

<210> SEQ ID NO 339
<211> LENGTH: 58
<212> TYPE: DNA
<213> ORGANISM: Glycine max

<400> SEQUENCE: 339
acttgtactt atcaaaattc ggaactgaca cacgacgatg gaacgtgact aaggtggg        58

<210> SEQ ID NO 340
<211> LENGTH: 58
<212> TYPE: DNA
<213> ORGANISM: Glycine max

<400> SEQUENCE: 340
acttgtactt atcaaaattc ggaactgaca cacggtgatg gaacgtgact aaggtggg        58

<210> SEQ ID NO 341
<211> LENGTH: 57
<212> TYPE: DNA
<213> ORGANISM: Glycine max

<400> SEQUENCE: 341
acttgtactt atcaaaattc ggaactgaca cacatgatgg aacgtgacta aggtggg        57

<210> SEQ ID NO 342
<211> LENGTH: 57
<212> TYPE: DNA
<213> ORGANISM: Glycine max

<400> SEQUENCE: 342
acttgtactt atcaaaattc ggaactgaca cacgtgatgg aacgtgacta aggtggg        57

<210> SEQ ID NO 343
<211> LENGTH: 56
<212> TYPE: DNA
<213> ORGANISM: Glycine max

<400> SEQUENCE: 343
acttgtactt atcaaaattc ggaactgaca cactgatgga acgtgactaa ggtggg        56

<210> SEQ ID NO 344
<211> LENGTH: 56
<212> TYPE: DNA
<213> ORGANISM: Glycine max

<400> SEQUENCE: 344
acttgtactt atcaaaattc ggaactgaca cacggatgga acgtgactaa ggtggg        56

<210> SEQ ID NO 345
<211> LENGTH: 55
<212> TYPE: DNA
<213> ORGANISM: Glycine max

<400> SEQUENCE: 345
acttgtactt atcaaaattc ggaactgaca cacgatggaa cgtgactaag gtggg        55
```

<210> SEQ ID NO 346
<211> LENGTH: 55
<212> TYPE: DNA
<213> ORGANISM: Glycine max

<400> SEQUENCE: 346
acttgtactt atcaaaattc ggaactgaca catgatggaa cgtgactaag gtggg    55

<210> SEQ ID NO 347
<211> LENGTH: 54
<212> TYPE: DNA
<213> ORGANISM: Glycine max

<400> SEQUENCE: 347
acttgtactt atcaaaattc ggaactgaca cacatggaac gtgactaagg tggg    54

<210> SEQ ID NO 348
<211> LENGTH: 54
<212> TYPE: DNA
<213> ORGANISM: Glycine max

<400> SEQUENCE: 348
acttgtactt atcaaaattc ggaactgaca ctgatggaac gtgactaagg tggg    54

<210> SEQ ID NO 349
<211> LENGTH: 53
<212> TYPE: DNA
<213> ORGANISM: Glycine max

<400> SEQUENCE: 349
acttgtactt atcaaaattc ggaactgaca cgatggaacg tgactaaggt ggg    53

<210> SEQ ID NO 350
<211> LENGTH: 51
<212> TYPE: DNA
<213> ORGANISM: Glycine max

<400> SEQUENCE: 350
acttgtactt atcaaaattc ggaactgatg atggaacgtg actaaggtgg g    51

<210> SEQ ID NO 351
<211> LENGTH: 50
<212> TYPE: DNA
<213> ORGANISM: Glycine max

<400> SEQUENCE: 351
acttgtactt atcaaaattc ggaactgaca tggaacgtga ctaaggtggg    50

<210> SEQ ID NO 352
<211> LENGTH: 50
<212> TYPE: DNA
<213> ORGANISM: Glycine max

<400> SEQUENCE: 352
acttgtactt atcaaaattc ggaactgtga tggaacgtga ctaaggtggg    50

<210> SEQ ID NO 353
<211> LENGTH: 51
<212> TYPE: DNA
<213> ORGANISM: Glycine max

<400> SEQUENCE: 353
acttgtactt atcaaaattc ggaactgaca cacgaacgtg actaaggtgg g        51

<210> SEQ ID NO 354
<211> LENGTH: 50
<212> TYPE: DNA
<213> ORGANISM: Glycine max

<400> SEQUENCE: 354
acttgtactt atcaaaattc ggaactgaca cggaacgtga ctaaggtggg          50

<210> SEQ ID NO 355
<211> LENGTH: 49
<212> TYPE: DNA
<213> ORGANISM: Glycine max

<400> SEQUENCE: 355
acttgtacct atcaaaattc ggaactgaat ggaacgtgac taaggtggg           49

<210> SEQ ID NO 356
<211> LENGTH: 48
<212> TYPE: DNA
<213> ORGANISM: Glycine max

<400> SEQUENCE: 356
acttgtactt atcaaaattc ggaactgatg gaacgtgact aaggtggg            48

<210> SEQ ID NO 357
<211> LENGTH: 46
<212> TYPE: DNA
<213> ORGANISM: Glycine max

<400> SEQUENCE: 357
acttgtactt atcaaaattc ggaactgaga acgtgactaa ggtggg              46

<210> SEQ ID NO 358
<211> LENGTH: 38
<212> TYPE: DNA
<213> ORGANISM: Glycine max

<400> SEQUENCE: 358
acttgtactt atcaaaattc ggaactgaca cacgacat                       38

<210> SEQ ID NO 359
<211> LENGTH: 38
<212> TYPE: DNA
<213> ORGANISM: Glycine max

<400> SEQUENCE: 359
acttgtactt atcaaaattc ggaactgaca aggtggg                        38

<210> SEQ ID NO 360
<211> LENGTH: 39
<212> TYPE: DNA
<213> ORGANISM: Glycine max

<400> SEQUENCE: 360
acttgtactt atcaaaattc ggaacgtgac taaggtggg                      39

<210> SEQ ID NO 361
<211> LENGTH: 24
<212> TYPE: DNA
<213> ORGANISM: Glycine max

<400> SEQUENCE: 361

```
actatggaac gtgactaagg tggg                                              24

<210> SEQ ID NO 362
<211> LENGTH: 211
<212> TYPE: DNA
<213> ORGANISM: Glycine max

<400> SEQUENCE: 362
acttgtactt atcaaaattc ggaactgaca cacggccggt gatggattgg tggatgagtg       60
ttgcgtcgag cacctccttg gtggaggtgt atctcttcct gtcaatggtg gtgtcgaagt      120
acttgaaggc agcaggggct cccaagtttg tgagggtaaa caggtggata atgttttcag      180
cctgctcgcg atggaacgtg actaaggtgg g                                     211

<210> SEQ ID NO 363
<211> LENGTH: 90
<212> TYPE: DNA
<213> ORGANISM: Glycine max

<400> SEQUENCE: 363
acttgtactt atcaaaaact acttgtgctg taaaaaaaaa gaggaacaat cttcactcat       60
caataagtga tggaacgcga ctaaggtggg                                        90

<210> SEQ ID NO 364
<211> LENGTH: 57
<212> TYPE: DNA
<213> ORGANISM: Glycine max
<220> FEATURE:
<221> NAME/KEY: misc_feature
<222> LOCATION: (1)..(57)
<223> OTHER INFORMATION: soybean genomic DD20CR2 target region

<400> SEQUENCE: 364
gacacacgac atgatggaac gtgactaagg tgggtttttg actttgcatg tcgaagt          57

<210> SEQ ID NO 365
<211> LENGTH: 61
<212> TYPE: DNA
<213> ORGANISM: Glycine max

<400> SEQUENCE: 365
actgacacac gacatgatgg aacgtgaact aaggtgggtt tttgactttg catgtcgaag       60
t                                                                       61

<210> SEQ ID NO 366
<211> LENGTH: 59
<212> TYPE: DNA
<213> ORGANISM: Glycine max

<400> SEQUENCE: 366
actgacacac gacatgatgg aacgtactaa ggtgggtttt tgactttgca tgtcgaagt       59

<210> SEQ ID NO 367
<211> LENGTH: 58
<212> TYPE: DNA
<213> ORGANISM: Glycine max

<400> SEQUENCE: 367
actgacacac gacatgatgg aacgtctaag gtgggttttt gactttgcat gtcgaagt       58

<210> SEQ ID NO 368
```

```
<211> LENGTH: 58
<212> TYPE: DNA
<213> ORGANISM: Glycine max

<400> SEQUENCE: 368
actgacacac gacatgatgg aacgtgaaag gtgggttttt gactttgcat gtcgaagt      58

<210> SEQ ID NO 369
<211> LENGTH: 57
<212> TYPE: DNA
<213> ORGANISM: Glycine max

<400> SEQUENCE: 369
actgacacac gacatgatgg aacgctaagg tgggttttg actttgcatg tcgaagt        57

<210> SEQ ID NO 370
<211> LENGTH: 57
<212> TYPE: DNA
<213> ORGANISM: Glycine max

<400> SEQUENCE: 370
actgacacac gacatgatgg aacgtgaagg tgggttttg actttgcatg tcgaagt        57

<210> SEQ ID NO 371
<211> LENGTH: 56
<212> TYPE: DNA
<213> ORGANISM: Glycine max

<400> SEQUENCE: 371
actgacacac gacatgatgg aacgtgaggt gggttttga ctttgcatgt cgaagt         56

<210> SEQ ID NO 372
<211> LENGTH: 56
<212> TYPE: DNA
<213> ORGANISM: Glycine max

<400> SEQUENCE: 372
actgacacac gacatgatgg aacgtaaggt gggttttga ctttgcatgt cgaagt         56

<210> SEQ ID NO 373
<211> LENGTH: 56
<212> TYPE: DNA
<213> ORGANISM: Glycine max

<400> SEQUENCE: 373
actgacacac gacatgatgg aacctaaggt gggttttga ctttgcatgt cgaagt         56

<210> SEQ ID NO 374
<211> LENGTH: 56
<212> TYPE: DNA
<213> ORGANISM: Glycine max

<400> SEQUENCE: 374
actgacacac gacatgatgg aacgtgaggt gggttttga ctttgcatgt cgaagt         56

<210> SEQ ID NO 375
<211> LENGTH: 55
<212> TYPE: DNA
<213> ORGANISM: Glycine max

<400> SEQUENCE: 375
actgacacac gacatgatgg aactaaggtg ggttttgac tttgcatgtc gaagt          55
```

```
<210> SEQ ID NO 376
<211> LENGTH: 54
<212> TYPE: DNA
<213> ORGANISM: Glycine max

<400> SEQUENCE: 376
actgacacac gacatgatgg aataaggtgg gttttttgact ttgcatgtcg aagt        54

<210> SEQ ID NO 377
<211> LENGTH: 53
<212> TYPE: DNA
<213> ORGANISM: Glycine max

<400> SEQUENCE: 377
actgacacac gacatgatgg ctaaggtggg tttttgactt tgcatgtcga agt          53

<210> SEQ ID NO 378
<211> LENGTH: 53
<212> TYPE: DNA
<213> ORGANISM: Glycine max

<400> SEQUENCE: 378
actgacacac gacatgatgg ataaggtggg tttttgactt tgcatgtcga agt          53

<210> SEQ ID NO 379
<211> LENGTH: 51
<212> TYPE: DNA
<213> ORGANISM: Glycine max

<400> SEQUENCE: 379
actgacacac gacatgatgg aaggtgggtt tttgactttg catgtcgaag t            51

<210> SEQ ID NO 380
<211> LENGTH: 50
<212> TYPE: DNA
<213> ORGANISM: Glycine max

<400> SEQUENCE: 380
actgacacac gacatgatgg aggtgggttt ttgactttgc atgtcgaagt              50

<210> SEQ ID NO 381
<211> LENGTH: 44
<212> TYPE: DNA
<213> ORGANISM: Glycine max

<400> SEQUENCE: 381
actgacacac gacatgatgg gttttttgact ttgcatgtcg aagt                   44

<210> SEQ ID NO 382
<211> LENGTH: 43
<212> TYPE: DNA
<213> ORGANISM: Glycine max

<400> SEQUENCE: 382
actgacacac gacaggtggg tttttgactt tgcatgtcga agt                     43

<210> SEQ ID NO 383
<211> LENGTH: 40
<212> TYPE: DNA
<213> ORGANISM: Glycine max

<400> SEQUENCE: 383
actgacacta aggtgggttt ttgactttgc atgtcgaagt                         40
```

```
<210> SEQ ID NO 384
<211> LENGTH: 25
<212> TYPE: DNA
<213> ORGANISM: Glycine max

<400> SEQUENCE: 384
actgacacac gacatgatgg aacgt                                        25

<210> SEQ ID NO 385
<211> LENGTH: 20
<212> TYPE: DNA
<213> ORGANISM: Glycine max

<400> SEQUENCE: 385
actgacacac gacatgatgg                                              20

<210> SEQ ID NO 386
<211> LENGTH: 60
<212> TYPE: DNA
<213> ORGANISM: Glycine max
<220> FEATURE:
<221> NAME/KEY: misc_feature
<222> LOCATION: (1)..(60)
<223> OTHER INFORMATION: soybean genomic DD43CR1 target region

<400> SEQUENCE: 386
agccttacaa ctcacaagtc ccttgtactt gtacgtacgg agggtattct agaaaagagg  60

<210> SEQ ID NO 387
<211> LENGTH: 59
<212> TYPE: DNA
<213> ORGANISM: Glycine max

<400> SEQUENCE: 387
agccttacaa ctcacaagtc ccttgtactt gtactacgga gggtattcta gaaaagagg   59

<210> SEQ ID NO 388
<211> LENGTH: 59
<212> TYPE: DNA
<213> ORGANISM: Glycine max

<400> SEQUENCE: 388
agccttacaa ctcacaagtc ccttgtactt gtagtacgga gggtattcta gaaaagagg   59

<210> SEQ ID NO 389
<211> LENGTH: 58
<212> TYPE: DNA
<213> ORGANISM: Glycine max

<400> SEQUENCE: 389
agccttacaa ctcacaagtc ccttgtactt gtgtacggag ggtattctag aaaagagg    58

<210> SEQ ID NO 390
<211> LENGTH: 58
<212> TYPE: DNA
<213> ORGANISM: Glycine max

<400> SEQUENCE: 390
agccttacaa ctcacaagtc ccttgtactt gcgtacggag ggtattctag aaaagagg    58

<210> SEQ ID NO 391
<211> LENGTH: 57
<212> TYPE: DNA
<213> ORGANISM: Glycine max
```

```
<400> SEQUENCE: 391
agccttacaa ctcacaagtc ccttgtactt ggtacggagg gtattctaga aaagagg            57

<210> SEQ ID NO 392
<211> LENGTH: 57
<212> TYPE: DNA
<213> ORGANISM: Glycine max

<400> SEQUENCE: 392
agccttacaa ctcacaagtc ccttgtactt gttacggagg gtattctaga aaagagg            57

<210> SEQ ID NO 393
<211> LENGTH: 56
<212> TYPE: DNA
<213> ORGANISM: Glycine max

<400> SEQUENCE: 393
agccttacaa ctcacaagtc ccttgtactt gtacggaggg tattctagaa aagagg             56

<210> SEQ ID NO 394
<211> LENGTH: 55
<212> TYPE: DNA
<213> ORGANISM: Glycine max

<400> SEQUENCE: 394
agccttacaa ctcacaagtc ccttgtactt tacggagggt attctagaaa agagg              55

<210> SEQ ID NO 395
<211> LENGTH: 55
<212> TYPE: DNA
<213> ORGANISM: Glycine max

<400> SEQUENCE: 395
agccttacaa ctcacaagtc ccttgtactg tacggagggt attctagaaa agagg              55

<210> SEQ ID NO 396
<211> LENGTH: 54
<212> TYPE: DNA
<213> ORGANISM: Glycine max

<400> SEQUENCE: 396
agccttacaa ctcacaagcc ccttgtactt acggagggta ttctagaaaa gagg               54

<210> SEQ ID NO 397
<211> LENGTH: 52
<212> TYPE: DNA
<213> ORGANISM: Glycine max

<400> SEQUENCE: 397
agccttacaa ctcacaagtc ccttgtatac ggagggtatt ctagaaaaga gg                 52

<210> SEQ ID NO 398
<211> LENGTH: 52
<212> TYPE: DNA
<213> ORGANISM: Glycine max

<400> SEQUENCE: 398
agccttacaa ctcacaagtc ccttgtgtac ggagggtatt ctagaaaaga gg                 52

<210> SEQ ID NO 399
<211> LENGTH: 50
<212> TYPE: DNA
```

<213> ORGANISM: Glycine max

<400> SEQUENCE: 399
agccttacaa ctcacaagtc ccttgtacgg agggtattct agaaaagagg            50

<210> SEQ ID NO 400
<211> LENGTH: 49
<212> TYPE: DNA
<213> ORGANISM: Glycine max

<400> SEQUENCE: 400
agccttacaa ctcacaagtc cctttacgga gggtattcta gaaaagagg             49

<210> SEQ ID NO 401
<211> LENGTH: 48
<212> TYPE: DNA
<213> ORGANISM: Glycine max

<400> SEQUENCE: 401
agccttacaa ctcacaagtc ccttacggag ggtattctag aaaagagg              48

<210> SEQ ID NO 402
<211> LENGTH: 47
<212> TYPE: DNA
<213> ORGANISM: Glycine max

<400> SEQUENCE: 402
agccttacaa ctcacaagtc cctacggagg gtattctaga aaagagg               47

<210> SEQ ID NO 403
<211> LENGTH: 43
<212> TYPE: DNA
<213> ORGANISM: Glycine max

<400> SEQUENCE: 403
agccttacaa ctcacaagtc ccttgtactt gtaagaaaag agg                   43

<210> SEQ ID NO 404
<211> LENGTH: 49
<212> TYPE: DNA
<213> ORGANISM: Glycine max

<400> SEQUENCE: 404
agccttacaa ctcacaagtc ctaaattaaa ggttattcta gaaaagagg             49

<210> SEQ ID NO 405
<211> LENGTH: 227
<212> TYPE: DNA
<213> ORGANISM: Glycine max

<400> SEQUENCE: 405
agccttacaa ctcacaagtc ccttgtactt gtagaatcca gttcataaaa caagtgacac     60
acaacagata tgaactggac tacgtcgaac ccacaaatcc cacaaagcgc gtgaaatcaa    120
atcgctcaaa ccacaaaaaa gaacaacgcg tttgttacac gctaatacca aaattatacc    180
caaatcttaa gctatttatg cgtacggagg gtattctaga aaagagg                  227

<210> SEQ ID NO 406
<211> LENGTH: 97
<212> TYPE: DNA
<213> ORGANISM: Glycine max

<400> SEQUENCE: 406

```
agccttacaa ctcacaagtc ccttgtactt gtaatgctcc cctctaaact cgtatcgctt      60
cagagttgag agtacggagg gtattctaga aaagagg                               97
```

<210> SEQ ID NO 407
<211> LENGTH: 183
<212> TYPE: DNA
<213> ORGANISM: Glycine max

<400> SEQUENCE: 407

```
agccttacaa ctcacaagtc ccttgtatat agatacccac aaaataagta aacccgatcc      60
aaaatcttaa atgatgtgga ggaagggaaa ttgttaatta ttcccctctt ctcctacatg     120
gatatacctg aaacatgcaa tggatggatt agattttgta cggagggtat tctagaaaag     180
agg                                                                  183
```

<210> SEQ ID NO 408
<211> LENGTH: 234
<212> TYPE: DNA
<213> ORGANISM: Glycine max

<400> SEQUENCE: 408

```
agccttacaa ctcacaagtc ccttgtactt gtaccagggg atgttttta tttacattca       60 cgtcttttgg aaagagccgc taaattaagt tctcagttag gcgaaggaag tatgactgct     120
ttaccaatag ttgaaactca atcgggagat gtttcagctt atattcctac taatgtaatt     180
tccattacag atggccaaat attcttacgt acggagggta ttctagaaaa gagg           234
```

<210> SEQ ID NO 409
<211> LENGTH: 280
<212> TYPE: DNA
<213> ORGANISM: Glycine max

<400> SEQUENCE: 409

```
agccttacaa ctcacaagtc ccttgtactt gtaccgaaaa tttcagccat aaaaaaagtt      60
ataatagaat ttaaagcaaa agtttcattt tttaaacata tatactgaca cgctccgata    120
aaaatagagg caagtccgac aacgtcccct ccgaggaggt cgtgaagaag atgaaaaact    180
actggagaca gctcttgaac gccaagctca tcacccagcg taagctcgac aacctgacta    240
aggctgagag aggtgtacgg agggtattct agaaaagagg                          280
```

<210> SEQ ID NO 410
<211> LENGTH: 250
<212> TYPE: DNA
<213> ORGANISM: Glycine max

<400> SEQUENCE: 410

```
agccttacaa ctcacaagtc ccttgtactt gtactggatt tggtgaggga tgcttccgtt      60
gtcgaaggtt tctgcttcc tcaacaggtc ctctctgttc aacttcacca acagctcctc     120
ggtaccgtcc atcttctcaa ggatgaagat cgagtgcttc gactccgtcg agatctctgg    180
tgtcgaggac aggttcaacg cctcccttgg gacttgccac gatcgtacgg agggtattct    240
agaaaagagg                                                           250
```

<210> SEQ ID NO 411
<211> LENGTH: 161
<212> TYPE: DNA
<213> ORGANISM: Glycine max

<400> SEQUENCE: 411
agccttacaa ctcacaagtc ccttatgacc tcaaaaaaaa gattcacctc caacacacca    60
aataactcga aaatctcttt cctattctct agaaagtata ggaacttcca ctagtccatg   120
aaaaagcctg aactcgtacg gagggtattc tagaaaagag g                       161

<210> SEQ ID NO 412
<211> LENGTH: 185
<212> TYPE: DNA
<213> ORGANISM: Glycine max

<400> SEQUENCE: 412
agccttacaa ctcacaagtc ccttgtactt gtacacctgg ggcatggaga gcaccttcct    60
cacagtagcg aaatccctcc ctttgtccca cacgatctct ccagtctcac cgttggtctc   120
gatcagtggg cgcttcctga tctcaccgtt ggcgagagtg tacggagggt attctagaaa   180
agagg                                                              185

<210> SEQ ID NO 413
<211> LENGTH: 212
<212> TYPE: DNA
<213> ORGANISM: Glycine max

<400> SEQUENCE: 413
agccttacaa ctcacaagtc ccttgtactt gtgctaggtt agccgaaaga tggttatcgg    60
ttcaaggacg caaggtgccc ctgcttttc agggtaataa ggggtagaga aaatgcctcg   120
agccaaagtt cgagtaccag cgctacagc gctgaagtaa tccatgccat actcccagga   180
aaagccgtac ggagggtatt ctagaaaaga gg                                 212

<210> SEQ ID NO 414
<211> LENGTH: 231
<212> TYPE: DNA
<213> ORGANISM: Glycine max

<400> SEQUENCE: 414
agccttacaa ctcacaagtc ccttgtactt gtactcaagt tcttattta tttcatattt    60 tttcctataa aaggttaatg ctctataaa ggttgagtga cggatccggt cacctaagtg   120
actagggtca cgtgacccta gtcacttatt cccgggcaac tttattatac aaagttgata   180
gatctcgaat tcattccgat taatcgtggc gagggtattc tagaaaagag g            231

<210> SEQ ID NO 415
<211> LENGTH: 98
<212> TYPE: DNA
<213> ORGANISM: Zea mays

<400> SEQUENCE: 415
tcctctgtaa cgatttacgc acctgctggg aattgtaccg tacgtgcccc ggtcggagga    60
tatatatacc tcacacgtac gcgtacgcgt atatatac                           98

<210> SEQ ID NO 416
<211> LENGTH: 98
<212> TYPE: DNA
<213> ORGANISM: Zea mays

<400> SEQUENCE: 416
tcctctgtaa cgatttacgc acctgctggg aattgtaccg tacgtgcccc ggacggagga    60
tatatatacc tcacacgtac gcgtacgcgt atatatac                           98

<210> SEQ ID NO 417
<211> LENGTH: 98
<212> TYPE: DNA
<213> ORGANISM: Zea mays

<400> SEQUENCE: 417
tcctctgtaa cgatttacgc acctgctggg aattgtaccg tacgtgcccc gggcggagga    60
tatatatacc tcacacgtac gcgtacgcgt atatatac                            98

<210> SEQ ID NO 418
<211> LENGTH: 98
<212> TYPE: DNA
<213> ORGANISM: Zea mays

<400> SEQUENCE: 418
tcctctgtaa cgatttacgc acctgctggg aattgtaccg tacgtgcccc ggccggagga    60
tatatatacc tcacacgtac gcgtacgcgt atatatac                            98

<210> SEQ ID NO 419
<211> LENGTH: 99
<212> TYPE: DNA
<213> ORGANISM: Zea mays

<400> SEQUENCE: 419
tcctctgtaa cgatttacgc acctgctggg aattgtaccg tacgtgcccc ggatcggagg    60
atatatatac ctcacacgta cgcgtacgcg tatatatac                           99

<210> SEQ ID NO 420
<211> LENGTH: 94
<212> TYPE: DNA
<213> ORGANISM: Zea mays

<400> SEQUENCE: 420
tcctctgtaa cgatttacgc acctgctggg aattgtaccg tacgtgcccc ggaggatata    60
tatacctcac acgtacgcgt acgcgtatat atac                                94

<210> SEQ ID NO 421
<211> LENGTH: 81
<212> TYPE: DNA
<213> ORGANISM: Zea mays

<400> SEQUENCE: 421
tcctctgtaa cgatttacgc acctgctggg aattgtaccg tacgtgcccc ggttcacacg    60
tacgcgtacg cgtatatata c                                              81

<210> SEQ ID NO 422
<211> LENGTH: 65
<212> TYPE: DNA
<213> ORGANISM: Zea mays

<400> SEQUENCE: 422
tcctctgtaa cgatttacgc acctgctggg aattgtaccg tacgtacgcg tacgcgtata    60
tatac                                                                65

<210> SEQ ID NO 423
<211> LENGTH: 99
<212> TYPE: DNA
<213> ORGANISM: Zea mays

```
<400> SEQUENCE: 423
tcctctgtaa cgatttacgc acctgctggg aattgtaccg tacgtgcccc ggttcggagg      60
atatatatac ctcacacgta cgcgtacgcg tatatatac                            99

<210> SEQ ID NO 424
<211> LENGTH: 95
<212> TYPE: DNA
<213> ORGANISM: Zea mays

<400> SEQUENCE: 424
tcctctgtaa cgatttacgc acctgctggg aattgtaccg tacgtgcccc cggaggatat      60
atatacctca cacgtacgcg tacgcgtata tatac                                95

<210> SEQ ID NO 425
<211> LENGTH: 98
<212> TYPE: DNA
<213> ORGANISM: Zea mays

<400> SEQUENCE: 425
gaagctgtaa cgatttacgc acctgctggg aattgtaccg tacgtgaccc cggcggagga      60
tatatatacc tcacacgtac gcgtacgcgt atatatac                             98

<210> SEQ ID NO 426
<211> LENGTH: 98
<212> TYPE: DNA
<213> ORGANISM: Zea mays

<400> SEQUENCE: 426
gaagctgtaa cgatttacgc acctgctggg aattgtaccg tacgtgtccc cggcggagga      60
tatatatacc tcacacgtac gcgtacgcgt atatatac                             98

<210> SEQ ID NO 427
<211> LENGTH: 96
<212> TYPE: DNA
<213> ORGANISM: Zea mays

<400> SEQUENCE: 427
gaagctgtaa cgatttacgc acctgctggg aattgtaccg tacgtccccg gcggaggata      60 tatataccte acacgtacgc gtacgcgtat atatac                               96

<210> SEQ ID NO 428
<211> LENGTH: 98
<212> TYPE: DNA
<213> ORGANISM: Zea mays

<400> SEQUENCE: 428
gaagctgtaa cgatttacgc acctgctggg aattgtaccg tacgtggccc cggcggagga      60
tatatatacc tcacacgtac gcgtacgcgt atatatac                             98

<210> SEQ ID NO 429
<211> LENGTH: 99
<212> TYPE: DNA
<213> ORGANISM: Zea mays

<400> SEQUENCE: 429
gaagctgtaa cgatttacgc acctgctggg aattgtaccg tacgtgcacc ccggcggagg      60
atatatatac ctcacacgta cgcgtacgcg tatatatac                            99
```

<210> SEQ ID NO 430
<211> LENGTH: 87
<212> TYPE: DNA
<213> ORGANISM: Zea mays

<400> SEQUENCE: 430
gaagctgtaa cgatttacgc acctgctggg aattgtaccc ggcggaggat atatatacct    60
cacacgtacg cgtacgcgta tatatac                                       87

<210> SEQ ID NO 431
<211> LENGTH: 92
<212> TYPE: DNA
<213> ORGANISM: Zea mays

<400> SEQUENCE: 431
gaagctgtaa cgatttacgc acctgctggg aattgtaccg tccccggcgg aggatatata    60
tacctcacac gtacgcgtac gcgtatatat ac                                 92

<210> SEQ ID NO 432
<211> LENGTH: 94
<212> TYPE: DNA
<213> ORGANISM: Zea mays

<400> SEQUENCE: 432
gaagctgtaa cgatttacgc acctgctggg aattgtaccg taccccggc ggaggatata     60 tatacctcac acgtacgcgt acgcgtatat atac                               94

<210> SEQ ID NO 433
<211> LENGTH: 95
<212> TYPE: DNA
<213> ORGANISM: Zea mays

<400> SEQUENCE: 433
gaagctgtaa cgatttacgc acctgctggg aattgtaccg tacgccccgg cggaggatat    60
atatacctca cacgtacgcg tacgcgtata tatac                              95

<210> SEQ ID NO 434
<211> LENGTH: 88
<212> TYPE: DNA
<213> ORGANISM: Zea mays

<400> SEQUENCE: 434
gaagctgtaa cgatttacgc acctgctggg aattgtaccc cggcggagga tatatatacc    60
tcacacgtac gcgtacgcgt atatatac                                      88

<210> SEQ ID NO 435
<211> LENGTH: 98
<212> TYPE: DNA
<213> ORGANISM: Zea mays

<400> SEQUENCE: 435
aaggcgcaaa tgagtagcag cgcacgtata tatacgcgta cgcgtacgtt gtgaggtata    60
tatatcctcc gccggggcac gtacggtaca attcccag                           98

<210> SEQ ID NO 436
<211> LENGTH: 96
<212> TYPE: DNA
<213> ORGANISM: Zea mays

<400> SEQUENCE: 436

```
aaggcgcaaa tgagtagcag cgcacgtata tatacgcgta cgcgtacggt gaggtatata    60
tatcctccgc cggggcacgt acggtacaat tcccag                              96

<210> SEQ ID NO 437
<211> LENGTH: 95
<212> TYPE: DNA
<213> ORGANISM: Zea mays

<400> SEQUENCE: 437
aaggcgcaaa tgagtagcag cgcacgtata tatacgcgta cgcgtacgtg aggtatatat    60
atcctccgcc ggggcacgta cggtacaatt cccag                               95

<210> SEQ ID NO 438
<211> LENGTH: 96
<212> TYPE: DNA
<213> ORGANISM: Zea mays

<400> SEQUENCE: 438
aaggcgcaaa tgagtagcag cgcacgtata tatacgcgta cgcgtactgt gaggtatata    60
tatcctccgc cggggcacgt acggtacaat tcccag                              96

<210> SEQ ID NO 439
<211> LENGTH: 68
<212> TYPE: DNA
<213> ORGANISM: Zea mays

<400> SEQUENCE: 439
aaggcgcaaa tgagtagcag cgcacgtata tatatcctcc gccggggcac gtacggtaca    60
attcccag                                                             68

<210> SEQ ID NO 440
<211> LENGTH: 93
<212> TYPE: DNA
<213> ORGANISM: Zea mays

<400> SEQUENCE: 440
aaggcgcaaa tgagtagcag cgcacgtata tatacgcgta cgcgtgtgag gtatatatat    60
cctccgccgg ggcacgtacg gtacaattcc cag                                 93

<210> SEQ ID NO 441
<211> LENGTH: 89
<212> TYPE: DNA
<213> ORGANISM: Zea mays

<400> SEQUENCE: 441
aaggcgcaaa tgagtagcag cgcacgtata tatacgcgta cgtgaggtat atatatcctc    60
cgccggggca cgtacggtac aattcccag                                      89

<210> SEQ ID NO 442
<211> LENGTH: 89
<212> TYPE: DNA
<213> ORGANISM: Zea mays

<400> SEQUENCE: 442
aaggcgcaaa tgagtagcag cgcacgtata tatacgcgta cgcgtactat atatatcctc    60
cgccggggca cgtacggtac aattcccag                                      89

<210> SEQ ID NO 443
<211> LENGTH: 94
```

<212> TYPE: DNA
<213> ORGANISM: Zea mays

<400> SEQUENCE: 443
aaggcgcaaa tgagtagcag cgcacgtata tatacgcgta cgcgtacgga ggtatatata     60
tcctccgccg gggcacgtac ggtacaattc ccag                                94

<210> SEQ ID NO 444
<211> LENGTH: 96
<212> TYPE: DNA
<213> ORGANISM: Zea mays

<400> SEQUENCE: 444
aaggcgcaaa tgagtagcag cgcacgtata tatacgcgta cgcgtacgat gaggtatata     60
tatcctccgc cggggcacgt acggtacaat cccag                               96

<210> SEQ ID NO 445
<211> LENGTH: 1051
<212> TYPE: DNA
<213> ORGANISM: Artificial sequence
<220> FEATURE:
<223> OTHER INFORMATION: synthesized sequence-
      LIGCas-1_crRNA_Expression_Cassette

<400> SEQUENCE: 445
tgagagtaca atgatgaacc tagattaatc aatgccaaag tctgaaaaat gcaccctcag     60
tctatgatcc agaaaatcaa gattgcttga ggccctgttc ggttgttccg gattagagcc    120
ccggattaat tcctagccgg attacttctc taatttatat agattttgat gagctggaat    180
gaatcctggc ttattccggt acaaccgaac aggccctgaa ggataccagt aatcgctgag    240
ctaaattggc atgctgtcag agtgtcagta ttgcagcaag gtagtgagat aaccggcatc    300
atggtgccag tttgatggca ccattagggt tagagatggt ggccatgggc gcatgtcctg    360
gccaactttg tatgatatat ggcagggtga ataggaaagt aaaattgtat tgtaaaaagg    420
gatttcttct gtttgttagc gcatgtacaa ggaatgcaag ttttgagcga ggggcatca     480 aagatctggc tgtgtttcca gctgtttttg ttagccccat cgaatccttg acataatgat    540
cccgcttaaa taagcaacct cgcttgtata gttccttgtg ctctaacaca cgatgatgat    600
aagtcgtaaa atagtggtgt ccaaagaatt tccaggccca gttgtaaaag ctaaaatgct    660
attcgaattt ctactagcag taagtcgtgt ttagaaatta tttttttata tacctttttt    720
ccttctatgt acagtaggac acagtgtcag cgccgcgttg acggagaata tttgcaaaaa    780
agtaaaagag aaagtcatag cggcgtatgt gccaaaaact tcgtcacaga gagggccata    840
agaaacatgg cccacggccc aatacgaagc accgcgacga agcccaaaca gcagtccgta    900
ggtggagcaa agcgctgggt aatacgcaaa cgttttgtcc caccttgact aatcacaaga    960
gtggagcgta ccttataaac cgagccgcaa gcaccgaatt gtaccgtacg tgccccggcg   1020
ggttttagag ctatgctgtt ttgtttttttt t                                 1051

<210> SEQ ID NO 446
<211> LENGTH: 1051
<212> TYPE: DNA
<213> ORGANISM: Artificial sequence
<220> FEATURE:
<223> OTHER INFORMATION: synthesized sequence-
      LIGCas-2_crRNA_Expression_Cassette

<400> SEQUENCE: 446

```
tgagagtaca atgatgaacc tagattaatc aatgccaaag tctgaaaaat gcaccctcag    60
tctatgatcc agaaaatcaa gattgcttga ggccctgttc ggttgttccg gattagagcc   120
ccggattaat tcctagccgg attacttctc taatttatat agattttgat gagctggaat   180
gaatcctggc ttattccggt acaaccgaac aggccctgaa ggataccagt aatcgctgag   240
ctaaattggc atgctgtcag agtgtcagta ttgcagcaag gtagtgagat aaccggcatc   300
atggtgccag tttgatggca ccattagggt tagagatggt ggccatgggc gcatgtcctg   360
gccaactttg tatgatatat ggcagggtga ataggaaagt aaaattgtat tgtaaaaagg   420
gatttcttct gtttgttagc gcatgtacaa ggaatgcaag ttttgagcga gggggcatca   480
aagatctggc tgtgtttcca gctgtttttg ttagccccat cgaatccttg acataatgat   540
cccgcttaaa taagcaacct cgcttgtata gttccttgtg ctctaacaca cgatgatgat   600
aagtcgtaaa atagtggtgt ccaaagaatt tccaggccca gttgtaaaag ctaaaatgct   660
attcgaattt ctactagcag taagtcgtgt ttagaaatta tttttttata tacctttttt   720
ccttctatgt acagtaggac acagtgtcag cgccgcgttg acggagaata tttgcaaaaa   780
agtaaaagag aaagtcatag cggcgtatgt gccaaaaact tcgtcacaga gagggccata   840
agaaacatgg cccacggccc aatacgaagc accgcgacga agcccaaaca gcagtccgta   900
ggtggagcaa agcgctgggt aatacgcaaa cgttttgtcc caccttgact aatcacaaga   960
gtggagcgta ccttataaac cgagccgcaa gcaccgaatt ggaattgtac cgtacgtgcc  1020
cgttttagag ctatgctgtt ttgttttttt t                                 1051
```

<210> SEQ ID NO 447
<211> LENGTH: 1047
<212> TYPE: DNA
<213> ORGANISM: Artificial sequence
<220> FEATURE:
<223> OTHER INFORMATION: synthesized sequence-
      LIGCas-3_crRNA_Expression_Cassette

<400> SEQUENCE: 447

```
tgagagtaca atgatgaacc tagattaatc aatgccaaag tctgaaaaat gcaccctcag    60
tctatgatcc agaaaatcaa gattgcttga ggccctgttc ggttgttccg gattagagcc   120
ccggattaat tcctagccgg attacttctc taatttatat agattttgat gagctggaat   180
gaatcctggc ttattccggt acaaccgaac aggccctgaa ggataccagt aatcgctgag   240
ctaaattggc atgctgtcag agtgtcagta ttgcagcaag gtagtgagat aaccggcatc   300
atggtgccag tttgatggca ccattagggt tagagatggt ggccatgggc gcatgtcctg   360
gccaactttg tatgatatat ggcagggtga ataggaaagt aaaattgtat tgtaaaaagg   420
gatttcttct gtttgttagc gcatgtacaa ggaatgcaag ttttgagcga gggggcatca   480
aagatctggc tgtgtttcca gctgtttttg ttagccccat cgaatccttg acataatgat   540
cccgcttaaa taagcaacct cgcttgtata gttccttgtg ctctaacaca cgatgatgat   600
aagtcgtaaa atagtggtgt ccaaagaatt tccaggccca gttgtaaaag ctaaaatgct   660
attcgaattt ctactagcag taagtcgtgt ttagaaatta tttttttata tacctttttt   720
ccttctatgt acagtaggac acagtgtcag cgccgcgttg acggagaata tttgcaaaaa   780
agtaaaagag aaagtcatag cggcgtatgt gccaaaaact tcgtcacaga gagggccata   840
agaaacatgg cccacggccc aatacgaagc accgcgacga agcccaaaca gcagtccgta   900
ggtggagcaa agcgctgggt aatacgcaaa cgttttgtcc caccttgact aatcacaaga   960
```

<210> SEQ ID NO 448
<211> LENGTH: 1087
<212> TYPE: DNA
<213> ORGANISM: Artificial sequence
<220> FEATURE:
<223> OTHER INFORMATION: synthesized sequence-
      tracrRNA_Expression_Cassette

<400> SEQUENCE: 448

```
tgagagtaca atgatgaacc tagattaatc aatgccaaag tctgaaaaat gcaccctcag      60
tctatgatcc agaaaatcaa gattgcttga ggccctgttc ggttgttccg gattagagcc     120
ccggattaat tcctagccgg attacttctc taatttatat agattttgat gagctggaat     180
gaatcctggc ttattccggt acaaccgaac aggccctgaa ggataccagt aatcgctgag     240
ctaaattggc atgctgtcag agtgtcagta ttgcagcaag gtagtgagat aaccggcatc     300
atggtgccag tttgatggca ccattagggt tagagatggt ggccatgggc gcatgtcctg     360
gccaactttg tatgatatat ggcagggtga ataggaaagt aaaattgtat tgtaaaaagg     420
gatttcttct gtttgttagc gcatgtacaa ggaatgcaag ttttgagcga ggggcatca      480
aagatctggc tgtgtttcca gctgtttttg ttagccccat cgaatccttg acataatgat     540
cccgcttaaa taagcaacct cgcttgtata gttccttgtg ctctaacaca cgatgatgat     600
aagtcgtaaa atagtggtgt ccaaagaatt tccaggccca gttgtaaaag ctaaaatgct     660
attcgaattt ctactagcag taagtcgtgt ttagaaatta tttttttata tacctttttt     720
ccttctatgt acagtaggac acagtgtcag cgccgcgttg acggagaata tttgcaaaaa     780
agtaaaagag aaagtcatag cggcgtatgt gccaaaaact tcgtcacaga gagggccata     840
agaaacatgg cccacggccc aatacgaagc accgcgacga agcccaaaca gcagtccgta     900
ggtggagcaa agcgctgggt aatacgcaaa cgttttgtcc caccttgact aatcacaaga     960
gtggagcgta ccttataaac cgagccgcaa gcaccgaatt ggaaccattc aaaacagcat    1020
agcaagttaa aataaggcta gtccgttatc aacttgaaaa agtggcaccg agtcggtgct    1080
ttttttt                                                              1087
```

<210> SEQ ID NO 449
<211> LENGTH: 63
<212> TYPE: DNA
<213> ORGANISM: Artificial Sequence
<220> FEATURE:
<223> OTHER INFORMATION: synthesized sequence- LIGCas-2 forward primer
      for primary

<400> SEQUENCE: 449

```
ctacactctt tccctacacg acgctcttcc gatctgaagc tgtaacgatt tacgcacctg      60
ctg                                                                    63
```

<210> SEQ ID NO 450
<211> LENGTH: 60
<212> TYPE: DNA
<213> ORGANISM: Artificial Sequence
<220> FEATURE:
<223> OTHER INFORMATION: synthesized sequence- LIGCas-3 forward primer
      for primary PCR

<400> SEQUENCE: 450
ctacactctt tccctacacg acgtcttcc gatctttccc gcaaatgagt agcagcgcac    60

<210> SEQ ID NO 451
<211> LENGTH: 19
<212> TYPE: DNA
<213> ORGANISM: Zea mays

<400> SEQUENCE: 451
gcgtgcatcg atccatcgc    19

<210> SEQ ID NO 452
<211> LENGTH: 21
<212> TYPE: DNA
<213> ORGANISM: Zea mays

<400> SEQUENCE: 452
ggctacggat agatatgatg c    21

<210> SEQ ID NO 453
<211> LENGTH: 20
<212> TYPE: DNA
<213> ORGANISM: Zea mays

<400> SEQUENCE: 453
gttacttctc taagcacggc    20

<210> SEQ ID NO 454
<211> LENGTH: 21
<212> TYPE: DNA
<213> ORGANISM: Artificial sequence
<220> FEATURE:
<223> OTHER INFORMATION: synthesized sequence- P1, Forward_primer

<400> SEQUENCE: 454
gcgccattcc ctaaaggtaa c    21

<210> SEQ ID NO 455
<211> LENGTH: 23
<212> TYPE: DNA
<213> ORGANISM: Artificial sequence
<220> FEATURE:
<223> OTHER INFORMATION: synthesized sequence- P2, Reverse_primer

<400> SEQUENCE: 455
gctaatcgta agtgacgctt gga    23

<210> SEQ ID NO 456
<211> LENGTH: 31
<212> TYPE: DNA
<213> ORGANISM: Artificial sequence
<220> FEATURE:
<223> OTHER INFORMATION: synthesized sequence- P3, Forward_primer

<400> SEQUENCE: 456
gctcgtgtcc aagcgtcact tacgattagc t    31

<210> SEQ ID NO 457
<211> LENGTH: 20
<212> TYPE: DNA
<213> ORGANISM: Artificial sequence
<220> FEATURE:
<223> OTHER INFORMATION: synthesized sequence- P4, Reverse_primer

<400> SEQUENCE: 457
ctgcgaactg cttgattccg    20

<210> SEQ ID NO 458
<211> LENGTH: 24
<212> TYPE: DNA
<213> ORGANISM: Artificial sequence
<220> FEATURE:
<223> OTHER INFORMATION: synthesized sequence- P5, Forward_primer

<400> SEQUENCE: 458 accgtccta tctctgcatc atct                                    24

<210> SEQ ID NO 459
<211> LENGTH: 31
<212> TYPE: DNA
<213> ORGANISM: Artificial sequence
<220> FEATURE:
<223> OTHER INFORMATION: synthesized sequence- PBS, Primer Binding Site

<400> SEQUENCE: 459
gctcgtgtcc aagcgtcact tacgattagc t                           31

<210> SEQ ID NO 460
<211> LENGTH: 1823
<212> TYPE: DNA
<213> ORGANISM: Zea mays
<220> FEATURE:
<221> NAME/KEY: misc_feature
<222> LOCATION: (1)..(1823)
<223> OTHER INFORMATION: Zm-GOS2 PRO-GOS2 INTRON, maize GOS2 promoter
      and GOS2 intron1 including the promoter, 5'-UTR1, INTRON1 and
      5'-UTR2 sequence

<400> SEQUENCE: 460
taattattgg ctgtaggatt ctaaacagag cctaaatagc tggaatagct ctagccctca    60
atccaaacta atgatatcta tacttatgca actctaaatt tttattctaa aagtaatatt   120
tcatttttgt caacgagatt ctctactcta ttccacaatc ttttgaagct atatttacct   180
taaatctgta ctctatacca ataatcatat attctattat ttattttat ctctctccta    240 aggagcatcc ctctatgtct gcatggcccc cgcctcgggt cccaatctct tgctctgcta   300
gtagcacaga agaaaacact agaaatgact tgcttgactt agagtatcag ataaacatca   360
tgtttactta actttaattt gtatcggttt ctactatttt tataatattt ttgtctctat   420
agatactacg tgcaacagta taatcaacct agtttaatcc agagcgaagg atttttact    480 aagtacgtga ctccatatgc acagcgttcc ttttatggtt cctcactggg cacagcataa   540
acgaaccctg tccaatgttt tcagcgcgaa caaacagaaa ttccatcagc gaacaaacaa   600
catacatgcg agatgaaaat aaataataaa aaaagctccg tctcgatagg ccggcacgaa   660
tcgagagcct ccatagccag ttttttccat cggaacggcg gttcgcgcac ctaattatat   720
gcaccacacg cctataaagc caaccaaccc gtcggagggg cgcaagccag acagaagaca   780
gcccgtcagc ccctctcgtt tttcatccgc cttcgcctcc aaccgcgtgc gctccacgcc   840
tcctccagga aagcgagagg tgagcgcagt ccccttccc ctccttccaa ttcaattcgt    900
cttctcgttc gcagccctag gatttggggg tctggagggg tttgatcgtt tctcgccgtg   960
aatctgcttt ggtgtaaacc aacgatctc ggatcgtagt cttcagaaga tcccggattt   1020
tgcggtttgg ccctcctgg attcaattcg tcgtatcgtt cgcagcccta ggatttgggg   1080
atctggaggg gtttgatcgt ttctcgccgc gaatctgctc tggtgtaaac caacggatct   1140
cgggtcgtag tcttcagaag gtcccggatt ttgcggtttg gccctcctg gattcaattc   1200

-continued

```
gtcgtatcgt tcgcagccct aggatttggg gatctggagg ggtttgatcc tttctcgccg    1260
cgaatctgct ctggtataac caacggatct cgggtcgtag tcttcagaag gtcccggatt    1320
ttgcggtttg gtggttcttg ctctatgaat cagagggatg gttcttcccg gatttatgcc    1380
ttgcggccac tctgtcgaat catggggttt cgacccgatt cgtaggcgtg ctccctgttt    1440
tggatgggaa gtaggcgtgt ttgtagtatt cgtgcttcga ttcgtcaacg gagattagaa    1500
gacctgggat gggatttgag gaaatctagg tatctgtcta gcacgtttct agatctattc    1560
ttcagctgtt atatgagagt aattttggaa ccctggtggg gtatgtttga ccgagtattc    1620
tgtagattat tgtccgtgac ttgctggctg ttaccgtcct tatctctgca tcatctatct    1680
gtgctagttt ctgcgtgctt ctcaaatatt tccggcctgt gtagcatgtg actgataata    1740
tgattttggc agcttctgca taagaacaac aaatcaaaag cttgatcagc tcggtgccta    1800
caaaacctca acaaccaagt ttc                                            1823
```

<210> SEQ ID NO 461
<211> LENGTH: 556
<212> TYPE: DNA
<213> ORGANISM: Zea mays
<220> FEATURE:
<221> NAME/KEY: misc_feature
<222> LOCATION: (1)..(556)
<223> OTHER INFORMATION: Zm-ARGOS8 promoter

<400> SEQUENCE: 461

```
gttacttctc taagcacggc tggatttcag gcctctagtc ctctactagt actagctaca     60
cgacgtgcac gcatgcatca cagcatcaac aactagacac gcacacgctg cacgcggccg    120
gggaacccac tgattccccc cttcccgcg cgcggtttga tttcctttcc tggtacggat    180
ccatatctga gggcttgttc ggttattccc aacacacatg tattggatgg gattgaaaaa    240
aaaatgagaa gaagtttgac ttgtttggga ttcaaaccca tccaatccca ctcaatccac    300
atggattgag agctaaccga acaagccctc atagtacata cctggtacgg atccatatca    360
tagtacatag atccagtaga atagaaggtg atccgaccgc cggcgcttgc gttgttttcc    420
ccggtccatt gaacctgcca accctcctaa ccacaggcac gccaaaccgc gggctccggc    480
caccaccgcc accgccacct gccctgccgc acctctccaa ccccaaatcc aggggggggg    540 ggggcacca tgcgtg                                                     556
```

<210> SEQ ID NO 462
<211> LENGTH: 155
<212> TYPE: DNA
<213> ORGANISM: Zea mays
<220> FEATURE:
<221> NAME/KEY: misc_feature
<222> LOCATION: (1)..(155)
<223> OTHER INFORMATION: Zm-ARGOS8 5'-UTR

<400> SEQUENCE: 462

```
catcgatcca tcgctggcgc gcgggtccgg cggggcggtc tgtgagggca aatttatata     60
ggtctagtgg gtacccggct acggatagat atgatgctgc actgcacatt ggctatatct    120
gaggctcctg cgcgcgcctt ggccaggtgt ctgtc                               155
```

<210> SEQ ID NO 463
<211> LENGTH: 285
<212> TYPE: DNA
<213> ORGANISM: Zea mays

<400> SEQUENCE: 463

```
atgcgggcga tgccgcagga agaggaagcc gcggtggcga cgacgaccat ggccgggggc    60
aaggtggcgg cgctgctggc cacggcggcc gcgctgctgc tgctgctccc gctggcgctg   120
ccgccgctgc cgccgccgcc cacgcagctg ttgttcgtcc ccgtggtctt gctgctcctc   180
gtggcgtccc tcgcgttctg ccccgccgcg accccctcgc cgtcgccgat gcatgccgcc   240
gaccacgggt cgttcgggac cactggatca ccgcacctat gttga                   285
```

<210> SEQ ID NO 464
<211> LENGTH: 2843
<212> TYPE: DNA
<213> ORGANISM: Zea mays
<220> FEATURE:
<221> NAME/KEY: misc_feature
<222> LOCATION: (1)..(2843)
<223> OTHER INFORMATION: Zm-GOS2 gene, including promoter, 5'-UTR, CDS, 3'-UTR and introns sequence

<400> SEQUENCE: 464

```
taattattgg ctgtaggatt ctaaacagag cctaaatagc tggaatagct ctagccctca    60
atccaaacta atgatatcta tacttatgca actctaaatt tttattctaa aagtaatatt   120
tcatttttgt caacgagatt ctctactcta ttccacaatc ttttgaagct atatttacct   180
taaatctgta ctctatacca ataatcatat attctattat ttatttttat ctctctccta   240
aggagcatcc ctctatgtct gcatggcccc cgcctcgggt cccaatctct tgctctgcta   300
gtagcacaga agaaaacact agaaatgact tgcttgactt agagtatcag ataaacatca   360
tgtttactta actttaattt gtatcggttt ctactatttt tataatattt ttgtctctat   420
agatactacg tgcaacagta taatcaacct agtttaatcc agagcgaagg attttttact   480
aagtacgtga ctccatatgc acagcgttcc ttttatggtt cctcactggg cacagcataa   540
acgaaccctg tccaatgttt tcagcgcgaa caaacagaaa ttccatcagc gaacaaacaa   600
catacatgcg agatgaaaat aaataataaa aaaagctccg tctcgatagg ccggcacgaa   660
tcgagagcct ccatagccag ttttttccat cggaacggcg gttcgcgcac ctaattatat   720
gcaccacacg cctataaagc caaccaaccc gtcggagggg cgcaagccag acagaagaca   780
gcccgtcagc ccctctcgtt tttcatccgc cttcgcctcc aaccgcgtgc gctccacgcc   840
tcctccagga aagcgagagg tgagcgcagt ccccttccc ctccttccaa ttcaattcgt    900
cttctcgttc gcagccctag gatttggggg tctggagggg tttgatcgtt tctcgccgtg   960
aatctgcttt ggtgtaaacc aacggatctc ggatcgtagt cttcagaaga tcccggattt  1020
tgcggtttgg ccctcctgg attcaattcg tcgtatcgtt cgcagcccta ggatttgggg   1080
atctggaggg gtttgatcgt ttctcgccgc gaatctgctc tggtgtaaac caacggatct  1140
cgggtcgtag tcttcagaag gtcccggatt tgcggtttg ccctcctg gattcaattc    1200 gtcgtatcgt tcgcagccct aggatttggg gatctgagg ggtttgatcc tttctcgccg   1260
cgaatctgct ctggtataac caacggatct cgggtcgtag tcttcagaag gtcccggatt  1320
ttgcggtttg gtggttcttg ctctatgaat cagagggatg gttcttcccg gatttatgcc  1380
ttgcggccac tctgtcgaat catggggttt cgacccgatt cgtaggcgtg ctccctgttt  1440
tggatgggaa gtaggcgtgt ttgtagtatt cgtgcttcga ttcgtcaacg gagattagaa  1500
gacctgggat gggatttgag gaaatctagg tatctgtcta gcacgtttct agatctattc  1560
ttcagctgtt atatgagagt aattttggaa ccctggtggg gtatgtttga ccgagtattc  1620
tgtagattat tgtccgtgac ttgctggctg ttaccgtcct tatctctgca tcatctatct  1680
```

```
gtgctagttt ctgcgtgctt ctcaaatatt tccggcctgt gtagcatgtg actgataata   1740
tgattttggc agcttctgca taagaacaac aaatcaaaag cttgatcagc tcggtgccta   1800
caaaacctca acaaccaagt ttcatgtctg atctcgacgt ccagcttcca tctgcctttg   1860
gtatggctac ttctcaattc atgatgccat gttttttttt atattgtggt tttacataat   1920
acatagcatc ttccagcttc ctgaagagta ttactgaata gattgataac atcatacaca   1980
cgaagttcat cttgaacatg cttattagtg ttctgtttgc atctgatggt atggcatcat   2040
ctttgataga tccgtttgct gaggcaaatg ctgaggactc tggtgctggt cctggaacga   2100
aggattatgt gcatgtgcgc atccagcagc gcaacggcag aaagagtctg actacagtcc   2160
agggtctgaa gaaagagttc agctataaca agatcctcaa ggatctgaag aaggaattct   2220
gctgcaatgg tactgtagtt caggacccag agctaggcca ggtaagatac gagaacaatg   2280
catttcaagc ttgtaaaaat ggtatctgcc ggttggtgga tatactgatc tgtttgtccg   2340
ctgcaggtca ttcagctcca aggtgaccag cgcaagaatg ttgctacttt cctagttcag   2400
gtattcagaa tcttcagacc tggccagctg aatactgttt taccataccg atagatgttc   2460
aatctgttaa tactgatcgt gcaattatta cttgtcttgg taggctggga ttgcgaagaa   2520
agagaacatc aagattcacg ggttctaagg gacctgtaaa tgcttgtgcc ctatattgtg   2580
tgcctccaca tattggggag cttgaagcat cgacagttac tagtcattgc ttacttatat   2640
aagaacataa gtagtatttg ctattgtcaa gtgtgccttg cttgatgcaa gttgtgtttt   2700
cgtatcatta ttattatgca cggccatcgt acgtgtatgg cttgtatggg ttattgccaa   2760
cttaataaaa gcacactctg tttgcctata agcactgatg tttgcctcgt catgcacatg   2820
ttgagtcggg tttttatttgt att                                          2843
```

<210> SEQ ID NO 465
<211> LENGTH: 800
<212> TYPE: DNA
<213> ORGANISM: Zea mays
<220> FEATURE:
<221> NAME/KEY: misc_feature
<222> LOCATION: (1)..(800)
<223> OTHER INFORMATION: Zm-GOS2 PRO, maize GOS2 promoter

<400> SEQUENCE: 465

```
taattattgg ctgtaggatt ctaaacagag cctaaatagc tggaatagct ctagccctca     60
atccaaacta atgatatcta tacttatgca actctaaatt tttattctaa aagtaatatt    120 tcattttgt caacgagatt ctctactcta ttccacaatc ttttgaagct atatttacct    180
taaatctgta ctctatacca ataatcatat attctattat ttatttttat ctctctccta    240
aggagcatcc ctctatgtct gcatggcccc cgcctcgggt cccaatctct tgctctgcta    300
gtagcacaga agaaaacact agaaatgact tgcttgactt agagtatcag ataaacatca    360
tgtttactta actttaattt gtatcggttt ctactatttt tataatattt ttgtctctat    420
agatactacg tgcaacagta taatcaacct agtttaatcc agagcgaagg attttttact    480
aagtacgtga ctccatatgc acagcgttcc ttttatggtt cctcactggg cacagcataa    540
acgaaccctg tccaatgttt tcagcgcgaa caaacagaaa ttccatcagc gaacaaacaa    600
catacatgcg agatgaaaat aaataataaa aaaagctccg tctcgatagg ccggcacgaa    660
tcgagagcct ccatagccag tttttttccat cggaacggcg gttcgcgcac ctaattatat    720
gcaccacacg cctataaagc caaccaaccc gtcggagggg cgcaagccag acagaagaca    780
```

```
gcccgtcagc ccctctcgtt                                              800
```

<210> SEQ ID NO 466
<211> LENGTH: 1023
<212> TYPE: DNA
<213> ORGANISM: Zea mays
<220> FEATURE:
<221> NAME/KEY: misc_feature
<222> LOCATION: (1)..(1023)
<223> OTHER INFORMATION: GOS2 INTRON, maize GOS2 5'-UTR1 and intron1 and
      5'-UTR2 sequence

<400> SEQUENCE: 466

```
tttcatccgc cttcgcctcc aaccgcgtgc gctccacgcc tcctccagga aagcgagagg    60
tgagcgcagt cccctttccc ctccttccaa ttcaattcgt cttctcgttc gcagccctag   120
gatttggggg tctggagggg tttgatcgtt tctcgccgtg aatctgcttt ggtgtaaacc   180
aacggatctc ggatcgtagt cttcagaaga tcccggattt tgcggtttgg cccctcctgg   240
attcaattcg tcgtatcgtt cgcagcccta ggatttgggg atctggaggg gtttgatcgt   300
ttctcgccgc gaatctgctc tggtgtaaac caacggatct cgggtcgtag tcttcagaag   360
gtcccggatt ttgcggtttg gcccctcctg gattcaattc gtcgtatcgt tcgcagccct   420
aggatttggg gatctggagg ggtttgatcc tttctcgccg cgaatctgct ctggtataac   480
caacggatct cgggtcgtag tcttcagaag gtcccggatt ttgcggtttg gtggttcttg   540
ctctatgaat cagagggatg gttcttcccg gatttatgcc ttgcggccac tctgtcgaat   600
catgggggttt cgacccgatt cgtaggcgtg ctccctgttt tggatgggaa gtaggcgtgt   660
ttgtagtatt cgtgcttcga ttcgtcaacg gagattagaa gacctgggat gggatttgag   720
gaaatctagg tatctgtcta gcacgtttct agatctattc ttcagctgtt atatgagagt   780
aattttggaa ccctggtggg gtatgtttga ccgagtattc tgtagattat tgtccgtgac   840
ttgctggctg ttaccgtcct tatctctgca tcatctatct gtgctagttt ctgcgtgctt   900
ctcaaatatt tccggcctgt gtagcatgtg actgataata tgattttggc agcttctgca   960
taagaacaac aaatcaaaag cttgatcagc tcggtgccta caaaacctca acaaccaagt  1020
ttc                                                               1023
```

<210> SEQ ID NO 467
<211> LENGTH: 23
<212> TYPE: DNA
<213> ORGANISM: Glycine max

<400> SEQUENCE: 467

```
gcgtcctttg acagcagctg tgg                                           23
```

<210> SEQ ID NO 468
<211> LENGTH: 23
<212> TYPE: DNA
<213> ORGANISM: Glycine max

<400> SEQUENCE: 468

```
gcaaccacag ctgctgtcaa agg                                           23
```

<210> SEQ ID NO 469
<211> LENGTH: 434
<212> TYPE: DNA
<213> ORGANISM: Glycine max

<400> SEQUENCE: 469

```
ccgggtgtga tttagtataa agtgaagtaa tggtcaaaag aaaaagtgta aaacgaagta    60
cctagtaata agtaatattg aacaaaataa atggtaaagt gtcagatata taaaataggc   120
tttaataaaa ggaagaaaaa aaacaaacaa aaaataggtt gcaatggggc agagcagagt   180
catcatgaag ctagaaaggc taccgataga taaactatag ttaattaaat acattaaaaa   240
atacttggat ctttctctta ccctgtttat attgagacct gaaacttgag agagatacac   300
taatcttgcc ttgttgtttc attccctaac ttacaggact cagcgcatgt catgtggtct   360
cgttccccat ttaagtccca caccgtctaa acttattaaa ttattaatgt ttataactag   420
atgcacaaca acaa                                                    434

<210> SEQ ID NO 470
<211> LENGTH: 9093
<212> TYPE: DNA
<213> ORGANISM: Artificial sequence
<220> FEATURE:
<223> OTHER INFORMATION: synthesized sequence- QC878

<400> SEQUENCE: 470
ccgggtgtga tttagtataa agtgaagtaa tggtcaaaag aaaaagtgta aaacgaagta    60
cctagtaata agtaatattg aacaaaataa atggtaaagt gtcagatata taaaataggc   120
tttaataaaa ggaagaaaaa aaacaaacaa aaaataggtt gcaatggggc agagcagagt   180
catcatgaag ctagaaaggc taccgataga taaactatag ttaattaaat acattaaaaa   240
atacttggat ctttctctta ccctgtttat attgagacct gaaacttgag agagatacac   300
taatcttgcc ttgttgtttc attccctaac ttacaggact cagcgcatgt catgtggtct   360
cgttccccat ttaagtccca caccgtctaa acttattaaa ttattaatgt ttataactag   420
atgcacaaca acaaagcttg cgtcctttga cagcagctgg ttttagagct agaaatagca   480
agttaaaata aggctagtcc gttatcaact tgaaaaagtg caccgagtc ggtgcttttt    540 tttgcggccg caattggatc gggtttactt attttgtggg tatctatact tttattagat   600
ttttaatcag gctcctgatt tcttttttatt tcgattgaat tcctgaactt gtattattca   660
gtagatcgaa taaattataa aaagataaaa tcataaaata atattttatc ctatcaatca   720
tattaaagca atgaatatgt aaaattaatc ttatctttat tttaaaaaat catataggtt   780
tagtattttt ttaaaaataa agataggatt agttttacta ttcactgctt attacttttta   840 aaaaaatcat aaaggtttag tattttttta aaataaatat aggaatagtt ttactattca   900
ctgctttaat agaaaaatag tttaaaattt aagatagttt taatcccagc atttgccacg   960
tttgaacgtg agccgaaacg atgtcgttac attatcttaa cctagctgaa acgatgtcgt  1020
cataatatcg ccaaatgcca actggactac gtcgaaccca caaatcccac aaagcgcgtg  1080
aaatcaaatc gctcaaacca caaaaaagaa caacgcgttt gttacacgct caatcccacg  1140
cgagtagagc acagtaacct tcaaataagc gaatggggca taatcagaaa tccgaaataa  1200
acctaggggc attatcggaa atgaaaagta gctcactcaa tataaaaatc taggaaccct  1260
agttttcgtt atcactctgt gctccctcgc tctatttctc agtctctgtg tttgcggctg  1320
aggattccga acgagtgacc ttcttcgttt ctcgcaaagg taacagcctc tgctcttgtc  1380
tcttcgattc gatctatgcc tgtctcttat ttacgatgat gtttcttcgg ttatgttttt  1440
ttatttatgc tttatgctgt tgatgttcgg ttgtttgttt cgctttgttt ttgtggttca  1500
gttttttagg attctttttgg tttttgaatc gattaatcgg aagagatttt cgagttattt  1560
ggtgtgttgg aggtgaatct ttttttttgag gtcatagatc tgttgtattt gtgttataaa  1620
```

```
catgcgactt tgtatgattt tttacgaggt tatgatgttc tggttgtttt attatgaatc    1680
tgttgagaca gaaccatgat ttttgttgat gttcgtttac actattaaag gtttgtttta    1740
acaggattaa aagttttta agcatgttga aggagtcttg tagatatgta accgtcgata    1800
gttttttgt gggtttgttc acatgttatc aagcttaatc ttttactatg tatgcgacca    1860
tatctggatc cagcaaaggc gattttttaa ttccttgtga aacttttgta atatgaagtt    1920
gaaattttgt tattggtaaa ctataaatgt gtgaagttgg agtataccttt taccttctta    1980
tttggctttg tgatagtttaa atttatatgt attttgagtt ctgacttgta tttctttgaa    2040
ttgattctag tttaagtaat ccatggacaa aaagtactca atagggctcg acatagggac    2100
taactccgtt ggatgggccg tcatcaccga cgagtacaag gtgcctcca agaagttcaa    2160
ggtgttggga aacaccgaca ggcacagcat aaagaagaat ttgatcggtg ccctcctctt    2220
cgactccgga gagaccgctg aggctaccag gctcaagagg accgctagaa ggcgctacac    2280
cagaaggaag aacagaatct gctacctgca ggagatcttc tccaacgaga tggccaaggt    2340
ggacgactcc ttcttccacc gccttgagga atcattcctg gtggaggagg ataaaaagca    2400
cgagagacac ccaatcttcg gaacatcgt cgacgaggtg gcctaccatg aaaagtaccc    2460
taccatctac cacctgagga gaagctggt cgactctacc gacaaggctg acttgcgctt    2520
gatttacctg gctctcgctc acatgataaa gttccgcgga cacttcctca ttgagggaga    2580
cctgaaccca gacaactccg acgtggacaa gctcttcatc cagctcgttc agacctacaa    2640
ccagcttttc gaggagaacc caatcaacgc cagtggagtt gacgccaagg ctatcctctc    2700
tgctcgtctg tcaaagtcca ggaggcttga gaacttgatt gcccagctgc ctggcgaaaa    2760
gaagaacgga ctgttcggaa acttgatcgc tctctccctg ggattgactc ccaacttcaa    2820
gtccaacttc gacctcgccg aggacgctaa gttgcagttg tctaaagaca cctacgacga    2880
tgacctcgac aacttgctgg cccagatagg cgaccaatac gccgatctct cctcgccgc    2940
taagaacttg tccgacgcaa tcctgctgtc cgacatcctg agagtcaaca ctgagattac    3000
caaagctcct ctgtctgctt ccatgattaa gcgctacgac gagcaccacc aagatctgac    3060
cctgctcaag gccctggtga cacagcagct gcccgagaag tacaaggaga tcttttcga    3120
ccagtccaag aacggctacg ccggatacat tgacggaggc gcctcccagg aagagttcta    3180
caagttcatc aagcccatcc ttgagaagat ggacggtacc gaggagctgt tggtgaagtt    3240
gaacagagag gacctgttga ggaagcagag aaccttcgac aacggaagca tccctcacca    3300
aatccacctg ggagagctcc acgccatctt gaggaggcag gaggatttct atcccttcct    3360
gaaggacaac cgcgagaaga ttgagaagat cttgaccttc agaattcctt actacgtcgg    3420
gccactcgcc agaggaaact ctaggttcgc ctggatgacc cgcaaatctg aagagaccat    3480
tactcctgg aacttcgagg aagtcgtgga caagggcgct tccgctcagt ctttcatcga    3540
gaggatgacc aacttcgata aaatctgcc caacgagaag gtgctgccca gcactccct    3600
gttgtacgag tatttcacag tgtacaacga gctcaccaag gtgaagtacg tcacagaggg    3660
aatgaggaag cctgccttct tgtccggaga gcagaagaag gccatcgtcg acctgctctt    3720
caagaccaac aggaaggtga ctgtcaagca gctgaaggag gactacttca agaagatcga    3780
gtgcttcgac tccgtcgaga tctctggtgt cgaggacagg ttcaacgcct cccttgggac    3840
ttaccacgat ctgctcaaga ttattaaaga caaggacttc ctggacaacg aggagaacga    3900
ggacatcctt gaggacatcg tgctcaccct gaccttgttc gaagacaggg aaatgatcga    3960
```

```
agagaggctc aagacctacg cccacctctt cgacgacaag gtgatgaaac agctgaagag    4020
acgcagatat accggctggg gaaggctctc ccgcaaattg atcaacggga tcagggacaa    4080
gcagtcaggg aagactatac tcgacttcct gaagtccgac ggattcgcca acaggaactt    4140
catgcagctc attcacgacg actccttgac cttcaaggag gacatccaga aggctcaggt    4200
gtctggacag ggtgactcct tgcatgagca cattgctaac ttggccggct ctcccgctat    4260
taagaagggc attttgcaga ccgtgaaggt cgttgacgag ctcgtgaagg tgatgggacg    4320
ccacaagcca gagaacatcg ttattgagat ggctcgcgag aaccaaacta cccagaaagg    4380
gcagaagaat tcccgcgaga ggatgaagcg cattgaggag ggcataaaag agcttggctc    4440
tcagatcctc aaggagcacc ccgtcgagaa cactcagctg cagaacgaga agctgtacct    4500
gtactacctc caaaacggaa gggacatgta cgtggaccag gagctggaca tcaacaggtt    4560
gtccgactac gacgtcgacc acatcgtgcc tcagtccttc ctgaaggatg actccatcga    4620
caataaagtg ctgacacgct ccgataaaaa tagaggcaag tccgacaacg tcccctccga    4680
ggaggtcgtg aagaagatga aaaactactg gagacagctc ttgaacgcca agctcatcac    4740
ccagcgtaag ttcgacaacc tgactaaggc tgagagagga ggattgtccg agctcgataa    4800
ggccggattc atcaagagac agctcgtcga acccgccaa attaccaagc acgtggccca    4860
aattctggat tcccgcatga acaccaagta cgatgaaaat gacaagctga tccgcgaggt    4920
caaggtgatc accttgaagt ccaagctggt ctccgacttc gcaaggact tccagttcta    4980
caaggtgagg gagatcaaca actaccacca cgcacacgac gcctacctca acgctgtcgt    5040
tggaaccgcc ctcatcaaaa atatccctaa gctggagtct gagttcgtct acggcgacta    5100
caaggtgtac gacgtgagga agatgatcgc taagtctgag caggagatcg gcaaggccac    5160
cgccaagtac ttcttctact ccaacatcat gaacttcttc aagaccgaga tcactctcgc    5220
caacggtgag atcaggaagc gcccactgat cgagaccaac ggtgagactg gagagatcgt    5280
gtgggacaaa gggaagggatt tcgctactgt gaggaaggtg ctctccatgc ctcaggtgaa    5340
catcgtcaag aagaccgaag ttcagaccgg aggattctcc aaggagtcca tcctcccaa    5400
gagaaactcc gacaagctga tcgctagaaa gaaagactgg gaccctaaga agtacgagg    5460
cttcgattct cctaccgtgg cctactctgt gctggtcgtg gccaaggtgg agaagggcaa    5520
gtccaagaag ctgaaatccg tcaaggagct cctcgggatt accatcatgg agaggagttc    5580
cttcgagaag aaccctatcg acttcctgga ggccaaggga tataaagagg tgaagaagga    5640
cctcatcatc aagctgccca agtactccct cttcgagttg gagaacggaa ggaagaggat    5700
gctggcttct gccggagagt tgcagaaggg aaatgagctc gcccttccct ccaagtacgt    5760
gaacttcctg tacctcgcct ctcactatga aaagttgaag gctctcctg aggacaacga    5820
gcagaagcag ctcttcgtgg agcagcacaa gcactacctg gacgaaatta cgagcagat    5880
ctctgagttc tccaagcgcg tgatattggc cgacgccaac ctcgacaagg tgctgtccgc    5940
ctacaacaag cacagggata agcccattcg cgagcaggct gaaaacatta tccacctgtt    6000
taccctcaca aacttgggag cccctgctgc cttcaagtac ttcgacacca ccattgacag    6060
gaagagatac acctccacca aggaggtgct cgacgcaaca ctcatccacc aatccatcac    6120
cggcctctat gaaacaagga ttgacttgtc ccagctggga ggcgactcta gagccgatcc    6180
caagaagaag agaaaggtgt aggttaacct agacttgtcc atcttctgga ttggccaact    6240
taattaatgt atgaaataaa aggatgcaca catagtgaca tgctaatcac tataatgtgg    6300
gcatcaaagt tgtgtgttat gtgtaattac tagttatctg aataaaagag aaagagatca    6360
```

```
tccatatttc ttatcctaaa tgaatgtcac gtgtctttat aattctttga tgaaccagat    6420
gcatttcatt aaccaaatcc atatacatat aaatattaat catatataat taatatcaat    6480
tgggttagca aaacaaatct agtctaggtg tgttttgcga attcgatatc aagcttatcg    6540
ataccgtcga gggggggccc ggtaccggcg cgccgttcta tagtgtcacc taaatcgtat    6600
gtgtatgata cataaggtta tgtattaatt gtagccgcgt tctaacgaca atatgtccat    6660
atggtgcact ctcagtacaa tctgctctga tgccgcatag ttaagccagc ccgacaccc     6720 gccaacaccc gctgacgcgc cctgacgggc ttgtctgctc ccggcatccg cttacagaca    6780
agctgtgacc gtctccggga gctgcatgtg tcagaggttt tcaccgtcat caccgaaacg    6840
cgcgagacga aagggcctcg tgatacgcct attttatag gttaatgtca tgaccaaaat    6900
cccttaacgt gagttttcgt tccactgagc gtcagacccc gtagaaaaga tcaaaggatc    6960
ttcttgagat cctttttttc tgcgcgtaat ctgctgcttg caaacaaaaa aaccaccgct    7020
accagcggtg gtttgtttgc cggatcaaga gctaccaact ctttttccga aggtaactgg    7080
cttcagcaga gcgcagatac caaatactgt ccttctagtg tagccgtagt taggccacca    7140
cttcaagaac tctgtagcac cgcctacata cctcgctctg ctaatcctgt taccagtggc    7200
tgctgccagt ggcgataagt cgtgtcttac cgggttggac tcaagacgat agttaccgga    7260
taaggcgcag cggtcgggct gaacggggg ttcgtgcaca cagcccagct tggagcgaac     7320
gacctacacc gaactgagat acctacagcg tgagcattga gaaagcgcca cgcttcccga    7380
agggagaaag gcggacaggt atccggtaag cggcagggtc ggaacaggag agcgcacgag    7440
ggagcttcca gggggaaacg cctggtatct ttatagtcct gtcgggtttc gccacctctg    7500
acttgagcgt cgatttttgt gatgctcgtc aggggggcgg agcctatgga aaaacgccag    7560
caacgcggcc tttttacggt tcctggcctt ttgctggcct tttgctcaca tgttctttcc    7620
tgcgttatcc cctgattctg tggataaccg tattaccgcc tttgagtgag ctgataccgc    7680
tcgccgcagc cgaacgaccg agcgcagcga gtcagtgagc gaggaagcgg aagagcgccc    7740
aatacgcaaa ccgcctctcc ccgcgcgttg gccgattcat taatgcaggt tgatcagatc    7800
tcgatcccgc gaaattaata cgactcacta tagggagacc acaacggttt ccctctagaa    7860
ataattttgt ttaactttaa gaaggagata tacccatgga aaagcctgaa ctcaccgcga    7920
cgtctgtcga agtttctg atcgaaaagt tcgacagcgt ctccgacctg atgcagctct      7980
cggagggcga agaatctcgt gctttcagct tcgatgtagg agggcgtgga tatgtcctgc    8040
gggtaaatag ctgcgccgat ggtttctaca aagatcgtta tgtttatcgg cactttgcat    8100
cggccgcgct cccgattccg gaagtgcttg acattgggga attcagcgag agcctgacct    8160
attgcatctc ccgccgtgca cagggtgtca cgttgcaaga cctgcctgaa accgaactgc    8220
ccgctgttct gcagccggtc gcggaggcta tggatgcgat cgctgcggcc gatcttagcc    8280
agacgagcgg gttcggccca ttcggaccgc aaggaatcgg tcaatacact acatggcgtg    8340
atttcatatg cgcgattgct gatccccatg tgtatcactg gcaaactgtg atggacgaca    8400
ccgtcagtgc gtccgtcgcg caggctctcg atgagctgat gctttgggcc gaggactgcc    8460
ccgaagtccg gcacctcgtg cacgcggatt tcggctccaa caatgtcctg acggacaatg    8520
gccgcataac agcggtcatt gactggagcg aggcgatgtt cggggattcc caatacgagg    8580
tcgccaacat cttcttctgg aggccgtggt tggcttgtat ggagcagcag acgcgctact    8640
tcgagcggag gcatccggag cttgcaggat cgccgcggct ccgggcgtat atgctccgca    8700
```

```
ttggtcttga ccaactctat cagagcttgg ttgacggcaa tttcgatgat gcagcttggg   8760
cgcagggtcg atgcgacgca atcgtccgat ccggagccgg gactgtcggg cgtacacaaa   8820
tcgcccgcag aagcgcggcc gtctggaccg atggctgtgt agaagtactc gccgatagtg   8880
gaaaccgacg ccccagcact cgtccgaggg caaaggaata gtgaggtaca gcttggatcg   8940
atccggctgc taacaaagcc cgaaaggaag ctgagttggc tgctgccacc gctgagcaat   9000
aactagcata accccttggg gcctctaaac gggtcttgag gggttttttg ctgaaggag    9060 gaactatatc cggatgatcg ggcgcgccgg tac                                9093
```

<210> SEQ ID NO 471
<211> LENGTH: 9093
<212> TYPE: DNA
<213> ORGANISM: Artificial sequence
<220> FEATURE:
<223> OTHER INFORMATION: synthesized sequence- QC879

<400> SEQUENCE: 471

```
ccgggtgtga tttagtataa agtgaagtaa tggtcaaaag aaaaagtgta aaacgaagta     60
cctagtaata agtaatattg aacaaaataa atggtaaagt gtcagatata taaaataggc    120
tttaataaaa ggaagaaaaa aaacaaacaa aaaataggtt gcaatggggc agagcagagt    180
catcatgaag ctagaaaggc taccgataga taaactatag ttaattaaat acattaaaaa    240
atacttggat ctttctctta ccctgtttat attgagacct gaaacttgag agagatacac    300
taatcttgcc ttgttgtttc attccctaac ttacaggact cagcgcatgt catgtggtct    360
cgttccccat ttaagtccca caccgtctaa acttattaaa ttattaatgt ttataactag    420
atgcacaaca acaaagcttg caaccacagc tgctgtcaag ttttagagct agaaatagca    480
agttaaaata aggctagtcc gttatcaact tgaaaaagtg gcaccgagtc ggtgcttttt    540
tttgcggccg caattggatc gggtttactt attttgtggg tatctatact tttattagat    600
ttttaatcag gctcctgatt tctttttatt tcgattgaat tcctgaactt gtattattca    660
gtagatcgaa taaattataa aaagataaaa tcataaaata atatttatc ctatcaatca    720 tattaaagca atgaatatgt aaaattaatc ttatctttat tttaaaaaat catataggtt    780
tagtattttt ttaaaaataa agataggatt agttttacta ttcactgctt attactttta    840
aaaaaatcat aaaggtttag tattttttta aaataaatat aggaatagtt ttactattca    900
ctgctttaat agaaaaatag tttaaaattt aagtagtttt taatcccagc atttgccacg    960
tttgaacgtg agccgaaacg atgtcgttac attatcttaa cctagctgaa acgatgtcgt   1020
cataatatcg ccaaatgcca actggactac gtcgaaccca caaatcccac aaagcgcgtg   1080
aaatcaaatc gctcaaacca caaaaaagaa caacgcgttt gttacacgct caatcccacg   1140
cgagtagagc acagtaacct tcaaataagc gaatggggca taatcagaaa tccgaaataa   1200
acctaggggc attatcggaa atgaaaagta gctcactcaa tataaaaatc taggaaccct   1260
agttttcgtt atcactctgt gctccctcgc tctatttctc agtctctgtg tttgcggctg   1320
aggattccga acgagtgacc ttcttcgttt ctcgcaaagg taacagcctc tgctcttgtc   1380
tcttcgattc gatctatgcc tgtctcttat ttacgatgat gtttcttcgg ttatgttttt   1440
ttatttatgc tttatgctgt tgatgttcgg ttgtttgttt cgctttgttt ttgtggttca   1500
gttttttagg attcttttgg tttttgaatc gattaatcgg aagagatttt cgagttattt   1560
ggtgtgttgg aggtgaatct ttttttttgag gtcatagatc tgttgtattt gtgttataaa   1620
catgcgactt tgtatgattt tttacgaggt tatgatgttc tggttgtttt attatgaatc   1680
```

```
tgttgagaca gaaccatgat ttttgttgat gttcgtttac actattaaag gtttgtttta   1740
acaggattaa aagttttta agcatgttga aggagtcttg tagatatgta accgtcgata    1800
gttttttgt gggtttgttc acatgttatc aagcttaatc ttttactatg tatgcgacca    1860
tatctggatc cagcaaaggc gattttttaa ttccttgtga aacttttgta atatgaagtt   1920
gaaattttgt tattggtaaa ctataaatgt gtgaagttgg agtataccctt taccttctta  1980
tttggctttg tgatagttta atttatatgt attttgagtt ctgacttgta tttctttgaa   2040
ttgattctag tttaagtaat ccatggacaa aaagtactca atagggctcg acatagggac   2100
taactccgtt ggatgggccg tcatcaccga cgagtacaag gtgccctcca agaagttcaa   2160
ggtgttggga acaccgaca ggcacagcat aaagaagaat ttgatcggtg ccctcctctt    2220
cgactccgga gagaccgctg aggctaccag gctcaagagg accgctagaa ggcgctacac   2280
cagaaggaag aacagaatct gctacctgca ggagatcttc tccaacgaga tggccaaggt   2340
ggacgactcc ttcttccacc gccttgagga atcattcctg gtggaggag ataaaaagca    2400
cgagagacac ccaatcttcg gaacatcgt cgacgaggtg gcctaccatg aaaagtaccc    2460
taccatctac cacctgagga gaagctggt cgactctacc gacaaggctg acttgcgctt    2520
gatttacctg gctctcgctc acatgataaa gttccgcgga cacttcctca ttgagggaga   2580
cctgaaccca gacaactccg acgtggacaa gctcttcatc cagctcgttc agacctacaa   2640
ccagcttttc gaggagaacc caatcaacgc cagtggagtt gacgccaagg ctatcctctc   2700
tgctcgtctg tcaaagtcca ggaggcttga aacttgatt gcccagctgc ctggcgaaaa    2760
gaagaacgga ctgttcggaa acttgatcgc tctctccctg ggattgactc ccaacttcaa   2820
gtccaacttc gacctcgccg aggacgctaa gttgcagttg tctaaagaca cctacgacga   2880
tgacctcgac aacttgctgg cccagatagg cgaccaatac gccgatctct tcctcgccgc   2940
taagaacttg tccgacgcaa tcctgctgtc cgacatcctg agagtcaaca ctgagattac   3000
caaagctcct ctgtctgctt ccatgattaa gcgctacgac gagcaccacc aagatctgac   3060
cctgctcaag gccctggtga acagcagct gcccgagaag tacaaggaga tcttttcga    3120
ccagtccaag aacggctacg ccggatacat tgacggaggc gcctcccagg aagagttcta   3180
caagttcatc aagcccatcc ttgagaagat ggacggtacc gaggagctgt tggtgaagtt   3240
gaacagagag gacctgttga ggaagcagag aaccttcgac aacggaagca tccctcacca   3300
aatccacctg ggagagctcc acgccatctt gaggaggcag gaggatttct atccccttcct  3360
gaaggacaac cgcgagaaga ttgagaagat cttgaccttc agaattcctt actacgtcgg   3420
gccactcgcc agaggaaact ctaggttcgc ctggatgacc cgcaaatctg aagagaccat   3480
tactccctgg aacttcgagg aagtcgtgga caagggcgct tccgctcagt ctttcatcga   3540
gaggatgacc aacttcgata aaaatctgcc caacgagaag gtgctgccca gcactccct    3600
gttgtacgag tatttcacag tgtacaacga gctcaccaag gtgaagtacg tcacagaggg   3660
aatgaggaag cctgccttct tgtccggaga gcagaagaag gccatcgtcg acctgctctt   3720
caagaccaac aggaaggtga ctgtcaagca gctgaaggag gactacttca agaagatcga   3780
gtgcttcgac tccgtcgaga tctctggtgt cgaggacagg ttcaacgcct cccttgggac   3840
ttaccacgat ctgctcaaga ttattaaaga caaggacttc ctggacaacg aggagaacga   3900
ggacatcctt gaggacatcg tgctcaccct gaccttgttc gaagacaggg aaatgatcga   3960
agagaggctc aagacctacg cccacctctt cgacgacaag gtgatgaaac agctgaagag   4020
```

-continued

```
acgcagatat accggctggg gaaggctctc ccgcaaattg atcaacggga tcaggacaa    4080 gcagtcaggg aagactatac tcgacttcct gaagtccgac ggattcgcca acaggaactt    4140
catgcagctc attcacgacg actccttgac cttcaaggag gacatccaga aggctcaggt    4200
gtctggacag ggtgactcct tgcatgagca cattgctaac ttggccggct ctcccgctat    4260
taagaagggc attttgcaga ccgtgaaggt cgttgacgag ctcgtgaagg tgatgggacg    4320
ccacaagcca gagaacatcg ttattgagat ggctcgcgag aaccaaacta cccagaaagg    4380
gcagaagaat tcccgcgaga ggatgaagcg cattgaggag ggcataaaag agcttggctc    4440
tcagatcctc aaggagcacc ccgtcgaaa cactcagctg cagaacgaga agctgtacct    4500
gtactacctc caaaacggaa gggacatgta cgtggaccag gagctggaca tcaacaggtt    4560
gtccgactac gacgtcgacc acatcgtgcc tcagtccttc ctgaaggatg actccatcga    4620
caataaagtg ctgacacgct ccgataaaaa tagaggcaag tccgacaacg tcccctccga    4680
ggaggtcgtg aagaagatga aaaactactg gagacagctc ttgaacgcca agctcatcac    4740
ccagcgtaag ttcgacaacc tgactaaggc tgagagagga ggattgtccg agctcgataa    4800
ggccggattc atcaagagac agctcgtcga aacccgccaa attaccaagc acgtggccca    4860
aattctggat tcccgcatga acaccaagta cgatgaaaat gacaagctga tccgcgaggt    4920
caaggtgatc accttgaagt ccaagctggt ctccgacttc cgcaaggact tccagttcta    4980
caaggtgagg gagatcaaca actaccacca cgcacacgac gcctacctca acgctgtcgt    5040
tggaaccgcc ctcatcaaaa aatatcctaa gctggagtct gagttcgtct acggcgacta    5100
caaggtgtac gacgtgagga gatgatcgc taagtctgag caggagatcg gcaaggccac    5160
cgccaagtac ttcttctact ccaacatcat gaacttcttc aagaccgaga tcactctcgc    5220
caacggtgag atcaggaagc gcccactgat cgagaccaac ggtgagactg gagagatcgt    5280
gtgggacaaa gggagggatt tcgctactgt gaggaaggtg ctctccatgc ctcaggtgaa    5340
catcgtcaag aagaccgaag ttcagaccgg aggattctcc aaggagtcca tcctccccaa    5400
gagaaactcc gacaagctga tcgctagaaa gaaagactgg gaccctaaga agtacggagg    5460
cttcgattct cctaccgtgg cctactctgt gctggtcgtg gccaaggtgg agaagggcaa    5520
gtccaagaag ctgaaatccg tcaaggagct cctcgggatt accatcatgg agaggagttc    5580
cttcgagaag aaccctatcg acttcctgga ggccaaggga tataaagagg tgaagaagga    5640
cctcatcatc aagctgccca gtactccct cttcgagttg gagaacggaa ggaagaggat    5700
gctggcttct gccggagagt tgcagaaggg aaatgagctc gcccttccct ccaagtacgt    5760
gaacttcctg tacctcgcct ctcactatga aaagttgaag ggctctcctg aggacaacga    5820
gcagaagcag ctcttcgtgg agcagcacaa gcactacctg gacgaaatta tcgagcagat    5880
ctctgagttc tccaagcgcg tgatattggc cgacgccaac ctcgacaagg tgctgtccgc    5940
ctacaacaag cacagggata agcccattcg cgagcaggct gaaaacatta tccacctgtt    6000
taccctcaca aacttgggag ccctgctgc cttcaagtac ttcgacacca ccattgacag    6060
gaagagatac acctccacca aggaggtgct cgacgcaaca ctcatccacc aatccatcac    6120
cggcctctat gaaacaagga ttgacttgtc ccagctggga ggcgactcta gagccgatcc    6180
caagaagaag agaaaggtgt aggttaacct agacttgtcc atcttctgga ttggccaact    6240
taattaatgt atgaaataaa aggatgcaca catagtgaca tgctaatcac tataatgtgg    6300
gcatcaaagt tgtgtgttat gtgtaattac tagttatctg aataaaagag aaagagatca    6360
tccatatttc ttatcctaaa tgaatgtcac gtgtctttat aattctttga tgaaccagat    6420
```

```
gcatttcatt aaccaaatcc atatacatat aaatattaat catatataat taatatcaat    6480
tgggttagca aaacaaatct agtctaggtg tgttttgcga attcgatatc aagcttatcg    6540
ataccgtcga ggggggggccc ggtaccggcg cgccgttcta tagtgtcacc taaatcgtat    6600
gtgtatgata cataaggtta tgtattaatt gtagccgcgt tctaacgaca atatgtccat    6660
atggtgcact ctcagtacaa tctgctctga tgccgcatag ttaagccagc cccgacaccc    6720
gccaacaccc gctgacgcgc cctgacgggc ttgtctgctc ccggcatccg cttacagaca    6780
agctgtgacc gtctccggga gctgcatgtg tcagaggttt tcaccgtcat caccgaaacg    6840
cgcgagacga aagggcctcg tgatacgcct atttttatag gttaatgtca tgaccaaaat    6900
cccttaacgt gagttttcgt tccactgagc gtcagacccc gtagaaaaga tcaaaggatc    6960
ttcttgagat ccttttttc tgcgcgtaat ctgctgcttg caaacaaaaa aaccaccgct    7020
accagcggtg gtttgtttgc cggatcaaga gctaccaact cttttttccga aggtaactgg    7080
cttcagcaga gcgcagatac caaatactgt ccttctagtg tagccgtagt taggccacca    7140
cttcaagaac tctgtagcac cgcctacata cctcgctctg ctaatcctgt taccagtggc    7200
tgctgccagt ggcgataagt cgtgtcttac cgggttggac tcaagacgat agttaccgga    7260
taaggcgcag cggtcgggct gaacgggggg ttcgtgcaca cagcccagct tggagcgaac    7320
gacctacacc gaactgagat acctacagcg tgagcattga gaaagcgcca cgcttcccga    7380
agggagaaag gcggacaggt atccggtaag cggcagggtc ggaacaggag agcgcacgag    7440
ggagcttcca gggggaaacg cctggtatct ttatagtcct gtcgggtttc gccacctctg    7500
acttgagcgt cgatttttgt gatgctcgtc aggggggcgg agcctatgga aaaacgccag    7560
caacgcggcc ttttacggtt cctggccctt ttgctggcct tttgctcaca tgttctttcc    7620
tgcgttatcc cctgattctg tggataaccg tattaccgcc tttgagtgag ctgataccgc    7680
tcgccgcagc cgaacgaccg agcgcagcga gtcagtgagc gaggaagcgg aagagcgccc    7740
aatacgcaaa ccgcctctcc ccgcgcgttg gccgattcat taatgcaggt tgatcagatc    7800
tcgatcccgc gaaattaata cgactcacta tagggagacc acaacggttt ccctctagaa    7860
ataattttgt ttaactttaa gaaggagata tacccatgga aaagcctgaa ctcaccgcga    7920
cgtctgtcga agtttctctg atcgaaaagt tcgacagcgt ctccgacctg atgcagctct    7980
cggagggcga agaatctcgt gctttcagct tcgatgtagg agggcgtgga tatgtcctgc    8040
gggtaaatag ctgcgccgat ggtttctaca aagatcgtta tgtttatcgg cactttgcat    8100
cggccgcgct cccgattccg gaagtgcttg acattgggga attcagcgag agcctgacct    8160
attgcatctc ccgccgtgca cagggtgtca cgttgcaaga cctgcctgaa accgaactgc    8220
ccgctgttct gcagccggtc gcggaggcta tggatgcgat cgctgcggcc gatcttagcc    8280
agacgagcgg gttcggccca ttcggaccgc aaggaatcgg tcaatacact acatggcgtg    8340
atttcatatg cgcgattgct gatccccatg tgtatcactg gcaaactgtg atggacgaca    8400
ccgtcagtgc gtccgtcgcg caggctctcg atgagctgat gctttgggcc gaggactgcc    8460
ccgaagtccg gcacctcgtg cacgcggatt tcggctccaa caatgtcctg acggacaatg    8520
gccgcataac agcggtcatt gactggagcg aggcgatgtt cggggattcc caatacgagg    8580
tcgccaacat cttcttctgg aggccgtggt tggcttgtat ggagcagcag acgcgctact    8640
tcgagcggag gcatccggag cttgcaggat cgccgcggct ccgggcgtat atgctccgca    8700
ttggtcttga ccaactctat cagagcttgg ttgacggcaa tttcgatgat gcagcttggg    8760
```

```
cgcagggtcg atgcgacgca atcgtccgat ccggagccgg gactgtcggg cgtacacaaa    8820
tcgcccgcag aagcgcggcc gtctggaccg atggctgtgt agaagtactc gccgatagtg    8880
gaaaccgacg ccccagcact cgtccgaggg caaaggaata gtgaggtaca gcttggatcg    8940
atccggctgc taacaaagcc cgaaaggaag ctgagttggc tgctgccacc gctgagcaat    9000
aactagcata accccttggg gcctctaaac gggtcttgag gggttttttg ctgaaggag     9060 gaactatatc cggatgatcg ggcgcgccgg tac                                 9093
```

<210> SEQ ID NO 472
<211> LENGTH: 1357
<212> TYPE: DNA
<213> ORGANISM: Artificial sequence
<220> FEATURE:
<223> OTHER INFORMATION: synthesized sequence- RTW1013A

<400> SEQUENCE: 472

```
ctagaagata aaccctcccc caaaacacaa attagaatga catttcaagt tccatgtatg     60
tcactttcat tctattattt ttacaacttt tagttactta acagatgtct tgttcagcat    120
aaattataat ttattctgtt tttttttagg gaacaactgt tgtagacaac ttgttgtata    180
gtgaggatat tcattacatg cttggtgcat taaggaccct tggactgcgt gtggaagatg    240
acaaaacaac caaacaagca attgttgaag gctgtggggg attgtttccc actagtaagg    300
aatctaaaga tgaaatcaat ttattccttg gaaatgctgg tattgcaatg agatctttga    360
cagcagctgt tgttgctgca ggtggaaatg caaggtctgt tttttttttt tttgttcagc    420
ataatctttg aattgttcct cgtataacta atcacaacag agtacgtgtt cttcttcctg    480
ttataatcta aaaatctcat ccagattagt catcctttct tcttaaaagg aacctttaat    540
tatcaatgta tttatttaat atttaaatta gcttgtcaaa gtctagcata tacatatttt    600
gattatattc tgagaaatgc acctgagggt gttcctcatg atctacttca acctctgtta    660
ttattagatt ttctatcatg attactggtt tgagtctcta agtagaccat cttgatgttc    720
aaaatatttc agctacgtac ttgatggggt gccccgaatg agagagaggc caattgggga    780
tttggttgct ggtcttaagc aacttggtgc agatgttgat tgctttcttg gcacaaactg    840
tccacctgtt cgtgtaaatg ggaagggagg acttcctggc ggaaaggtat ggtttggatt    900
tcatttagaa taaggtggag taactttcct ggatcaaaat tctaatttaa gaagcctccc    960
tgttttcctc tctttagaat aagactaagg gtaggtttag gagttgggtt ttggagagaa   1020
atggaaggga gagcaatttt tttcttcttc taataaatat tctttaattt gatacatttt   1080
ttaagtaaaa gaatataaag atagattagc ataacttaat gttttaatct tttatttatt   1140
tttataaata ttatatacct gtctatttaa aaatcaaata tttgtcctcc attcccttc    1200 ccttcaaaac ctcagttcca aatataccgt agttgaatta tattttggaa ggcctattgg   1260
ttggagactt ttcctttca gagattatcc ctcacctta ttatagcctt tctatttta     1320 aacttcatat agacgccatt cttggggcgg ccgcgat                            1357
```

<210> SEQ ID NO 473
<211> LENGTH: 1357
<212> TYPE: DNA
<213> ORGANISM: Artificial sequence
<220> FEATURE:
<223> OTHER INFORMATION: synthesized sequence- RTW1012A

<400> SEQUENCE: 473

```
ctagaagata aaccctcccc caaaacacaa attagaatga catttcaagt tccatgtatg     60
```

-continued

```
tcactttcat tctattattt ttacaacttt tagttactta acagatgtct tgttcagcat    120
aaattataat ttattctgtt tttttttagg gaacaactgt tgtagacaac ttgttgtata    180
gtgaggatat tcattacatg cttggtgcat taaggaccct tggactgcgt gtggaagatg    240
acaaaacaac caaacaagca attgttgaag gctgtggggg attgtttccc actagtaagg    300
aatctaaaga tgaaatcaat ttattccttg gaaatgctgg tattgcaatg agatctttga    360
cagcagctgt ggttgctgca ggtggaaatg caaggtctgt ttttttttt tttgttcagc     420 ataatctttg aattgttcct cgtataacta atcacaacag agtacgtgtt cttcttcctg    480
ttataatcta aaaatctcat ccagattagt catcctttct tcttaaaagg aacctttaat    540
tatcaatgta tttatttaat atttaaatta gcttgtcaaa gtctagcata tacatatttt    600
gattatattc tgagaaatgc acctgagggt gttcctcatg atctacttca acctctgtta    660
ttattagatt ttctatcatg attactggtt tgagtctcta agtagaccat cttgatgttc    720
aaaatatttc agctacgtac ttgatggggt gccccgaatg agagagaggc caattgggga    780
tttggttgct ggtcttaagc aacttggtgc agatgttgat tgctttcttg gcacaaactg    840
tccacctgtt cgtgtaaatg ggaagggagg acttcctggc ggaaaggtat ggtttggatt    900
tcatttagaa taaggtggag taactttcct ggatcaaaat tctaatttaa gaagcctccc    960
tgttttcctc tctttagaat aagactaagg gtaggtttag gagttgggtt ttggagagaa   1020
atggaaggga gagcaatttt tttcttcttc taataaatat tctttaatt gatacatttt     1080 ttaagtaaaa gaatataaag atagattagc ataacttaat gttttaatct tttatttatt    1140
tttataaata ttatatacct gtctatttaa aaatcaaata tttgtcctcc attcccttc     1200 ccttcaaaac ctcagttcca aatataccgt agttgaatta tattttggaa ggcctattgg    1260
ttggagactt ttccttttca gagattatcc ctcacccttta ttatagcctt tctattttta   1320
aacttcatat agacgccatt cttggggcgg ccgcgat                             1357
```

<210> SEQ ID NO 474
<211> LENGTH: 30
<212> TYPE: DNA
<213> ORGANISM: Artificial sequence
<220> FEATURE:
<223> OTHER INFORMATION: synthesized sequence- primer, soy1-F1

<400> SEQUENCE: 474

```
ccactagtaa ggaatctaaa gatgaaatca                                       30
```

<210> SEQ ID NO 475
<211> LENGTH: 24
<212> TYPE: DNA
<213> ORGANISM: Artificial sequence
<220> FEATURE:
<223> OTHER INFORMATION: synthesized sequence- primer, soy1-R2

<400> SEQUENCE: 475

```
cctgcagcaa ccacagctgc tgtc                                             24
```

<210> SEQ ID NO 476
<211> LENGTH: 15
<212> TYPE: DNA
<213> ORGANISM: Artificial sequence
<220> FEATURE:
<223> OTHER INFORMATION: synthesized sequence- probe, soy1-T1(FAM-MGB

<400> SEQUENCE: 476
ctgcaatgcg tcctt                                                    15

<210> SEQ ID NO 477
<211> LENGTH: 19
<212> TYPE: DNA
<213> ORGANISM: Artificial sequence
<220> FEATURE:
<223> OTHER INFORMATION: synthesized sequence- primer, cas9-F

<400> SEQUENCE: 477
ccttcttcca ccgccttga                                                19

<210> SEQ ID NO 478
<211> LENGTH: 21
<212> TYPE: DNA
<213> ORGANISM: Artificial sequence
<220> FEATURE:
<223> OTHER INFORMATION: synthesized sequence- primer, Cas9-R

<400> SEQUENCE: 478
tgggtgtctc tcgtgctttt t                                             21

<210> SEQ ID NO 479
<211> LENGTH: 19
<212> TYPE: DNA
<213> ORGANISM: Artificial sequence
<220> FEATURE:
<223> OTHER INFORMATION: synthesized sequence- probe, Cas9-T(FAM-MGB)

<400> SEQUENCE: 479
aatcattcct ggtggagga                                                19

<210> SEQ ID NO 480
<211> LENGTH: 25
<212> TYPE: DNA
<213> ORGANISM: Artificial sequence
<220> FEATURE:
<223> OTHER INFORMATION: synthesized sequence- primer, pINII-99F

<400> SEQUENCE: 480
tgatgcccac attatagtga ttagc                                         25

<210> SEQ ID NO 481
<211> LENGTH: 22
<212> TYPE: DNA
<213> ORGANISM: Artificial sequence
<220> FEATURE:
<223> OTHER INFORMATION: synthesized sequence- primer, pINII-13R

<400> SEQUENCE: 481
catcttctgg attggccaac tt                                            22

<210> SEQ ID NO 482
<211> LENGTH: 17
<212> TYPE: DNA
<213> ORGANISM: Artificial sequence
<220> FEATURE:
<223> OTHER INFORMATION: synthesized sequence- probe, pINII-69T(FAM-MGB)

<400> SEQUENCE: 482
actatgtgtg catcctt                                                  17

<210> SEQ ID NO 483
<211> LENGTH: 23
<212> TYPE: DNA
<213> ORGANISM: Artificial sequence

```
<220> FEATURE:
<223> OTHER INFORMATION: synthesized sequence- primer, SIP-130F

<400> SEQUENCE: 483
ttcaagttgg gcttttcag aag                                              23

<210> SEQ ID NO 484
<211> LENGTH: 22
<212> TYPE: DNA
<213> ORGANISM: Artificial sequence
<220> FEATURE:
<223> OTHER INFORMATION: synthesized sequence- primer, SIP-198R

<400> SEQUENCE: 484
tctccttggt gctctcatca ca                                              22

<210> SEQ ID NO 485
<211> LENGTH: 15
<212> TYPE: DNA
<213> ORGANISM: Artificial sequence
<220> FEATURE:
<223> OTHER INFORMATION: synthesized sequence-  probe, SIP-170T(VIC-MGB)

<400> SEQUENCE: 485
ctgcagcaga accaa                                                      15

<210> SEQ ID NO 486
<211> LENGTH: 24
<212> TYPE: DNA
<213> ORGANISM: Artificial
<220> FEATURE:
<223> OTHER INFORMATION: synthesized sequence- WOL569, Forward_primer

<400> SEQUENCE: 486
ggacccatta ggtgagagcg tggg                                            24

<210> SEQ ID NO 487
<211> LENGTH: 19
<212> TYPE: DNA
<213> ORGANISM: Artificial
<220> FEATURE:
<223> OTHER INFORMATION: synthesized sequence- WOL876, Reverse_primer

<400> SEQUENCE: 487
cagctgctgt caaagatct                                                  19

<210> SEQ ID NO 488
<211> LENGTH: 29
<212> TYPE: DNA
<213> ORGANISM: Artificial
<220> FEATURE:
<223> OTHER INFORMATION: synthesized sequence- WOL570, Reverse_primer

<400> SEQUENCE: 488
tctaataata acagaggttg aagtagatc                                       29

<210> SEQ ID NO 489
<211> LENGTH: 4104
<212> TYPE: DNA
<213> ORGANISM: Glycine max

<400> SEQUENCE: 489
atggacaaaa agtactcaat agggctcgac ataggggacta actccgttgg atgggccgtc    60
atcaccgacg agtacaaggt gccctccaag aagttcaagg tgttgggaaa caccgacagg   120
```

```
cacagcataa agaagaattt gatcggtgcc ctcctcttcg actccggaga gaccgctgag    180
gctaccaggc tcaagaggac cgctagaagg cgctacacca gaaggaagaa cagaatctgc    240
tacctgcagg agatcttctc caacgagatg gccaaggtgg acgactcctt cttccaccgc    300
cttgaggaat cattcctggt ggaggaggat aaaaagcacg agagacaccc aatcttcggg    360
aacatcgtcg acgaggtggc ctaccatgaa aagtacccta ccatctacca cctgaggaag    420
aagctggtcg actctaccga caaggctgac ttgcgcttga tttacctggc tctcgctcac    480
atgataaagt tccgcggaca cttcctcatt gagggagacc tgaacccaga caactccgac    540
gtggacaagc tcttcatcca gctcgttcag acctacaacc agcttttcga ggagaaccca    600
atcaacgcca gtggagttga cgccaaggct atcctctctg ctcgtctgtc aaagtccagg    660
aggcttgaga acttgattgc ccagctgcct ggcgaaaaga gaacggact gttcggaaac     720 ttgatcgctc tctccctggg attgactccc aacttcaagt ccaacttcga cctcgccgag    780
gacgctaagt tgcagttgtc taaagacacc tacgacgatg acctcgacaa cttgctggcc    840
cagataggcg accaatacgc cgatctcttc ctcgccgcta gaaacttgtc cgacgcaatc    900
ctgctgtccg acatcctgag agtcaacact gagattacca agctcctct gtctgcttcc     960 atgattaagc gctacgacga gcaccaccaa gatctgaccc tgctcaaggc cctggtgaga   1020
cagcagctgc ccgagaagta caaggagatc ttttttcgacc agtccaagaa cggctacgcc   1080
ggatacattg acggaggcgc ctcccaggaa gagttctaca gttcatcaa gcccatcctt    1140 gagaagatgg acgtaccga ggagctgttg gtgaagttga acagagagga cctgttgagg    1200
aagcagagaa ccttcgacaa cggaagcatc cctcaccaaa tccacctggg agagctccac   1260
gccatcttga ggaggcagga ggatttctat cccttcctga aggacaaccg cgagaagatt   1320
gagaagatct tgaccttcag aattccttac tacgtcgggc cactcgccag aggaaactct   1380
aggttcgcct ggatgacccg caaatctgaa gagaccatta ctcccctggaa cttcgaggaa  1440 gtcgtggaca agggcgcttc cgctcagtct ttcatcgaga ggatgaccaa cttcgataaa   1500
aatctgccca acgagaaggt gctgcccaag cactccctgt tgtacgagta tttcacagtg   1560
tacaacgagc tcaccaaggt gaagtacgtc acagagggaa tgaggaagcc tgccttcttg   1620
tccggagagc agaagaaggc catcgtcgac ctgctcttca gaccaacag gaaggtgact    1680 gtcaagcagc tgaaggagga ctacttcaag aagatcgagt gcttcgactc cgtcgagatc   1740
tctggtgtcg aggacaggtt caacgcctcc cttgggactt accacgatct gctcaagatt   1800
attaaagaca aggacttcct ggacaacgag gagaacgagg acatccttga ggacatcgtg   1860
ctcaccctga ccttgttcga agacagggaa atgatcgaag agaggctcaa gacctacgcc   1920
cacctcttcg acgacaaggt gatgaaacag ctgaagagac gcagatatac cggctgggga   1980
aggctctccc gcaaattgat caacgggatc agggacaagc agtcagggaa gactatactc   2040
gacttcctga gtccgacgg attcgccaac aggaacttca tgcagctcat tcacgacgac    2100
tccttgacct tcaaggagga catccagaag gctcaggtgt ctggacaggg tgactccttg   2160
catgagcaca ttgctaactt ggccggctct cccgctatta gaagggcat tttgcagacc    2220 gtgaaggtcg ttgacgagct cgtgaaggtg atgggacgcc acaagccaga gaacatcgtt   2280
attgagatgg ctcgcgagaa ccaaactacc cagaaagggc agaagaattc ccgcgagagg   2340
atgaagcgca ttgaggaggg cataaaagag cttggctctc agatcctcaa ggagcacccc   2400
gtcgagaaca ctcagctgca gaacgagaag ctgtacctgt actacctcca aaacggaagg   2460
gacatgtacg tggaccagga gctggacatc aacaggttgt ccgactacga cgtcgaccac   2520
```

```
atcgtgcctc agtccttcct gaaggatgac tccatcgaca ataaagtgct gacacgctcc    2580
gataaaaata gaggcaagtc cgacaacgtc cctccgagg aggtcgtgaa gaagatgaaa     2640
aactactgga cacagctctt gaacgccaag ctcatcaccc agcgtaagtt cgacaacctg    2700
actaaggctg agagaggagg attgtccgag ctcgataagg ccggattcat caagagacag   2760
ctcgtcgaaa cccgccaaat taccaagcac gtggcccaaa ttctggattc ccgcatgaac    2820
accaagtacg atgaaaatga caagctgatc cgcgaggtca aggtgatcac cttgaagtcc    2880
aagctggtct ccgacttccg caaggacttc cagttctaca aggtgaggga gatcaacaac    2940
taccaccacg cacacgacgc ctacctcaac gctgtcgttg gaaccgccct catcaaaaaa    3000
tatcctaagc tggagtctga gttcgtctac ggcgactaca aggtgtacga cgtgaggaag    3060
atgatcgcta agtctgagca ggagatcggc aaggccaccg ccaagtactt cttctactcc    3120
aacatcatga acttcttcaa gaccgagatc actctcgcca acggtgagat caggaagcgc    3180
ccactgatcg agaccaacgg tgagactgga gagatcgtgt gggacaaagg gagggatttc    3240
gctactgtga ggaaggtgct ctccatgcct caggtgaaca tcgtcaagaa gaccgaagtt    3300
cagaccggag gattctccaa ggagtccatc ctccccaaga gaaactccga caagctgatc    3360
gctagaaaga aagactggga ccctaagaag tacggaggct tcgattctcc taccgtggcc    3420
tactctgtgc tggtcgtggc caaggtggag aagggcaagt ccaagaagct gaaatccgtc    3480
aaggagctcc tcgggattac catcatggag aggagttcct tcgagaagaa ccctatcgac    3540
ttcctggagg ccaagggata taagaggtg aagaaggacc tcatcatcaa gctgcccaag    3600
tactccctct tcgagttgga gaacggaagg aagaggatgc tggcttctgc cggagagttg    3660
cagaagggaa atgagctcgc ccttccctcc aagtacgtga acttcctgta cctcgccctct    3720
cactatgaaa agttgaaggg ctctcctgag gacaacgagc agaagcagct cttcgtggag    3780
cagcacaagc actacctgga cgaaattatc gagcagatct ctgagttctc caagcgcgtg    3840
atattggccg acgccaacct cgacaaggtg ctgtccgcct acaacaagca cagggataag    3900
cccattcgcg agcaggctga aacattatc cacctgtttta ccctcacaaa cttgggagcc    3960
cctgctgcct tcaagtactt cgacaccacc attgacagga agagatacac ctccaccaag    4020
gaggtgctcg acgcaacact catccaccaa tccatcaccg gcctctatga aacaaggatt    4080
gacttgtccc agctgggagg cgac                                           4104

<210> SEQ ID NO 490
<211> LENGTH: 23
<212> TYPE: DNA
<213> ORGANISM: Glycine max

<400> SEQUENCE: 490
gtttgtttgt tgttgggtgt ggg                                             23

<210> SEQ ID NO 491
<211> LENGTH: 22
<212> TYPE: DNA
<213> ORGANISM: Glycine max

<400> SEQUENCE: 491
tgttgttggg tgtgggaata gg                                              22

<210> SEQ ID NO 492
<211> LENGTH: 9174
<212> TYPE: DNA
```

<213> ORGANISM: Artificial sequence
<220> FEATURE:
<223> OTHER INFORMATION: synthesized sequence- RTW1199

<400> SEQUENCE: 492

| | | | | | |
|---|---|---|---|---|---|
| ccgggtgtga | tttagtataa | agtgaagtaa | tggtcaaaag | aaaaagtgta | aaacgaagta | 60 |
| cctagtaata | agtaatattg | aacaaaataa | atggtaaagt | gtcagatata | taaaataggc | 120 |
| tttaataaaa | ggaagaaaaa | aaacaaacaa | aaaataggtt | gcaatggggc | agagcagagt | 180 |
| catcatgaag | ctagaaaggc | taccgataga | taaactatag | ttaattaaat | acattaaaaa | 240 |
| atacttggat | ctttctctta | ccctgtttat | attgagacct | gaaacttgag | agagatacac | 300 |
| taatcttgcc | ttgttgtttc | attccctaac | ttacaggact | cagcgcatgt | catgtggtct | 360 |
| cgttccccat | ttaagtccca | caccgtctaa | acttattaaa | ttattaatgt | ttataactag | 420 |
| atgcacaaca | acaaagcttg | tttgtttgtt | gttgggtgtg | ttttagagct | agaaatagca | 480 |
| agttaaaata | aggctagtcc | gttatcaact | tgaaaaagtg | gcaccgagtc | ggtgcttttt | 540 |
| tttgcggccg | caattggatc | gggtttactt | attttgtggg | tatctatact | ttttattgat | 600 |
| ttttaatcag | gctcctgatt | tcttttttatt | tcgattgaat | tcctgaactt | gtattattca | 660 |
| gtagatcgaa | taaattataa | aaagataaaa | tcataaaata | atattttatc | ctatcaatca | 720 |
| tattaaagca | atgaatatgt | aaaattaatc | ttatctttat | tttaaaaaat | catataggtt | 780 |
| tagtattttt | ttaaaaataa | agataggatt | agttttacta | ttcactgctt | attacttta | 840 |
| aaaaaatcat | aaaggtttag | tatttttttta | aaataaatat | aggaatagtt | ttactattca | 900 |
| ctgctttaat | agaaaaatag | tttaaaattt | aagatagttt | taatcccagc | atttgccacg | 960 |
| tttgaacgtg | agccgaaacg | atgtcgttac | attatcttaa | cctagctgaa | acgatgtcgt | 1020 |
| cataatatcg | ccaaatgcca | actggactac | gtcgaaccca | caaatcccac | aaagcgcgtg | 1080 |
| aaatcaaatc | gctcaaacca | caaaaagaa | caacgcgttt | gttacacgct | caatcccacg | 1140 |
| cgagtagagc | acagtaacct | tcaaataagc | gaatggggca | taatcagaaa | tccgaaataa | 1200 |
| acctaggggc | attatcggaa | atgaaagta | gctcactcaa | tataaaaatc | taggaaccct | 1260 |
| agttttcgtt | atcactctgt | gctccctcgc | tctatttctc | agtctctgtg | tttgcggctg | 1320 |
| aggattccga | acgagtgacc | ttcttcgttt | ctcgcaaagg | taacagcctc | tgctcttgtc | 1380 |
| tcttcgattc | gatctatgcc | tgtctcttat | ttacgatgat | gtttcttcgg | ttatgttttt | 1440 |
| ttatttatgc | tttatgctgt | tgatgttcgg | ttgtttgttt | cgctttgttt | ttgtggttca | 1500 |
| gtttttagg | attcttttgg | ttttgaatc | gattaatcgg | aagagatttt | cgagttattt | 1560 |
| ggtgtgttgg | aggtgaatct | tttttttgag | gtcatagatc | tgttgtattt | gtgttataaa | 1620 |
| catgcgactt | tgtatgattt | tttacgaggt | tatgatgttc | tggttgtttt | attatgaatc | 1680 |
| tgttgagaca | gaaccatgat | ttttgttgat | gttcgtttac | actattaaag | gtttgtttta | 1740 |
| acaggattaa | aagttttta | agcatgttga | aggagtcttg | tagatatgta | accgtcgata | 1800 |
| gttttttttgt | gggtttgttc | acatgttatc | aagcttaatc | ttttactatg | tatgcgacca | 1860 |
| tatctggatc | cagcaaaggc | gattttttaa | ttccttgtga | aacttttgta | atatgaagtt | 1920 |
| gaaatttttgt | tattggtaaa | ctataaatgt | gtgaagttgg | agtataccttt | taccttctta | 1980 |
| tttggctttg | tgatagttta | atttatatgt | attttgagtt | ctgacttgta | tttctttgaa | 2040 |
| ttgattctag | tttaagtaat | ccatggcacc | gaagaagaag | cgcaaggtga | tggacaaaaa | 2100 |
| gtactcaata | gggctcgaca | tagggactaa | ctccgttgga | tgggccgtca | tcaccgcacga | 2160 |
| gtacaaggtg | ccctccaaga | agttcaaggt | gttgggaaac | accgacaggc | acagcataaa | 2220 |

```
gaagaatttg atcggtgccc tcctcttcga ctccggagag accgctgagg ctaccaggct    2280
caagaggacc gctagaaggc gctacaccag aaggaagaac agaatctgct acctgcagga    2340
gatcttctcc aacgagatgg ccaaggtgga cgactccttc ttccaccgcc ttgaggaatc    2400
attcctggtg gaggaggata aaagcacga gagacaccca atcttcggga acatcgtcga    2460
cgaggtggcc taccatgaaa agtaccctac catctaccac ctgaggaaga agctggtcga    2520
ctctaccgac aaggctgact tgcgcttgat ttacctggct ctcgctcaca tgataaagtt    2580
ccgcggacac ttcctcattg agggagacct gaacccagac aactccgacg tggacaagct    2640
cttcatccag ctcgttcaga cctacaacca gcttttcgag gagaacccaa tcaacgccag    2700
tggagttgac gccaaggcta tcctctctgc tcgtctgtca aagtccagga ggcttgagaa    2760
cttgattgcc cagctgcctg cgaaaagaa gaacggactg ttcggaaact tgatcgctct    2820
ctccctggga ttgactccca acttcaagtc caacttcgac ctcgccgagg acgctaagtt    2880
gcagttgtct aaagacacct acgacgatga cctcgacaac ttgctggccc agataggcga    2940
ccaatacgcc gatctcttcc tcgccgctaa gaacttgtcc gacgcaatcc tgctgtccga    3000
catcctgaga gtcaacactg agattaccaa agctcctctg tctgcttcca tgattaagcg    3060
ctacgacgag caccaccaag atctgaccct gctcaaggcc ctggtgagac agcagctgcc    3120
cgagaagtac aaggagatct ttttcgacca gtccaagaac ggctacgccg atacattga    3180 cggaggcgcc tcccaggaag agttctacaa gttcatcaag cccatccttg agaagatgga    3240
cggtaccgag gagctgttgg tgaagttgaa cagagaggac ctgttgagga agcagagaac    3300
cttcgacaac ggaagcatcc ctcaccaaat ccacctggga gagctccacg ccatcttgag    3360
gaggcaggag gatttctatc ccttcctgaa ggacaaccgc gagaagattg agaagatctt    3420
gaccttcaga attccttact acgtcgggcc actcgccaga ggaaactcta ggttcgcctg    3480
gatgacccgc aaatctgaag agaccattac tccctggaac ttcgaggaag tcgtggacaa    3540
gggcgcttcc gctcagtctt tcatcgagag gatgaccaac ttcgataaaa atctgcccaa    3600
cgagaaggtg ctgcccaagc actccctgtt gtacgagtat ttcacagtgt acaacgagct    3660
caccaaggtg aagtacgtca cagagggaat gaggaagcct gccttcttgt ccggagagca    3720
gaagaaggcc atcgtcgacc tgctcttcaa gaccaacagg aaggtgactg tcaagcagct    3780
gaaggaggac tacttcaaga agatcgagtg cttcgactcc gtcgagatct ctggtgtcga    3840
ggacaggttc aacgcctccc ttgggactta ccacgatctg ctcaagatta ttaaagacaa    3900
ggacttcctg gacaacgagg agaacgagga catccttgag gacatcgtgc tcaccctgac    3960
cttgttcgaa gacagggaaa tgatcgaaga gaggctcaag acctacgccc acctcttcga    4020
cgacaaggtg atgaaacagc tgaagagacg cagatatacc ggctggggaa ggctctcccg    4080
caaattgatc aacgggatca gggacaagca gtcaggaag actatactcg acttcctgaa    4140
gtccgacgga ttcgccaaca ggaacttcat gcagctcatt cacgacgact ccttgacctt    4200
caaggaggac atccagaagg ctcaggtgtc tggacagggt gactccttgc atgagcacat    4260
tgctaacttg gccggctctc ccgctattaa gaagggcatt ttgcagaccg tgaaggtcgt    4320
tgacgagctc gtgaaggtga tgggacgcca caagccagaa acatcgtta ttgagatggc    4380 tcgcgagaac caaactaccc agaaagggca agaattcc cgcgagagga tgaagcgcat    4440
tgaggagggc ataaaagagc ttggctctca gatcctcaag gagcacccg tcgagaacac    4500 tcagctgcag aacgagaagc tgtacctgta ctacctccaa aacggaaggg acatgtacgt    4560
```

```
ggaccaggag ctggacatca acaggttgtc cgactacgac gtcgaccaca tcgtgcctca    4620
gtccttcctg aaggatgact ccatcgacaa taaagtgctg acacgctccg ataaaaatag    4680
aggcaagtcc gacaacgtcc cctccgagga ggtcgtgaag aagatgaaaa actactggag    4740
acagctcttg aacgccaagc tcatcaccca gcgtaagttc gacaacctga ctaaggctga    4800
gagaggagga ttgtccgagc tcgataaggc cggattcatc aagagacagc tcgtcgaaac    4860
ccgccaaatt accaagcacg tggcccaaat tctggattcc cgcatgaaca ccaagtacga    4920
tgaaaatgac aagctgatcc gcgaggtcaa ggtgatcacc ttgaagtcca agctggtctc    4980
cgacttccgc aaggacttcc agttctacaa ggtgagggag atcaacaact accaccacgc    5040
acacgacgcc tacctcaacg ctgtcgttgg aaccgccctc atcaaaaaat atcctaagct    5100
ggagtctgag ttcgtctacg gcgactacaa ggtgtacgac gtgaggaaga tgatcgctaa    5160
gtctgagcag gagatcggca aggccaccgc caagtacttc ttctactcca acatcatgaa    5220
cttcttcaag accgagatca ctctcgccaa cggtgagatc aggaagcgcc cactgatcga    5280
gaccaacggt gagactggag agatcgtgtg ggacaaaggg agggatttcg ctactgtgag    5340
gaaggtgctc tccatgcctc aggtgaacat cgtcaagaag accgaagttc agaccggagg    5400
attctccaag gagtccatcc tccccaagag aaactccgac aagctgatcg ctagaaagaa    5460
agactgggac cctaagaagt acggaggctt cgattctcct accgtggcct actctgtgct    5520
ggtcgtggcc aaggtggaga gggcaagtc caagaagctg aaatccgtca aggagctcct    5580
cgggattacc atcatggaga ggagttcctt cgagaagaac cctatcgact tcctggaggc    5640
caagggatat aaagaggtga agaaggacct catcatcaag ctgcccaagt actccctctt    5700
cgagttggag aacggaagga agaggatgct ggcttctgcc ggagagttgc agaagggaaa    5760
tgagctcgcc cttccctcca gtacgtgaa cttcctgtac ctcgcctctc actatgaaaa    5820
gttgaagggc tctcctgagg acaacgagca gaagcagctc ttcgtggagc agcacaagca    5880
ctacctggac gaaattatcg agcagatctc tgagttctcc aagcgcgtga tattggccga    5940
cgccaacctc gacaaggtgc tgtccgccta caacaagcac agggataagc ccattcgcga    6000
gcaggctgaa acattatcc acctgtttac cctcacaaac ttgggagccc ctgctgcctt    6060
caagtacttc gacaccacca ttgacaggaa gagatacacc tccaccaagg aggtgctcga    6120
cgcaacactc atccaccaat ccatcaccgg cctctatgaa acaaggattg acttgtccca    6180
gctgggaggc gactctagag ccgatcccaa gaagaagaga aaggtgaaga gaccacggga    6240
ccgccacgat ggcgagctgg gaggccgcaa gcgggcaagg taggttaacc tagacttgtc    6300
catcttctgg attggccaac ttaattaatg tatgaaataa aaggatgcac acatagtgac    6360
atgctaatca ctataatgtg ggcatcaaag ttgtgtgtta tgtgtaatta ctagttatct    6420
gaataaaaga gaaagagatc atccatattt cttatcctaa atgaatgtca cgtgtcttta    6480
taattctttg atgaaccaga tgcatttcat taaccaaatc catatacata taaatattaa    6540
tcatatataa ttaatatcaa ttgggttagc aaaacaaatc tagtctaggt gtgttttgcg    6600
aattcgatat caagcttatc gataccgtcg aggggggggcc cggtaccggc gcgccgttct    6660
atagtgtcac ctaaatcgta tgtgtatgat acataaggtt atgtattaat tgtagccgcg    6720
ttctaacgac aatatgtcca tatggtgcac tctcagtaca atctgctctg atgccgcata    6780
gttaagccag ccccgacacc cgccaacacc cgctgacgcg ccctgacggg cttgtctgct    6840
cccggcatcc gcttacagac aagctgtgac cgtctccggg agctgcatgt gtcagaggtt    6900
ttcaccgtca tcaccgaaac gcgcgagacg aaagggcctc gtgatacgcc tatttttata    6960
```

```
ggttaatgtc atgaccaaaa tcccttaacg tgagttttcg ttccactgag cgtcagaccc    7020
cgtagaaaag atcaaaggat cttcttgaga tcctttttt ctgcgcgtaa tctgctgctt    7080
gcaaacaaaa aaaccaccgc taccagcggt ggtttgtttg ccggatcaag agctaccaac    7140
tcttttccg aaggtaactg gcttcagcag agcgcagata ccaaatactg ttcttctagt    7200
gtagccgtag ttaggccacc acttcaagaa ctctgtagca ccgcctacat acctcgctct    7260
gctaatcctg ttaccagtgg ctgctgccag tggcgataag tcgtgtctta ccgggttgga    7320
ctcaagacga tagttaccgg ataaggcgca gcggtcgggc tgaacggggg gttcgtgcac    7380
acagcccagc ttggagcgaa cgacctacac cgaactgaga tacctacagc gtgagctatg    7440
agaaagcgcc acgcttcccg aagggagaaa ggcggacagg tatccggtaa gcggcagggt    7500
cggaacagga gagcgcacga gggagcttcc agggggaaac gcctggtatc tttatagtcc    7560
tgtcgggttt cgccacctct gacttgagcg tcgatttttg tgatgctcgt caggggggcg    7620
gagcctatgg aaaaacgcca gcaacgcggc ctttttacgg ttcctggcct tttgctggcc    7680
ttttgctcac atgttctttc ctgcgttatc ccctgattct gtggataacc gtattaccgc    7740
ctttgagtga gctgataccg ctcgccgcag ccgaacgacc gagcgcagcg agtcagtgag    7800
cgaggaagcg gaagagcgcc caatacgcaa accgcctctc cccgcgcgtt ggccgattca    7860
ttaatgcagg ttgatcagat ctcgatcccg cgaaattaat acgactcact atagggagac    7920
cacaacggtt tccctctaga ataattttg tttaactta agaaggagat atacccatgg    7980
aaaagcctga actcaccgcg acgtctgtcg agaagtttct gatcgaaaag ttcgacagcg    8040
tctccgacct gatgcagctc tcggagggcg aagaatctcg tgctttcagc ttcgatgtag    8100
gagggcgtgg atatgtcctg cgggtaaata gctgcgccga tggtttctac aaagatcgtt    8160
atgtttatcg gcactttgca tcggccgcgc tcccgattcc ggaagtgctt gacattgggg    8220
aattcagcga gagcctgacc tattgcatct cccgccgtgc acagggtgtc acgttgcaag    8280
acctgcctga aaccgaactg cccgctgttc tgcagccggt cgcggaggct atggatgcga    8340
tcgctgcggc cgatcttagc cagacgagcg ggttcggccc attcggaccg caaggaatcg    8400
gtcaatacac tacatggcgt gatttcatat gcgcgattgc tgatccccat gtgtatcact    8460
ggcaaactgt gatggacgac accgtcagtg cgtccgtcgc gcaggctctc gatgagctga    8520
tgctttgggc cgaggactgc cccgaagtcc ggcacctcgt gcacgcggat ttcggctcca    8580
acaatgtcct gacggacaat ggccgcataa cagcggtcat tgactggagc gaggcgatgt    8640
tcggggattc ccaatacgag gtcgccaaca tcttcttctg gaggccgtgg ttggcttgta    8700
tggagcagca gacgcgctac ttcgagcgga ggcatccgga gcttgcagga tcgccgcggc    8760
tccgggcgta tatgctccgc attggtcttg accaactcta tcagagcttg gttgacggca    8820
atttcgatga tgcagcttgg gcgcagggtc gatgcgacgc aatcgtccga tccggagccg    8880
ggactgtcgg gcgtacacaa atcgcccgca gaagcgcggc cgtctggacc gatggctgtg    8940
tagaagtact cgccgatagt ggaaaccgac gccccagcac tcgtccgagg gcaaaggaat    9000
agtgaggtac agcttggatc gatccggctg ctaacaaagc ccgaaaggaa gctgagttgg    9060
ctgctgccac cgctgagcaa taactagcat aaccccttgg ggcctctaaa cgggtcttga    9120
ggggttttt gctgaaagga ggaactatat ccggatgctc gggcgcgccg gtac          9174
```

<210> SEQ ID NO 493
<211> LENGTH: 9174
<212> TYPE: DNA

<213> ORGANISM: Artificial sequence
<220> FEATURE:
<223> OTHER INFORMATION: synthesized sequence- RTW1200

<400> SEQUENCE: 493

| | | | | | |
|---|---|---|---|---|---|
| ccgggtgtga | tttagtataa | agtgaagtaa | tggtcaaaag | aaaaagtgta | aaacgaagta | 60 |
| cctagtaata | agtaatattg | aacaaaataa | atggtaaagt | gtcagatata | taaaataggc | 120 |
| tttaataaaa | ggaagaaaaa | aaacaaacaa | aaaataggtt | gcaatggggc | agagcagagt | 180 |
| catcatgaag | ctagaaaggc | taccgataga | taaactatag | ttaattaaat | acattaaaaa | 240 |
| atacttggat | ctttctctta | ccctgtttat | attgagacct | gaaacttgag | agagatacac | 300 |
| taatcttgcc | ttgttgtttc | attccctaac | ttacaggact | cagcgcatgt | catgtggtct | 360 |
| cgttccccat | ttaagtccca | caccgtctaa | acttattaaa | ttattaatgt | ttataactag | 420 |
| atgcacaaca | acaaagcttg | tgttgttggg | tgtgggaatg | ttttagagct | agaaatagca | 480 |
| agttaaaata | aggctagtcc | gttatcaact | tgaaaaagtg | gcaccgagtc | ggtgcttttt | 540 |
| tttgcggccg | caattggatc | gggtttactt | attttgtggg | tatctatact | tttattagat | 600 |
| ttttaatcag | gctcctgatt | tcttttttatt | tcgattgaat | tcctgaactt | gtattattca | 660 |
| gtagatcgaa | taaattataa | aaagataaaa | tcataaaata | atattttatc | ctatcaatca | 720 |
| tattaaagca | atgaatatgt | aaaattaatc | ttatctttat | tttaaaaaat | cataggtt | 780 |
| tagtattttt | ttaaaaataa | agataggatt | agttttacta | ttcactgctt | attacttta | 840 |
| aaaaaatcat | aaaggtttag | tatttttttta | aaataaatat | aggaatagtt | ttactattca | 900 |
| ctgctttaat | agaaaaatag | tttaaaattt | aagatagttt | taatcccagc | atttgccacg | 960 |
| tttgaacgtg | agccgaaacg | atgtcgttac | attatcttaa | cctagctgaa | acgatgtcgt | 1020 |
| cataatatcg | ccaaatgcca | actggactac | gtcgaaccca | caaatcccac | aaagcgcgtg | 1080 |
| aaatcaaatc | gctcaaacca | caaaaagaa | caacgcgttt | gttacacgct | caatcccacg | 1140 |
| cgagtagagc | acagtaacct | tcaaataagc | gaatggggca | taatcagaaa | tccgaaataa | 1200 |
| acctaggggc | attatcggaa | atgaaaagta | gctcactcaa | tataaaaatc | taggaaccct | 1260 |
| agttttcgtt | atcactctgt | gctccctcgc | tctatttctc | agtctctgtg | tttgcggctg | 1320 |
| aggattccga | acgagtgacc | ttcttcgttt | ctcgcaaagg | taacagcctc | tgctcttgtc | 1380 |
| tcttcgattc | gatctatgcc | tgtctcttat | ttacgatgat | gtttcttcgg | ttatgttttt | 1440 |
| ttatttatgc | tttatgctgt | tgatgttcgg | ttgtttgttt | cgctttgttt | ttgtggttca | 1500 |
| gttttttagg | attcttttgg | tttttgaatc | gattaatcgg | aagagatttt | cgagttattt | 1560 |
| ggtgtgttgg | aggtgaatct | tttttttgag | gtcatagatc | tgttgtattt | gtgttataaa | 1620 |
| catgcgactt | tgtatgattt | tttacgaggt | tatgatgttc | tggttgtttt | attatgaatc | 1680 |
| tgttgagaca | gaaccatgat | ttttgttgat | gttcgtttac | actattaaag | gtttgtttta | 1740 |
| acaggattaa | aagtttttta | agcatgttga | aggagtcttg | tagatatgta | accgtcgata | 1800 |
| gtttttttgt | gggtttgttc | acatgttatc | aagcttaatc | ttttactatg | tatgcgacca | 1860 |
| tatctggatc | cagcaaaggc | gattttttaa | ttccttgtga | aacttttgta | atatgaagtt | 1920 |
| gaaattttgt | tattggtaaa | ctataaatgt | gtgaagttgg | agtataccctt | taccttctta | 1980 |
| tttggctttg | tgatagttta | atttatatgt | attttgagtt | ctgacttgta | tttctttgaa | 2040 |
| ttgattctag | tttaagtaat | ccatggcacc | gaagaagaag | cgcaaggtga | tggacaaaaa | 2100 |
| gtactcaata | gggctcgaca | tagggactaa | ctccgttgga | tgggccgtca | tcaccgacga | 2160 |
| gtacaaggtg | ccctccaaga | agttcaaggt | gttgggaaac | accgacaggc | acagcataaa | 2220 |

```
gaagaatttg atcggtgccc tcctcttcga ctccggagag accgctgagg ctaccaggct    2280
caagaggacc gctagaaggc gctacaccag aaggaagaac agaatctgct acctgcagga    2340
gatcttctcc aacgagatgg ccaaggtgga cgactccttc ttccaccgcc ttgaggaatc    2400
attcctggtg gaggaggata aaagcacga gagacaccca atcttcggga acatcgtcga     2460
cgaggtggcc taccatgaaa agtaccctac catctaccac ctgaggaaga agctggtcga    2520
ctctaccgac aaggctgact tgcgcttgat ttacctggct ctcgctcaca tgataaagtt    2580
ccgcggacac ttcctcattg agggagacct gaacccagac aactccgacg tggacaagct    2640
cttcatccag ctcgttcaga cctacaacca gcttttcgag gagaacccaa tcaacgccag    2700
tggagttgac gccaaggcta tcctctctgc tcgtctgtca aagtccagga ggcttgagaa    2760
cttgattgcc cagctgcctg cgaaaagaa gaacggactg ttcggaaact tgatcgctct     2820
ctccctggga ttgactccca acttcaagtc caacttcgac ctcgccgagg acgctaagtt    2880
gcagttgtct aaagacacct acgacgatga cctcgacaac ttgctggccc agataggcga    2940
ccaatacgcc gatctcttcc tcgccgctaa gaacttgtcc gacgcaatcc tgctgtccga    3000
catcctgaga gtcaacactg agattaccaa agctcctctg tctgcttcca tgattaagcg    3060
ctacgacgag caccaccaag atctgaccct gctcaaggcc ctggtgagac agcagctgcc    3120
cgagaagtac aaggagatct ttttcgacca gtccaagaac ggctacgccg atacattga    3180 cggaggcgcc tcccaggaag agttctacaa gttcatcaag cccatccttg agaagatgga    3240
cggtaccgag gagctgttgg tgaagttgaa cagagaggac ctgttgagga agcagagaac    3300
cttcgacaac ggaagcatcc ctcaccaaat ccacctggga gagctccacg ccatcttgag    3360
gaggcaggag gatttctatc ccttcctgaa ggacaaccgc gagaagattg agaagatctt    3420
gaccttcaga attccttact acgtcgggcc actcgccaga ggaaactcta ggttcgcctg    3480
gatgacccgc aaatctgaag agaccattac tccctggaac ttcgaggaag tcgtggacaa    3540
gggcgcttcc gctcagtctt tcatcgagag gatgaccaac ttcgataaaa atctgcccaa    3600
cgagaaggtg ctgcccaagc actccctgtt gtacgagtat ttcacagtgt acaacgagct    3660
caccaaggtg aagtacgtca cagagggaat gaggaagcct gccttcttgt ccggagagca    3720
gaagaaggcc atcgtcgacc tgctcttcaa gaccaacagg aaggtgactg tcaagcagct    3780
gaaggaggac tacttcaaga agatcgagtg cttcgactcc gtcgagatct ctggtgtcga    3840
ggacaggttc aacgcctccc ttgggactta ccacgatctg ctcaagatta ttaaagacaa    3900
ggacttcctg gacaacgagg agaacgagga catccttgag gacatcgtgc tcaccctgac    3960
cttgttcgaa gacagggaaa tgatcgaaga gaggctcaag acctacgccc acctcttcga    4020
cgacaaggtg atgaaacagc tgaagagacg cagatatacc ggctggggaa ggctctcccg    4080
caaattgatc aacgggatca gggacaagca gtcaggaag actatactcg acttcctgaa     4140
gtccgacgga ttcgccaaca ggaacttcat gcagctcatt cacgacgact ccttgacctt    4200
caaggaggac atccagaagg ctcaggtgtc tggacagggt gactccttgc atgagcacat    4260
tgctaacttg gccggctctc ccgctattaa gaagggcatt ttgcagaccg tgaaggtcgt    4320
tgacgagctc gtgaaggtga tgggacgcca caagccagaa acatcgtta ttgagatggc     4380 tcgcgagaac caaactaccc agaaagggca gaagaattcc cgcgagagga tgaagcgcat    4440
tgaggagggc ataaaagagc ttggctctca gatcctcaag gagcacccg tcgagaacac     4500 tcagctgcag aacgagaagc tgtacctgta ctacctccaa aacggaaggg acatgtacgt    4560
```

```
ggaccaggag ctggacatca acaggttgtc cgactacgac gtcgaccaca tcgtgcctca      4620
gtccttcctg aaggatgact ccatcgacaa taaagtgctg acacgctccg ataaaaatag      4680
aggcaagtcc gacaacgtcc cctccgagga ggtcgtgaag aagatgaaaa actactggag      4740
acagctcttg aacgccaagc tcatcaccca gcgtaagttc gacaacctga ctaaggctga      4800
gagaggagga ttgtccgagc tcgataaggc cggattcatc aagagacagc tcgtcgaaac      4860
ccgccaaatt accaagcacg tggcccaaat tctggattcc cgcatgaaca ccaagtacga      4920
tgaaaatgac aagctgatcc gcgaggtcaa ggtgatcacc ttgaagtcca agctggtctc      4980
cgacttccgc aaggacttcc agttctacaa ggtgagggag atcaacaact accaccacgc      5040
acacgacgcc tacctcaacg ctgtcgttgg aaccgccctc atcaaaaaat atcctaagct      5100
ggagtctgag ttcgtctacg gcgactacaa ggtgtacgac gtgaggaaga tgatcgctaa      5160
gtctgagcag gagatcggca aggccaccgc caagtacttc ttctactcca acatcatgaa      5220
cttcttcaag accgagatca ctctcgccaa cggtgagatc aggaagcgcc cactgatcga      5280
gaccaacggt gagactggag agatcgtgtg ggacaaaggg agggatttcg ctactgtgag      5340
gaaggtgctc tccatgcctc aggtgaacat cgtcaagaag accgaagttc agaccggagg      5400
attctccaag gagtccatcc tccccaagag aaactccgac aagctgatcg ctagaaagaa      5460
agactgggac cctaagaagt acggaggctt cgattctcct accgtggcct actctgtgct      5520
ggtcgtggcc aaggtggaga agggcaagtc caagaagctg aaatccgtca aggagctcct      5580
cgggattacc atcatggaga ggagttcctt cgagaagaac cctatcgact tcctggaggc      5640
caagggatat aaagaggtga agaaggacct catcatcaag ctgcccaagt actccctctt      5700
cgagttggag aacggaagga gaggatgct ggcttctgcc ggagagttgc agaagggaaa      5760
tgagctcgcc cttccctcca gtacgtgaa cttcctgtac ctcgcctctc actatgaaaa      5820
gttgaagggc tctcctgagg acaacgagca gaagcagctc ttcgtggagc agcacaagca      5880
ctacctggac gaaattatcg agcagatctc tgagttctcc aagcgcgtga tattggccga      5940
cgccaacctc gacaaggtgc tgtccgccta caacaagcac agggataagc ccattcgcga      6000
gcaggctgaa acattatcc acctgtttac cctcacaaac ttgggagccc ctgctgcctt      6060
caagtacttc gacaccacca ttgacaggaa gagatacacc tccaccaagg aggtgctcga      6120
cgcaacactc atccaccaat ccatcaccgg cctctatgaa acaaggattg acttgtccca      6180
gctgggaggc gactctagag ccgatcccaa gaagaagaga aggtgaaga gaccacggga      6240 ccgccacgat ggcgagctgg gaggccgcaa gcgggcaagg taggttaacc tagacttgtc      6300
catcttctgg attggccaac ttaattaatg tatgaaataa aaggatgcac acatagtgac      6360
atgctaatca ctataatgtg ggcatcaaag ttgtgtgtta tgtgtaatta ctagttatct      6420
gaataaaaga gaaagagatc atccatattt cttatcctaa atgaatgtca cgtgtcttta      6480
taattctttg atgaaccaga tgcatttcat taaccaaatc catatacata taaatattaa      6540
tcatatataa ttaatatcaa ttgggttagc aaaacaaatc tagtctaggt gtgttttgcg      6600
aattcgatat caagcttatc gataccgtcg agggggggcc cggtaccggc gcgccgttct      6660
atagtgtcac ctaaatcgta tgtgtatgat acataaggtt atgtattaat tgtagccgcg      6720
ttctaacgac aatatgtcca tatggtgcac tctcagtaca atctgctctg atgccgcata      6780
gttaagccag ccccgacacc cgccaacacc cgctgacgcg ccctgacggg cttgtctgct      6840
cccggcatcc gcttacagac aagctgtgac cgtctccggg agctgcatgt gtcagaggtt      6900
ttcaccgtca tcaccgaaac gcgcgagacg aaagggcctc gtgatacgcc tatttttata      6960
```

```
ggttaatgtc atgaccaaaa tcccttaacg tgagttttcg ttccactgag cgtcagaccc   7020
cgtagaaaag atcaaaggat cttcttgaga tccttttttt ctgcgcgtaa tctgctgctt   7080
gcaaacaaaa aaaccaccgc taccagcggt ggtttgtttg ccggatcaag agctaccaac   7140 tcttttccg  aaggtaactg gcttcagcag agcgcagata ccaaatactg ttcttctagt   7200
gtagccgtag ttaggccacc acttcaagaa ctctgtagca ccgcctacat acctcgctct   7260
gctaatcctg ttaccagtgg ctgctgccag tggcgataag tcgtgtctta ccgggttgga   7320
ctcaagacga tagttaccgg ataaggcgca gcggtcgggc tgaacggggg gttcgtgcac   7380
acagcccagc ttggagcgaa cgacctacac cgaactgaga tacctacagc gtgagctatg   7440
agaaagcgcc acgcttcccg aagggagaaa ggcggacagg tatccggtaa gcggcagggt   7500
cggaacagga gagcgcacga gggagcttcc agggggaaac gcctggtatc tttatagtcc   7560
tgtcgggttt cgccacctct gacttgagcg tcgatttttg tgatgctcgt caggggggcg   7620
gagcctatgg aaaaacgcca gcaacgcggc cttttacgg  ttcctggcct tttgctggcc   7680
ttttgctcac atgttctttc ctgcgttatc ccctgattct gtggataacc gtattaccgc   7740
ctttgagtga gctgataccg ctcgccgcag ccgaacgacc gagcgcagcg agtcagtgag   7800
cgaggaagcg gaagagcgcc caatacgcaa accgcctctc cccgcgcgtt ggccgattca   7860
ttaatgcagg ttgatcagat ctcgatcccg cgaaattaat acgactcact atagggagac   7920
cacaacggtt tccctctaga ataattttg  tttaacttta agaaggagat atacccatgg   7980
aaaagcctga actcaccgcg acgtctgtcg agaagtttct gatcgaaaag ttcgacagcg   8040
tctccgacct gatgcagctc tcggagggcg aagaatctcg tgctttcagc ttcgatgtag   8100
gagggcgtgg atatgtcctg cgggtaaata gctgcgccga tggtttctac aaagatcgtt   8160
atgtttatcg gcactttgca tcggccgcgc tcccgattcc ggaagtgctt gacattgggg   8220
aattcagcga gagcctgacc tattgcatct cccgccgtgc acagggtgtc acgttgcaag   8280
acctgcctga aaccgaactg cccgctgttc tgcagccggt cgcggaggct atggatgcga   8340
tcgctgcggc cgatcttagc cagacgagcg ggttcggccc attcggaccg caaggaatcg   8400
gtcaatacac tacatggcgt gatttcatat gcgcgattgc tgatccccat gtgtatcact   8460
ggcaaactgt gatggacgac accgtcagtg cgtccgtcgc gcaggctctc gatgagctga   8520
tgctttgggc cgaggactgc cccgaagtcc ggcacctcgt gcacgcggat ttcggctcca   8580
acaatgtcct gacggacaat ggccgcataa cagcggtcat tgactggagc gaggcgatgt   8640
tcggggattc ccaatacgag gtcgccaaca tcttcttctg gaggccgtgg ttggcttgta   8700
tggagcagca gacgcgctac ttcgagcgga ggcatccgga gcttgcagga tcgccgcggc   8760 tccggcgta  tatgctccgc attggtcttg accaactcta tcagagcttg gttgacggca   8820
atttcgatga tgcagcttgg gcgcagggtc gatgcgacgc aatcgtccga tccggagccg   8880
ggactgtcgg gcgtacacaa atcgcccgca gaagcgcggc cgtctggacc gatggctgtg   8940
tagaagtact cgccgatagt ggaaaccgac gccccagcac tcgtccgagg gcaaaggaat   9000
agtgaggtac agcttggatc gatccggctg ctaacaaagc ccgaaaggaa gctgagttgg   9060
ctgctgccac cgctgagcaa taactagcat aaccccttgg ggcctctaaa cgggtcttga   9120 ggggttttt  gctgaaagga ggaactatat ccggatgctc gggcgcgccg gtac           9174
```

<210> SEQ ID NO 494
<211> LENGTH: 3175
<212> TYPE: DNA

<213> ORGANISM: Artificial sequence
<220> FEATURE:
<223> OTHER INFORMATION: synthesized sequence- RTW1190A

<400> SEQUENCE: 494

```
cgaattctac aggtcactaa taccatctaa gtagttggtt catagtgact gcatatgtaa      60
aaattatcct tattttaagg aaattaaaaa ttatcatata tatataagtt ttaaattaat     120
tatcttatat atgtaccaaa aagttttaaa gcaattatta taaaaattaa taaatttatc     180
atataaaata atttataatt aaattttaaa ttatcaattc attaaattaa attatttaaa     240
attttttgaat gataatataa taattttatc ctctactaag tcccaacgtt tcctatttta     300
ttccactttt agcaataaat tttgtcataa acacttataa caaaaaagt aagtaaaaaa      360
taaaaaaaag tttttcaata agtataaac taatttgtat aaactttttag aaaaaataaa     420
gttatacatt gataatataa attttttaca taattatccg atcaactcat tatatatgat     480
aaatttattg attttttaaa ataattatct taaaataatt taaacaatga tttgcaatta     540
gatgataata taaaattatt ttacacacta catgtattaa actcaaactt ttatatatta     600
gttttttctaa aaactaattt ttaactcaaa aaaaatgtta cttataattt tcttatcttc     660
ttttttata agtattttt aagaaattta ttgaaacatg accatgcttg ggtcaataat       720
actactctct tagacaccaa acaacccttc ccaaactata atctaatcca aaagccatca     780
ttcattttcc ttggtaggta aagttccaag accttcacca acttttttcac tcaattgttt    840
tggtgtaagc aattcgacat gtgttagtgt tagttggcaa ccaaaaatcc ctttatgtga    900
ctcaatccaa caaccactca caccaccaac ccccataacc atttctcaca ataccctttca    960
tttacacatt atcatcacca aaaataaata aaaaaaacct ctcatttcag agagagagag   1020
agagacttca cagaccaaag tgcagagaac aacaaagttc acaactttaa ggaaaattga   1080
aatggcccaa gtgagcagag tgcacaatct tgctcaaagc actcaaattt ttggccattc   1140
ttccaactcc aacaaactca aatcggtgaa ttcggtttca ttgaggccac gcctttgggg   1200
ggcctcaaaa tctcgcatcc cgatgcataa aaatggaagc tttatgggaa attttaatgt   1260
ggggaaggga aattccggcg tgtttaaggt ttctgcatcg gtcgccgccg cagagaagcc   1320
gtcaacgtcg ccggagatcg tgttggaacc catcaaagac ttctcgggta ccatcacatt   1380
gccagggtcc aagtctctgt ccaatcgaat tttgcttctt gctgctctct ctgaggttcg   1440
tagatttctt ccgtttttt tcttcttct ttattgtttg ttctacatca gcatgatgtt     1500
gatttgattg tgttttctat cgtttcatcg attataaatt ttcataatca gaagattcag   1560
ctttttattaa tgcaagaacg tccttaattg atgatttat aaccgtaaat taggtctaat   1620
tagagttttt ttcataaaga ttttcagatc cgtttacaac aagccttaat tgttgattct   1680
gtagtcgtag attaaggttt ttttcatgaa ctacttcaga tccgttaaac aacagcctta   1740
tttgttgata cttcagtcgt ttttcaagaa attgttcaga tccgttgata aaagccttat   1800
tcgttgattc tgtatggtat ttcaagagat attgctcagg tcctttagca actaccttat   1860
ttgttgattc tgtggccata gattaggatt ttttttcacg aaattgcttc ttgaaattac   1920
gtgatggatt tgattctga tttatcttgt gattgttgac tctacaggga caactgttg    1980
tagacaactt gttgtatagt gaggatattc attacatgct tggtgcatta aggacccttg   2040
gactgcgtgt ggaagatgac aaaacaacca acaagcaat tgttgaaggc tgtgggggat    2100
tgtttcccac tagtaaggaa tctaaagatg aaatcaattt attccttgga aatgctggta   2160
ttgcaatgag atctttgaca gcagctgttg ttgctgcagg tggaaatgca aggtctgttt   2220
```

```
tttttttttt tgttcagcat aatctttgaa ttgttcctcg tataactaat cacaacagag    2280
tacgtgttct tcttcctgtt ataatctaaa aatctcatcc agattagtca tcctttcttc    2340
ttaaaaggaa cctttaatta tcaatgtatt tatttaatat ttaaattagc ttgtcaaagt    2400
ctagcatata catattttga ttatattctg agaaatgcac ctgagggtgt tcctcatgat    2460
ctacttcaac ctctgttatt attagatttt ctatcatgat tactggtttg agtctctaag    2520
tagaccatct tgatgttcaa aatatttcag ctacgtactt gatggggtgc cccgaatgag    2580
agagaggcca attggggatt tggttgctgg tcttaagcaa cttggtgcag atgttgattg    2640 cttttcttggc acaaactgtc cacctgttcg tgtaaatggg aagggaggac ttcctggcgg    2700
aaaggtatgg tttggatttc atttagaata aggtggagta actttcctgg atcaaaattc    2760
taatttaaga agcctccctg ttttcctctc tttagaataa gactaagggt aggtttagga    2820
gttgggtttt ggagagaaat ggaagggaga gcaattttt tcttcttcta ataaatattc    2880
tttaatttga tacatttttt aagtaaaaga atataaagat agattagcat aacttaatgt    2940
tttaatcttt tatttatttt tataaatatt atatacctgt ctatttaaaa atcaaatatt    3000
tgtcctccat tccctttccc ttcaaaacct cagttccaaa tataccgtag ttgaattata    3060
ttttggaagg cctattggtt ggagactttt ccttttcaga gattatccct cacctttatt    3120
atagcctttc tattttaaa cttcatatag acgccattct tggggcggcc gcgat          3175

<210> SEQ ID NO 495
<211> LENGTH: 23
<212> TYPE: DNA
<213> ORGANISM: Artificial sequence
<220> FEATURE:
<223> OTHER INFORMATION: synthesized sequence- primer, soy1-F3

<400> SEQUENCE: 495
gtttgtttgt tgttgggtgt ggg                                              23

<210> SEQ ID NO 496
<211> LENGTH: 25
<212> TYPE: DNA
<213> ORGANISM: Artificial sequence
<220> FEATURE:
<223> OTHER INFORMATION: synthesized sequence- primer, soy1-R3

<400> SEQUENCE: 496
gacatgatgc ttcattttca cagaa                                            25

<210> SEQ ID NO 497
<211> LENGTH: 18
<212> TYPE: DNA
<213> ORGANISM: Artificial sequence
<220> FEATURE:
<223> OTHER INFORMATION: synthesized sequence- probe, soy1-T2(FAM-MGB)

<400> SEQUENCE: 497
tgtgtagagt ggattttg                                                    18

<210> SEQ ID NO 498
<211> LENGTH: 22
<212> TYPE: DNA
<213> ORGANISM: Artificial sequence
<220> FEATURE:
<223> OTHER INFORMATION: synthesized sequence- primer, soy1-F2

<400> SEQUENCE: 498
```

```
tgttgttggg tgtgggaata gg                                              22

<210> SEQ ID NO 499
<211> LENGTH: 31
<212> TYPE: DNA
<213> ORGANISM: Artificial sequence
<220> FEATURE:
<223> OTHER INFORMATION: synthesized sequence- WOL1001, Forward_primer

<400> SEQUENCE: 499
aggtttaatt ttatataatg ttagcataca g                                    31

<210> SEQ ID NO 500
<211> LENGTH: 28
<212> TYPE: DNA
<213> ORGANISM: Artificial sequence
<220> FEATURE:
<223> OTHER INFORMATION: synthesized sequence- 500 WOL1002,
      Reverse_primer

<400> SEQUENCE: 500
atcaacatca tgctgatgta gaacaaac                                        28

<210> SEQ ID NO 501
<211> LENGTH: 29
<212> TYPE: DNA
<213> ORGANISM: Artificial sequence
<220> FEATURE:
<223> OTHER INFORMATION: synthesized sequence- 501 WOL1003,
      Forward_primer

<400> SEQUENCE: 501
attctgattt atcttgtgat tgttgactc                                       29

<210> SEQ ID NO 502
<211> LENGTH: 27
<212> TYPE: DNA
<213> ORGANISM: Artificial sequence
<220> FEATURE:
<223> OTHER INFORMATION: synthesized sequence- WOL1004, Reverse_primer

<400> SEQUENCE: 502
atttactttg gagagaataa ggagggg                                         27

<210> SEQ ID NO 503
<211> LENGTH: 23
<212> TYPE: DNA
<213> ORGANISM: Glycine max

<400> SEQUENCE: 503
gaaacgttgg gacttagtag agg                                             23

<210> SEQ ID NO 504
<211> LENGTH: 23
<212> TYPE: DNA
<213> ORGANISM: Glycine max

<400> SEQUENCE: 504
ggaataaaat aggaaacgtt ggg                                             23

<210> SEQ ID NO 505
<211> LENGTH: 9174
<212> TYPE: DNA
<213> ORGANISM: Artificial sequence
<220> FEATURE:
<223> OTHER INFORMATION: synthesized sequence- RTW1201
```

<400> SEQUENCE: 505

```
ccgggtgtga tttagtataa agtgaagtaa tggtcaaaag aaaaagtgta aaacgaagta      60
cctagtaata agtaatattg aacaaaataa atggtaaagt gtcagatata taaaataggc     120
tttaataaaa ggaagaaaaa aaacaaacaa aaaataggtt gcaatggggc agagcagagt     180
catcatgaag ctagaaaggc taccgataga taaactatag ttaattaaat acattaaaaa     240
atacttggat ctttctctta ccctgtttat attgagacct gaaacttgag agagatacac     300
taatcttgcc ttgttgtttc attccctaac ttacaggact cagcgcatgt catgtggtct     360
cgttccccat ttaagtccca caccgtctaa acttattaaa ttattaatgt ttataactag     420
atgcacaaca acaaagcttg aaacgttggg acttagtagg ttttagagct agaaatagca     480
agttaaaata aggctagtcc gttatcaact tgaaaagtg gcaccgagtc ggtgcttttt      540
tttgcggccg caattggatc gggtttactt attttgtggg tatctatact tttattagat     600
tttaatcag gctcctgatt tctttttatt tcgattgaat tcctgaactt gtattattca      660
gtagatcgaa taaattataa aaagataaaa tcataaaata atatttatc ctatcaatca      720
tattaaagca atgaatatgt aaaattaatc ttatctttat tttaaaaaat catataggtt     780
tagtattttt ttaaaaataa agataggatt agttttacta ttcactgctt attactttta     840
aaaaaatcat aaaggtttag tattttttta aaataaatat aggaatagtt ttactattca     900
ctgctttaat agaaaaatag tttaaaattt aagtagttt taatcccagc atttgccacg      960
tttgaacgtg agccgaaacg atgtcgttac attatcttaa cctagctgaa acgatgtcgt    1020
cataatatcg ccaaatgcca actggactac gtcgaaccca caaatcccac aaagcgcgtg    1080
aaatcaaatc gctcaaacca caaaaaagaa caacgcgttt gttacacgct caatcccacg    1140
cgagtagagc acagtaacct tcaaataagc gaatggggca taatcagaaa tccgaaataa    1200
acctaggggc attatcggaa atgaaaagta gctcactcaa tataaaaatc taggaaccct    1260
agttttcgtt atcactctgt gctccctcgc tctatttctc agtctctgtg tttgcggctg    1320
aggattccga acgagtgacc ttcttcgttt ctcgcaaagg taacagcctc tgctcttgtc    1380
tcttcgattc gatctatgcc tgtctcttat ttacgatgat gtttcttcgg ttatgttttt    1440
ttatttatgc tttatgctgt tgatgttcgg ttgtttgttt cgctttgttt ttgtggttca    1500
gttttttagg attcttttgg tttttgaatc gattaatcgg aagagatttt cgagttattt    1560
ggtgtgttgg aggtgaatct tttttttgag gtcatagatc tgttgtattt gtgttataaa    1620
catgcgactt tgtatgattt tttacgaggt tatgatgttc tggttgtttt attatgaatc    1680
tgttgagaca gaaccatgat ttttgttgat gttcgtttac actattaaag gtttgtttta    1740
acaggattaa agtttttta agcatgttga aggagtcttg tagatatgta accgtcgata    1800
gttttttttgt gggtttgttc acatgttatc aagcttaatc ttttactatg tatgcgacca    1860
tatctggatc cagcaaaggc gattttttaa ttccttgtga aacttttgta atatgaagtt    1920
gaaattttgt tattggtaaa ctataaatgt gtgaagttgg agtatacctt taccttctta    1980
tttggctttg tgatagttta atttatatgt attttgagtt ctgacttgta tttctttgaa    2040
ttgattctag tttaagtaat ccatggcacc gaagaagaag cgcaaggtga tggacaaaaa    2100
gtactcaata gggctcgaca tagggactaa ctccgttgga tgggccgtca tcaccgacga    2160
gtacaaggtg ccctccaaga agttcaaggt gttgggaaac accgacaggc acagcataaa    2220
gaagaatttg atcggtgccc tcctcttcga ctccggagag accgctgagg ctaccaggct    2280
```

-continued

```
caagaggacc gctagaaggc gctacaccag aaggaagaac agaatctgct acctgcagga    2340
gatcttctcc aacgagatgg ccaaggtgga cgactccttc ttccaccgcc ttgaggaatc    2400
attcctggtg gaggaggata aaaagcacga gagacaccca atcttcggga acatcgtcga    2460
cgaggtggcc taccatgaaa agtaccctac catctaccac ctgaggaaga agctggtcga    2520
ctctaccgac aaggctgact tgcgcttgat ttacctggct ctcgctcaca tgataaagtt    2580
ccgcggacac ttcctcattg agggagacct gaacccagac aactccgacg tggacaagct    2640
cttcatccag ctcgttcaga cctacaacca gcttttcgag gagaacccaa tcaacgccag    2700
tggagttgac gccaaggcta tcctctctgc tcgtctgtca aagtccagga ggcttgagaa    2760
cttgattgcc cagctgcctg gcgaaaagaa gaacggactg ttcggaaact tgatcgctct    2820
ctccctggga ttgactccca acttcaagtc caacttcgac ctcgccgagg acgctaagtt    2880
gcagttgtct aaagacacct acgacgatga cctcgacaac ttgctggccc agataggcga    2940
ccaatacgcc gatctcttcc tcgccgctaa gaacttgtcc gacgcaatcc tgctgtccga    3000
catcctgaga gtcaacactg agattaccaa agctcctctg tctgcttcca tgattaagcg    3060
ctacgacgag caccaccaag atctgaccct gctcaaggcc ctggtgagac agcagctgcc    3120
cgagaagtac aaggagatct ttttcgacca gtccaagaac ggctacgccg atacattga    3180 cggaggcgcc tcccaggaag agttctacaa gttcatcaag cccatccttg agaagatgga    3240
cggtaccgag gagctgttgg tgaagttgaa cagagaggac ctgttgagga agcagagaac    3300
cttcgacaac ggaagcatcc ctcaccaaat ccacctggga gagctccacg ccatcttgag    3360
gaggcaggag gatttctatc ccttcctgaa ggacaaccgc gagaagattg agaagatctt    3420
gaccttcaga attccttact acgtcgggcc actcgccaga ggaaactcta ggttcgcctg    3480
gatgacccgc aaatctgaag agaccattac tccctggaac ttcgaggaag tcgtggacaa    3540
gggcgcttcc gctcagtctt tcatcgagag gatgaccaac ttcgataaaa atctgcccaa    3600
cgagaaggtc ctgcccaagc actccctgtt gtacgagtat ttcacagtgt acaacgagct    3660
caccaaggtg aagtacgtca cagagggaat gaggaagcct gccttcttgt ccggagagca    3720
gaagaaggcc atcgtcgacc tgctcttcaa gaccaacagg aaggtgactg tcaagcagct    3780
gaaggaggac tacttcaaga agatcgagtg cttcgactcc gtcgagatct ctggtgtcga    3840
ggacaggttc aacgcctccc ttgggactta ccacgatctg ctcaagatta ttaaagacaa    3900
ggacttcctg gacaacgagg agaacgagga catccttgag gacatcgtgc tcaccctgac    3960
cttgttcgaa gacagggaaa tgatcgaaga gaggctcaag acctacgccc acctcttcga    4020
cgacaaggtg atgaaacagc tgaagagacg cagatatacc ggctggggaa ggctctcccg    4080
caaattgatc aacgggatca gggacaagca gtcaggaagg actatactcg acttcctgaa    4140
gtccgacgga ttcgccaaca ggaacttcat gcagctcatt cacgacgact ccttgacctt    4200
caaggaggac atccagaagg ctcaggtgtc tggacagggt gactccttgc atgagcacat    4260
tgctaacttg gccggctctc ccgctattaa gaagggcatt ttgcagaccg tgaaggtcgt    4320
tgacgagctc gtgaaggtga tgggacgcca caagccagag aacatcgtta ttgagatggc    4380
tcgcgagaac caaactaccc agaaagggca gaagaattcc cgcgagagga tgaagcgcat    4440
tgaggagggc ataaaagagc ttggctctca gatcctcaag gagcaccccg tcgagaacac    4500
tcagctgcag aacgagaagc tgtacctgta ctacctccaa aacggaaggg acatgtacgt    4560
ggaccaggag ctggacatca acaggttgtc cgactacgac gtcgaccaca tcgtgcctca    4620
gtccttcctg aaggatgact ccatcgacaa taaagtgctg acacgctccg ataaaaatag    4680
```

```
aggcaagtcc gacaacgtcc cctccgagga ggtcgtgaag aagatgaaaa actactggag   4740
acagctcttg aacgccaagc tcatcaccca gcgtaagttc gacaacctga ctaaggctga   4800
gagaggagga ttgtccgagc tcgataaggc cggattcatc aagagacagc tcgtcgaaac   4860
ccgccaaatt accaagcacg tggcccaaat tctggattcc cgcatgaaca ccaagtacga   4920
tgaaaatgac aagctgatcc gcgaggtcaa ggtgatcacc ttgaagtcca agctggtctc   4980
cgacttccgc aaggacttcc agttctacaa ggtgagggag atcaacaact accaccacgc   5040
acacgacgcc tacctcaacg ctgtcgttgg aaccgccctc atcaaaaaat atcctaagct   5100
ggagtctgag ttcgtctacg gcgactacaa ggtgtacgac gtgaggaaga tgatcgctaa   5160
gtctgagcag gagatcggca aggccaccgc caagtacttc ttctactcca acatcatgaa   5220
cttcttcaag accagatca ctctcgccaa cggtgagatc aggaagcgcc cactgatcga   5280
gaccaacggt gagactggag agatcgtgtg ggacaaaggg agggatttcg ctactgtgag   5340
gaaggtgctc tccatgcctc aggtgaacat cgtcaagaag accgaagttc agaccggagg   5400
attctccaag gagtccatcc tccccaagag aaactccgac aagctgatcg ctagaaagaa   5460
agactgggac cctaagaagt acggaggctt cgattctcct accgtggcct actctgtgct   5520
ggtcgtggcc aaggtggaga agggcaagtc caagaagctg aaatccgtca aggagctcct   5580
cgggattacc atcatggaga ggagttcctt cgagaagaac cctatcgact tcctggaggc   5640
caagggatat aaagaggtga agaaggacct catcatcaag ctgcccaagt actccctctt   5700
cgagttggag aacggaagga agaggatgct ggcttctgcc ggagagttgc agaagggaaa   5760
tgagctcgcc cttccctcca gtacgtgaa cttcctgtac ctcgcctctc actatgaaaa   5820
gttgaagggc tctcctgagg acaacgagca gaagcagctc ttcgtggagc agcacaagca   5880
ctacctggac gaaattatcg agcagatctc tgagttctcc aagcgcgtga tattggccga   5940
cgccaacctc gacaaggtgc tgtccgccta caacaagcac agggataagc ccattcgcga   6000
gcaggctgaa aacattatcc acctgtttac cctcacaaac ttgggagccc ctgctgcctt   6060
caagtacttc gacaccacca ttgacaggaa gagatacacc tccaccaagg aggtgctcga   6120
cgcaacactc atccaccaat ccatcaccgg cctctatgaa acaaggattg acttgtccca   6180
gctgggaggc gactctagag ccgatcccaa gaagaagaga aggtgaaga gaccacggga   6240 ccgccacgat ggcgagctgg gaggccgcaa gcgggcaagg taggttaacc tagacttgtc   6300
catcttctgg attggccaac ttaattaatg tatgaaataa aaggatgcac acatagtgac   6360
atgctaatca ctataatgtg ggcatcaaag ttgtgtgtta tgtgtaatta ctagttatct   6420
gaataaaaga gaaagagatc atccatattt cttatcctaa atgaatgtca cgtgtcttta   6480
taattctttg atgaaccaga tgcatttcat taaccaaatc catatacata taaatattaa   6540
tcatatataa ttaatatcaa ttgggttagc aaaacaaatc tagtctaggt gtgttttgcg   6600
aattcgatat caagcttatc gataccgtcg aggggggcc cggtaccggc gcgccgttct   6660
atagtgtcac ctaaatcgta tgtgtatgat acataaggtt atgtattaat tgtagccgcg   6720
ttctaacgac aatatgtcca tatggtgcac tctcagtaca atctgctctg atgccgcata   6780
gttaagccag ccccgacacc cgccaacacc cgctgacgcg ccctgacggg cttgtctgct   6840
cccggcatcc gcttacagac aagctgtgac cgtctccggg agctgcatgt gtcagaggtt   6900
ttcaccgtca tcaccgaaac gcgcgagacg aaagggcctc gtgatacgcc tatttttata   6960
ggttaatgtc atgaccaaaa tcccttaacg tgagttttcg ttccactgag cgtcagaccc   7020
```

-continued

```
cgtagaaaag atcaaaggat cttcttgaga tccttttttt ctgcgcgtaa tctgctgctt    7080
gcaaacaaaa aaaccaccgc taccagcggt ggtttgtttg ccggatcaag agctaccaac    7140 tcttttccg aaggtaactg gcttcagcag agcgcagata ccaaatactg ttcttctagt    7200
gtagccgtag ttaggccacc acttcaagaa ctctgtagca ccgcctacat acctcgctct    7260
gctaatcctg ttaccagtgg ctgctgccag tggcgataag tcgtgtctta ccgggttgga    7320
ctcaagacga tagttaccgg ataaggcgca gcggtcgggc tgaacggggg gttcgtgcac    7380
acagcccagc ttggagcgaa cgacctacac cgaactgaga tacctacagc gtgagctatg    7440
agaaagcgcc acgcttcccg aagggagaaa ggcggacagg tatccggtaa gcggcagggt    7500
cggaacagga gagcgcacga gggagcttcc agggggaaac gcctggtatc tttatagtcc    7560
tgtcgggttt cgccacctct gacttgagcg tcgatttttg tgatgctcgt caggggggcg    7620
gagcctatgg aaaaacgcca gcaacgcggc ctttttacgg ttcctggcct tttgctggcc    7680
ttttgctcac atgttctttc ctgcgttatc ccctgattct gtggataacc gtattaccgc    7740
ctttgagtga gctgataccg ctcgccgcag ccgaacgacc gagcgcagcg agtcagtgag    7800
cgaggaagcg gaagagcgcc caatacgcaa accgcctctc ccgcgcgtt ggccgattca    7860 ttaatgcagg ttgatcagat ctcgatcccg cgaaattaat acgactcact ataggagac    7920 cacaacggtt ccctctaga aataattttg tttaacttta agaaggagat atacccatgg    7980
aaaagcctga actcaccgcg acgtctgtcg agaagtttct gatcgaaaag ttcgacagcg    8040
tctccgacct gatgcagctc tcggagggcg aagaatctcg tgctttcagc ttcgatgtag    8100
gagggcgtgg atatgtcctg cgggtaaata gctgcgccga tggtttctac aaagatcgtt    8160
atgtttatcg gcactttgca tcggccgcgc tcccgattcc ggaagtgctt gacattgggg    8220
aattcagcga gagcctgacc tattgcatct cccgccgtgc acagggtgtc acgttgcaag    8280
acctgcctga aaccgaactg cccgctgttc tgcagccggt cgcggaggct atggatgcga    8340
tcgctgcggc cgatcttagc cagacgagcg gttcggccc attcggaccg caaggaatcg    8400
gtcaatacac tacatggcgt gatttcatat gcgcgattgc tgatccccat gtgtatcact    8460
ggcaaactgt gatggacgac accgtcagtg cgtccgtcgc gcaggctctc gatgagctga    8520
tgctttgggc cgaggactgc cccgaagtcc ggcacctcgt gcacgcggat tcggctcca    8580 acaatgtcct gacggacaat ggccgcataa cagcggtcat tgactggagc gaggcgatgt    8640
tcggggattc ccaatacgag gtcgccaaca tcttcttctg gaggccgtgg ttggcttgta    8700
tggagcagca gacgcgctac ttcgagcgga ggcatccgga gcttgcagga tcgccgcggc    8760
tccgggcgta tatgctccgc attggtcttg accaactcta tcagagcttg gttgacggca    8820
atttcgatga tgcagcttgg gcgcagggtc gatgcgacgc aatcgtccga tccggagccg    8880
ggactgtcgg gcgtacacaa atcgcccgca gaagcgcggc cgtctggacc gatggctgtg    8940
tagaagtact cgccgatagt ggaaaccgac gccccagcac tcgtccgagg caaaggaat    9000 agtgaggtac agcttggatc gatccggctg ctaacaaagc ccgaaaggaa gctgagttgg    9060
ctgctgccac cgctgagcaa taactagcat aaccccttgg ggcctctaaa cgggtcttga    9120 ggggttttt gctgaaagga ggaactatat ccggatgctc gggcgcgccg gtac          9174
```

<210> SEQ ID NO 506
<211> LENGTH: 9174
<212> TYPE: DNA
<213> ORGANISM: Artificial sequence
<220> FEATURE:
<223> OTHER INFORMATION: synthesized sequence- RTW1202

<400> SEQUENCE: 506

```
ccgggtgtga tttagtataa agtgaagtaa tggtcaaaag aaaaagtgta aaacgaagta      60
cctagtaata agtaatattg aacaaaataa atggtaaagt gtcagatata taaaataggc     120
tttaataaaa ggaagaaaaa aaacaaacaa aaaataggtt gcaatggggc agagcagagt     180
catcatgaag ctagaaaggc taccgataga taaactatag ttaattaaat acattaaaaa     240
atacttggat ctttctctta ccctgtttat attgagacct gaaacttgag agagatacac     300
taatcttgcc ttgttgtttc attccctaac ttacaggact cagcgcatgt catgtggtct     360
cgttccccat ttaagtccca caccgtctaa acttattaaa ttattaatgt ttataactag     420
atgcacaaca acaaagcttg gaataaaata ggaaacgttg ttttagagct agaaatagca     480
agttaaaata aggctagtcc gttatcaact tgaaaaagtg gcaccgagtc ggtgcttttt     540
tttgcggccg caattggatc gggtttactt attttgtggg tatctatact tttattagat     600
ttttaatcag gctcctgatt tcttttatt tcgattgaat tcctgaactt gtattattca     660
gtagatcgaa taaattataa aaagataaaa tcataaaata atattttatc ctatcaatca     720
tattaaagca atgaatatgt aaaattaatc ttatctttat tttaaaaaat catataggtt     780
tagtatttt ttaaaaataa agataggatt agttttacta ttcactgctt attactttta     840
aaaaaatcat aaaggtttag tatttttta aaataaatat aggaatagtt ttactattca     900
ctgctttaat agaaaaatag tttaaaattt aagtagtttt taatcccagc atttgccacg     960
tttgaacgtg agccgaaacg atgtcgttac attatcttaa cctagctgaa acgatgtcgt    1020
cataatatcg ccaaatgcca actggactac gtcgaaccca caatcccac aaagcgcgtg    1080
aaatcaaatc gctcaaacca caaaaaagaa caacgcgttt gttacacgct caatcccacg    1140
cgagtagagc acagtaacct tcaaataagc gaatggggca taatcagaaa tccgaaataa    1200
acctaggggc attatcggaa atgaaaagta gctcactcaa tataaaaatc taggaaccct    1260
agttttcgtt atcactctgt gctccctcgc tctatttctc agtctctgtg tttgcggctg    1320
aggattccga acgagtgacc ttcttcgttt ctcgcaaagg taacagcctc tgctcttgtc    1380
tcttcgattc gatctatgcc tgtctcttat ttacgatgat gtttcttcgg ttatgttttt    1440
ttatttatgc tttatgctgt tgatgttcgg ttgtttgttt cgctttgttt ttgtggttca    1500
gttttttagg attcttttgg tttttgaatc gattaatcgg aagagatttt cgagttattt    1560
ggtgtgttgg aggtgaatct tttttttgag gtcatagatc tgttgtattt gtgttataaa    1620
catgcgactt tgtatgattt tttacgaggt tatgatgttc tggttgtttt attatgaatc    1680
tgttgagaca gaaccatgat ttttgttgat gttcgtttac actattaaag gtttgtttta    1740
acaggattaa agttttttta agcatgttga aggagtcttg tagatatgta accgtcgata    1800
gttttttgt gggtttgttc acatgttatc aagcttaatc ttttactatg tatgcgacca    1860
tatctggatc cagcaaaggc gatttttaa ttccttgtga aacttttgta atatgaagtt    1920
gaaattttgt tattggtaaa ctataaatgt gtgaagttgg agtataccct taccttctta    1980
tttggctttg tgatagttta atttatatgt attttgagtt ctgacttgta tttctttgaa    2040
ttgattctag tttaagtaat ccatggcacc gaagaagaag cgcaaggtga tggacaaaaa    2100
gtactcaata gggctcgaca tagggactaa ctccgttgga tgggccgtca tcaccgacga    2160
gtacaaggtg ccctccaaga agttcaaggt ggtttgggaaac accgacaggc acagcataaa    2220
gaagaatttg atcggtgccc tcctcttcga ctccggagag accgctgagg ctaccaggct    2280
```

```
caagaggacc gctagaaggc gctacaccag aaggaagaac agaatctgct acctgcagga    2340
gatcttctcc aacgagatgg ccaaggtgga cgactccttc ttccaccgcc ttgaggaatc    2400
attcctggtg gaggaggata aaaagcacga gagacaccca atcttcggga acatcgtcga    2460
cgaggtggcc taccatgaaa agtaccctac catctaccac ctgaggaaga agctggtcga    2520
ctctaccgac aaggctgact tgcgcttgat ttacctggct ctcgctcaca tgataaagtt    2580
ccgcggacac ttcctcattg agggagacct gaacccagac aactccgacg tggacaagct    2640
cttcatccag ctcgttcaga cctacaacca gcttttcgag gagaacccaa tcaacgccag    2700
tggagttgac gccaaggcta tcctctctgc tcgtctgtca aagtccagga ggcttgagaa    2760
cttgattgcc cagctgcctg gcgaaaagaa gaacggactg ttcggaaact tgatcgctct    2820
ctccctggga ttgactccca acttcaagtc caacttcgac ctcgccgagg acgctaagtt    2880
gcagttgtct aaagacacct acgacgatga cctcgacaac ttgctggccc agataggcga    2940
ccaatacgcc gatctcttcc tcgccgctaa gaacttgtcc gacgcaatcc tgctgtccga    3000
catcctgaga gtcaacactg agattaccaa agctcctctg tctgcttcca tgattaagcg    3060
ctacgacgag caccaccaag atctgaccct gctcaaggcc ctggtgagac agcagctgcc    3120
cgagaagtac aaggagatct ttttcgacca gtccaagaac ggctacgccg atacattga    3180 cggaggcgcc tcccaggaag agttctacaa gttcatcaag cccatccttg agaagatgga    3240
cggtaccgag gagctgttgg tgaagttgaa cagagaggac ctgttgagga agcagagaac    3300
cttcgacaac ggaagcatcc ctcaccaaat ccacctggga gagctccacg ccatcttgag    3360
gaggcaggag gatttctatc ccttcctgaa ggacaaccgc gagaagattg agaagatctt    3420
gaccttcaga attccttact acgtcgggcc actcgccaga ggaaactcta ggttcgcctg    3480
gatgacccgc aaatctgaag agaccattac tccctggaac ttcgaggaag tcgtggacaa    3540
gggcgcttcc gctcagtctt tcatcgagag gatgaccaac ttcgataaaa atctgcccaa    3600
cgagaaggtc ctgcccaagc actccctgtt gtacgagtat ttcacagtgt acaacgagct    3660
caccaaggtg aagtacgtca cagagggaat gaggaagcct gccttcttgt ccggagagca    3720
gaagaaggcc atcgtcgacc tgctcttcaa gaccaacagg aaggtgactg tcaagcagct    3780
gaaggaggac tacttcaaga agatcgagtg cttcgactcc gtcgagatct ctggtgtcga    3840
ggacaggttc aacgcctccc ttgggactta ccacgatctg ctcaagatta ttaaagacaa    3900
ggacttcctg gacaacgagg agaacgagga catccttgag gacatcgtgc tcaccctgac    3960
cttgttcgaa gacagggaaa tgatcgaaga gaggctcaag acctacgccc acctcttcga    4020
cgacaaggtg atgaaacagc tgaagagacg cagatatacc ggctggggaa ggctctcccg    4080
caaattgatc aacgggatca gggacaagca gtcaggaag actatactcg acttcctgaa    4140
gtccgacgga ttcgccaaca ggaacttcat gcagctcatt cacgacgact ccttgacctt    4200
caaggaggac atccagaagg ctcaggtgtc tggacagggt gactccttgc atgagcacat    4260
tgctaacttg gccggctctc ccgctattaa gaagggcatt ttgcagaccg tgaaggtcgt    4320
tgacgagctc gtgaaggtga tgggacgcca caagccagag aacatcgtta ttgagatggc    4380
tcgcgagaac caaactaccc agaaagggca gaagaattcc cgcgagagga tgaagcgcat    4440
tgaggagggc ataaaagagc ttggctctca gatcctcaag gagcaccccg tcgagaacac    4500
tcagctgcag aacgagaagc tgtacctgta ctacctccaa aacggaaggg acatgtacgt    4560
ggaccaggag ctggacatca acaggttgtc cgactacgac gtcgaccaca tcgtgcctca    4620
gtccttcctg aaggatgact ccatcgacaa taaagtgctg acacgctccg ataaaaatag    4680
```

```
aggcaagtcc gacaacgtcc cctccgagga ggtcgtgaag aagatgaaaa actactggag   4740
acagctcttg aacgccaagc tcatcaccca gcgtaagttc gacaacctga ctaaggctga   4800
gagaggagga ttgtccgagc tcgataaggc cggattcatc aagagacagc tcgtcgaaac   4860
ccgccaaatt accaagcacg tggcccaaat tctggattcc cgcatgaaca ccaagtacga   4920
tgaaaatgac aagctgatcc gcgaggtcaa ggtgatcacc ttgaagtcca agctggtctc   4980
cgacttccgc aaggacttcc agttctacaa ggtgagggag atcaacaact accaccacgc   5040
acacgacgcc tacctcaacg ctgtcgttgg aaccgccctc atcaaaaaat atcctaagct   5100
ggagtctgag ttcgtctacg gcgactacaa ggtgtacgac gtgaggaaga tgatcgctaa   5160
gtctgagcag gagatcggca aggccaccgc caagtacttc ttctactcca acatcatgaa   5220
cttcttcaag accagatca ctctcgccaa cggtgagatc aggaagcgcc cactgatcga   5280
gaccaacggt gagactggag agatcgtgtg ggacaaaggg agggatttcg ctactgtgag   5340
gaaggtgctc tccatgcctc aggtgaacat cgtcaagaag accgaagttc agaccggagg   5400
attctccaag gagtccatcc tccccaagag aaactccgac aagctgatcg ctagaaagaa   5460
agactgggac cctaagaagt acggaggctt cgattctcct accgtggcct actctgtgct   5520
ggtcgtggcc aaggtggaga agggcaagtc caagaagctg aaatccgtca aggagctcct   5580
cgggattacc atcatggaga ggagttcctt cgagaagaac cctatcgact tcctggaggc   5640
caagggatat aaagaggtga agaaggacct catcatcaag ctgcccaagt actccctctt   5700
cgagttggag aacggaagga agaggatgct ggcttctgcc ggagagttgc agaagggaaa   5760
tgagctcgcc cttccctcca agtacgtgaa cttcctgtac ctcgcctctc actatgaaaa   5820
gttgaagggc tctcctgagg acaacgagca gaagcagctc ttcgtggagc agcacaagca   5880
ctacctggac gaaattatcg agcagatctc tgagttctcc aagcgcgtga tattggccga   5940
cgccaacctc gacaaggtgc tgtccgccta caacaagcac agggataagc ccattcgcga   6000
gcaggctgaa aacattatcc acctgtttac cctcacaaac ttgggagccc ctgctgcctt   6060
caagtacttc gacaccacca ttgacaggaa gagatacacc tccaccaagg aggtgctcga   6120
cgcaacactc atccaccaat ccatcaccgg cctctatgaa acaaggattg acttgtccca   6180
gctgggaggc gactctagag ccgatcccaa gaagaagaga aaggtgaaga gaccacggga   6240
ccgccacgat ggcgagctgg gaggccgcaa gcgggcaagg taggttaacc tagacttgtc   6300
catcttctgg attggccaac ttaattaatg tatgaaataa aaggatgcac acatagtgac   6360
atgctaatca ctataatgtg ggcatcaaag ttgtgtgtta tgtgtaatta ctagttatct   6420
gaataaaaga gaaagagatc atccatattt cttatcctaa atgaatgtca cgtgtcttta   6480
taattctttg atgaaccaga tgcatttcat taaccaaatc catatacata taaatattaa   6540
tcatatataa ttaatatcaa ttgggttagc aaaacaaatc tagtctaggt gtgttttgcg   6600
aattcgatat caagcttatc gataccgtcg agggggggcc cggtaccggc gcgccgttct   6660
atagtgtcac ctaaatcgta tgtgtatgat acataaggtt atgtattaat tgtagccgcg   6720
ttctaacgac aatatgtcca tatggtgcac tctcagtaca atctgctctg atgccgcata   6780
gttaagccag ccccgacacc cgccaacacc cgctgacgcg ccctgacggg cttgtctgct   6840
cccggcatcc gcttacagac aagctgtgac cgtctccggg agctgcatgt gtcagaggtt   6900
ttcaccgtca tcaccgaaac gcgcgagacg aaagggcctc gtgatacgcc tatttttata   6960
ggttaatgtc atgaccaaaa tcccttaacg tgagttttcg ttccactgag cgtcagaccc   7020
```

| | |
|---|---|
| cgtagaaaag atcaaaggat cttcttgaga tccttttttt ctgcgcgtaa tctgctgctt | 7080 |
| gcaaacaaaa aaaccaccgc taccagcggt ggtttgtttg ccggatcaag agctaccaac | 7140 |
| tcttttccg aaggtaactg gcttcagcag agcgcagata ccaaatactg ttcttctagt | 7200 |
| gtagccgtag ttaggccacc acttcaagaa ctctgtagca ccgcctacat acctcgctct | 7260 |
| gctaatcctg ttaccagtgg ctgctgccag tggcgataag tcgtgtctta ccgggttgga | 7320 |
| ctcaagacga tagttaccgg ataaggcgca gcggtcgggc tgaacggggg gttcgtgcac | 7380 |
| acagcccagc ttggagcgaa cgacctacac cgaactgaga tacctacagc gtgagctatg | 7440 |
| agaaagcgcc acgcttcccg aagggagaaa ggcggacagg tatccggtaa gcggcagggt | 7500 |
| cggaacagga gagcgcacga gggagcttcc aggggaaac gcctggtatc tttatagtcc | 7560 |
| tgtcgggttt cgccacctct gacttgagcg tcgattttg tgatgctcgt caggggggcg | 7620 |
| gagcctatgg aaaaacgcca gcaacgcggc cttttacgg ttcctggcct tttgctggcc | 7680 |
| ttttgctcac atgttctttc ctgcgttatc ccctgattct gtggataacc gtattaccgc | 7740 |
| ctttgagtga gctgataccg ctcgccgcag ccgaacgacc gagcgcagcg agtcagtgag | 7800 |
| cgaggaagcg gaagagcgcc caatacgcaa accgcctctc cccgcgcgtt ggccgattca | 7860 |
| ttaatgcagg ttgatcagat ctcgatcccg cgaaattaat acgactcact ataggagac | 7920 |
| cacaacggtt ccctctaga aataattttg tttaacttta agaaggagat atacccatgg | 7980 |
| aaaagcctga actcaccgcg acgtctgtcg agaagtttct gatcgaaaag ttcgacagcg | 8040 |
| tctccgacct gatgcagctc tcggagggcg aagaatctcg tgctttcagc ttcgatgtag | 8100 |
| gagggcgtgg atatgtcctg cgggtaaata gctgcgccga tggtttctac aaagatcgtt | 8160 |
| atgtttatcg gcactttgca tcggccgcgc tcccgattcc ggaagtgctt gacattgggg | 8220 |
| aattcagcga gagcctgacc tattgcatct cccgccgtgc acagggtgtc acgttgcaag | 8280 |
| acctgcctga aaccgaactg cccgctgttc tgcagccggt cgcggaggct atggatgcga | 8340 |
| tcgctgcggc cgatcttagc cagacgagcg ggttcggccc attcggaccg caaggaatcg | 8400 |
| gtcaatacac tacatggcgt gatttcatat gcgcgattgc tgatccccat gtgtatcact | 8460 |
| ggcaaactgt gatggacgac accgtcagtg cgtccgtcgc gcaggctctc gatgagctga | 8520 |
| tgctttgggc cgaggactgc cccgaagtcc ggcacctcgt gcacgcggat ttcggctcca | 8580 |
| acaatgtcct gacggacaat ggccgcataa cagcggtcat tgactggagc gaggcgatgt | 8640 |
| tcggggattc ccaatacgag gtcgccaaca tcttcttctg gaggccgtgg ttggcttgta | 8700 |
| tggagcagca gacgcgctac ttcgagcgga ggcatccgga gcttgcagga tcgccgcggc | 8760 |
| tccgggcgta tatgctccgc attggtcttg accaactcta tcagagcttg gttgacggca | 8820 |
| atttcgatga tgcagcttgg gcgcagggtc gatgcgacgc aatcgtccga tccggagccg | 8880 |
| ggactgtcgg gcgtacacaa atcgcccgca gaagcgcggc cgtctggacc gatggctgtg | 8940 |
| tagaagtact cgccgatagt ggaaaccgac gccccagcac tcgtccgagg caaaggaat | 9000 |
| agtgaggtac agcttggatc gatccggctg ctaacaaagc ccgaaaggaa gctgagttgg | 9060 |
| ctgctgccac cgctgagcaa taactagcat aaccccttgg ggcctctaaa cgggtcttga | 9120 |
| ggggttttt gctgaaagga ggaactatat ccggatgctc gggcgcgccg gtac | 9174 |

<210> SEQ ID NO 507
<211> LENGTH: 6113
<212> TYPE: DNA
<213> ORGANISM: Artificial sequence
<220> FEATURE:
<223> OTHER INFORMATION: synthesized sequence- RTW1192A

<400> SEQUENCE: 507

```
caagtagttc tagtcttaat acaaatgtca aatggcacaa gtgagatttt gaatttctga      60
tgttgtaaaa atctcaggac atgaatacta ttgggaagca attattcata cttcaccaat     120
ccaaactgac ccaaaattct caaatcacat gaaagcaaaa atgcatataa cacgaagaat     180
aagaagaaga ggaactaacc tggggtttcg atgattaaag cgttgttgtt gatgatgaaa     240
acgatgatta tggagagaaa ttgttgttga atggtgaaat tgttatagaa agagaacgaa     300
gatagagaaa aagatatata gatttttcaa ggctcaaacc ctaaaatcac catgagagag     360
aacaaagatt gagaaaccta caaccactat gagagagaat gagcagaaca gaagcgtgag     420
atagagaacg agagttaagg tgcgagagga cacgaagaac aaaaggtgtg agagaaagaa     480
caaaggagcc tacggtgtga gatgagagaa tttgaaattc ttaccatttta ggtggaattt     540
caattctaca attttattct attaaaatta ttttaaaaaa tgatgtcatt ttaaattctt     600
taaaatctca tatccaacaa ctgaattatg atagaggtat ttcaaattca cttaaaaaaa     660
ttatcttatt taaataccc atccaaacat agcgaaatgt tcatgagaag gatcaagtgg      720
tttggaaaca tagtactaat ggtgtttata cagttcatgg aatccttgat agataattta     780
aaggttgctg gaaattggat gaaggtgtgg agattaaata ttcttccaaa ataaagcgt     840
tttatttgga gagtgttgtg tggttgtctc ccctgtaggc aaaagcttcg atgtaaagga     900
gttcaatgtc caataaccta tgctttctat ccctcgatta ttgaaaatga atgacacatt     960
ttatttggtt gaaatcaaga ataagcatg tggcaagcaa cgggtatttg acaattcata    1020
gaacaaaagg tgaatgcagc aaaagaatta atgaactcct tttcgatcta cttggatcac    1080
tacatggaga tattatcaac aaatttgatg ttactttatg gagcagttgg aattcttgga    1140
atgacaagat atgaaatgaa cataccaacc ctcctcttgt ttctgtttcg gtttctatgc    1200
agtatttttgt tgaatggcaa agtgcaaggt aatatgctcc tcaacatcaa ttaacaaatg    1260
ttcatgacat ctcttaccag ctccaacttg gggacgtttg acaaacacca ccgtcaagtt    1320
tccttaaatg caacattaat gttgctcatt tcaaggagga gaatagtttt ggtgtcggca    1380
tgatactcca tcaaggaaga ttcgtcaaag ctcactcacg ttttcgacat gggtcgacat    1440
gggttacctg acccaaaggc tgaggcttag gcttgggttt gcttcaagta ttgatctggg    1500
cccagactat tggtttacat aatatcattt ttgaaaacct aacatctaaa actcaaggtt    1560
gtttagaggt gcgccattcc aaaataagat tatcctattt gtgcatgaat gcgaccaact    1620
atctcctgtt tcagcattat aaagtataaa caacaaactt ctttaatcaa gggactaaaa    1680
gatattggac atacaagcta aaagtgatag aatttgagaa aacaaatatt gacaacaata    1740
ttcaagagga cactaaaaca taattctcaa attttttttg tttatttaaa ataaagtggt    1800
tcattaggta gctccgggtg attgcggtta catcatgtac ggaaaaataa ttctaatcct    1860
tgatttaaat ttgaacttga ctattttattt attctttatt tcattttgta aatcatttta    1920
tgtatctcct ggcaagcaat tttatccacc ttgcaccaac accttcgggt tccataatca    1980
aaccaccta acttcacacc atgctgtaac tcacaccgcc cagcatctcc aatgtgaaag    2040
aagctaaaat ttaataaaca atcatacgaa gcagtgacaa ataccagat ggtattaatg    2100
cttcgataaa attaattgga aagtataaaa tggtagaaaa taataaatta aattaattt    2160
aagtaagata aaaataatt aaaaactaaa atgttaaaat tttaaaaaaa ttattttaaa    2220
taatatttaa aaacattaaa aatcatttta aaaaatttat ttatagaaca attaaataaa    2280
```

-continued

```
tatttcagct aataaaaaac aaaagcttac ctagccttag aagacaactt gtccaacaat    2340
tagatgatac ccattgccct tacgttttct ttaacatcaa ttattgtttt tgtcaacaag    2400
ctatctttta gttttatttt attggtaaaa aatatgtcgc cttcaagttg catcatttaa    2460
cacatctcgt cattagaaaa ataaaactct tccctaaacg attagtagaa aaaatcattc    2520
gataataaat aagaaagaaa aattagaaaa aaataacttc attttaaaaa aatcattaag    2580
gctatatttt ttaaatgact aattttatat agactgtaac taaaagtata caatttatta    2640
tgctatgtat cttaaagaat tacttataaa aatctacgga agaatatctt acaaagtgaa    2700
aaacaaatga gaaagaattt agtgggatga ttatgatttt atttgaaaat tgaaaaaata    2760
attattaaag actttagtgg agtaagaaag ctttcctatt agtcttttct tatccataaa    2820
aaaaaaaaaa aaaatctagc gtgacagctt ttccatagat tttaataatg taaaatactg    2880
gtagcagccg accgttcagg taatggacac tgtggtccta acttgcaacg ggtgcgggcc    2940
caatttaata acgccgtggt aacggataaa gccaagcgtg aagcggtgaa ggtacatctc    3000
tgactccgtc aagattacga aaccgtcaac tacgaaggac tccccgaaat atcatctgtg    3060
tcataaacac caagtcacac catacatggg cacgcgtcac aatatgattg gagaacggtt    3120
ccaccgcata tgctataaaa tgcccccaca cccctcgacc ctaatcgcac ttcaattgca    3180
atcaaattag ttcattctct ttgcgcagtt ccctacctct cctttcaagg ttcgtagatt    3240
tcttccgttt tttttttcttc ttctttattg tttgttctac atcagcatga tgttgatttg    3300
attgtgtttt ctatcgtttc atcgattata aattttcata atcagaagat tcagctttta    3360
ttaatgcaag aacgtcctta attgatgatt ttataaccgt aaattaggtc taattagagt    3420
ttttttcata aagattttca gatccgttta caacaagcct taattgttga ttctgtagtc    3480
gtagattaag gttttttttca tgaactactt cagatccgtt aaacaacagc cttatttgtt    3540
gatacttcag tcgttttttca agaaattgtt cagatccgtt gataaaagcc ttattcgttg    3600
attctgtatg gtatttcaag agatattgct caggtccttt agcaactacc ttatttgttg    3660
attctgtggc catagattag gattttttttt cacgaaattg cttcttgaaa ttacgtgatg    3720
gattttgatt ctgatttatc ttgtgattgt tgactctaca gatggcccaa gtgagcagag    3780
tgcacaatct tgctcaaagc actcaaattt ttggccattc ttccaactcc aacaaactca    3840
aatcggtgaa ttcggtttca ttgaggccac gcctttgggg ggcctcaaaa tctcgcatcc    3900
cgatgcataa aaatggaagc tttatgggaa attttaatgt ggggaaggga aattccggcg    3960
tgtttaaggt ttctgcatcg gtcgccgccg cagagaagcc gtcaacgtcg ccggagatcg    4020
tgttggaacc catcaaagac ttctcgggta ccatcacatt gccagggtcc aagtctctgt    4080
ccaatcgaat tttgcttctt gctgctctct ctgaggtgaa gtttatttat ttatttattt    4140
gtttgtttgt tgttgggtgt gggaatagga gtttgatgtg tagagtggat tttgaatatt    4200
tgatttttttt ttgtattatt ctgtgaaaat gaagcatcat gtcccatgaa agaaatggac    4260
acgaaattaa gtggcttatg atgtgaaatg aggatagaaa tgtgtgtagg gttttttaat    4320
gggtagcaat aagcatattc aatatctgga ttgatttgga cgtttctgta taaggagta    4380
tgctagcaat gtgttaatgt atggcttgct aaaatactcc taaaaatcaa gtgggagtag    4440
tatacatatc tacagcaaat gtattaggtg aggcatttgg cttctctatt gtaaggaaca    4500
aataatatca gttaatgtga aaatcaatgg ttgatattcc aatacattca tgatgtgtta    4560
tttatatgta cctaatattg actgttgttt ttctccgcaa tgaccaagat tatttatttt    4620
atcctctaaa gtgactaatt gagttgctta ctttagagaa gttggaccca ttaggtgaga    4680
```

```
gcgtgggggg aactaatctt gaatatacaa tctgagtctt gattatccaa gtatggttgt    4740
atgaacaatg ttagctctag aagataaacc ctcccccaaa acacaaatta gaatgacatt    4800
tcaagttcca tgtatgtcac tttcattcta ttatttttac aacttttagt tacttaacag    4860
atgtcttgtt cagcataaat tataatttat tctgtttttt tttagggaac aactgttgta    4920
gacaacttgt tgtatagtga ggatattcat tacatgcttg gtgcattaag gacccttgga    4980
ctgcgtgtgg aagatgacaa aacaaccaaa caagcaattg ttgaaggctg tggggattg     5040 tttcccacta gtaaggaatc taaagatgaa atcaatttat tccttggaaa tgctggtatt    5100
gcaatgagat ctttgacagc agctgttgtt gctgcaggtg gaaatgcaag gtctgttttt    5160
tttttttttg ttcagcataa tctttgaatt gttcctcgta taactaatca caacagagta    5220
cgtgttcttc ttcctgttat aatctaaaaa tctcatccag attagtcatc ctttcttctt    5280
aaaaggaacc tttaattatc aatgtattta tttaatattt aaattagctt gtcaaagtct    5340
agcatataca tattttgatt atattctgag aaatgcacct gagggtgttc ctcatgatct    5400
acttcaacct ctgttattat tagattttct atcatgatta ctggtttgag tctctaagta    5460
gaccatcttg atgttcaaaa tatttcagct acgtacttga tggggtgccc cgaatgagag    5520
agaggccaat tggggatttg gttgctggtc ttaagcaact tggtgcagat gttgattgct    5580
ttcttggcac aaactgtcca cctgttcgtg taaatgggaa gggaggactt cctggcggaa    5640
aggtatggtt tggatttcat ttagaataag gtggagtaac tttcctggat caaaattcta    5700
atttaagaag cctccctgtt ttcctctctt tagaataaga ctaagggtag gtttaggagt    5760
tgggttttgg agagaaatgg aagggagagc aattttttc ttcttctaat aaatattctt     5820
taatttgata catttttaa gtaaaagaat ataagatag attagcataa cttaatgttt      5880
taatctttta tttattttta taaatattat ataccgtgtct atttaaaaat caaatatttg   5940
tcctccattc cctttccctt caaaacctca gttccaaata taccgtagtt gaattatatt    6000
ttggaaggcc tattggttgg agacttttcc ttttcagaga ttatccctca cctttattat    6060
agcctttcta ttttttaaact tcatatagac gccattcttg gggcggccgc gat          6113
```

<210> SEQ ID NO 508
<211> LENGTH: 32
<212> TYPE: DNA
<213> ORGANISM: Artificial sequence
<220> FEATURE:
<223> OTHER INFORMATION: synthesized sequence- primer, soy1-F4

<400> SEQUENCE: 508
tcaataatac tactctctta gacaccaaac aa                                  32

<210> SEQ ID NO 509
<211> LENGTH: 23
<212> TYPE: DNA
<213> ORGANISM: Artificial sequence
<220> FEATURE:
<223> OTHER INFORMATION: synthesized sequence- primer, soy1-R4

<400> SEQUENCE: 509
caaggaaaat gaatgatggc ttt                                            23

<210> SEQ ID NO 510
<211> LENGTH: 18
<212> TYPE: DNA
<213> ORGANISM: Artificial sequence
<220> FEATURE:

<223> OTHER INFORMATION: synthesized sequence- probe, soy1-T3(FAM-MGB)

<400> SEQUENCE: 510
ccttcccaaa ctataatc                                                         18

<210> SEQ ID NO 511
<211> LENGTH: 27
<212> TYPE: DNA
<213> ORGANISM: Artificial sequence
<220> FEATURE:
<223> OTHER INFORMATION: synthesized sequence- WOL1005, Forward_primer

<400> SEQUENCE: 511
aaatgttatc agaggaacat gagctgc                                               27

<210> SEQ ID NO 512
<211> LENGTH: 28
<212> TYPE: DNA
<213> ORGANISM: Artificial sequence
<220> FEATURE:
<223> OTHER INFORMATION: synthesized sequence- WOL1006, Reverse_primer

<400> SEQUENCE: 512
attatttttc cgtacatgat gtaaccgc                                              28

<210> SEQ ID NO 513
<211> LENGTH: 438
<212> TYPE: DNA
<213> ORGANISM: Cauliflower mosaic virus

<400> SEQUENCE: 513
cccatggagt caaagattca atagaggac ctaacagaac tcgccgtaaa gactggcgaa            60
cagttcatac agagtctctt acgactcaat gacaagaaga aaatcttcgt caacatggtg         120
gagcacgaca cgcttgtcta ctccaaaaat atcaagata cagtctcaga agaccaaagg          180
gcaattgaga cttttcaaca aagggtaata tccggaaacc tcctcggatt ccattgccca         240
gctatctgtc actttattgt gaagatagtg gaaaggaag gtggctccta caaatgccat          300
cattgcgata aaggaaaggc catcgttgaa gatgcctctg ccgacagtgg tcccaaagat         360 ggaccccccac ccacgaggag catcgtggaa aagaagacg ttccaaccac gtcttcaaag        420
caagtggatt gatgtgat                                                       438

<210> SEQ ID NO 514
<211> LENGTH: 19
<212> TYPE: DNA
<213> ORGANISM: Cauliflower mosaic virus

<400> SEQUENCE: 514
gtctcagaag accaaaggg                                                        19

<210> SEQ ID NO 515
<211> LENGTH: 25
<212> TYPE: DNA
<213> ORGANISM: Cauliflower mosaic virus

<400> SEQUENCE: 515
tgccatcatt gcgataaagg aaagg                                                 25

<210> SEQ ID NO 516
<211> LENGTH: 20
<212> TYPE: DNA
<213> ORGANISM: Cauliflower mosaic virus

<400> SEQUENCE: 516
gatgcctctg ccgacagtgg                                          20

<210> SEQ ID NO 517
<211> LENGTH: 3708
<212> TYPE: DNA
<213> ORGANISM: Zea mays

<400> SEQUENCE: 517

```
ctgcagccca tcaaggagat ctccggcacc gtcaagctgc ggggtccaa gtcgctttcc     60 aacaggatcc tcctgctcgc cgccctgtcc gaggtgagcg attttggtgc ttgctgcgct   120
gccctgtctc actgctacct aaatgttttg cctgtcgaat accatggatt ctcggtgtaa   180
tccatctcac gatcagatgc accgcatgtc gcatgcctag ctctctctaa tttgtctagt   240
agtttgtata cggattaaga ttgataaatc ggtaccgcaa aagctaggtg taaataaaca   300
ctacaaaatt ggatgttccc ctatcggcct gtactcggct actcgttctt gtgatggcat   360
gttatttctt cttggtgttt ggtgaactcc cttatgaaat ttgggcgcaa agaaatcgcc   420
ctcaagggtt gatcttatgc catcgtcatg ataaacagtg aagcacggat gatcctttac   480
gttgttttta acaaactttg tcagaaaact agcaatgtta acttcttaat gatgatttca   540
caacaaaaaa ggtaaccttg ctactaacat aacaaaagac ttgttgctta ttaattatat   600
gtttttttaa tctttgatca ggggacaaca gtggttgata acctgttgaa cagtgaggat   660
gtccactaca tgctcggggc cttgaggact cttggtctct ctgtcgaagc ggacaaagct   720
gccaaaagag ctgtagttgt tggctgtggt ggaaagttcc cagttgagga tgctagagag   780
gaagtgcagc tcttcttggg gaatgctgga tcgcaatgc ggtcattgac agcagctgtt   840
actgctgctg gtggaaatgc aacgtatgtt tcctctctct ctctacaata cttgttggag   900
ttagtatgaa acccatgtgt atgtctagtg gcttatggtg tattggtttt tgaacttcag   960
ttacgtgctt gatggagtac caagaatgag ggagagaccc attggcgact tggttgtcgg  1020
attgaagcag cttggtgcag atgttgattg tttccttggc actgactgcc cacctgttcg  1080
tgtcaatgga atcggagggc tacctggtgg caaggttagt tactaagggc acatgttac   1140 attcttctgt aaatggtaca actattgtcg agcttttgca tttgtaagga aaacattgat  1200
tgatctgaat ttgatgctac accacaaaat atctacaaat ggtcatccct aactagcaaa  1260
ccatgtctcc attaagctca atgaagtaat acttggcatg tgtttatcaa cttaatttcc  1320
atcttctggg gtattgcctg tttctagtc taatagcatt tgttttaga attagctctt  1380 acaactgtta tgttctacag gtcaagctgt ctggctccat cagcagtcag tacttgagtg  1440
ccttgctgat ggctgctcct ttggctcttg ggatgtgga gattgaaatc attgataaat  1500
taatctccat tccctacgtc gaaatgacat tgagattgat ggagcgtttt ggtgtgaaag  1560
cagagcattc tgatagctgg gacagattct acattaaggg aggtcaaaaa tacaagtaag  1620
ctctgtaatg tatttcacta ctttgatgcc aatgtttcag ttttcagttt tccaaacagt  1680
cgcatcaata tttgaataga tgcactgtag aaaaaaatca ttgcagggaa aaactagtac  1740
tgagtatttt gactgtaaat tatttaacca gtcggaatat agtcagtcta ttggagtcaa  1800
gagcgtgaac cgaaatagcc agttaattat cccattatac agaggacaac catgtatact  1860
attgaaactt ggtttaagag aatctaggta gctggactcg tagctgcttg gcatggatac  1920
cttcttatct ttaggaaaag acacttgatt tttttctgt ggccctctat gatgtgtgaa  1980
```

```
cctgcttctc tattgctttta gaaggatata tctatgtcgt tatgcaacat gcttccctta    2040
gtcatttgta ctgaaatcag tttcataagt tcgttagtgg ttccctaaac gaaaccttgt    2100
ttttctttgc aatcaacagg tcccctaaaa atgcctatgt tgaaggtgat gcctcaagcg    2160
caagctattt cttggctggt gctgcaatta ctggagggac tgtgactgtg aaggttgtg     2220 gcaccaccag tttgcaggta agatttctt ggctggtgct acgataactg cttttgtctt    2280
tttggtttca gcattgttct cagagtcact aaataacatt atcatctgca aacgtcaaat    2340
agacatactt aggtgaatgg atattcatgt aaccgtttcc ttacaaattt gctgaaacct    2400
cagggtgatg tgaagtttgc tgaggtactg gagatgatgg gagcgaaggt tacatggacc    2460
gagactagcg taactgttac tggcccaccg cgggagccat ttgggaggaa cacctcaag    2520 gcgattgatg tcaacatgaa caagatgcct gatgtcgcca tgactcttgc tgtggttgcc    2580
ctctttgccg atggcccgac agccatcaga gacggtaaaa cattctcagc cctacaacca    2640
tgcctcttct acatcactac ttgacaagac taaaaactat tggctcgttg gcagtggctt    2700
cctggagagt aaaggagacc gagaggatgg ttgcgatccg gacggagcta accaaggtaa    2760
ggctacatac ttcacatgtc tcacgtcgtc tttccatagc tcgctgcctc ttagcggctt    2820
gcctgcggtc gctccatcct cggttgctgt ctgtgttttc cacagctggg agcatctgtt    2880
gaggaagggc cggactactg catcatcacg ccgccggaga agctgaacgt gacggcgatc    2940
gacacgtacg acgaccacag gatggccatg gccttctccc ttgccgcctg tgccgaggtc    3000
cccgtgacca tccgggaccc tgggtgcacc cggaagacct tccccgacta cttcgatgtg    3060
ctgagcactt tcgtcaagaa ttaataaagc gtgcgatact accacgcagc ttgattgaag    3120
tgataggctt gtgctgagga aatacatttc ttttgttctg ttttttctct ttcacgggat    3180
taagttttga gtctgtaacg ttagttgttt gtagcaagtt tctatttcgg atcttaagtt    3240
tgtgcactgt aagccaaatt tcatttcaag agtggttcgt tggaataata agaataataa    3300
attacgtttc agtggctgtc aagcctgctg ctacgttta ggagatggca ttagacattc    3360
atcatcaaca acaataaaac cttttagcct caaacaataa tagtgaagtt attttttagt    3420
cctaaacaag ttgcattagg atatagttaa aacacaaaag aagctaaagt tagggtttag    3480
acatgtggat attgttttcc atgtatagta tgttctttct ttgagtctca tttaactacc    3540
tctacacata ccaactttag ttttttttct acctcttcat gttactatgg tgccttctta    3600
tcccactgag cattggtata tttagaggtt tttgttgaac atgcctaaat catctcaatc    3660
aacgatggac aatcttttct tcgattgagc tgaggtacgt catctaga                 3708
```

<210> SEQ ID NO 518
<211> LENGTH: 3714
<212> TYPE: DNA
<213> ORGANISM: Zea mays

<400> SEQUENCE: 518

```
ctgcagccca tcaaggagat ctccggcacc gtcaagctgc cggggtccaa gtcgctttcc     60
aacaggatcc tcctgctcgc cgccctgtcc gaggtgagcg attttggtgc ttgctgcgct    120
gccctgtctc actgctacct aaatgttttg cctgtcgaat accatggatt tcggtgtaa    180 tccatatctg cacgatcaga tatgcaccgc atgtcgcata tctgagctct ctctaatttg    240
tctagtagtt tgtatacgga ttaagattga taaatcggta ccgcaaaagc taggtgtaaa    300
taaacactac aaaattggat gttccccta t cggcctgtac tcggctactc gttcttgtga    360
tggcatgtta tttcttcttg gtgtttggtg aactccctta tgaaatttgg gcgcaaagaa    420
```

```
atcgccctca agggttgatc ttatgccatc gtcatgataa acagtgaagc acgatgatc      480 ctttacgttg ttttaacaa actttgtcag aaaactagca atgttaactt cttaatgatg      540
atttcacaac aaaaaaggta accttgctac taacataaca aaagacttgt tgcttattaa     600
ttatatgttt ttttaatctt tgatcagggg acaacagtgg ttgataacct gttgaacagt    660
gaggatgtcc actacatgct cggggccttg aggactcttg gtctctctgt cgaagcggac    720
aaagctgcca aaagagctgt agttgttggc tgtggtggaa agttcccagt tgaggatgct   780
aaagaggaag tgcagctctt cttggggaat gctggaatcg caatgcggtc attgacagca    840
gctgttactg ctgctggtgg aaatgcaacg tatgtttcct ctctctctct acaatacttg    900
ttggagttag tatgaaaccc atgtgtatgt ctagtggctt atggtgtatt ggttttgaa    960 cttcagttac gtgcttgatg gagtaccaag aatgagggag agacccattg gcgacttggt   1020
tgtcggattg aagcagcttg gtgcagatgt tgattgtttc cttggcactg actgcccacc    1080
tgttcgtgtc aatggaatcg gagggctacc tggtggcaag gttagttact aagggccaca  1140
tgttacattc ttctgtaaat ggtacaacta ttgtcgagct tttgcatttg taaggaaaac    1200
attgattgat ctgaatttga tgctacacca caaaatatct acaaatggtc atccctaact   1260
agcaaaccat gtctccatta agctcaatga agtaatactt ggcatgtgtt tatcaactta    1320
atttccatct tctggggtat tgcctgtttt ctagtctaat agcatttgtt tttagaatta    1380
gctcttacaa ctgttatgtt ctacaggtca agctgtctgg ctccatcagc agtcagtact    1440
tgagtgcctt gctgatggct gctccttttgg ctcttgggga tgtggagatt gaaatcattg   1500
ataaattaat ctccattccc tacgtcgaaa tgacattgag attgatggag cgttttggtg    1560
tgaaagcaga gcattctgat agctgggaca gattctacat taagggaggt caaaaatac a  1620 agtaagctct gtaatgtatt tcactacttt gatgccaatg tttcagtttt cagttttcca    1680
aacagtcgca tcaatatttg aatagatgca ctgtagaaaa aaatcattgc agggaaaaac    1740
tagtactgag tattttgact gtaaattatt taaccagtcg gaatatagtc agtctattgg    1800
agtcaagagc gtgaaccgaa atagccagtt aattatccca ttatacagag gacaaccatg   1860
tatactattg aaacttggtt taagagaatc taggtagctg gactcgtagc tgcttggcat    1920
ggataccttc ttatctttag gaaaagacac ttgatttttt ttctgtggcc ctctatgatg   1980
tgtgaacctg cttctctatt gctttagaag gatatatcta tgtcgttatg caacatgctt   2040
cccttagtca tttgtactga aatcagtttc ataagttcgt tagtggttcc ctaaacgaaa    2100
ccttgttttt ctttgcaatc aacaggtccc ctaaaaatgc ctatgttgaa ggtgatgcct    2160
caagcgcaag ctatttcttg gctggtgctg caattactgg agggactgtg actgtggaag   2220
gttgtggcac caccagtttg caggtaaaga tttcttggct ggtgctacga taactgcttt    2280 tgtcttttg gtttcagcat tgttctcaga gtcactaaat aacattatca tctgcaaacg    2340
tcaaatagac atacttaggt gaatggatat tcatgtaacc gtttccttac aaatttgctg    2400
aaacctcagg gtgatgtgaa gtttgctgag gtactggaga tgatgggagc gaaggttaca   2460
tggaccgaga ctagcgtaac tgttactggc ccaccgcggg agccatttgg gaggaaacac    2520
ctcaaggcga ttgatgtcaa catgaacaag atgcctgatg tcgccatgac tcttgctgtg    2580
gttgccctct tgccgatggg cccgacagcc atcagagacg gtaaaacatt ctcagcccta   2640
caaccatgcc tcttctacat cactacttga caagactaaa aactattggc tcgttggcag   2700
tggcttcctg gagagtaaag gagaccgaga ggatggttgc gatccggacg gagctaacca   2760
```

| | |
|---|---|
| aggtaaggct acatacttca catgtctcac gtcgtctttc catagctcgc tgcctcttag | 2820 |
| cggcttgcct gcggtcgctc catcctcggt tgctgtctgt gttttccaca gctgggagca | 2880 |
| tctgttgagg aagggccgga ctactgcatc atcacgccgc cggagaagct gaacgtgacg | 2940 |
| gcgatcgaca cgtacgacga ccacaggatg gccatggcct tctcccttgc cgcctgtgcc | 3000 |
| gaggtccccg tgaccatccg ggaccctggg tgcacccgga agaccttccc cgactacttc | 3060 |
| gatgtgctga gcactttcgt caagaattaa taaagcgtgc gatactacca cgcagcttga | 3120 |
| ttgaagtgat aggcttgtgc tgaggaaata catttctttt gttctgtttt ttctctttca | 3180 |
| cgggattaag ttttgagtct gtaacgttag ttgtttgtag caagtttcta tttcggatct | 3240 |
| taagtttgtg cactgtaagc caaatttcat ttcaagagtg gttcgttgga ataataagaa | 3300 |
| taataaatta cgtttcagtg gctgtcaagc ctgctgctac gttttaggag atggcattag | 3360 |
| acattcatca tcaacaacaa taaaaccttt tagcctcaaa caataatagt gaagttattt | 3420 |
| tttagtccta aacaagttgc attaggatat agttaaaaca caaagaagc taaagttagg | 3480 |
| gtttagacat gtggatattg ttttccatgt atagtatgtt ctttctttga gtctcattta | 3540 |
| actacctcta cacataccaa ctttagtttt ttttctacct cttcatgtta ctatggtgcc | 3600 |
| ttcttatccc actgagcatt ggtatattta gaggttttg ttgaacatgc ctaaatcatc | 3660 |
| tcaatcaacg atggacaatc ttttcttcga ttgagctgag gtacgtcatc taga | 3714 |

<210> SEQ ID NO 519
<211> LENGTH: 3708
<212> TYPE: DNA
<213> ORGANISM: Zea mays

<400> SEQUENCE: 519

| | |
|---|---|
| ctgcagccca tcaaggagat ctccggcacc gtcaagctgc cggggtccaa gtcgctttcc | 60 |
| aacaggatcc tcctgctcgc cgccctgtcc gaggtgagcg atttttggtgc ttgctgcgct | 120 |
| gccctgtctc actgctacct aaatgttttg cctgtcgaat accatggatt tcggtgtaa | 180 |
| tccatctcac gatcagatgc accgcatgtc gcatgcctag ctctctctaa tttgtctagt | 240 |
| agtttgtata cggattaaga ttgataaatc ggtaccgcaa aagctaggtg taaataaaca | 300 |
| ctacaaaatt ggatgttccc ctatcggcct gtactcggct actcgttctt gtgatggcat | 360 |
| gttatttctt cttggtgttt ggtgaactcc cttatgaaat ttgggcgcaa agaaatcgcc | 420 |
| ctcaagggtt gatcttatgc catcgtcatg ataaacagtg aagcacggat gatcctttac | 480 |
| gttgttttta acaaactttg tcagaaaact agcaatgtta acttcttaat gatgatttca | 540 |
| caacaaaaaa ggtaaccttg ctactaacat aacaaaagac ttgttgctta ttaattatat | 600 |
| gttttttttaa tctttgatca ggggacaaca gtggttgata acctgttgaa cagtgaggat | 660 |
| gtccactaca tgctcggggc cttgaggact cttggtctct ctgtcgaagc ggacaaagct | 720 |
| gccaaaagag ctgtagttgt tggctgtggt ggaaagttcc cagttgagga tgctagaaag | 780 |
| gaagtgcagc tcttcttggg gaatgctgga atcgcaatgc ggtcattgac agcagctgtt | 840 |
| actgctgctg gtggaaatgc aacgtatgtt tcctctctct ctctacaata cttgttggag | 900 |
| ttagtatgaa acccatgtgt atgtctagtg gcttatggtg tattggtttt tgaacttcag | 960 |
| gtacgtgctt gatggagtac caagaatgag ggagagaccc attggcgact tggttgtcgg | 1020 |
| attgaagcag cttggtgcag atgttgattg tttccttggc actgactgcc cacctgttcg | 1080 |
| tgtcaatgga atcggagggc tacctggtgg caaggttagt tactaagggc cacatgttac | 1140 |
| attcttctgt aaatggtaca actattgtcg agcttttgca tttgtaagga aaacattgat | 1200 |

```
tgatctgaat tgatgctac accacaaaat atctacaaat ggtcatccct aactagcaaa    1260
ccatgtctcc attaagctca atgaagtaat acttggcatg tgtttatcaa cttaatttcc    1320
atcttctggg gtattgcctg ttttctagtc taatagcatt tgtttttaga attagctctt    1380
acaactgtta tgttctacag gtcaagctgt ctggctccat cagcagtcag tacttgagtg    1440
ccttgctgat ggctgctcct ttggctcttg gggatgtgga gattgaaatc attgataaat    1500
taatctccat tccctacgtc gaaatgacat tgagattgat ggagcgtttt ggtgtgaaag    1560
cagagcattc tgatagctgg gacagattct acattaaggg aggtcaaaaa tacaagtaag    1620
ctctgtaatg tatttcacta ctttgatgcc aatgtttcag ttttcagttt tccaaacagt    1680
cgcatcaata tttgaataga tgcactgtag aaaaaaatca ttgcagggaa aaactagtac    1740
tgagtatttt gactgtaaat tatttaacca gtcggaatat agtcagtcta ttggagtcaa    1800
gagcgtgaac cgaaatagcc agttaattat cccattatac agaggacaac catgtatact    1860
attgaaactt ggtttaagag aatctaggta gctggactcg tagctgcttg gcatggatac    1920
cttcttatct ttaggaaaag acacttgatt ttttttctgt ggccctctat gatgtgtgaa    1980
cctgcttctc tattgcttta gaaggatata tctatgtcgt tatgcaacat gcttccctta    2040
gtcatttgta ctgaaatcag tttcataagt tcgttagtgg ttccctaaac gaaaccttgt    2100 tttctttgc aatcaacagg tcccctaaaa atgcctatgt tgaaggtgat gcctcaagcg    2160
caagctattt cttggctggt gctgcaatta ctggagggac tgtgactgtg aaggttgtg    2220 gcaccaccag tttgcaggta aagatttctt ggctggtgct acgataactg cttttgtctt    2280
tttggtttca gcattgttct cagagtcact aaataacatt atcatctgca aacgtcaaat    2340
agacatactt aggtgaatgg atattcatgt aaccgtttcc ttacaaattt gctgaaacct    2400
cagggtgatg tgaagtttgc tgaggtactg gagatgatgg gagcgaaggt tacatggacc    2460
gagactagcg taactgttac tggcccaccg cgggagccat ttgggaggaa cacctcaag    2520 gcgattgatg tcaacatgaa caagatgcct gatgtcgcca tgactcttgc tgtggttgcc    2580
ctctttgccg atgggcccgac agccatcaga gacggtaaaa cattctcagc cctacaacca    2640
tgcctcttct acatcactac ttgacaagac taaaaactat tggctcgttg gcagtggctt    2700
cctggagagt aaaggagacc gagaggatgg ttgcgatccg gacggagcta accaaggtaa    2760
ggctacatac ttcacatgtc tcacgtcgtc tttccatagc tcgctgcctc ttagcggctt    2820
gcctgcggtc gctccatcct cggttgctgt ctgtgttttc cacagctggg agcatctgtt    2880
gaggaagggc cggactactg catcatcacg ccgccggaga agctgaacgt gacggcgatc    2940
gacacgtacg acgaccacag gatggccatg gccttctccc ttgccgcctg tgccgaggtc    3000
cccgtgacca tccgggaccc tgggtgcacc cggaagacct tccccgacta cttcgatgtg    3060
ctgagcactt tcgtcaagaa ttaataaagc gtgcgatact accacgcagc ttgattgaag    3120
tgataggctt gtgctgagga aatacatttc ttttgttctg tttttttctct ttcacgggat    3180 taagttttga gtctgtaacg ttagttgttt gtagcaagtt tctatttcgg atcttaagtt    3240
tgtgcactgt aagccaaatt tcatttcaag agtggttcgt tggaataata agaataataa    3300
attacgtttc agtggctgtc aagcctgctg ctacgtttta ggagatggca ttagacattc    3360
atcatcaaca acaataaaac cttttagcct caaacaataa tagtgaagtt atttttttagt    3420 cctaaacaag ttgcattagg atatagttaa aacacaaaag aagctaaagt tagggtttag    3480
acatgtggat attgtttcc atgtatagta tgttctttct ttgagtctca tttaactacc    3540
```

```
tctacacata ccaactttag ttttttttct acctcttcat gttactatgg tgccttctta    3600
tcccactgag cattggtata tttagaggtt tttgttgaac atgcctaaat catctcaatc    3660
aacgatggac aatcttttct tcgattgagc tgaggtacgt catctaga                3708
```

<210> SEQ ID NO 520
<211> LENGTH: 464
<212> TYPE: PRT
<213> ORGANISM: zea mays

<400> SEQUENCE: 520

```
Met Gln Leu Asp Leu Asn Val Ala Glu Ala Pro Pro Val Glu Met
1               5                   10                  15

Glu Ala Ser Asp Ser Gly Ser Ser Val Leu Asn Ala Ser Glu Ala Ala
            20                  25                  30

Ser Ala Gly Gly Ala Pro Ala Pro Ala Glu Glu Gly Ser Ser Ser Thr
        35                  40                  45

Pro Ala Val Leu Glu Phe Ser Ile Leu Ile Arg Ser Asp Ser Asp Ala
    50                  55                  60

Ala Gly Ala Asp Glu Asp Glu Asp Ala Thr Pro Ser Pro Pro Pro Arg
65                  70                  75                  80

His Arg His Gln His Gln Gln Leu Val Thr Arg Glu Leu Phe Pro
                85                  90                  95

Ala Gly Ala Gly Pro Pro Ala Pro Thr Pro Arg His Trp Ala Glu Leu
            100                 105                 110

Gly Phe Phe Arg Ala Asp Leu Gln Gln Gln Gln Ala Pro Gly Pro Arg
        115                 120                 125

Ile Val Pro His Pro His Ala Ala Pro Pro Ala Lys Lys Ser Arg
130                 135                 140

Arg Gly Pro Arg Ser Arg Ser Ser Gln Tyr Arg Gly Val Thr Phe Tyr
145                 150                 155                 160

Arg Arg Thr Gly Arg Trp Glu Ser His Ile Trp Asp Cys Gly Lys Gln
                165                 170                 175

Val Tyr Leu Gly Gly Phe Asp Thr Ala His Ala Ala Arg Ala Tyr
            180                 185                 190

Asp Arg Ala Ala Ile Lys Phe Arg Gly Val Asp Ala Asp Ile Asn Phe
        195                 200                 205

Asn Leu Ser Asp Tyr Glu Asp Asp Met Lys Gln Met Gly Ser Leu Ser
    210                 215                 220

Lys Glu Glu Phe Val His Val Leu Arg Arg Gln Ser Thr Gly Phe Ser
225                 230                 235                 240

Arg Gly Ser Ser Arg Tyr Arg Gly Val Thr Leu His Lys Cys Gly Arg
                245                 250                 255

Trp Glu Ala Arg Met Gly Gln Phe Leu Gly Lys Lys Tyr Ile Tyr Leu
            260                 265                 270

Gly Leu Phe Asp Ser Glu Val Glu Ala Ala Arg Ala Tyr Asp Lys Ala
        275                 280                 285

Ala Ile Lys Cys Asn Gly Arg Glu Ala Val Thr Asn Phe Glu Pro Ser
    290                 295                 300

Thr Tyr His Gly Glu Leu Pro Thr Glu Val Ala Asp Val Asp Leu Asn
305                 310                 315                 320

Leu Ser Ile Ser Gln Pro Ser Pro Gln Arg Asp Lys Asn Ser Cys Leu
                325                 330                 335

Gly Leu Gln Leu His His Gly Pro Phe Glu Gly Ser Glu Leu Lys Lys
            340                 345                 350
```

```
          Thr Lys Ile Asp Asp Ala Pro Ser Glu Leu Pro Gly Arg Pro Arg Gln
                  355                 360                 365

Leu Ser Pro Leu Val Ala Glu His Pro Pro Ala Trp Pro Ala Gln Pro
              370                 375                 380

Pro His Pro Phe Phe Val Phe Thr Asn His Glu Met Ser Ala Ser Gly
          385                 390                 395                 400

Asp Leu His Arg Arg Pro Ala Gly Ala Val Pro Ser Trp Ala Trp Gln
                          405                 410                 415

Val Ala Ala Ala Pro Pro Ala Ala Leu Pro Ser Ser Ala Ala
                      420                 425                 430

Ala Ser Ser Gly Phe Ser Asn Thr Ala Thr Ala Ala Thr Thr Ala
                      435                 440                 445

Pro Ser Ala Ser Ser Leu Arg Tyr Cys Pro Pro Pro Pro Pro Ser
          450                 455                 460

<210> SEQ ID NO 521
<211> LENGTH: 1413
<212> TYPE: DNA
<213> ORGANISM: Zea mays

<400> SEQUENCE: 521
```

| | | | | |
|---|---|---|---|---|
| atgcagttgg atctgaacgt ggccgaggcg ccgccgccgg tggagatgga ggcgagcgac | 60 |
| tcggggtcgt cggtgctgaa cgcgtcggaa gcggcgtcgg cgggcggcgc gcccgcgccg | 120 |
| gcggaggagg gatctagctc aacgccggcc gtgctggagt tcagcatcct catccggagc | 180 |
| gatagcgacg cggccggcgc ggacgaggac gaggacgcca cgccatcgcc tcctcctcgc | 240 |
| caccgccacc agcaccagca gcagctcgtg acccgcgagc tgttcccggc cggcgccggt | 300 |
| ccgccggccc cgacgccgcg gcattgggcc gagctcggct tcttccgcgc cgacctgcag | 360 |
| cagcaacagg cgccgggccc caggatcgtg ccgcacccac acgccgcgcc gccgccggcc | 420 |
| aagaagagcc gccgcggccc cgcgctcccg cagctcgcag taccgcggcg tcaccttctac | 480 |
| cgccgcacag gccgctggga gtcccacatc tgggattgcg gcaagcaggt gtacctaggt | 540 |
| ggattcgaca ccgctcacgc cgctgcaagg gcgtacgacc gggcggcgat caagttccgc | 600 |
| ggcgtcgacg ccgacatcaa cttcaacctc agcgactacg aggacgacat gaagcagatg | 660 |
| gggagcctgt ccaaggagga gttcgtgcac gtcctgcgcc gtcagagcac cggcttctcg | 720 |
| agaggcagct ccaggtacag aggcgtcacc ctgcacaagt gcggccgctg ggaggcgcgc | 780 |
| atggggcagt cctcggcaa gaagtacata taccttgggc tattcgacag cgaagtagag | 840 |
| gctgcaagag cctacgacaa ggccgccatc aaatgcaatg cagagaggc cgtgacgaac | 900 |
| ttcgagccga gcacgtatca cggggagctg ccgactgaag ttgctgatgt cgatctgaac | 960 |
| ctgagcatat ctcagccgag ccccaaaga gacaagaaca gctgcctagg tctgcagctc | 1020 |
| caccacggac cattcgaggg ctccgaactg aagaaaacca agatcgacga tgctcccctct | 1080 |
| gagctaccgg gccgccctcg tcagctgtct cctctcgtgg ctgagcatcc gcggcctgg | 1140 |
| cctgcgcagc cgcctcaccc cttcttcgtc ttcacaaacc atgagatgag tgcatcagga | 1200 |
| gatctccaca ggaggcctgc aggggctgtt cccagctggg catggcaggt ggcagcagca | 1260 |
| gctcctcctc ctgccgccct gccgtcgtcc gctgcagcat catcaggatt ctccaacacc | 1320 |
| gccacgacag ctgccaccac cgccccatcg gcctcctccc tccggtactg cccgccgccg | 1380 |
| ccgccgccgt cgagccatca ccatccccgc tga | 1413 |

<210> SEQ ID NO 522
<211> LENGTH: 514
<212> TYPE: PRT
<213> ORGANISM: Zea Mays

<400> SEQUENCE: 522

```
Met Thr Thr Ser Thr Thr Ala Lys Gln Leu Arg Arg Val Arg Thr Leu
1               5                   10                  15

Gly Arg Gly Ala Ser Gly Ala Val Val Trp Leu Ala Ser Asp Glu Ala
            20                  25                  30

Ser Gly Glu Leu Val Ala Val Lys Ser Ala Arg Ala Ala Gly Ala Ala
        35                  40                  45

Ala Gln Leu Gln Arg Glu Gly Arg Val Leu Arg Gly Leu Ser Ser Pro
    50                  55                  60

His Ile Val Pro Cys Leu Gly Ser Arg Ala Ala Ala Gly Gly Glu Tyr
65                  70                  75                  80

Gln Leu Leu Leu Glu Phe Ala Pro Gly Gly Ser Leu Ala Asp Glu Ala
                85                  90                  95

Ala Arg Ser Gly Gly Gly Arg Leu Ala Glu Arg Ala Ile Gly Ala Tyr
            100                 105                 110

Ala Gly Asp Val Ala Arg Gly Leu Ala Tyr Leu His Gly Arg Ser Leu
        115                 120                 125

Val His Gly Asp Val Lys Ala Arg Asn Val Val Ile Gly Gly Asp Gly
    130                 135                 140

Arg Ala Arg Leu Thr Asp Phe Gly Cys Ala Arg Pro Ala Gly Gly Ser
145                 150                 155                 160

Thr Arg Pro Val Gly Gly Thr Pro Ala Phe Met Ala Pro Glu Val Ala
                165                 170                 175

Arg Gly Gln Glu Gln Gly Pro Ala Ala Asp Val Trp Ala Leu Gly Cys
            180                 185                 190

Met Val Val Glu Leu Ala Thr Gly Arg Ala Pro Trp Ser Asp Val Glu
        195                 200                 205

Gly Asp Asp Leu Leu Ala Ala Leu His Arg Ile Gly Tyr Thr Asp Asp
    210                 215                 220

Val Pro Glu Val Pro Ala Trp Leu Ser Pro Glu Ala Lys Asp Phe Leu
225                 230                 235                 240

Ala Gly Cys Phe Glu Arg Arg Ala Ala Ala Arg Pro Thr Ala Ala Gln
                245                 250                 255

Pro Ala Ala His Pro Phe Val Val Ala Ser Ala Ser Ala Ala Ala Ala
            260                 265                 270

Ile Arg Gly Pro Ala Lys Gln Glu Val Val Pro Ser Pro Lys Ser Thr
        275                 280                 285

Leu His Asp Ala Phe Trp Asp Ser Asp Ala Glu Asp Glu Ala Asp Glu
    290                 295                 300

Met Ser Thr Gly Ala Ala Ala Glu Arg Ile Gly Ala Leu Ala Cys Ala
305                 310                 315                 320

Ala Ser Ala Leu Pro Asp Trp Asp Thr Glu Gly Trp Ile Asp Leu
                325                 330                 335

Gln Asp Asp His Ser Ala Gly Thr Ala Asp Ala Pro Pro Ala Pro Val
            340                 345                 350

Ala Asp Tyr Phe Ile Ser Trp Ala Glu Pro Ser Asp Ala Glu Leu Glu
        355                 360                 365

Pro Phe Val Ala Val Ala Ala Ala Gly Leu Pro His Val Ala Gly
    370                 375                 380
```

```
Val Ala Leu Ala Gly Ala Thr Ala Val Asn Leu Gln Gly Ser Tyr Tyr
385                 390                 395                 400

Tyr Tyr Pro Pro Met His Leu Gly Val Arg Gly Asn Glu Ile Pro Arg
            405                 410                 415

Pro Leu Asp His His Gly Asp Gly Leu Glu Lys Gly Gln Gly Ser
        420                 425                 430

His Arg Val Cys Asn Arg Glu Thr Glu Lys Val Thr Met Lys Arg Ile
            435                 440                 445

Ser Leu Lys Arg Arg Ala Ala Phe Leu Leu Asp Gln His His Val Arg
        450                 455                 460

Ser Leu Asp Lys Leu Glu Tyr Arg Pro Arg His Asp Arg Met Leu Arg
465                 470                 475                 480

Arg Arg Gln Ser Ile Tyr Arg Ser Asn Ser Val Leu Gly Tyr Asp Val
                485                 490                 495

Ser Lys Gly Arg Gln Val Arg Trp Arg Arg Ala Val Cys Ile Ala Val
            500                 505                 510

Ala Ala
```

<210> SEQ ID NO 523
<211> LENGTH: 1545
<212> TYPE: DNA
<213> ORGANISM: Zea mays

<400> SEQUENCE: 523

```
atgacgacgt cgaccacggc gaagcagctc cggcgcgtgc gcacgctcgg ccgcggcgcg   60
tcgggcgccg tggtgtggct ggcctccgac gaggcctcgg gcgagctggt ggcggtcaag  120
tcggcgcgcg ccgccggggc cgcggcgcag ctgcagcgcg agggccgcgt cctccggggc  180
ctctcgtcgc cgcacatcgt gccctgcctc ggctcccgcg ccgcggcggg cggcgagtac  240
cagctcctgc tggagttcgc gccgggcggg tcgctggccg acgaggccgc caggagcggc  300
gggggccgcc tcgcggagcg cgccatcggc gcctacgccg ggacgtggc gcgcgggctg  360
gcgtacctcc acggccggtc gctcgtgcac ggggacgtca aggcccggaa cgtggtcatc  420
ggcggcgacg ggcgcgccag gctgaccgac ttcgggtgcg cgaggccggc cggcgggtcg  480
acgcgccccg tcggggcac cccggcgttc atggcgcccg aggtggcgcg cggccaggag  540
cagggccccg ccgccgacgt ctgggcgctc ggtgcatgg tcgtcgagct ggccacgggc  600
cgcgcgccct ggagcgacgt ggagggcgac gacctcctcg ccgcgctcca ccggatcggg  660
tacacggacg acgtgccgga ggtgcccgcg tggctgtcgc ccgaggccaa ggacttcctg  720
gccggctgct cgagcgccg cgccgccgcc cggcccacgg ccgcgcagcc cgcggcgcac  780
ccgttcgtcg tcgcctccgc ctccgccgcc gccgccatcc gcggcccggc gaagcaggag  840
gtggtcccgt cacccaagag cacgctgcac gacgcgttct gggactcgga cgccgaggac  900
gaagcggacg agatgtcgac gggcgcggcg gccgagagga tcggggcatt ggcgtgcgcc  960
gcctccgcgc tgcctgactg ggacaccgag gaaggctgga tcgacctcca ggacgaccac 1020
tcggccggaa ctgccgacgc accgccggcg cccgtcgcgg actacttcat cagctgggcg 1080
gagccgtcag acgcagagct ggaaccattc gtcgccgtcg ccgccgccgc aggtctcccg 1140
cacgttgcag gagttgcatt agcaggcgcc accgccgtta acctgcaggg cagttattat 1200
tattacccgc ctatgcatct aggcgtccgg ggaaacgaga ttccacgccc gttgttggat 1260
catcatggcg acgggttaga aaaggggcag ggatcccacc gcgtttgtaa cagagaaaca 1320
gaaaaggtaa caatgaaacg aatttcgtta aaaagaagag ctgctttcct tctcgaccag 1380
```

```
catcacgtgc gatcgctgga caaactggaa tatcgtccac gtcacgaccg aatgctgcgt   1440
cgacggcaat ctatatatcg gagcaatagc gtccttggtt acgacgttag caaaggtagg   1500
caggtccgtt ggcgccgtgc ggtttgcatt gccgttgctg cctga                  1545
```

<210> SEQ ID NO 524
<211> LENGTH: 671
<212> TYPE: DNA
<213> ORGANISM: Zea mays

<400> SEQUENCE: 524

```
cggatccact agtaacggcc gccagtgtgc tggaattcgc ccttgacggc ccgggctggt   60
atttcaaaac tatagtattt taaaattgca ttaacaaaca tgtcctaatt ggtactcctg   120
agatactata ccctcctgtt ttaaaatagt tggcattatc gaattatcat tttactttt    180 aatgttttct cttctttaa tatattttat gaattttaat gtattttaaa atgttatgca    240
gttcgctctg acttttctg ctgcgcctac acttgggtgt actgggccta aattcagcct    300
gaccgaccgc ctgcattgaa taatggatga gcaccggtaa aatccgcgta cccaactttc    360
gagaagaacc gagacgtggc gggccgggcc accgacgcac ggcaccagcg actgcacacg    420
tcccgccggc gtacgtgtac gtgctgttcc ctcactggcc gcccaatcca ctcatgcatg    480
cccacgtaca cccctgccgt ggcgcgccca gatcctaatc ctttcgccgt tctgcacttc    540
tgctgcctat aaatggcggc atcgaccgtc acctgcttca ccaccggcga gccacatcga    600
gaacacgatc gagcacacaa gcacgaagac tcgtttagga gaaaccacaa accaccaagc    660
cgtgcaagca c                                                         671
```

<210> SEQ ID NO 525
<211> LENGTH: 245
<212> TYPE: PRT
<213> ORGANISM: zea mays

<400> SEQUENCE: 525

```
Met Gly Arg Gly Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Ile Ile Phe
        35                  40                  45

Ser Thr Lys Gly Lys Leu Tyr Glu Tyr Ser Thr Asp Ser Cys Met Asp
    50                  55                  60

Lys Ile Leu Glu Arg Tyr Glu Arg Tyr Ser Tyr Ala Glu Lys Val Leu
65                  70                  75                  80

Ile Ser Ala Glu Tyr Glu Thr Gln Gly Asn Trp Cys His Glu Tyr Arg
                85                  90                  95

Lys Leu Lys Ala Lys Val Glu Thr Ile Gln Lys Cys Gln Lys His Leu
            100                 105                 110

Met Gly Glu Asp Leu Glu Thr Leu Asn Leu Lys Glu Leu Gln Gln Leu
        115                 120                 125

Glu Gln Gln Leu Glu Ser Ser Leu Lys His Ile Arg Thr Arg Lys Ser
    130                 135                 140

Gln Leu Met Val Glu Ser Ile Ser Ala Leu Gln Arg Lys Glu Lys Ser
145                 150                 155                 160

Leu Gln Glu Glu Asn Lys Val Leu Gln Lys Glu Leu Ala Glu Lys Gln
                165                 170                 175
```

Lys Asp Gln Arg Gln Val Gln Arg Asp Gln Thr Gln Gln Thr
            180                 185                 190

Ser Ser Ser Ser Thr Ser Phe Met Leu Arg Glu Ala Ala Pro Thr Thr
                195                 200                 205

Asn Val Ser Ile Phe Pro Val Ala Ala Gly Gly Arg Val Val Glu Gly
210                 215                 220

Ala Ala Ala Gln Pro Gln Ala Arg Val Gly Leu Pro Pro Trp Met Leu
225                 230                 235                 240

Ser His Leu Ser Cys
                245

<210> SEQ ID NO 526
<211> LENGTH: 738
<212> TYPE: DNA
<213> ORGANISM: zea mays

<400> SEQUENCE: 526

```
atggggcgcg ggaaggtgca gctgaagcgg atcgagaaca agatcaaccg ccaggtgaca      60
ttctccaagc gccgctcggg gctactcaag aaggcgcacg agatctccgt gctctgcgac     120
gccgaggtcg cgctcatcat cttctccacc aagggcaagc tctacgagta ctctaccgat     180
tcatgtatgg acaaaattct gaacggtat gagcgctact cctatgcaga aaaggttctc     240
atttccgcag aatatgaaac tcagggcaat tggtgccatg aatatagaaa actaaaggcg     300
aaggtcgaga caatacagaa atgtcaaaag cacctcatgg gagaggatct tgaaactttg     360
aatctcaaag agcttcagca actagagcag cagctggaga gttcactgaa acatatcaga     420
acaaggaaga gccagcttat ggtcgagtca atttcagcgc tccaacggaa ggagaagtca     480
ctgcaggagg agaacaaggt tctgcagaag gagctcgcgg agaagcagaa agaccagcgg     540
cagcaagtgc aacgggacca aactcaacag cagaccagtt cgtcttccac gtccttcatg     600
ttaagggaag ctgccccaac aacaaatgtc agcatcttcc ctgtggcagc aggcggggag     660
gtggtggaag gggcagcagc gcagccgcag gctcgcgttg gactgccacc atggatgctt     720
agccatctga gctgctga                                                   738
```

<210> SEQ ID NO 527
<211> LENGTH: 80
<212> TYPE: DNA
<213> ORGANISM: zea mays
<220> FEATURE:
<221> NAME/KEY: misc_feature
<222> LOCATION: (1)..(80)
<223> OTHER INFORMATION: sequence of Figure 34B

<400> SEQUENCE: 527

```
gctaaagagg aagtgcagct cttcttgggg aatgctggaa ctgcaatgcg gccattgaca      60
gcagctgtta ctgctgctgg                                                  80
```

<210> SEQ ID NO 528
<211> LENGTH: 80
<212> TYPE: DNA
<213> ORGANISM: zea mays
<220> FEATURE:
<221> NAME/KEY: misc_feature
<222> LOCATION: (1)..(80)
<223> OTHER INFORMATION: sequence of Figure 34c

<400> SEQUENCE: 528

```
gctagagagg aagtgcagct cttcttgggg aatgctggaa tcgcaatgcg gtcattgaca      60
```

```
gcagctgtta ctgctgctgg                                               80
```

```
<210> SEQ ID NO 529
<211> LENGTH: 37
<212> TYPE: DNA
<213> ORGANISM: zea mays
<220> FEATURE:
<221> NAME/KEY: misc_feature
<222> LOCATION: (1)..(37)
<223> OTHER INFORMATION: sequence of Figure 35b

<400> SEQUENCE: 529
catctcacga tcagatgcac cgcatgtcgc atgccta                            37
```

```
<210> SEQ ID NO 530
<211> LENGTH: 42
<212> TYPE: DNA
<213> ORGANISM: zea mays
<220> FEATURE:
<221> NAME/KEY: misc_feature
<222> LOCATION: (1)..(42)
<223> OTHER INFORMATION: sequence of Figure 35c

<400> SEQUENCE: 530
catatctgca cgatcagata tgcaccgcat gtcgcatatc tg                      42
```

```
<210> SEQ ID NO 531
<211> LENGTH: 31
<212> TYPE: DNA
<213> ORGANISM: zea mays
<220> FEATURE:
<221> NAME/KEY: misc_feature
<222> LOCATION: (1)..(31)
<223> OTHER INFORMATION: sequence of Figure 37

<400> SEQUENCE: 531
gtttttgaac ttcagttacg tgcttgatgg a                                  31
```

```
<210> SEQ ID NO 532
<211> LENGTH: 31
<212> TYPE: DNA
<213> ORGANISM: zea mays
<220> FEATURE:
<221> NAME/KEY: misc_feature
<222> LOCATION: (1)..(31)
<223> OTHER INFORMATION: sequence of Figure 37

<400> SEQUENCE: 532
gtttttgaac ttcaggtacg tgcttgatgg a                                  31
```

```
<210> SEQ ID NO 533
<211> LENGTH: 459
<212> TYPE: DNA
<213> ORGANISM: Artificial Sequence
<220> FEATURE:
<223> OTHER INFORMATION: synthesized sequence- Southern genomic probe

<400> SEQUENCE: 533
agctttatcc atccatccat cgcgctagct ggctgcaggc acgggttatc ttatcttgtc   60
gtccagagga cgacacacgg ccggccggtg aagtaaaagg gagtaatctt attttgccag  120
gacgaggggc ggtacatgat attacacacg taccatgcat gcatatatgc atggacaagg  180
tacgtcgtcg tcgatcgacg tcgatgcata tgtgtgtatg tatgtacgtg cataatgcat  240
ggtaccagct gctggcttat atatatttgt caccgatcga tgcatgctgc tgctctacac  300
```

```
ggtttgacac tttaatttga ctcatcgatg accttgctag atagtagcgg ctcgtcaatt    360
aatgagccat caagttaaca agagggcacg ggcttgcgcg actgattcca ccttattaac    420
atacgccctg cgcccgcgcg tgctgtacgt acgagaatt                           459
```

<210> SEQ ID NO 534
<211> LENGTH: 446
<212> TYPE: DNA
<213> ORGANISM: Artificial Sequence
<220> FEATURE:
<223> OTHER INFORMATION: synthesized sequence- Southern MoPAT probe

<400> SEQUENCE: 534

```
tcgaagtcgc gctgccagaa gccgacgtcg tgccagccgc cgtgcttgta gccggcggcg     60
cggagggtgc cgcgggcggt gtagccgagg gcctcgtgga ggcgcacgga cgggtcgttc    120
gggaggccga tcacggccac cacggacttg aagccctggg cctccatgct cttgaggagg    180
tgggtgtaga gggtggagcc gaggccgagg cgctggtggc ggtgggacac gtacacggtg    240
gactccacgg tccagtcgta ggcgttgcgg gccttccacg ggccggcgta ggcgatgccg    300
gccaccacgc cctccacctc ggccacgagc cacgggtagc ggtcctggag gcgctccagg    360
tcgtcgatcc actcctgcgg ggtctgcggc tcggtgcgga agttcacggt ggaggtctcg    420
atgtagtggt tcacgatgtc gcacac                                        446
```

<210> SEQ ID NO 535
<211> LENGTH: 20
<212> TYPE: DNA
<213> ORGANISM: Artificial Sequence
<220> FEATURE:
<223> OTHER INFORMATION: synthesized sequence- RF-FPCas-1

<400> SEQUENCE: 535

```
gcaggtctca cgacggttgg                                                20
```

<210> SEQ ID NO 536
<211> LENGTH: 23
<212> TYPE: DNA
<213> ORGANISM: Artificial Sequence
<220> FEATURE:
<223> OTHER INFORMATION: synthesized sequence- RF-FPCas-2

<400> SEQUENCE: 536

```
gtaaagtacg cgtacgtgtg agg                                            23
```

<210> SEQ ID NO 537
<211> LENGTH: 23
<212> TYPE: DNA
<213> ORGANISM: Artificial Sequence
<220> FEATURE:
<223> OTHER INFORMATION: synthesized sequence- ALSCas-4

<400> SEQUENCE: 537

```
gctgctcgat tccgtcccca tgg                                            23
```

<210> SEQ ID NO 538
<211> LENGTH: 804
<212> TYPE: DNA
<213> ORGANISM: Artificial Sequence
<220> FEATURE:
<223> OTHER INFORMATION: synthesized sequence- ALS modification repair
      template 804

<400> SEQUENCE: 538

-continued

| | |
|---|---|
| agcttacagc cgccgcaacc atggccaccg ccgccgccgc gtctaccgcg ctcactggcg | 60 |
| ccactaccgc tgccgcccaag gcgaggcgcc gggcgcacct cctggccacc cgccgcgccc | 120 |
| tcgccgcgcc catcaggtgc tcagcggcgt cacccgccat gccgatggct ccccggcca | 180 |
| ccccgctccg gccgtggggc cccaccgatc cccgcaaggg cgccgacatc ctcgtcgagt | 240 |
| ccctcgagcg ctgcggcgtc cgcgacgtct tcgcctaccc cggcggcgcg tccatggaga | 300 |
| tccaccaggc actcacccgc tcccccgtca tcgccaacca cctcttccgc cacgagcaag | 360 |
| gggaggcctt tgcggcctcc ggctacgcgc gctcctcggg ccgcgtcggc gtctgcatcg | 420 |
| ccacctccgg ccccggcgcc accaaccttg tctccgcgct cgccgacgcg ttgctcgact | 480 |
| ccgtccccat tgtcgccatc acgggacagg tgtcgcgacg catgattggc accgacgcct | 540 |
| tccaggagac gccatcgtc gaggtcaccc gctccatcac caagcacaac tacctggtcc | 600 |
| tcgacgtcga cgacatcccc cgcgtcgtgc aggaggcttt cttcctcgcc tcctctggtc | 660 |
| gaccagggcc ggtgcttgtc gacatcccca aggacatcca gcagcagatg gcggtgcctg | 720 |
| tctgggacaa gcccatgagt ctgcctgggt acattgcgcg ccttccaag ccccctgcga | 780 |
| ctgagttgct tgagcagaag ggcg | 804 |

```
<210> SEQ ID NO 539
<211> LENGTH: 127
<212> TYPE: DNA
<213> ORGANISM: Artificial Sequence
<220> FEATURE:
<223> OTHER INFORMATION: synthesized sequence- ALS modification repair
      template 127

<400> SEQUENCE: 539
```

| | |
|---|---|
| aaccttgtct ccgcgctcgc cgacgcgttg ctcgactccg tccccattgt cgccatcacg | 60 |
| ggacaggtgt cgcgacgcat gattggcacc gacgccttcc aggagacgcc catcgtcgag | 120 |
| gtcaccc | 127 |

```
<210> SEQ ID NO 540
<211> LENGTH: 25
<212> TYPE: DNA
<213> ORGANISM: Artificial Sequence
<220> FEATURE:
<223> OTHER INFORMATION: synthesized sequence- ALS Forward_primer;

<400> SEQUENCE: 540
```

| | |
|---|---|
| ctacgcacat ccccctttct cccac | 25 |

```
<210> SEQ ID NO 541
<211> LENGTH: 36
<212> TYPE: DNA
<213> ORGANISM: Artificial Sequence
<220> FEATURE:
<223> OTHER INFORMATION: synthesized sequence- ALS Reverse_primer

<400> SEQUENCE: 541
```

| | |
|---|---|
| atgcatacct agcatgcgca gagacagtgg gtcgtc | 36 |

```
<210> SEQ ID NO 542
<211> LENGTH: 22
<212> TYPE: DNA
<213> ORGANISM: Glycine max

<400> SEQUENCE: 542
```

| | |
|---|---|
| caccggccag gtcccccgcc gg | 22 |

<210> SEQ ID NO 543
<211> LENGTH: 22
<212> TYPE: DNA
<213> ORGANISM: Glycine max

<400> SEQUENCE: 543
ggcgtcggtg ccgatcatcc gg                                             22

<210> SEQ ID NO 544
<211> LENGTH: 9093
<212> TYPE: DNA
<213> ORGANISM: Artificial sequence
<220> FEATURE:
<223> OTHER INFORMATION: synthesized sequence- QC880

<400> SEQUENCE: 544

| | |
|---|---|
| ccgggtgtga tttagtataa agtgaagtaa tggtcaaaag aaaaagtgta aaacgaagta | 60 |
| cctagtaata agtaatattg aacaaaataa atggtaaagt gtcagatata taaaataggc | 120 |
| tttaataaaa ggaagaaaaa aaacaaacaa aaaataggtt gcaatggggc agagcagagt | 180 |
| catcatgaag ctagaaaggc taccgataga taaactatag ttaattaaat acattaaaaa | 240 |
| atacttggat cttctctta ccctgtttat attgagacct gaaacttgag agagatacac | 300 |
| taatcttgcc ttgttgtttc attccctaac ttacaggact cagcgcatgt catgtggtct | 360 |
| cgttccccat ttagtcccca caccgtctaa acttattaaa ttattaatgt ttataactag | 420 |
| atgcacaaca acaaagcttg caccggccag gtcccccgcg ttttagagct agaaatagca | 480 |
| agttaaaata aggctagtcc gttatcaact tgaaaaagtg gcaccgagtc ggtgcttttt | 540 |
| tttgcggccg caattggatc gggtttactt attttgtggg tatctatact tttattagat | 600 |
| ttttaatcag gctcctgatt tcttttttatt tcgattgaat tcctgaactt gtattattca | 660 |
| gtagatcgaa taaattataa aaagataaaa tcataaaata atattttatc ctatcaatca | 720 |
| tattaaagca atgaatatgt aaaattaatc ttatctttat tttaaaaaat catataggtt | 780 |
| tagtattttt ttaaaaataa agataggatt agttttacta ttcactgctt attacttta | 840 |
| aaaaaatcat aaaggtttag tattttttta aaataaatat aggaatagtt ttactattca | 900 |
| ctgctttaat agaaaaatag tttaaaattt aagatagttt taatcccagc atttgccacg | 960 |
| tttgaacgtg agccgaaacg atgtcgttac attatcttaa cctagctgaa acgatgtcgt | 1020 |
| cataatatcg ccaaatgcca actggactac gtcgaaccca caaatcccac aaagcgcgtg | 1080 |
| aaatcaaatc gctcaaacca caaaaaagaa caacgcgttt gttacacgct caatcccacg | 1140 |
| cgagtagagc acagtaacct tcaaataagc gaatggggca taatcagaaa tccgaaataa | 1200 |
| acctaggggc attatcggaa atgaaaagta gctcactcaa tataaaaatc taggaaccct | 1260 |
| agttttcgtt atcactctgt gctccctcgc tctatttctc agtctctgtg tttgcggctg | 1320 |
| aggattccga acgagtgacc ttcttcgttt ctcgcaaagg taacagcctc tgctcttgtc | 1380 |
| tcttcgattc gatctatgcc tgtctcttat ttacgatgat gtttcttcgg ttatgttttt | 1440 |
| ttatttatgc tttatgctgt tgatgttcgg ttgtttgttt cgctttgttt ttgtggttca | 1500 |
| gttttttagg attcttttgg tttttgaatc gattaatcgg aagagatttt cgagttattt | 1560 |
| ggtgtgttgg aggtgaatct ttttttgag gtcatagatc tgttgtattt gtgttataaa | 1620 |
| catgcgactt tgtatgattt tttacgaggt tatgatgttc tggttgtttt attatgaatc | 1680 |
| tgttgagaca gaaccatgat ttttgttgat gttcgtttac actattaaag gtttgtttta | 1740 |
| acaggattaa aagttttta agcatgttga aggagtcttg tagatatgta accgtcgata | 1800 |

```
gttttttttgt gggtttgttc acatgttatc aagcttaatc ttttactatg tatgcgacca    1860
tatctggatc cagcaaaggc gattttttaa ttccttgtga aactttttgta atatgaagtt    1920 gaaattttgt tattggtaaa ctataaatgt gtgaagttgg agtataccct taccttctta    1980
tttggctttg tgatagttta atttatatgt attttgagtt ctgacttgta tttcttttgaa   2040 ttgattctag tttaagtaat ccatggacaa aaagtactca atagggctcg catagggac     2100 taactccgtt ggatgggccg tcatcaccga cgagtacaag gtgccctcca agaagttcaa    2160
ggtgttggga acaccgaca ggcacagcat aaagaagaat ttgatcggtg ccctcctctt     2220
cgactccgga gagaccgctg aggctaccag gctcaagagg accgctagaa ggcgctacac    2280
cagaaggaag aacagaatct gctacctgca ggagatcttc ccaacgaga tggccaaggt     2340 ggacgactcc ttcttccacc gccttgagga atcattcctg gtggaggagg ataaaaagca    2400
cgagagacac ccaatcttcg gaacatcgt cgacgaggtg gcctaccatg aaaagtaccc     2460
taccatctac cacctgagga agaagctggt cgactctacc gacaaggctg acttgcgctt    2520
gatttacctg gctctcgctc acatgataaa gttccgcgga cacttcctca ttgagggaga    2580
cctgaaccca gacaactccg acgtggacaa gctcttcatc cagctcgttc agacctacaa    2640
ccagcttttc gaggagaacc caatcaacgc cagtggagtt gacgccaagg ctatcctctc    2700
tgctcgtctg tcaaagtcca ggaggcttga gaacttgatt gcccagctgc ctggcgaaaa    2760
gaagaacgga ctgttcggaa acttgatcgc tctctccctg ggattgactc ccaacttcaa    2820
gtccaacttc gacctcgccg aggacgctaa gttgcagttg tctaaagaca cctacgacga    2880
tgacctcgac aacttgctgg cccagatagg cgaccaatac gccgatctct cctcgccgc    2940 taagaacttg tccgacgcaa tcctgctgtc cgacatcctg agagtcaaca ctgagattac    3000
caaagctcct ctgtctgctt ccatgattaa gcgctacgac gagcaccacc aagatctgac    3060
cctgctcaag gccctggtga acagcagct gcccgagaag tacaaggaga tcttttttcga   3120 ccagtccaag aacggctacg ccggatacat tgacggaggc gcctcccagg aagagttcta    3180
caagttcatc aagcccatcc ttgagaagat ggacggtacc gaggagctgt tggtgaagtt    3240
gaacagagag gacctgttga ggaagcagag aaccttcgac aacggaagca tccctcacca    3300
aatccacctg ggagagctcc acgccatctt gaggaggcag gaggatttct atccttcct    3360 gaaggacaac cgcgagaaga ttgagaagat cttgaccttc agaattcctt actacgtcgg    3420
gccactcgcc agaggaaact ctaggttcgc ctggatgacc cgcaaatctg aagagaccat    3480
tactccctgg aacttcgagg aagtcgtgga caagggcgct tccgctcagt ctttcatcga    3540
gaggatgacc aacttcgata aaaatctgcc caacgagaag gtgctgccca gcactccct    3600 gttgtacgag tatttcacag tgtacaacga gctcaccaag gtgaagtacg tcacagaggg    3660
aatgaggaag cctgccttct tgtccggaga gcagaagaag gccatcgtcg acctgctctt    3720
caagaccaac aggaaggtga ctgtcaagca gctgaaggag gactacttca agaagatcga    3780
gtgcttcgac tccgtcgaga tctctggtgt cgaggacagg ttcaacgcct cccttgggac    3840
ttaccacgat ctgctcaaga ttattaaaga caaggacttc ctggacaacg aggaaacga    3900 ggacatcctt gaggacatcg tgctcaccct gaccttgttc aagacaggg aaatgatcga    3960 agagaggctc aagacctacg cccacctctt cgacgacaag gtgatgaaac agctgaagag    4020
acgcagatat accggctggg gaaggctctc ccgcaaattg atcaacggga tcagggcaa    4080 gcagtcaggg aagactatac tcgacttcct gaagtccgac ggattcgcca acaggaactt    4140
```

```
catgcagctc attcacgacg actccttgac cttcaaggag gacatccaga aggctcaggt    4200
gtctggacag ggtgactcct tgcatgagca cattgctaac ttggccggct ctcccgctat    4260
taagaagggc attttgcaga ccgtgaaggt cgttgacgag ctcgtgaagg tgatgggacg    4320
ccacaagcca gagaacatcg ttattgagat ggctcgcgag aaccaaacta cccagaaagg    4380
gcagaagaat tcccgcgaga ggatgaagcg cattgaggag ggcataaaag agcttggctc    4440
tcagatcctc aaggagcacc ccgtcgaaa cactcagctg cagaacgaga agctgtacct    4500
gtactacctc caaaacggaa gggacatgta cgtggaccag gagctggaca tcaacaggtt    4560
gtccgactac gacgtcgacc acatcgtgcc tcagtccttc ctgaaggatg actccatcga    4620
caataaagtg ctgacacgct ccgataaaaa tagaggcaag tccgacaacg tcccctccga    4680
ggaggtcgtg aagaagatga aaaactactg gagacagctc ttgaacgcca agctcatcac    4740
ccagcgtaag ttcgacaacc tgactaaggc tgagagagga ggattgtccg agctcgataa    4800
ggccggattc atcaagagac agctcgtcga aacccgccaa attaccaagc acgtggccca    4860
aattctggat tcccgcatga acaccaagta cgatgaaaat gacaagctga tccgcgaggt    4920
caaggtgatc accttgaagt ccaagctggt ctccgacttc cgcaaggact ccagttctca    4980
caaggtgagg gagatcaaca actaccacca cgcacacgac gcctacctca cgctgtcgt    5040 tggaaccgcc ctcatcaaaa aatatcctaa gctggagtct gagttcgtct acggcgacta    5100
caaggtgtac gacgtgagga agatgatcgc taagtctgag caggagatcg gcaaggccac    5160
cgccaagtac ttcttctact ccaacatcat gaacttcttc aagaccgaga tcactctcgc    5220
caacggtgag atcaggaagc gcccactgat cgagaccaac ggtgagactg gagagatcgt    5280
gtgggacaaa gggagggatt tcgctactgt gaggaaggtg ctctccatgc ctcaggtgaa    5340
catcgtcaag aagaccgaag ttcagaccgg aggattctcc aaggagtcca tcctccccaa    5400
gagaaactcc gacaagctga tcgctagaaa gaaagactgg gaccctaaga agtacggagg    5460
cttcgattct cctaccgtgg cctactctgt gctggtcgtg gccaaggtgg agaagggcaa    5520
gtccaagaag ctgaaatccg tcaaggagct cctcgggatt accatcatgg agaggagttc    5580
cttcgagaag aaccctatcg acttcctgga ggccaaggga tataaagagg tgaagaagga    5640
cctcatcatc aagctgccca gtactcccct cttcgagttg gagaacggaa ggaagaggat    5700
gctggcttct gccggagagt tgcagaaggg aaatgagctc gcccttccct ccaagtacgt    5760
gaacttcctg tacctcgcct ctcactatga aaagttgaag ggctctcctg aggacaacga    5820
gcagaagcag ctcttcgtgg agcagcacaa gcactacctg gacgaaatta tcgagcagat    5880
ctctgagttc tccaagcgcg tgatattggc cgacgccaac ctcgacaagg tgctgtccgc    5940
ctacaacaag cacagggata agcccattcg cgagcaggct gaaaacatta tccacctgtt    6000
taccctcaca aacttgggag ccctgctgc cttcaagtac ttcgacacca ccattgacag    6060
gaagagatac acctccacca aggaggtgct cgacgcaaca ctcatccacc aatccatcac    6120
cggcctctat gaaacaagga ttgacttgtc ccagctggga ggcgactcta gagccgatcc    6180
caagaagaag agaaaggtgt aggttaacct agacttgtcc atcttctgga ttggccaact    6240
taattaatgt atgaaataaa aggatgcaca catagtgaca tgctaatcac tataatgtgg    6300
gcatcaaagt tgtgtgttat gtgtaattac tagttatctg aataaaagag aaagagatca    6360
tccatatttc ttatcctaaa tgaatgtcac gtgtctttat aattctttga tgaaccagat    6420
gcatttcatt aaccaaatcc atatacatat aaatattaat catatataat taatatcaat    6480
tgggttagca aaacaaatct agtctaggtg tgttttgcga attcgatatc aagcttatcg    6540
```

-continued

```
ataccgtcga ggggggggccc ggtaccggcg cgccgttcta tagtgtcacc taaatcgtat    6600
gtgtatgata cataaggtta tgtattaatt gtagccgcgt tctaacgaca atatgtccat    6660
atggtgcact ctcagtacaa tctgctctga tgccgcatag ttaagccagc cccgacaccc    6720
gccaacaccc gctgacgcgc cctgacgggc ttgtctgctc ccggcatccg cttacagaca    6780
agctgtgacc gtctccggga gctgcatgtg tcagaggttt tcaccgtcat caccgaaacg    6840
cgcgagacga aagggcctcg tgatacgcct attttatag gttaatgtca tgaccaaaat     6900
cccttaacgt gagttttcgt tccactgagc gtcagacccc gtagaaaaga tcaaaggatc    6960
ttcttgagat ccttttttc tgcgcgtaat ctgctgcttg caaacaaaaa aaccaccgct     7020
accagcggtg gtttgtttgc cggatcaaga gctaccaact cttttccga aggtaactgg     7080
cttcagcaga gcgcagatac caaatactgt ccttctagtg tagccgtagt taggccacca    7140
cttcaagaac tctgtagcac cgcctacata cctcgctctg ctaatcctgt taccagtggc    7200
tgctgccagt ggcgataagt cgtgtcttac cgggttggac tcaagacgat agttaccgga    7260
taaggcgcag cggtcgggct gaacgggggg ttcgtgcaca gcccagct tggagcgaac      7320
gacctacacc gaactgagat acctacagcg tgagcattga aaagcgcca cgcttcccga     7380
agggagaaag gcggacaggt atccggtaag cggcagggtc ggaacaggag agcgcacgag    7440
ggagcttcca gggggaaacg cctggtatct ttatagtcct gtcgggtttc gccacctctg    7500
acttgagcgt cgatttttgt gatgctcgtc aggggggcgg agcctatgga aaacgccag    7560
caacgcggcc ttttacggt tcctggcctt ttgctggcct tttgctcaca tgttctttcc     7620
tgcgttatcc cctgattctg tggataaccg tattaccgcc tttgagtgag ctgataccgc    7680
tcgccgcagc cgaacgaccg agcgcagcga gtcagtgagc gaggaagcgg aagagcgccc    7740
aatacgcaaa ccgcctctcc ccgcgcgttg gccgattcat taatgcaggt tgatcagatc    7800
tcgatcccgc gaaattaata cgactcacta tagggagacc acaacggttt ccctctagaa    7860
ataattttgt ttaactttaa gaaggagata tacccatgga aaagcctgaa ctcaccgcga    7920
cgtctgtcga gaagtttctg atcgaaaagt tcgacagcgt ctccgacctg atgcagctct    7980
cggagggcga agaatctcgt gctttcagct tcgatgtagg agggcgtgga tatgtcctgc    8040
gggtaaatag ctgcgccgat ggtttctaca aagatcgtta tgtttatcgg cactttgcat    8100
cggccgcgct cccgattccg gaagtgcttg acattgggga attcagcgag agcctgacct    8160
attgcatctc ccgccgtgca cagggtgtca cgttgcaaga cctgcctgaa accgaactgc    8220
ccgctgttct gcagccggtc gcggaggcta tggatgcgat cgctgcggcc gatcttagcc    8280
agacgagcgg gttcggccca ttcggaccgc aaggaatcgg tcaatacact acatggcgtg    8340
atttcatatg cgcgattgct gatccccatg tgtatcactg gcaaactgtg atggacgaca    8400
ccgtcagtgc gtccgtcgcg caggctctcg atgagctgat gctttgggcc gaggactgcc    8460
ccgaagtccg gcacctcgtg cacgcggatt tcggctccaa caatgtcctg acggacaatg    8520
gccgcataac agcggtcatt gactggagcg aggcgatgtt cggggattcc caatacgagg    8580
tcgccaacat cttcttctgg aggccgtggt tggcttgtat ggagcagcag acgcgctact    8640
tcgagcggag gcatccggag cttgcaggat cgccgcggct ccgggcgtat atgctccgca    8700
ttggtcttga ccaactctat cagagcttgg ttgacggcaa tttcgatgat gcagcttggg    8760
cgcagggtcg atgcgacgca atcgtccgat ccggagccgg gactgtcggg cgtacacaaa    8820
tcgcccgcag aagcgcggcc gtctggaccg atggctgtgt agaagtactc gccgatagtg    8880
```

| gaaaccgacg cccagcact cgtccgaggg caaaggaata gtgaggtaca gcttggatcg | 8940 |
| atccggctgc taacaaagcc cgaaaggaag ctgagttggc tgctgccacc gctgagcaat | 9000 |
| aactagcata accccttggg gcctctaaac gggtcttgag gggttttttg ctgaaaggag | 9060 |
| gaactatatc cggatgatcg ggcgcgccgg tac | 9093 |

<210> SEQ ID NO 545
<211> LENGTH: 9093
<212> TYPE: DNA
<213> ORGANISM: Artificial sequence
<220> FEATURE:
<223> OTHER INFORMATION: synthesized sequence- QC881

<400> SEQUENCE: 545

| ccgggtgtga tttagtataa agtgaagtaa tggtcaaaag aaaaagtgta aaacgaagta | 60 |
| cctagtaata agtaatattg aacaaaataa atggtaaagt gtcagatata taaaataggc | 120 |
| tttaataaaa ggaagaaaaa aaacaaacaa aaaataggtt gcaatggggc agagcagagt | 180 |
| catcatgaag ctagaaaggc taccgataga taaactatag ttaattaaat acattaaaaa | 240 |
| atacttggat ctttctctta ccctgtttat attgagacct gaaacttgag agagatacac | 300 |
| taatcttgcc ttgttgtttc attccctaac ttacaggact cagcgcatgt catgtggtct | 360 |
| cgttccccat ttaagtccca caccgtctaa acttattaaa ttattaatgt ttataactag | 420 |
| atgcacaaca acaaagcttg ggcgtcggtg ccgatcatcg ttttagagct agaaatagca | 480 |
| agttaaaata aggctagtcc gttatcaact tgaaaaagtg gcaccgagtc ggtgcttttt | 540 |
| tttgcggccg caattggatc gggtttactt attttgtggg tatctatact tttattagat | 600 |
| ttttaatcag gctcctgatt tcttttttatt tcgattgaat tcctgaactt gtattattca | 660 |
| gtagatcgaa taaattataa aaagataaaa tcataaaata atattttatc ctatcaatca | 720 |
| tattaaagca atgaatatgt aaaattaatc ttatctttat tttaaaaaat catataggtt | 780 |
| tagtattttt ttaaaaataa agataggatt agttttacta ttcactgctt attacttta | 840 |
| aaaaaatcat aaaggtttag tatttttta aaataaatat aggaatagtt ttactattca | 900 |
| ctgctttaat agaaaaatag tttaaaattt aagatagttt taatcccagc atttgccacg | 960 |
| tttgaacgtg agccgaaacg atgtcgttac attatcttaa cctagctgaa acgatgtcgt | 1020 |
| cataatatcg ccaaatgcca actggactac gtcgaaccca caaatcccac aaagcgcgtg | 1080 |
| aaatcaaatc gctcaaacca caaaaaagaa caacgcgttt gttacacgct caatcccacg | 1140 |
| cgagtagagc acagtaacct tcaaataagc gaatggggca taatcagaaa tccgaaataa | 1200 |
| acctaggggc attatcggaa atgaaaagta gctcactcaa tataaaaatc taggaaccct | 1260 |
| agttttcgtt atcactctgt gctccctcgc tctatttctc agtctctgtg tttgcggctg | 1320 |
| aggattccga acgagtgacc ttcttcgttt ctcgcaaagg taacagcctc tgctcttgtc | 1380 |
| tcttcgattc gatctatgcc tgtctcttat ttacgatgat gtttcttcgg ttatgttttt | 1440 |
| ttatttatgc tttatgctgt tgatgttcgg ttgtttgttt cgctttgttt ttgtggttca | 1500 |
| gttttttagg attcttttgg tttttgaatc gattaatcgg aagagatttt cgagttattt | 1560 |
| ggtgtgttgg aggtgaatct ttttttttgag gtcatagatc tgttgtattt gtgttataaa | 1620 |
| catgcgactt tgtatgattt tttacgaggt tatgatgttc tggttgtttt attatgaatc | 1680 |
| tgttgagaca gaaccatgat ttttgttgat gttcgtttac actattaaag gtttgtttta | 1740 |
| acaggattaa aagttttttta agcatgttga aggagtcttg tagatatgta accgtcgata | 1800 |
| gttttttttgt gggtttgttc acatgttatc aagcttaatc ttttactatg tatgcgacca | 1860 |

```
tatctggatc cagcaaaggc gatttttaa ttccttgtga aacttttgta atatgaagtt    1920
gaaattttgt tattggtaaa ctataaatgt gtgaagttgg agtataccct taccttctta    1980
tttggctttg tgatagttta atttatatgt attttgagtt ctgacttgta tttctttgaa    2040
ttgattctag tttaagtaat ccatggacaa aaagtactca atagggctcg ataggggac    2100 taactccgtt ggatgggccg tcatcaccga cgagtacaag gtgccctcca agaagttcaa    2160
ggtgttggga acaccgaca ggcacagcat aaagaagaat ttgatcggtg ccctcctctt     2220
cgactccgga gagaccgctg aggctaccag gctcaagagg accgctagaa ggcgctacac    2280
cagaaggaag aacagaatct gctacctgca ggagatcttc ccaacgaga tggccaaggt     2340 ggacgactcc ttcttccacc gccttgagga atcattcctg gtggaggagg ataaaaagca    2400
cgagagacac ccaatcttcg gaacatcgt cgacgaggtg gcctaccatg aaaagtaccc     2460
taccatctac cacctgagga agaagctggt cgactctacc gacaaggctg acttgcgctt    2520
gatttacctg gctctcgctc acatgataaa gttccgcgga cacttcctca ttgagggaga    2580
cctgaaccca gacaactccg acgtggacaa gctcttcatc cagctcgttc agacctacaa    2640 ccagctttc gaggagaacc caatcaacgc cagtggagtt gacgccaagg ctatcctctc     2700
tgctcgtctg tcaaagtcca ggaggcttga aacttgatt gcccagctgc ctggcgaaaa    2760
gaagaacgga ctgttcggaa acttgatcgc tctctccctg ggattgactc ccaacttcaa    2820
gtccaacttc gacctcgccg aggacgctaa gttgcagttg tctaaagaca cctacgacga    2880
tgacctcgac aacttgctgg cccagatagg cgaccaatac gccgatctct tcctcgccgc    2940
taagaacttg tccgacgcaa tcctgctgtc cgacatcctg agagtcaaca ctgagattac    3000
caaagctcct ctgtctgctt ccatgattaa gcgctacgac gagcaccacc aagatctgac    3060
cctgctcaag gccctggtga cacagcagct gcccgagaag tacaaggaga tcttttcga    3120 ccagtccaag aacggctacg ccggatacat tgacggaggc gcctcccagg aagagttcta    3180
caagttcatc aagcccatcc ttgagaagat ggacggtacc gaggagctgt tggtgaagtt    3240
gaacagagag gacctgttga ggaagcagag aaccttcgac aacggaagca tccctcacca    3300
aatccacctg ggagagctcc acgccatctt gaggaggcag gaggatttct atcccttcct    3360
gaaggacaac cgcgaagaga ttgagaagat cttgaccttc agaattcctt actacgtcgg    3420
gccactcgcc agaggaaact ctaggttcgc ctggatgacc cgcaaatctg aagagaccat    3480
tactccctgg aacttcgagg aagtcgtgga caagggcgct tccgctcagt ctttcatcga    3540
gaggatgacc aacttcgata aaatctgcc caacgagaag gtgctgccca gcactccct    3600 gttgtacgag tatttcacag tgtacaacga gctcaccaag gtgaagtacg tcacagaggg    3660
aatgaggaag cctgccttct gtccggaga gcagaagaag gccatcgtcg acctgctctt    3720
caagaccaac aggaaggtga ctgtcaagca gctgaaggag gactacttca gaagatcga    3780 gtgcttcgac tccgtcgaga tctctggtgt cgaggacagg ttcaacgcct cccttgggac    3840
ttaccacgat ctgctcaaga ttattaaaga caaggacttc ctggacaacg aggagaacga    3900
ggacatcctt gaggacatcg tgctcaccct gaccttgttc gaagacaggg aaatgatcga    3960
agagaggctc aagacctacg cccacctctt cgacgacaag gtgatgaaac agctgaagag    4020
acgcagatat accggctggg gaaggctctc ccgcaaattg atcaacggga tcagggacaa    4080
gcagtcaggg aagactatac tcgacttcct gaagtccgac ggattcgcca acaggaactt    4140
catgcagctc attcacgacg actccttgac cttcaaggag gacatccaga aggctcaggt    4200
```

```
gtctggacag ggtgactcct tgcatgagca cattgctaac ttggccggct ctcccgctat   4260
taagaagggc attttgcaga ccgtgaaggt cgttgacgag ctcgtgaagg tgatgggacg   4320
ccacaagcca gagaacatcg ttattgagat ggctcgcgag aaccaaacta cccagaaagg   4380
gcagaagaat tcccgcgaga ggatgaagcg cattgaggag ggcataaaag agcttggctc   4440
tcagatcctc aaggagcacc ccgtcgagaa cactcagctg cagaacgaga agctgtacct   4500
gtactacctc caaaacggaa gggacatgta cgtggaccag gagctggaca tcaacaggtt   4560
gtccgactac gacgtcgacc acatcgtgcc tcagtccttc ctgaaggatg actccatcga   4620
caataaagtg ctgacacgct ccgataaaaa tagaggcaag tccgacaacg tcccctccga   4680
ggaggtcgtg aagaagatga aaaactactg gagacagctc ttgaacgcca agctcatcac   4740
ccagcgtaag ttcgacaacc tgactaaggc tgagagagga ggattgtccg agctcgataa   4800
ggccggattc atcaagagac agctcgtcga acccgccaa attaccaagc acgtggccca   4860
aattctggat tcccgcatga acaccaagta cgatgaaaat gacaagctga tccgcgaggt   4920
caaggtgatc acccttgaagt ccaagctggt ctccgacttc cgcaaggact ccagttcta   4980
caaggtgagg gagatcaaca actaccacca cgcacacgac gcctacctca cgctgtcgt   5040
tggaaccgcc ctcatcaaaa aatatcctaa gctggagtct gagttcgtct acggcgacta   5100
caaggtgtac gacgtgagga agatgatcgc taagtctgag caggagatcg gcaaggccac   5160
cgccaagtac ttcttctact ccaacatcat gaacttcttc aagaccgaga tcactctcgc   5220
caacggtgag atcaggaagc gcccactgat cgagaccaac ggtgagactg gagagatcgt   5280
gtgggacaaa ggggagggatt cgctactgt gaggaaggtg ctctccatgc ctcaggtgaa   5340
catcgtcaag aagaccgaag ttcagaccgg aggattctcc aaggagtcca tcctccccaa   5400
gagaaactcc gacaagctga tcgctagaaa gaaagactgg gaccctaaga agtacggagg   5460
cttcgattct cctaccgtgg cctactctgt gctggtcgtg gccaaggtgg agaagggcaa   5520
gtccaagaag ctgaaatccg tcaaggagct cctcgggatt accatcatgg agaggagttc   5580
cttcgagaag aaccctatcg acttcctgga ggccaaggga tataaagagg tgaagaagga   5640
cctcatcatc aagctgccca agtactccct cttcgagttg gagaacggaa ggaagaggat   5700
gctggcttct gccggagagt tgcagaaggg aaatgagctc gcccttccct ccaagtacgt   5760
gaacttcctg tacctcgcct ctcactatga aaagttgaag gctctcctg aggacaacga   5820
gcagaagcag ctcttcgtgg agcagcacaa gcactacctg gacgaaatta tcgagcagat   5880
ctctgagttc tccaagcgcg tgatattggc cgacgccaac ctcgacaagg tgctgtccgc   5940
ctacaacaag cacagggata agcccattcg cgagcaggct gaaaacatta tccacctgtt   6000
taccctcaca acttgggag cccctgctgc cttcaagtac ttcgacacca ccattgacag   6060
gaagagatac acctccacca aggaggtgct cgacgcaaca ctcatccacc aatccatcac   6120
cggcctctat gaaacaagga ttgacttgtc ccagctggga ggcgactcta gagccgatcc   6180
caagaagaag agaaaggtgt aggttaacct agacttgtcc atcttctgga ttggccaact   6240
taattaatgt atgaaataaa aggatgcaca catagtgaca tgctaatcac tataatgtgg   6300
gcatcaaagt tgtgtgttat gtgtaattac tagttatctg aataaaagag aaagagatca   6360
tccatatttc ttatcctaaa tgaatgtcac gtgtctttat aattctttga tgaaccagat   6420
gcatttcatt aaccaaatcc atatacatat aaatattaat catatataat taatatcaat   6480
tgggttagca aaacaaatct agtctaggtg tgttttgcga attcgatatc aagcttatcg   6540
ataccgtcga gggggggccc ggtaccggcg cgccgttcta tagtgtcacc taaatcgtat   6600
```

```
gtgtatgata cataaggtta tgtattaatt gtagccgcgt tctaacgaca atatgtccat    6660
atggtgcact ctcagtacaa tctgctctga tgccgcatag ttaagccagc cccgacaccc    6720
gccaacaccc gctgacgcgc cctgacgggc ttgtctgctc ccggcatccg cttacagaca    6780
agctgtgacc gtctccggga gctgcatgtg tcagaggttt tcaccgtcat caccgaaacg    6840
cgcgagacga aagggcctcg tgatacgcct attttatag gttaatgtca tgaccaaaat    6900
cccttaacgt gagttttcgt tccactgagc gtcagacccc gtagaaaaga tcaaaggatc    6960
ttcttgagat cctttttttc tgcgcgtaat ctgctgcttg caaacaaaaa aaccaccgct    7020
accagcggtg gtttgtttgc cggatcaaga gctaccaact ctttttccga aggtaactgg    7080
cttcagcaga gcgcagatac caaatactgt ccttctagtg tagccgtagt taggccacca    7140
cttcaagaac tctgtagcac cgcctacata cctcgctctg ctaatcctgt taccagtggc    7200
tgctgccagt ggcgataagt cgtgtcttac cgggttggac tcaagacgat agttaccgga    7260
taaggcgcag cggtcgggct gaacgggggg ttcgtgcaca cagcccagct tggagcgaac    7320
gacctacacc gaactgagat acctacagcg tgagcattga gaaagcgcca cgcttcccga    7380
agggagaaag gcggacaggt atccggtaag cggcagggtc ggaacaggag agcgcacgag    7440
ggagcttcca gggggaaacg cctggtatct ttatagtcct gtcgggtttc gccacctctg    7500
acttgagcgt cgatttttgt gatgctcgtc agggggggcgg agcctatgga aaaacgccag    7560
caacgcggcc ttttttacggt tcctggcctt ttgctggcct tttgctcaca tgttctttcc    7620
tgcgttatcc cctgattctg tggataaccg tattaccgcc tttgagtgag ctgataccgc    7680
tcgccgcagc cgaacgaccg agcgcagcga gtcagtgagc gaggaagcgg aagagcgccc    7740
aatacgcaaa ccgcctctcc ccgcgcgttg gccgattcat taatgcaggt tgatcagatc    7800
tcgatcccgc gaaattaata cgactcacta tagggagacc acaacggttt ccctctagaa    7860
ataattttgt ttaactttaa gaaggagata tacccatgga aaagcctgaa ctcaccgcga    7920
cgtctgtcga agtttctg atcgaaaagt tcgacagcgt ctccgacctg atgcagctct    7980
cggagggcga agaatctcgt gctttcagct tcgatgtagg agggcgtgga tatgtcctgc    8040
gggtaaatag ctgcgccgat ggtttctaca aagatcgtta tgtttatcgg cactttgcat    8100
cggccgcgct cccgattccg gaagtgcttg acattgggga attcagcgag agcctgacct    8160
attgcatctc ccgccgtgca cagggtgtca cgttgcaaga cctgcctgaa accgaactgc    8220
ccgctgttct gcagccggtc gcggaggcta tggatgcgat cgctgcggcc gatcttagcc    8280
agacgagcgg gttcggccca ttcggaccgc aaggaatcgg tcaatacact acatggcgtg    8340
atttcatatg cgcgattgct gatccccatg tgtatcactg gcaaactgtg atggacgaca    8400
ccgtcagtgc gtccgtcgcg caggctctcg atgagctgat gctttgggcc gaggactgcc    8460
ccgaagtccg gcacctcgtg cacgcggatt tcggctccaa caatgtcctg acggacaatg    8520
gccgcataac agcggtcatt gactggagcg aggcgatgtt cggggattcc caatacgagg    8580
tcgccaacat cttcttctgg aggccgtggt tggcttgtat ggagcagcag acgcgctact    8640
tcgagcggag gcatccggag cttgcaggat cgccgcggct ccgggcgtat atgctccgca    8700
ttggtcttga ccaactctat cagagcttgg ttgacggcaa tttcgatgat gcagcttggg    8760
cgcagggtcg atgcgacgca atcgtccgat ccggagccgg gactgtcggg cgtacacaaa    8820
tcgcccgcag aagcgcggcc gtctggaccg atggctgtgt agaagtactc gccgatagtg    8880
gaaaccgacg ccccagcact cgtccgaggg caaaggaata gtgaggtaca gcttggatcg    8940
```

```
atccggctgc taacaaagcc cgaaaggaag ctgagttggc tgctgccacc gctgagcaat    9000
aactagcata accccttggg gcctctaaac gggtcttgag gggttttttg ctgaaaggag    9060
gaactatatc cggatgatcg ggcgcgccgg tac                                 9093
```

<210> SEQ ID NO 546
<211> LENGTH: 1113
<212> TYPE: DNA
<213> ORGANISM: Artificial sequence
<220> FEATURE:
<223> OTHER INFORMATION: synthesized sequence- RTW1026A

<400> SEQUENCE: 546

```
agcttggtac cgagctcgga tccactagta tggcggccac cgcttccaga accacccgat     60
tctcttcttc ctcttcacac cccaccttcc ccaaacgcat tactagatcc ccctccctc    120 tctctcatca aaccctcacc aaacccaacc acgctctcaa atcaaatgt tccatctcca    180 aacccccac ggcggcgccc ttcaccaagg aagcgccgac cacggagccc ttcgtgtcac    240
ggttcgcctc cggcgaacct cgcaagggcg cggacatcct tgtggaggcg ctggagaggc    300
agggcgtgac gacggtgttc gcgtaccccg gcggtgcgtc gatggagatc caccaggcgc    360
tcacgcgctc cgccgccatc cgcaacgtgc tcccgcgcca cgagcagggc ggcgtcttcg    420
ccgccgaagg ctacgcgcgt tcctccggcc tccccggcgt ctgcattgcc acctccggcc    480
ccggcgccac caacctcgtg agcggcctcg ccgacgcttt aatggacagc gtcccagtcg    540
tcgccatcac cggccaggtc agccgtcgca tgatcggtac cgacgccttc aagaaaccc    600 cgatcgtgga ggtgagcaga tccatcacga agcacaacta cctcatcctc gacgtcgacg    660
acatcccccg cgtcgtcgcc gaggctttct tcgtcgccac ctccggccgc cccggtccgg    720
tcctcatcga cattcccaaa gacgttcagc agcaactcgc cgtgcctaat tgggacgagc    780
ccgttaacct ccccggttac ctcgccaggc tgcccaggcc cccgccgag gcccaattgg    840 aacacattgt cagactcatc atggaggccc aaaagcccgt tctctacgtc ggcggtggca    900
gtttgaattc cagtgctgaa ttgaggcgct tgttgaact cactggtatt cccgttgcta    960
gcactttaat gggtcttgga acttttccta ttggtgatga atattccctt cagatgctgg   1020
gtatgcatgg tactgtttat gctaactatg ctgttgacaa tagtgatttg ttgcttgcct   1080
ttggggtaag gtttgatgac cgtgttactg gga                                1113
```

<210> SEQ ID NO 547
<211> LENGTH: 17
<212> TYPE: DNA
<213> ORGANISM: Artificial
<220> FEATURE:
<223> OTHER INFORMATION: synthesized sequence- WOL900, Forward_primer

<400> SEQUENCE: 547

```
atcaccggcc aggtcag                                                    17
```

<210> SEQ ID NO 548
<211> LENGTH: 25
<212> TYPE: DNA
<213> ORGANISM: Artificial
<220> FEATURE:
<223> OTHER INFORMATION: synthesized sequence- WOL578, Reverse_primer

<400> SEQUENCE: 548

```
acttaccctc cactcctttc tcctc                                           25
```

```
<210> SEQ ID NO 549
<211> LENGTH: 29
<212> TYPE: DNA
<213> ORGANISM: Artificial
<220> FEATURE:
<223> OTHER INFORMATION: synthesized sequence- WOL573, Forward_primer

<400> SEQUENCE: 549
atggcggcca ccgcttccag aaccacccg                                    29

<210> SEQ ID NO 550
<211> LENGTH: 638
<212> TYPE: PRT
<213> ORGANISM: zea mays

<400> SEQUENCE: 550
```

Met Ala Thr Ala Ala Ala Ser Thr Ala Leu Thr Gly Ala Thr Thr
1               5                   10                  15

Ala Ala Pro Lys Ala Arg Arg Arg Ala His Leu Leu Ala Thr Arg Arg
            20                  25                  30

Ala Leu Ala Ala Pro Ile Arg Cys Ser Ala Ala Ser Pro Ala Met Pro
        35                  40                  45

Met Ala Pro Pro Ala Thr Pro Leu Arg Pro Trp Gly Pro Thr Glu Pro
    50                  55                  60

Arg Lys Gly Ala Asp Ile Leu Val Glu Ser Leu Glu Arg Cys Gly Val
65                  70                  75                  80

Arg Asp Val Phe Ala Tyr Pro Gly Gly Ala Ser Met Glu Ile His Gln
                85                  90                  95

Ala Leu Thr Arg Ser Pro Val Ile Ala Asn His Leu Phe Arg His Glu
            100                 105                 110

Gln Gly Glu Ala Phe Ala Ala Ser Gly Tyr Ala Arg Ser Ser Gly Arg
        115                 120                 125

Val Gly Val Cys Ile Ala Thr Ser Gly Pro Gly Ala Thr Asn Leu Val
    130                 135                 140

Ser Ala Leu Ala Asp Ala Leu Leu Asp Ser Val Pro Met Val Ala Ile
145                 150                 155                 160

Thr Gly Gln Val Pro Arg Arg Met Ile Gly Thr Asp Ala Phe Gln Glu
                165                 170                 175

Thr Pro Ile Val Glu Val Thr Arg Ser Ile Thr Lys His Asn Tyr Leu
            180                 185                 190

Val Leu Asp Val Asp Asp Ile Pro Arg Val Val Gln Glu Ala Phe Phe
        195                 200                 205

Leu Ala Ser Ser Gly Arg Pro Gly Pro Val Leu Val Asp Ile Pro Lys
    210                 215                 220

Asp Ile Gln Gln Gln Met Ala Val Pro Val Trp Asp Lys Pro Met Ser
225                 230                 235                 240

Leu Pro Gly Tyr Ile Ala Arg Leu Pro Lys Pro Pro Ala Thr Glu Leu
                245                 250                 255

Leu Glu Gln Val Leu Arg Leu Val Gly Glu Ser Arg Arg Pro Val Leu
            260                 265                 270

Tyr Val Gly Gly Gly Cys Ala Ala Ser Gly Glu Glu Leu Arg Arg Phe
        275                 280                 285

Val Glu Leu Thr Gly Ile Pro Val Thr Thr Thr Leu Met Gly Leu Gly
    290                 295                 300

Asn Phe Pro Ser Asp Asp Pro Leu Ser Leu Arg Met Leu Gly Met His
305                 310                 315                 320

-continued

```
Gly Thr Val Tyr Ala Asn Tyr Ala Val Asp Lys Ala Asp Leu Leu Leu
                325                 330                 335

Ala Leu Gly Val Arg Phe Asp Asp Arg Val Thr Gly Lys Ile Glu Ala
            340                 345                 350

Phe Ala Ser Arg Ala Lys Ile Val His Val Asp Ile Asp Pro Ala Glu
        355                 360                 365

Ile Gly Lys Asn Lys Gln Pro His Val Ser Ile Cys Ala Asp Val Lys
    370                 375                 380

Leu Ala Leu Gln Gly Met Asn Ala Leu Leu Glu Gly Ser Thr Ser Lys
385                 390                 395                 400

Lys Ser Phe Asp Phe Gly Ser Trp Asn Asp Glu Leu Asp Gln Gln Lys
                405                 410                 415

Arg Glu Phe Pro Leu Gly Tyr Lys Thr Ser Asn Glu Glu Ile Gln Pro
            420                 425                 430

Gln Tyr Ala Ile Gln Val Leu Asp Glu Leu Thr Lys Gly Glu Ala Ile
        435                 440                 445

Ile Gly Thr Gly Val Gly Gln His Gln Met Trp Ala Ala Gln Tyr Tyr
    450                 455                 460

Thr Tyr Lys Arg Pro Arg Gln Trp Leu Ser Ser Ala Gly Leu Gly Ala
465                 470                 475                 480

Met Gly Phe Gly Leu Pro Ala Ala Ala Gly Ala Ser Val Ala Asn Pro
                485                 490                 495

Gly Val Thr Val Val Asp Ile Asp Gly Asp Gly Ser Phe Leu Met Asn
            500                 505                 510

Val Gln Glu Leu Ala Met Ile Arg Ile Glu Asn Leu Pro Val Lys Val
        515                 520                 525

Phe Val Leu Asn Asn Gln His Leu Gly Met Val Val Gln Trp Glu Asp
    530                 535                 540

Arg Phe Tyr Lys Ala Asn Arg Ala His Thr Tyr Leu Gly Asn Pro Glu
545                 550                 555                 560

Asn Glu Ser Glu Ile Tyr Pro Asp Phe Val Thr Ile Ala Lys Gly Phe
                565                 570                 575

Asn Ile Pro Ala Val Arg Val Thr Lys Lys Asn Glu Val Arg Ala Ala
            580                 585                 590

Ile Lys Lys Met Leu Glu Thr Pro Gly Pro Tyr Leu Leu Asp Ile Ile
        595                 600                 605

Val Pro His Gln Glu His Val Leu Pro Met Ile Pro Ser Gly Gly Ala
    610                 615                 620

Phe Lys Asp Met Ile Leu Asp Gly Asp Gly Arg Thr Val Tyr
625                 630                 635

<210> SEQ ID NO 551
<211> LENGTH: 23
<212> TYPE: DNA
<213> ORGANISM: Glycine max

<400> SEQUENCE: 551
gtgtttggaa cccttgagag agg                                              23

<210> SEQ ID NO 552
<211> LENGTH: 22
<212> TYPE: DNA
<213> ORGANISM: Glycine max

<400> SEQUENCE: 552
caaagccacc attcactgtt gg                                               22
```

<210> SEQ ID NO 553
<211> LENGTH: 9174
<212> TYPE: DNA
<213> ORGANISM: Artificial sequence
<220> FEATURE:
<223> OTHER INFORMATION: synthesized sequence RTW1211

<400> SEQUENCE: 553

| | | | | | |
|---|---|---|---|---|---|
| atgagaaagc | gccacgcttc | ccgaagggag | aaaggcggac | aggtatccgg | taagcggcag | 60 |
| ggtcggaaca | ggagagcgca | cgagggagct | ccaggggga | aacgcctggt | atctttatag | 120 |
| tcctgtcggg | tttcgccacc | tctgacttga | gcgtcgattt | tgtgatgct | cgtcaggggg | 180 |
| gcggagccta | tggaaaaacg | ccagcaacgc | ggccttttta | cggttcctgg | cctttgctg | 240 |
| gccttttgct | cacatgttct | ttcctgcgtt | atccctgat | tctgtggata | accgtattac | 300 |
| cgcctttgag | tgagctgata | ccgctcgccg | cagccgaacg | accgagcgca | gcgagtcagt | 360 |
| gagcgaggaa | gcggaagagc | gcccaatacg | caaaccgcct | ctccccgcgc | gttggccgat | 420 |
| tcattaatgc | aggttgatca | gatctcgatc | ccgcgaaatt | aatacgactc | actataggga | 480 |
| gaccacaacg | gtttccctct | agaaataatt | ttgtttaact | ttaagaagga | gatatacca | 540 |
| tggaaaagcc | tgaactcacc | gcgacgtctg | tcgagaagtt | tctgatcgaa | aagttcgaca | 600 |
| gcgtctccga | cctgatgcag | ctctcggagg | gcgaagaatc | tcgtgctttc | agcttcgatg | 660 |
| taggagggcg | tggatatgtc | ctgcgggtaa | atagctgcgc | cgatggtttc | tacaaagatc | 720 |
| gttatgttta | tcggcacttt | gcatcggccg | cgctcccgat | tccggaagtg | cttgacattg | 780 |
| gggaattcag | cgagagcctg | acctattgca | tctcccgccg | tgcacagggt | gtcacgttgc | 840 |
| aagacctgcc | tgaaaccgaa | ctgcccgctg | ttctgcagcc | ggtcgcggag | gctatggatg | 900 |
| cgatcgctgc | ggccgatctt | agccagacga | gcgggttcgg | cccattcgga | ccgcaaggaa | 960 |
| tcggtcaata | cactacatgg | cgtgatttca | tatgcgcgat | tgctgatccc | catgtgtatc | 1020 |
| actggcaaac | tgtgatggac | gacaccgtca | gtgcgtccgt | cgcgcaggct | ctcgatgagc | 1080 |
| tgatgctttg | ggccgaggac | tgccccgaag | tccggcacct | cgtgcacgcg | gatttcggct | 1140 |
| ccaacaatgt | cctgacggac | aatggccgca | taacagcggt | cattgactgg | agcgaggcga | 1200 |
| tgttcgggga | ttcccaatac | gaggtcgcca | acatcttctt | ctggaggccg | tggttggctt | 1260 |
| gtatggagca | gcagacgcgc | tacttcgagc | ggaggcatcc | ggagcttgca | ggatcgccgc | 1320 |
| ggctccgggc | gtatatgctc | cgcattggtc | ttgaccaact | ctatcagagc | ttggttgacg | 1380 |
| gcaatttcga | tgatgcagct | tgggcgcagg | tcgatgcga | cgcaatcgtc | cgatccggag | 1440 |
| ccgggactgt | cgggcgtaca | caaatcgccc | gcagaagcgc | ggccgtctgg | accgatggct | 1500 |
| gtgtagaagt | actcgccgat | agtggaaacc | gacgccccag | cactcgtccg | agggcaaagg | 1560 |
| aatagtgagg | tacagcttgg | atcgatccgg | ctgctaacaa | agcccgaaag | gaagctgagt | 1620 |
| tggctgctgc | caccgctgag | caataactag | cataaccct | tggggcctct | aaacgggtct | 1680 |
| tgaggggttt | tttgctgaaa | ggaggaacta | tatccggatg | ctcgggcgcg | ccggtacccg | 1740 |
| ggtgtgattt | agtataaagt | gaagtaatgg | tcaaaagaaa | aagtgtaaaa | cgaagtacct | 1800 |
| agtaataagt | aatattgaac | aaaataaatg | gtaaagtgtc | agatatataa | aataggcttt | 1860 |
| aataaaagga | agaaaaaaa | caaacaaaaa | ataggttgca | atgggcaga | gcagagtcat | 1920 |
| catgaagcta | gaaaggctac | cgatagataa | actatagtta | attaaataca | ttaaaaaata | 1980 |
| cttggatctt | tctcttaccc | tgtttatatt | gagacctgaa | acttgagaga | gatacactaa | 2040 |

```
tcttgccttg ttgtttcatt ccctaactta caggactcag cgcatgtcat gtggtctcgt    2100
tccccattta agtcccacac cgtctaaact tattaaatta ttaatgttta taactagatg    2160
cacaacaaca aagcttgtgt ttggaaccct tgagaggttt tagagctaga aatagcaagt    2220
taaaataagg ctagtccgtt atcaacttga aaaagtggca ccgagtcggt gcttttttt     2280 gcggccgcaa ttggatcggg tttacttatt ttgtgggtat ctatactttt attagatttt    2340
taatcaggct cctgatttct ttttatttcg attgaattcc tgaacttgta ttattcagta    2400
gatcgaataa attataaaaa gataaaatca taaaataata ttttatccta tcaatcatat    2460
taaagcaatg aatatgtaaa attaatctta tctttatttt aaaaaatcat ataggtttag    2520
tattttttta aaaataaaga taggattagt tttactattc actgcttatt acttttaaaa    2580
aaatcataaa ggtttagtat ttttttaaaa taaatatagg aatagtttta ctattcactg    2640
ctttaataga aaaatagttt aaaatttaag atagttttaa tcccagcatt tgccacgttt    2700
gaacgtgagc cgaaacgatg tcgttacatt atcttaacct agctgaaacg atgtcgtcat    2760
aatatcgcca aatgccaact ggactacgtc gaacccacaa atcccacaaa gcgcgtgaaa    2820
tcaaatcgct caaccacaa aaaagaacaa cgcgtttgtt acacgctcaa tcccacgcga    2880
gtagagcaca gtaaccttca aataagcgaa tggggcataa tcagaaatcc gaaataaacc    2940
taggggcatt atcggaaatg aaaagtagct cactcaatat aaaaatctag gaaccctagt    3000
tttcgttatc actctgtgct ccctcgctct atttctcagt ctctgtgttt gcggctgagg    3060
attccgaacg agtgaccttc ttcgtttctc gcaaaggtaa cagcctctgc tcttgtctct    3120
tcgattcgat ctatgcctgt ctcttatta cgatgatgtt tcttcggtta tgttttttta    3180
tttatgcttt atgctgttga tgttcggttg tttgtttcgc tttgttttg tggttcagtt    3240 ttttaggatt cttttggttt ttgaatcgat taatcggaag agattttcga gttatttggt    3300
gtgttggagg tgaatctttt ttttgaggtc atagatctgt tgtatttgtg ttataaacat    3360
gcgactttgt atgattttt acgaggttat gatgttctgg ttgtttttatt atgaatctgt    3420 tgagacagaa ccatgatttt tgttgatgtt cgtttacact attaaaggtt tgttttaaca    3480
ggattaaaag ttttttaagc atgttgaagg agtcttgtag atatgtaacc gtcgatagtt    3540
tttttgtggg tttgttcaca tgttatcaag cttaatcttt tactatgtat gcgaccatat    3600
ctggatccag caaaggcgat tttttaattc cttgtgaaac ttttgtaata tgaagttgaa    3660
attttgttat tggtaaacta taaatgtgtg aagttggagt ataccttac cttcttattt     3720 ggctttgtga tagtttaatt tatatgtatt ttgagttctg acttgtattt ctttgaattg    3780
attctagttt aagtaatcca tggcaccgaa gaagaagcgc aaggtgatgg acaaaaagta    3840
ctcaataggg ctcgacatag ggactaactc cgttggatgg gccgtcatca ccgacgagta    3900
caaggtgccc tccaagaagt tcaaggtgtt gggaaacacc gacaggcaca gcataaagaa    3960
gaatttgatc ggtgccctcc tcttcgactc cggagagacc gctgaggcta ccaggctcaa    4020
gaggaccgct agaaggcgct acaccagaag gaagaacaga atctgctacc tgcaggagat    4080
cttctccaac gagatggcca aggtggacga ctccttcttc caccgccttg aggaatcatt    4140
cctggtggag gaggataaaa agcacgagag acacccaatc ttcgggaaca tcgtcgacga    4200
ggtggcctac catgaaaagt accctaccat ctaccacctg aggaagaagc tggtcgactc    4260
taccgacaag gctgacttgc gcttgattta cctggctctc gctcacatga taaagttccg    4320
cggacacttc ctcattgagg gagacctgaa cccagacaac tccgacgtgg acaagctctt    4380
catccagctc gttcagacct acaaccagct tttcgaggag aacccaatca cgccagtgg    4440
```

```
agttgacgcc aaggctatcc tctctgctcg tctgtcaaag tccaggaggc ttgagaactt    4500
gattgcccag ctgcctggcg aaaagaagaa cggactgttc ggaaacttga tcgctctctc    4560
cctgggattg actcccaact tcaagtccaa cttcgacctc gccgaggacg ctaagttgca    4620
gttgtctaaa gacacctacg acgatgacct cgacaacttg ctggcccaga taggcgacca    4680
atacgccgat ctcttcctcg ccgctaagaa cttgtccgac gcaatcctgc tgtccgacat    4740
cctgagagtc aacactgaga ttaccaaagc tcctctgtct gcttccatga ttaagcgcta    4800
cgacgagcac caccaagatc tgaccctgct caaggccctg gtgagacagc agctgcccga    4860
gaagtacaag gagatctttt tcgaccagtc caagaacggc tacgccggat acattgacgg    4920
aggcgcctcc caggaagagt tctacaagtt catcaagccc atccttgaga gatggacgg    4980
taccgaggag ctgttggtga agttgaacag agaggacctg ttgaggaagc agagaacctt    5040
cgacaacgga agcatccctc accaaatcca cctgggagag ctccacgcca tcttgaggag    5100
gcaggaggat ttctatccct tcctgaagga caaccgcgag aagattgaga agatcttgac    5160
cttcagaatt ccttactacg tcgggccact cgccagagga aactctaggt tcgcctggat    5220
gacccgcaaa tctgaagaga ccattactcc ctggaacttc gaggaagtcg tggacaaggg    5280
cgcttccgct cagtctttca tcgagaggat gaccaacttc gataaaaatc tgcccaacga    5340
gaaggtgctg cccaagcact ccctgttgta cgagtatttc acagtgtaca acagctcac    5400
caaggtgaag tacgtcacag agggaatgag gaagcctgcc ttcttgtccg gagagcagaa    5460
gaaggccatc gtcgacctgc tcttcaagac caacaggaag gtgactgtca agcagctgaa    5520
ggaggactac ttcaagaaga tcgagtgctt cgactccgtc gagatctctg tgtcgagga    5580
caggttcaac gcctcccttg ggacttacca cgatctgctc aagattatta agacaaggga    5640
cttcctggac aacgaggaga acgaggacat ccttgaggac atcgtgctca ccctgacctt    5700
gttcgaagac agggaaatga tcgaagagag gctcaagacc tacgcccacc tcttcgacga    5760
caaggtgatg aaacagctga agagacgcag atataccggc tggggaaggc tctcccgcaa    5820
attgatcaac gggatcagg acaagcagtc agggaagact atactcgact tcctgaagtc    5880
cgacggattc gccaacagga acttcatgca gctcattcac gacgactcct tgaccttcaa    5940
ggaggacatc cagaaggctc aggtgtctgg acagggtgac tccttgcatg agcacattgc    6000
taacttggcc ggctctcccg ctattaagaa gggcattttg cagaccgtga aggtcgttga    6060
cgagctcgtg aaggtgatgg gacgccacaa gccagagaac atcgttattg agatggctcg    6120
cgagaaccaa actacccaga aagggcagaa gaattcccgc gagaggatga gcgcattga    6180
ggagggcata aaagagcttg gctctcagat cctcaaggag caccccgtcg agaacactca    6240
gctgcagaac gagaagctgt acctgtacta cctccaaaac ggaagggaca tgtacgtgga    6300
ccaggagctg gacatcaaca ggttgtccga ctacgacgtc gaccacatcg tgcctcagtc    6360
cttcctgaag gatgactcca tcgacaataa agtgctgaca cgctccgata aaaatagagg    6420
caagtccgac aacgtcccct ccgaggaggt cgtgaagaag atgaaaaact actggagaca    6480
gctcttgaac gccaagctca tcacccagcg taagttcgac aacctgacta aggctgagag    6540
aggaggattg tccgagctcg ataaggccgg attcatcaag agacagctcg tcgaaacccg    6600
ccaaattacc aagcacgtgg cccaaattct ggattcccgc atgaacacca agtacgatga    6660
aaatgacaag ctgatccgcg aggtcaaggt gatcaccttg aagtccaagc tggtctccga    6720
cttccgcaag gacttccagt tctacaaggt gagggagatc aacaactacc accacgcaca    6780
```

```
cgacgcctac ctcaacgctg tcgttggaac cgccctcatc aaaaaatatc ctaagctgga      6840
gtctgagttc gtctacggcg actacaaggt gtacgacgtg aggaagatga tcgctaagtc      6900
tgagcaggag atcggcaagg ccaccgccaa gtacttcttc tactccaaca tcatgaactt      6960
cttcaagacc gagatcactc tcgccaacgg tgagatcagg aagcgcccac tgatcgagac      7020
caacggtgag actggagaga tcgtgtggga caaagggagg gatttcgcta ctgtgaggaa      7080
ggtgctctcc atgcctcagg tgaacatcgt caagaagacc gaagttcaga ccggaggatt      7140
ctccaaggag tccatcctcc ccaagagaaa ctccgacaag ctgatcgcta gaaagaaaga      7200
ctgggaccct aagaagtacg gaggcttcga ttctcctacc gtggcctact ctgtgctggt      7260
cgtggccaag gtggagaagg gcaagtccaa gaagctgaaa tccgtcaagg agctcctcgg      7320
gattaccatc atggagagga gttccttcga agaaccccct atcgacttcc tggaggccaa      7380
gggatataaa gaggtgaaga aggacctcat catcaagctg cccaagtact ccctcttcga      7440
gttggagaac ggaaggaaga ggatgctggc ttctgccgga gagttgcaga agggaaatga      7500
gctcgcccct ccctccaagt acgtgaactt cctgtacctc gcctctcact atgaaaagtt      7560
gaagggctct cctgaggaca cgagcagaa gcagctcttc gtggagcagc acaagcacta      7620
cctggacgaa attatcgagc agatctctga gttctccaag cgcgtgatat tggccgacgc      7680
caacctcgac aaggtgctgt ccgcctacaa caagcacagg gataagccca ttcgcgagca      7740
ggctgaaaac attatccacc tgtttaccct cacaaacttg ggagcccctg ctgccttcaa      7800
gtacttcgac accaccattg acaggaagag atacacctcc accaaggagg tgctcgacgc      7860
aacactcatc caccaatcca tcaccggcct ctatgaaaca aggattgact tgtcccagct      7920
gggaggcgac tctagagccg atcccaagaa gaagagaaag gtgaagagac cacgggaccg      7980
ccacgatggc gagctgggag ccgcaagcg ggcaaggtag gttaacctag acttgtccat      8040
cttctggatt ggccaactta attaatgtat gaaataaaag gatgcacaca tagtgacatg      8100
ctaatcacta taatgtgggc atcaaagttg tgtgttatgt gtaattacta gttatctgaa      8160
taaaagagaa agagatcatc catatttctt atcctaaatg aatgtcacgt gtctttataa      8220
ttctttgatg aaccagatgc atttcattaa ccaaatccat atacatataa atattaatca      8280
tatataatta atatcaattg ggttagcaaa acaaatctag tctaggtgtg ttttgcgaat      8340
tcgatatcaa gcttatcgat accgtcgagg ggggcccgg taccggcgcg ccgttctata      8400
gtgtcaccta atcgtatgt gtatgataca taaggttatg tattaattgt agccgcgttc      8460
taacgacaat atgtccatat ggtgcactct cagtacaatc tgctctgatg ccgcatagtt      8520
aagccagccc cgacacccgc caacacccgc tgacgcgccc tgacgggctt gtctgctccc      8580
ggcatccgct tacagacaag ctgtgaccgt ctccgggagc tgcatgtgtc agaggttttc      8640
accgtcatca ccgaaacgcg cgagacgaaa gggcctcgtg atacgcctat ttttataggt      8700
taatgtcatg accaaaatcc cttaacgtga gttttcgttc cactgagcgt cagaccccgt      8760
agaaaagatc aaaggatctt cttgagatcc ttttttctg cgcgtaatct gctgcttgca      8820
aacaaaaaaa ccaccgctac cagcggtggt ttgtttgccg gatcaagagc taccaactct      8880
ttttccgaag gtaactggct tcagcagagc gcagatacca atactgttc ttctagtgta      8940
gccgtagtta ggccaccact tcaagaactc tgtagcaccg cctacatacc tcgctctgct      9000
aatcctgtta ccagtggctg ctgccagtgg cgataagtcg tgtcttaccg ggttggactc      9060
aagacgatag ttaccggata aggcgcagcg gtcgggctga acggggggtt cgtgcacaca      9120
gcccagcttg gagcgaacga cctacaccga actgagatac ctacagcgtg agct            9174
```

<210> SEQ ID NO 554
<211> LENGTH: 9174
<212> TYPE: DNA
<213> ORGANISM: Artificial sequence
<220> FEATURE:
<223> OTHER INFORMATION: synthesized sequence RTW1212

<400> SEQUENCE: 554

```
tgcacacagc ccagcttgga gcgaacgacc tacaccgaac tgagatacct acagcgtgag      60
ctatgagaaa gcgccacgct tcccgaaggg agaaaggcgg acaggtatcc ggtaagcggc     120
agggtcggaa caggagagcg cacgagggag cttccagggg gaaacgcctg gtatctttat     180
agtcctgtcg ggtttcgcca cctctgactt gagcgtcgat ttttgtgatg ctcgtcaggg     240
gggcggagcc tatggaaaaa cgccagcaac gcggcctttt tacggttcct ggccttttgc     300
tggccttttg ctcacatgtt ctttcctgcg ttatcccctg attctgtgga taaccgtatt     360
accgcctttg agtgagctga taccgctcgc cgcagccgaa cgaccgagcg cagcgagtca     420
gtgagcgagg aagcggaaga gcgcccaata cgcaaaccgc ctctccccgc gcgttggccg     480
attcattaat gcaggttgat cagatctcga tcccgcgaaa ttaatacgac tcactatagg     540
gagaccacaa cggtttccct ctagaaataa ttttgtttaa ctttaagaag gagatatacc     600
catggaaaag cctgaactca ccgcgacgtc tgtcgagaag tttctgatcg aaaagttcga     660
cagcgtctcc gacctgatgc agctctcgga gggcgaagaa tctcgtgctt tcagcttcga     720
tgtaggaggg cgtggatatg tcctgcgggt aaatagctgc gccgatggtt tctacaaaga     780
tcgttatgtt tatcggcact ttgcatcggc cgcgctcccg attccggaag tgcttgacat     840
tggggaattc agcgagagcc tgacctattg catctcccgc cgtgcacagg gtgtcacgtt     900
gcaagacctg cctgaaaccg aactgcccgc tgttctgcag ccggtcgcgg aggctatgga     960
tgcgatcgct gcggccgatc ttagccagac gagcgggttc ggcccattcg gaccgcaagg    1020
aatcggtcaa tacactacat ggcgtgattt catatgcgcg attgctgatc cccatgtgta    1080
tcactggcaa actgtgatgg acgacaccgt cagtgcgtcc gtcgcgcagg ctctcgatga    1140
gctgatgctt tgggccgagg actgccccga agtccggcac ctcgtgcacg cggatttcgg    1200
ctccaacaat gtcctgacgg acaatggccg cataacagcg gtcattgact ggagcgaggc    1260
gatgttcggg gattcccaat acgaggtcgc caacatcttc ttctggaggc cgtggttggc    1320
ttgtatggag cagcagacgc gctacttcga gcggaggcat ccggagcttg caggatcgcc    1380
gcggctccgg gcgtatatgc tccgcattgg tcttgaccaa ctctatcaga gcttggttga    1440
cggcaatttc gatgatgcag cttgggcgca gggtcgatgc gacgcaatcg tccgatccgg    1500
agccgggact gtcgggcgta cacaaatcgc ccgcagaagc gcggccgtct ggaccgatgg    1560
ctgtgtagaa gtactcgccg atagtggaaa ccgacgcccc agcactcgtc cgagggcaaa    1620
ggaatagtga ggtacagctt ggatcgatcc ggctgctaac aaagcccgaa aggaagctga    1680
gttggctgct gccaccgctg agcaataact agcataaccc cttggggcct ctaaacgggt    1740
cttgaggggt tttttgctga aggaggaac tatatccgga tgctcgggcg cgccggtacc    1800
cgggtgtgat ttagtataaa gtgaagtaat ggtcaaaaga aaaagtgtaa aacgaagtac    1860
ctagtaataa gtaatattga acaaaataaa tggtaaagtg tcagatatat aaaataggct    1920
ttaataaaag gaagaaaaaa acaaacaaa aaataggttg caatgggca gagcagagtc    1980
atcatgaagc tagaaaggct accgatagat aaactatagt taattaaata cattaaaaaa    2040
```

```
tacttggatc tttctcttac cctgtttata ttgagacctg aaacttgaga gagatacact    2100
aatcttgcct tgttgtttca ttccctaact tacaggactc agcgcatgtc atgtggtctc    2160
gttccccatt taagtcccac accgtctaaa cttattaaat tattaatgtt tataactaga    2220
tgcacaacaa caaagcttgc aaagccacca ttcactgtgt tttagagcta gaaatagcaa    2280
gttaaaataa ggctagtccg ttatcaactt gaaaaagtgg caccgagtcg gtgcttttttt   2340
ttgcggccgc aattggatcg ggtttactta ttttgtgggt atctatactt ttattagatt    2400
tttaatcagg ctcctgattt cttttattt cgattgaatt cctgaacttg tattattcag     2460
tagatcgaat aaattataaa aagataaaat catgaaataa tatttatcc tatcaatcat     2520
attaaagcaa tgaatatgta aaattaatct tatctttatt ttaaaaaatc ataggtttt     2580
agtatttttt taaaaataaa gataggatta gttttactat tcactgctta ttacttttaa    2640
aaaaatcata aaggtttagt attttttttaa aataaatata ggaatagttt tactattcac   2700
tgctttaata gaaaaatagt ttaaaattta agatagtttt aatcccagca tttgccacgt    2760
ttgaacgtga gccgaaacga tgtcgttaca ttatcttaac ctagctgaaa cgatgtcgtc    2820
ataatatcgc caaatgccaa ctggactacg tcgaacccac aaatcccaca agcgcgtga    2880
aatcaaatcg ctcaaaccac aaaaaagaac aacgcgtttg ttacacgctc aatcccacgc    2940
gagtagagca cagtaacctt caaataagcg aatggggcat aatcagaaat ccgaaataaa    3000
cctagggca ttatcggaaa tgaaagtag ctcactcaat ataaaaatct aggaacccta      3060
gttttcgtta tcactctgtg ctccctcgct ctatttctca gtctctgtgt ttgcggctga    3120
ggattccgaa cgagtgacct tcttcgtttc tcgcaaaggt aacagcctct gctcttgtct    3180
cttcgattcg atctatgcct gtctcttatt tacgatgatg tttcttcggt tatgtttttt    3240
tatttatgct ttatgctgtt gatgttcggt tgtttgtttc gctttgtttt tgtggttcag    3300
ttttttagga ttcttttggt ttttgaatcg attaatcgga agagattttc gagttatttg    3360
gtgtgttgga ggtgaatctt ttttttgagg tcatagatct gttgtatttg tgttataaac    3420
atgcgacttt gtatgatttt ttacgaggtt atgatgttct ggttgtttta ttatgaatct    3480
gttgagacag aaccatgatt tttgttgatg ttcgttaca ctattaaagg tttgttttaa     3540
caggattaaa agttttttaa gcatgttgaa ggagtcttgt agatatgtaa ccgtcgatag    3600
ttttttgtg ggtttgttca catgttatca agcttaatct tttactatgt atgcgaccat     3660
atctggatcc agcaaaggcg atttttttaat tccttgtgaa acttttgtaa tatgaagttg    3720
aaatttttgtt attggtaaac tataaatgtg tgaagttgga gtataccttt accttcttat   3780
ttggctttgt gatagtttaa tttatatgta ttttgagttc tgacttgtat ttctttgaat    3840
tgattctagt ttaagtaatc catggcaccg aagaagaagc gcaaggtgat ggacaaaaag    3900
tactcaatag ggctcgacat agggactaac tccgttggat gggccgtcat caccgacgag    3960
tacaaggtgc cctccaagaa gttcaaggtg ttgggaaaca ccgacaggca cagcataaag    4020
aagaatttga tcggtgccct cctcttcgac tccggagaga ccgctgaggc taccaggctc    4080
aagaggaccg ctagaaggcg ctacaccaga aggaagaaca gaatctgcta cctgcaggag    4140
atcttctcca acgagatggc caaggtggac gactccttct tccaccgcct tgaggaatca    4200
ttcctggtgg aggaggataa aaagcacgag agacacccaa tcttcgggaa catcgtcgac    4260
gaggtggcct accatgaaaa gtaccctacc atctaccacc tgaggaagaa gctggtcgac    4320
tctaccgaca aggctgactt gcgcttgatt tacctggctc tcgctcacat gataaagttc    4380
cgcggacact tcctcattga gggagacctg aacccagaca actccgacgt ggacaagctc    4440
```

```
ttcatccagc tcgttcagac ctacaaccag cttttcgagg agaacccaat caacgccagt    4500
ggagttgacg ccaaggctat cctctctgct cgtctgtcaa agtccaggag gcttgagaac    4560
ttgattgccc agctgcctgg cgaaaagaag aacggactgt tcggaaactt gatcgctctc    4620
tccctgggat tgactcccaa cttcaagtcc aacttcgacc tcgccgagga cgctaagttg    4680
cagttgtcta agacaccta cgacgatgac ctcgacaact tgctggccca gataggcgac    4740
caatacgccg atctcttcct cgccgctaag aacttgtccg acgcaatcct gctgtccgac    4800
atcctgagag tcaacactga gattaccaaa gctcctctgt ctgcttccat gattaagcgc    4860
tacgacgagc accaccaaga tctgaccctg ctcaaggccc tggtgagaca gcagctgccc    4920
gagaagtaca aggagatctt tttcgaccag tccaagaacg gctacgccgg atacattgac    4980
ggaggcgcct cccaggaaga gttctacaag ttcatcaagc ccatccttga gaagatggac    5040
ggtaccgagg agctgttggt gaagttgaac agagaggacc tgttgaggaa gcagagaacc    5100
ttcgacaacg gaagcatccc tcaccaaatc cacctgggag agctccacgc catcttgagg    5160
aggcaggagg atttctatcc cttcctgaag gacaaccgcg agaagattga agatcttg     5220 accttcagaa ttccttacta cgtcgggcca ctcgccagag gaaactctag gttcgcctgg    5280
atgacccgca atctgaaga gaccattact ccctggaact tcgaggaagt cgtggacaag    5340
ggcgcttccg ctcagtcttt catcgagagg atgaccaact tcgataaaaa tctgcccaac    5400
gagaaggtgc tgcccaagca ctccctgttg tacgagtatt tcacagtgta caacgagctc    5460
accaaggtga agtacgtcac agagggaatg aggaagcctg ccttcttgtc cggagagcag    5520
aagaaggcca tcgtcgacct gctctcttcaag accaacagga aggtgactgt caagcagctg    5580
aaggaggact acttcaagaa gatcgagtgc ttcgactccg tcgagatctc tggtgtcgag    5640
gacaggttca acgcctccct tgggacttac cacgatctgc tcaagattat taaagacaag    5700
gacttcctgg acaacgagga gaacgaggac atccttgagg catcgtgct cacccctgacc    5760 ttgttcgaag acagggaaat gatcgaagag aggctcaaga cctacgccca cctcttcgac    5820
gacaaggtga tgaaacagct gaagagacgc agatataccg gctggggaag gctctcccgc    5880
aaattgatca acgggatcag ggacaagcag tcagggaaga ctatactcga cttcctgaag    5940
tccgacggat tcgccaacag gaacttcatg cagctcattc acgacgactc cttgaccttc    6000
aaggaggaca tccagaaggc tcaggtgtct ggacagggtg actccttgca tgagcacatt    6060
gctaacttgg ccggctctcc cgctattaag aagggcattt tgcagaccgt gaaggtcgtt    6120
gacgagctcg tgaaggtgat gggacgccac aagccagaga acatcgttat tgagatggct    6180
cgcgagaacc aaactaccca gaaagggcag aagaattccc gcgagaggat gaagcgcatt    6240
gaggagggca taaagagct tggctctcag atcctcaagg agcacccgt cgagaacact    6300 cagctgcaga acgagaagct gtacctgtac tacctccaaa acggaaggga catgtacgtg    6360
gaccaggagc tggacatcaa caggttgtcc gactacgacg tcgaccacat cgtgcctcag    6420
tccttcctga aggatgactc catcgacaat aaagtgctga cacgctccga taaaaataga    6480
ggcaagtccg acaacgtccc ctccgaggag gtcgtgaaga gatgaaaaa ctactggaga    6540 cagctcttga cgccaagct catcacccag cgtaagttcg acaacctgac taaggctgag    6600
agaggaggat tgtccgagct cgataaggcc ggattcatca agagacagct cgtcgaaacc    6660
cgccaaatta ccaagcacgt ggcccaaatt ctggattccc gcatgaacac caagtacgat    6720
gaaaatgaca agctgatccg cgaggtcaag gtgatcacct tgaagtccaa gctggtctcc    6780
```

```
gacttccgca aggacttcca gttctacaag gtgagggaga tcaacaacta ccaccacgca    6840
cacgacgcct acctcaacgc tgtcgttgga accgccctca tcaaaaaata tcctaagctg    6900
gagtctgagt tcgtctacgg cgactacaag gtgtacgacg tgaggaagat gatcgctaag    6960
tctgagcagg agatcggcaa ggccaccgcc aagtacttct tctactccaa catcatgaac    7020
ttcttcaaga ccgagatcac tctcgccaac ggtgagatca ggaagcgccc actgatcgag    7080
accaacggtg agactggaga gatcgtgtgg gacaaaggga gggatttcgc tactgtgagg    7140
aaggtgctct ccatgcctca ggtgaacatc gtcaagaaga ccgaagttca gaccggagga    7200
ttctccaagg agtccatcct ccccaagaga aactccgaca agctgatcgc tagaaagaaa    7260
gactgggacc ctaagaagta cggaggcttc gattctccta ccgtggccta ctctgtgctg    7320
gtcgtggcca aggtggagaa gggcaagtcc aagaagctga atccgtcaa ggagctcctc     7380
gggattacca tcatggagag gagttccttc gagaagaacc ctatcgactt cctggaggcc    7440
aagggatata agaggtgaa gaaggacctc atcatcaagc tgcccaagta ctccctcttc     7500
gagttggaga acgaaggaa gaggatgctg gcttctgccg agagttgca gaagggaaat     7560
gagctcgccc ttccctccaa gtacgtgaac ttcctgtacc tcgcctctca ctatgaaaag    7620
ttgaagggct ctcctgagga caacgagcag aagcagctct tcgtggagca gcacaagcac    7680
tacctggacg aaattatcga gcagatctct gagttctcca gcgcgtgat attggccgac    7740
gccaacctcg acaaggtgct gtccgcctac aacaagcaca gggataagcc cattcgcgag    7800
caggctgaaa acattatcca cctgtttacc ctcacaaact gggagcccc tgctgccttc     7860
aagtacttcg acaccaccat tgacaggaag agatacacct ccaccaagga ggtgctcgac    7920
gcaacactca tccaccaatc catcaccggc ctctatgaaa caaggattga cttgtcccag    7980
ctgggaggcg actctagagc cgatcccaag aagaagagaa aggtgaagag accacgggac    8040
cgccacgatg gcgagctggg aggccgcaag cgggcaaggt aggttaacct agacttgtcc    8100
atcttctgga ttggccaact taattaatgt atgaaataaa aggatgcaca catagtgaca    8160
tgctaatcac tataatgtgg gcatcaaagt tgtgtgttat gtgtaattac tagttatctg    8220
aataaaagag aaagagatca tccatatttc ttatcctaaa tgaatgtcac gtgtcttat     8280
aattctttga tgaaccagat gcatttcatt aaccaaatcc atatacatat aaatattaat    8340
catatataat taatatcaat tggggttagca aaacaaatct agtctaggtg tgttttgcga    8400
attcgatatc aagcttatcg ataccgtcga ggggggggccc ggtaccggcg cgccgttcta   8460
tagtgtcacc taaatcgtat gtgtatgata cataaggtta tgtattaatt gtagccgcgt    8520
tctaacgaca atatgtccat atggtgcact ctcagtacaa tctgctctga tgccgcatag    8580
ttaagccagc cccgacaccc gccaacaccc gctgacgcgc cctgacgggc ttgtctgctc    8640
ccggcatccg cttacagaca agctgtgacc gtctccggga gctgcatgtg tcagaggttt    8700
tcaccgtcat caccgaaacg cgcgagacga aagggcctcg tgatacgcct attttttatag   8760
gttaatgtca tgaccaaaat cccttaacgt gagttttcgt tccactgagc gtcagacccc    8820
gtagaaaaga tcaaaggatc ttcttgagat cctttttttc tgcgcgtaat ctgctgcttg    8880
caaacaaaaa aaccaccgct accagcggtg gtttgtttgc cggatcaaga gctaccaact    8940
cttttccga aggtaactgg cttcagcaga gcgcagatac caaatactgt tcttctagtg     9000
tagccgtagt taggccacca cttcaagaac tctgtagcac cgcctacata cctcgctctg    9060
ctaatcctgt taccagtggc tgctgccagt ggcgataagt cgtgtcttac cgggttggac    9120
tcaagacgat agttaccgga taaggcgcag cggtcgggct gaacggggg ttcg           9174
```

```
<210> SEQ ID NO 555
<211> LENGTH: 43
<212> TYPE: DNA
<213> ORGANISM: Zea mays

<400> SEQUENCE: 555
gatatatata cctcacacgt acgcgtacgc gtatatatac gtg          43

<210> SEQ ID NO 556
<211> LENGTH: 43
<212> TYPE: DNA
<213> ORGANISM: Zea mays

<400> SEQUENCE: 556
cacgtatata tacgcgtacg cgtacgtgtg aggtatatat atc          43

<210> SEQ ID NO 557
<211> LENGTH: 104
<212> TYPE: DNA
<213> ORGANISM: Artificial sequence
<220> FEATURE:
<223> OTHER INFORMATION: synthesized sequence- sequence of Figure

<400> SEQUENCE: 557
gtcccttgta cttgtacgta gttttagagc tagaaatagc aagttaaaat aaggctagtc    60
cgttatcaac ttgaaaaagt ggcaccgagt cggtgctttt tttt                    104

<210> SEQ ID NO 558
<211> LENGTH: 70
<212> TYPE: DNA
<213> ORGANISM: Glycine max

<400> SEQUENCE: 558
atcaaaattc ggaactgaca cacgacatga tggaacgtga ctaaggtggg tttttgactt    60
tgcatgtcga                                                           70

<210> SEQ ID NO 559
<211> LENGTH: 70
<212> TYPE: DNA
<213> ORGANISM: Glycine max

<400> SEQUENCE: 559
tcgacatgca aagtcaaaaa cccaccttag tcacgttcca tcatgtcgtg tgtcagttcc    60
gaattttgat                                                           70

<210> SEQ ID NO 560
<211> LENGTH: 70
<212> TYPE: DNA
<213> ORGANISM: Glycine max

<400> SEQUENCE: 560
ggcagactcc aattcctctt ttctagaata ccctccgtac gtacaagtac aagggacttg    60
tgagttgtaa                                                           70

<210> SEQ ID NO 561
<211> LENGTH: 70
<212> TYPE: DNA
<213> ORGANISM: Glycine max

<400> SEQUENCE: 561
```

```
ttacaactca caagtccctt gtacttgtac gtacggaggg tattctagaa aagaggaatt    60
ggagtctgcc                                                          70
```

<210> SEQ ID NO 562
<211> LENGTH: 8
<212> TYPE: PRT
<213> ORGANISM: Zea mays

<400> SEQUENCE: 562

Val Glu Asp Ala Lys Glu Glu Val
1               5

<210> SEQ ID NO 563
<211> LENGTH: 8
<212> TYPE: PRT
<213> ORGANISM: Petunia hybrida

<400> SEQUENCE: 563

Gly Lys Glu Ser Lys Glu Glu Ile
1               5

<210> SEQ ID NO 564
<211> LENGTH: 8
<212> TYPE: PRT
<213> ORGANISM: Solanum lycopersicum

<400> SEQUENCE: 564

Gly Lys Lys Ser Glu Glu Glu Ile
1               5

<210> SEQ ID NO 565
<211> LENGTH: 8
<212> TYPE: PRT
<213> ORGANISM: Sorghum bicolor

<400> SEQUENCE: 565

Glu Lys Asp Ala Lys Glu Glu Val
1               5

<210> SEQ ID NO 566
<211> LENGTH: 8
<212> TYPE: PRT
<213> ORGANISM: Oryza sativa

<400> SEQUENCE: 566

Val Glu Asp Ser Lys Glu Glu Val
1               5

<210> SEQ ID NO 567
<211> LENGTH: 8
<212> TYPE: PRT
<213> ORGANISM: Amaranthus floridanus

<400> SEQUENCE: 567

Gly Lys Asp Gly Lys Glu Glu Ile
1               5

<210> SEQ ID NO 568
<211> LENGTH: 80
<212> TYPE: DNA
<213> ORGANISM: Zea mays

<400> SEQUENCE: 568

```
gctaaagagg aagtgcagct cttcttgggg aatgctggaa ctgcaatgcg gccattgaca    60
```

```
gcagctgtta ctgctgctgg                                                      80

<210> SEQ ID NO 569
<211> LENGTH: 80
<212> TYPE: DNA
<213> ORGANISM: Zea mays

<400> SEQUENCE: 569
gctagagagg aagtgcagct cttcttgggg aatgctggaa tcgcaatgcg gtcattgaca          60
gcagctgtta ctgctgctgg                                                      80

<210> SEQ ID NO 570
<211> LENGTH: 37
<212> TYPE: DNA
<213> ORGANISM: Zea mays

<400> SEQUENCE: 570
catctcacga tcagatgcac cgcatgtcgc atgccta                                   37

<210> SEQ ID NO 571
<211> LENGTH: 42
<212> TYPE: DNA
<213> ORGANISM: Zea mays

<400> SEQUENCE: 571
catatctgca cgatcagata tgcaccgcat gtcgcatatc tg                             42
```

US 11,773,400 B2

METHODS FOR PRODUCING GENETIC MODIFICATIONS IN A PLANT GENOME WITHOUT INCORPORATING A SELECTABLE TRANSGENE MARKER, AND COMPOSITIONS THEREOF

This application claims the benefit of U.S. Provisional Application No. 61/868,706, filed Aug. 22, 2013, U.S. Provisional Application No. 61/882,532, filed Sep. 25, 2013, U.S. Provisional Application No. 61/937,045, filed Feb. 7, 2014, U.S. Provisional Application No. 61/953,090, filed Mar. 14, 2014, and U.S. Provisional Application No. 62/023,239, filed Jul. 11, 2014; all of which are hereby incorporated herein in their entirety by reference.

FIELD

The disclosure relates to the field of plant molecular biology, in particular, to methods for altering the genome of a plant cell.

REFERENCE TO SEQUENCE LISTING SUBMITTED ELECTRONICALLY

The official copy of the sequence listing is submitted electronically via EFS-Web as an ASCII formatted sequence listing with a file named 20140814_BB2365PCT_ST25_SequenceListing created on Aug. 14, 2014 and having a size of 584 kilobytes and is filed concurrently with the specification. The sequence listing contained in this ASCII formatted document is part of the specification and is herein incorporated by reference in its entirety.

BACKGROUND

Recombinant DNA technology has made it possible to insert foreign DNA sequences into the genome of an organism, thus, altering the organism's phenotype. The most commonly used plant transformation methods are *Agrobacterium* infection and biolistic particle bombardment in which transgenes integrate into a plant genome in a random fashion and in an unpredictable copy number. Thus, efforts are undertaken to control transgene integration in plants.

One method for inserting or modifying a DNA sequence involves homologous DNA recombination by introducing a transgenic DNA sequence flanked by sequences homologous to the genomic target. U.S. Pat. No. 5,527,695 describes transforming eukaryotic cells with DNA sequences that are targeted to a predetermined sequence of the eukaryote's DNA. Specifically, the use of site-specific recombination is discussed. Transformed cells are identified through use of a selectable marker included as a part of the introduced DNA sequences.

It was shown that artificially induced site-specific genomic double-stranded breaks in plant cells were repaired by homologous recombination with exogenously supplied DNA using two different pathways. (Puchta et al., (1996) *Proc. Natl. Acad. Sci. USA* 93:5055-5060; U.S. Patent Application Publication No. 2005/0172365A1 published Aug. 4, 2005; U.S. Patent Application Publication No. 2006/0282914 published Dec. 14, 2006; WO 2005/028942 published Jun. 2, 2005).

Since the isolation, cloning, transfer and recombination of DNA segments, including coding sequences and non-coding sequences, is most conveniently carried out using restriction endonuclease enzymes. Much research has focused on studying and designing endonucleases such as WO 2004/067736 published Aug. 12, 2004; U.S. Pat. No. 5,792,632 issued to Dujon et al., Aug. 11, 1998; U.S. Pat. No. 6,610,545 B2 issued to Dujon et al., Aug. 26, 2003; Chevalier et al., (2002) *Mol Cell* 10:895-905; Chevalier et al., (2001) *Nucleic Acids Res* 29:3757-3774; Seligman et al., (2002) *Nucleic Acids Res* 30:3870-3879.

Although several approaches have been developed to target a specific site for modification in the genome of a plant, there still remains a need for more efficient and effective methods for producing a fertile plant, having an altered genome comprising specific modifications in a defined region of the genome of the plant.

There remains a need to develop a genetic modification system that can modify a genomic location without incorporating a selectable transgene marker.

BRIEF SUMMARY

Compositions and methods are provided employing a guide polynucleotide/Cas endonuclease system in plants for genome modification of a target sequence in the genome of a plant or plant cell, for selecting plants, for gene editing, and for inserting a polynucleotide of interest into the genome of a plant without incorporating a selectable transgene marker.

The methods and compositions employ a guide polynucleotide/Cas endonuclease system to provide for an effective system for modifying or altering target sites and nucleotide of interest within the genome of a plant, plant cell or seed without incorporating a selectable transgene marker.

Once a genomic target site is identified, a variety of methods can be employed to further modify the target sites such that they contain a variety of polynucleotides of interest. Breeding methods and methods for selecting plants utilizing a two component RNA guide and Cas endonuclease system are also disclosed. Also provided are nucleic acid constructs, plants, plant cells, explants, seeds and grain having the guide polynucleotide/Cas endonuclease system. The methods and compositions employ a guide polynucleotide/Cas endonuclease system to provide for an effective system for modifying or altering target sites and editing nucleotide sequences of interest within the genome of a cell, wherein the guide polynucleotide is comprised of a RNA sequence, a DNA sequence, or a DNA-RNA combination sequence.

Thus in one embodiment of the disclosure, the method comprises a method for producing a genetic modification into a second gene of a plant genome without introducing an exogenous selectable marker into said plant genome, the method comprising providing a first guide polynucleotide, a polynucleotide modification template, a second guide polynucleotide, and a Cas endonuclease to a plant cell comprising a first endogenous gene that can be modified to confer herbicide resistance, wherein said first guide polynucleotide and Cas endonuclease are capable of forming a first complex that enables the Cas endonuclease to introduce a double strand break at a first target site, located in or near said first endogenous gene in the genome of said plant cell, wherein said second guide polynucleotide and Cas endonuclease are capable of forming a second complex that enables the Cas endonuclease to introduce a double strand break at a second target site in the genome of said plant cell, wherein said polynucleotide modification template comprises at least one nucleotide alteration when compared to the first endogenous gene.

In one embodiment of the disclosure, the method comprises a method for introducing a polynucleotide of interest into a plant genome without introducing an exogenous selectable marker into said plant genome, the method comprising providing a first guide RNA, a first polynucleotide modification template, a second guide RNA, a second polynucleotide modification template, and a Cas endonuclease to a plant cell comprising a first endogenous gene that can be modified to confer herbicide resistance, wherein said first guide RNA and Cas endonuclease are capable of forming a first complex that enables the Cas endonuclease to introduce a double strand break at a first target site located in or near said first endogenous gene in the genome of said plant cell, wherein said first polynucleotide modification template comprises at least one nucleotide modification of said first endogenous gene to render said endogenous gene capable of conferring herbicide resistance to a plant cell, wherein said second guide RNA and Cas endonuclease are capable of forming a second complex that enables the Cas endonuclease to introduce a double strand break at a second target site in the genome of said plant cell, wherein said second polynucleotide modification template comprises at least one polynucleotide of interest to be introduced into said plant genome.

In one embodiment of the disclosure, the method comprises a method for editing a second gene of a plant genome without introducing an exogenous selectable marker into said plant genome, the method comprising providing a first guide RNA, a first polynucleotide modification template, a second guide RNA, a second polynucleotide modification template, and a Cas endonuclease to a plant cell comprising a first endogenous gene that can be modified to confer herbicide resistance, wherein said first guide RNA and Cas endonuclease are capable of forming a complex that enables the Cas endonuclease to introduce a double strand break at a first target site (located in or near said first endogenous gene) in the genome of said plant cell, wherein said first polynucleotide modification template comprises at least one nucleotide modification of said first endogenous gene to render said endogenous gene capable of conferring herbicide resistance to a plant cell, wherein said second guide RNA and Cas endonuclease are capable of forming a complex that enables the Cas endonuclease to introduce a double strand break at a second target site (located at a different locus than said first endogenous gene) in the genome of said plant cell, wherein said second polynucleotide modification template comprises at least one nucleotide alteration when compared to the second gene to be edited.

Additional embodiments of the methods and compositions of the present invention are disclosed herein.

BRIEF DESCRIPTION OF THE DRAWINGS AND THE SEQUENCE LISTING

The disclosure can be more fully understood from the following detailed description and the accompanying drawings and Sequence Listing, which form a part of this application. The sequence descriptions and sequence listing attached hereto comply with the rules governing nucleotide and amino acid sequence disclosures in patent applications as set forth in 37 C.F.R. §§ 1.821-1.825. The sequence descriptions contain the three letter codes for amino acids as defined in 37 C.F.R. §§ 1.821-1.825, which are incorporated herein by reference.

FIGURES

FIG. 1A shows a maize optimized Cas9 gene (encoding a Cas9 endonuclease) containing a potato ST-LS1 intron, a SV40 amino terminal nuclear localization sequence (NLS), and a VirD2 carboxyl terminal NLS, operably linked to a plant ubiquitin promoter (SEQ ID NO: 5). The maize optimized Cas9 gene (just Cas9 coding sequence, no NLSs) corresponds to nucleotide positions 2037-2411 and 2601-6329 of SEQ ID NO: 5 with the potato intron residing at positions 2412-2600 of SEQ ID NO: 5.SV40 NLS is at positions 2010-2036 of SEQ ID NO: 5. VirD2 NLS is at positions 6330-6386 of SEQ ID NO: 5. FIG. 1 B shows a long guide RNA operably linked to a maize U6 polymerase III promoter terminating with a maize U6 terminator (SEQ ID NO: 12). The long guide RNA containing the variable targeting domain corresponding to the maize LIGCas-3 target site (SEQ ID NO: 8) is transcribed from/corresponds to positions 1001-1094 of SEQ ID NO: 12. FIG. 1 C shows the maize optimized Cas9 and long guide RNA expression cassettes combined on a single vector DNA (SEQ ID NO: 102).

Figure 2:
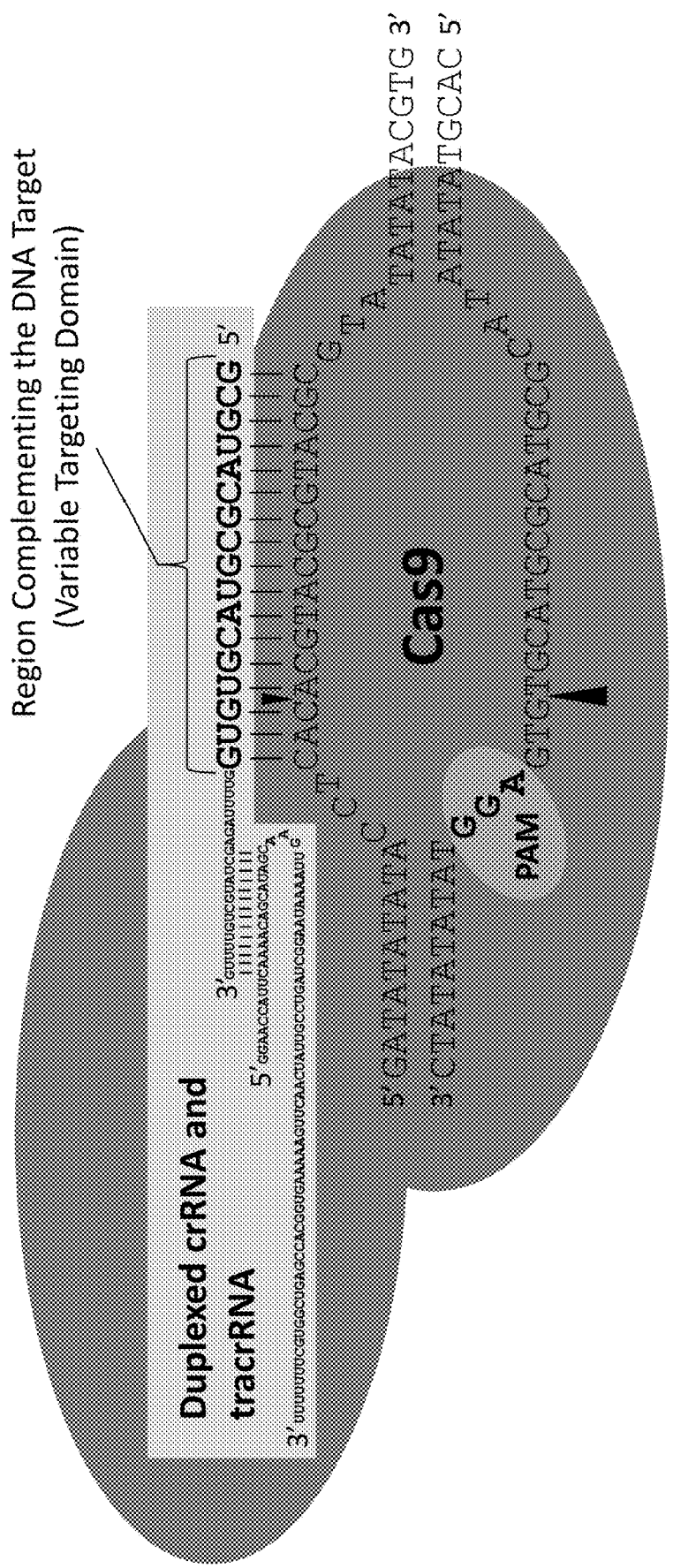
Figure 2:
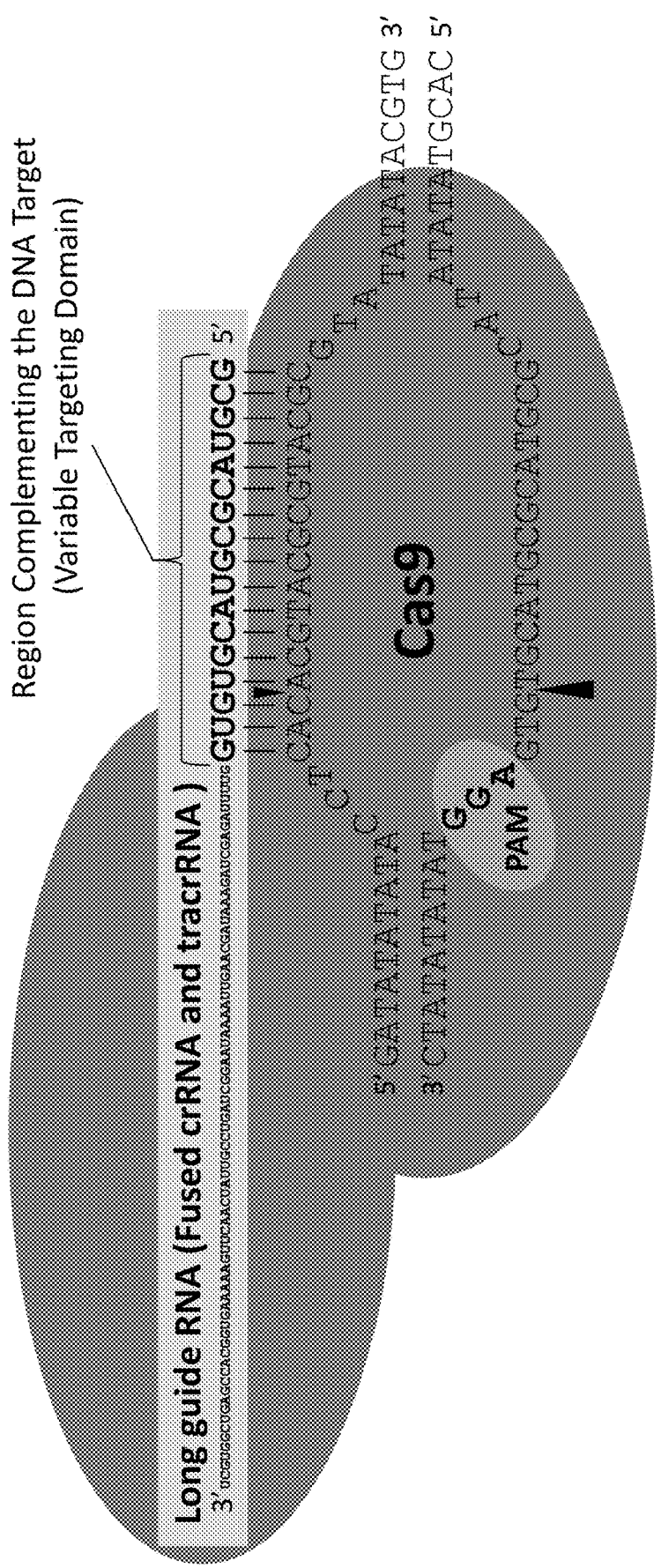

FIG. 2A illustrates the duplexed crRNA (SEQ ID NO:6)-tracrRNA (SEQ ID NO:7)/Cas9 endonuclease system and target DNA complex relative to the appropriately oriented PAM sequence at the maize LIGCas-3 (SEQ ID NO: 18, Table 1) target site with triangles pointing towards the expected site of cleavage on both sense and anti-sense DNA strands. FIG. 2 B illustrates the guide RNA/Cas9 endonuclease complex interacting with the genomic target site relative to the appropriately oriented PAM sequence (GGA) at the maize genomic LIGCas-3 target site (SEQ ID NO:18, Table 1). The guide RNA (shown as boxed-in in light gray, SEQ ID NO:8) is a fusion between a crRNA and tracrRNA and comprises a variable targeting domain that is complementary to one DNA strand of the double strand DNA genomic target site. The Cas9 endonuclease is shown in dark gray. Triangles point towards the expected site of DNA cleavage on both sense and anti-sense DNA strands. The sense genome sequence shown in FIGS. 2A and 2B is listed in SEQ ID NO: 555, while the complementary genome sequence shown in FIGS. 2A and 2B is listed in SEQ ID NO: 556.

FIG. 3A-3B shows an alignment and count of the top 10 most frequent NHEJ mutations induced by the maize optimized guide RNA/Cas endonuclease system described herein compared to a LIG3-4 homing endonuclease control at the maize genomic Liguleless 1 locus. The mutations were identified by deep sequencing. The reference sequence represents the unmodified locus with each target site underlined. The PAM sequence and expected site of cleavage are also indicated. Deletions or insertions as a result of imperfect NHEJ are shown by a "−" or an italicized underlined nucleotide, respectively. The reference and mutations 1-10 of the LIGCas-1 target site correspond to SEQ ID NOs: 55-65, respectively. The reference and mutations 1-10 of the LIGCas-2 correspond to SEQ ID NOs: 55, 65-75, respectively. The reference and mutations 1-10 of the LIGCas-3 correspond to SEQ ID NOs: 76-86, respectively. The reference and mutations 1-10 of the LIG3-4 homing endonuclease target site correspond to SEQ ID NOs: 76, 87-96, respectively.

Figure 4:
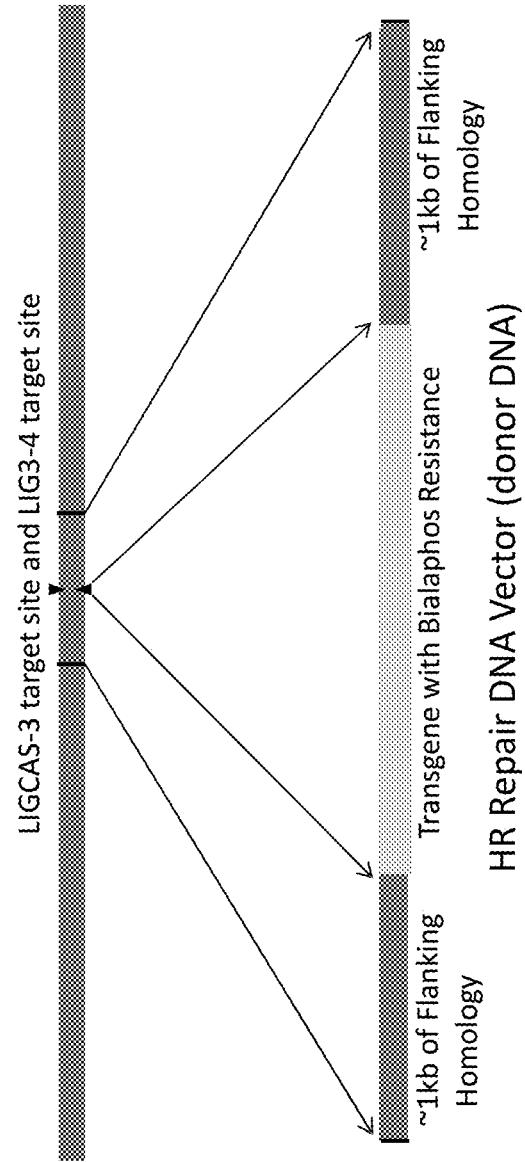

FIG. 4 illustrates how the homologous recombination (HR) repair DNA vector (SEQ ID NO: 97) was constructed. To promote site-specific transgene insertion by homologous recombination, the transgene (shown in light gray) was flanked on either side by approximately 1 kb of DNA with homology to the maize genomic regions immediately adjacent to the LIGCas3 and LIG3-4 homing endonuclease expected sites of cleavage.

Figure 5:
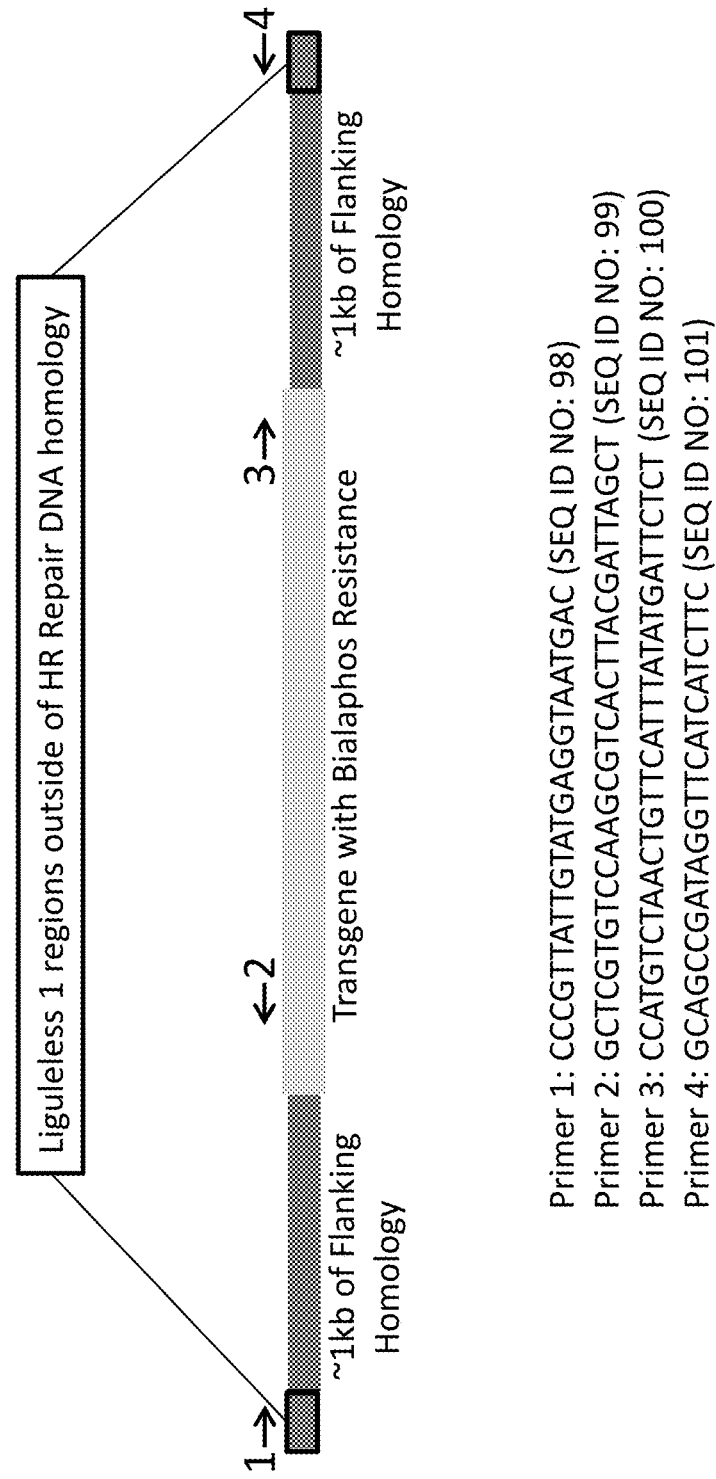

FIG. 5 illustrates how genomic DNA extracted from stable transformants was screened for site-specific transgene insertion by PCR. Genomic primers (corresponding to SEQ ID NOs: 98 and 101) within the Liguleless 1 locus were designed outside of the regions used in constructing the HR repair DNA vector (SEQ ID NO: 97) and were paired with primers inside the transgene (corresponding to SEQ ID NOs: 99 and 100) to facilitate PCR detection of unique genomic DNA junctions created by appropriately oriented site-specific transgene integration.

FIG. 6 shows an alignment of the NHEJ mutations induced by the maize optimized guide RNA/Cas endonuclease system, described herein, when the short guide RNA was delivered directly as RNA. The mutations were identified by deep sequencing. The reference illustrates the unmodified locus with the genomic target site underlined. The PAM sequence and expected site of cleavage are also indicated. Deletions or insertions as a result of imperfect NHEJ are shown by a "–" or an italicized underlined nucleotide, respectively. The reference and mutations 1-6 for 55CasRNA-1 correspond to SEQ ID NOs: 104-110, respectively.

Figure 7:
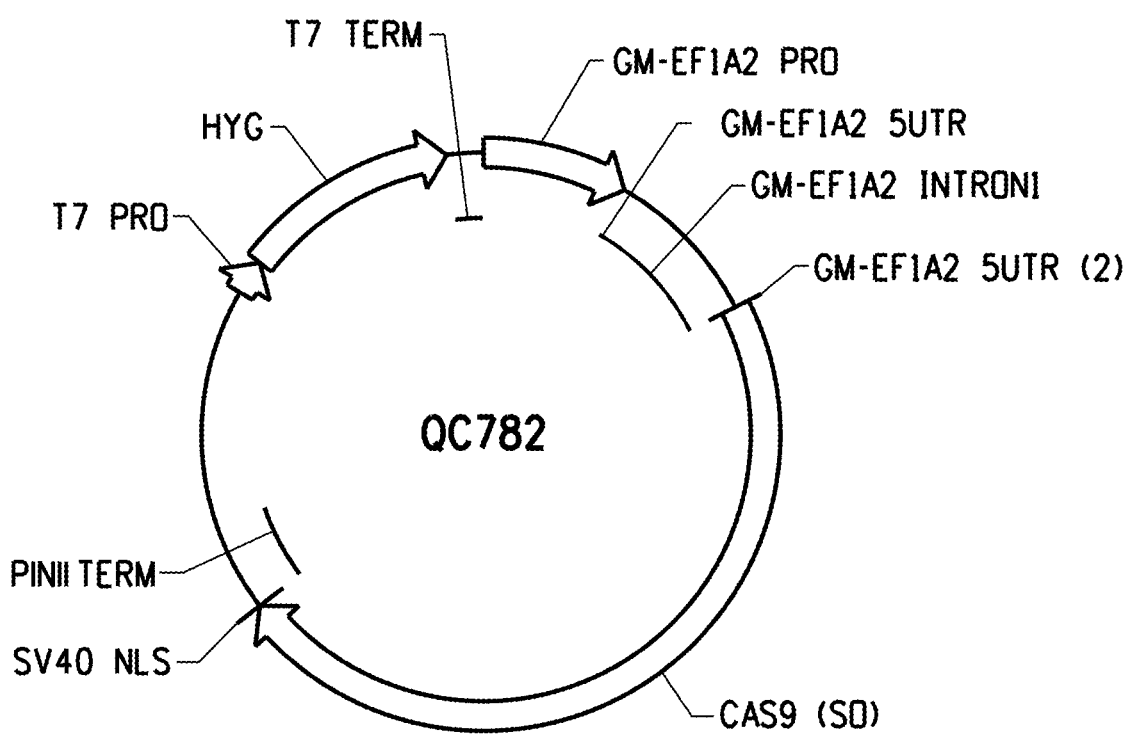

FIG. 7 shows the QC782 vector comprising the Cas9 expression cassette.

Figure 8A:
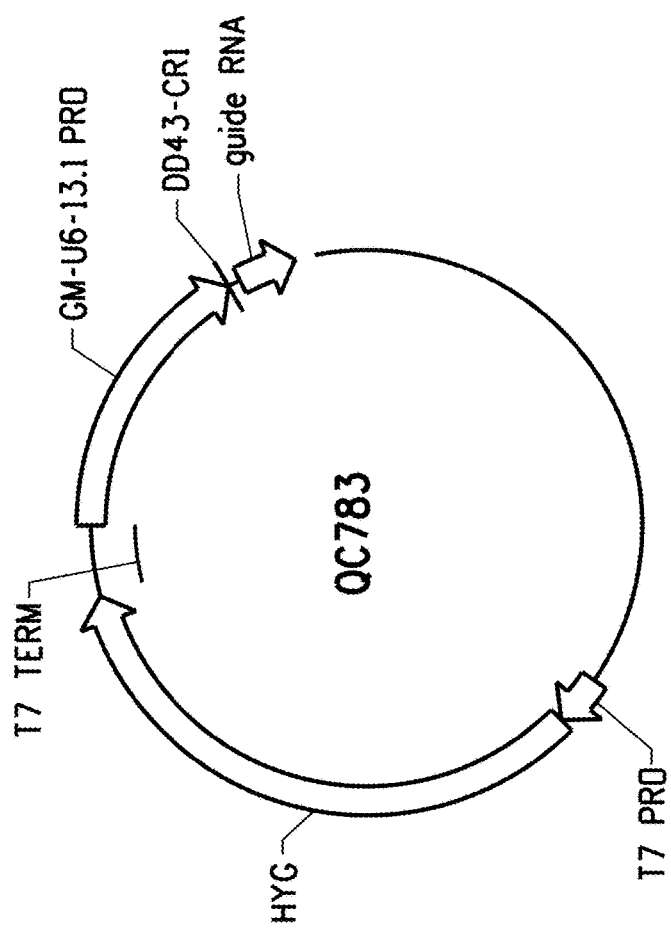
Figure 8B:

FIG. 8A shows the QC783 vector comprising the guide RNA expression cassette. FIG. 8B show the DNA sequence (coding sequence) of the DD43CR1 (20 bp) variable targeting domain of the guide RNA, as well as the terminator sequence linked to the guide RNA. The 20 bp variable targeting domain DD43CR1 is in bold. The sequence shown in FIG. 8B is listed in SEQ ID NO: 557

Figure 9:
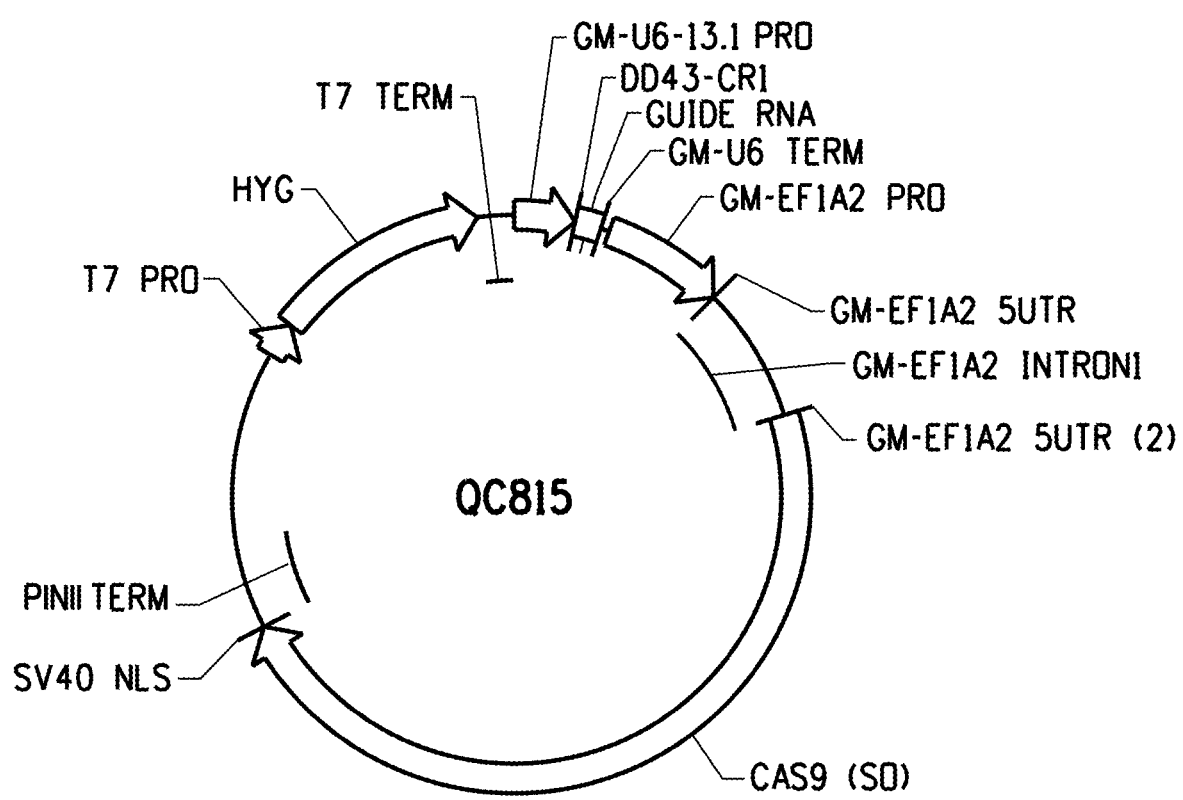

FIG. 9 shows the map of a linked soybean optimized Cas9 and guide RNA construct QC815.

FIG. 10A shows the DD20 soybean locus on chromosome 4 and the DD20CR1 and DD20CR2 genomic target sites (indicated by bold arrows). The sense sequence shown in FIG. 10A is listed in SEQ ID NO: 558 and the complementary sequence shown in FIG. 10A is listed in SEQ ID NO: 559. FIG. 10B shows the DD43 soybean locus on chromosome 4 and the DD43CR1 and DD43CR2 genomic target sites (indicated by bold arrows). The sense sequence shown in FIG. 10B is listed in SEQ ID NO: 560 and the complementary sequence shown in FIG. 10B is listed in SEQ ID NO: 561.

Figures 11A, 11B:
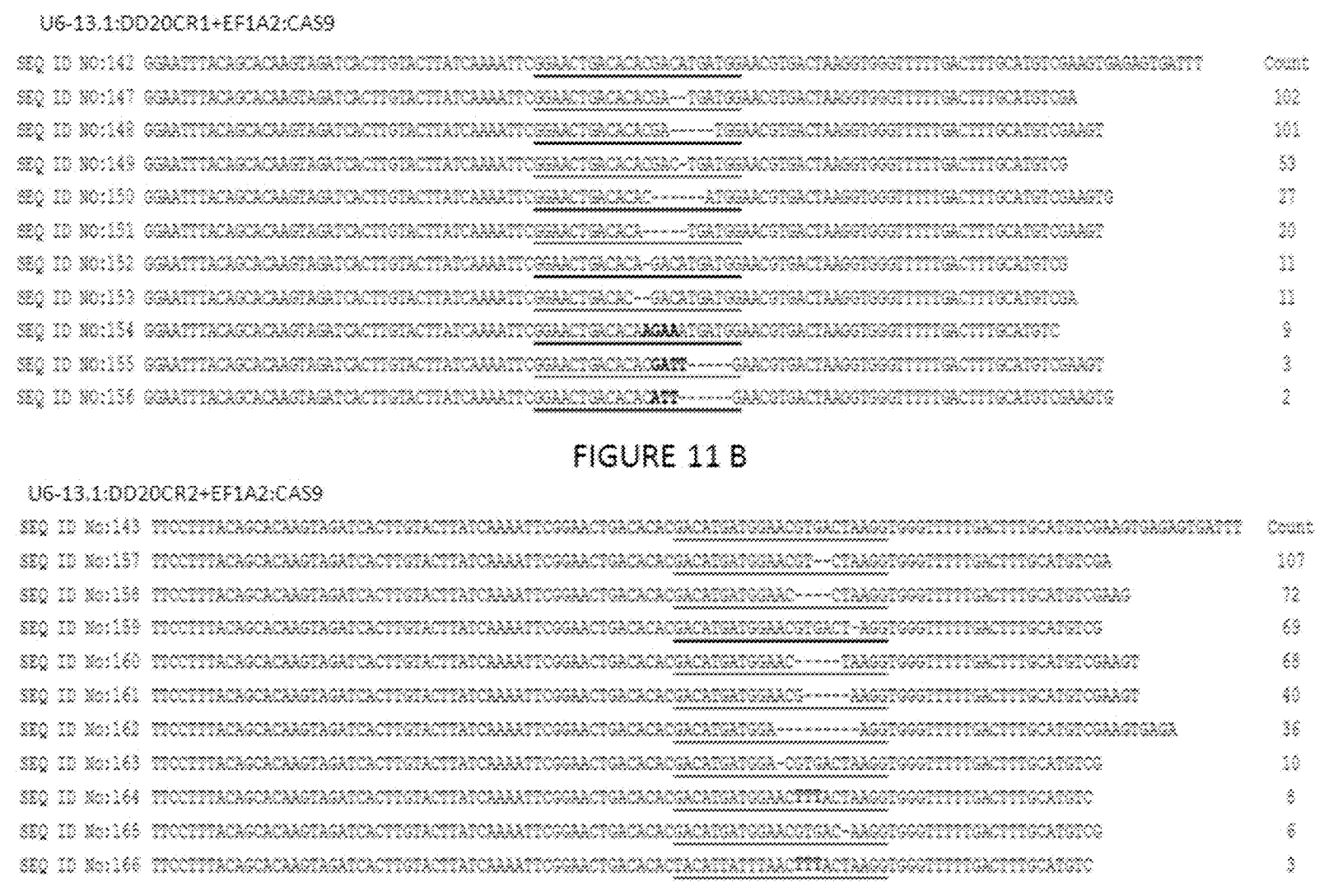
Figures 11C, 11D:
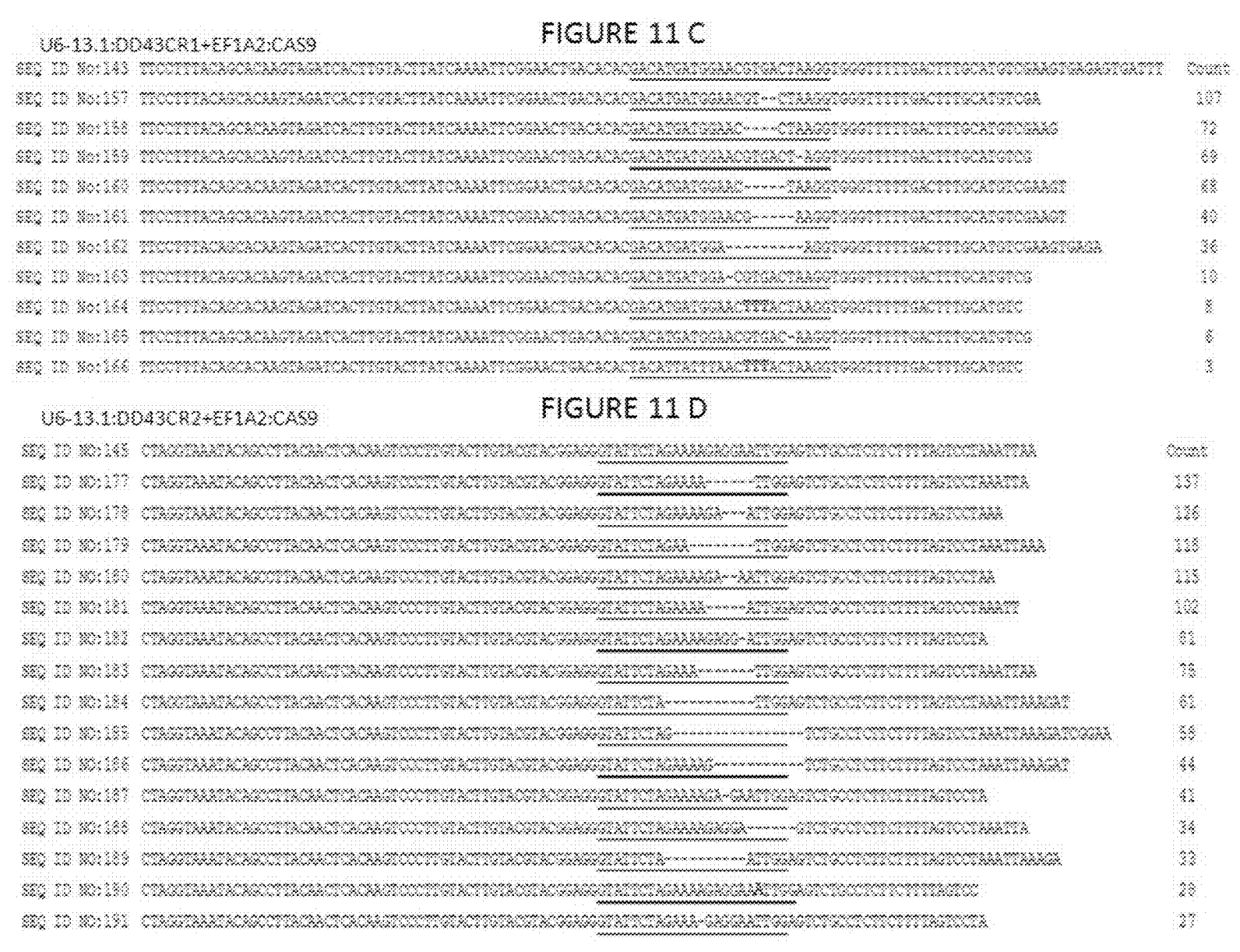

FIG. 11A-11D. Alignments of expected target site sequences with mutant target sequences detected in four guide RNAs induced NHEJ experiments. FIG. 11A shows the DD20CR1 PCR amplicon (reference sequence, SEQ ID NO:142, genomic target site is underlined) and the 10 mutations (SEQ ID NOs: 147-156) induced by the guideRNA/Cas endonuclease system at the DD20CR1 genomic target site. FIG. 11B shows the DD20CR2 PCR amplicon (reference sequence, SEQ ID NO:143) and the 10 mutations (SEQ ID NOs 157-166) induced by the guide RNA/Cas endonuclease system at the DD20CR2 genomic target site. FIG. 11C shows the DD43CR1 PCR amplicon (reference sequence, SEQ ID NO:144) and the 10 mutations (SEQ ID NOs:167-176) induced by the guide RNA/Cas endonuclease system at the DD43CR1 genomic target site. FIG. 11D shows the DD43CR2 PCR amplicon (reference sequence, SEQ ID NO:145) and the 10 mutations (SEQ ID NOs: 177-191) induced by the guide RNA/Cas endonuclease system at the DD43CR2 genomic target site. The target sequences corresponding different guide RNAs are underlined. Each nucleotide deletions is indicated by "–". Inserted and replaced sequences are in bold. The total number of each mutant sequence is listed in the last column.

FIG. 12A-12B shows a schematic representation of the guide RNA/Cas endonuclease system used for editing a nucleotide sequence of interest. To enable specific nucleotide editing, a polynucleotide modification template that includes at least one nucleotide modification (when compared to the nucleotide sequence to be edited) is introduced into a cell together with the guide RNA and Cas endonuclease expression cassettes. For example, as shown herein, the nucleotide sequence to be edited is an endogenous wild type enolpyruvylshikimate-3-phosphate synthase (EPSPS) gene in maize cells. The Cas endonuclease (shaded circle) is a maize optimized Cas9 endonuclease that cleaves a moCas9 target sequence within the epsps genomic locus using a guide RNA of SEQ ID NO:194. FIG. 12-A shows a polynucleotide modification template that includes three nucleotide modifications (when compared to the wild type epsps locus depicted in FIG. 12-B) flanked by two homology regions HR-1 and HR-2. FIG. 12-B shows the guide RNA/ maize optimized Cas9 endonuclease complex interacting with the epsps locus. The original nucleotide codons of the EPSPS gene that needed to be edited are show as aCT and Cca (FIG. 12-B). The nucleotide codons with modified nucleotides (shown in capitals) are shown as aTC and Tca (FIG. 12-B).

Figure 13:
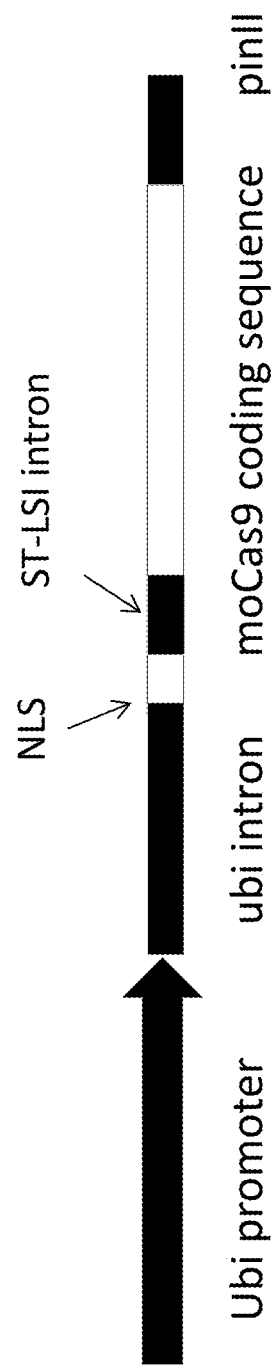

FIG. 13 shows a diagram of a maize optimized Cas9 endonuclease expression cassette. The bacterial cas9 coding sequence was codon optimized for expression in maize cells and supplemented with the ST-LS1 potato intron (moCas9 coding sequence, SEQ ID NO: 193). A DNA fragment encoding the SV40 nuclear localization signal (NLS) was fused to the 5'-end of the moCas9 coding sequence. A maize ubiquitin promoter (Ubi promoter) and its cognate intron (ubi intron) provided controlling elements for the expression of moCas9 in maize cells. The pinII transcription termination sequence (pinII) completed the maize moCAS9 gene design.

Figure 15:
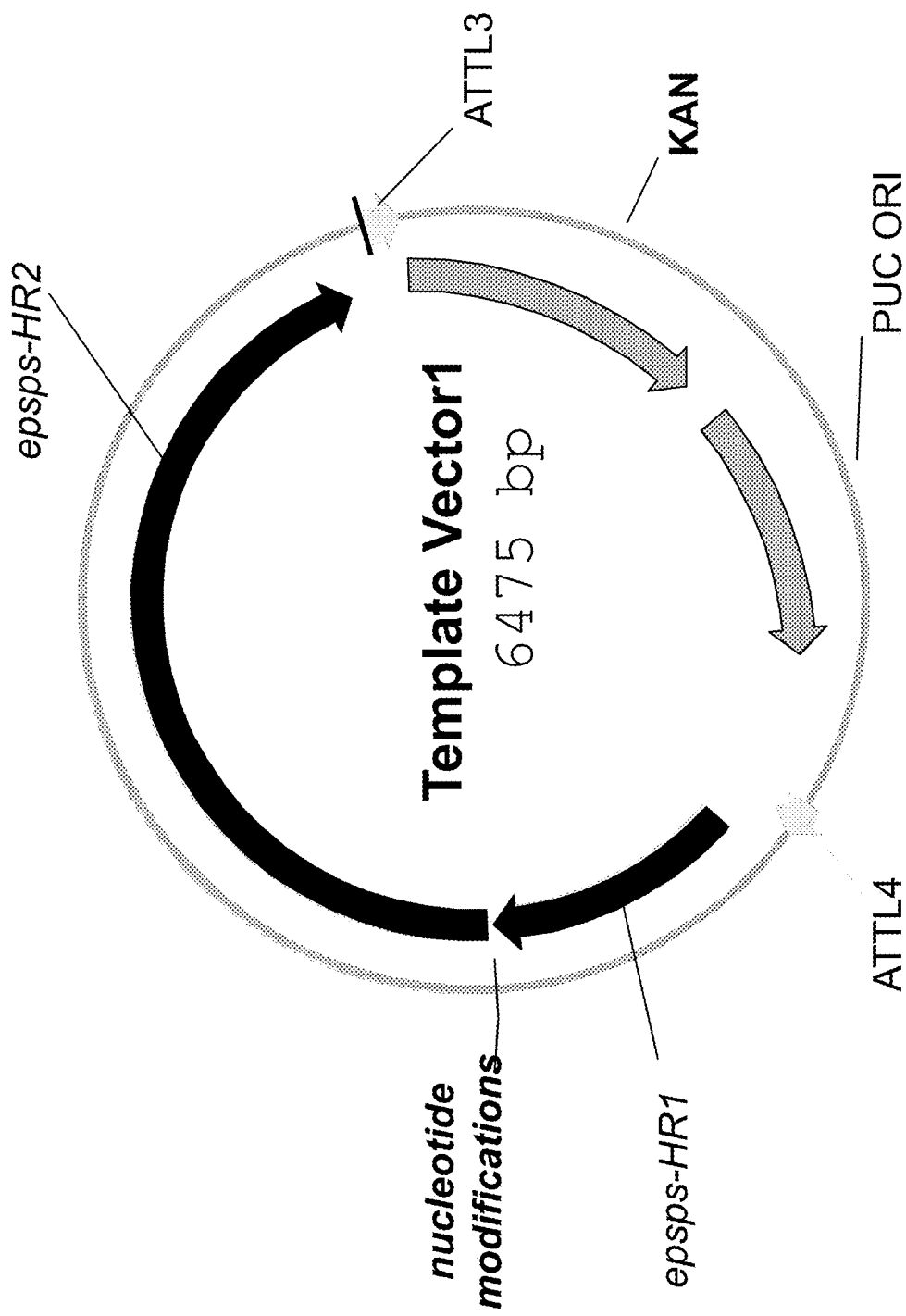

FIG. 14 shows some examples of the moCas9 target sequence (underlined), located on EPSPS DNA fragments, mutagenized by the introduction of double-strand breaks at the cleavage site of the moCas9 endonuclease (thick arrow) in maize cells. In SEQ ID NO: 206, three nucleotides were deleted (dashes) next to the moCas9 cleavage site. SEQ ID NOs: 207-208 indicate that the nucleotide deletion can expand beyond the moCAs9 cleavage site FIG. 15 depicts an EPSPS template vector used for delivery of the EPSPS polynucleotide modification template containing the three TIPS nucleotide modifications. The EPSP polynucleotide modification template includes a partial fragment of the EPSPS gene. The vector was 6,475 bp in length and consisted of two homology regions to the epsps locus (epsps-HR1 and epsps-HR2). Two Gateway cloning sites (ATTL4 and ATTL3), an antibiotic resistance gene (KAN), and the pUC origin of replication (PUC ORI) completed synthesis of the EPSPS template vector1.

FIG. 16 illustrates the PCR-based screening strategy for the identification of maize events with TIPS nucleotide modifications in maize cells. Two pairs of PCR primers were used to amplify the genomic fragments of the epsps locus (upper section). Both of them contained the TIPS specific primers (an arrow with a dot indicating the site of the three TIPS modifications). The shorter fragment (780 bp F-E2) was produced by amplification of the EPSPS polynucleotide modification template fragment (template detection). The amplified EPSPS polynucleotide modification template fragment was found in all but 4 analyzed events (panel F-E2). The longer fragment (839 bp H-T) was produced by amplification of the genomic EPSPS sequence providing that the epsps locus contained the three nucleotide modifications responsible for the TIPS modifications. Six events were identified as containing the three nucleotide modifications (panel H-T). The white arrows point to events that contain both the amplified EPSPS polynucleotide modification template and the nucleotide modifications responsible for the TIPS modification.

Figure 17:
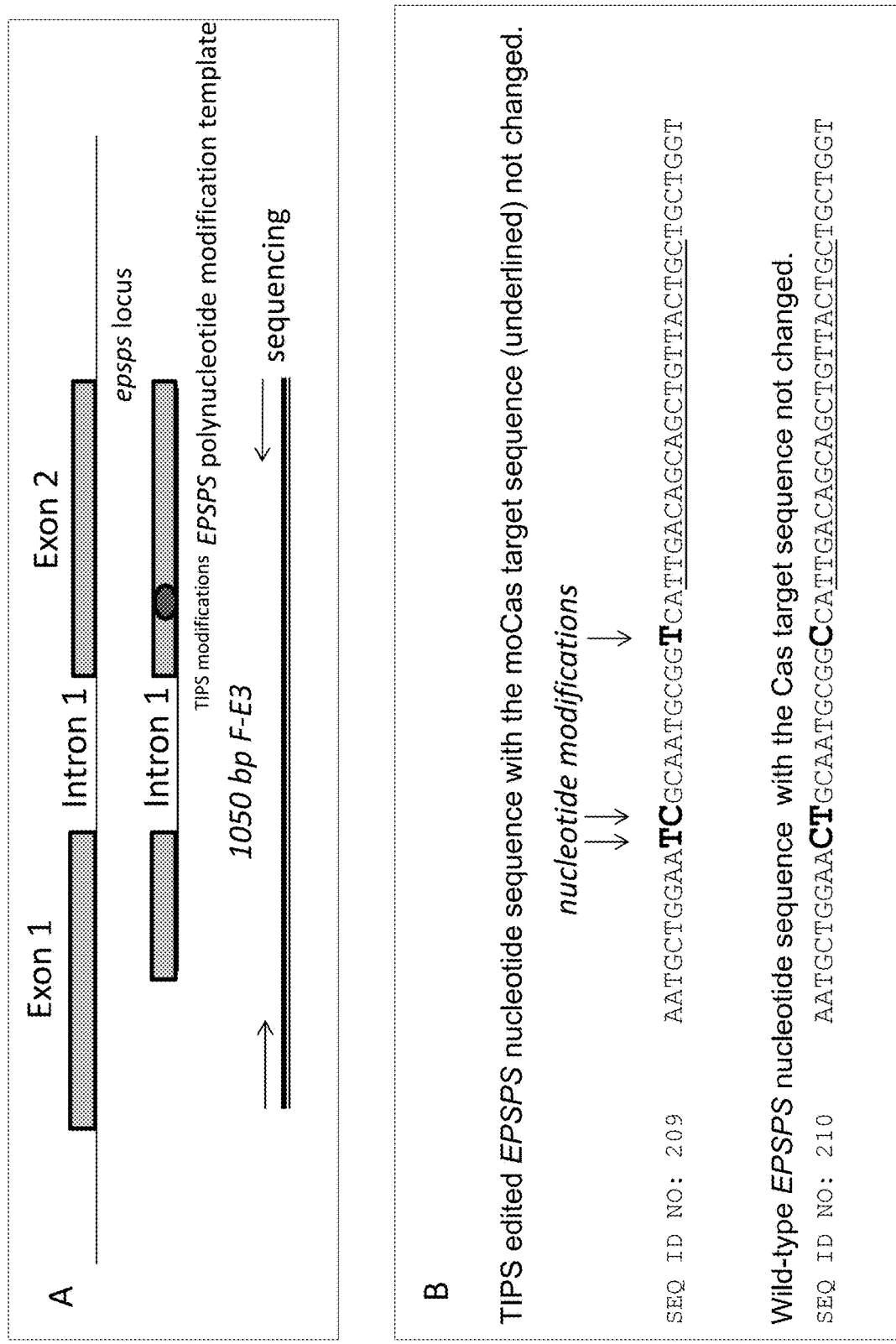

FIG. 17 A shows a schematic diagram of the PCR protocol used to identify edited EPSPS DNA fragments in selected events. A partial genomic fragment, comprising parts of Exon1, Intron 1 and Exon2 of the epsps locus, was amplified regardless of the editing product (panel A, 1050 bp F-E3). The amplification products, representing only partial EPSPS gene sequences having one or more mutations, were cloned and sequenced. FIG. 17-B shows 2 examples of sequenced amplification products. In some amplification products, the epsps nucleotides and the moCas9 target sequence (underlined) were unchanged indicating that one EPSPS allele was not edited (wild type allele; SEQ ID NO: 210). In other amplification products, three specific nucleotide substitutions (representing the TIPS modifications) were identified with no mutations at the moCas9 target sequence (underlined) (SEQ ID NO: 209).

Figure 18:
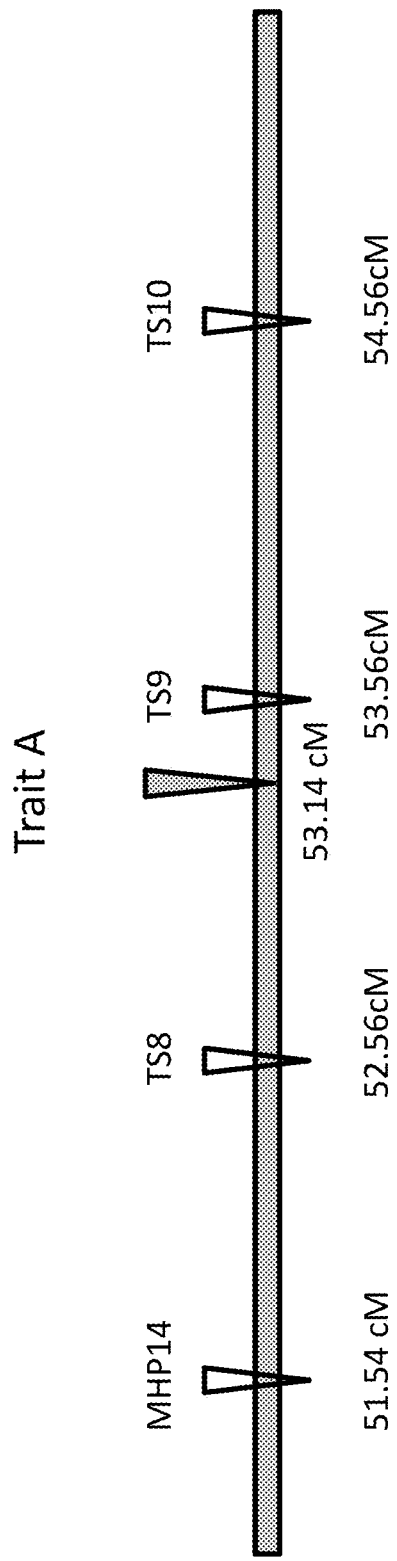

FIG. 18 shows the location of MHP14, TS8, TS9 and TS10 loci comprising target sites for the guide RNA/Cas endonuclease system near trait A (located at 53.14 cM) on chromosome 1 of maize.

Figure 19:
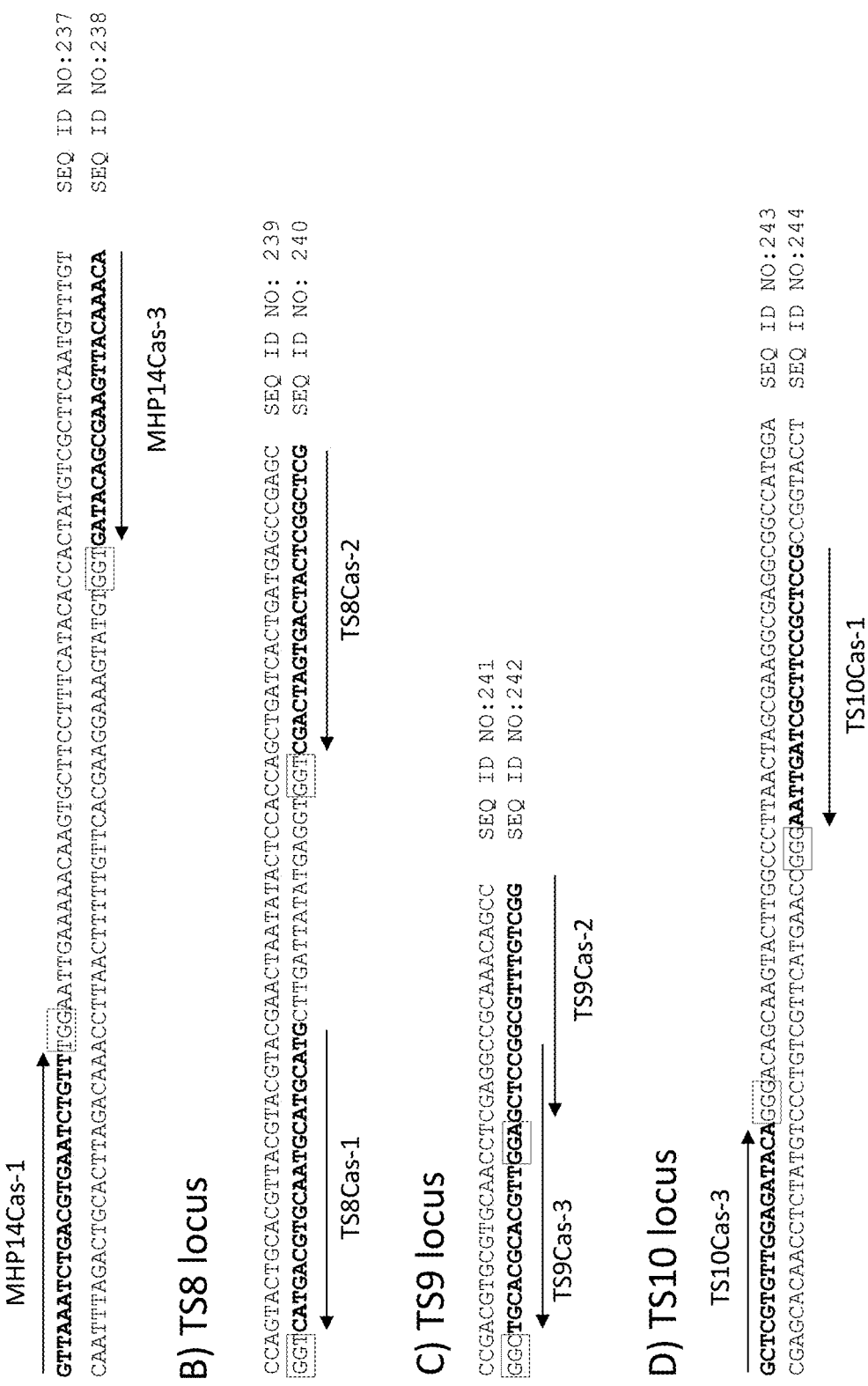

FIG. 19A shows the location of the MHP14Cas1 maize genomic target sequence (SEQ ID NO: 229) and the MSP14Cas-3 maize genomic target sequence (SEQ ID NO: 230) on the MHP14 maize genomic DNA locus on chromosome1. The 5' to 3' sequence. FIG. 19B shows the location of the TS8Cas-1 (SEQ ID NO: 231) and TS8Cas-2 (SEQ ID NO: 232) maize genomic target sequences located on the TS8 locus. FIG. 19-C shows the location of the TS9Cas-2 (SEQ ID NO: 233) and TS9Cas-3 (SEQ ID NO: 234) maize genomic target sequences located on the TS8 locus. FIG. 19-D shows the location of the TS10Cas-1 (SEQ ID NO: 235), and TS10Cas-3 (SEQ ID NO: 236) maize genomic target sequences located on the TS10 locus. All these maize genomic target sites are recognized are recognized and cleaved by a guide RNA/Cas endonuclease system described herein. Each maize genomic target sequence (indicated by an arrow) is highlighted in bold and followed by the NGG PAM sequence shown boxed in.

Figure 20:
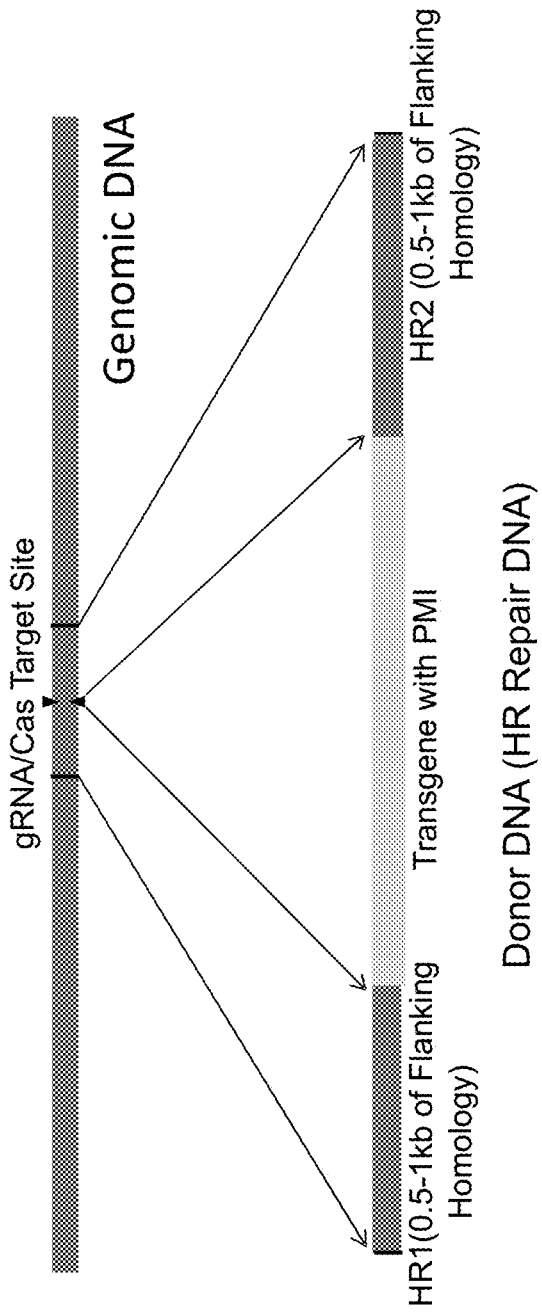

FIG. 20 shows a schematic of a donor DNA (also referred to as HR repair DNA) comprising a transgene cassette with a selectable marker (phosphomannose isomerase, depicted in grey), flanked by homologous recombination sequences (HR1 and HR2) of about 0.5 to 1 kb in length, used to introduce the transgene cassette into a genomic target site for the guide RNA/Cas endonuclease system. The arrows indicate the sections of the genomic DNA sequence on either side of the endonuclease cleavage site that corresponds to the homologous regions of the donor DNA. This schematic is representative for homologous recombination occurring at any one of the 8 target sites (4 loci) located on chromosome 1 from 51.54cM to 54.56cM in maize genome.

Figure 21:
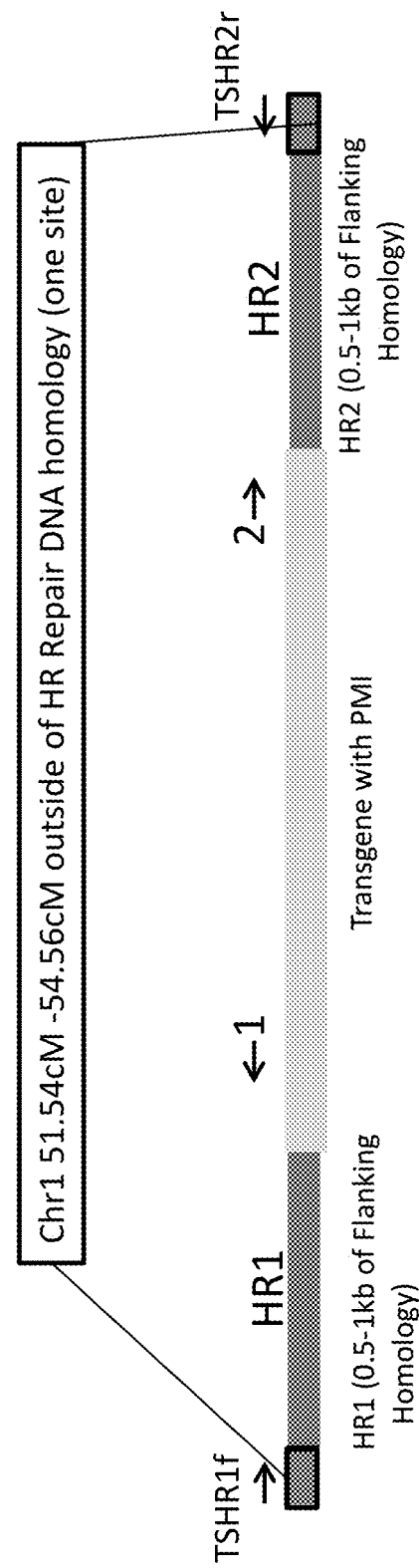

FIG. 21 shows the junction PCR screen for identification of insertion events. Primer 1 and 2 located on the transgene donor are common for all target sites. Primer TSHR1f is located on the genomic region outside of the homologous sequence HR1. Primer combination THR1f/primer1 amplify junction 1. Primer TSHR2r is located on the genomic region outside of the HR2 region. Primer combination primer2/TSHR2r amplify junction 2.

Figure 22:
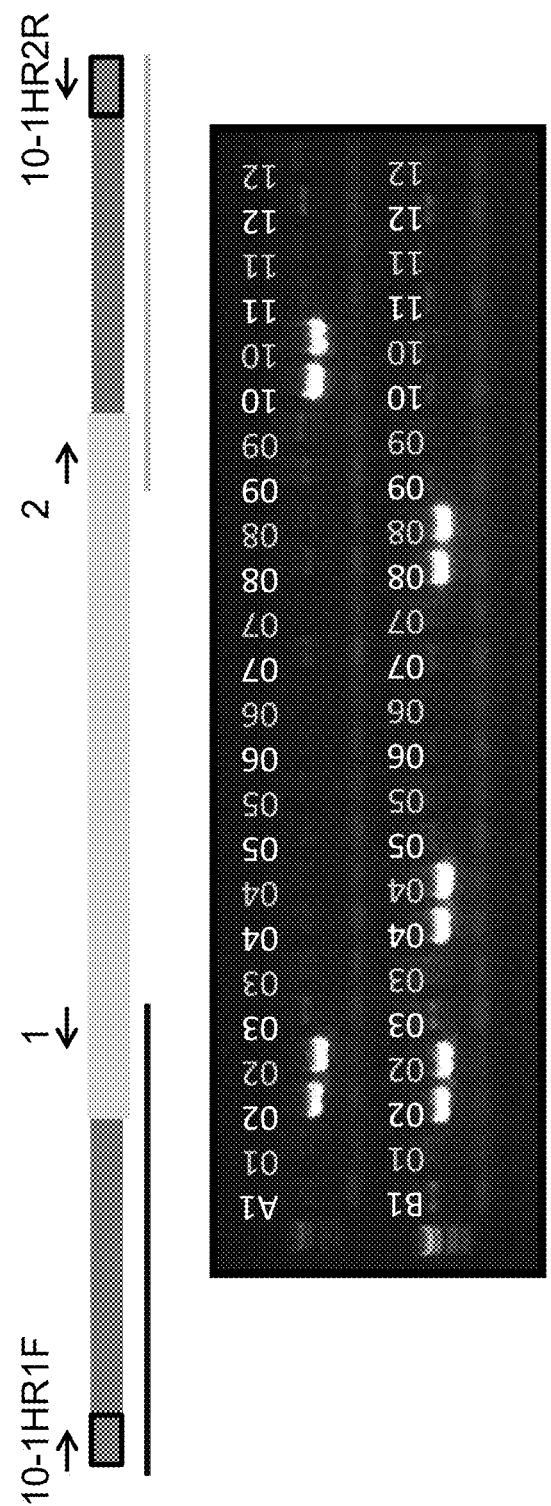

FIG. 22 shows a junction PCR screen for identification of insertion events at the TS10Cas10 locus. A gel picture indicates the presence of insertion events at the TS10Cas10-1 target site (lane 02 A1). PCR reaction of HR1 and HR2 junction loaded next to each other (lane 02-white label and lane 02-gray label), with white label representing HR1 junction PCR, gray label representing HR2 junction PCR.

FIG. 23 A-B. DNA expression cassettes used in gRNA/Cas9 mediated genome modification experiments. A) The Cas9 endonuclease cassette (EF1A2:CAS9) comprising a soybean EF1A2 promoter (GM-EF1A2 PRO) driving the soybean codon optimized Cas9 endonucleases (CAS9(SO), a soybean optimized SV40 nuclear localization signal (SV40 NLS(SO)) and a PINII terminator (PINII TERM) was linked to a guide RNA expression cassette (U6-9.1:DD20CR1, comprising a soybean U6 promoter driving the DD20CR1 guide RNA) used in experiment U6-9.1DD20CR1 (Table 27). Other Guide RNA/Cas9 cassettes listed in Table 27 are identical except for the 20 bp variable targeting domains of the guide RNA targeting the genomic target sites DD20CR2, DD43CR1, or DD43CR2. B) The donor DNA cassette (DD20HR1-SAMS:HPT-DD20HR2) used in experiment U6-9.1DD20CR1 (Table 27). DD20HR1 and DD20HR2 homologous DNA regions between the donor DNA cassette and the genomic DNA sequences flanking the DD20 target site). Other Donor DNA cassettes listed in Table 27 are identical except for the DD43HR1 and DD43HR2 regions in two of them.

Figure 24:
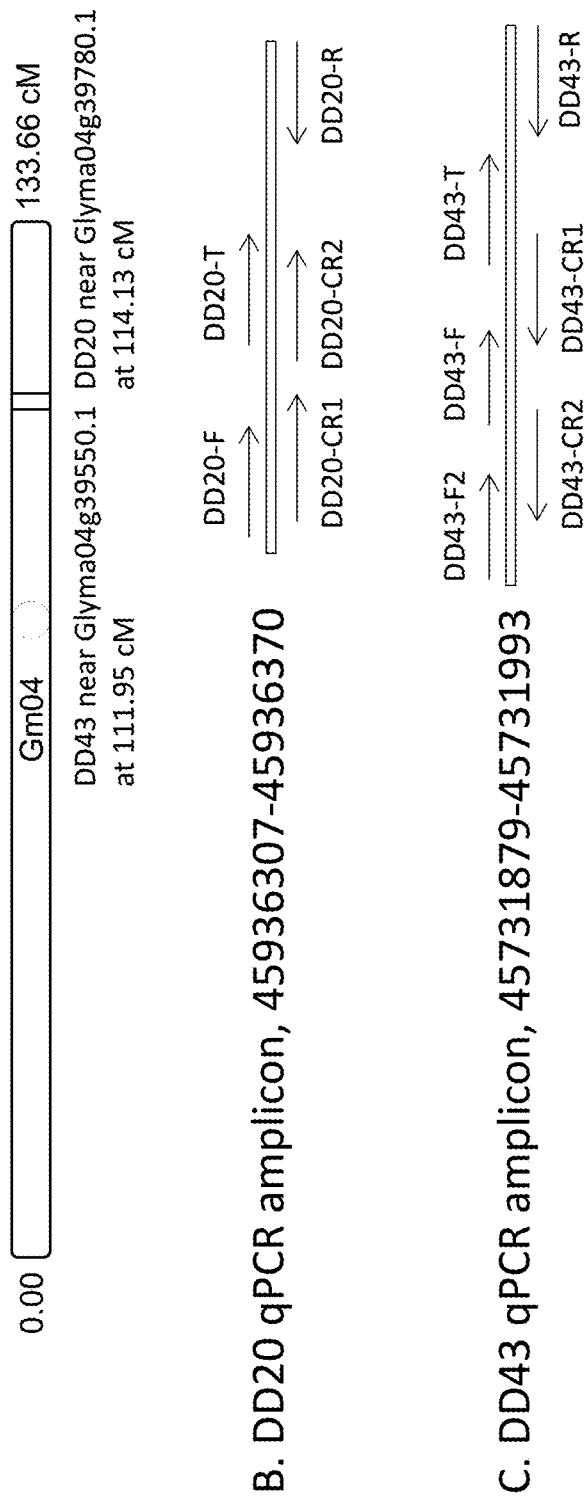

FIG. 24 A-C. DD20 and DD43 soybean genomic target sites locations and qPCR amplicons. A) Diagram of *Glycine max* chromosome 04 indicating relative positions of DD20 and DD43 target sites. Genetic mapping positions of DD20 and DD43 sites are the positions of the most nearby genes Glyma04g39780.1 and Glyma04g39550.1. B) DD20 qPCR 64 bp amplicon 45936307-45936370 from chromosome 04 (SEQ ID NO: 304). Relative positions of the target sites DD20-CR1 and DD20-CR2, qPCR primers and probe DD20-F, DD20-R, and DD20-T are marked. C) DD43 qPCR 115 bp amplicon 45731879-45731993 from chromosome 04 (SEQ ID NO: 305). Relative positions of the target sites DD43-CR1 and DD43-CR2, qPCR primers and probe DD43-F2, DD43-F, DD43-R, and DD43-T are marked.

Figure 25:
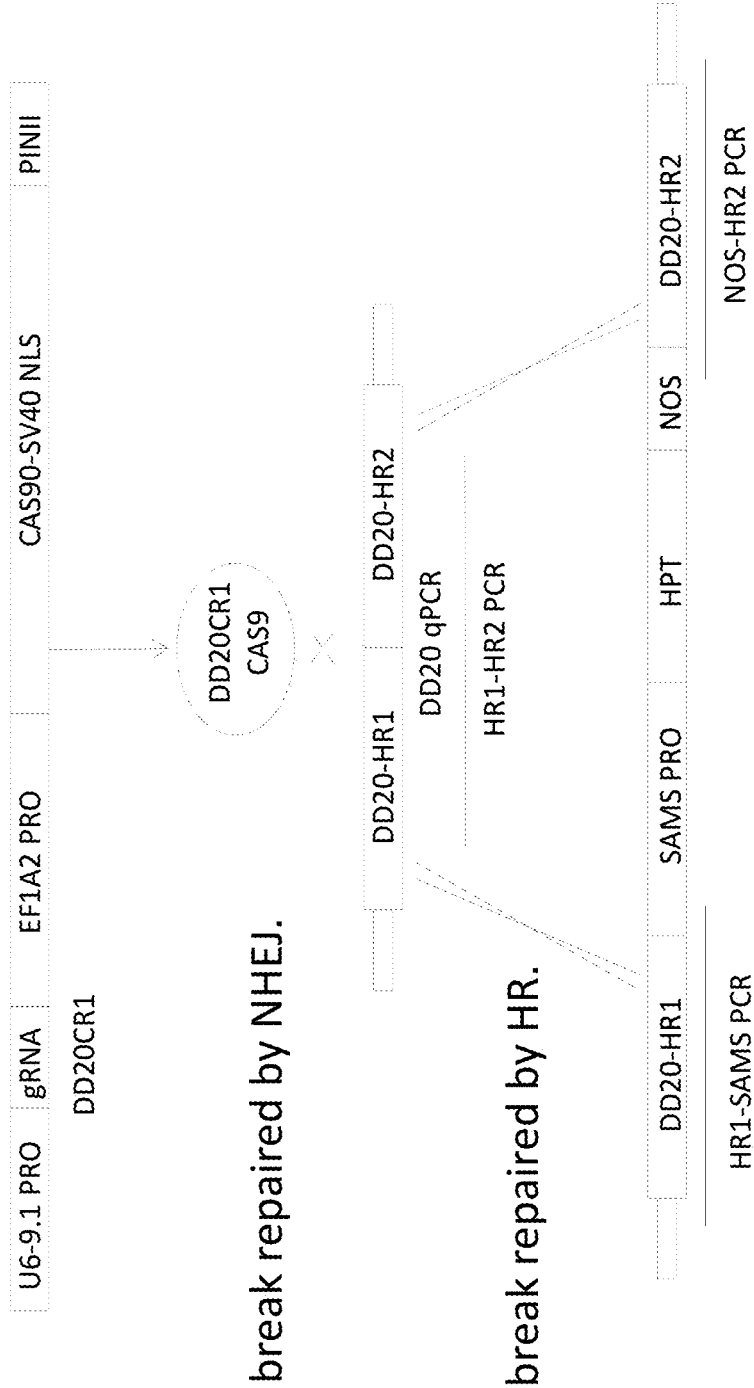

FIG. 25 A-C. Schematic of guide RNA/Cas9 system mediated site-specific non-homologous end joining (NHEJ) and transgene insertion via homologous recombination (HR) at DD20CR1 site. A) Soybean plants are co-transformed with guide RNA/Cas9 and donor DNA cassettes as listed in Table 27. The DD20CR1 guide RNA/Cas9 complex transcribed from the linked guide RNA/Cas9 DNA cassettes will cleave specifically the DD20CR1 target site on chromosome 04 to make DNA double strand breaks. The breaks can be repaired spontaneously as NHEJs or repaired as a HR event by the donor DNA facilitated by the flanking homologous regions DD20-HR1 and DD20HR2. B) NHEJs are detected by DD20-specific qPCR and the mutated sequences are assessed by sequencing cloned HR1-HR2 PCR fragments. C) HR events are revealed by two border-specific PCR analyses HR1-SAMS and NOS-HR2, noting that the primers are only able to amplify DNA recombined between the DD20CR1 region of chromosome 04 and the donor DNA. Guide RNA/Cas9 mediated NHEJ and HR at DD20-CR2 site follow the same process except for using DD20-CR2 guide RNA. Guide RNA/Cas9 mediated site-specific NHEJ and HR at DD43CR1 and DD43CR2 sites follow the same process except for using guide RNA and homologous regions specific to the DD43 sites.

FIG. 26 A-C. Sequences of gRNA/Cas9 system mediated NHEJs. Only 60 bp sequences surrounding the genomic target site shown in bold case are aligned to show the mutations. The PAM sequence is shown boxed in. Insertion sequences are indicated by symbol ˆ marking the insertion position followed by the size of the insert. Actual insertion sequences are listed in the sequences listing. A) U6-9.1 DD20CR1 sequences. Three colonies were sequenced for each of 54 events from experiment U6-9.1 DD20CR1. A total of 150 sequences were returned, of which 26 were found to be short unique deletions while 2 of the events contained small insertions. B) U6-9.1DD20CR2 sequences. Three colonies were sequenced for each of 28 events from experiment U6-9.1DD20CR2. A total of 84 sequences were returned, of which 20 were found to be short unique deletions while 1 of the events contained a single by insertion. C) U6-9.1DD43CR1 sequences. Three colonies were sequenced for each of 46 events from experiment U6-9.1DD43CR1. A total of 132 sequences were returned, of which 18 were found to be short unique deletions while 10 of the events contained small insertions. D) U6-9.1DD43CR2 sequences.

FIG. 27 A-C shows the ten most prevalent types of NHEJ mutations recovered based on the crRNA/tracrRNA/Cas endonuclease system. FIG. 27A shows NHEJ mutations for LIGCas-1 target site, corresponding to SEQ ID NOs: 415-424), FIG. 27B shows NHEJ mutations for LIGCas-2 target site corresponding to SEQ ID NOs: 425-434) and FIG. 27V shows NHEJ mutations (for LIGCas-3 target site corresponding to SEQ ID NOs: 435-444).

Figure 28:
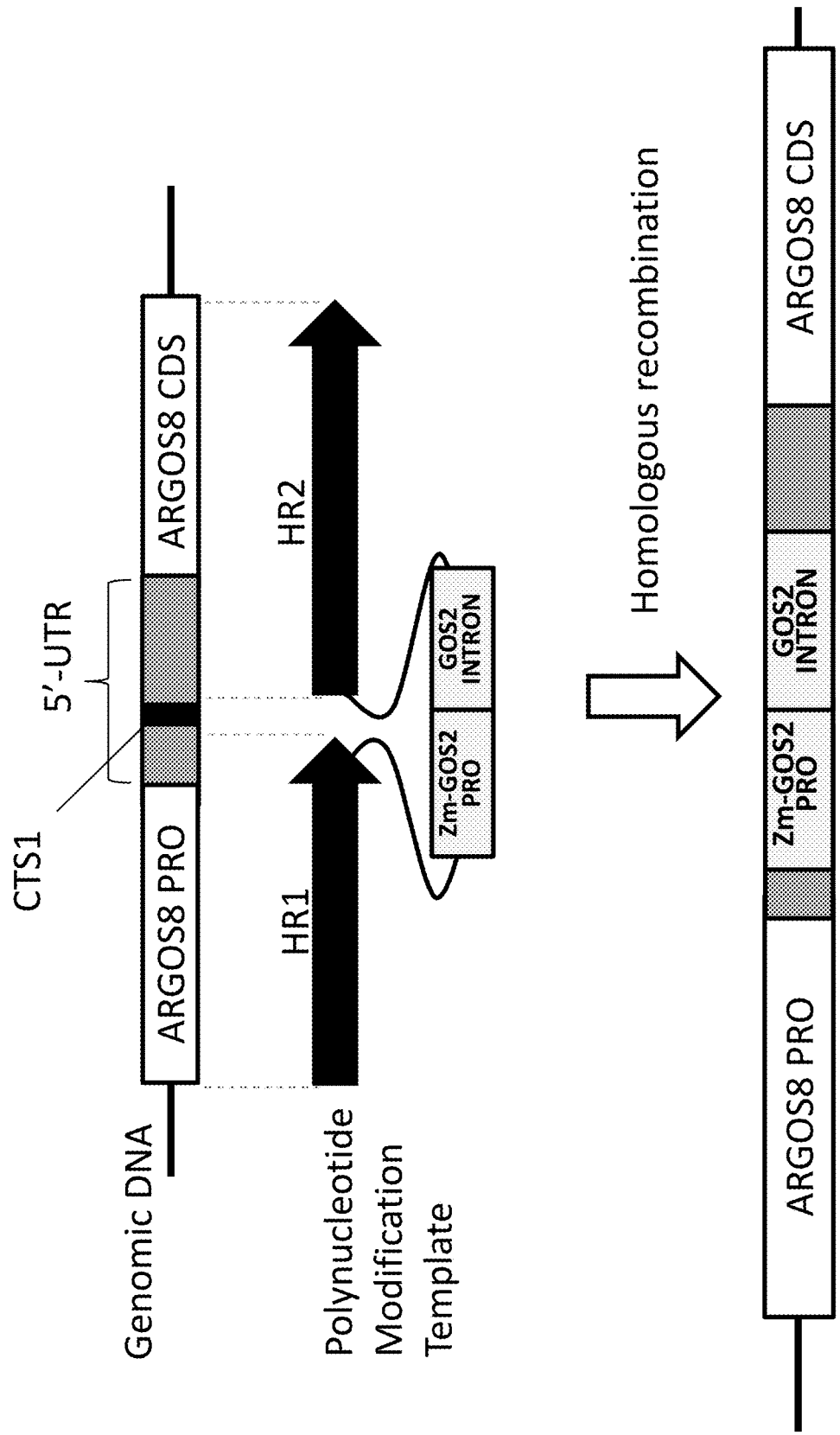

FIG. 28. Schematic representation of Zm-GOS2 PRO: GOS2 INTRON insertion in the 5'-UTR of maize ARGOS8 gene by targeting the guide RNA/Cas9 target sequence 1 (CTS1, SEQ ID NO: 1) with the gRNA1/Cas9 endonuclease system, described herein. HR1 and HR2 indicate homologous recombination regions.

FIG. 29A-29C. Identification and analysis of Zm-GOS2 PRO:GOS2 INTRON insertion events in maize plants. (A) Schematic representation of Zm-GOS2 PRO:GOS2 INTRON insertion in the 5'-UTR of Zm-ARGOS8. CTS1 was targeted with the gRNA1/Cas9 endonuclease system, described herein. HR1 and HR2 indicate homologous recombination regions. P1 to P4 indicate PCR primers. (B) PCR screening of PMI-resistance calli to identify insertion events. PCR results are shown for 13 representative calli. The left and right junction PCRs were carried out with the primer pair P1+P2 and P3+P4, respectively. (C) PCR analysis of a T0 plant. A PCR product with the expected size (2.4 kb, Lane T0) was amplified with the primer P3 and P4.

Figure 30:
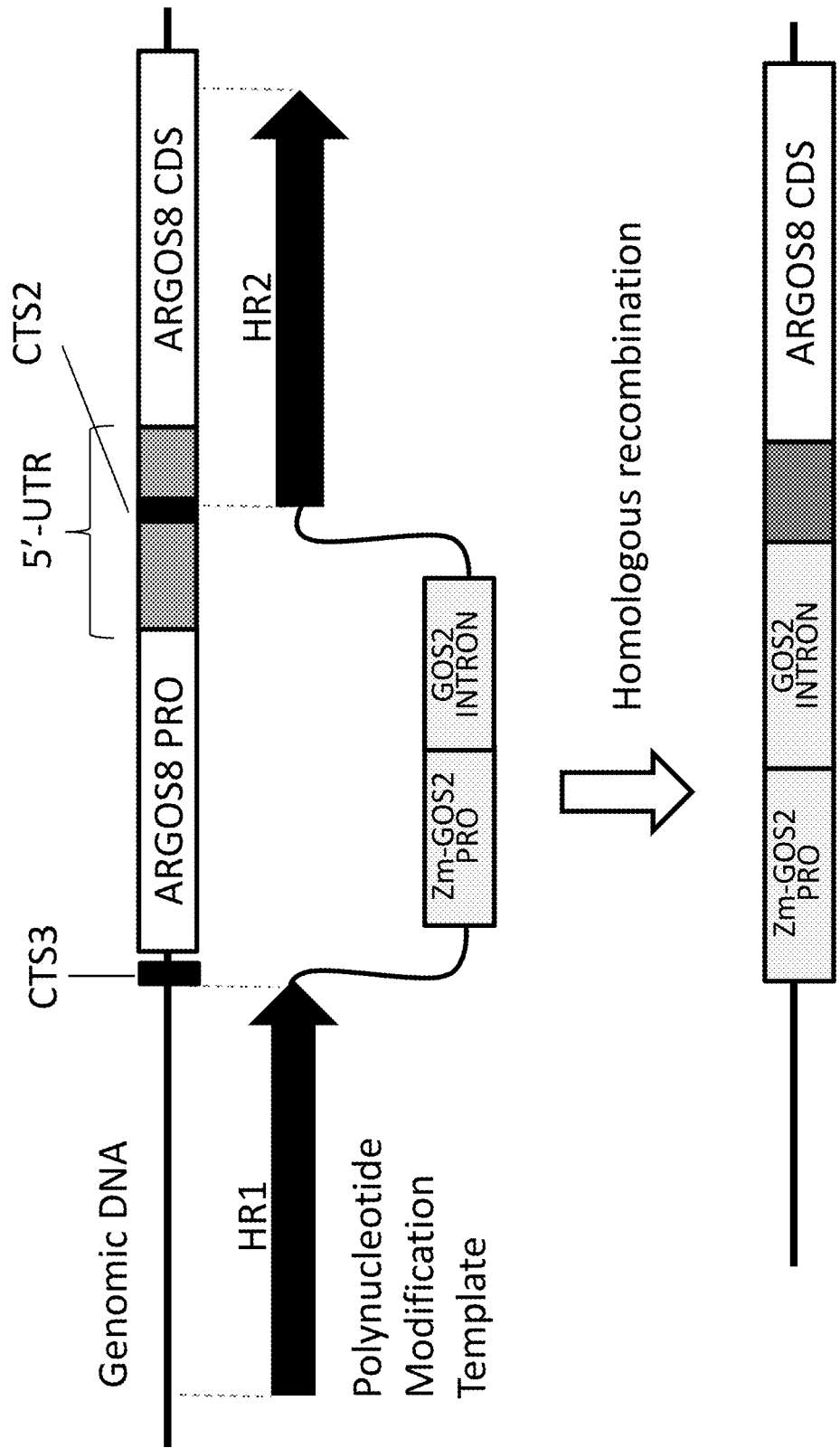

FIG. 30. Schematic representation of Zm-ARGOS8 promoter substitution with Zm-GOS2 PRO:GOS2 INTRON by targeting CTS3 (SEQ ID NO: 3) and CTS2 (SEQ ID NO:2). HR1 and HR2 indicate homologous recombination regions.

FIG. 31A-31D. Substitution of the native promoter of the ARGOS8 gene with Zm-GOS2 PRO:GOS2 INTRON in maize plants. (A) Schematic representation of the Zm-GOS2 PRO:GOS2 INTRON:ARGOS8 allele generated by promoter swap. Two guide RNA/Cas9 target sites, CTS3 (SEQ ID NO:3) and CTS2 (SEQ ID NO:2), were targeted with a gRNA3/gRNA2/Cas9 system. HR1 and HR2 indicate homologous recombination regions. P1 to P5 indicate PCR primers. (B) PCR screening of PMI-resistance calli to identify swap events. PCR results are shown for 10 representative calli. One callus sample, 12A09, is positive for both left junction (L, primer P1+P2) and right junction (R, primer P5+P4) PCR, indicating that 12A09 is a swap event. (C) PCR analysis of the callus events identified in primary screening. PCR products with the expected size (2.4 kb) were amplified using the primer P3 and P4 from event #3, 4, 6, 8 and 9, indicating presence of the Zm-GOS2 PRO: GOS2 INTRON:ARGOS8 allele. (D) PCR analysis of a T0 plant. A PCR product with the expected size (2.4 kb, Lane T0) was amplified with the primer P3 and P4.

Figure 32A:
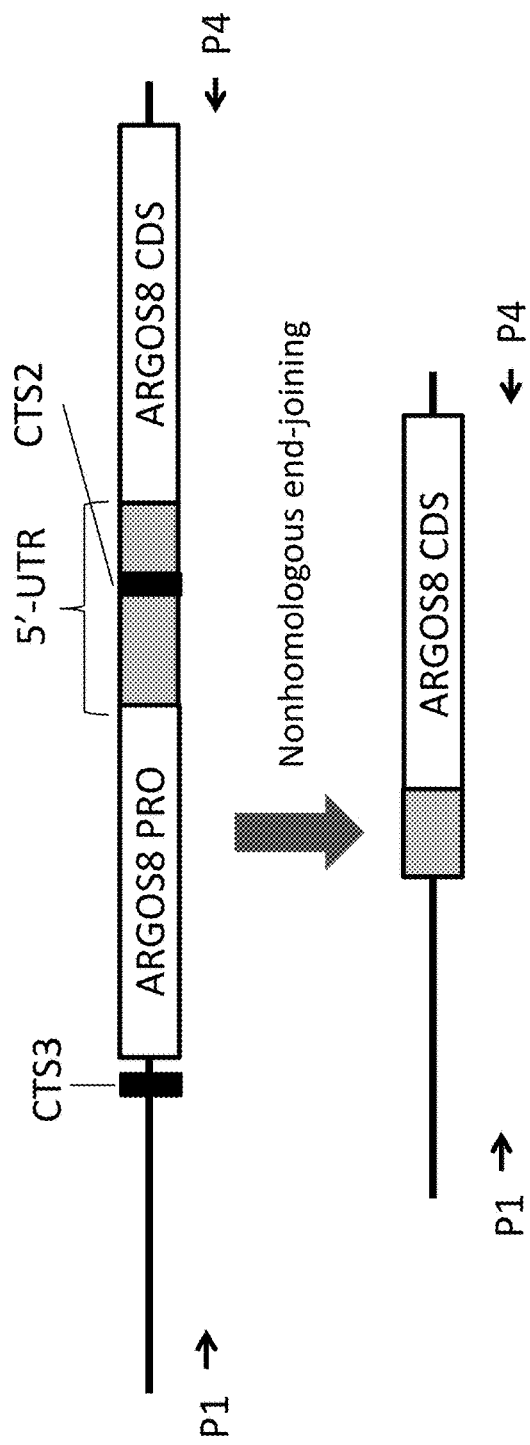
Figure 32B:
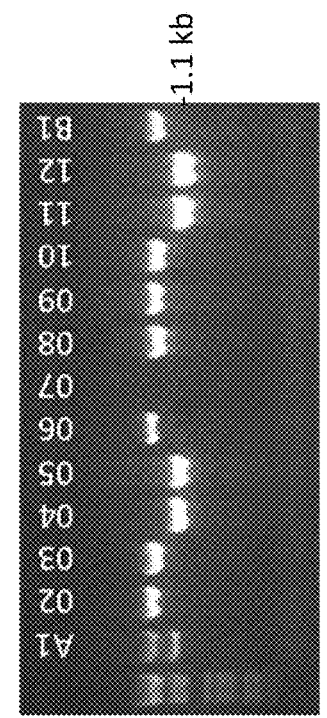

FIG. 32A-32B. Deletion of the native promoter of the ARGOS8 gene in maize plants. (A) Schematic representation of promoter deletion. Two guide RNA's and a Cas9 endonuclease system, referred to as a gRNA3/gRNA2/Cas9 system, were used to target the CTS3 and CTS2 sites in Zm-ARGOS8. P1 and P4 indicate PCR primers for deletion event screening. (B) PCR screening of PMI-resistance calli to identify deletion events. PCR results are shown for 15 representative calli. A 1.1-kp PCR product indicates deletion of the CTS3/CTS2 fragment.

Figure 33:
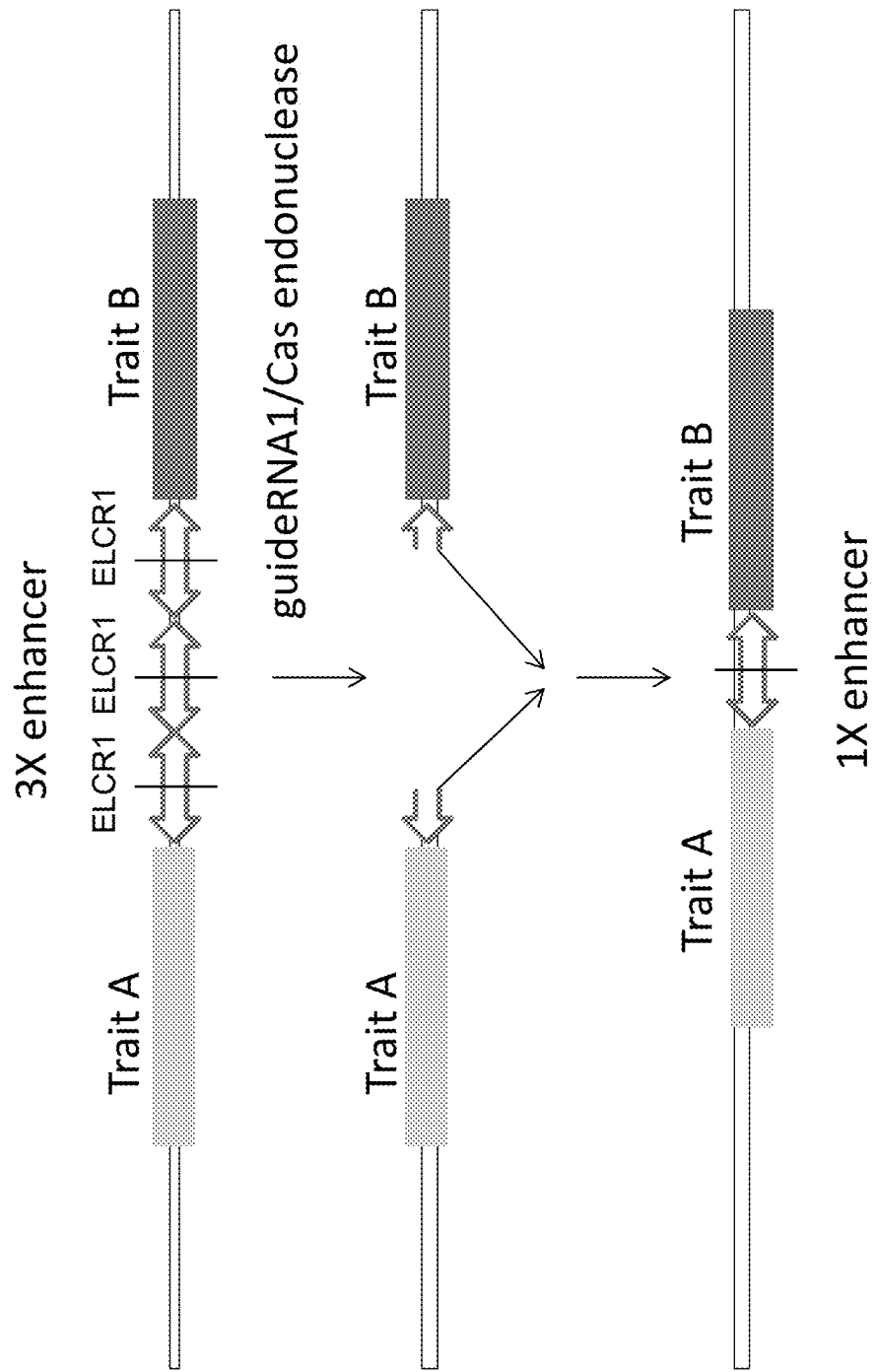

FIG. 33. Schematic representation of enhancer element deletions using the guide RNA/Cas9 target sequence. The enhancer element to be deleted can be, but is not limited to, a 35S enhancer element.

FIG. 34A-C. Modification of a maize EPSPS polyubiquitination site. (A) The selected maize EPSPS polyubiquitination site is compared to the analogous sites of other plant species (SEQ ID NOs: 562-567) (B) The nucleotides to be edited in the maize EPSPS coding sequence (underlined, encoded amino acid shown in bold). The sequence shown in FIG. 34B is listed in SEQ ID NO: 568 (C) The edited EPSPS coding sequence identified in the selected TO plant. The sequence shown in FIG. 34C is listed in SEQ ID NO: 569

FIG. 35A-C. The intron mediated enhanced element (A). The 5' section of the first intron of the EPSPS gene (editing: substitutions underlined and deletions represented by dots) (B) and its edited version conferring three IMEs elements (underlined). The edited nucleotides are shown in bold (C). The sequence shown in FIG. 35B is listed in SEQ ID NO: 570. The sequence shown in FIG. 35 C is listed in SEQ ID NO: 571

Figure 36:
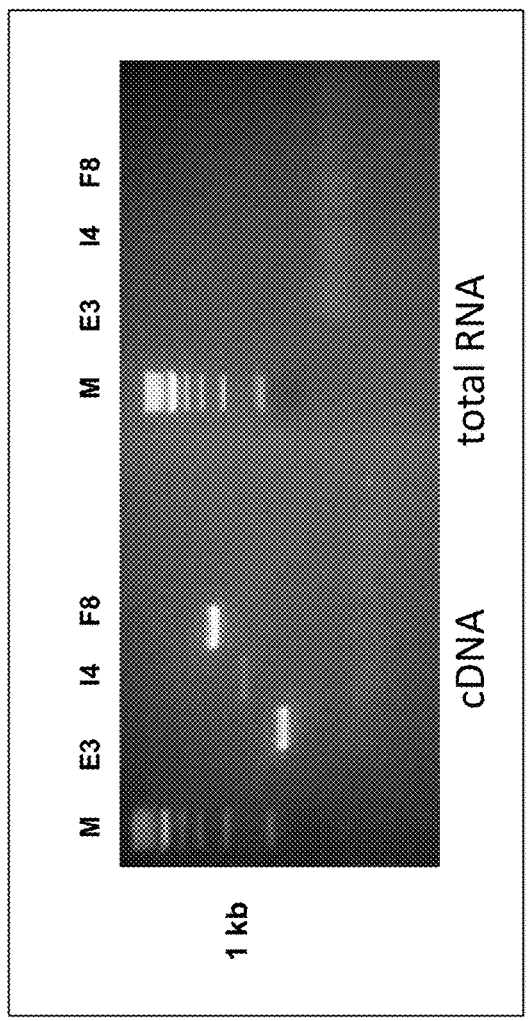
Figure 36:
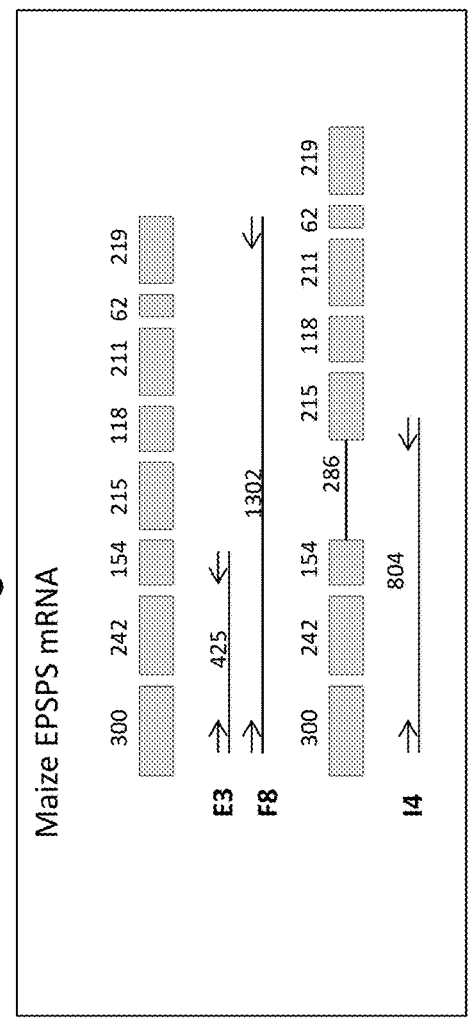

FIG. 36A-36B. Alternatively spliced EPSPS mRNA in maize cells. (A) left panel represents analysis of EPSPS cDNA. The lane 14 in FIG. 36A shows amplification of the EPSPS pre-mRNA containing the $3^{rd}$ intron unspliced (the 804 bp diagnostic fragment as shown in FIG. 36 B indicates an alternate splicing event). Lanes E3 and F8 show the EPSPS PCR amplified fragments with spliced introns. These diagnostic fragments are not amplified unless cDNA is synthesized (as is evident by the absence of bands in lanes E3, 14, and F8 comprising total RNA (shown in the total RNA panel on right of FIG. 36A). The grey boxes in FIG. 36 B represent the eight EPSPS exons (their sizes are indicated above each of them).

Figure 37:
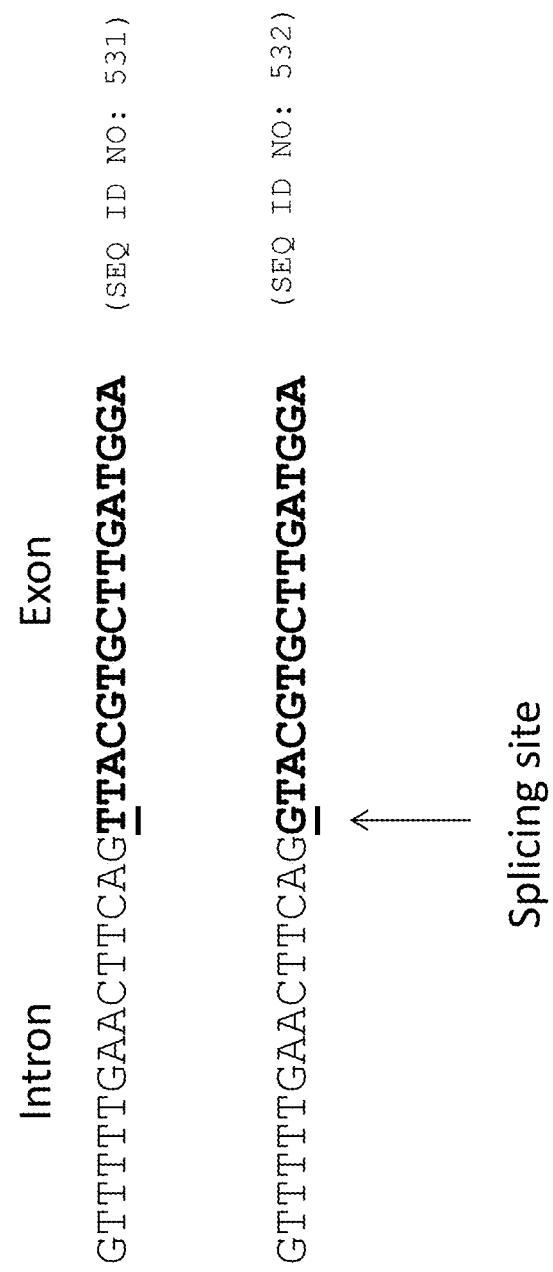

FIG. 37. Splicing site at the junction between the second EPSPS intron and the third exon (bolded). The nucleotide to be edited is underlined.

Figure 38:
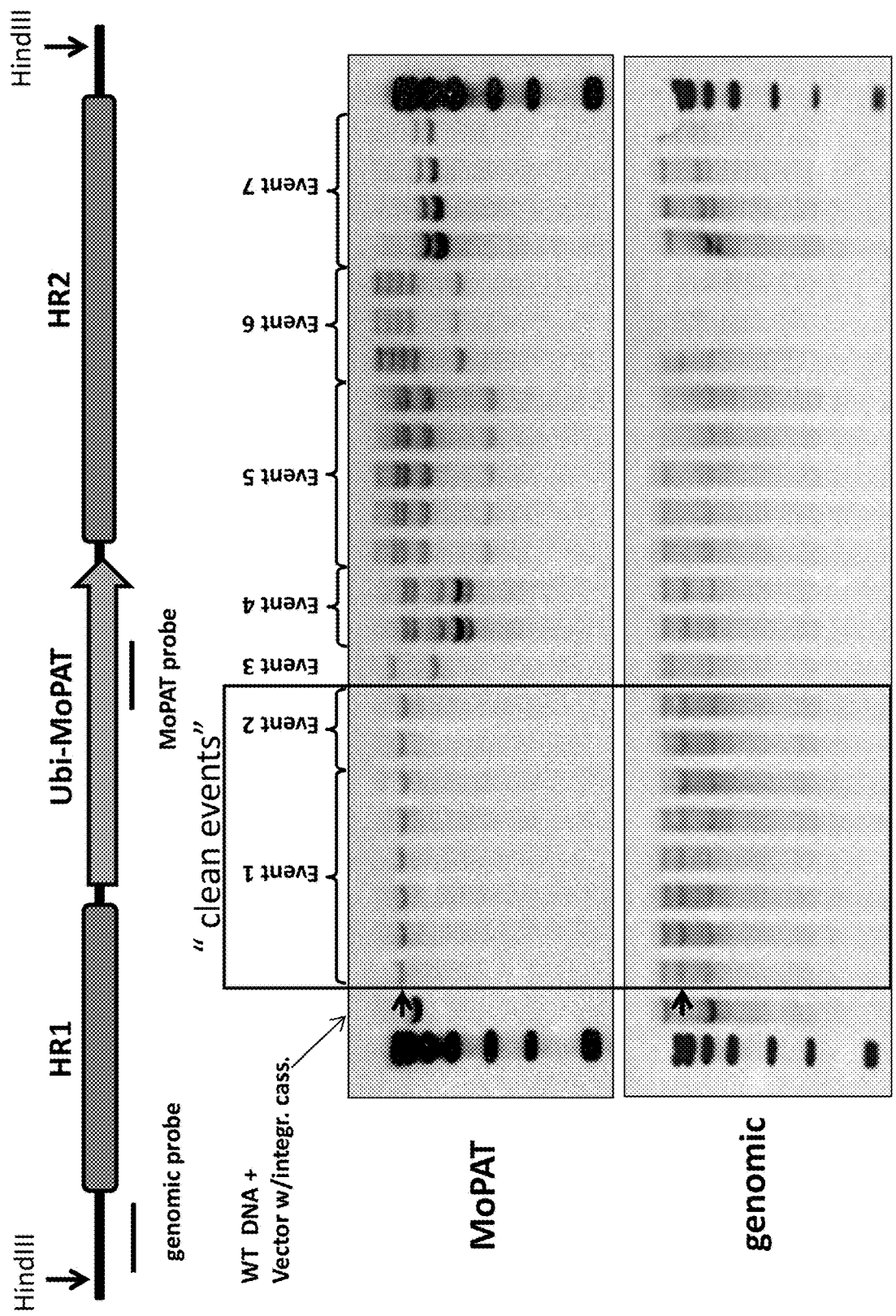

FIG. 38. Schematic representation of Southern hybridization analysis of T0 and T1 plants.

Figure 39:
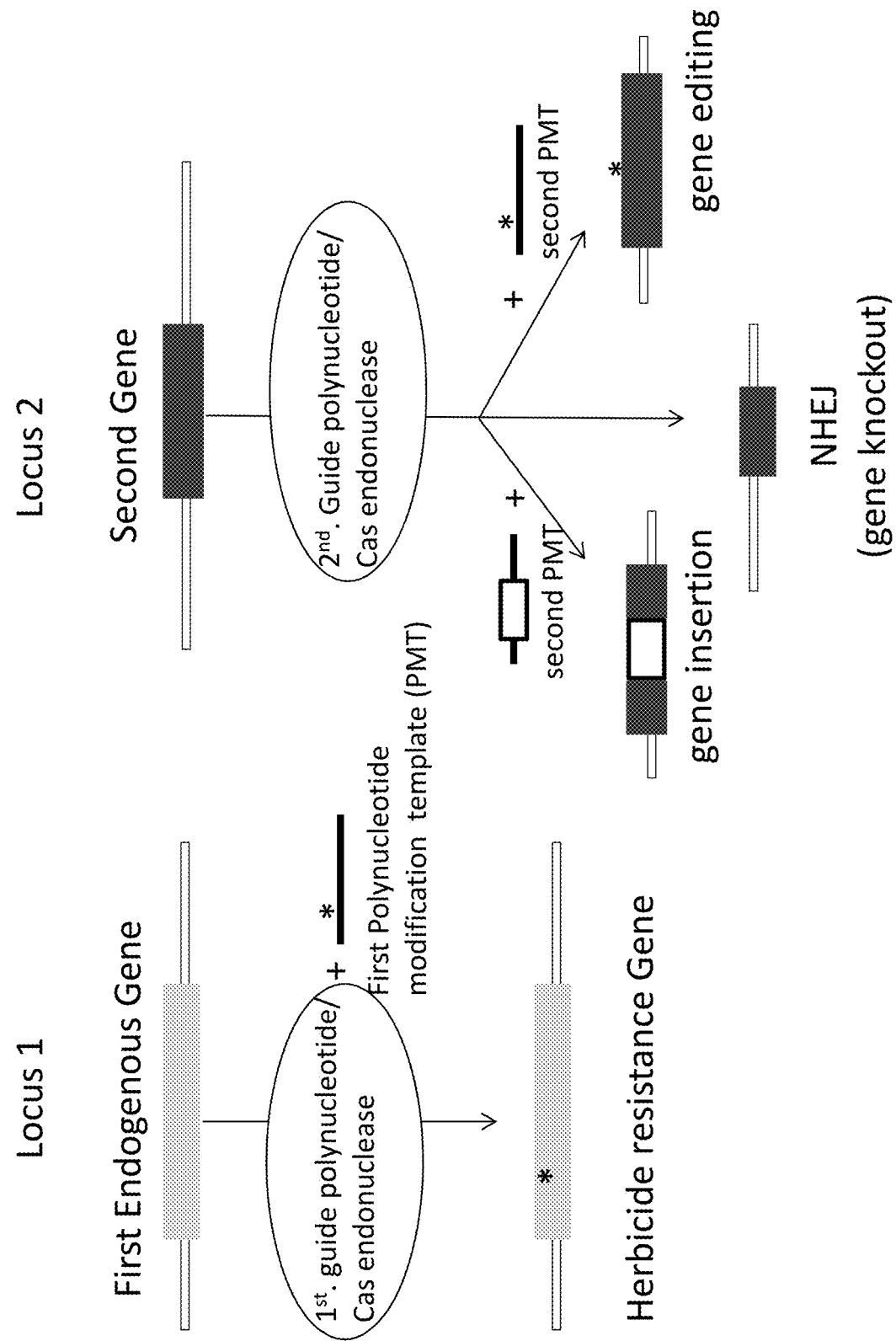

FIG. 39. Schematic representation of methods for producing a genetic modification (a gene insertion, a gene knockout via non-homologous-end-joining (NHEJ), a gene editing, or any combination thereof) into a second gene of a plant genome without introducing an exogenous selectable marker into said plant genome. A first endogenous gene (located in a first locus-locus 1) can be modified to confer herbicide resistance using a first guide polynucleotide/Cas endonuclease system together with a first polynucleotide modification template. At the same time, a second guide polynucleotide/Cas endonuclease system is provided to the same cell, with or without a second polynucleotide modification template to enable the second guide polynucleotide/Cas endonuclease system to introduce a double strand break at a second target site in the genome of said plant cell, resulting in either a gene insertion, gene knockout (NHEJ) or a gene editing. The second gene can be located at different locus (say locus 2) than the first endogenous gene. A "*" represents at least one nucleotide alteration in the polynucleotide modification template (PMT). A second PMT can comprise a polynucleotide of interest (shown by a white box) for gene insertion.

SEQUENCES

SEQ ID NO: 1 is the nucleotide sequence of the Cas9 gene from *Streptococcus pyogenes* M1 GAS (SF370).

SEQ ID NO: 2 is the nucleotide sequence of the potato ST-LS1 intron.

SEQ ID NO: 3 is the amino acid sequence of SV40 amino N-terminal.

SEQ ID NO: 4 is the amino acid sequence of *Agrobacterium tumefaciens* bipartite VirD2 T-DNA border endonuclease carboxyl terminal.

SEQ ID NO: 5 is the nucleotide sequence of an expression cassette expressing the maize optimized Cas9.

SEQ ID NO: 6 is the nucleotide sequence of crRNA containing the LIGCas-3 target sequence in the variable targeting domain.

SEQ ID NO: 7 is the nucleotide sequence of the tracrRNA.

SEQ ID NO: 8 is the nucleotide sequence of a long guide RNA containing the LIGCas-3 target sequence in the variable targeting domain.

SEQ ID NO: 9 is the nucleotide sequence of the Chromosome 8 maize U6 polymerase III promoter.

SEQ ID NO: 10 list two copies of the nucleotide sequence of the maize U6 polymerase III terminator.

SEQ ID NO: 11 is the nucleotide sequence of the maize optimized short guide RNA containing the LIGCas-3 variable targeting domain.

SEQ ID NO: 12 is the nucleotide sequence of the maize optimized long guide RNA expression cassette containing the LIGCas-3 variable targeting domain.

SEQ ID NO: 13 is the nucleotide sequence of the Maize genomic target site MS26Cas-1 plus PAM sequence.

SEQ ID NO: 14 is the nucleotide sequence of the Maize genomic target site MS26Cas-2 plus PAM sequence.

SEQ ID NO: 15 is the nucleotide sequence of the Maize genomic target site MS26Cas-3 plus PAM sequence.

SEQ ID NO: 16 is the nucleotide sequence of the Maize genomic target site LIGCas-2 plus PAM sequence.

SEQ ID NO: 17 is the nucleotide sequence of the Maize genomic target site LIGCas-3 plus PAM sequence.

SEQ ID NO: 18 is the nucleotide sequence of the Maize genomic target site LIGCas-4 plus PAM sequence.

SEQ ID NO: 19 is the nucleotide sequence of the Maize genomic target site MS45Cas-1 plus PAM sequence.

SEQ ID NO: 20 is the nucleotide sequence of the Maize genomic target site MS45Cas-2 plus PAM sequence.

SEQ ID NO: 21 is the nucleotide sequence of the Maize genomic target site MS45Cas-3 plus PAM sequence.

SEQ ID NO: 22 is the nucleotide sequence of the Maize genomic target site ALSCas-1 plus PAM sequence.

SEQ ID NO: 23 is the nucleotide sequence of the Maize genomic target site ALSCas-2 plus PAM sequence.

SEQ ID NO: 24 is the nucleotide sequence of the Maize genomic target site ALSCas-3 plus PAM sequence.

SEQ ID NO: 25 is the nucleotide sequence of the Maize genomic target site EPSPSCas-1 plus PAM sequence.

SEQ ID NO: 26 is the nucleotide sequence of the Maize genomic target site EPSPSCas-2 plus PAM sequence.

SEQ ID NO: 27 is the nucleotide sequence of the Maize genomic target site EPSPSCas-3 plus PAM sequence.

SEQ ID NOs: 28-52 are the nucleotide sequence of target site specific forward primers for primary PCR as shown in Table 2.

SEQ ID NO: 53 is the nucleotide sequence of the forward primer for secondary PCR.

SEQ ID NO: 54 is the nucleotide sequence of Reverse primer for secondary PCR

SEQ ID NO: 55 is the nucleotide sequence of the unmodified reference sequence for LIGCas-1 and LIGCas-2 locus.

SEQ ID NOs: 56-65 are the nucleotide sequences of mutations 1-10 for LIGCas-1.

SEQ ID NOs: 66-75 are the nucleotide sequences of mutations 1-10 for LIGCas-2.

SEQ ID NO: 76 is the nucleotide sequence of the unmodified reference sequence for the LIGCas-3 and LIG3-4 homing endonuclease locus.

SEQ ID NOs: 77-86 are the nucleotide sequences of mutations 1-10 for LIGCas-3.

SEQ ID NOs: 88-96 are the nucleotide sequences of mutations 1-10 for LIG3-4 homing endonuclease locus.

SEQ ID NO: 97 is the nucleotide sequence of a donor vector referred to as an HR Repair DNA.

SEQ ID NO: 98 is the nucleotide sequence of forward PCR primer for site-specific transgene insertion at junction 1.

SEQ ID NO: 99 is the nucleotide sequence of reverse PCR primer for site-specific transgene insertion at junction 1.

SEQ ID NO: 100 is the nucleotide sequence of forward PCR primer for site-specific transgene insertion at junction 2.

SEQ ID NO: 101 is the nucleotide sequence of reverse PCR primer for site-specific transgene insertion at junction 2.

SEQ ID NO: 102 is the nucleotide sequence of the linked Cas9 endonuclease and LIGCas-3 long guide RNA expression cassettes SEQ ID NO: 103 is the nucleotide sequence of Maize genomic target site 55CasRNA-1 plus PAM sequence.

SEQ ID NO: 104 is the nucleotide sequence of the unmodified reference sequence for 55CasRNA-1 locus.

SEQ ID NOs: 105-110 are the nucleotide sequences of mutations 1-6 for 55CasRNA-1.

SEQ ID NO: 111 is the nucleotide sequence of LIG3-4 homing endonuclease target site SEQ ID NO: 112 is the nucleotide sequence of LIG3-4 homing endonuclease coding sequence.

SEQ ID NO: 113 is the nucleotide sequence of the MS26++ homing endonuclease target site.

SEQ ID NO: 114 is the nucleotide sequence of MS26++ homing endonuclease coding sequence SEQ ID NO: 115 is the nucleotide sequence of the soybean codon optimized Cas9 gene.

SEQ ID NO: 116 is the nucleotide sequence of the soybean constitutive promoter GM-EF1A2.

SEQ ID NO: 117 is the nucleotide sequence of linker SV40 NLS.

SEQ ID NO: 118 is the amino acid sequence of soybean optimized Cas9 with a SV40 NLS.

SEQ ID NO: 119 is the nucleotide sequence of vector QC782.

SEQ ID NO: 120 is the nucleotide sequence of soybean U6 polymerase III promoter described herein, GM-U6-13.1 PRO.

SEQ ID NO: 121 is the nucleotide sequence of the guide RNA in FIG. 8B.

SEQ ID NO: 122 is the nucleotide sequence of vector QC783.

SEQ ID NO: 123 is the nucleotide sequence of vector QC815.

SEQ ID NO: 124 is the nucleotide sequence of a Cas9 endonuclease (cas9-2) from S. pyogenes.

SEQ ID NO: 125 is the nucleotide sequence of the DD20CR1 soybean target site

SEQ ID NO: 126 is the nucleotide sequence of the DD20CR2 soybean target site

SEQ ID NO: 127 is the nucleotide sequence of the DD43CR1 soybean target site

SEQ ID NO: 128 is the nucleotide sequence of the DD43CR2 soybean target site

SEQ ID NO: 129 is the nucleotide sequence of the DD20 sequence in FIG. 10A.

SEQ ID NO: 130 is the nucleotide sequence of the DD20 sequence complementary in FIG. 10A.

SEQ ID NO: 131 is the nucleotide sequence of DD43 sequence.

SEQ ID NO: 132 is the nucleotide sequence of the DD43 complementary sequence.

SEQ ID NO: 133-141 are primer sequences.

SEQ ID NO: 142 is the nucleotide sequence of the DD20CR1 PCR amplicon.

SEQ ID NO: 143 is the nucleotide sequence of the DD20CR2 PCR amplicon.

SEQ ID NO: 144 is the nucleotide sequence of the DD43CR1 PCR amplicon.

SEQ ID NO: 145 is the nucleotide sequence of the DD43CR2 PCR amplicon.

SEQ ID NO: 146 is the nucleotide sequence of the DD43CR2 PCR amplicon.

SEQ ID NO: 147-156 are the nucleotide sequence of mutations 1 to 10 for the DD20CR1 target site SEQ ID NO: 157-166 are the nucleotide sequence of mutations 1 to 10 for the DD20CR2 target site SEQ ID NO: 167-176 are the nucleotide sequence of mutations 1 to 10 for the DD43CR1 target site SEQ ID NO: 177-191 are the nucleotide sequence of mutations 1 to 10 for the DD43CR2 target site.

SEQ ID NO: 192 is the amino acid sequence of a maize optimized version of the Cas9 protein.

SEQ ID NO: 193 is the nucleotide sequence of the maize optimized version of the Cas9 gene of SEQ ID NO: 192.

SEQ ID NO: 194 is the DNA version of guide RNA (EPSPS sgRNA).

SEQ ID NO: 195 is the EPSPS polynucleotide modification template.

SEQ ID NO: 196 is a nucleotide fragment comprising the TIPS nucleotide modifications.

SEQ ID NO: 197-204 are primer sequences shown in Table 15.

SEQ ID NO: 205-208 are nucleotide fragments shown in FIG. 14.

SEQ ID NO: 209 is an example of a TIPS edited EPSPS nucleotide sequence fragment shown in FIG. 17.

SEQ ID NO: 210 is an example of a Wild-type EPSPS nucleotide sequence fragment shown in FIG. 17.

SEQ ID NO: 211 is the nucleotide sequence of a maize enolpyruvylshikimate-3-phosphate synthase (epsps) locus SEQ ID NO: 212 is the nucleotide sequence of a Cas9 endonuclease (genbank CS571758.1) from S. thermophiles.

SEQ ID NO: 213 is the nucleotide sequence of a Cas9 endonuclease (genbank CS571770.1) from S. thermophiles.

SEQ ID NO: 214 is the nucleotide sequence of a Cas9 endonuclease (genbank CS571785.1) from S. agalactiae.

SEQ ID NO: 215 is the nucleotide sequence of a Cas9 endonuclease, (genbank CS571790.1) from S. agalactiae.

SEQ ID NO: 216 is the nucleotide sequence of a Cas9 endonuclease (genbank CS571790.1) from S. mutant.

SEQ ID NOs: 217-228 are primer and probe nucleotide sequences described in Example 17.

SEQ ID NOs: 229 is the nucleotide sequence of the MHP14Cas1 target site.

SEQ ID NOs: 230 is the nucleotide sequence of the MHP14Cas3 target site.

SEQ ID NOs: 231 is the nucleotide sequence of the TS8Cas1 target site.

SEQ ID NOs: 232 is the nucleotide sequence of the TS8Cas2 target site.

SEQ ID NOs: 233 is the nucleotide sequence of the TS9Cas2 target site.

SEQ ID NOs: 234 is the nucleotide sequence of the TS9Cas3 target site.

SEQ ID NOs: 235 is the nucleotide sequence of the TS10Cas1 target site.

SEQ ID NOs: 236 is the nucleotide sequence of the TS10Cas3 target site.

SEQ ID NOs: 237-244 are the nucleotide sequences shown in FIG. 19A-D.

SEQ ID NOs: 245-252 are the nucleotide sequences of the guide RNA expression cassettes described in Example 18.

SEQ ID NOs: 253-260 are the nucleotide sequences of donor DNA expression cassettes described in Example 18.

SEQ ID NOs: 261-270 are the nucleotide sequences of the primers described in Example 18.

SEQ ID NOs: 271-294 are the nucleotide sequences of the primers and probes described in Example 18.

SEQ ID NO: 295 is the nucleotide sequence of GM-U6-13.1 PRO, a soybean U6 polymerase III promoter described herein, SEQ ID NOs: 298, 300, 301 and 303 are the nucleotide sequences of the linked guideRNA/Cas9 expression cassettes.

SEQ ID NOs: 299 and 302 are the nucleotide sequences of the donor DNA expression cassettes.

SEQ ID NOs: 271-294 are the nucleotide sequences of the primers and probes described in Example 18.

SEQ ID NO: 304 is the nucleotide sequence of the DD20 qPCR amplicon.

SEQ ID NO: 305 is the nucleotide sequence of the DD43 qPCR amplicon.

SEQ ID NOs: 306-328 are the nucleotide sequences of the primers and probes described herein.

SEQ ID NOs: 329-334 are the nucleotide sequences of PCR amplicons described herein.

SEQ ID NO: 335 is the nucleotide sequence of a soybean genomic region comprising the DD20CR1 target site.

SEQ ID NO: 364 is the nucleotide sequence of a soybean genomic region comprising the DD20CR2 target site.

SEQ ID NO: 386 is the nucleotide sequence of a soybean genomic region comprising the DD43CR1 target site.

SEQ ID NOs: 336-363, 365-385 and 387-414 are the nucleotide sequences of shown in FIG. 26 A-C.

SEQ ID NOs: 415-444 are the nucleotide sequences of NHEJ mutations recovered based on the crRNA/tracrRNA/Cas endonuclease system shown in FIG. 27A-C.

SEQ ID NO: 445-447 are the nucleotide sequence of the LIGCas-1, LIGCas2 and LIGCas3 crRNA expression cassettes, respectively.

SEQ ID NO: 448 is the nucleotide sequence of the tracrRNA expression cassette.

SEQ ID NO: 449 is the nucleotide sequence of LIGCas-2 forward primer for primary PCR SEQ ID NO: 450 is the nucleotide sequence of LIGCas-3 forward primer for primary PCR.

SEQ ID NO: 451 is the nucleotide sequence of the maize genomic Cas9 endonuclease target site Zm-ARGOS8-CTS1.

SEQ ID NO: 452 is the nucleotide sequence of the maize genomic Cas9 endonuclease target site Zm-ARGOS8-CTS2.

SEQ ID NO: 453 is the nucleotide sequence of the maize genomic Cas9 endonuclease target site Zm-ARGOS8-CTS3

SEQ ID NOs: 454-458 are the nucleotide sequence of primers P1, P2, P3, P4, P5, respectively.

SEQ ID NO: 459 is the nucleotide sequence of a Primer Binding Site (PBS), a sequence to facilitate event screening.

SEQ ID NO: 460 is the nucleotide sequence of the Zm-GOS2 PRO-GOS2 INTRON, the maize GOS2 promoter and GOS2 intron1 including the promoter, 5'-UTR1, INTRON1 and 5'-UTR2.

SEQ ID NO:461 is the nucleotide sequence of the maize Zm-ARGOS8 promoter.

SEQ ID NO:462 is the nucleotide sequence of the maize Zm-ARGOS8 5'-UTR.

SEQ ID NO:463 is the nucleotide sequence of the maize Zm-ARGOS8 codon sequence

SEQ ID NO:464 is the nucleotide sequence of the maize Zm-GOS2 gene, including promoter, 5'-UTR, CDS, 3'-UTR and introns.

SEQ ID NO:465 is the nucleotide sequence of the maize Zm-GOS2 PRO promoter.

SEQ ID NO:466 is the nucleotide sequence of the maize GOS2 INTRON, maize GOS2 5'-UTR1 and intron1 and 5'-UTR2.

SEQ ID NOs: 467-468, 490-491, 503-504 are the nucleotide sequence of the soybean genomic Cas endonuclease target sequences soy EPSPS-CR1, soy EPSPS-CR2, soy EPSPS-CR4, soy EPSPS-CR5, soy EPSPS-CR6, soy EPSPS-CR7, respectively SEQ ID NO:469 is the nucleotide sequence of the soybean U6 small nuclear RNA promoter GM-U6-13.1.

SEQ ID NOs:470, 471 are the nucleotide sequences of the QC868, QC879 plasmids, respectively.

SEQ ID NOs:472, 473, 492, 493, 494, 505, 506, 507 are the nucleotide sequences of the RTW1013A, RTW1012A, RTW1199, RTW1200, RTW1190A, RTW1201, RTW1202, RTW1192A respectively.

SEQ ID NOs:474-488, 495-402, 508-512 are the nucleotide sequences of primers and probes.

SEQ ID NO: 489 is the nucleotide sequence of the soybean codon optimized Cas9.

SEQ ID NO: 513 is the nucleotide sequence of the 35S enhancer.

SEQ ID NO: 514 is the nucleotide sequence of the 35S-CRTS for gRNA1 at 163-181 (including pam at 3'end).

SEQ ID NO: 515 is the nucleotide sequence of the 35S-CRTS for gRNA2 at 295-319 (including pam at 3'end).

SEQ ID NO: 516 is the nucleotide sequence of the 35S-CRT for gRNA3 at 331-350 (including pam at 3'end).

SEQ ID NO: 517 is the nucleotide sequence of the EPSPS-K90R template.

SEQ ID NO: 518 is the nucleotide sequence of the EPSPS-IME template. S

SEQ ID NO: 519 is the nucleotide sequence of the EPSPS-Tspliced template.

SEQ ID NO: 520 is the amino acid sequence of ZM-RAP2.7 peptide

SEQ ID NO: 521 is the nucleotide sequence zM-RAP2.7 coding DNA sequence

SEQ ID NOs: 522 is the amino acid sequence of ZM-NPK1B peptide

SEQ ID NO: 523 is the nucleotide sequence of the ZM-NPK1B coding DNA sequence

SEQ ID NOs: 524 is the nucleotide sequence of the RAB17 promoter

SEQ ID NOs: 525 is the amino acid sequence of the Maize FTM1.

SEQ ID NO: 526 is the nucleotide sequence of the Maize FTM1 coding DNA sequence.

SEQ ID NOs: 527-532 are the nucleotide sequences shown in FIGS. 34, 35 and 37.

SEQ ID NOs: 533-534 are the nucleotide sequences of the Southern genomic probe and Southern MoPAT probe of FIG. 38, respectively. SEQ ID NOs: 535-541 are the nucleotide sequences of the RF-FPCas-1, RF-FPCas-2, ALSCas-4, ALS modification repair template 804, ALS modification repair template 127, ALS Forward_primer and ALS Reverse_primer, respectively.

SEQ ID NOs: 542-549 are the nucleotide sequences of the soy ALS1-CR1, Cas9 target sequence, soy ALS2-CR2, Cas9 target sequence, QC880, QC881, RTW1026A, WOL900, Forward_primer, WOL578, Reverse_primer and WOL573, Forward_primer, respectively.

SEQ ID NO: 550 is the nucleotide sequence of a maize ALS protein.

SEQ ID NOs: 551-554 are the nucleotide sequences of the soy FAD2-1-CR1, Cas9 target sequence, soy FAD2-1-CR2, Cas9 target sequence, RTW1211 and RTW1212.

DETAILED DESCRIPTION

The present disclosure includes compositions and methods for genome modification of a target sequence in the genome of a plant or plant cell, for selecting plants, for gene editing, and for inserting a polynucleotide of interest into the genome of a plant without incorporating a selectable transgene marker. The methods employ a guide polynucleotide/Cas endonuclease system, wherein the Cas endonuclease is guided by at least two guide polynucleotides to recognize and optionally introduce a double strand break at a specific first and second target site into the genome of a cell. The guide polynucleotide/Cas endonuclease system provides for an effective system for modifying target sites within the genome of a plant, plant cell or seed. Further provided are methods and compositions employing a guide polynucleotide/Cas endonuclease for editing a nucleotide sequence in the genome of a cell. Once a genomic target site is identified, a variety of methods can be employed to further modify the target sites such that they contain a variety of polynucleotides of interest. Breeding methods utilizing a two component guide RNA/Cas endonuclease system are also disclosed. Compositions and methods are also provided for editing a nucleotide sequence in the genome of a cell. The nucleotide sequence to be edited (the nucleotide sequence of interest) can be located within or outside a target site that is recognized by a Cas endonuclease.

CRISPR loci (Clustered Regularly Interspaced Short Palindromic Repeats) (also known as SPIDRs—SPacer Interspersed Direct Repeats) constitute a family of recently described DNA loci. CRISPR loci consist of short and highly conserved DNA repeats (typically 24 to 40 bp, repeated from 1 to 140 times—also referred to as CRISPR-repeats) which are partially palindromic. The repeated sequences (usually specific to a species) are interspaced by variable sequences of constant length (typically 20 to 58 bp depending on the CRISPR locus (WO2007/025097 published Mar. 1, 2007).

CRISPR loci were first recognized in *E. coli* (Ishino et al. (1987) J. Bacterial. 169:5429-5433; Nakata et al. (1989) J. Bacterial. 171:3553-3556). Similar interspersed short sequence repeats have been identified in *Haloferax mediterranei*, *Streptococcus pyogenes*, *Anabaena*, and *Mycobacterium tuberculosis* (Groenen et al. (1993) Mol. Microbiol. 10:1057-1065; Hoe et al. (1999) Emerg. Infect. Dis. 5:254-263; Masepohl et al. (1996) Biochim. Biophys. Acta 1307: 26-30; Mojica et al. (1995) Mol. Microbiol. 17:85-93). The CRISPR loci differ from other SSRs by the structure of the repeats, which have been termed short regularly spaced repeats (SRSRs) (Janssen et al. (2002) OMICS J. Integ. Biol. 6:23-33; Mojica et al. (2000) Mol. Microbiol. 36:244-246). The repeats are short elements that occur in clusters, which are always regularly spaced by variable sequences of constant length (Mojica et al. (2000) Mol. Microbiol. 36:244-246).

Cas gene includes a gene that is generally coupled, associated or close to or in the vicinity of flanking CRISPR loci. The terms "Cas gene", "CRISPR-associated (Cas) gene" are used interchangeably herein. A comprehensive review of the Cas protein family is presented in Haft et al. (2005) Computational Biology, PLoS Comput Biol 1(6): e60. doi:10.1371/journal.pcbi.0010060.

As described therein, 41 CRISPR-associated (Cas) gene families are described, in addition to the four previously known gene families. It shows that CRISPR systems belong to different classes, with different repeat patterns, sets of genes, and species ranges. The number of Cas genes at a given CRISPR locus can vary between species.

Cas endonuclease relates to a Cas protein encoded by a Cas gene, wherein said Cas protein is capable of introducing a double strand break into a DNA target sequence. The Cas endonuclease is guided by the guide polynucleotide to recognize and optionally introduce a double strand break at a specific target site into the genome of a cell. As used herein, the tem "guide polynucleotide/Cas endonuclease system" includes a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide RNA, but only if the correct protospacer-adjacent motif (PAM) is approximately oriented at the 3' end of the target sequence (FIG. 2A, FIG. 2B).

In one embodiment, the Cas endonuclease gene is a Cas9 endonuclease, such as but not limited to, Cas9 genes listed in SEQ ID NOs: 462, 474, 489, 494, 499, 505, and 518 of WO2007/025097 published Mar. 1, 2007, and incorporated herein by reference. In another embodiment, the Cas endonuclease gene is plant, maize or soybean optimized Cas9 endonuclease (FIG. 1 A). In another embodiment, the Cas endonuclease gene is operably linked to a SV40 nuclear targeting signal upstream of the Cas codon region and a bipartite VirD2 nuclear localization signal (Tinland et al. (1992) Proc. Natl. Acad. Sci. USA 89:7442-6) downstream of the Cas codon region.

In one embodiment, the Cas endonuclease gene is a Cas9 endonuclease gene of SEQ ID NO:1, 124, 212, 213, 214, 215, 216, 193 or nucleotides 2037-6329 of SEQ ID NO:5, or any functional fragment or variant thereof.

The terms "functional fragment", "fragment that is functionally equivalent" and "functionally equivalent fragment" are used interchangeably herein. These terms refer to a portion or subsequence of the Cas endonuclease sequence of the present disclosure in which the ability to create a double-strand break is retained.

The terms "functional variant", "Variant that is functionally equivalent" and "functionally equivalent variant" are used interchangeably herein. These terms refer to a variant of the Cas endonuclease of the present disclosure in which the ability create a double-strand break is retained. Fragments and variants can be obtained via methods such as site-directed mutagenesis and synthetic construction.

In one embodiment, the Cas endonuclease gene is a plant codon optimized *Streptococcus pyogenes* Cas9 gene that can recognize any genomic sequence of the form N(12-30)NGG can in principle be targeted.

In one embodiment, the Cas endonuclease is introduced directly into a cell by any method known in the art, for example, but not limited to transient introduction methods, transfection and/or topical application.

Endonucleases are enzymes that cleave the phosphodiester bond within a polynucleotide chain, and include restriction endonucleases that cleave DNA at specific sites without damaging the bases. Restriction endonucleases include Type I, Type II, Type III, and Type IV endonucleases, which further include subtypes. In the Type I and Type III systems, both the methylase and restriction activities are contained in a single complex. Endonucleases also include meganucleases, also known as homing endonucleases (HEases), which like restriction endonucleases, bind and cut at a specific recognition site, however the recognition sites for meganucleases are typically longer, about 18 bp or more. (patent application WO-PCT PCT/US12/30061 filed on Mar. 22, 2012) Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. This cleaving activity can be used to produce a double-strand break. For reviews of site-specific recombinases and their recognition sites, see, Sauer (1994) Curr Op Biotechnol 5:521-7; and Sadowski (1993) FASEB 7:760-7. In some examples the recombinase is from the Integrase or Resolvase families.

TAL effector nucleases are a new class of sequence-specific nucleases that can be used to make double-strand breaks at specific target sequences in the genome of a plant or other organism. (Miller et al. (2011) *Nature Biotechnology* 29:143-148). Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind an 18 nucleotide recognition sequence.

Bacteria and archaea have evolved adaptive immune defenses termed clustered regularly interspaced short palindromic repeats (CRISPR)/CRISPR-associated (Cas) systems that use short RNA to direct degradation of foreign nucleic acids ((WO2007/025097 published Mar. 1, 2007). The type II CRISPR/Cas system from bacteria employs a crRNA and tracrRNA to guide the Cas endonuclease to its DNA target. The crRNA (CRISPR RNA) contains the region complementary to one strand of the double strand DNA target and base pairs with the tracrRNA (trans-activating CRISPR RNA) forming a RNA duplex that directs the Cas endonuclease to cleave the DNA target (FIG. 2 B).

As used herein, the term "guide RNA" includes a synthetic fusion of two RNA molecules, a crRNA (CRISPR RNA) comprising a variable targeting domain, and a tracrRNA (FIG. 2 B). In one embodiment, the guide RNA comprises a variable targeting domain of 12 to 30 nucleotide sequences and a RNA fragment that can interact with a Cas endonuclease.

As used herein, the term "guide polynucleotide", includes a polynucleotide sequence that can form a complex with a Cas endonuclease and enables the Cas endonuclease to recognize and optionally cleave a DNA target site. The guide polynucleotide can be included a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited to, Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA".

The guide polynucleotide can be a double molecule (also referred to as duplex guide polynucleotide) comprising a first nucleotide sequence domain (referred to as Variable Targeting domain or VT domain) that is complementary to a nucleotide sequence in a target DNA and a second nucleotide sequence domain (referred to as as endonuclease recognition domain or CER domain) that interacts with a Cas endonuclease polypeptide. The CER domain of the double molecule guide polynucleotide comprises two separate molecules that are hybridized along a region of complementarity. The two separate molecules can be RNA, DNA, and/or RNA-DNA-combination sequences. In some embodiments, the first molecule of the duplex guide polynucleotide comprising a VT domain linked to a CER domain is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the cRNA naturally occurring in Bacteria and Archaea. In one embodiment, the size of the fragment of the cRNA naturally occurring in Bacteria and Archaea that is present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides In one embodiment, the RNA that guides the RNA/Cas9 endonuclease complex, is a duplexed RNA comprising a duplex crRNA-tracrRNA.

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. In some embodiments the single guide polynucleotide comprises a crNucleotide (comprising a VT domain linked to a CER domain) linked to a tracrNucleotide (comprising a CER domain), wherein the linkage is a nucleotide sequence comprising a RNA sequence, a DNA sequence, or a RNA-DNA combination sequence. The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). In one embodiment of the disclosure, the single guide RNA comprises a cRNA or cRNA fragment and a tracrRNA or tracrRNA fragment of the type II CRISP R/Cas system that can form a complex with a type II Cas endonuclease, wherein said guide RNA/Cas endonuclease complex can direct the Cas endonuclease to a plant genomic target site, enabling the Cas endonuclease to introduce a double strand break into the genomic target site. One aspect of using a single guide polynucleotide versus a duplex guide polynucleotide is that only one expression cassette needs to be made to express the single guide polynucleotide.

The term "variable targeting domain" or "VT domain" is used interchangeably herein and includes a nucleotide sequence that is complementary to one strand (nucleotide sequence) of a double strand DNA target site (FIGS. 2 A and 2 B). The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

In one embodiment, the guide RNA and Cas endonuclease are capable of forming a complex that enables the Cas endonuclease to introduce a double strand break at a DNA target site In one embodiment of the disclosure the variable target domain is 12, 13, 14, 15, 16, 17, 18, 19, 20, 21, 22, 23, 24, 25, 26, 27, 28, 29 or 30 nucleotides in length.

In one embodiment of the disclosure, the guide RNA comprises a cRNA (or cRNA fragment) and a tracrRNA (or tracrRNA fragment) of the type II CRISPR/Cas system that can form a complex with a type II Cas endonuclease, wherein said guide RNA/Cas endonuclease complex can direct the Cas endonuclease to a plant genomic target site, enabling the Cas endonuclease to introduce a double strand break into the genomic target site.

In one embodiment the guide RNA can be introduced into a plant or plant cell directly using any method known in the art such as, but not limited to, particle bombardment or topical applications.

In another embodiment the guide RNA can be introduced indirectly by introducing a recombinant DNA molecule comprising the corresponding guide DNA sequence operably linked to a plant specific promoter (as shown in FIG. 1 B) that is capable of transcribing the guide RNA in said plant cell. The term "corresponding guide DNA" includes a DNA molecule that is identical to the RNA molecule but has a "T" substituted for each "U" of the RNA molecule.

In some embodiments, the guide RNA is introduced via particle bombardment or Agrobacterium transformation of a recombinant DNA construct comprising the corresponding guide DNA operably linked to a plant U6 polymerase III promoter.

In one embodiment, the RNA that guides the RNA/Cas9 endonuclease complex, is a duplexed RNA comprising a duplex crRNA-tracrRNA (as shown in FIG. 2B). One advantage of using a guide RNA versus a duplexed crRNA-tracrRNA is that only one expression cassette needs to be made to express the fused guide RNA.

The terms "target site", "target sequence", "target DNA", "target locus", "genomic target site", "genomic target sequence", and "genomic target locus" are used interchangeably herein and refer to a polynucleotide sequence in the genome (including choloroplastic and mitochondrial DNA) of a plant cell at which a double-strand break is induced in the plant cell genome by a Cas endonuclease. The target site can be an endogenous site in the plant genome, or alternatively, the target site can be heterologous to the plant and thereby not be naturally occurring in the genome, or the target site can be found in a heterologous genomic location compared to where it occurs in nature. As used herein, terms "endogenous target sequence" and "native target sequence" are used interchangeable herein to refer to a target sequence that is endogenous or native to the genome of a plant and is at the endogenous or native position of that target sequence in the genome of the plant.

In one embodiments, the target site can be similar to a DNA recognition site or target site that that is specifically recognized and/or bound by a double-strand break inducing agent such as a LIG3-4 endonuclease (US patent publication 2009-0133152 A1 (published May 21, 2009) or a MS26++ meganuclease (U.S. patent application Ser. No. 13/526,912 filed Jun. 19, 2012).

An "artificial target site" or "artificial target sequence" are used interchangeably herein and refer to a target sequence that has been introduced into the genome of a plant. Such an artificial target sequence can be identical in sequence to an endogenous or native target sequence in the genome of a plant but be located in a different position (i.e., a non-endogenous or non-native position) in the genome of a plant.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Methods for modifying a plant genomic target site are disclosed herein. In one embodiment, the method comprises a method for producing a genetic modification into a second gene of a plant genome without introducing an exogenous selectable marker into said plant genome, the method comprising providing a first guide polynucleotide, a polynucleotide modification template, a second guide polynucleotide, and a Cas endonuclease to a plant cell comprising a first endogenous gene that can be modified to confer herbicide resistance, wherein said first guide polynucleotide and Cas endonuclease are capable of forming a first complex that enables the Cas endonuclease to introduce a double strand break at a first target site, located in or near said first endogenous gene in the genome of said plant cell, wherein said second guide polynucleotide and Cas endonuclease are capable of forming a second complex that enables the Cas endonuclease to introduce a double strand break at a second target site in the genome of said plant cell, wherein said polynucleotide modification template comprises at least one nucleotide alteration when compared to the first endogenous gene.

Also provided is a method for modifying a target site in the genome of a plant cell, the method comprising introducing a guide RNA and a Cas endonuclease into said plant, wherein said guide RNA and Cas endonuclease are capable of forming a complex that enables the Cas endonuclease to introduce a double strand break at said target site.

Further provided is a method for modifying a target site in the genome of a plant cell, the method comprising introducing a guide RNA and a donor DNA into a plant cell having a Cas endonuclease, wherein said guide RNA and Cas endonuclease are capable of forming a complex that enables the Cas endonuclease to introduce a double strand break at said target site, wherein said donor DNA comprises a polynucleotide of interest.

Further provided is a method for modifying a target site in the genome of a plant cell, the method comprising: a) introducing into a plant cell a guide RNA comprising a variable targeting domain and a Cas endonuclease, wherein said guide RNA and Cas endonuclease are capable of forming a complex that enables the Cas endonuclease to introduce a double strand break at said target site; and, b) identifying at least one plant cell that has a modification at said target, wherein the modification includes at least one deletion or substitution of one or more nucleotides in said target site.

Further provided, a method for modifying a target DNA sequence in the genome of a plant cell, the method comprising: a) introducing into a plant cell a first recombinant DNA construct capable of expressing a guide RNA and a second recombinant DNA construct capable of expressing a Cas endonuclease, wherein said guide RNA and Cas endonuclease are capable of forming a complex that enables the Cas endonuclease to introduce a double strand break at said target site; and, b) identifying at least one plant cell that has a modification at said target, wherein the modification includes at least one deletion or substitution of one or more nucleotides in said target site.

The length of the target site can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The nick/cleavage site can be within the target sequence or the nick/cleavage site could be outside of the target sequence. In another variation, the cleavage could occur at nucleotide positions immediately opposite each other to produce a blunt end cut or, in other Cases, the incisions could be staggered to produce single-stranded overhangs, also called "sticky ends", which can be either 5' overhangs, or 3' overhangs.

In some embodiment, the genomic target site capable of being cleaved by a Cas endonuclease comprises a 12 to 30 nucleotide fragment of a male fertility gene such as MS26 (see for example U.S. Pat. Nos. 7,098,388, 7,517,975, 7,612,251), MS45 (see for example U.S. Pat. Nos. 5,478, 369, 6,265,640) or MSCA1 (see for example U.S. Pat. No. 7,919,676), ALS or ESPS genes.

Active variants of genomic target sites can also be used. Such active variants can comprise at least 65%, 70%, 75%, 80%, 85%, 90%, 91%, 92%, 93%, 94%, 95%, 96%, 97%, 98%, 99% or more sequence identity to the given target site, wherein the active variants retain biological activity and hence are capable of being recognized and cleaved by an Cas endonuclease. Assays to measure the double-strand break of a target site by an endonuclease are known in the art and generally measure the overall activity and specificity of the agent on DNA substrates containing recognition sites.

Various methods and compositions can be employed to obtain a plant having a polynucleotide of interest inserted in a target site for a Cas endonuclease. Such methods can employ homologous recombination to provide integration of the polynucleotide of Interest at the target site. In one method provided, a polynucleotide of interest is provided to the plant cell in a donor DNA construct. As used herein, "donor DNA" is a DNA construct that comprises a polynucleotide of Interest to be inserted into the target site of a Cas endonuclease. The donor DNA construct further comprises a first and a second region of homology that flank the polynucleotide of Interest. The first and second regions of homology of the donor DNA share homology to a first and a second genomic region, respectively, present in or flanking the target site of the plant genome. By "homology" is meant DNA sequences that are similar. For example, a "region of homology to a genomic region" that is found on the donor DNA is a region of DNA that has a similar sequence to a given "genomic region" in the plant genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases in length such that the region of homology has sufficient homology to undergo homologous recombination with the corresponding genomic region. "Sufficient homology" indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of homology or sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bp. The amount of homology can also described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook et al., (1989) *Molecular Cloning: A Laboratory Manual*, (Cold Spring Harbor Laboratory Press, NY); *Current Protocols in Molecular Biology*, Ausubel et al., Eds (1994) Current Protocols, (Greene Publishing Associates, Inc. and John Wiley & Sons, Inc); and, Tijssen (1993) *Laboratory Techniques in Biochemistry and Molecular Biology—Hybridization with Nucleic Acid Probes*, (Elsevier, New York).

As used herein, a "genomic region" is a segment of a chromosome in the genome of a plant cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

Polynucleotides of interest and/or traits can be stacked together in a complex trait locus as described in US-2013-0263324-A1, published 3 Oct. 2013 and in PCT/US13/22891, published Jan. 24, 2013, both applications are hereby incorporated by reference. The guide polynucleotide/Cas9 endonuclease system described herein provides for an efficient system to generate double strand breaks and allows for traits to be stacked in a complex trait locus.

In one embodiment, the guide polynucleotide/Cas endonuclease system is used for introducing one or more polynucleotides of interest or one or more traits of interest into one or more target sites by providing one or more guide polynucleotides, one Cas endonuclease, and optionally one or more donor DNAs to a plant cell without incorporating a selectable transgene marker. A fertile plant can be produced from that plant cell that comprises an alteration at said one or more target sites, wherein the alteration is selected from the group consisting of (i) replacement of at least one nucleotide, (ii) a deletion of at least one nucleotide, (iii) an insertion of at least one nucleotide, and (iv) any combination of (i)-(iii). Plants comprising these altered target sites can be crossed with plants comprising at least one gene or trait of interest in the same complex trait locus, thereby further stacking traits in said complex trait locus. (see also US-2013-0263324-A1, published 3 Oct. 2013 and in PCT/US13/22891, published Jan. 24, 2013).

In one embodiment, the method comprises a method for producing in a plant a complex trait locus without incorporating a selectable transgene marker comprising at least two altered target sequences in a genomic region of interest, said method comprising: (a) selecting a genomic region in a plant, wherein the genomic region comprises a first target sequence and a second target sequence; (b) contacting at least one plant cell with at least a first guide polynucleotide, a second polynucleotide, and optionally at least one donor DNA, and a Cas endonuclease, wherein the first and second guide polynucleotide and the Cas endonuclease can form a complex that enables the Cas endonuclease to introduce a double strand break in at least a first and a second target sequence; (c) identifying a cell from (b) comprising a first alteration at the first target sequence and a second alteration at the second target sequence; and (d) recovering a first fertile plant from the cell of (c) said fertile plant comprising the first alteration and the second alteration, wherein the first alteration and the second alteration are physically linked.

In one embodiment, the method comprises a method for producing in a plant a complex trait locus without incorporating a selectable transgene marker comprising at least two altered target sequences in a genomic region of interest, said method comprising: (a) selecting a genomic region in a plant, wherein the genomic region comprises a first target sequence and a second target sequence; (b) contacting at least one plant cell with a first guide polynucleotide, a Cas endonuclease, and optionally a first donor DNA, wherein the first guide polynucleotide and the Cas endonuclease can form a complex that enables the Cas endonuclease to introduce a double strand break a first target sequence; (c) identifying a cell from (b) comprising a first alteration at the first target sequence; (d) recovering a first fertile plant from the cell of (c), said first fertile plant comprising the first alteration; (e) contacting at least one plant cell with a second guide polynucleotide, a Cas endonuclease and optionally a second Donor DNA; (f) identifying a cell from (e) comprising a second alteration at the second target sequence; (g) recovering a second fertile plant from the cell of (f), said second fertile plant comprising the second alteration; and, (h) obtaining a fertile progeny plant from the second fertile plant of (g), said fertile progeny plant comprising the first alteration and the second alteration, wherein the first alteration and the second alteration are physically linked.

The structural similarity between a given genomic region and the corresponding region of homology found on the donor DNA can be any degree of sequence identity that allows for homologous recombination to occur. For example, the amount of homology or sequence identity shared by the "region of homology" of the donor DNA and the "genomic region" of the plant genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination The region of homology on the donor DNA can have homology to any sequence flanking the target site. While in some embodiments the regions of homology share significant sequence homology to the genomic sequence immediately flanking the target site, it is recognized that the regions of homology can be designed to have sufficient homology to regions that may be further 5' or 3' to the target site. In still other embodiments, the regions of homology can also have homology with a fragment of the target site along with downstream genomic regions. In one embodiment, the first region of homology further comprises a first fragment of the target site and the second region of homology comprises a second fragment of the target site, wherein the first and second fragments are dissimilar.

As used herein, "homologous recombination" includes the exchange of DNA fragments between two DNA molecules at the sites of homology. The frequency of homologous recombination is influenced by a number of factors. Different organisms vary with respect to the amount of homologous recombination and the relative proportion of homologous to non-homologous recombination. Generally, the length of the region of homology affects the frequency of homologous recombination events: the longer the region of homology, the greater the frequency. The length of the homology region needed to observe homologous recombination is also species-variable. In many cases, at least 5 kb of homology has been utilized, but homologous recombination has been observed with as little as 25-50 bp of homology. See, for example, Singer et al., (1982) Cell 31:25-33; Shen and Huang, (1986) Genetics 112:441-57; Watt et al., (1985) Proc. Natl. Acad. Sci. USA 82:4768-72, Sugawara and Haber, (1992) Mol Cell Biol 12:563-75, Rubnitz and Subramani, (1984) Mol Cell Biol 4:2253-8; Ayares et al., (1986) Proc. Natl. Acad. Sci. USA 83:5199-203; Liskay et al., (1987) Genetics 115:161-7.

Homology-directed repair (HDR) is a mechanism in cells to repair double-stranded and single stranded DNA breaks. Homology-directed repair includes homologous recombination (HR) and single-strand annealing (SSA) (Lieber. 2010 Annu. Rev. Biochem. 79:181-211). The most common form of HDR is called homologous recombination (HR), which has the longest sequence homology requirements between the donor and acceptor DNA. Other forms of HDR include single-stranded annealing (SSA) and breakage-induced replication, and these require shorter sequence homology relative to HR. Homology-directed repair at nicks (single-stranded breaks) can occur via a mechanism distinct from HDR at double-strand breaks (Davis and Maizels. PNAS (0027-8424), 111 (10), p. E924-E932.

Alteration of the genome of a plant cell, for example, through homologous recombination (HR), is a powerful tool for genetic engineering. Despite the low frequency of homologous recombination in higher plants, there are a few examples of successful homologous recombination of plant endogenous genes. The parameters for homologous recombination in plants have primarily been investigated by rescuing introduced truncated selectable marker genes. In these experiments, the homologous DNA fragments were typically between 0.3 kb to 2 kb. Observed frequencies for homologous recombination were on the order of $10^{-4}$ to $10^{-5}$. See, for example, Halfter et al., (1992) Mol Gen Genet 231:186-93; Offringa et al., (1990) EMBO J 9:3077-84; Offringa et al., (1993) Proc. Natl. Acad. Sci. USA 90:7346-50; Paszkowski et al., (1988) EMBO J 7:4021-6; Hourda and Paszkowski, (1994) Mol Gen Genet 243:106-11; and Risseeuw et al., (1995) Plant J 7:109-19.

Homologous recombination has been demonstrated in insects. In Drosophila, Dray and Gloor found that as little as 3 kb of total template:target homology sufficed to copy a large non-homologous segment of DNA into the target with reasonable efficiency (Dray and Gloor, (1997) Genetics 147:689-99). Using FLP-mediated DNA integration at a target FRT in Drosophila, Golic et al., showed integration was approximately 10-fold more efficient when the donor and target shared 4.1 kb of homology as compared to 1.1 kb of homology (Golic et al., (1997) Nucleic Acids Res 25:3665). Data from Drosophila indicates that 2-4 kb of homology is sufficient for efficient targeting, but there is some evidence that much less homology may suffice, on the order of about 30 bp to about 100 bp (Nassif and Engels, (1993) Proc. Natl. Acad. Sci. USA 90:1262-6; Keeler and Gloor, (1997) Mol Cell Biol 17:627-34).

Homologous recombination has also been accomplished in other organisms. For example, at least 150-200 bp of homology was required for homologous recombination in the parasitic protozoan Leishmania (Papadopoulou and Dumas, (1997) Nucleic Acids Res 25:4278-86). In the filamentous fungus Aspergillus nidulans, gene replacement has been accomplished with as little as 50 bp flanking homology (Chaveroche et al., (2000) Nucleic Acids Res 28:e97). Targeted gene replacement has also been demonstrated in the ciliate Tetrahymena thermophila (Gaertig et al., (1994) Nucleic Acids Res 22:5391-8). In mammals, homologous recombination has been most successful in the mouse using pluripotent embryonic stem cell lines (ES) that can be grown in culture, transformed, selected and introduced into a mouse embryo. Embryos bearing inserted transgenic ES cells develop as genetically offspring. By interbreeding siblings, homozygous mice carrying the selected genes can be obtained. An overview of the process is provided in Watson et al., (1992) Recombinant DNA, 2nd Ed., (Scientific American Books distributed by WH Freeman & Co.); Capecchi, (1989) Trends Genet 5:70-6; and Bronson, (1994) J Biol Chem 269:27155-8. Homologous recombination in mammals other than mouse has been limited by the lack of stem cells capable of being transplanted to oocytes or developing embryos. However, McCreath et al., Nature 405:1066-9 (2000) reported successful homologous recombination in sheep by transformation and selection in primary embryo fibroblast cells.

Error-prone DNA repair mechanisms can produce mutations at double-strand break sites. The nonhomologous end-joining (NHEJ) pathways are the most common repair mechanism to bring the broken ends together (Bleuyard et al., (2006) DNA Repair 5:1-12). The structural integrity of chromosomes is typically preserved by the repair, but deletions, insertions, or other rearrangements are possible. The two ends of one double-strand break are the most prevalent substrates of NHEJ (Kirik et al., (2000) EMBO J 19:5562-6), however if two different double-strand breaks occur, the free ends from different breaks can be ligated and result in chromosomal deletions (Siebert and Puchta, (2002) Plant Cell 14:1121-31), or chromosomal translocations between different chromosomes (Pacher et al., (2007) Genetics 175: 21-9).

Episomal DNA molecules can also be ligated into the double-strand break, for example, integration of T-DNAs into chromosomal double-strand breaks (Chilton and Que, (2003) Plant Physiol 133:956-65; Salomon and Puchta, (1998) EMBO J 17:6086-95). Once the sequence around the double-strand breaks is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (Molinier et al., (2004) Plant Cell 16:342-52). Ectopic and/or epigenic DNA sequences may also serve as a DNA repair template for homologous recombination (Puchta, (1999) Genetics 152: 1173-81).

Once a double-strand break is induced in the DNA, the cell's DNA repair mechanism is activated to repair the break. Error-prone DNA repair mechanisms can produce mutations at double-strand break sites. The most common repair mechanism to bring the broken ends together is the nonhomologous end-joining (NHEJ) pathway (Bleuyard et al., (2006) DNA Repair 5:1-12). The structural integrity of chromosomes is typically preserved by the repair, but deletions, insertions, or other rearrangements are possible (Siebert and Puchta, (2002) Plant Cell 14:1121-31; Pacher et al., (2007) Genetics 175:21-9).

Alternatively, the double-strand break can be repaired by homologous recombination between homologous DNA sequences. Once the sequence around the double-strand break is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (Molinier et al., (2004) Plant Cell 16:342-52). Ectopic and/or epigenic DNA sequences may also serve as a DNA repair template for homologous recombination (Puchta, (1999) Genetics 152:1173-81).

DNA double-strand breaks appear to be an effective factor to stimulate homologous recombination pathways (Puchta et al., (1995) Plant Mol Biol 28:281-92; Tzfira and White, (2005) Trends Biotechnol 23:567-9; Puchta, (2005) J Exp Bot 56:1-14). Using DNA-breaking agents, a two- to nine-fold increase of homologous recombination was observed between artificially constructed homologous DNA repeats in plants (Puchta et al., (1995) Plant Mol Biol 28:281-92). In maize protoplasts, experiments with linear DNA molecules demonstrated enhanced homologous recombination between plasmids (Lyznik et al., (1991) Mol Gen Genet 230:209-18).

In one embodiment provided herein, the method comprises contacting a plant cell with the donor DNA and the endonuclease. Once a double-strand break is introduced in the target site by the endonuclease, the first and second regions of homology of the donor DNA can undergo homologous recombination with their corresponding genomic regions of homology resulting in exchange of DNA between the donor and the genome. As such, the provided methods result in the integration of the polynucleotide of interest of the donor DNA into the double-strand break in the target site in the plant genome, thereby altering the original target site and producing an altered genomic target site.

The donor DNA may be introduced by any means known in the art. For example, a plant having a target site is provided. The donor DNA may be provided by any transformation method known in the art including, for example, *Agrobacterium*-mediated transformation or biolistic particle bombardment. The donor DNA may be present transiently in the cell or it could be introduced via a viral replicon. In the presence of the Cas endonuclease and the target site, the donor DNA is inserted into the transformed plant's genome.

Another approach uses protein engineering of existing homing endonucleases to alter their target specificities. Homing endonucleases, such as I-SceI or I-CreI, bind to and cleave relatively long DNA recognition sequences (18 bp and 22 bp, respectively). These sequences are predicted to naturally occur infrequently in a genome, typically only 1 or 2 sites/genome. The cleavage specificity of a homing endonuclease can be changed by rational design of amino acid substitutions at the DNA binding domain and/or combinatorial assembly and selection of mutated monomers (see, for example, Arnould et al., (2006) J Mol Biol 355:443-58; Ashworth et al., (2006) Nature 441:656-9; Doyon et al., (2006) J Am Chem Soc 128:2477-84; Rosen et al., (2006) Nucleic Acids Res 34:4791-800; and Smith et al., (2006) Nucleic Acids Res 34:e149; Lyznik et al., (2009) U.S. Patent Application Publication No. 20090133152A1; Smith et al., (2007) U.S. Patent Application Publication No. 20070117128A1). Engineered meganucleases have been demonstrated that can cleave cognate mutant sites without broadening their specificity. An artificial recognition site specific to the wild type yeast I-SceI homing nuclease was introduced in maize genome and mutations of the recognition sequence were detected in 1% of analyzed F1 plants when a transgenic I-SceI was introduced by crossing and activated by gene excision (Yang et al., (2009) Plant Mol Biol 70:669-79). More practically, the maize liguleless locus was targeted using an engineered single-chain endonuclease designed based on the I-CreI meganuclease sequence. Mutations of the selected liguleless locus recognition sequence were detected in 3% of the T0 transgenic plants when the designed homing nuclease was introduced by *Agrobacterium*-mediated transformation of immature embryos (Gao et al., (2010) Plant J 61:176-87).

Polynucleotides of interest are further described herein and are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for genetic engineering will change accordingly.

Genome Editing Using the Guide RNA/Cas Endonuclease System

As described herein, the guide RNA/Cas endonuclease system can be used in combination with a co-delivered polynucleotide modification template to allow for editing of a genomic nucleotide sequence of interest. Also, as described herein, for each embodiment that uses a guide RNA/Cas endonuclease system, a similar guide polynucleotide/Cas endonuclease system can be deployed where the guide polynucleotide does not solely comprise ribonucleic acids but wherein the guide polynucleotide comprises a combination of RNA-DNA molecules or solely comprise DNA molecules.

While numerous double-strand break-making systems exist, their practical applications for gene editing may be restricted due to the relatively low frequency of induced double-strand breaks (DSBs). To date, many genome modification methods rely on the homologous recombination system. Homologous recombination (HR) can provide molecular means for finding genomic DNA sequences of interest and modifying them according to the experimental specifications. Homologous recombination takes place in plant somatic cells at low frequency. The process can be enhanced to a practical level for genome engineering by introducing double-strand breaks (DSBs) at selected endonuclease target sites. The challenge has been to efficiently make DSBs at genomic sites of interest since there is a bias in the directionality of information transfer between two interacting DNA molecules (the broken one acts as an acceptor of genetic information). Described herein is the use of a guide RNA/Cas system which provides flexible genome cleavage specificity and results in a high frequency of double-strand breaks at a DNA target site, thereby enabling efficient gene editing in a nucleotide sequence of interest, wherein the nucleotide sequence of interest to be edited can be located within or outside the target site recognized and cleaved by a Cas endonuclease.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

In one embodiment, the disclosure describes a method for editing a nucleotide sequence in the genome of a cell without incorporating a selectable transgene marker, the method comprising providing at least one guide RNA, at least one polynucleotide modification template, and at least one Cas endonuclease to a cell, wherein the Cas endonuclease is capable of introducing a double-strand break at a target sequence in the genome of said cell, wherein said polynucleotide modification template includes at least one nucleotide modification of said nucleotide sequence to be edited. Cells include, but are not limited to, human, animal, bacterial, fungal, insect, and plant cells as well as plants and seeds produced by the methods described herein. The nucleotide to be edited can be located within or outside a target site recognized and cleaved by a Cas endonuclease. In one embodiment, the at least one nucleotide modification is not a modification at a target site recognized and cleaved by a Cas endonuclease. In another embodiment, there are at least 1, 2, 3, 4, 5, 6, 7, 8, 9, 10, 11, 12, 13, 14, 15, 16, 17, 18, 19, 20, 21, 22, 23, 24, 25, 26, 27, 30, 40, 50, 100, 200, 300, 400, 500, 600, 700, 900 or 1000 nucleotides between the at least one nucleotide to be edited and the genomic target site.

In one embodiment, the method comprises a method for editing a second gene of a plant genome without introducing an exogenous selectable marker into said plant genome, the method comprising providing a first guide RNA, a first polynucleotide modification template, a second guide RNA, a second polynucleotide modification template, and a Cas endonuclease to a plant cell comprising a first endogenous gene that can be modified to confer herbicide resistance, wherein said first guide RNA and Cas endonuclease are capable of forming a complex that enables the Cas endonuclease to introduce a double strand break at a first target site (located in or near said first endogenous gene) in the genome of said plant cell, wherein said first polynucleotide modification template comprises at least one nucleotide modification of said first endogenous gene to render said endogenous gene capable of conferring herbicide resistance to a plant cell, wherein said second guide RNA and Cas endonuclease are capable of forming a complex that enables the Cas endonuclease to introduce a double strand break at a second target site (located at a different locus than said first endogenous gene) in the genome of said plant cell, wherein said second polynucleotide modification template comprises at least one nucleotide alteration when compared to the second gene to be edited.

In one embodiment of genome editing, editing of the endogenous enolpyruvylshikimate-3-phosphate synthase (EPSPS) gene is disclosed herein wherein, the polynucleotide modification template (EPSPS polynucleotide modification template) includes a partial fragment of the EPSPS gene (and therefore does not encode a fully functional EPSPS polypeptide by itself). The EPSPS polynucleotide modification template contained three point mutations that were responsible for the creation of the T102I/P106S (TIPS) double mutant (Funke, T et al., J. Biol. Chem. 2009, 284: 9854-9860), which provide glyphosate tolerance to transgenic plants expressing as EPSPS double mutant transgene.

As defined herein "Glyphosate" includes any herbicidally effective form of N-phosphonomethylglycine (including any salt thereof), other forms which result in the production of the glyphosate anion in plants and any other herbicides of the phosphonomethylglycine family.

Increased resistance to a herbicide is demonstrated when plants which display the increased resistance to a herbicide are subjected to the herbicide and a dose/response curve is shifted to the right when compared with that provided by an appropriate control plant. Such dose/response curves have "dose" plotted on the x-axis and "percentage injury", "herbicidal effect" etc. plotted on the y-axis. Plants which are substantially resistant to the herbicide exhibit few, if any, bleached, necrotic, lytic, chlorotic or other lesions and are not stunted, wilted or deformed when subjected to the herbicide at concentrations and rates which are typically employed by the agricultural community to kill weeds in the field. The terms resistance and tolerance may be used interchangeably.

FIG. 12 shows a schematic representation of components used in the genome editing procedure. A maize optimized Cas endonuclease, a guide RNA and a polynucleotide modification template were provided to a plant cell. For example, as shown in FIG. 12, the polynucleotide modification template included three nucleotide modifications (indicated by arrows) when compared to the EPSPS genomic sequence to be edited. These three nucleotide modifications are referred to as TIPS mutations as these nucleotide modifications result in the amino acid changes T-102 to I-102 and P-106 to S-106. The first point mutation results from the substitution of the C nucleotide in the codon sequence ACT with a T nucleotide, a second mutation results from the substitution of the T nucleotide on the same codon sequence ACT with a C nucleotide to form the isoleucine codon ATC, the third point mutation results from the substitution of the first C nucleotide in the codon sequence CCA with a T nucleotide in order to form a serine codon TCA (FIG. 12).

The nucleotide sequence to be edited can be a sequence that is endogenous, artificial, pre-existing, or transgenic to the cell that is being edited. For example, the nucleotide sequence in the genome of a cell can be a native gene, a mutated gene, a non-native gene, a foreign gene, or a transgene that is stably incorporated into the genome of a cell. Editing of such nucleotide may result in a further desired phenotype or genotype.

Regulatory Sequence Modifications Using the Guide Polynucleotide/Cas Endonuclease System In one embodiment the nucleotide sequence to be modified can be a regulatory sequence such as a promoter wherein the editing of the promoter comprises replacing the promoter (also referred to as a "promoter swap" or "promoter replacement") or promoter fragment with a different promoter (also referred to as replacement promoter) or promoter fragment (also referred to as replacement promoter fragment), wherein the promoter replacement results in any one of the following or any one combination of the following: an increased promoter activity, an increased promoter tissue specificity, a decreased promoter activity, a decreased promoter tissue specificity, a new promoter activity, an inducible promoter activity, an extended window of gene expression, a modification of the timing or developmental progress of gene expression in the same cell layer or other cell layer (such as but not limiting to extending the timing of gene expression in the tapetum of maize anthers (U.S. Pat. No. 5,837,850 issued Nov. 17, 1998), a mutation of DNA binding elements and/or a deletion or addition of DNA binding elements. The promoter (or promoter fragment) to be modified can be a promoter (or promoter fragment) that is endogenous, artificial, pre-existing, or transgenic to the cell that is being edited. The replacement promoter (or replacement promoter fragment) can be a promoter (or promoter fragment) that is endogenous, artificial, pre-existing, or transgenic to the cell that is being edited.

In one embodiment the nucleotide sequence can be a promoter wherein the editing of the promoter comprises replacing a native EPSPS1 promoter from with a plant ubiquitin promoter.

In one embodiment the nucleotide sequence can be a promoter wherein the promoter to be edited is selected from the group comprising *Zea mays*-PEPC1 promoter (Kausch et al, Plant Molecular Biology, 45: 1-15, 2001), *Zea mays* Ubiquitin promoter (UBI1ZM PRO, Christensen et al, plant Molecular Biology 18: 675-689, 1992), *Zea mays*-Rootmet2 promoter (U.S. Pat. No. 7,214,855), Rice actin promoter (OS-ACTIN PRO, U.S. Pat. No. 5,641,876; McElroy et al, The Plant Cell, Vol 2, 163-171, February 1990), Sorghum RCC3 promoter (US 2012/0210463 filed on 13 Feb. 2012), *Zea mays*-GOS2 promoter (U.S. Pat. No. 6,504,083), *Zea mays*-ACO2 promoter (U.S. application Ser. No. 14/210,711 filed 14 Mar. 2014) or *Zea mays*-oleosin promoter (U.S. Pat. No. 8,466,341 B2).

In one embodiment, the guide polynucleotide/Cas endonuclease system can be used in combination with a co-delivered polynucleotide modification template or donor DNA sequence to allow for the insertion of a promoter or promoter element into a genomic nucleotide sequence of interest without incorporating a selectable transgene marker, wherein the promoter insertion (or promoter element insertion) results in any one of the following or any one combination of the following: an increased promoter activity (increased promoter strength), an increased promoter tissue specificity, a decreased promoter activity, a decreased promoter tissue specificity, a new promoter activity, an inducible promoter activity, an extended window of gene expression, a modification of the timing or developmental progress of gene expression a mutation of DNA binding elements and/or an addition of DNA binding elements. Promoter elements to be inserted can be, but are not limited to, promoter core elements (such as, but not limited to, a CAAT box, a CCAAT box, a Pribnow box, a and/or TATA box, translational regulation sequences and/or a repressor system for inducible expression (such as TET operator repressor/operator/inducer elements, or sulphonylurea (Su) repressor/operator/inducer elements. The dehydration-responsive element (DRE) was first identified as a cis-acting promoter element in the promoter of the drought-responsive gene rd29A, which contains a 9 bp conserved core sequence, TACCGACAT (Yamaguchi-Shinozaki, K., and Shinozaki, K. (1994) *Plant Cell* 6, 251-264). Insertion of DRE into an endogenous promoter may confer a drought inducible expression of the downstream gene. Another example is ABA-responsive elements (ABREs) which contains a (C/T) ACGTGGC consensus sequence found to be present in numerous ABA and/or stress-regulated genes (Busk P. K., Pages M. (1998) Plant Mol. Biol. 37:425-435). Insertion of 35S enhancer or MMV enhancer into an endogenous promoter region will increase gene expression (U.S. Pat. No. 5,196,525). The promoter (or promoter element) to be inserted can be a promoter (or promoter element) that is endogenous, artificial, pre-existing, or transgenic to the cell that is being edited.

In one embodiment, the guide polynucleotide/Cas endonuclease system can be used to insert an enhancer element, such as but not limited to a Cauliflower Mosaic Virus 35 S enhancer, in front of an endogenous FMT1 promoter to enhance expression of the FTM1.

In one embodiment, the guide polynucleotide/Cas endonuclease system can be used to insert a component of the TET operator repressor/operator/inducer system, or a component of the sulphonylurea (Su) repressor/operator/inducer system into plant genomes to generate or control inducible expression systems without incorporating a selectable transgene marker.

In another embodiment, the guide polynucleotide/Cas endonuclease system can be used to allow for the deletion of a promoter or promoter element, wherein the promoter deletion (or promoter element deletion) results in any one of the following or any one combination of the following: a permanently inactivated gene locus, an increased promoter activity (increased promoter strength), an increased promoter tissue specificity, a decreased promoter activity, a decreased promoter tissue specificity, a new promoter activity, an inducible promoter activity, an extended window of gene expression, a modification of the timing or developmental progress of gene expression, a mutation of DNA binding elements and/or an addition of DNA binding elements. Promoter elements to be deleted can be, but are not limited to, promoter core elements, promoter enhancer elements or 35 S enhancer elements (as described in Example 32) The promoter or promoter fragment to be deleted can be endogenous, artificial, pre-existing, or transgenic to the cell that is being edited.

Terminator Modifications Using the Guide Polynucleotide/Cas Endonuclease System

In one embodiment the nucleotide sequence to be modified can be a terminator wherein the editing of the terminator comprises replacing the terminator (also referred to as a "terminator swap" or "terminator replacement") or terminator fragment with a different terminator (also referred to as replacement terminator) or terminator fragment (also referred to as replacement terminator fragment), wherein the terminator replacement results in any one of the following or any one combination of the following: an increased terminator activity, an increased terminator tissue specificity, a decreased terminator activity, a decreased terminator tissue specificity, a mutation of DNA binding elements and/or a deletion or addition of DNA binding elements." The terminator (or terminator fragment) to be modified can be a terminator (or terminator fragment) that is endogenous, artificial, pre-existing, or transgenic to the cell that is being edited. The replacement terminator (or replacement terminator fragment) can be a terminator (or terminator fragment) that is endogenous, artificial, pre-existing, or transgenic to the cell that is being edited.

In one embodiment the nucleotide sequence to be modified can be a terminator wherein the terminator to be edited is selected from the group comprising terminators from maize Argos 8 or SRTF18 genes, or other terminators, such as potato PinII terminator, sorghum actin terminator (SB-ACTIN TERM, WO 2013/184537 A1 published December 2013), sorghum SB-GKAF TERM (WO2013019461), rice T28 terminator (OS-T28 TERM, WO 2013/012729 A2), AT-T9 TERM (WO 2013/012729 A2) or GZ-W64A TERM (U.S. Pat. No. 7,053,282).

In one embodiment, the guide polynucleotide/Cas endonuclease system can be used in combination with a co-delivered polynucleotide modification template or donor DNA sequence to allow for the insertion of a terminator or terminator element into a genomic nucleotide sequence of interest, wherein the terminator insertion (or terminator element insertion) results in any one of the following or any one combination of the following: an increased terminator activity (increased terminator strength), an increased terminator tissue specificity, a decreased terminator activity, a decreased terminator tissue specificity, a mutation of DNA binding elements and/or an addition of DNA binding elements.

The terminator (or terminator element) to be inserted can be a terminator (or terminator element) that is endogenous, artificial, pre-existing, or transgenic to the cell that is being edited.

In another embodiment, the guide polynucleotide/Cas endonuclease system can be used to allow for the deletion of a terminator or terminator element, wherein the terminator deletion (or terminator element deletion) results in any one of the following or any one combination of the following: an increased terminator activity (increased terminator strength), an increased terminator tissue specificity, a decreased terminator activity, a decreased terminator tissue specificity, a mutation of DNA binding elements and/or an addition of DNA binding elements. The terminator or terminator fragment to be deleted can be endogenous, artificial, pre-existing, or transgenic to the cell that is being edited.

Additional Regulatory Sequence Modifications Using the Guide Polynucleotide/Cas Endonuclease System In one embodiment, the guide polynucleotide/Cas endonuclease system can be used to modify or replace a regulatory sequence in the genome of a cell without incorporating a selectable transgene marker. A regulatory sequence is a segment of a nucleic acid molecule which is capable of increasing or decreasing the expression of specific genes within an organism and/or is capable of altering tissue specific expression of genes within an organism. Examples of regulatory sequences include, but are not limited to, 3' UTR (untranslated region) region, 5' UTR region, transcription activators, transcriptional enhancers transcriptions repressors, translational repressors, splicing factors, miRNAs, siRNA, artificial miRNAs, promoter elements, CAMV 35 S enhancer, MMV enhancer elements (PCT/US14/23451 filed Mar. 11, 2013), SECIS elements, polyadenylation signals, and polyubiquitination sites. In some embodiments the editing (modification) or replacement of a regulatory element results in altered protein translation, RNA cleavage, RNA splicing, transcriptional termination or post translational modification. In one embodiment, regulatory elements can be identified within a promoter and these regulatory elements can be edited or modified do to optimize these regulatory elements for up or down regulation of the promoter.

In one embodiment, the genomic sequence of interest to be modified is a polyubiquitination site, wherein the modification of the polyubiquitination sites results in a modified rate of protein degradation. The ubiquitin tag condemns proteins to be degraded by proteasomes or autophagy. Proteasome inhibitors are known to cause a protein overproduction. Modifications made to a DNA sequence encoding a protein of interest can result in at least one amino acid modification of the protein of interest, wherein said modification allows for the polyubiquitination of the protein (a post translational modification) resulting in a modification of the protein degradation In one embodiment, the genomic sequence of interest to be modified is a polyubiquitination site on a maize EPSPS gene, wherein the polyubiquitination site modified resulting in an increased protein content due to a slower rate of EPSPS protein degradation.

In one embodiment, the genomic sequence of interest to be modified is a an intron site, wherein the modification consist of inserting an intron enhancing motif into the intron which results in modulation of the transcriptional activity of the gene comprising said intron.

In one embodiment, the genomic sequence of interest to be modified is a an intron site, wherein the modification consist of replacing a soybean EPSP1 intron with a soybean ubiquitin intron 1 as described herein (Example 25)

In one embodiment, the genomic sequence of interest to be modified is a an intron or UTR site, wherein the modification consist of inserting at least one microRNA into said intron or UTR site, wherein expression of the gene comprising the intron or UTR site also results in expression of said microRNA, which in turn can silence any gene targeted by the microRNA without disrupting the gene expression of the native/transgene comprising said intron.

In one embodiment, the guide polynucleotide/Cas endonuclease system can be used to allow for the deletion or mutation of a Zinc Finger transcription factor, wherein the deletion or mutation of the Zinc Finger transcription factor results in or allows for the creation of a dominant negative Zinc Finger transcription factor mutant (Li et al 2013 Rice zinc finger protein DST enhances grain production through controlling Gn1a/OsCKX2 expression PNAS 110:3167-3172). Insertion of a single base pair downstream zinc finger domain will result in a frame shift and produces a new protein which still can bind to DNA without transcription activity. The mutant protein will compete to bind to cytokinin oxidase gene promoters and block the expression of cytokinin oxidase gene. Reduction of cytokinin oxidase gene expression will increase cytokinin level and promote panicle growth in rice and ear growth in maize, and increase yield under normal and stress conditions.

Modifications of Splicing Sites and/or Introducing Alternate Splicing Sites Using the Guide Polynucleotide/Cas Endonuclease System Protein synthesis utilizes mRNA molecules that emerge from pre-mRNA molecules subjected to the maturation process. The pre-mRNA molecules are capped, spliced and stabilized by addition of polyA tails. Eukaryotic cells developed a complex process of splicing that result in alternative variants of the original pre-mRNA molecules. Some of them may not produce functional templates for protein synthesis. In maize cells, the splicing process is affected by splicing sites at the exon-intron junction sites. An example of a canonical splice site is AGGT. Gene coding sequences can contains a number of alternate splicing sites that may affect the overall efficiency of the pre-mRNA maturation process and as such may limit the protein accumulation in cells. The guide polynucleotide/Cas endonuclease system can be used in combination with a co-delivered polynucleotide modification template to edit a gene of interest to introduce a canonical splice site at a described junction or any variant of a splicing site that changes the splicing pattern of pre-mRNA molecules, without incorporating a selectable transgene marker.

In one embodiment, the nucleotide sequence of interest to be modified is a maize EPSPS gene, wherein the modification of the gene consists of modifying alternative splicing sites resulting in enhanced production of the functional gene transcripts and gene products (proteins).

In one embodiment, the nucleotide sequence of interest to be modified is a gene, wherein the modification of the gene consists of editing the intron borders of alternatively spliced genes to alter the accumulation of splice variants.

Modifications of Nucleotide Sequences Encoding a Protein of Interest Using the Guide Polynucleotide/Cas Endonuclease System In one embodiment, the guide polynucleotide/Cas endonuclease system can be used to modify or replace a coding sequence in the genome of a cell without incorporating a selectable transgene marker, wherein the modification or replacement results in any one of the following, or any one combination of the following: an increased protein (enzyme) activity, an increased protein functionality, a decreased protein activity, a decreased protein functionality, a site specific mutation, a protein domain swap, a protein knockout, a new protein functionality, a modified protein functionality.

In one embodiment the protein knockout is due to the introduction of a stop codon into the coding sequence of interest.

In one embodiment the protein knockout is due to the deletion of a start codon into the coding sequence of interest.

Amino Acid and/or Protein Fusions Using the Guide Polynucleotide/Cas Endonuclease System In one embodiment, the guide polynucleotide/Cas endonuclease system can be used with or without a co-delivered polynucleotide sequence to fuse a first coding sequence encoding a first protein to a second coding sequence encoding a second protein in the genome of a cell, without incorporating a selectable transgene marker, wherein the protein fusion results in any one of the following or any one combination of the following: an increased protein (enzyme) activity, an increased protein functionality, a decreased protein activity, a decreased protein functionality, a new protein functionality, a modified protein functionality, a new protein localization, a new timing of protein expression, a modified protein expression pattern, a chimeric protein, or a modified protein with dominant phenotype functionality.

In one embodiment, the guide polynucleotide/Cas endonuclease system can be used with or without a co-delivered polynucleotide sequence to fuse a first coding sequence encoding a chloroplast localization signal to a second coding sequence encoding a protein of interest, wherein the protein fusion results in targeting the protein of interest to the chloroplast.

In one embodiment, the guide polynucleotide/Cas endonuclease system can be used with or without a co-delivered polynucleotide sequence to fuse a first coding sequence encoding a chloroplast localization signal to a second coding sequence encoding a protein of interest, wherein the protein fusion results in targeting the protein of interest to the chloroplast.

In one embodiment, the guide polynucleotide/Cas endonuclease system can be used with or without a co-delivered polynucleotide sequence to fuse a first coding sequence encoding a chloroplast localization signal (e.g., a chloroplast transit peptide) to a second coding sequence, wherein the protein fusion results in a modified protein with dominant phenotype functionality Gene Silencing by Expressing an Inverted Repeat into a Gene of Interest Using the Guide Polynucleotide/Cas Endonuclease System In one embodiment, the guide polynucleotide/Cas endonuclease system can be used in combination with a co-delivered polynucleotide sequence to insert an inverted gene fragment into a gene of interest in the genome of an organism, without incorporating a selectable transgene marker, wherein the insertion of the inverted gene fragment can allow for an in-vivo creation of an inverted repeat (hairpin) and results in the silencing of said endogenous gene.

In one embodiment the insertion of the inverted gene fragment can result in the formation of an in-vivo created inverted repeat (hairpin) in a native (or modified) promoter of a gene and/or in a native 5' end of the native gene. The inverted gene fragment can further comprise an intron which can result in an enhanced silencing of the targeted gene.

Genome Deletion for Trait Locus Characterization

Trait mapping in plant breeding often results in the detection of chromosomal regions housing one or more genes controlling expression of a trait of interest. For a qualitative trait, the guide polynucleotide/Cas endonuclease system can be used to eliminate candidate genes in the identified chromosomal regions to determine if deletion of the gene affects expression of the trait. For quantitative traits, expression of a trait of interest is governed by multiple quantitative trait loci (QTL) of varying effect-size, complexity, and statistical significance across one or more chromosomes. In cases of negative effect or deleterious QTL regions affecting a complex trait, the guide polynucleotide/Cas endonuclease system can be used to eliminate whole regions delimited by marker-assisted fine mapping, and to target specific regions for their selective elimination or rearrangement. Similarly, presence/absence variation (PAV) or copy number variation (CNV) can be manipulated with selective genome deletion using the guide polynucleotide/Cas endonuclease system.

In one embodiment, the region of interest can be flanked by two independent guide polynucleotide/CAS endonuclease target sequences. Cutting would be done concurrently. The deletion event would be the repair of the two chromosomal ends without the region of interest. Alternative results would include inversions of the region of interest, mutations at the cut sites and duplication of the region of interest.

Methods for Identifying at Least One Plant Cell Comprising in its Genome a Polynucleotide of Interest Integrated at the Target Site.

Further provided are methods for identifying at least one plant cell comprising in its genome a polynucleotide of Interest integrated at the target site. A variety of methods are available for identifying those plant cells with insertion into the genome at or near to the target site without using a screenable marker phenotype. Such methods can be viewed as directly analyzing a target sequence to detect any change in the target sequence, including but not limited to PCR methods, sequencing methods, nuclease digestion, Southern blots, and any combination thereof. See, for example, U.S. patent application Ser. No. 12/147,834, herein incorporated by reference to the extent necessary for the methods described herein. The method also comprises recovering a plant from the plant cell comprising a polynucleotide of Interest integrated into its genome. The plant may be sterile or fertile. It is recognized that any polynucleotide of interest can be provided, integrated into the plant genome at the target site, and expressed in a plant.

Polynucleotides/polypeptides of interest include, but are not limited to, herbicide-resistance coding sequences, insecticidal coding sequences, nematicidal coding sequences, antimicrobial coding sequences, antifungal coding sequences, antiviral coding sequences, abiotic and biotic stress tolerance coding sequences, or sequences modifying plant traits such as yield, grain quality, nutrient content, starch quality and quantity, nitrogen fixation and/or utilization, fatty acids, and oil content and/or composition. More specific polynucleotides of interest include, but are not limited to, genes that improve crop yield, polypeptides that improve desirability of crops, genes encoding proteins conferring resistance to abiotic stress, such as drought, nitrogen, temperature, salinity, toxic metals or trace elements, or those conferring resistance to toxins such as pesticides and herbicides, or to biotic stress, such as attacks by fungi, viruses, bacteria, insects, and nematodes, and development of diseases associated with these organisms. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, fertility or sterility, grain characteristics, and commercial products. Genes of interest include, generally, those involved in oil, starch, carbohydrate, or nutrient metabolism as well as those affecting kernel size, sucrose loading, and the like that can be stacked or used in combination with glyphosate resistance described herein.

The terms "FAD" and fatty acid desaturase are used interchangeably and refer to membrane bound microsomal oleoyl- and linoleoyl-phosphatidylcholine desaturases that convert oleic acid to linoleic acid and linoleic acid to linolenic acid, respectively, in reactions that reduce molecular oxygen to water and require the presence of NADH. The gene for microsomal delta 12 fatty acid desaturases described in WO 94/11516, can be used to make a high oleic acid soybean variety. The resulting high oleic acid soybean variety was one in which the polyunsaturated fatty acids were reduced from 70% of the total fatty acids to less than 5%.

Plant having a high oleic phenotype (a high oleic acid phenotype) and a herbicide tolerance phenotype conferred by suppression of a FAD2 gene in conjunction with the expression of a sequence that confers tolerance to inhibitors of ALS have been described in U.S. Pat. No. 8,609,935, issued 2013 Dec. 17)

Two soybean fatty acid desaturases, designated FAD2-1 and FAD2-2, are Δ 12 desaturases that introduce a second double bond into oleic acid to form linoleic acid, a polyunsaturated fatty acid. FAD2-1 is expressed only in the developing seed (Heppard et al. (1996) Plant Physiol. 110:311-319). The expression of this gene increases during the period of oil deposition, starting around 19 days after flowering, and its gene product is responsible for the synthesis of the polyunsaturated fatty acids found in soybean oil. Gm Fad 2-1 is described in detail by Okuley, J. et al. (1994) Plant Cell 6:147 158 and in WO94/11516. It is available from the ATCC in the form of plasmid pSF2 169K (ATCC accession number 69092). FAD 2-2 is expressed in the seed, leaf, root and stem of the soy plant at a constant level and is the "housekeeping" 12-desaturase gene. The Fad 2-2 gene product is responsible for the synthesis of polyunsaturated fatty acids for cell membranes.

Since FAD2-1 is the major enzyme of this type in soybean seeds, reduction in the expression of FAD2-1 results in increased accumulation of oleic acid (18:1) and a corresponding decrease in polyunsaturated fatty acid content. Reduction of expression of FAD2-2 in combination with FAD2-1 leads to a greater accumulation of oleic acid and corresponding decrease in polyunsaturated fatty acid content. FAD3 is a Δ 15 desaturase that introduces a third double bond into linoleic acid (18:2) to form linolenic acid (18:3). Reduction of expression of FAD3 in combination with reduction of FAD2-1 and FAD2-2 leads to a greater accumulation of oleic acid and corresponding decrease in polyunsaturated fatty acid content, especially linolenic acid.

Nucleic acid fragments encoding FAD2-1, FAD2-2, and FAD3 have been described in WO 94/11516 and WO 93/11245. Chimeric recombinant constructs comprising all or a part of these nucleic acid fragments or the reverse complements thereof operably linked to at least one suitable regulatory sequence can be constructed wherein expression of the chimeric gene results in an altered fatty acid phenotype. A chimeric recombinant construct can be introduced into soybean plants via transformation techniques well known to those skilled in the art. Transgenic soybean plants resulting from a transformation with a recombinant DNA are assayed to select plants with altered fatty acid profiles. The recombinant construct may contain all or part of 1) the FAD2-1 gene or 2) the FAD2-2 gene or 3) the FAD3 gene or 4) combinations of all or portions of the FAD2-1, Fad2-2, or FAD3 genes.

Recombinant constructs comprising all or part of 1) the FAD2-1 gene with or without 2) all or part of the Fad2-2 gene with or without all or part of the FAD3 gene can be used in making a transgenic soybean plant having a high oleic phenotype. An altered fatty acid profile, specifically an increase in the proportion of oleic acid and a decrease in the proportion of the polyunsaturated fatty acids, indicates that one or more of the soybean seed FAD genes (FAD2-1, Fad2-2, FAD3) have been suppressed. Assays may be conducted on soybean somatic embryo cultures and seeds to determine suppression of FAD2-1, Fad2-2, or FAD3.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J. Biochem.* 165:99-106, the disclosures of which are herein incorporated by reference.

Commercial traits can also be encoded on a polynucleotide of interest that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxybutyrate synthase), and acetoacetyl-CoA reductase (see Schubert et al. (1988) J. Bacteriol. 170:5837-5847) facilitate expression of polyhydroxyalkanoates (PHAs).

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed.

Applewhite (American Oil Chemists Society, Champaign, Ill.), pp. 497-502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Polynucleotides that improve crop yield include dwarfing genes, such as Rht1 and Rht2 (Peng et al. (1999) Nature 400:256-261), and those that increase plant growth, such as ammonium-inducible glutamate dehydrogenase. Polynucleotides that improve desirability of crops include, for example, those that allow plants to have reduced saturated fat content, those that boost the nutritional value of plants, and those that increase grain protein. Polynucleotides that improve salt tolerance are those that increase or allow plant growth in an environment of higher salinity than the native environment of the plant into which the salt-tolerant gene(s) has been introduced.

Polynucleotides/polypeptides that influence amino acid biosynthesis include, for example, anthranilate synthase (AS; EC 4.1.3.27) which catalyzes the first reaction branching from the aromatic amino acid pathway to the biosynthesis of tryptophan in plants, fungi, and bacteria. In plants, the chemical processes for the biosynthesis of tryptophan are compartmentalized in the chloroplast. See, for example, US Pub. 20080050506, herein incorporated by reference. Additional sequences of interest include Chorismate Pyruvate Lyase (CPL) which includes a gene encoding an enzyme which catalyzes the conversion of chorismate to pyruvate and pHBA. The most well characterized CPL gene has been isolated from *E. coli* and bears the GenBank accession number M96268. See, U.S. Pat. No. 7,361,811, herein incorporated by reference.

Polynucleotide sequences of interest may encode proteins involved in providing disease or pest resistance. By "disease resistance" or "pest resistance" is intended that the plants avoid the harmful symptoms that are the outcome of the plant-pathogen interactions. Pest resistance genes may encode resistance to pests that have great yield drag such as rootworm, cutworm, European Corn Borer, and the like. Disease resistance and insect resistance genes such as lysozymes or cecropins for antibacterial protection, or proteins such as defensins, glucanases or chitinases for antifungal protection, or *Bacillus thuringiensis* endotoxins, protease inhibitors, collagenases, lectins, or glycosidases for controlling nematodes or insects are all examples of useful gene products. Genes encoding disease resistance traits include detoxification genes, such as against fumonisin (U.S. Pat. No. 5,792,931); avirulence (avr) and disease resistance (R) genes (Jones et al. (1994) Science 266:789; Martin et al. (1993) Science 262:1432; and Mindrinos et al. (1994) Cell 78:1089); and the like. Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) Gene 48:109); and the like.

An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer period of time than cells that do not express the protein. Herbicide resistance traits may be introduced into plants by genes coding for resistance to herbicides that act to inhibit the action of acetolactate synthase (ALS), in particular the sulfonylurea-type herbicides, genes coding for resistance to herbicides that act to inhibit the action of glutamine synthase, such as phosphinothricin or basta (e.g., the bar gene), glyphosate (e.g., the EPSP synthase gene and the GAT gene), HPPD inhibitors (e.g, the HPPD gene) or other such genes known in the art. See, for example, U.S. Pat. Nos. 7,626,077, 5,310,667, 5,866,775, 6,225,114, 6,248,876, 7,169,970, 6,867,293, and U.S. Provisional Application No. 61/401,456, each of which is herein incorporated by reference. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male fertility genes such as MS26 (see for example U.S. Pat. Nos. 7,098,388, 7,517,975, 7,612,251), MS45 (see for example U.S. Pat. Nos. 5,478,369, 6,265,640) or MSCA1 (see for example U.S. Pat. No. 7,919,676). Maize plants (*Zea mays* L.) can be bred by both self-pollination and cross-pollination techniques. Maize has male flowers, located on the tassel, and female flowers, located on the ear, on the same plant. It can self-pollinate ("selfing") or cross pollinate. Natural pollination occurs in maize when wind blows pollen from the tassels to the silks that protrude from the tops of the incipient ears. Pollination may be readily controlled by techniques known to those of skill in the art. The development of maize hybrids requires the development of homozygous inbred lines, the crossing of these lines, and the evaluation of the crosses. Pedigree breeding and recurrent selections are two of the breeding methods used to develop inbred lines from populations. Breeding programs combine desirable traits from two or more inbred lines or various broad-based sources into breeding pools from which new inbred lines are developed by selfing and selection of desired phenotypes. A hybrid maize variety is the cross of two such inbred lines, each of which may have one or more desirable characteristics lacked by the other or which complement the other. The new inbreds are crossed with other inbred lines and the hybrids from these crosses are evaluated to determine which have commercial potential. The hybrid progeny of the first generation is designated F1. The F1 hybrid is more vigorous than its inbred parents. This hybrid vigor, or heterosis, can be manifested in many ways, including increased vegetative growth and increased yield.

Hybrid maize seed can be produced by a male sterility system incorporating manual detasseling. To produce hybrid seed, the male tassel is removed from the growing female inbred parent, which can be planted in various alternating row patterns with the male inbred parent. Consequently, providing that there is sufficient isolation from sources of foreign maize pollen, the ears of the female inbred will be fertilized only with pollen from the male inbred. The resulting seed is therefore hybrid (F1) and will form hybrid plants.

Field variation impacting plant development can result in plants tasseling after manual detasseling of the female parent is completed. Or, a female inbred plant tassel may not be completely removed during the detasseling process. In any event, the result is that the female plant will successfully shed pollen and some female plants will be self-pollinated. This will result in seed of the female inbred being harvested along with the hybrid seed which is normally produced.

Female inbred seed does not exhibit heterosis and therefore is not as productive as F1 seed. In addition, the presence of female inbred seed can represent a germplasm security risk for the company producing the hybrid.

Alternatively, the female inbred can be mechanically detasseled by machine. Mechanical detasseling is approximately as reliable as hand detasseling, but is faster and less costly. However, most detasseling machines produce more damage to the plants than hand detasseling. Thus, no form of detasseling is presently entirely satisfactory, and a need continues to exist for alternatives which further reduce production costs and to eliminate self-pollination of the female parent in the production of hybrid seed.

Mutations that cause male sterility in plants have the potential to be useful in methods for hybrid seed production for crop plants such as maize and can lower production costs by eliminating the need for the labor-intensive removal of male flowers (also known as de-tasseling) from the maternal parent plants used as a hybrid parent. Mutations that cause male sterility in maize have been produced by a variety of methods such as X-rays or UV-irradiations, chemical treatments, or transposable element insertions (ms23, ms25, ms26, ms32) (Chaubal et al. (2000) Am J Bot 87:1193-1201). Conditional regulation of fertility genes through fertility/sterility "molecular switches" could enhance the options for designing new male-sterility systems for crop improvement (Unger et al. (2002) Transgenic Res 11:455-465).

Besides identification of novel genes impacting male fertility, there remains a need to provide a reliable system of producing genetic male sterility.

In U.S. Pat. No. 5,478,369, a method is described by which the Ms45 male fertility gene was tagged and cloned on maize chromosome 9. Previously, there had been described a male fertility gene on chromosome 9, ms2, which had never been cloned and sequenced. It is not allelic to the gene referred to in the '369 patent. See Albertsen, M. and Phillips, R. L., "Developmental Cytology of 13 Genetic Male Sterile Loci in Maize" Canadian Journal of Genetics & Cytology 23:195-208 (January 1981). The only fertility gene cloned before that had been the *Arabidopsis* gene described at Aarts, et al., supra.

Examples of genes that have been discovered subsequently that are important to male fertility are numerous and include the *Arabidopsis* ABORTED MICROSPORES (AMS) gene, Sorensen et al., The Plant Journal (2003) 33(2):413-423); the *Arabidopsis* MS1 gene (Wilson et al., The Plant Journal (2001) 39(2):170-181); the NEF1 gene (Ariizumi et al., The Plant Journal (2004) 39(2):170-181); *Arabidopsis* AtGPAT1 gene (Zheng et al., The Plant Cell (2003) 15:1872-1887); the *Arabidopsis* dde2-2 mutation was shown to be defective in the allene oxide syntase gene (Malek et al., Planta (2002)216:187-192); the *Arabidopsis* faceless pollen-1 gene (flp1) (Ariizumi et al, Plant Mol. Biol. (2003) 53:107-116); the *Arabidopsis* MALE MEIOCYTE DEATH1 gene (Yang et al., The Plant Cell (2003) 15:1281-1295); the tapetum-specific zinc finger gene, TAZ1 (Kapoor et al., The Plant Cell (2002) 14:2353-2367); and the TAPETUM DETERMINANT1 gene (Lan et al, The Plant Cell (2003) 15:2792-2804).

Other known male fertility mutants or genes from *Zea mays* are listed in U.S. Pat. No. 7,919,676 incorporated herein by reference.

Other genes include kinases and those encoding compounds toxic to either male or female gametophytic development.

Furthermore, it is recognized that the polynucleotide of interest may also comprise antisense sequences complementary to at least a portion of the messenger RNA (mRNA) for a targeted gene sequence of interest. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, 80%, or 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

In addition, the polynucleotide of interest may also be used in the sense orientation to suppress the expression of endogenous genes in plants. Methods for suppressing gene expression in plants using polynucleotides in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, generally greater than about 65% sequence identity, about 85% sequence identity, or greater than about 95% sequence identity. See, U.S. Pat. Nos. 5,283,184 and 5,034,323; herein incorporated by reference.

The polynucleotide of interest can also be a phenotypic marker. A phenotypic marker is screenable or a selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as glufosinate ammonium, bromoxynil, imidazolinones, and 2,4-dichlorophenoxyacetate (2,4-D). See for example, Yarranton, (1992) Curr Opin Biotech 3:506-11; Christopherson et al., (1992) Proc. Natl. Acad. Sci. USA 89:6314-8; Yao et al., (1992)

Cell 71:63-72; Reznikoff, (1992) Mol Microbiol 6:2419-22; Hu et al., (1987) Cell 48:555-66; Brown et al., (1987) Cell 49:603-12; Figge et al., (1988) Cell 52:713-22; Deuschle et al., (1989) Proc. Natl. Acad. Sci. USA 86:5400-4; Fuerst et al., (1989) Proc. Natl. Acad. Sci. USA 86:2549-53; Deuschle et al., (1990) Science 248:480-3; Gossen, (1993) Ph.D. Thesis, University of Heidelberg; Reines et al., (1993) Proc. Natl. Acad. Sci. USA 90:1917-21; Labow et al., (1990) Mol Cell Biol 10:3343-56; Zambretti et al., (1992) Proc. Natl. Acad. Sci. USA 89:3952-6; Bairn et al., (1991) Proc. Natl. Acad. Sci. USA 88:5072-6; Wyborski et al., (1991) Nucleic Acids Res 19:4647-53; Hillen and Wissman, (1989) Topics Mol Struc Biol 10:143-62; Degenkolb et al., (1991) Antimicrob Agents Chemother 35:1591-5; Kleinschnidt et al., (1988) Biochemistry 27:1094-104; Bonin, (1993) Ph.D. Thesis, University of Heidelberg; Gossen et al., (1992) Proc. Natl. Acad. Sci. USA 89:5547-51; Oliva et al., (1992) Antimicrob Agents Chemother 36:913-9; Hlavka et al., (1985) Handbook of Experimental Pharmacology, Vol. 78 (Springer-Verlag, Berlin); Gill et al., (1988) Nature 334:721-4. Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) J. Bacteriol. 170:5837-5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

The transgenes, recombinant DNA molecules, DNA sequences of interest, and polynucleotides of interest can be comprise one or more DNA sequences for gene silencing. Methods for gene silencing involving the expression of DNA sequences in plant are known in the art include, but are not limited to, cosuppression, antisense suppression, double-stranded RNA (dsRNA) interference, hairpin RNA (hpRNA) interference, intron-containing hairpin RNA (ihpRNA) interference, transcriptional gene silencing, and micro RNA (miRNA) interference As used herein, "nucleic acid" means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" and "nucleic acid fragment" are used interchangeably to denote a polymer of RNA and/or DNA that is single- or double-stranded, optionally containing synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide.

"Open reading frame" is abbreviated ORF.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of genes to produce the desired phenotype in a transformed plant. genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential to the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

Polynucleotide and polypeptide sequences, variants thereof, and the structural relationships of these sequences can be described by the terms "homology", "homologous", "substantially identical", "substantially similar" and "corresponding substantially" which are used interchangeably herein. These refer to polypeptide or nucleic acid fragments wherein changes in one or more amino acids or nucleotide bases do not affect the function of the molecule, such as the ability to mediate gene expression or to produce a certain phenotype. These terms also refer to modification(s) of nucleic acid fragments that do not substantially alter the functional properties of the resulting nucleic acid fragment relative to the initial, unmodified fragment. These modifications include deletion, substitution, and/or insertion of one or more nucleotides in the nucleic acid fragment.

Substantially similar nucleic acid sequences encompassed may be defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence in an in vitro hybridization assay. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salt(s)) at pH 7.0 to 8.3, and at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

"Sequence identity" or "identity" in the context of nucleic acid or polypeptide sequences includes the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, (1989) CABIOS 5:151-153; Higgins et al., (1992) *Comput Appl Biosci* 8:189-191) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, (1989) *CABIOS* 5:151-153; Higgins et al., (1992) *Comput Appl Biosci* 8:189-191) and found in the MegAlign™ v6.1 program of the LASERGENE bioinformatics computing suite (DNASTAR Inc., Madison, Wis.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

Unless otherwise stated, sequence identity/similarity values provided herein refer to the value obtained using GAP Version 10 (GCG, Accelrys, San Diego, Calif.) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff and Henikoff, (1989) *Proc. Natl. Acad. Sci. USA* 89:10915). GAP uses the algorithm of Needleman and Wunsch, (1970) *J Mol Biol* 48:443-53, to find an alignment of two complete sequences that maximizes the number of matches and minimizes the number of gaps. GAP considers all possible alignments and gap positions and creates the alignment with the largest number of matched bases and the fewest gaps, using a gap creation penalty and a gap extension penalty in units of matched bases.

"BLAST" is a searching algorithm provided by the National Center for Biotechnology Information (NCBI) used to find regions of similarity between biological sequences. The program compares nucleotide or protein sequences to sequence databases and calculates the statistical significance of matches to identify sequences having sufficient similarity to a query sequence such that the similarity would not be predicted to have occurred randomly. BLAST reports the identified sequences and their local alignment to the query sequence.

It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90% or 95%, or any integer percentage from 50% to 100%. Indeed, any integer amino acid identity from 50% to 100% may be useful in describing the present disclosure, such as 51%, 52%, 53%, 54%, 55%, 56%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

"Gene" includes a nucleic acid fragment that expresses a functional molecule such as, but not limited to, a specific protein, including regulatory sequences preceding (5' non-coding sequences) and following (3' non-coding sequences) the coding sequence. "Native gene" refers to a gene as found in nature with its own regulatory sequences.

A "mutated gene" is a gene that has been altered through human intervention. Such a "mutated gene" has a sequence that differs from the sequence of the corresponding non-mutated gene by at least one nucleotide addition, deletion, or substitution. In certain embodiments of the disclosure, the mutated gene comprises an alteration that results from a guide polynucleotide/Cas endonuclease system as disclosed herein. A mutated plant is a plant comprising a mutated gene.

Targeted mutation includes a mutation in a native gene that was made by altering a target sequence within the native gene using a method involving a double-strand-break-inducing agent that is capable of inducing a double-strand break in the DNA of the target sequence as disclosed herein or known in the art.

In one embodiment, the targeted mutation is the result of a guideRNA/Cas endonuclease induced gene editing, without incorporating a selectable transgene marker, as described herein. The guide RNA/Cas endonuclease induced targeted mutation can occur in a nucleotide sequence that is located within or outside a genomic target site that is recognized and cleaved by a Cas endonuclease.

The term "genome" as it applies to a plant cells encompasses not only chromosomal DNA found within the nucleus, but organelle DNA found within subcellular components (e.g., mitochondria, or plastid) of the cell.

A "codon-modified gene" or "codon-preferred gene" or "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus.

"Coding sequence" refers to a polynucleotide sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, 5' untranslated sequences, 3' untranslated sequences, introns, polyadenylation target sequences, RNA processing sites, effector binding sites, and stem-loop structures.

"A plant-optimized nucleotide sequence" is nucleotide sequence that has been optimized for increased expression in plants, particularly for increased expression in plants or in one or more plants of interest. For example, a plant-optimized nucleotide sequence can be synthesized by modifying a nucleotide sequence encoding a protein such as, for example, double-strand-break-inducing agent (e.g., an endonuclease) as disclosed herein, using one or more plant-preferred codons for improved expression. See, for example, Campbell and Gowri (1990) *Plant Physiol.* 92:1-11 for a discussion of host-preferred codon usage.

Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference. Additional sequence modifications are known to enhance gene expression in a plant host. These include, for example, elimination of: one or more sequences encoding spurious polyadenylation signals, one or more exon-intron splice site signals, one or more transposon-like repeats, and other such well-characterized sequences that may be deleterious to gene expression. The G-C content of the sequence may be adjusted to levels average for a given plant host, as calculated by reference to known genes expressed in the host plant cell. When possible, the sequence is modified to avoid one or more predicted hairpin secondary mRNA structures. Thus, "a plant-optimized nucleotide sequence" of the present disclosure comprises one or more of such sequence modifications.

"Promoter" refers to a DNA sequence capable of controlling the expression of a coding sequence or functional RNA. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters".

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters" if the promoters direct RNA synthesis preferably in certain tissues but also in other tissues at reduced levels. Since patterns of expression of a chimeric gene (or genes) introduced into a plant are controlled using promoters, there is an ongoing interest in the isolation of novel promoters which are capable of controlling the expression of a chimeric gene or (genes) at certain levels in specific tissue types or at specific plant developmental stages.

New promoters of various types useful in plant cells are constantly being discovered; numerous examples may be found in the compilation by Okamuro and Goldberg, (1989) In *The Biochemistry of Plants*, Vol. 115, Stumpf and Conn, eds (New York, N.Y.: Academic Press), pp. 1-82.

"Translation leader sequence" refers to a polynucleotide sequence located between the promoter sequence of a gene and the coding sequence. The translation leader sequence is present in the mRNA upstream of the translation start sequence. The translation leader sequence may affect processing of the primary transcript to mRNA, mRNA stability or translation efficiency. Examples of translation leader sequences have been described (e.g., Turner and Foster, (1995) *Mol Biotechnol* 3:225-236).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

"RNA transcript" refers to the product resulting from RNA polymerase-catalyzed transcription of a DNA sequence. When the RNA transcript is a perfect complimentary copy of the DNA sequence, it is referred to as the primary transcript or pre-mRNA. A RNA transcript is referred to as the mature RNA or mRNA when it is a RNA sequence derived from post-transcriptional processing of the primary transcript pre mRNAt. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (see, e.g., U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" includes antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions can be operably linked, either directly or indirectly, 5' to the target mRNA, or 3' to the target mRNA, or within the target mRNA, or a first complementary region is 5' and its complement is 3' to the target m RNA.

Standard recombinant DNA and molecular cloning techniques used herein are well known in the art and are described more fully in Sambrook et al., *Molecular Cloning: A Laboratory Manual; Cold Spring Harbor Laboratory*: Cold Spring Harbor, NY (1989). Transformation methods are well known to those skilled in the art and are described infra.

"PCR" or "polymerase chain reaction" is a technique for the synthesis of specific DNA segments and consists of a series of repetitive denaturation, annealing, and extension cycles. Typically, a double-stranded DNA is heat denatured, and two primers complementary to the 3' boundaries of the target segment are annealed to the DNA at low temperature, and then extended at an intermediate temperature. One set of these three consecutive steps is referred to as a "cycle".

The term "recombinant" refers to an artificial combination of two otherwise separated segments of sequence, e.g., by chemical synthesis, or manipulation of isolated segments of nucleic acids by genetic engineering techniques.

The terms "plasmid", "vector" and "cassette" refer to an extra chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell. "Transformation cassette" refers to a specific vector containing a gene and having elements in addition to the gene that facilitates transformation of a particular host cell. "Expression cassette" refers to a specific vector containing a gene and having elements in addition to the gene that allow for expression of that gene in a host.

The terms "recombinant DNA molecule", "recombinant construct", "expression construct", "construct", "construct", and "recombinant DNA construct" are used interchangeably herein. A recombinant construct comprises an artificial combination of nucleic acid fragments, e.g., regulatory and coding sequences that are not all found together in nature. For example, a construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells. The skilled artisan will also recognize that different independent transformation events may result in different levels and patterns of expression (Jones et al., (1985) *EMBO J* 4:2411-2418; De Almeida et al., (1989) *Mol Gen Genetics* 218:78-86), and thus that multiple events are typically screened in order to obtain lines displaying the desired expression level and pattern. Such screening may be accomplished standard molecular biological, biochemical, and other assays including Southern analysis of DNA, Northern analysis of mRNA expression, PCR, real time quantitative PCR (qPCR), reverse transcription PCR (RT-PCR), immunoblotting analysis of protein expression, enzyme or activity assays, and/or phenotypic analysis.

The term "expression", as used herein, refers to the production of a functional end-product (e.g., an mRNA, guide RNA, or a protein) in either precursor or mature form.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid, or mitochondrial DNA), converted into an autonomous replicon, or transiently expressed (e.g., transfected mRNA).

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or other DNA-containing organelle, of a host organism resulting in gene expression without integration or stable inheritance. Host organisms containing the transformed nucleic acid fragments are referred to as "transgenic" organisms.

The commercial development of genetically improved germplasm has also advanced to the stage of introducing multiple traits into crop plants, often referred to as a gene stacking approach. In this approach, multiple genes conferring different characteristics of interest can be introduced into a plant. Gene stacking can be accomplished by many means including but not limited to co-transformation, retransformation, and crossing lines with different genes of interest.

The term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollens, seeds, tumor tissue and various forms of cells and culture (e.g., single cells, protoplasts, embryos, and callus tissue). The plant tissue may be in plant or in a plant organ, tissue or cell culture. The term "plant organ" refers to plant tissue or a group of tissues that constitute a morphologically and functionally distinct part of a plant. The term "genome" refers to the entire complement of genetic material (genes and non-coding sequences) that is present in each cell of an organism, or virus or organelle; and/or a complete set of chromosomes inherited as a (haploid) unit from one parent. "Progeny" comprises any subsequent generation of a plant.

A transgenic plant includes, for example, a plant which comprises within its genome a heterologous polynucleotide introduced by a transformation step. The heterologous polynucleotide can be stably integrated within the genome such that the polynucleotide is passed on to successive generations. The heterologous polynucleotide may be integrated into the genome alone or as part of a recombinant DNA construct. A transgenic plant can also comprise more than one heterologous polynucleotide within its genome. Each heterologous polynucleotide may confer a different trait to the transgenic plant. A heterologous polynucleotide can include a sequence that originates from a foreign species, or, if from the same species, can be substantially modified from its native form. Transgenic can include any cell, cell line, callus, tissue, plant part or plant, the genotype of which has been altered by the presence of heterologous nucleic acid including those transgenics initially so altered as well as those created by sexual crosses or asexual propagation from the initial transgenic. The alterations of the genome (chromosomal or extra-chromosomal) by conventional plant breeding methods, by the genome editing procedure described herein that does not result in an insertion of a foreign polynucleotide, or by naturally occurring events such as random cross-fertilization, non-recombinant viral infection, non-recombinant bacterial transformation, non-recombinant transposition, or spontaneous mutation are not intended to be regarded as transgenic.

In certain embodiments of the disclosure, a fertile plant is a plant that produces viable male and female gametes and is self-fertile. Such a self-fertile plant can produce a progeny plant without the contribution from any other plant of a gamete and the genetic material contained therein. Other embodiments of the disclosure can involve the use of a plant that is not self-fertile because the plant does not produce male gametes, or female gametes, or both, that are viable or otherwise capable of fertilization. As used herein, a "male sterile plant" is a plant that does not produce male gametes that are viable or otherwise capable of fertilization. As used herein, a "female sterile plant" is a plant that does not produce female gametes that are viable or otherwise capable of fertilization. It is recognized that male-sterile and female-sterile plants can be female-fertile and male-fertile, respectively. It is further recognized that a male fertile (but female sterile) plant can produce viable progeny when crossed with a female fertile plant and that a female fertile (but male sterile) plant can produce viable progeny when crossed with a male fertile plant.

A "centimorgan" (cM) or "map unit" is the distance between two linked genes, markers, target sites, loci, or any pair thereof, wherein 1% of the products of meiosis are recombinant. Thus, a centimorgan is equivalent to a distance equal to an 1% average recombination frequency between the two linked genes, markers, target sites, loci, or any pair thereof.

Breeding Methods and Methods for Selecting Plants Utilizing a Two Component RNA Guide and Cas Endonuclease System The present disclosure finds use in the breeding of plants comprising one or more transgenic traits. Most commonly, transgenic traits are randomly inserted throughout the plant genome as a consequence of transformation systems based on *Agrobacterium*, biolistics, or other commonly used procedures. More recently, gene targeting protocols have been developed that enable directed transgene insertion. One important technology, site-specific integration (SSI) enables the targeting of a transgene to the same chromosomal location as a previously inserted transgene. Custom-designed meganucleases and custom-designed zinc finger meganucleases allow researchers to design nucleases to target specific chromosomal locations, and these reagents allow the targeting of transgenes at the chromosomal site cleaved by these nucleases.

The currently used systems for precision genetic engineering of eukaryotic genomes, e.g. plant genomes, rely upon homing endonucleases, meganucleases, zinc finger nucleases, and transcription activator-like effector nucleases (TALENs), which require de novo protein engineering for every new target locus. The highly specific, RNA-directed DNA nuclease, guide RNA/Cas9 endonuclease system described herein, is more easily customizable and therefore more useful when modification of many different target sequences is the goal. This disclosure takes further advantage of the two component nature of the guide RNA/Cas system, with its constant protein component, the Cas endonuclease, and its variable and easily reprogrammable targeting component, the guide RNA or the crRNA.

The guide RNA/Cas system described herein is especially useful for genome engineering, especially plant genome engineering, in circumstances where nuclease off-target cutting can be toxic to the targeted cells. In one embodiment of the guide RNA/Cas system described herein, the constant component, in the form of an expression-optimized Cas9 gene, is stably integrated into the target genome, e.g. plant genome. Expression of the Cas9 gene is under control of a promoter, e.g. plant promoter, which can be a constitutive promoter, tissue-specific promoter or inducible promoter, e.g. temperature-inducible, stress-inducible, developmental stage inducible, or chemically inducible promoter. In the absence of the variable component, i.e. the guide RNA or crRNA, the Cas9 protein is not able to cut DNA and therefore its presence in the plant cell should have little or no consequence. Hence a key advantage of the guide RNA/Cas system described herein is the ability to create and maintain a cell line or transgenic organism capable of efficient expression of the Cas9 protein with little or no consequence to cell viability. In order to induce cutting at desired genomic sites to achieve targeted genetic modifications, guide RNAs or crRNAs can be introduced by a variety of methods into cells containing the stably-integrated and expressed cas9 gene. For example, guide RNAs or crRNAs can be chemically or enzymatically synthesized, and introduced into the Cas9 expressing cells via direct delivery methods such a particle bombardment or electroporation.

Alternatively, genes capable of efficiently expressing guide RNAs or crRNAs in the target cells can be synthesized chemically, enzymatically or in a biological system, and these genes can be introduced into the Cas9 expressing cells via direct delivery methods such a particle bombardment, electroporation or biological delivery methods such as *Agrobacterium* mediated DNA delivery.

In one embodiment, the method comprises a method for introducing a polynucleotide of interest into a plant genome without introducing an exogenous selectable marker into said plant genome, the method comprising providing a first guide RNA, a first polynucleotide modification template, a second guide RNA, a second polynucleotide modification template, and a Cas endonuclease to a plant cell comprising a first endogenous gene that can be modified to confer herbicide resistance, wherein said first guide RNA and Cas endonuclease are capable of forming a first complex that enables the Cas endonuclease to introduce a double strand break at a first target site located in or near said first endogenous gene in the genome of said plant cell, wherein said first polynucleotide modification template comprises at least one nucleotide modification of said first endogenous gene to render said endogenous gene capable of conferring herbicide resistance to a plant cell, wherein said second guide RNA and Cas endonuclease are capable of forming a second complex that enables the Cas endonuclease to introduce a double strand break at a second target site in the genome of said plant cell, wherein said second polynucleotide modification template comprises at least one polynucleotide of interest to be introduced into said plant genome.

As disclosed herein, a guide RNA/Cas system mediating gene targeting without incorporating a selectable transgene marker can be used in methods for directing transgene insertion and/or for producing complex transgenic trait loci comprising multiple transgenes in a fashion similar as disclosed in WO2013/0198888 (published Aug. 1, 2013) where instead of using a double strand break inducing agent to introduce a gene of interest, a guide RNA/Cas system or a guide polynucleotide/Cas system as disclosed herein is used. In one embodiment, a complex transgenic trait locus is a genomic locus that has multiple transgenes genetically linked to each other. By inserting independent transgenes within 0.1, 0.2, 0.3, 04, 0.5, 1, 2, or even 5 centimorgans (cM) from each other, the transgenes can be bred as a single genetic locus (see, for example, U.S. patent application Ser. No. 13/427,138) or PCT application PCT/US2012/030061. After selecting a plant comprising a transgene, plants containing (at least) one transgenes can be crossed to form an F1 that contains both transgenes. In progeny from these F1 (F2 or BC1) 1/500 progeny would have the two different transgenes recombined onto the same chromosome. The complex locus can then be bred as single genetic locus with both transgene traits. This process can be repeated to stack as many traits as desired.

Chromosomal intervals that correlate with a phenotype or trait of interest can be identified. A variety of methods well known in the art are available for identifying chromosomal intervals. The boundaries of such chromosomal intervals are drawn to encompass markers that will be linked to the gene controlling the trait of interest. In other words, the chromosomal interval is drawn such that any marker that lies within that interval (including the terminal markers that define the boundaries of the interval) can be used as a marker for northern leaf blight resistance. In one embodiment, the chromosomal interval comprises at least one QTL, and furthermore, may indeed comprise more than one QTL. Close proximity of multiple QTLs in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identify the same QTL or two different QTL. The term "quantitative trait locus" or "QTL" refers to a region of DNA that is associated with the differential expression of a quantitative phenotypic trait in at least one genetic background, e.g., in at least one breeding population. The region of the QTL encompasses or is closely linked to the gene or genes that affect the trait in question. An "allele of a QTL" can comprise multiple genes or other genetic factors within a contiguous genomic region or linkage group, such as a haplotype. An allele of a QTL can denote a haplotype within a specified window wherein said window is a contiguous genomic region that can be defined, and tracked, with a set of one or more polymorphic markers. A haplotype can be defined by the unique fingerprint of alleles at each marker within the specified window.

A variety of methods are available to identify those cells having an altered genome at or near a target site without using a screenable marker phenotype. Such methods can be viewed as directly analyzing a target sequence to detect any change in the target sequence, including but not limited to PCR methods, sequencing methods, nuclease digestion, Southern blots, and any combination thereof.

Proteins may be altered in various ways including amino acid substitutions, deletions, truncations, and insertions. Methods for such manipulations are generally known. For example, amino acid sequence variants of the protein(s) can be prepared by mutations in the DNA. Methods for mutagenesis and nucleotide sequence alterations include, for example, Kunkel, (1985) *Proc. Natl. Acad. Sci. USA* 82:488-92; Kunkel et al., (1987) *Meth Enzymol* 154:367-82; U.S. Pat. No. 4,873,192; Walker and Gaastra, eds. (1983) *Techniques in Molecular Biology* (MacMillan Publishing Company, New York) and the references cited therein. Guidance regarding amino acid substitutions not likely to affect biological activity of the protein is found, for example, in the model of Dayhoff et al., (1978) *Atlas of Protein Sequence and Structure* (Natl Biomed Res Found, Washington, D.C.). Conservative substitutions, such as exchanging one amino acid with another having similar properties, may be preferable. Conservative deletions, insertions, and amino acid substitutions are not expected to produce radical changes in the characteristics of the protein, and the effect of any substitution, deletion, insertion, or combination thereof can be evaluated by routine screening assays. Assays for double-strand-break-inducing activity are known and generally measure the overall activity and specificity of the agent on DNA substrates containing target sites.

A variety of methods are known for the introduction of nucleotide sequences and polypeptides into an organism, including, for example, transformation, sexual crossing, and the introduction of the polypeptide, DNA, or mRNA into the cell.

Methods for contacting, providing, and/or introducing a composition into various organisms are known and include but are not limited to, stable transformation methods, transient transformation methods, virus-mediated methods, and sexual breeding. Stable transformation indicates that the introduced polynucleotide integrates into the genome of the organism and is capable of being inherited by progeny thereof. Transient transformation indicates that the introduced composition is only temporarily expressed or present in the organism.

Protocols for introducing polynucleotides and polypeptides into plants may vary depending on the type of plant or plant cell targeted for transformation, such as monocot or dicot. Suitable methods of introducing polynucleotides and polypeptides into plant cells and subsequent insertion into the plant genome include microinjection (Crossway et al., (1986) *Biotechniques* 4:320-34 and U.S. Pat. No. 6,300, 543), meristem transformation (U.S. Pat. No. 5,736,369), electroporation (Riggs et al., (1986) *Proc. Natl. Acad. Sci. USA* 83:5602-6, *Agrobacterium*-mediated transformation (U.S. Pat. Nos. 5,563,055 and 5,981,840), direct gene transfer (Paszkowski et al., (1984) *EMBO J* 3:2717-22), and ballistic particle acceleration (U.S. Pat. Nos. 4,945,050; 5,879,918; 5,886,244; 5,932,782; Tomes et al., (1995) "Direct DNA Transfer into Intact Plant Cells via Microprojectile Bombardment" in *Plant Cell, Tissue, and Organ Culture: Fundamental Methods*, ed. Gamborg & Phillips (Springer-Verlag, Berlin); McCabe et al., (1988) *Biotechnology* 6:923-6; Weissinger et al., (1988) *Ann Rev Genet* 22:421-77; Sanford et al., (1987) *Particulate Science and Technology* 5:27-37 (onion); Christou et al., (1988) *Plant Physiol* 87:671-4 (soybean); Finer and McMullen, (1991) *In Vitro Cell Dev Biol* 27P:175-82 (soybean); Singh et al., (1998) *Theor Appl Genet* 96:319-24 (soybean); Datta et al., (1990) *Biotechnology* 8:736-40 (rice); Klein et al., (1988) *Proc. Natl. Acad. Sci. USA* 85:4305-9 (maize); Klein et al., (1988) *Biotechnology* 6:559-63 (maize); U.S. Pat. Nos. 5,240,855; 5,322,783 and 5,324,646; Klein et al., (1988) *Plant Physiol* 91:440-4 (maize); Fromm et al., (1990) *Biotechnology* 8:833-9 (maize); Hooykaas-Van Slogteren et al., (1984) *Nature* 311:763-4; U.S. Pat. No. 5,736,369 (cereals); Bytebier et al., (1987) *Proc. Natl. Acad. Sci. USA* 84:5345-9 (Liliaceae); De Wet et al., (1985) in *The Experimental Manipulation of Ovule Tissues*, ed. Chapman et al., (Longman, N.Y.), pp. 197-209 (pollen); Kaeppler et al., (1990) *Plant Cell Rep* 9:415-8) and Kaeppler et al., (1992) *Theor Appl Genet* 84:560-6 (whisker-mediated transformation);

D'Halluin et al., (1992) *Plant Cell* 4:1495-505 (electroporation); Li et al., (1993) *Plant Cell Rep* 12:250-5; Christou and Ford (1995) *Annals Botany* 75:407-13 (rice) and Osjoda et al., (1996) *Nat Biotechnol* 14:745-50 (maize via *Agrobacterium tumefaciens*).

Alternatively, polynucleotides may be introduced into plants by contacting plants with a virus or viral nucleic acids. Generally, such methods involve incorporating a polynucleotide within a viral DNA or RNA molecule. In some examples a polypeptide of interest may be initially synthesized as part of a viral polyprotein, which is later processed by proteolysis in vivo or in vitro to produce the desired recombinant protein. Methods for introducing polynucleotides into plants and expressing a protein encoded therein, involving viral DNA or RNA molecules, are known, see, for example, U.S. Pat. Nos. 5,889,191, 5,889,190, 5,866,785, 5,589,367 and 5,316,931. Transient transformation methods include, but are not limited to, the introduction of polypeptides, such as a double-strand break inducing agent, directly into the organism, the introduction of polynucleotides such as DNA and/or RNA polynucleotides, and the introduction of the RNA transcript, such as an mRNA encoding a double-strand break inducing agent, into the organism. Such methods include, for example, microinjection or particle bombardment. See, for example Crossway et al., (1986) *Mol Gen Genet* 202:179-85; Nomura et al., (1986) *Plant Sci* 44:53-8; Hepler et al., (1994) *Proc. Natl. Acad. Sci. USA* 91:2176-80; and, Hush et al., (1994) *J Cell Sci* 107:775-84.

The term "dicot" refers to the subclass of angiosperm plants also knows as "dicotyledoneae" and includes reference to whole plants, plant organs (e.g., leaves, stems, roots, etc.), seeds, plant cells, and progeny of the same. Plant cell, as used herein includes, without limitation, seeds, suspension cultures, embryos, meristematic regions, callus tissue, leaves, roots, shoots, gametophytes, sporophytes, pollen, and microspores.

The term "crossed" or "cross" or "crossing" in the context of this disclosure means the fusion of gametes via pollination to produce progeny (i.e., cells, seeds, or plants). The term encompasses both sexual crosses (the pollination of one plant by another) and selfing (self-pollination, i.e., when the pollen and ovule (or microspores and megaspores) are from the same plant or genetically identical plants).

The term "introgression" refers to the transmission of a desired allele of a genetic locus from one genetic background to another. For example, introgression of a desired allele at a specified locus can be transmitted to at least one progeny plant via a sexual cross between two parent plants, where at least one of the parent plants has the desired allele within its genome. Alternatively, for example, transmission of an allele can occur by recombination between two donor genomes, e.g., in a fused protoplast, where at least one of the donor protoplasts has the desired allele in its genome. The desired allele can be, e.g., a transgene, a modified (mutated or edited) native allele, or a selected allele of a marker or QTL.

Standard DNA isolation, purification, molecular cloning, vector construction, and verification/characterization methods are well established, see, for example Sambrook et al., (1989) *Molecular Cloning: A Laboratory Manual*, (Cold Spring Harbor Laboratory Press, NY). Vectors and constructs include circular plasmids, and linear polynucleotides, comprising a polynucleotide of interest and optionally other components including linkers, adapters, regulatory regions, introns, restriction sites, enhancers, insulators, selectable markers, nucleotide sequences of interest, promoters, and/or other sites that aid in vector construction or analysis. In some examples a recognition site and/or target site can be contained within an intron, coding sequence, 5' UTRs, 3' UTRs, and/or regulatory regions.

The present disclosure further provides expression constructs for expressing in a plant, plant cell, or plant part a guide RNA/Cas system that is capable of binding to and creating a double strand break in a target site. In one embodiment, the expression constructs of the disclosure comprise a promoter operably linked to a nucleotide sequence encoding a Cas gene and a promoter operably linked to a guide RNA of the present disclosure. The promoter is capable of driving expression of an operably linked nucleotide sequence in a plant cell.

A promoter is a region of DNA involved in recognition and binding of RNA polymerase and other proteins to initiate transcription. A plant promoter is a promoter capable of initiating transcription in a plant cell, for a review of plant promoters, see, Potenza et al., (2004) *In Vitro Cell Dev Biol* 40:1-22. Constitutive promoters include, for example, the core promoter of the Rsyn7 promoter and other constitutive promoters disclosed in WO99/43838 and U.S. Pat. No. 6,072,050; the core CaMV 35S promoter (Odell et al., (1985) *Nature* 313:810-2); rice actin (McElroy et al., (1990) *Plant Cell* 2:163-71); ubiquitin (Christensen et al., (1989) *Plant Mol Biol* 12:619-32; Christensen et al., (1992) *Plant Mol Biol* 18:675-89); pEMU (Last et al., (1991) *Theor Appl Genet* 81:581-8); MAS (Velten et al., (1984) *EMBO J* 3:2723-30); ALS promoter (U.S. Pat. No. 5,659,026), and the like. Other constitutive promoters are described in, for example, U.S. Pat. Nos. 5,608,149; 5,608,144; 5,604,121; 5,569,597; 5,466,785; 5,399,680; 5,268,463; 5,608,142 and 6,177,611. In some examples an inducible promoter may be used. Pathogen-inducible promoters induced following infection by a pathogen include, but are not limited to those regulating expression of PR proteins, SAR proteins, beta-1, 3-glucanase, chitinase, etc.

Chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. Chemical-inducible promoters include, but are not limited to, the maize In2-2 promoter, activated by benzene sulfonamide herbicide safeners (De Veylder et al., (1997) *Plant Cell Physiol* 38:568-77), the maize GST promoter (GST-II-27, WO93/01294), activated by hydrophobic electrophilic compounds used as pre-emergent herbicides, and the tobacco PR-1a promoter (Ono et al., (2004) *Biosci Biotechnol Biochem* 68:803-7) activated by salicylic acid. Other chemical-regulated promoters include steroid-responsive promoters (see, for example, the glucocorticoid-inducible promoter (Schena et al., (1991) *Proc. Natl. Acad. Sci. USA* 88:10421-5; McNellis et al., (1998) *Plant J* 14:247-257); tetracycline-inducible and tetracycline-repressible promoters (Gatz et al., (1991) *Mol Gen Genet* 227:229-37; U.S. Pat. Nos. 5,814,618 and 5,789,156).

Tissue-preferred promoters can be utilized to target enhanced expression within a particular plant tissue. Tissue-preferred promoters include, for example, Kawamata et al., (1997) *Plant Cell Physiol* 38:792-803; Hansen et al., (1997) *Mol Gen Genet* 254:337-43; Russell et al., (1997) *Transgenic Res* 6:157-68; Rinehart et al., (1996) *Plant Physiol* 112:1331-41; Van Camp et al., (1996) *Plant Physiol* 112:525-35; Canevascini et al., (1996) *Plant Physiol* 112:513-524; Lam, (1994) *Results Probl Cell Differ* 20:181-96; and Guevara-Garcia et al., (1993) *Plant J* 4:495-505. Leaf-preferred promoters include, for example, Yamamoto et al., (1997) *Plant J* 12:255-65; Kwon et al., (1994) *Plant Physiol* 105:357-67; Yamamoto et al., (1994) *Plant Cell Physiol* 35:773-8; Gotor et al., (1993) *Plant J* 3:509-18; Orozco et al., (1993) *Plant Mol Biol* 23:1129-38; Matsuoka et al., (1993) *Proc. Natl. Acad. Sci. USA* 90:9586-90; Simpson et al., (1958) *EMBO J* 4:2723-9; Timko et al., (1988) *Nature* 318:57-8. Root-preferred promoters include, for example, Hire et al., (1992) *Plant Mol Biol* 20:207-18 (soybean root-specific glutamine synthase gene); Miao et al., (1991) *Plant Cell* 3:11-22 (cytosolic glutamine synthase (GS)); Keller and Baumgartner, (1991) *Plant Cell* 3:1051-61 (root-specific control element in the GRP 1.8 gene of French bean); Sanger et al., (1990) *Plant Mol Biol* 14:433-43 (root-specific promoter of *A. tumefaciens* mannopine synthase (MAS)); Bogusz et al., (1990) *Plant Cell* 2:633-41 (root-specific promoters isolated from *Parasponia andersonii* and *Trema tomentosa*); Leach and Aoyagi, (1991) *Plant Sci* 79:69-76 (*A. rhizogenes* rolC and rolD root-inducing genes); Teeri et al., (1989) *EMBO J* 8:343-50 (*Agrobacterium* wound-induced TR1' and TR2' genes); VfENOD-GRP3 gene promoter (Kuster et al., (1995) *Plant Mol Biol* 29:759-72); and rolB promoter (Capana et al., (1994) *Plant Mol Biol* 25:681-91; phaseolin gene (Murai et al., (1983) *Science* 23:476-82; Sengopta-Gopalen et al., (1988) *Proc. Natl. Acad. Sci. USA* 82:3320-4). See also, U.S. Pat. Nos. 5,837,876; 5,750,386; 5,633,363; 5,459,252; 5,401,836; 5,110,732 and 5,023,179.

Seed-preferred promoters include both seed-specific promoters active during seed development, as well as seed-germinating promoters active during seed germination. See, Thompson et al., (1989) *BioEssays* 10:108. Seed-preferred promoters include, but are not limited to, Cim1 (cytokinin-induced message); cZ19B1 (maize 19 kDa zein); and milps (myo-inositol-1-phosphate synthase); (WO00/11177; and U.S. Pat. No. 6,225,529). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa gamma zein, waxy, shrunken 1, shrunken 2, globulin 1, oleosin, and nuc1. See also, WO00/12733, where seed-preferred promoters from END1 and END2 genes are disclosed.

A phenotypic marker is a screenable or selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as glufosinate ammonium, bromoxynil, imidazolinones, and 2,4-dichlorophenoxyacetate (2,4-D). See for example, Yarranton, (1992) *Curr Opin Biotech* 3:506-11; Christopherson et al., (1992) *Proc. Natl. Acad. Sci. USA* 89:6314-8; Yao et al., (1992) *Cell* 71:63-72; Reznikoff, (1992) *Mol Microbiol* 6:2419-22; Hu et al., (1987) *Cell* 48:555-66; Brown et al., (1987) *Cell* 49:603-12; Figge et al., (1988) *Cell* 52:713-22; Deuschle et al., (1989) *Proc. Natl. Acad. Sci. USA* 86:5400-4; Fuerst et al., (1989) *Proc. Natl. Acad. Sci. USA* 86:2549-53; Deuschle et al., (1990) *Science* 248:480-3; Gossen, (1993) Ph.D. Thesis, University of Heidelberg; Reines et al., (1993) *Proc. Natl. Acad. Sci. USA* 90:1917-21; Labow et al., (1990) *Mol Cell Biol* 10:3343-56; Zambretti et al., (1992) *Proc. Natl. Acad. Sci. USA* 89:3952-6; Bairn et al., (1991) *Proc. Natl. Acad. Sci. USA* 88:5072-6; Wyborski et al., (1991) *Nucleic Acids Res* 19:4647-53; Hillen and Wissman, (1989) *Topics Mol Struc Biol* 10:143-62; Degenkolb et al., (1991) *Antimicrob Agents Chemother* 35:1591-5; Kleinschnidt et al., (1988) *Biochemistry* 27:1094-104; Bonin, (1993) Ph.D. Thesis, University of Heidelberg; Gossen et al., (1992) *Proc. Natl. Acad. Sci. USA* 89:5547-51; Oliva et al., (1992) *Antimicrob Agents Chemother* 36:913-9; Hlavka et al., (1985) *Handbook of Experimental Pharmacology*, Vol. 78 (Springer-Verlag, Berlin); Gill et al., (1988) *Nature* 334:721-4.

The cells having the introduced sequence may be grown or regenerated into plants using conventional conditions, see for example, McCormick et al., (1986) *Plant Cell Rep* 5:81-4. These plants may then be grown, and either pollinated with the same transformed strain or with a different transformed or untransformed strain, and the resulting progeny having the desired characteristic and/or comprising the introduced polynucleotide or polypeptide identified. Two or more generations may be grown to ensure that the polynucleotide is stably maintained and inherited, and seeds harvested.

Any plant can be used, including monocot and dicot plants. Examples of monocot plants that can be used include, but are not limited to, corn (*Zea mays*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), wheat (*Triticum aestivum*), sugarcane (*Saccharum* spp.), oats (*Avena*), barley (*Hordeum*), switchgrass (*Panicum virgatum*), pineapple (*Ananas comosus*), banana (*Musa* spp.), palm, ornamentals, turfgrasses, and other grasses. Examples of dicot plants that can be used include, but are not limited to, soybean (*Glycine max*), canola (*Brassica napus* and *B. campestris*), alfalfa (*Medicago sativa*), tobacco (*Nicotiana tabacum*), Arabidopsis (*Arabidopsis thaliana*), sunflower (*Helianthus annuus*), cotton (*Gossypium arboreum*), and peanut (*Arachis hypogaea*), tomato (*Solanum lycopersicum*), potato (*Solanum tuberosum*) etc.

The transgenes, recombinant DNA molecules, DNA sequences of interest, and polynucleotides of interest can comprise one or more genes of interest. Such genes of interest can encode, for example, a protein that provides agronomic advantage to the plant.

Marker Assisted Selection and Breeding of Plants

A primary motivation for development of molecular markers in crop species is the potential for increased efficiency in plant breeding through marker assisted selection (MAS). Genetic marker alleles, or alternatively, quantitative trait loci (QTL alleles, are used to identify plants that contain a desired genotype at one or more loci, and that are expected to transfer the desired genotype, along with a desired phenotype to their progeny. Genetic marker alleles (or QTL alleles) can be used to identify plants that contain a desired genotype at one locus, or at several unlinked or linked loci (e.g., a haplotype), and that would be expected to transfer the desired genotype, along with a desired phenotype to their progeny. It will be appreciated that for the purposes of MAS, the term marker can encompass both marker and QTL loci.

After a desired phenotype and a polymorphic chromosomal locus, e.g., a marker locus or QTL, are determined to segregate together, it is possible to use those polymorphic loci to select for alleles corresponding to the desired phenotype—a process called marker-assisted selection (MAS). In brief, a nucleic acid corresponding to the marker nucleic acid is detected in a biological sample from a plant to be selected. This detection can take the form of hybridization of a probe nucleic acid to a marker, e.g., using allele-specific hybridization, southern blot analysis, northern blot analysis, in situ hybridization, hybridization of primers followed by PCR amplification of a region of the marker or the like. A variety of procedures for detecting markers are well known in the art. After the presence (or absence) of a particular marker in the biological sample is verified, the plant is selected, i.e., used to make progeny plants by selective breeding.

Plant breeders need to combine traits of interest with genes for high yield and other desirable traits to develop improved plant varieties. Screening for large numbers of samples can be expensive, time consuming, and unreliable. Use of markers, and/or genetically-linked nucleic acids is an effective method for selecting plant having the desired traits in breeding programs. For example, one advantage of marker-assisted selection over field evaluations is that MAS can be done at any time of year regardless of the growing season. Moreover, environmental effects are irrelevant to marker-assisted selection.

When a population is segregating for multiple loci affecting one or multiple traits, the efficiency of MAS compared to phenotypic screening becomes even greater because all the loci can be processed in the lab together from a single sample of DNA.

The DNA repair mechanisms of cells are the basis to introduce extraneous DNA or induce mutations on endogenous genes. DNA homologous recombination is a specialized way of DNA repair that the cells repair DNA damages using a homologous sequence. In plants, DNA homologous recombination happens at frequencies too low to be routinely used in gene targeting or gene editing until it has been found that the process can be stimulated by DNA double-strand breaks (Bibikova et al., (2001) *Mol. Cell Biol.* 21:289-297; Puchta and Baltimore, (2003) *Science* 300:763; Wright et al., (2005) *Plant J.* 44:693-705).

The meaning of abbreviations is as follows: "sec" means second(s), "min" means minute(s), "h" means hour(s), "d" means day(s), "µL" means microliter(s), "m L" means milliliter(s), "L" means liter(s), "µM" means micromolar, "mM" means millimolar, "M" means molar, "mmol" means millimole(s), "µmole" mean micromole(s), "g" means gram(s), "pg" means microgram(s), "ng" means nanogram(s), "U" means unit(s), "bp" means base pair(s) and "kb" means kilobase(s).

Also, as described herein, for each example or embodiment that cites a guide RNA, a similar guide polynucleotide can be designed wherein the guide polynucleotide does not solely comprise ribonucleic acids but wherein the guide polynucleotide comprises a combination of RNA-DNA molecules or solely comprises DNA molecules.

Non-limiting examples of compositions and methods disclosed herein are as follows:

1. A method for producing a genetic modification into a second gene of a plant genome without introducing an exogenous selectable marker into said plant genome, the method comprising providing a first guide polynucleotide, a polynucleotide modification template, a second guide polynucleotide, and a Cas endonuclease to a plant cell comprising a first endogenous gene that can be modified to confer herbicide resistance, wherein said first guide polynucleotide and Cas endonuclease are capable of forming a first complex that enables the Cas endonuclease to introduce a double strand break at a first target site, located in or near said first endogenous gene in the genome of said plant cell, wherein said second guide polynucleotide and Cas endonuclease are capable of forming a second complex that enables the Cas endonuclease to introduce a double strand break at a second target site in the genome of said plant cell, wherein said polynucleotide modification template comprises at least one nucleotide alteration when compared to the first endogenous gene.
2. The method of embodiment 1, wherein said at least one nucleotide alteration encodes for an amino acid change in first endogenous gene.
3. The method of embodiment 1, wherein said first endogenous gene is modified to confer herbicide resistance to a plant cell.
4. The method of embodiment 1, wherein said first endogenous gene is selected from the group consisting of an acetolactate synthase (ALS) and an enolpyruvylshikimate-3-phosphate synthase (EPSPS) gene.
5. The method of embodiment 1, wherein the first target site and the second target site are located at two different genomic loci.
6. The method of embodiment 4, wherein the endogenous ALS gene is modified to confer sulfonylurea resistance.
7. The method of embodiment 4, wherein the endogenous EPSPS gene is modified to confer glyphosate resistance.
8. The method of embodiment 1, wherein Cas endonuclease is a Cas9 endonuclease
9. The method of embodiment 1, further comprising selecting at least one plant cell that has resistance to an herbicide and comprises a modification into said second gene, wherein said modification includes at least one deletion, insertion or substitution of one or more nucleotides in said second gene of the plant genome.
10. The method of embodiment 9, wherein said herbicide is a sulphonylurea, such as chlorsulfuron or an imidazolinone herbicide.
11. The method of embodiment 9, wherein said modification into said second gene includes at least one deletion, insertion, or substitution of one or more nucleotides in a FAD2-1 gene.
12. A plant grown or cultured from the plant cell of embodiment 9, a seed thereof, or progeny thereof
13. The plant of embodiment 12, wherein the plant is a monocot or a dicot.
14. The plant of embodiment 13, wherein the monocot is selected from the group consisting of maize, rice, sorghum, rye, barley, wheat, millet, oats, sugarcane, turfgrass, or switchgrass.
15. The plant of embodiment 13, wherein the dicot is selected from the group consisting of soybean, canola, alfalfa, sunflower, cotton, tobacco, peanut, potato, tobacco, *Arabidopsis*, or safflower.
16. An herbicide resistant plant grown or cultured from the plant cell of embodiment 9, a seed thereof, or progeny thereof having herbicide resistance and a high oleic phenotype.
17. A method for introducing a polynucleotide of interest into a plant genome without introducing an exogenous selectable marker into said plant genome, the method comprising providing a first guide RNA, a first polynucleotide modification template, a second guide RNA, a second polynucleotide modification template, and a Cas endonuclease to a plant cell comprising a first endogenous gene that can be modified to confer herbicide resistance, wherein said first guide RNA and Cas endonuclease are capable of forming a first complex that enables the Cas endonuclease to introduce a double strand break at a first target site located in or near said first endogenous gene in the genome of said plant cell, wherein said first polynucleotide modification template comprises at least one nucleotide modification of said first endogenous gene to render said endogenous gene capable of conferring herbicide resistance to a plant cell, wherein said second guide RNA and Cas endonuclease are capable of forming a second complex that enables the Cas endonuclease to introduce a double strand break at a second target site in the genome of said plant cell, wherein said second polynucleotide modification template comprises at least one polynucleotide of interest to be introduced into said plant genome.
18. The method of embodiment 17, wherein the first target site and the second target site are located at two different genomic loci.
19. The method of embodiment 17, wherein said first endogenous gene is selected from the group consisting of a plant acetolactate synthase (ALS) and a plant enolpyruvylshikimate-3-phosphate synthase (EPSPS) gene.
20. The method of embodiment 17, wherein the endogenous ALS gene is modified to confer sulfonylurea resistance.
21. The method of embodiment 17, wherein the endogenous EPSPS gene is modified to confer glyphosate resistance.
22. The method of embodiment 17, wherein Cas endonuclease is a Cas9 endonuclease
23. The method of embodiment 17, further comprising selecting at least one plant cell that has resistance to an herbicide and comprises said at least one polynucleotide of interest in said plant genome.
24. The method of embodiment 17, wherein the at least one polynucleotide of interest is selected from the group consisting of herbicide-tolerance coding sequences, insecticidal coding sequences, nematicidal coding sequences, antimicrobial coding sequences, antifungal coding sequences, antiviral coding sequences, abiotic and biotic stress tolerance coding sequences, or sequences modifying plant traits such as yield, grain quality, nutrient content, starch quality and quantity, nitrogen fixation and/or utilization, and oil content and/or composition.
25. The method of embodiment 23, wherein said herbicide is a sulphonylurea, such as chlorsulfuron or an imidazolinone herbicide.

26. A plant grown or cultured from the plant cell of embodiment 23, a seed thereof, or progeny thereof
27. The plant of embodiment 26, wherein the plant is a monocot or a dicot.
28. An herbicide resistant plant grown or cultured from the plant cell of embodiment 23, a seed thereof, or progeny thereof having herbicide resistance and stably inherited the at least one polynucleotide of interest in said plant genome.
29. A method for editing a second gene of a plant genome without introducing an exogenous selectable marker into said plant genome, the method comprising providing a first guide RNA, a first polynucleotide modification template, a second guide RNA, a second polynucleotide modification template, and a Cas endonuclease to a plant cell comprising a first endogenous gene that can be modified to confer herbicide resistance, wherein said first guide RNA and Cas endonuclease are capable of forming a complex that enables the Cas endonuclease to introduce a double strand break at a first target site (located in or near said first endogenous gene) in the genome of said plant cell, wherein said first polynucleotide modification template comprises at least one nucleotide modification of said first endogenous gene to render said endogenous gene capable of conferring herbicide resistance to a plant cell, wherein said second guide RNA and Cas endonuclease are capable of forming a complex that enables the Cas endonuclease to introduce a double strand break at a second target site (located at a different locus than said first endogenous gene) in the genome of said plant cell, wherein said second polynucleotide modification template comprises at least one nucleotide alteration when compared to the second gene to be edited.
30. The method of embodiment 29, wherein said first endogenous gene is an acetolactate synthase (ALS) gene.
31. The method of embodiment 29, wherein the endogenous ALS gene is modified to confer sulfonylurea resistance.
32. The method of embodiment 29, wherein the second gene is an EPSPS gene modified to confer glyphosate resistance.
33. The method of embodiment 29, wherein Cas endonuclease is a Cas9 endonuclease
34. The method of embodiment 29, further comprising selecting at least one plant cell that has resistance to an herbicide and comprises a modified EPSPS gene that confers glyphosate resistance.
35. The method of embodiment 34, wherein said herbicide is a sulphonylurea, such as chlorsulfuron or an imidazolinone herbicide.
36. A plant grown or cultured from the plant cell of embodiment 34, a seed thereof, or progeny thereof
37. The plant of embodiment 36, wherein the plant is a monocot or a dicot.
38. A method of generating a glyphosate resistant soybean plant without introducing an exogenous selectable marker into said plant genome the method comprising providing a maize plant cell wherein its endogenous chromosomal ALS gene and endogenous chromosomal EPSPS gene have been modified through a guide RNA/Cas endonuclease system to produce a glyphosate resistant EPSPS protein and growing a maize plant from said maize plant cell, wherein said plant is resistant to glyphosate.

EXAMPLES

In the following Examples, unless otherwise stated, parts and percentages are by weight and degrees are Celsius. It should be understood that these Examples, while indicating embodiments of the disclosure, are given by way of illustration only. From the above discussion and these Examples, one skilled in the art can make various changes and modifications of the disclosure to adapt it to various usages and conditions. Such modifications are also intended to fall within the scope of the appended claims.

Example 1

Maize Optimized Expression Cassettes for Guide RNA/Cas Endonuclease Based Genome Modification in Maize Plants For genome engineering applications, the type II CRISPR/Cas system minimally requires the Cas9 protein and a duplexed crRNA/tracrRNA molecule or a synthetically fused crRNA and tracrRNA (guide RNA) molecule for DNA target site recognition and cleavage (Gasiunas et al. (2012) *Proc. Natl. Acad. Sci. USA* 109:E2579-86, Jinek et al. (2012) *Science* 337:816-21, Mali et al. (2013) *Science* 339:823-26, and Cong et al. (2013) *Science* 339:819-23). Described herein is a guideRNA/Cas endonuclease system that is based on the type II CRISPR/Cas system and consists of a Cas endonuclease and a guide RNA (or duplexed crRNA and tracrRNA) that together can form a complex that recognizes a genomic target site in a plant and introduces a double-strand-break into said target site.

To test the guide RNA/Cas endonuclease system in maize, the Cas9 gene from *Streptococcus pyogenes* M1 GAS (SF370) (SEQ ID NO: 1) was maize codon optimized per standard techniques known in the art and the potato ST-LS1 intron (SEQ ID NO: 2) was introduced in order to eliminate its expression in *E. coli* and *Agrobacterium* (FIG. 1 A). To facilitate nuclear localization of the Cas9 protein in maize cells, Simian virus 40 (SV40) monopartite amino terminal nuclear localization signal (MAPKKKRKV, SEQ ID NO: 3) and *Agrobacterium tumefaciens* bipartite VirD2 T-DNA border endonuclease carboxyl terminal nuclear localization signal (KRPRDRHDGELGGRKRAR, SEQ ID NO: 4) were incorporated at the amino and carboxyl-termini of the Cas9 open reading frame (FIG. 1 A), respectively. The maize optimized Cas9 gene was operably linked to a maize constitutive or regulated promoter by standard molecular biological techniques. An example of the maize optimized Cas9 expression cassette (SEQ ID NO: 5) is illustrated in FIG. 1 A. FIG. 1A shows a maize optimized Cas9 gene containing the ST-LS1 intron, SV40 amino terminal nuclear localization signal (NLS) and VirD2 carboxyl terminal NLS driven by a plant Ubiquitin promoter.

The second component necessary to form a functional guide RNA/Cas endonuclease system for genome engineering applications is a duplex of the crRNA and tracrRNA molecules or a synthetic fusing of the crRNA and tracrRNA molecules, a guide RNA. To confer efficient guide RNA expression (or expression of the duplexed crRNA and tracrRNA) in maize, the maize U6 polymerase III promoter (SEQ ID NO: 9) and maize U6 polymerase III terminator (first 8 bases of SEQ ID NO: 10) residing on chromosome 8 were isolated and operably fused to the termini of a guide RNA (FIG. 1 B) using standard molecular biology techniques. Two different guide RNA configurations were developed for testing in maize, a short guide RNA (SEQ ID NO: 11) based on Jinek et al. (2012) *Science* 337:816-21 and a long guide RNA (SEQ ID NO: 8) based on Mali et al. (2013) *Science* 339:823-26. An example expression cassette (SEQ ID NO: 12) is shown in FIG. 1 B which illustrates a maize U6 polymerase III promoter driving expression of a long guide RNA terminated with a U6 polymerase III terminator.

As shown in FIGS. 2A and 2B, the guide RNA or crRNA molecule contains a region complementary to one strand of the double strand DNA target (referred to as the variable targeting domain) that is approximately 12-30 nucleotides in length and upstream of a PAM sequence (5'NGG3' on antisense strand of FIG. 2A-2B, corresponding to 5'CCN3' on sense strand of FIG. 2A-2B) for target site recognition and cleavage (Gasiunas et al. (2012) *Proc. Natl. Acad. Sci. USA* 109:E2579-86, Jinek et al. (2012) *Science* 337:816-21, Mali et al. (2013) *Science* 339:823-26, and Cong et al. (2013) *Science* 339:819-23). To facilitate the rapid introduction of maize genomic DNA target sequences into the crRNA or guide RNA expression constructs, two Type IIS BbsI restriction endonuclease target sites were introduced in an inverted tandem orientation with cleavage orientated in an outward direction as described in Cong et al. (2013) *Science* 339:819-23. Upon cleavage, the Type IIS restriction endonuclease excises its target sites from the crRNA or guide RNA expression plasmid, generating overhangs allowing for the in-frame directional cloning of duplexed oligos containing the desired maize genomic DNA target site into the variable targeting domain. In this example, only target sequences starting with a G nucleotide were used to promote favorable polymerase III expression of the guide RNA or crRNA.

Expression of both the Cas endonuclease gene and the guide RNA then allows for the formation of the guide RNA/Cas complex depicted in FIG. 2 B (SEQ ID NO: 8). Alternatively, expression of the Cas endonucleases gene, crRNA, and tracrRNA allow for the formation of the crRNA/tracrRNA/Cas complex as depicted in FIG. 2 A, (SEQ ID NOs: 6-7).

Example 2

The Guide RNA/Cas Endonuclease System Cleaves Chromosomal DNA in Maize and Introduces Mutations by Imperfect Non-Homologous End-Joining To test whether the maize optimized guide RNA/Cas endonuclease described in example 1 could recognize, cleave, and mutate maize chromosomal DNA through imprecise non-homologous end-joining (NHEJ) repair pathways, three different genomic target sequences in 5 maize loci were targeted for cleavage (see Table 1) and examined by deep sequencing for the presence of NHEJ mutations.

TABLE 1

Maize genomic target sites targeted by a guideRNA/Cas endonuclease system.

| Locus | Location | Guide RNA Used | Target Site Designation | Maize Genomic Target Site Sequence | PAM Sequence | SEQ ID NO: |
|---|---|---|---|---|---|---|
| MS26 | Chr. 1: 51.81cM | Long | MS26Cas-1 | GTACTCCATCCGCCCCATCGAGTA | GGG | 13 |
|  |  | Long | MS26Cas-2 | GCACGTACGTCACCATCCCGC | CGG | 14 |
|  |  | Long | MS26Cas-3 | GACGTACGTGCCCTACTCGAT | GGG | 15 |
| LIG | Chr. 2: 28.45cM | Long | LIGCas-1 | GTACCGTACGTGCCCCGGCGG | AGG | 16 |
|  |  | Long | LIGCas-2 | GGAATTGTACCGTACGTGCCC | CGG | 17 |
|  |  | Long | LIGCas-3 | GCGTACGCGTACGTGTG | AGG | 18 |
| MS45 | Chr. 9: 119.15cM | Long | MS45Cas-1 | GCTGGCCGAGGTCGACTAC | CGG | 19 |
|  |  | Long | MS45Cas-2 | GGCCGAGGTCGACTACCGGC | CGG | 20 |
|  |  | Long | MS45Cas-3 | GGCGCGAGCTCGTGCTTCAC | CGG | 21 |
| ALS | Chr. 4: 107.73cM and Chr. 5: 115.49cM | Long | ALSCas-1 | GGTGCCAATCATGCGTCG | CGG | 22 |
|  |  | Long | ALSCas-2 | GGTCGCCATCACGGGAC | AGG | 23 |
|  |  | Long | ALSCas-3 | GTCGCGGCACCTGTCCCGTGA | TGG | 24 |
| EPSPS | Chr. 9: 69.43cM | Long | EPSPSCas-1 | GGAATGCTGGAACTGCAATG | CGG | 25 |
|  |  | Long | EPSPSCas-2 | GCAGCTCTTCTTGGGGAATGC | TGG | 26 |
|  |  | Long | EPSPSCas-3 | GCAGTAACAGCTGCTGTCAA | TGG | 27 |

MS26 = Male Sterility Gene 26,
LIG = Liguleless 1 Gene Promoter,
MS45 = Male Sterility Gene 45,
ALS = Acetolactate Synthase Gene,
EPSPS = Enolpyruvylshikimate Phosphate Synthase Gene The maize optimized Cas9 endonuclease and long guide RNA expression cassettes containing the specific maize variable targeting domains were co-delivered to 60-90 Hi-II immature maize embryos by particle-mediated delivery (see Example 10) in the presence of BBM and WUS2 genes (see Example 11). Hi-II maize embryos transformed with either the LIG3-4 or MS26++ homing endonucleases (see Example 9) targeting the same maize genomic loci as the LIGCas or MS26Cas target sites served as a positive control and embryos transformed with only the Cas9 or guide RNA expression cassette served as negative controls. After 7 days, the 20-30 most uniformly transformed embryos from each treatment were pooled and total genomic DNA was extracted. The region surrounding the intended target site was PCR amplified with Phusion® High Fidelity PCR Master Mix (New England Biolabs, M0531L) adding on the sequences necessary for amplicon-specific barcodes and Illumnia sequencing using "tailed" primers through two rounds of PCR. The primers used in the primary PCR reaction are shown in Table 2 and the primers used in the secondary PCR reaction were AATGATACGGCGAC-CACCGAGATCTACACTCTTTCCCTACACG (forward, SEQ ID NO: 53) and CAAGCAGAAGACGGCATA (reverse, SEQ ID NO: 54).

TABLE 2

PCR primer sequences

| Target Site | Primer Orientation | Primary PCR Primer Sequence | SEQ ID NO: |
|---|---|---|---|
| MS26Cas-1 | Forward | CTACACTCTTTCCCTACACGACGCTCTTCCGATCTAGGACCGGAAGCTCGCCGCGT | 28 |
| MS26Cas-1 | Reverse | CAAGCAGAAGACGGCATACGAGCTCTTCCGATCTTCCTGGAGGACGACGTGCTG | 29 |
| MS26Cas-2 | Forward | CTACACTCTTTCCCTACACGACGCTCTTCCGATCTAAGGTCCTGGAGGACGACGTGCTG | 30 |
| MS26Cas-2 | Reverse | CAAGCAGAAGACGGCATACGAGCTCTTCCGATCTCCGGAAGCTCGCCGCGT | 31 |
| MS26Cas-3 | Forward | CTACACTCTTTCCCTACACGACGCTCTTCCGATCTTCCTCCGGAAGCTCGCCGCGT | 32 |
| MS26Cas-3 | Reverse | CAAGCAGAAGACGGCATACGAGCTCTTCCGATCTTCCTGGAGGACGACGTGCTG | 29 |
| MS26 Meganuclease | Forward | CTACACTCTTTCCCTACACGACGCTCTTCCGATCTTTCCTCCTGGAGGACGACGTGCTG | 33 |
| MS26 Meganuclease | Reverse | CAAGCAGAAGACGGCATACGAGCTCTTCCGATCTCCGGAAGCTCGCCGCGT | 31 |
| LIGCas-1 | Forward | CTACACTCTTTCCCTACACGACGCTCTTCCGATCTAGGACTGTAACGATTTACGCACCTGCTG | 34 |
| LIGCas-1 | Reverse | CAAGCAGAAGACGGCATACGAGCTCTTCCGATCTGCAAATGAGTAGCAGCGCACGTAT | 35 |
| LIGCas-2 | Forward | CTACACTCTTTCCCTACACGACGCTCTTCCGATCTTCCTCTGTAACGATTTACGCACCTGCTG | 36 |
| LIGCas-2 | Reverse | CAAGCAGAAGACGGCATACGAGCTCTTCCGATCTGCAAATGAGTAGCAGCGCACGTAT | 35 |
| LIGCas-3 | Forward | CTACACTCTTTCCCTACACGACGCTCTTCCGATCTAAGGCGCAAATGAGTAGCAGCGCAC | 37 |
| LIGCas-3 | Reverse | CAAGCAGAAGACGGCATACGAGCTCTTCCGATCTCACCTGCTGGGAATTGTACCGTA | 38 |
| LIG3-4 Meganuclease | Forward | CTACACTCTTTCCCTACACGACGCTCTTCCGATCTCCTTCGCAAATGAGTAGCAGCGCAC | 39 |
| LIG3-4 Meganuclease | Reverse | CAAGCAGAAGACGGCATACGAGCTCTTCCGATCTCACCTGCTGGGAATTGTACCGTA | 38 |
| MS45Cas-1 | Forward | CTACACTCTTTCCCTACACGACGCTCTTCCGATCTAGGAGGACCCGTTCGGCCTCAGT | 40 |
| MS45Cas-1 | Reverse | CAAGCAGAAGACGGCATACGAGCTCTTCCGATCTGCCGGCTGGCATTGTCTCTG | 41 |
| MS45Cas-2 | Forward | CTACACTCTTTCCCTACACGACGCTCTTCCGATCTTCCTGGACCCGTTCGGCCTCAGT | 42 |
| MS45Cas-2 | Reverse | CAAGCAGAAGACGGCATACGAGCTCTTCCGATCTGCCGGCTGGCATTGTCTCTG | 41 |
| MS45Cas-3 | Forward | CTACACTCTTTCCCTACACGACGCTCTTCCGATCTGAAGGGACCCGTTCGGCCTCAGT | 43 |
| MS45Cas-3 | Reverse | CAAGCAGAAGACGGCATACGAGCTCTTCCGATCTGCCGGCTGGCATTGTCTCTG | 41 |
| ALSCas-1 | Forward | CTACACTCTTTCCCTACACGACGCTCTTCCGATCTAAGGCGACGATGGGCGTCTCCTG | 44 |

TABLE 2-continued

PCR primer sequences

| Target Site | Primer Orientation | Primary PCR Primer Sequence | SEQ ID NO: |
|---|---|---|---|
| ALSCas-1 | Reverse | CAAGCAGAAGACGGCATACGAGCTCTTCCGATCTGCGTCTGCATCGCCACCTC | 45 |
| ALSCas-2 | Forward | CTACACTCTTTCCCTACACGACGCTCTTCCGATCTTTCCCGACGATGGGCGTCTCCTG | 46 |
| ALSCas-2 | Reverse | CAAGCAGAAGACGGCATACGAGCTCTTCCGATCTGCGTCTGCATCGCCACCTC | 45 |
| ALSCas-3 | Forward | CTACACTCTTTCCCTACACGACGCTCTTCCGATCTGGAACGACGATGGGCGTCTCCTG | 47 |
| ALSCas-3 | Reverse | CAAGCAGAAGACGGCATACGAGCTCTTCCGATCTGCGTCTGCATCGCCACCTC | 45 |
| EPSPSCas-1 | Forward | CTACACTCTTTCCCTACACGACGCTCTTCCGATCTGGAAGAGGAAACATACGTTGCATTTCCA | 48 |
| EPSPSCas-1 | Reverse | CAAGCAGAAGACGGCATACGAGCTCTTCCGATCTGGTGGAAAGTTCCCAGTTGAGGA | 49 |
| EPSPSCas-2 | Forward | CTACACTCTTTCCCTACACGACGCTCTTCCGATCTAAGCGGTGGAAAGTTCCCAGTTGAGGA | 50 |
| EPSPSCas-2 | Reverse | CAAGCAGAAGACGGCATACGAGCTCTTCCGATCTGAGGAAACATACGTTGCATTTCCA | 51 |
| EPSPSCas-3 | Forward | CTACACTCTTTCCCTACACGACGCTCTTCCGATCTCCTTGAGGAAACATACGTTGCATTTCCA | 52 |
| EPSPSCas-3 | Reverse | CAAGCAGAAGACGGCATACGAGCTCTTCCGATCTGGTGGAAAGTTCCCAGTTGAGGA | 49 |

The resulting PCR amplifications were purified with a Qiagen PCR purification spin column, concentration measured with a Hoechst dye-based fluorometric assay, combined in an equimolar ratio, and single read 100 nucleotide-length deep sequencing was performed on Illumina's MiSeq Personal Sequencer with a 30-40% (v/v) spike of PhiX control v3 (Illumina, FC-110-3001) to off-set sequence bias. Only those reads with a ≥1 nucleotide indel arising within the 10 nucleotide window centered over the expected site of cleavage and not found in a similar level in the negative control were classified as NHEJ mutations. NHEJ mutant reads with the same mutation were counted and collapsed into a single read and the top 10 most prevalent mutations were visually confirmed as arising within the expected site of cleavage. The total numbers of visually confirmed NHEJ mutations were then used to calculate the % mutant reads based on the total number of reads of an appropriate length containing a perfect match to the barcode and forward primer.

The frequency of NHEJ mutations recovered by deep sequencing for the guide RNA/Cas endonuclease system targeting the three LIGCas targets (SEQ ID NOS: 16, 17, 18) compared to the LIG3-4 homing endonuclease targeting the same locus is shown in Table 3. The ten most prevalent types of NHEJ mutations recovered based on the guide RNA/Cas endonuclease system compared to the LIG3-4 homing endonuclease are shown in FIG. 3 A (corresponding to SEQ ID NOs: 55-75) and FIG. 3 B (corresponding to SEQ ID NOs: 76-96). Approximately, 12-23 fold higher frequencies of NHEJ mutations were observed when using a guide RNA/Cas system to introduce a double strand break at a maize genomic target site (Cas target sites), relative to the LIG3-4 homing endonuclease control. As shown in Table 4, a similar difference between the guide RNA/Cas system and meganuclease double-strand break technologies was observed at the MS26 locus with approximately 14-25 fold higher frequencies of NHEJ mutations when a guide RNA/Cas endonuclease system was used. High frequencies of NHEJ mutations were also recovered at the MS45, ALS and EPSPS Cas targets (see Table 5) when using a guide RNA/Cas endonuclease system. This data indicates that the guide RNA/Cas9 endonuclease system described herein can be effectively used to introduce an alteration at genomic sites of interest such as those related to male fertility, wherein an alteration results in the creation of a male sterile gene locus and male sterile plants. Altering the EPSPS target can result in the production of plants that are tolerant and/or resistant against glyphosate based herbicides. Altering the acetolactate synthase (ALS) gene target site can result in the production of plants that are tolerant and/or resistant to imidazolinone and sulphonylurea herbicides.

TABLE 3

Percent (%) mutant reads at maize Liguleless 1 target locus produced by a guide RNA/Cas system versus a homing endonuclease system.

| System | Total Number of Reads | Number of Mutant Reads | % Mutant Reads |
|---|---|---|---|
| Cas9 Only Control | 640,063 | 1 | 0.00% |
| guide RNA Only Control | 646,774 | 1 | 0.00% |
| LIG3-4 Homing Endonuclease | 616,536 | 1,211 | 0.20% |

TABLE 3-continued

Percent (%) mutant reads at maize Liguleless 1 target locus produced by a guide RNA/Cas system versus a homing endonuclease system.

| System | Total Number of Reads | Number of Mutant Reads | % Mutant Reads |
|---|---|---|---|
| LIGCas-1 guide/Cas9 | 716,854 | 33,050 | 4.61% |
| LIGCas-2 guide/Cas9 | 711,047 | 16,675 | 2.35% |
| LIGCas-3 guide/Cas9 | 713,183 | 27,959 | 3.92% |

TABLE 4

Percent (%) mutant reads at maize Male Sterility 26 target locus produced by a guide RNA/Cas system versus a homing endonuclease.

| System | Total Number of Reads | Number of Mutant Reads | % Mutant Reads |
|---|---|---|---|
| Cas9 Only Control | 403,123 | 15 | 0.00% |
| MS26++ Homing Endonuclease | 512,784 | 642 | 0.13% |
| MS26Cas-1 guide/Cas9 | 575,671 | 10,073 | 1.75% |
| MS26Cas-2 guide/Cas9 | 543,856 | 16,930 | 3.11% |
| MS26Cas-3 guide/Cas9 | 538,141 | 13,879 | 2.58% |

TABLE 5

Percent (%) mutant reads at maize Male Sterility 45, Acetolactate Synthase and Enolpyruvylshikimate Phosphate Synthase target loci produced by the guide RNA/Cas system.

| System | Total Number of Reads | Number of Mutant Reads | % Mutant Reads |
|---|---|---|---|
| Cas9 Only Control (MS45) | 899,500 | 27 | 0.00% |
| MS45Cas-1 guide/Cas9 | 812,644 | 3,795 | 0.47% |
| MS45Cas-2 guide/Cas9 | 785,183 | 14,704 | 1.87% |
| MS45Cas-3 guide/Cas9 | 728,023 | 9,203 | 1.26% |
| Cas9 Only Control (ALS) | 534,764 | 19 | 0.00% |
| ALSCas-1 guide/Cas9 | 434,452 | 9,669 | 2.23% |
| ALSCas-2 guide/Cas9 | 472,351 | 6,352 | 1.345% |
| ALSCas-3 guide/Cas9 | 497,786 | 8,535 | 1.715% |
| Cas9 Only Control (EPSPS) | 1,347,086 | 6 | 0.00% |
| EPSPSCas-1 guide/Cas9 | 1,420,274 | 13,051 | 0.92% |
| EPSPSCas-2 guide/Cas9 | 1,225,082 | 26,340 | 2.15% |
| EPSPSCas-3 guide/Cas9 | 1,406,905 | 53,603 | 3.81% |

Taken together, our data indicate that the maize optimized guide RNA/Cas endonuclease system described herein using a long guide RNA expression cassette efficiently cleaves maize chromosomal DNA and generates imperfect NHEJ mutations at frequencies greater than the engineered LIG3-4 and MS26++ homing endonucleases.

Example 3

Long Guide RNA of the Maize Optimized Guide RNA/Cas Endonuclease System Cleaves Maize Chromosomal DNA More Efficiently than the Short Guide RNA To determine the most effective guide RNA (comprising a fusion of the crRNA and tracrRNA) for use in maize, the recovery of NHEJ mutations using a short guide RNA (SEQ ID NO: 11) based on Jinek et al. (2012) Science 337:816-21 and a long guide RNA (SEQ ID NO: 8) based on Mali et al. (2013) Science 339:823-26 was examined.

The variable targeting domains of the guide RNA targeting the maize genomic target sites at the LIG locus (LIGCas-1, LIGCas-2 and LIGCas-3, SEQ ID NOs: 16, 17 and 18, Table1) were introduced into both the maize optimized long and short guide RNA expression cassettes as described in Example 1 and co-transformed along with the maize optimized Cas9 endonuclease expression cassette into immature maize embryos and deep sequenced for NHEJ mutations as described in Example 2. Embryos transformed with only the Cas9 endonuclease expression cassette served as a negative control.

As shown in Table 6 below, the frequency of NHEJ mutations recovered with the long guide RNA far exceeded those obtained with the short guide RNA. This data indicates that the long guide RNA paired with the maize optimized Cas9 endonuclease gene described herein more efficiently cleaves maize chromosomal DNA.

TABLE 6

Percent (%) mutant reads at the maize Liguleless 1 target locus produced by a guide RNA/Cas system with a long versus a short guide RNA.

| System | guide RNA Used | Total Number of Reads | Number of Mutant Reads | % Mutant Reads |
|---|---|---|---|---|
| Cas9 Only | N/A | 640,063 | 1 | 0.00% |
| LIGCas-1 guide/Cas9 | Short | 676,870 | 43 | 0.01% |
| LIGCas-2 guide/Cas9 | Short | 747,945 | 91 | 0.01% |
| LIGCas-3 guide/Cas9 | Short | 655,157 | 10 | 0.00% |
| LIGCas-1 guide/Cas9 | Long | 716,854 | 33,050 | 4.61% |
| LIGCas-2 guide/cas9 | Long | 711,047 | 16,675 | 2.35% |
| LIGCas-3 guide/Cas9 | Long | 713,183 | 27,959 | 3.92% |

Example 4

The Guide RNA/Cas Endonuclease System May be Multiplexed to Simultaneously Target Multiple Chromosomal Loci in Maize for Mutagenesis by Imperfect Non-Homologous End-Joining To test if multiple chromosomal loci may be simultaneously mutagenized with the guide RNA/maize optimized Cas endonuclease system described herein, the long guide RNA expression cassettes targeting the MS26Cas-2 target site (SEQ ID NO: 14), the LIGCas-3 target site (SEQ ID NO: 18) and the MS45Cas-2 target site (SEQ ID NO: 20), were co-transformed into maize embryos either in duplex or in triplex along with the Cas9 endonuclease expression cassette and examined by deep sequencing for the presence of imprecise NHEJ mutations as described in Example 2.

Hi-II maize embryos co-transformed with the Cas9 expression cassette and the corresponding guide RNA expression cassette singly served as a positive control and embryos transformed with only the Cas9 expression cassette served as a negative control.

As shown in Table 7 below, mutations resulting from imprecise NHEJ were recovered at all relevant loci when multiple guide RNA expression cassettes were simultaneously introduced either in duplex or triplex with frequencies of mutant reads near those of the positive control. Thus, demonstrating that the maize optimized guide RNA/Cas endonuclease system described herein may be used to simultaneously introduce imprecise NHEJ mutations at multiple loci in maize.

TABLE 7

Percent (%) mutant reads at maize target loci produced by a multiplexed guide RNA/Cas system.

| Target Site Examined for NHEJ Mutations | guide RNAs Co-transformed Individually, in Duplex, or in Triplex with Cas9 | Total Number of Reads | Number of Mutant Reads | % Mutant Reads |
|---|---|---|---|---|
| LIGCas-3, MS26Cas-2, MS45Cas-2 | None (Cas9 Only control) | 527,691 | 9 | 0.00% |
| LIGCas-3 | LIGCas-3 | 645,107 | 12,631 | 1.96% |
| | LIGCas-3 MS26Cas-2 | 579,992 | 10,348 | 1.78% |
| | LIGCas-3 MS26Cas-2 MS45Cas-2 | 648,901 | 12,094 | 1.86% |
| MS26Cas-2 | MS26 Cas 2 | 699,154 | 17,247 | 2.47% |
| | LIGCas-3 MS26Cas-2 | 717,158 | 10,256 | 1.43% |
| | MS26Cas-2 MS45Cas-2 | 613,431 | 9,931 | 1.62% |
| | LIGCas-3 MS26Cas-2 MS45Cas-2 | 471,890 | 7,311 | 1.55% |
| MS45Cas-2 | MS45Cas-2 | 503,423 | 10,034 | 1.99% |
| | MS26Cas-2 MS45Cas-2 | 480,178 | 8,008 | 1.67% |
| | LIGCas-3 MS26Cas-2 MS45Cas-2 | 416,711 | 7,190 | 1.73% |

Example 5

Guide RNA/Cas Endonuclease Mediated DNA Cleavage in Maize Chromosomal Loci can Stimulate Homologous Recombination Repair-Mediated Transgene Insertion To test the utility of the maize optimized guide RNA/Cas system described herein to cleave maize chromosomal loci and stimulate homologous recombination (HR) repair pathways to site-specifically insert a transgene, a HR repair DNA vector (also referred to as a donor DNA) (SEQ ID NO: 97) was constructed as illustrated in FIG. 4 using standard molecular biology techniques and co-transformed with a long guide RNA expression cassette, comprising a variable targeting domain corresponding to the LIGCas-3 genomic target site, and a Cas9 endonuclease expression cassette into immature maize embryos as described in Example 2.

Maize embryos co-transformed with the HR repair DNA vector and LIG3-4 homing endonuclease (see Example 9) targeting the same genomic target site as LIGCas-3 served as a positive control. Since successful delivery of the HR repair DNA vector confers bialaphos herbicide resistance, callus events containing putative HR-mediated transgenic insertions were selected by placing the callus on herbicide containing media. After selection, stable callus events were sampled, total genomic DNA extracted, and using the primer pairs shown in FIG. 5 (corresponding to SEQ ID NOs: 98-101), PCR amplification was carried out at both possible transgene genomic DNA junctions to identify putative HR-mediated transgenic insertions. The resulting amplifications were sequenced for confirmation.

Sequence confirmed PCR amplifications indicating site-specific transgene insertion for the guide RNA/Cas system were detected for 37 out of 384 stable transformants with 15 containing amplifications across both transgene genomic DNA junctions indicating near perfect site-specific transgene insertion. The LIG3-4 homing endonuclease positive control yielded PCR amplifications indicating site-specific transgene insertion for 3 out of 192 stable transformants with 1 containing amplifications across both transgene genomic DNA junctions. The data clearly demonstrates that maize chromosomal loci cleaved with the maize optimized guide RNA/Cas system described herein can be used to stimulate HR repair pathways to site-specifically insert transgenes at frequencies greater than the LIG3-4 homing endonuclease.

Example 6

Guide RNA/Cas Endonuclease System Transformed Together on a Single Vector Results in Greater Recovery of Imperfect Non-Homologous End-Joining Mutations To evaluate different delivery methods for the maize optimized guide RNA/Cas endonuclease system described herein, the recovery of NHEJ mutations when the guide RNA/Cas expression cassettes were either co-transformed as separate DNA vectors as in Examples 2, 3, 4 and 5 or transformed as a single vector DNA (comprising both guide RNA and Cas endonuclease expression cassettes, as shown in FIG. 1C) was examined.

The long guide RNA expression cassette for LIGCas-3 and the Cas9 expression cassette were consolidated onto a single vector DNA (FIG. 1 C, SEQ ID NO: 102) by standard molecular biology techniques and transformed into immature Hi-II maize embryos as described in Examples 10 and 11 by particle-mediated delivery. Hi-II embryos co-transformed with the Cas9 and LIGCas-3 long guide RNA expression cassettes served as a positive control while embryos transformed with only the Cas9 expression cassette served as a negative control. Deep sequencing for NHEJ mutations was performed as described in Example 2.

As shown in Table 8 below, the frequency of NHEJ mutations recovered when the Cas endonuclease and long guide RNA expression cassettes were delivered together as a single vector DNA was approximately 2-fold greater than that observed from the equivalent co-transformation experiment. This indicates that delivery of the guide RNA/Cas system expression cassettes together on a single vector DNA results in a greater recovery of imperfect non-homologous end-joining mutations.

TABLE 8

Percent (%) mutant reads at the maize Liguleless 1 target locus produced by a guide RNA/Cas system with Cas9 and guide RNA expression cassettes combined into one DNA vector versus two separate DNA vectors.

| System | Total Number of Reads | Number of Mutant Reads | % Mutant Reads |
|---|---|---|---|
| Cas9 Only Control | 1,519,162 | 97 | 0.01% |
| LIGCas-3 guide/Cas9 (Two vector DNAs) | 1,515,0607 | 36,346 | 2.40% |
| LIGCas-3 guide/Cas9 (Single vector DNA) | 1,860,031 | 105,854 | 5.69% |

Example 7

Delivery Methods for Plant Genome Editing Using the Guide RNA/Cas Endonuclease System This example describes methods to deliver or maintain and express the Cas9 endonuclease and guide RNA (or individual crRNA and tracrRNAs) into, or within plants, respectively, to enable directed DNA modification or gene insertion via homologous recombination. More specifically this example describes a variety of methods which include, but are not limited to, delivery of the Cas9 endonuclease as a DNA, RNA (5'-capped and polyadenylated) or protein molecule. In addition, the guide RNA may be delivered as a DNA or RNA molecule.

Shown in Example 2, a high mutation frequency was observed when Cas9 endonuclease and guide RNA were delivered as DNA vectors by biolistic transformation of immature corn embryos. Other embodiments of this disclosure can be to deliver the Cas9 endonuclease as a DNA, RNA or protein and the guide RNA as a DNA or RNA molecule or as a duplex crRNA/tracrRNA molecule as RNA or DNA or a combination. Various combinations of Cas9 endonuclease, guide RNA and crRNA/tracrRNA delivery methods can be, but are not limited to, the methods shown in Table 9.

TABLE 9

Various combinations of delivery of the cas9 endonuclease, guide RNA or cRNA + tracrRNA.

| combination | Components delivered. (Delivery method is shown between brackets) |
|---|---|
| 1 | Cas9 (DNA vector), guide RNA (DNA vector) |
| 2 | Cas9 (DNA vector), guide RNA (RNA) |
| 3 | Cas9 (RNA), guide RNA (DNA) |
| 4 | Cas9 (RNA), guide RNA (RNA) |
| 5 | Cas9 (Protein), guide RNA (DNA) |
| 6 | Cas9 (Protein), guide RNA (RNA) |
| 7 | Cas9 (DNA vector), crRNA (DNA), tracrRNA (DNA) |
| 8 | Cas9 (DNA vector), crRNA (RNA), tracrRNA (DNA) |
| 9 | Cas9 (DNA vector), crRNA (RNA), tracrRNA (RNA) |
| 10 | Cas9 (DNA vector) crRNA (DNA), tracrRNA (RNA) |
| 11 | Cas9 (RNA), crRNA (DNA), tracrRNA (DNA) |
| 12 | Cas9 (RNA), crRNA (RNA), tracrRNA (DNA) |
| 13 | Cas9 (RNA), crRNA (RNA), tracrRNA (RNA) |
| 14 | Cas9 (RNA), crRNA (DNA), tracrRNA (RNA) |
| 15 | Cas9 (Protein), crRNA (DNA), tracrRNA (DNA) |
| 16 | Cas9 (Protein), crRNA (RNA), tracrRNA (DNA) |
| 17 | Cas9 (Protein), crRNA (RNA), tracrRNA 18 (RNA) |
| 18 | Cas9 (Protein), crRNA (DNA), tracrRNA (RNA) |

Delivery of the Cas9 (as DNA vector) and guide RNA (as DNA vector) example (Table 9, combination1) can also be accomplished by co-delivering these DNA cassettes on a single or multiple *Agrobacterium* vectors and transforming plant tissues by *Agrobacterium* mediated transformation. In addition, a vector containing a constitutive, tissue-specific or conditionally regulated Cas9 gene can be first delivered to plant cells to allow for stable integration into the plant genome to establish a plant line that contains only the Cas9 gene in the plant genome. In this example, single or multiple guide RNAs, or single or multiple crRNA and a tracrRNA can be delivered as either DNA or RNA, or combination, to the plant line containing the genome-integrated version of the Cas9 gene for the purpose of generating mutations or promoting homologous recombination when HR repair DNA vectors for targeted integration are co-delivered with the guide RNAs. As extension of this example, plant line containing the genome-integrated version of the Cas9 gene and a tracrRNA as a DNA molecule can also be established. In this example single or multiple crRNA molecules can be delivered as RNA or DNA to promote the generation of mutations or to promote homologous recombination when HR repair DNA vectors for targeted integration are co-delivered with crRNA molecule(s) enabling the targeted mutagenesis or homologous recombination at single or multiple sites in the plant genome.

Example 8

Components of the Guide RNA/Cas Endonuclease System Delivered Directly as RNA in Plants This example illustrates the use of the methods as described in Table 9 configuration of Example 7 [Cas9 (DNA vector), guide RNA (RNA)] for modification or mutagenesis of chromosomal loci in plants. The maize optimized Cas9 endonuclease expression cassette described in Example 1 was co-delivered by particle gun as described in Example 2 along with single stranded RNA molecules (synthesized by Integrated DNA Technologies, Inc.) constituting a short guide RNA targeting the maize locus and sequence shown in Table 10. Embryos transformed with only the Cas9 expression cassette or short guide RNA molecules served as negative controls. Seven days post-bombardment, the immature embryos were harvested and analyzed by deep sequencing for NHEJ mutations as described in Example 2. Mutations not present in the negative controls were found at the site (FIG. 6, corresponding to SEQ ID NOs: 104-110). These mutations were similar to those found in Examples 2, 3, 4 and 6. This data indicates that component(s) of the maize optimized guide RNA/Cas endonuclease system described herein may be delivered directly as RNA.

TABLE 10

Maize genomic target site and location for short guide RNA delivered as RNA.

| Locus | Location | Guide RNA Used | Designation | Maize Target Site | PAM Sequence | SEQ ID NO |
|---|---|---|---|---|---|---|
| 55 | Chr. 1: 51.78 cM | Short | 55CasRNA-1 | TGGGCAGGTCTCACGACGGT | TGG | 103 |

Example 9

Creation of Rare Cutting Engineered Meganucleases

LIG3-4 Meganuclease and LIG3-4 Intended Recognition Sequence

An endogenous maize genomic target site comprising the LIG3-4 intended recognition sequence (SEQ ID NO: 111) was selected for design of a rare-cutting double-strand break inducing agent (SEQ ID NO: 112) as described in US patent publication 2009-0133152 A1 (published May 21, 2009). The LIG3-4 intended recognition sequence is a 22 bp polynucleotide having the following sequence: ATATACCT-CACACGTACGCGTA (SEQ ID NO: 111).

MS 26++Meganuclease

An endogenous maize genomic target site designated "TS-MS26" (SEQ ID NO: 113) was selected for design of a custom double-strand break inducing agent MS26++ as described in U.S. patent application Ser. No. 13/526,912 filed Jun. 19, 2012). The TS-MS26 target site is a 22 bp polynucleotide positioned 62 bps from the 5' end of the fifth exon of the maize MS26 gene and having the following sequence: gatggtgacqtac^gtgccctac (SEQ ID NO: 113). The double strand break site and overhang region is underlined, the enzyme cuts after C13, as indicated by the A. Plant optimized nucleotide sequences for an engineered endonuclease (SEQ ID NO: 114) encoding an engineered MS26++ endonuclease were designed to bind and make double-strand breaks at the selected TS-MS26 target site.

Example 10

Transformation of Maize Immature Embryos

Transformation can be accomplished by various methods known to be effective in plants, including particle-mediated delivery, *Agrobacterium*-mediated transformation, PEG-mediated delivery, and electroporation.

a. Particle-Mediated Delivery

Transformation of maize immature embryos using particle delivery is performed as follows. Media recipes follow below.

The ears are husked and surface sterilized in 30% Clorox bleach plus 0.5% Micro detergent for 20 minutes, and rinsed two times with sterile water. The immature embryos are isolated and placed embryo axis side down (scutellum side up), 25 embryos per plate, on 560Y medium for 4 hours and then aligned within the 2.5-cm target zone in preparation for bombardment. Alternatively, isolated embryos are placed on 560L (Initiation medium) and placed in the dark at temperatures ranging from 26° C. to 37° C. for 8 to 24 hours prior to placing on 560Y for 4 hours at 26° C. prior to bombardment as described above.

Plasmids containing the double strand brake inducing agent and donor DNA are constructed using standard molecular biology techniques and co-bombarded with plasmids containing the developmental genes ODP2 (AP2 domain transcription factor ODP2 (Ovule development protein 2); US20090328252 A1) and Wushel (US2011/0167516).

The plasmids and DNA of interest are precipitated onto 0.6 µm (average diameter) gold pellets using a water-soluble cationic lipid transfection reagent as follows. DNA solution is prepared on ice using 1 pg of plasmid DNA and optionally other constructs for co-bombardment such as 50 ng (0.5 µl) of each plasmid containing the developmental genes ODP2 (AP2 domain transcription factor ODP2 (Ovule development protein 2); US20090328252 A1) and Wushel. To the pre-mixed DNA, 20 µl of prepared gold particles (15 mg/ml) and 5 µl of the a water-soluble cationic lipid transfection reagent is added in water and mixed carefully. Gold particles are pelleted in a microfuge at 10,000 rpm for 1 min and supernatant is removed. The resulting pellet is carefully rinsed with 100 ml of 100% EtOH without resuspending the pellet and the EtOH rinse is carefully removed. 105 µl of 100% EtOH is added and the particles are resuspended by brief sonication. Then, 10 µl is spotted onto the center of each macrocarrier and allowed to dry about 2 minutes before bombardment.

Alternatively, the plasmids and DNA of interest are precipitated onto 1.1 µm (average diameter) tungsten pellets using a calcium chloride ($CaCl_2$) precipitation procedure by mixing 100 µl prepared tungsten particles in water, 10 µl (1 pg) DNA in Tris EDTA buffer (1 pg total DNA), 100 µl 2.5 M CaCl2, and 10 µl 0.1 M spermidine. Each reagent is added sequentially to the tungsten particle suspension, with mixing. The final mixture is sonicated briefly and allowed to incubate under constant vortexing for 10 minutes. After the precipitation period, the tubes are centrifuged briefly, liquid is removed, and the particles are washed with 500 ml 100% ethanol, followed by a 30 second centrifugation. Again, the liquid is removed, and 105 µl 100% ethanol is added to the final tungsten particle pellet. For particle gun bombardment, the tungsten/DNA particles are briefly sonicated. 10 µl of the tungsten/DNA particles is spotted onto the center of each macrocarrier, after which the spotted particles are allowed to dry about 2 minutes before bombardment.

The sample plates are bombarded at level #4 with a Biorad Helium Gun. All samples receive a single shot at 450 PSI, with a total of ten aliquots taken from each tube of prepared particles/DNA.

Following bombardment, the embryos are incubated on 560P (maintenance medium) for 12 to 48 hours at temperatures ranging from 26 C to 37 C, and then placed at 26 C. After 5 to 7 days the embryos are transferred to 560R selection medium containing 3 mg/liter Bialaphos, and subcultured every 2 weeks at 26 C. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to a lighted culture room. Approximately 7-10 days later, developing plantlets are transferred to 272V hormone-free medium in tubes for 7-10 days until plantlets are well established. Plants are then transferred to inserts in flats (equivalent to a 2.5" pot) containing potting soil and grown for 1 week in a growth chamber, subsequently grown an additional 1-2 weeks in the greenhouse, then transferred to Classic 600 pots (1.6 gallon) and grown to maturity. Plants are monitored and scored for transformation efficiency, and/or modification of regenerative capabilities.

Initiation medium (560L) comprises 4.0 g/l N6 basal salts (SIGMA C-1416), 1.0 ml/l Eriksson's Vitamin Mix (1000× SIGMA-1511), 0.5 mg/l thiamine HCl, 20.0 g/l sucrose, 1.0 mg/l 2,4-D, and 2.88 g/l L-proline (brought to volume with D-I H$_2$O following adjustment to pH 5.8 with KOH); 2.0 g/l Gelrite (added after bringing to volume with D-I H2O); and 8.5 mg/l silver nitrate (added after sterilizing the medium and cooling to room temperature).

Maintenance medium (560P) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, 2.0 mg/l 2,4-D, and 0.69 g/l L-proline (brought to volume with D-I H$_2$O following adjustment to pH 5.8 with KOH); 3.0 g/l Gelrite (added after bringing to volume with D-I H2O); and 0.85 mg/l silver nitrate (added after sterilizing the medium and cooling to room temperature).

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I H$_2$O following adjustment to pH 5.8 with KOH); 2.0 g/l Gelrite (added after bringing to volume with D-I H2O); and 8.5 mg/l silver nitrate (added after sterilizing the medium and cooling to room temperature).

Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I H$_2$O following adjustment to pH 5.8 with KOH); 3.0 g/l Gelrite (added after bringing to volume with D-I H2O); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H$_2$O) (Murashige and Skoog (1962) Physiol. Plant. 15:473), 100 mg/l myo-inositol, 0.5 mg/l zeatin, 60 g/l sucrose, and 1.0 ml/l of 0.1 mM abscisic acid (brought to volume with polished D-I H$_2$O after adjusting to pH 5.6); 3.0 g/l Gelrite (added after bringing to volume with D-I H2O); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H2O), 0.1 g/l myo-inositol, and 40.0 g/l sucrose (brought to volume with polished D-I H$_2$O after adjusting pH to 5.6); and 6 g/l bacto-agar (added after bringing to volume with polished D-I H2O), sterilized and cooled to 60° C.

b. *Agrobacterium*-Mediated Transformation

*Agrobacterium*-mediated transformation was performed essentially as described in Djukanovic et al. (2006) *Plant Biotech J* 4:345-57. Briefly, 10-12 day old immature embryos (0.8-2.5 mm in size) were dissected from sterilized kernels and placed into liquid medium (4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.690 g/L L-proline, 68.5 g/L sucrose, 36.0 g/L glucose, pH 5.2). After embryo collection, the medium was replaced with 1 ml *Agrobacterium* at a concentration of 0.35-0.45 OD550. Maize embryos were incubated with *Agrobacterium* for 5 min at room temperature, then the mixture was poured onto a media plate containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.690 g/L L-proline, 30.0 g/L sucrose, 0.85 mg/L silver nitrate, 0.1 nM acetosyringone, and 3.0 g/L Gelrite, pH 5.8. Embryos were incubated axis down, in the dark for 3 days at 20° C., then incubated 4 days in the dark at 28° C., then transferred onto new media plates containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.69 g/L L-proline, 30.0 g/L sucrose, 0.5 g/L MES buffer, 0.85 mg/L silver nitrate, 3.0 mg/L Bialaphos, 100 mg/L carbenicillin, and 6.0 g/L agar, pH 5.8. Embryos were subcultured every three weeks until transgenic events were identified. Somatic embryogenesis was induced by transferring a small amount of tissue onto regeneration medium (4.3 g/L MS salts (Gibco 11117), 5.0 ml/L MS Vitamins Stock Solution, 100 mg/L myo-inositol, 0.1 µM ABA, 1 mg/L IAA, 0.5 mg/L zeatin, 60.0 g/L sucrose, 1.5 mg/L Bialaphos, 100 mg/L carbenicillin, 3.0 g/L Gelrite, pH 5.6) and incubation in the dark for two weeks at 28° C. All material with visible shoots and roots were transferred onto media containing 4.3 g/L MS salts (Gibco 11117), 5.0 ml/L MS Vitamins Stock Solution, 100 mg/L myo-inositol, 40.0 g/L sucrose, 1.5 g/L Gelrite, pH 5.6, and incubated under artificial light at 28° C. One week later, plantlets were moved into glass tubes containing the same medium and grown until they were sampled and/or transplanted into soil.

Example 11

Transient Expression of BBM Enhances Transformation

Parameters of the transformation protocol can be modified to ensure that the BBM activity is transient. One such method involves precipitating the BBM-containing plasmid in a manner that allows for transcription and expression, but precludes subsequent release of the DNA, for example, by using the chemical PEI. In one example, the BBM plasmid is precipitated onto gold particles with PEI, while the transgenic expression cassette (UBI::moPAT~GFPm::PinII; moPAT is the maize optimized PAT gene) to be integrated is precipitated onto gold particles using the standard calcium chloride method.

Briefly, gold particles were coated with PEI as follows. First, the gold particles were washed. Thirty-five mg of gold particles, 1.0 in average diameter (A.S.I. #162-0010), were weighed out in a microcentrifuge tube, and 1.2 ml absolute EtOH was added and vortexed for one minute. The tube was incubated for 15 minutes at room temperature and then centrifuged at high speed using a microfuge for 15 minutes at 4° C. The supernatant was discarded and a fresh 1.2 ml aliquot of ethanol (EtOH) was added, vortexed for one minute, centrifuged for one minute, and the supernatant again discarded (this is repeated twice). A fresh 1.2 ml aliquot of EtOH was added, and this suspension (gold particles in EtOH) was stored at −20° C. for weeks. To coat particles with polyethylimine (PEI; Sigma #P3143), 250 μl of the washed gold particle/EtOH mix was centrifuged and the EtOH discarded. The particles were washed once in 100 μl ddH2O to remove residual ethanol, 250 μl of 0.25 mM PEI was added, followed by a pulse-sonication to suspend the particles and then the tube was plunged into a dry ice/EtOH bath to flash-freeze the suspension, which was then lyophilized overnight. At this point, dry, coated particles could be stored at −80° C. for at least 3 weeks. Before use, the particles were rinsed 3 times with 250 μl aliquots of 2.5 mM HEPES buffer, pH 7.1, with 1× pulse-sonication, and then a quick vortex before each centrifugation. The particles were then suspended in a final volume of 250 μl HEPES buffer. A 25 μl aliquot of the particles was added to fresh tubes before attaching DNA. To attach uncoated DNA, the particles were pulse-sonicated, then 1 pg of DNA (in 5 μl water) was added, followed by mixing by pipetting up and down a few times with a Pipetteman and incubated for 10 minutes. The particles were spun briefly (i.e. 10 seconds), the supernatant removed, and 60 μl EtOH added. The particles with PEI-precipitated DNA-1 were washed twice in 60 μl of EtOH. The particles were centrifuged, the supernatant discarded, and the particles were resuspended in 45 μl water. To attach the second DNA (DNA-2), precipitation using a water-soluble cationic lipid transfection reagent was used. The 45 μl of particles/DNA-1 suspension was briefly sonicated, and then 5 μl of 100 ng/μl of DNA-2 and 2.5 μl of a water-soluble cationic lipid transfection reagent were added. The solution was placed on a rotary shaker for 10 minutes, centrifuged at 10,000 g for 1 minute. The supernatant was removed, and the particles resuspended in 60 μl of EtOH. The solution was spotted onto macrocarriers and the gold particles onto which DNA-1 and DNA-2 had been sequentially attached were delivered into scutellar cells of 10 DAP Hi-II immature embryos using a standard protocol for the PDS-1000. For this experiment, the DNA-1 plasmid contained a UBI::RFP::pinII expression cassette, and DNA-2 contained a UBI::CFP::pinII expression cassette. Two days after bombardment, transient expression of both the CFP and RFP fluorescent markers was observed as numerous red & blue cells on the surface of the immature embryo. The embryos were then placed on non-selective culture medium and allowed to grow for 3 weeks before scoring for stable colonies. After this 3-week period, 10 multicellular, stably-expressing blue colonies were observed, in comparison to only one red colony. This demonstrated that PEI-precipitation could be used to effectively introduce DNA for transient expression while dramatically reducing integration of the PEI-introduced DNA and thus reducing the recovery of RFP-expressing transgenic events. In this manner, PEI-precipitation can be used to deliver transient expression of BBM and/or WUS2.

For example, the particles are first coated with UBI::BBM::pinII using PEI, then coated with UBI::moPAT-YFP using a water-soluble cationic lipid transfection reagent, and then bombarded into scutellar cells on the surface of immature embryos. PEI-mediated precipitation results in a high frequency of transiently expressing cells on the surface of the immature embryo and extremely low frequencies of recovery of stable transformants. Thus, it is expected that the PEI-precipitated BBM cassette expresses transiently and stimulates a burst of embryogenic growth on the bombarded surface of the tissue (i.e. the scutellar surface), but this plasmid will not integrate. The PAT~GFP plasmid released from the Ca++/gold particles is expected to integrate and express the selectable marker at a frequency that results in substantially improved recovery of transgenic events. As a control treatment, PEI-precipitated particles containing a UBI::GUS::pinII (instead of BBM) are mixed with the PAT~GFP/Ca++ particles. Immature embryos from both treatments are moved onto culture medium containing 3 mg/l bialaphos. After 6-8 weeks, it is expected that GFP+, bialaphos-resistant calli will be observed in the PEI/BBM treatment at a much higher frequency relative to the control treatment (PEI/GUS).

As an alternative method, the BBM plasmid is precipitated onto gold particles with PEI, and then introduced into scutellar cells on the surface of immature embryos, and subsequent transient expression of the BBM gene elicits a rapid proliferation of embryogenic growth. During this period of induced growth, the explants are treated with *Agrobacterium* using standard methods for maize (see Example 1), with T-DNA delivery into the cell introducing a transgenic expression cassette such as UBI::moPAT~GFPm::pinII. After co-cultivation, explants are allowed to recover on normal culture medium, and then are moved onto culture medium containing 3 mg/l bialaphos. After 6-8 weeks, it is expected that GFP+, bialaphos-resistant calli will be observed in the PEI/BBM treatment at a much higher frequency relative to the control treatment (PEI/GUS).

It may be desirable to "kick start" callus growth by transiently expressing the BBM and/or WUS2 polynucleotide products. This can be done by delivering BBM and WUS2 5'-capped polyadenylated RNA, expression cassettes containing BBM and WUS2 DNA, or BBM and/or WUS2 proteins. All of these molecules can be delivered using a biolistics particle gun. For example 5'-capped polyadenylated BBM and/or WUS2 RNA can easily be made in vitro using Ambion's mMessage mMachine kit. RNA is co-delivered along with DNA containing a polynucleotide of interest and a marker used for selection/screening such as Ubi::moPAT~GFPm::PinII. It is expected that the cells receiving the RNA will immediately begin dividing more rapidly and a large portion of these will have integrated the agronomic gene. These events can further be validated as being transgenic clonal colonies because they will also express the PAT~GFP fusion protein (and thus will display green fluorescence under appropriate illumination). Plants regenerated from these embryos can then be screened for the presence of the polynucleotide of interest.

Example 12

DNA Constructs to Test the Guide RNA/Cas Endonuclease System for Soybean Genome Modifications To test if a guide RNA/Cas endonuclease system, similar to that described in Example 1 for maize, is functional in a dicot such as soybean, a Cas9 (SO) gene (SEQ ID NO:115) soybean codon optimized from *Streptococcus pyogenes* M1 GAS (SF370) was expressed with a strong soybean constitutive promoter GM-EF1A2 (US patent application 20090133159 (SEQ ID NO: 116). A simian vacuolating virus 40 (SV40) large T-antigen nuclear localization signal (SEQ ID NO:117), representing the amino acid molecules of PKKKRKV (with a linker SRAD (SRADPKKKRKV), was added to the carboxyl terminus of the codon optimized Cas9 to facilitate transporting the codon optimized Cas9 protein (SEQ ID NO:118) to the nucleus. The codon optimized Cas9 gene was synthesized as two pieces by GenScript USA Inc. (Piscataway, N.J.) and cloned in frame downstream of the GM-EF1A2 promoter to make DNA construct QC782 shown in FIG. 7 (SEQ ID NO:119).

Plant U6 RNA polymerase III promoters have been cloned and characterized from such as *Arabidopsis* and *Medicago truncatula* (Waibel and Filipowicz, NAR 18:3451-3458 (1990); Li et al., J. Integrat. Plant Biol. 49:222-229 (2007); Kim and Nam, Plant Mol. Biol. Rep. 31:581-593 (2013); Wang et al., RNA 14:903-913 (2008)). Soybean U6 small nuclear RNA (snRNA) genes were identified herein by searching public soybean variety Williams82 genomic sequence using *Arabidopsis* U6 gene coding sequence. Approximately 0.5 kb genomic DNA sequence upstream of the first G nucleotide of a U6 gene was selected to be used as a RNA polymerase III promoter for example, GM-U6-13.1 promoter (SEQ ID NO:120), to express guide RNA to direct Cas9 nuclease to designated genomic site.

sites were selected one close to a predicted gene Glyma04g39780.1 at 114.13 cM herein named DD20 locus (FIG. 10A) and another close to Glyma04g39550.1 at 111.95 cM herein named DD43 locus (FIG. 10B). Each of the 20 bp variable targeting domain of the guide RNA started with a G residue required by RNA polymerase III and was followed in the soybean genome by a 3 bp PAM motif (Table 11). The chromosome positions of the soybean genomic targets sites in close proximity to the PAM sequences were determined by blast searching the public soybean variety Williams82 genomic sequence. The soybean genomic target sites DD20CR1 (SEQ ID NO: 125), DD20CR2 (SEQ ID NO: 126), and DD43CR1 (SEQ ID NO: 127) were identified as all unique in soybean genome while a second identical 23 bp genomic target site DD43CR2 (SEQ ID NO: 128) was found at Gm06:12072339-12072361 so there are two potential cleavage sites targeted by DD43CR2 guide RNA. Both DD43CR1 and DD43CR2 are complementary strand sequences indicated by "c" after the positions.

TABLE 11

Soybean genomic target sites for a guide RNA/Cas endonuclease system.

| Chromosome | Positions | Designation | Genomic Target Sites | PAM |
| --- | --- | --- | --- | --- |
| Gm04, 114.13 cM | 45936311-45936333 | DD20CR1 | GGAACTGACACACGACATGA | TGG |
| | 45936324-45936346 | DD20CR2 | GACATGATGGAACGTGACTA | AGG |
| Gm04, 111.95 cM | 45731921-45731943c | DD43CR1 | GTCCCTTGTACTTGTACGTA | CGG |
| | 45731895-45731917c | DD43CR2 | GTATTCTAGAAAAGAGGAAT | TGG |

The guide RNA coding sequence was 76 bp long (FIG. 8B) and comprised a 20 bp variable targeting domain from a chosen soybean genomic target site on the 5' end and a tract of 4 or more T residues as a transcription terminator on the 3' end. (SEQ ID NO:121, FIG. 8 B). The first nucleotide of the 20 bp variable targeting domain was a G residue to be used by RNA polymerase III for transcription. The U6 gene promoter and the complete guide RNA was synthesized and then cloned into an appropriate vector to make, for example, DNA construct QC783 shown in FIG. 8 A (SEQ ID NO:122). Other soybean U6 homologous genes promoters were similarly cloned and used for small RNA expression.

Since the Cas9 endonuclease and the guide RNA need to form a protein/RNA complex to mediate site-specific DNA double strand cleavage, the Cas9 endonuclease and guide RNA must be expressed in same cells. To improve their co-expression and presence, the Cas9 endonuclease and guide RNA expression cassettes were linked into a single DNA construct, for example, QC815 in FIG. 9 A (SEQ ID NO:123), which was then used to transform soybean cells to test the soybean optimized guide RNA/Cas system for genome modification. Similar DNA constructs were made to target different genomic sites using guide RNAs containing different target sequences.

Guide RNA expression cassette comprising a variable targeting domain targeting one of DD20CR1, DD20CR2, DD43CR2 genomic target sites were similarly constructed and linked to the soybean Cas9 expression cassette to make DNA constructs QC817, QC818, and QC816 that are similar to QC815 in FIG. 9 A (SEQ ID NO:123) except for the 20 bp variable targeting domain of the guide RNA Since up to six continuous mismatches in the 5' regions of the genomic target site (protospacer) with the 20 bp variable targeting domain can be tolerated, i.e., a continuous stretch of 14 base pairs between the variable targeting domain and the crRNA sequence proximate to the PAM is necessarily enough for efficient targets cleavage any 23 bp genomic DNA sequence following the pattern N(20)NGG can be selected as a target site for the guide RNA/Cas endonuclease system. The last NGG is the PAM sequence that should not be included in the 20 bp variable targeting domain of the guide RNA. If the first N is not endogenously a G residue it must be replaced with a G residue in guide RNA target sequence to accommodate RNA polymerase III, which should not sacrifice recognition specificity of the target site by the guide RNA.

Example 13

Selection of Soybean Genomic Sites to be Cleaved by the Guide RNA/Cas Endonuclease System A region of the soybean chromosome 4 (Gm04) was selected to test if the soybean optimized guide RNA/Cas endonuclease system could recognize, cleave, and mutate soybean chromosomal DNA through imprecise non-homologous end-joining (NHEJ) repair. Two genomic target Example 14

Delivery of the Guide RNA/Cas Endonuclease System DNA to Soybean by Transient Transformation The soybean optimized Cas9 endonuclease and guide RNA expression cassettes were delivered to young soybean somatic embryos in the form of embryogenic suspension cultures by particle gun bombardment. Soybean embryogenic suspension cultures were induced as follows. Cotyledons (~3 mm in length) were dissected from surface sterilized, immature seeds and were cultured for 6-10 weeks in the light at 26° C. on a Murashige and Skoog (MS) media containing 0.7% agar and supplemented with 10 mg/ml 2,4-D (2,4-Dichlorophenoxyacetic acid). Globular stage somatic embryos, which produced secondary embryos, were then excised and placed into flasks containing liquid MS medium supplemented with 2,4-D (10 mg/ml) and cultured in the light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (Bio-Rad Laboratories, Hercules, Calif.). To 50 µl of a 60 mg/ml 1.0 mm gold particle suspension were added (in order): 30 µl of 30 ng/µl QC815 DNA fragment U6-13.1:DD43CR1+EF1A2:CAS9 as an example, 20 µl of 0.1 M spermidine, and 25 µl of 5 M CaCl$_2$. The particle preparation was then agitated for 3 minutes, spun in a centrifuge for 10 seconds and the supernatant removed. The DNA-coated particles were then washed once in 400 µl 100% ethanol and resuspended in 45 µl of 100% ethanol. The DNA/particle suspension was sonicated three times for one second each. Then 5 µl of the DNA-coated gold particles was loaded on each macro carrier disk.

Approximately 100 mg of a two-week-old suspension cultures were placed in an empty 60×15 mm Petri dish and the residual liquid removed from the tissue with a pipette. Membrane rupture pressure was set at 1100 psi and the chamber was evacuated to a vacuum of 28 inches mercury. The tissue was placed approximately 3.5 inches away from the retaining screen and bombarded once. The tissue clumps were rearranged and bombarded another time. Minimum amount of liquid MS media without 2,4-D supplement was added to the tissue to prevent the cultures from drying or overgrowing. The 60×15 mm Petri dish was sealed in a 100×25 mm Petri dish containing agar solid MS media to as another measure to keep the tissues from drying up. The tissues were harvested seven days after and genomic DNA was extracted for PCR analysis.

Example 15

Analysis of Guide RNA/Cas Endonuclease System Mediated Site-Specific NHEJ by Deep Sequencing To evaluate DNA double strand cleavage at a soybean genomic target site mediated by the guide RNA/Cas endonuclease system, a region of approximately 100 bp genomic DNA surrounding the target site was amplified by PCR and the PCR product was then sequenced to check mutations at the target site as results of NHEJs. The region was first amplified by 20 cycles of PCR with Phusion High Fidelity mastermix (New England Biolabs) from 100 ng genomic DNA using gene-specific primers that also contain adaptors and amplicon-specific barcode sequences needed for a second round PCR and subsequence sequence analysis. For examples, the first PCR for the four experiments listed in Table 2 were done using primers DD20-S3 (SEQ ID NO:133)/DD20-A (SEQ ID NO:134), DD20-S4 (SEQ ID NO:135)/DD20-A, DD43-S3 (SEQ ID NO:136)/DD43-A (SEQ ID NO:137) and DD43-S4 (SEQ ID NO:138)/DD43-

A. One micro liter of the first round PCR products was further amplified by another 20 cycles of PCR using universal primers (SEQ ID NOs:140, 141) with Phusion High Fidelity mastermix. The resulting PCR products were separated on 1.5% agarose gel and the specific DNA bands were purified with Qiagen gel purification spin columns. DNA concentrations were measured with a DNA Bioanalyzer (Agilent) and equal molar amounts of DNA for up to 12 different samples each with specific barcode were mixed as one sample for Illumina deep sequencing analysis. Single read 100 nucleotide-length deep sequencing was performed at a DuPont core facility on a Illumnia's MiSeq Personal Sequencer with a 40% (v/v) spike of PhiX control v3 (Illumina, FC-110-3001) to off-set sequence bias.

Since the genomic target site is located in the middle of the ~100 bp long PCR amplicon (SEQ ID NOs: 142, 143, 144, 145), the 100 nucleotide-length deep sequencing is sufficient to cover the targets site region. A window of 10 nucleotides centered over the expected cleavage site, i.e., 3 bp upstream of the PAM, was selected for sequence analysis. Only those reads with one or more nucleotide indel arising within the 10 nucleotide window and not found in a similar level in negative controls were classified as NHEJ mutations. NHEJ mutant reads of different lengths but with the same mutation were counted into a single read and up to 10 most prevalent mutations were visually confirmed to be specific mutations before they were then used to calculate the % mutant reads based on the total analyzed reads containing specific barcode and forward primer.

The frequencies of NHEJ mutations revealed by deep sequencing for four target sites DD20CR1, DD20CR2, DD43CR1, DD43CR2 with one RNA polymerase III promoter GM-U6-13.1 are shown in Table 2. The visually confirmed most prevalent NHEJ mutations are shown in FIG. 11A-11D. The mutant sequences in FIG. 11A-11E are listed as SEQ ID NOs:147-201. The top row is the original reference sequence with the target site sequence underlined. Deletions in the mutated sequences are indicated by "---" while additions and replacements are indicated by bold letters. Total count of each mutation of different reads is given in the last column. Cas9 nuclease construct only, guide RNA construct only, and no DNA bombardment negative controls were similarly performed and analyzed but data not shown since no-specific mutations were detected. Other targets sites and guide RNAs were also tested with similar positive results and data not shown.

TABLE 12

Target site-specific mutations introduced by guide RNA/Cas endonuclease mediated NHEJ.

| Experiment | DNA | Mutant reads | Total reads | % Mutants |
|---|---|---|---|---|
| U6-13.1:DD20CR1 + EF1A2:CAS9 | QC817 | 339 | 710,339 | 0.048% |
| U6-13.1:DD20CR2 + EF1A2:CAS9 | QC818 | 419 | 693,483 | 0.060% |
| U6-13.1:DD43CR1 + EF1A2:CAS9 | QC815 | 489 | 682,207 | 0.072% |
| U6-13.1:DD43CR2 + EF1A2:CAS9 | QC816 | 917** | 539,681 | 0.170% |

**At least the top 15 reads are specific mutations but only the top 10 are counted in the table to be consistent with other experiments. If all top 15 mutations are counted, the total Mutant reads is 1080 and the % Mutants is 0.200%.

In conclusion, our data indicate that the soybean optimized guide RNA/Cas endonuclease system is able to effectively cleave soybean endogenous genomic DNA and create imperfect NHEJ mutations at the specified genomic target sites.

Example 16

The Guide RNA/Cas Endonuclease System Delivers Double-Strand Breaks (DBSs) to the Maize Epsps Locus Resulting in Desired Point Mutations Two maize optimized Cas9 endonucleases were developed and evaluated for their ability to introduce a double-strand break at a genomic target sequence. A first Cas9 endonuclease was as described in FIG. 1A (Example 2 and expression cassette SEQ ID NO:5). A second maize optimized Cas9 endonuclease (moCas9 endonuclease; SEQ ID NO:192) was supplemented with the SV40 nuclear localization signal by adding the signal coding sequence to the 5' end of the moCas9 coding sequence (FIG. 13). The plant moCas9 expression cassette was subsequently modified by the insertion of the ST-LS1 intron into the moCas9 coding sequence in order to enhance its expression in maize cells and to eliminate its expression in *E. coli* and *Agrobacterium*. The maize ubiquitin promoter and the potato proteinase inhibitor II gene terminator sequences complemented the moCas9 endonuclease gene designs. The structural elements of the moCas9 expression cassette are shown in FIG. 13 and its amino acid and nucleotide sequences are listed as SEQ ID Nos: 192 and 193.

A single guide RNA (sgRNA) expression cassette was essentially as described in Example 1 and shown in FIG. 1B. It consists of the U6 polymerase III maize promoter (SEQ ID NO: 9) and its cognate U6 polymerase III termination sequences (TTTTTTTT). The guide RNA (SEQ ID NO: 194) comprised a 20 nucleotide variable targeting domain (nucleotide1-20 of SEQ ID NO: 194) followed by a RNA sequence capable of interacting with the double strand break inducing endonuclease.

A maize optimized Cas9 endonuclease target sequence (moCas9 target sequence) within the EPSPS codon sequence was complementary to the 20 nucleotide variable sequence of the guide sgRNA determined the site of the Cas9 endonuclease cleavage within the EPSPS coding sequence.

The moCAS9 target sequence (nucleotides 25-44 of SEQ ID NO:209) was synthesized and cloned into the guide RNA-Cas9 expression vector designed for delivery of the components of the guide RNA-Cas9 system to the BMS (Black Mexican Sweet) cells through *Agrobacterium*-mediated transformation. *Agrobacterium* T-DNA delivered also the yeast FLP site-specific recombinase and the WDV (wheat dwarf virus) replication-associated protein (replicase). Since the moCas9 target sequences were flanked by the FLP recombination targets (FRT), they were excised by FLP in maize cells forming episomal (chromosome-like) structures. Such circular DNA fragments were replicated by the WDV replicase (the origin of replication was embedded into the WDV promoter) allowing their recovery in *E. coli* cells. If the maize optimizedCas9 endonuclease made a double-strand break at the moCas9 target sequence, its repair might produce mutations. The procedure is described in detail in: Lyznik, L. A., Djukanovic, V., Yang, M. and Jones, S. (2012) Double-strand break-induced targeted mutagenesis in plants. In: *Transgenic plants: Methods and Protocols* (Dunwell, J. M. and Wetten, A. C. eds). New York Heidelberg Dordrecht London: Springer, pp. 399-416.

The guideRNA/Cas endonuclease systems using either one of the maize optimized Cas9 endonucleases described herein, generated double-strand breaks in the moCas9 target sequence (Table 13). Table 13 shows the percent of the moCas9 target sequences mutagenized in the maize BMS cells using the moCas9 endonuclease of SEQ ID NO: 192 or the maize optimized cas9 endonuclease described in FIG. 1A and expressed by the expression cassette of SEQ ID NO:5. Both guideRNA/Cas endonuclease systems generated double-strand breaks (as judged by the number of targeted mutagenesis events) ranging from 67 to 84% of the moCas9 target sequences available on episomal DNA molecules in maize BMS cells. A sample of mutagenized EPSPS target sequences is shown in FIG. 14. This observation indicates that the maize optimized Cas9 endonuclease described herein is functional in maize cells and efficiently generates double-strand breaks at the moCas9 target sequence.

TABLE 13

Percent of the moCas9 target sequences mutagenized in the maize BMS cells by maize optimized Cas9 endonucleases.

| Cas9 endonuclease version | # of moCas9 target sequences analyzed | # of intact moCas9 target sequences recovered | # of mutagenized moCas9 target sequences found | Percent mutagenesis (%) |
| --- | --- | --- | --- | --- |
| SEQ ID NO: 193 (FIG. 13) | 81 | 13 | 68 | 84% |
| SEQ ID NO: 5 (FIG. 1A) | 93 | 31 | 62 | 67% |

In order to accomplish targeted genome editing of the maize chromosomal EPSPS gene, a polynucleotide modification template which provided genetic information for editing the EPSPS coding sequence was created (SEQ ID NO:195) and co-delivered with the guide RNA/Cas9 system components.

As shown in FIG. 12, the polynucleotide modification template comprised three nucleotide modifications (indicated by arrows) when compared to the EPSPS genomic sequence to be edited. These three nucleotide modifications are referred to as TIPS mutations as these nucleotide modifications result in the amino acid changes T-102 to 1-102 and P-106 to S-106. The first point mutation results from the substitution of the C nucleotide in the codon sequence ACT with a T nucleotide, a second mutation results from the substitution of the T nucleotide on the same codon sequence ACT with a C nucleotide to form the isoleucine codon (ATC), the third point mutation results from the substitution of the first C nucleotide in the codon sequence CCA with a T nucleotide in order to form a serine codon, TCA. (FIG. 12). Both codon sequences were located within 9 nucleotides of each other as shown in SEQ ID NO: 196: atcgcaatgcggtca. The three nucleotide modifications are shown in bold. The nucleotides between the two codon sequences were homologous to the non-edited EPSPS gene on the epsps locus. The polynucleotide modification template further comprised DNA fragments of maize EPSPS genomic sequence that were used as homologous sequence for the EPSPS gene editing. The short arm of homologous sequence (HR1-FIG. 12) was 810 base pairs long and the long arm of homologous sequence (HR2-FIG. 12) was 2,883 base pairs long (SEQ ID NO: 195).

In this example, the EPSPS polynucleotide modification template was co-delivered using particle gun bombardment as a plasmid (see template vector 1, FIG. 15) together with the guide sgRNA expression cassette and a maize optimized-Cas9 endonuclease expression vector which contained the maize optimized Cas9 endonuclease expression cassette described in FIG. 1A (Example 1, SEQ ID NO:5) and also contained a moPAT selectable marker gene. Ten to eleven day-old immature embryos were placed, embryo-axis down, onto plates containing the N6 medium (Table 14) and incubated at 28° C. for 4-6 hours before bombardment. The plates were placed on the third shelf from the bottom in the PDS-1000 apparatus and bombarded at 200 psi. Post-bombardment, embryos were incubated in the dark overnight at 28° C. and then transferred to plates containing the N6-2 media for 6-8 days at 28° C. The embryos were then transferred to plates containing the N6-3 media for three weeks, followed by transferring the responding callus to plates containing the N6-4 media for an additional three-week selection. After six total weeks of selection at 28° C., a small amount of selected tissue was transferred onto the MS regeneration medium and incubated for three weeks in the dark at 28° C.

DNA was eluted in 100 ul Elution Buffer (10 mM Tris-Ha pH 8.3) and centrifuged at 3000×g for 1 min. For each sample, four PCR reactions were run. They included approximately 40 ng genomic DNA, 10 ul REDExtract-N-Amp PCR ReadyMix (R4775, Sigma-Aldrich Co.), and 5 picomoles of each primer in a total volume of 20 ul. Primer combinations for each PCR reaction are listed in the Table 15.

TABLE 15

Primer combinations for PCR reactions.

| PCR reaction | Primer sequence | SEQ ID NO: | PCR product |
|---|---|---|---|
| F-E2 | CCGAGGAGATCGTGCTGCA | 197 | Template |
|  | CAATGGCCGCATTGCAGTTC | 198 | randomly integrated or gene editing event |
| F-T | CCGAGGAGATCGTGCTGCA | 199 | Wild-type |
|  | TGACCGCATTGCGATTCCAG | 200 | EPSPS allele |

TABLE 14

Composition of Culture Media.

| Culture medium | Composition |
|---|---|
| N6 | 4.0 g/L $N_6$ Basal Salts (Sigma C-1416; Sigma-Aldrich Co., St. Louis, MO, USA), 1.0 ml/L Ericksson's Vitamin Mix (Sigma E-1511), 0.5 mg/L thiamine HCl, 190 g/L sucrose, 1.0 mg/L 2,4-dichlorophenoxyacetic acid (2,4-D), 2.88 g/L L-proline, 8.5 mg/L silver nitrate, 25 mg/L cefotaxime, and 6.36 g/L Sigma agar at pH 5.8 |
| N6-2 | 4.0 g/L $N_6$ Basal Salts (Sigma C-1416), 1.0 ml/L Ericksson's Vitamin Mix (Sigma E-1511), 0.5 mg/L thiamine HCl, 20 g/L sucrose, 1.0 mg/L 2,4-D, 2.88 g/L L-proline, 8.5 mg/L silver nitrate, 25 mg/L cefotaxime, and 8.5 g/L Sigma agar at pH 5.8 |
| N6-3 | 4.0 g/L $N_6$ Basal Salts (Sigma C-1416), 1.0 ml/L Ericksson's Vitamin Mix (Sigma E-1511), 0.5 mg/L thiamine HCl, 30 g/L sucrose, 1.5 mg/L 2,4-D, 0.69 g/L L-proline, 0.5 g/L 2-(N-morpholino)ethanesulphonic acid (MES) buffer, 0.85 mg/L silver nitrate, 5 mg/L glufosinate $NH_4$, and 8.0 g/L Sigma agar at pH 5.8 |
| N6-4 | 4.0 g/L $N_6$ Basal Salts (Sigma C-1416), 1.0 ml/L Ericksson's Vitamin Mix (Sigma E-1511), 0.5 mg/L thiamine HCl, 30 g/L sucrose, 1.5 mg/L 2,4-D, 0.69 g/L L-proline, 0.5 g/L MES buffer, 0.85 mg/L silver nitrate, 3 mg/L bialophos, and 8.0 g/L Sigma agar at pH 5.8 |
| MS | 4.3 g/L Murashige and Skoog (MS) salts (Gibco 11117; Gibco, Grand Island, NY), 5.0 ml/L MS Vitamins Stock Solution (Sigma M3900), 100 mg/L myo-inositol, 0.1 μmol abscisic acid (ABA), 1 mg/L indoleacetic acid (IAA), 0.5 mg/L zeatin, 60.0 g/L sucrose, 3.0 mg/L Bialophos, and 8.0 g/L Sigma agar at pH 5.6 |

DNA was extracted by placing callus cell samples, two stainless-steel beads, and 450 ul of extraction buffer (250 mM NaCl, 200 mM Tris-HCl pH 7.4, 25 mM EDTA, 4.2 M Guanidine HCl) into each tube of a Mega titer rack. The rack was shaken in the Genogrinder at 1650 r.p.m. for 60 seconds and centrifuged at 3000×g for 20 min at 4° C. Three hundred μl of supernatant was transferred to the wells of the Unifilter 96-well DNA Binding GF/F Microplate (770-2810, Whatman, GE Healthcare). The plate was placed on the top of a Multi-well plate vacuum manifold (5017, Pall Life Sciences). A vacuum pressure was applied until the wells were completely dried. The vacuum filtration procedure was repeated one time with 100 ul extraction buffer and two times with 250 ul washing buffer (50 mM Tris-HCl pH 7.4, 200 mM NaCl, 70% ethanol). The residual ethanol was removed by placing the GF/F filter plate on an empty waste collection plate and centrifuged for 10 min at 3000×g. The TABLE 15-continued Primer combinations for PCR reactions.

| PCR reaction | Primer sequence | SEQ ID NO: | PCR product |
|---|---|---|---|
| H-T | TCCAAGTCGCTTTCCAACAGGATC | 201 | TIPS editing |
|  | TGACCGCATTGCGATTCCAG | 202 | event |
| F-E3 | CCGAGGAGATCGTGCTGCA | 203 | A fragment of |
|  | ACCAAGCTGCTTCAATCCGACAAC | 204 | the epsps locus for cloning and sequencing |

The same PCR reactions were done on five samples of genomic DNA obtained from untransformed maize inbred plantlets. After an initial denaturation at 95° C. for 5 minutes, each PCR amplification was carried out over 35 cycles using DNA Engine Tetrad2 Thermal Cycler (BioRad Laboratories, Hercules, Calif.) at 94° C. for 30 sec denaturation, 68° C. for 30 sec annealing, and 72° C. for 1 min extension. PCR products F-E2, F-T and H-T were separated in 1% agarose gel at 100 Volts for 45 minutes, with 100 bp DNA Ladder (N0467S, NewEngland Biolabs). For sequencing, the F-F3 PCR amplified fragments from selected calli were cloned into pCR 2.1-TOPO vectors using the TOPO TA Cloning Kit (Invitrogen Corp, Carlsbad, Calif.). DNA sequencing was done with BigDye Terminator chemistry on ABI 3700 capillary sequencing machines (Applied Biosystems, Foster City, Calif.). Each sample contained about 0.5 ug Topo plasmid DNA and 6.4 pmole primer E3-EPex3 Rev (ACCAAGCTGCTTCAATCCGACAAC, SEQ ID NO: 204). Sequences were analyzed using the Sequencer program.

A sample of thirty one callus events selected on media containing bialophos (the moPAT selectable marker gene was part of the guide RNA-moCas9 expression vector) were screened for the presence of the TIPS point mutations. Twenty four events contained the TIPS point mutations integrated into genomic DNA (FIG. 16, the F-E2 treatment). Among them, six events showed the PCR amplification product of the chromosomal EPSPS gene with TIPS mutations (FIG. 16, the H-T treatment). The pair of PCR primers (one that can hybridize to the genomic epsps sequence not present in the EPSPS polynucleotide modification template and the other one binding to the edited EPSPS sequence present in the EPSPS polynucleotide modification template) distinguished the EPSPS-TIPS editing products from the wild-type epsps alleles or random insertions of the TIPS mutations. If one EPSPS allele was edited to contain the TIPS substitutions, it should be detected as a DNA fragment originating from the genomic epsps locus, regardless whether the TIPS substitutions were selected for during the PCR amplification process. The TIPS primer was replaced with the wild-type EPSPS primer (Table 15, the F-E3 pair of primers) and the PCR amplification products were cloned into the TOPO cloning vectors and sequenced. The sequencing data represented a random sample of the genomic epsps locus sequences in one of the selected events (FIG. 17, callus A12 3360.92). FIG. 17 shows that the method disclosed herein resulted in the successful nucleotide editing of three nucleotides (FIG. 17 bold) responsible for the TIPS mutations without altering any of the other epsps nucleotides, while the moCas9 target sequence (the site of guide RNA binding underlined in FIG. 17) was not mutagenized.

Also, the other EPSPS allele was not edited indicating that only one EPSPS allele was edited in this particular event (FIG. 17, lower section).

This data further shows that the present disclosure of the use of the guide RNA/Cas system for the gene editing demonstrates the ability to recover gene editing events at a high efficiency of 1 out of fewer than 10 selected events.

Example 17

The Guide RNA/Cas Endonuclease System Delivers Double-Strand Breaks to the Maize Epsps Locus Resulting in Maize Plants Containing an EPSPS-TIPS Edited Gene The EPSPS gene edited events were produced and selected as described in the Example 16. In short, the EPSPS polynucleotide modification template was co-delivered using particle gun bombardment as a plasmid (see template vector 1, FIG. 15) together with the guide RNA expression cassette and a maize optimized Cas9 endonuclease expression vector which contained the maize optimized Cas9 endonuclease expression cassette described in FIG. 1A (Example 1, SEQ ID NO:5) and also contained a moPAT selectable marker gene.

After six weeks of selection at 28° C., a small amount of selected tissue was transferred onto the MS regeneration medium and incubated for three weeks in the dark at 28° C. After the three week incubation visible shoots were transferred to plates containing the MS-1 medium and incubated at 26° C. in the light for 1-2 weeks until they were ready to be sent to a greenhouse and transferred into soil flats. The Ms-1 medium contained: 4.3 g/L MS salts (Gibco 11117), 5.0 ml/L MS Vitamins Stock Solution (Sigma M3900), 100 mg/L myo-inositol, 40.0 g/L sucrose, and 6.0 g/L Bacto-Agar at pH 5.6.

Using the procedures described above, 390 T0 maize plants were produced originating from 3282 embryos, resulting in an overall transformation efficiency of 12%, further indicating that the guide RNA/Cas system used herein results in low or no toxicity (Table 16).

TABLE 16

Transformation efficiency of the EPSPS editing.

| Treatment | # Embryos | # Calli selected | Selection efficiency | T0 plants to GH | Overall Efficiency |
|---|---|---|---|---|---|
| Particle bombardment | 3282 | 489 | 15% | 390 | 12% |

DNA was extracted from each T0 plantlet 7-10 days after transfer to the greenhouse and PCR procedures were conducted as described in the Example 16 to screen the T0 plants for mutations at the epsps locus.

Seventy two percent of analyzed T0 plants (270/375, Table 17) contained mutagenized EPSPS alleles as determined by the end-point PCR procedure described in the Example 16. Most of the mutations (230/375 or 89%) were produced as a result of error-prone non-homologous end joining (NHEJ) while forty T0 plants (40/375 or 11%) contained the TIPS edited EPSPS alleles indicating the involvement of a tem plated double-strand break repair mechanism (Table 17).

TABLE 17

Mutations at the epsps locus.

| Transformation | T0 Plants Analyzed | Mutations at the epsps locus | Mutation rate | TIPS editing | Gene Editing Rate (TIPS) |
|---|---|---|---|---|---|
| Particle bombardment | 375 | 270 | 72% | 40 | 11% |

A pair of primers (Table 15, the F-E3 pair of primers) was used to amplify a native, endogenous fragment of the epsps locus containing the moCas6 target sequence and the EPSPS editing site from the genomic DNA of selected T0 plants. The PCR amplification products were cloned into the TOPO cloning vectors and sequenced as described in Example 16. The sequencing data represent a random sample of the genomic epsps locus sequences from a particular T0 plant (Table 18) and indicate the genotype of the selected T0 plants. The list of the EPSPS-TIPS allele-containing T0 plants transferred to the pots is presented in Table 18 (a selected set of T0 plants from the original 40 TIPS-containing events).

TABLE 18

The epsps locus genotypes observed in T0 plants. TIPS refers to a clone comprising the TIPS edited EPSPS sequence. NHEJ refers to the presence of a NHEJ mutation and WT refers to the presence of a wild-type EPSPS sequence amplified from the native epsps locus.

| Event (T0 plant) | Observed Sequences found at the epsps locus |
|---|---|
| E1 | 16 TIPS, 13 NHEJ |
| E2 | 28 TIPS, 0 NHEJ |
| E3 | 2 TIPS, 20 WT |
| E4 | 1 TIPS, 28 NHEJ |
| E5 | 2 TIPS, 2 NHEJ, 9 WT |
| E6 | 10 TIPS, 17 NHEJ |
| E7 | 12 TIPS, 17 NHEJ |
| E8 | 11 TIPS, 15 NHEJ |
| E9 | 17 TIPS, 10 NHEJ |

As presented in Table 18, the selected plants of E1 and E3 to E9 contained the EPSPS-TIPS edited version of the EPSPS gene either accompanied by a wild-type EPSPS allele (WT) or a NHEJ mutagenized EPSPS allele (NHEJ).

The numbers before TIPS, WT, NHEJ in Table18 indicate the frequency at which a particular version of the EPSPS allele was identified. If all clones contained the TIPS-edited EPSPS sequence, the analyzed plant was likely to be homozygous for the EPSPS-TIPS allele (see for example E2). If only about 50% of clones contained a TIPS-edited EPSPS sequence, the analyzed plant was likely to be hemizygous for the EPSPS-TIPS allele (see for example E1). Other plants, such as E3 or E4, were likely to be chimeric for TIPS. In one event, E2, the T0 plant contained only TIPS-edited sequence at the epsps locus indicating that the guide RNA/Cas endonuclease system disclosed herein resulted in the successful nucleotide editing of three nucleotides (FIG. 17 bold) responsible for the two EPSPS-TIPS alleles at the epsps locus in maize plants.

A qPCR analysis was performed on the selected T0 plants to estimate the copy number of the wild-type EPSPS genes and the moCas9 endonuclease sequences. Multiplex qPCR amplifications of the maize EPSPS gene and the ADH housekeeping gene were carried out on the DNA samples from T0 plants. The primers and probes used in the PCR reaction are shown in Table 19.

TABLE 19

Primers used in qPCR analysis of T0 plants.

| Primer/probe | Primary PCR Primer Sequence | SEQ ID NO: |
|---|---|---|
| primer qADH F | 5'-CAAGTCGCGGTTTTCAATCA-3 | SEQ ID NO: 217 |
| Primer qADH R | 5'-TGAAGGTGGAAGTCCCAACAA-3' | SEQ ID NO: 218 |
| probe ADH-VIC | VIC-TGGGAAGCCTATCTACCAC | SEQ ID NO: 219 |
| Probe wtEPSPS | 6FAM-CGGCCATTGACAGCA-MGB-NFQ | SEQ ID NO: 220 |
| Forward primer qEPSPS F | 5'-TCTTGGGGAATGCTGGAACT-3' | ,SEQ ID NO: 221 |
| reverse primer qEPSPSR | 5'-CACCAGCAGCAGTAACAGCTG-3' | SEQ ID NO: 222 |
| FAM-wtEPSPS R probe | 6FAM-TGCTGTCAATGGCCGCA | SEQ ID NO: 223 |
| forward primer qEPSPS F | 5'-TCTTGGGGAATGCTGGAACT-3' | SEQ ID NO: 224 |
| reverse primer q wtEPSPS RA | 5'-CCACCAGCAGCAGTAACAGC-3 | SEQ ID NO: 225) |

All analyses were conducted using the LightCycler 480 Real-Time PCR System (Roche Diagnostics). A threshold value for the wtEPSPS genotype was set at 1.76. Every sample showing less than 1.76 copies of EPSPS, with the end-point florescence measurements up to two times lower than the wild-type control, was categorized as the One Allele EPSPS genotype (hemizygous for the wild-type EPSPS allele).

A qPCR method was used to estimate the TIPS sequence copy number. The primers and probes used in the qPCR reaction are shown in Table 20.

TABLE 20

Primers used in qPCR analysis to estimate the TIPS sequence copy number.

| Primer/probe | Primary PCR Primer Sequence | SEQ ID NO: |
|---|---|---|
| forward primer q epTIPS F | 5'-GGAAGTGCAGCTCTTCTTGGG-3' | SEQ ID NO: 226 |

TABLE 20-continued

Primers used in qPCR analysis to estimate the TIPS sequence copy number.

| Primer/probe | Primary PCR Primer Sequence | SEQ ID NO: |
|---|---|---|
| reverse primer q epTIPS R | 5'-AGCTGCTGTCAATGACCGC-3' | SEQ ID NO: 227 |
| TIPS probe | 6FAM-AATGCTGGAATCGCA | SEQ ID NO: 228) |

A comparative Ct method with Delta Ct values normalized to the average Delta Ct from the bi-allelic TIPS genotypes provided a copy number estimation for the TIPS sequence detected in the analyzed plant samples.

TABLE 21 qPCR genotyping and copy number of selected T0 plants.

| Event name | TIPS EPSPS allele | Wild-type EPSPS allele # | TIPS copy # | moCas9 coding sequence |
|---|---|---|---|---|
| E1 | positive | Null | 5 | positive |
| E2 | positive | Null | 2 | positive |
| E7 | positive | Null | 6 | positive |
| E8 | positive | Null | 1 | positive |
| E9 | positive | Null | 3 | positive |

The qPCR genotyping indicated that no wild-type EPSPS alleles were detected in the selected T0 plants of Events E1, E2, E7, E8 and E9 (Table 21). Both, the TIPS template sequences and the moCas9 coding sequence were found in the selected T0 plants, presumably, as a result of random insertions associated with the transformation process (Table 21: for the TIPS template sequences E1, E7, and E9 T0 plants). Both genetic elements (the randomly inserted TIPS templates and the moCas9 expression cassette) can be segregated out by standard breeding procedures in the T1 progeny generation, if not linked to the edited EPSPS-TIPS gene.

T0 plants grew well in the greenhouse and were fertile. A sample of T0 plants was sprayed with a 1× dose of glyphosate (Roundup Powermax) at V3 growth stage using the spray booth setting of 20 gallons per acre. The 1× dose of glyphosate was prepared as follow: 2.55 ml Powermax in 300 ml water (active ingredient: glyphosate, N-(phosphonomethyl) glycine, in the form of its potassium salt at 48.7%). Seven days after glyphosate application, no leaf tissue damage was observed in some of the T0 plants. These plantlets were hemizygous for the EPSPS-TIPS alleles, while other plantlets were severely damaged. One plant showing no damage to the leaf tissue 14 days after herbicide application contained 21 EPSPS-TIPS alleles among 44 genomic clones of the epsps locus (cloned and sequenced as described in the Example 16).

These data indicate that a guide RNA/Cas system can be used to create a TIPS-edited EPSPS allele in maize. Maize plants homozygous at the epsps-tips locus (two EPSPS alleles edited) with no additional insertion of the TIPS template (plant E2) were obtained. Furthermore, some EPSPS-TIPS edited maize plants did show some level of tolerance against a 1× dose of glyphosate.

Example 18

Guide RNA/Cas Endonuclease Mediated DNA Cleavage in Maize Chromosomal Loci Enables Transgene Insertion in an Elite Maize Line To test whether a maize optimized guide RNA/Cas system can cleave an maize chromosomal locus and enable homologous recombination (HR) mediated pathways to site-specifically insert a transgene in an elite maize line, 4 loci were selected on the maize chromosome 1 located between 51.54cM to 54.56 cM (FIG. 18). Two target sites for a Cas endonuclease were identified at each of the four loci and are referred to as MHP14Cas-1, MHP14Cas-3, TS8Cas-1, TS8Cas2, TS9Cas-2, TS9Cas-3, TS10Cas-1 and TS10Cas-3 (FIG. 19, Table 22, SEQ ID NOs:229-236).

TABLE 22

Maize genomic target sites targeted by a guide RNA/Cas endonuclease.

| Locus | Location | Target Site | Maize Genomic Target Site Sequence | PAM | SEQ ID NO: |
|---|---|---|---|---|---|
| MHP14 | Chr. 1: 51.54cM | MHP14Cas-1 | gttaaatctgacgtgaatctgtt | TGG | 229 |
| | | MHP14Cas-3 | acaaacattgaagcgacatag | TGG | 230 |
| TS8 | Chr. 1: 52.56cM | TS8Cas-1 | gtacgtaacgtgcagtac | TGG | 231 |
| | | TS8Cas-2 | gctcatcagtgatcagctgg | TGG | 232 |
| TS9 | Chr. 1: 53.56cM | TS9Cas-2 | ggctgtttgcggcctcg | AGG | 233 |
| | | TS9Cas-3 | gcctcgaggttgcacgcacgt | CGG | 234 |
| TS10 | Chr.1: 54.56cM | TS10Cas-1 | gcctcgccttcgctagttaa | GGG | 235 |
| | | TS10Cas-3 | gctcgtgttggagataca | GGG | 236 |

The maize optimized Cas endonuclease cassette (SEQ ID NO: 5 was as prepared as describe in Example 1. Long guide RNA expression cassettes comprising a variable targeting domain targeting one of the 8 genomic target sites, driven by a maize U6 polymerase III promoter, and terminated by a maize U6 polymerase III terminator were designed as described in Example 1 and 3 and listed in Table 23. A donor DNA (HR repair DNA) containing a selectable marker (a phosphomannose-isomerase (PMI) expression cassette) flanked by two homologous regions was constructed using standard molecular biology techniques (FIG. 20).

TABLE 23

List of guide RNA (gRNA) and Donor DNA expression cassettes

| Locus | Target Site | gRNA (SEQ ID NO:) | Donor DNA (SEQ ID NO:) |
|---|---|---|---|
| MHP14 | MHP14Cas-1 | 245 | 253 |
|  | MHP14Cas-3 | 246 | 254 |
| TS8 | TS8Cas-1 | 247 | 255 |
|  | TS8Cas-2 | 248 | 256 |
| TS9 | TS9Cas-2 | 249 | 257 |
|  | TS9Cas-3 | 250 | 258 |
| TS10 | TS10Cas-1 | 251 | 259 |
|  | TS10Cas-3 | 252 | 260 |

A vector containing the maize optimized Cas9 endonuclease of SEQ ID NO: 5, a vector containing one of eight long guide RNA expression cassettes of SEQ ID NOs: 245-252, and a vector containing one of eight donor DNAs of SEQ ID NOs: 253-260 were co-delivered to maize elite line immature embryos by particle-mediated delivery as described in Example 10. About 1000 embryos were bombarded for each target site. Since the donor DNA contained a selectable marker, PMI, successful delivery of the donor DNA allowed for callus growth on mannose media. Putative HR-mediated transgenic insertions were selected by placing the callus on mannose containing media. After selection, stable shoots on maturation plates were sampled, total genomic DNA extracted, and using the primer pairs shown in Table 24 (corresponding to SEQ ID NOs: 261-270), PCR amplification was carried out at both possible transgene genomic DNA junctions to identify putative HR-mediated transgenic insertions.

The same genomic primers were used for each of the two target sites at one locus. The resulting amplifications were sequenced to determine if these sites were mutated or contained a transgene insertion.

The "Event Recovery frequency" was calculated using the number of events recovered divided by the total number of embryos bombarded, and may indicate if an endonuclease has some toxic effect or not (Table 26). Hence, if 1000 embryos were bombarded and 240 were recovered, the Event Recovery frequency is 24%. Table 26 indicates that for all target sites analyzed the Event Recovery frequency ranged between 17 and 28%, indicating that the guide RNA/Cas system used herein results in low or no toxicity. Cas endonuclease activity was measured in-planta by determining the "Target Site Mutation frequency" (Table 26) is defined as: (number of events with target site modification/total number recovered events)*100%. Hence, if 240 events were recovered and 180 events showed a mutation, the Target Site Mutation frequency is 75%. The target site mutation frequency was measured using target site allele copy number as described in Example 9 of U.S. application Ser. No. 13/886,317, filed on May 3, 2013. The primers and probes for obtaining the target site copy number using qPCR at each site were as listed in Table 25 (SEQ ID NO: 271-294).

TABLE 25

Primer and probe sequences used to assess DNA cleavage at 8 maize genomic target sites

| Target Site Designation | Probe primers | Primer sequence | SEQ ID NO: |
|---|---|---|---|
| MHP14Cas-1 | probe | CAGATTCACGTCAGATTT | 271 |
|  | forward | CATAGTGGTGTATGAAAGGAAGCACTT | 272 |
|  | reverse | CATTTTGGATTGTAATATGTGTACCTCATA | 273 |
| MHP14Cas-3 | probe | CACCACTATGTCGCTTC | 274 |
|  | forward | CGGATGCACGAAAATTGTAGGA | 275 |
|  | reverse | CTGACGTGAATCTGTTTGGAATTG | 276 |

TABLE 24

Primer sequences used for integration event screening at each target site

| Locus | Target Site | Junction | Primer | SEQ ID NO: |
|---|---|---|---|---|
| UBIR | donor | 1 |  CCATGTCTAACTGTTCATTTATATGATTCTCT | 261 |
| PSBF | donor | 2 | GCTCGTGTCCAAGCGTCACTTACGATTAGCT | 262 |
| MHP14 | MHP14Cas-1 | 14-1HR1f | CTCACATGAGGCTCTTCTTTGCTTGCT | 263 |
|  | MHP14Cas-3 | 14-1HR2r | AGGATCCTATTCCCCAATTTGTAGAT | 264 |
| CHR1-8 | TS8Cas-1 | 8HR1f | CAGTCCGTGGATTGAAGCCAT | 265 |
|  | TS8Cas-2 | 8HR2r | CTCTGTCTCCGAGACGTGCTTA | 266 |
| CHR1-9 | TS9Cas-2 | 9HR1f | GGAGCAAATGTTTTAGGTATGAAATG | 267 |
|  | TS9Cas-3 | 9HR2r | CGGATTCTAAAGATCATACGTAAATGAA | 268 |
| CHR1-10 | TS10Cas-1 | 10HR1f | TGGCTTGTCTATGCGCATCTC | 269 |
|  | TS10Cas-3 | 10HR2r | CCAGACCCAAACAGCAGGTT | 270 |

TABLE 25-continued

Primer and probe sequences used to assess DNA cleavage at 8 maize genomic target sites

| Target Site Designation | Probe primers | Primer sequence | SEQ ID NO: |
|---|---|---|---|
| TS8Cas-1 | probe | TACGTAACGTGCAGTACT | 277 |
|  | forward | ACGGACGGACCATACGTTATG | 278 |
|  | reverse | TCAGCTGGTGGAGTATATTAGTTCGT | 279 |
| TS8Cas-2 | probe | CCAGCTGATCACTGATGA | 280 |
|  | forward | ACGGACGGACCATACGTTATG | 281 |
|  | reverse | CGCACATGTTATAAATTACAATGCAT | 282 |
| TS9Cas-2 | probe | CTGTTTGCGGCCTC | 283 |
|  | forward | CTGCGGAGCTGCTGGCGAT | 284 |
|  | reverse | CTTGCTGGCTTCGTCTGTCA | 285 |
| TS9Cas-3 | probe | CCGACGTGCGTGCAA | 286 |
|  | forward | CTGCGGAGCTGCTGGCGAT | 287 |
|  | reverse | CTTGCTGGCTTCGTCTGTCA | 288 |
| TS10Cas-1 | probe | TCGCCTTCGCTAGTTAA | 289 |
|  | forward | AAGACCTGGCCGGTTTTCCA | 290 |
|  | reverse | TAGCGGCCATTGCCATCA | 291 |
| TS10Cas-3 | probe | CTGTATCTCCAACACGAGC | 292 |
|  | forward | AAGACCTGGCCGGTTTTCCA | 293 |
|  | reverse | TAGCGGCCATTGCCATCA | 294 |

As shown in Table 26, all 8 guide RNA/Cas9 systems were very efficient in cleaving their target DNA and inducing mutations (by non-homologous end joining (NHEJ) as is evidenced by a mutation frequency ranging from 33-90%.

All events were also screened for the presence of an inserted transgene. The insertion event screening for each target site is illustrated in FIG. 21. The primers used for insertion PCR analysis at each site are listed in Table 24. FIG. 22 shows one example of an insertion event screening PCR result. The frequency of transgene insertion was determined by calculating the "Insertion frequency" which is defined as: (number of events with target site insertion/total number recovered events)*100%. Hence, if 240 events were recovered and 21 events showed a transgene insertion, the Insertion frequency was 9%.

TABLE 26

Activity of the guide RNA/Cas 9 system at 8 target sites as determined by target site mutation frequency and transgene insertion frequency at the desired target site in maize plant tissue

| Target Site | Event Recovery (%) | Target Site Mutation (%) | Insertion frequency (%) |
|---|---|---|---|
| TS10Cas-1 | 24% | 75% | 9% (7*) |
| TS10Cas-3 | 22% | 83% | 16% (20*) |
| TS8Cas-1 | 17% | 90% | 14% (9*) |
| TS8Cas-2 | 27% | 84% | 8% (10*) |
| MHP14Cas-1 | 17% | 33% | 2% (2*) |
| MHP14Cas-3 | 28% | 68% | 4% (1*) |
| TS9Cas-2 | 23% | 62% | 8%** |
| TS9Cas-3 | 28% | 84% | 8%** |

*Number of events with HR1 and HR2 both junctions positive
**only HR2 junction available Sequence—confirmed-PCR amplifications indicated a site-specific transgene insertion for each of the 8 target sites as shown in Table 26 (column Insertion frequency). A transgene cassette was inserted at all 8 target sites with high efficiency (2-16%). The number of events containing amplifications across both transgene genomic DNA junctions, indicating near perfect site-specific transgene insertion, are show in brackets in Table 26.

Taken together, these data demonstrates that maize chromosomal loci cleaved with the maize optimized guide RNA/Cas system described herein can be used to insert transgenes at high frequencies in maize elite inbred line.

Example 19

Delivery of the Guide RNA/Cas9 Endonuclease System DNA to Soybean by Stable Transformation A soybean U6 small nuclear RNA promoter (GM-U6-9.1; SEQ ID NO: 295) was identified in a similar manner as the soybean promoter GM-U6-13.1 (SEQ ID NO:120) described in Example 12. The GM-U6-9.1 promoter was used to express guide RNA to direct Cas9 nuclease to designated genomic target site.

A soybean codon optimized Cas9 endonuclease expression cassette (such as for example EF1A2:CAS9, SEQ ID NO: 296) and a guide RNA expression cassette (such as for example U6-9.1:DD20CR1; SEQ ID NO: 297) were linked (such as U6-9.1: DD20CR1+EF1A2:CAS9; SEQ ID NO: 298, FIG. 23A) and integrated into a DNA plasmid that was co-delivered with another plasmid comprising a donor DNA (repair DNA) cassette (such as DD20HR1-SAMS:HPT-DD20HR2; SEQ ID NO: 299) to young soybean somatic embryos in the form of embryogenic suspension cultures by particle gun bombardment (FIGS. 23A and 23B). Other guide RNA/Cas9 DNA constructs targeting various soybean genomic sites and donor DNA constructs for site-specific transgene integration through homologous recombination were similarly configured and are listed in Table 27. The four gRNA/Cas9 constructs differed only in the 20 bp guide RNA targeting domain (variable targeting domain) targeting the soybean genomic target sites DD20CR1 (SEQ ID NO: 125), DD20CR2 (SEQ ID NO: 126), DD43CR1 (SEQ ID NO: 127), or DD43CR2 (SEQ ID NO: 128). The two donor DNA constructs differed only in the homologous regions such as DD20HR1 and DD20HR (FIG. 23B), or DD43HR1 and DD43HR2. These guide RNA/Cas9 DNA constructs and donor DNAs were co-delivered to an elite (93B86) or a non-elite (Jack) soybean genome by the stable transformation procedure described below.

TABLE 27

Guide RNA/Cas9 Mediated Soybean Stable Transformation.

| Experiment | Guide RNA/Cas9 | Donor DNA | SEQ ID NOs: |
|---|---|---|---|
| U6-9.1DD20CR1 | U6-9.1:DD20CR1 + EF1A2:CAS9 | DD20HR1-SAMS:HPT-DD20HR2 | 298, 299 |
| U6-9.1DD20CR2 | U6-9.1:DD20CR2 + EF1A2:CAS9 | DD20HR1-SAMS:HPT-DD20HR2 | 300, 299 |
| U6-9.1DD43CR1 | U6-9.1:DD43CR1 + EF1A2:CAS9 | DD43HR1-SAMS:HPT-DD43HR2 | 301, 302 |
| U6-9.1DD43CR2 | U6-9.1:DD43CR2 + EF1A2:CAS9 | DD43HR1-SAMS:HPT-DD43HR2 | 303, 302 |

Soybean somatic embryogenic suspension cultures were induced from a DuPont Pioneer proprietary elite cultivar 93B86 as follows. Cotyledons (~3 mm in length) were dissected from surface sterilized, immature seeds and were cultured for 6-10 weeks in the light at 26° C. on a Murashige and Skoog (MS) media containing 0.7% agar and supplemented with 10 mg/ml 2,4-D (2,4-Dichlorophenoxyacetic acid). Globular stage somatic embryos, which produced secondary embryos, were then excised and placed into flasks containing liquid MS medium supplemented with 2,4-D (10 mg/ml) and cultured in light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (Bio-Rad Laboratories, Hercules, Calif.). To 50 µl of a 60 mg/ml 1.0 mm gold particle suspension were added in order: 30 µl of equal amount (30 ng/µl) plasmid DNA comprising, for example, U6-9.1:DD20CR1+EF1A2:CAS9 (SEQ ID NO:298) and plasmid DNA comprising, for example, (DD20HR1-SAMS:HPT-DD20HR2, SEQ ID NO: 299) (Experiment U6-9.1 DD20CR1 listed in Table 27) 20 µl of 0.1 M spermidine, and 25 µl of 5 M $CaCl_2$. The particle preparation was then agitated for 3 minutes, spun in a centrifuge for 10 seconds and the supernatant removed. The DNA-coated particles were then washed once in 400 µl 100% ethanol and resuspended in 45 µl of 100% ethanol. The DNA/particle suspension was sonicated three times for one second each. Then 5 µl of the DNA-coated gold particles was loaded on each macro carrier disk.

Approximately 300-400 mg of a two-week-old suspension culture was placed in an empty 60×15 mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 30 mg/ml hygromycin as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 30 ng/ml hygromycin selection agent to increase mass. The embryogenic suspension cultures were then transferred to agar solid MS media plates without 2,4-D supplement to allow somatic embryos to develop. A sample of each event was collected at this stage for quantitative PCR analysis.

Cotyledon stage somatic embryos were dried-down (by transferring them into an empty small Petri dish that was seated on top of a 10 cm Petri dish containing some agar gel to allow slow dry down) to mimic the last stages of soybean seed development. Dried-down embryos were placed on germination solid media and transgenic soybean plantlets were regenerated. The transgenic plants were then transferred to soil and maintained in growth chambers for seed production. Transgenic events were sampled at somatic embryo stage or T0 leaf stage for molecular analysis.

Similar transformation experiments (U6-9.1DD20CR2, U6-9.1DD43CR1, U6-9.1DD43CR2) with the components listed in Table 27 and using the elite cultivar 93B86 were performed as described above.

Two transformation experiments, U6-9.1DD20CR1 and U6-9.1DD43CR1 listed in Table 27, were also performed in a non-elite soybean cultivar "Jack" to test the gRNA/Cas9 system performance in different soybean genotypes.

Example 20

Detection of Site-Specific NHEJ Mediated by the Guide RNA/Cas9 System in Stably Transformed Soybean Genomic DNA was extracted from somatic embryo samples and analyzed by quantitative PCR using a 7500 real time PCR system (Applied Biosystems, Foster City, Calif.) with target site-specific primers and FAM-labeled fluorescence probe to check copy number changes of the target site DD20 or DD43 (FIG. 24 A-C). The qPCR analysis was done in duplex reactions with a heat shock protein (HSP) gene as the endogenous controls and a wild type 93B86 genomic DNA sample that contains one copy of the target site with 2 alleles, as the single copy calibrator. The HSP endogenous control qPCR employed primer probe set HSP-F/HSP-T/HSP-R. The DD20-CR1 (SEQ ID NO:306) and DD20-CR2 (SEQ ID NO:307) specific qPCR employed primer probe set DD20-F (SEQ ID NO:308)/DD20-T(SEQ ID NO:309)/DD20-R(SEQ ID NO:310). The DD43-CR1 (SEQ ID NO:311) specific qPCR employed primer probe set DD43-F(SEQ ID NO:313)/DD43-T(SEQ ID NO:315)/DD43-R (SEQ ID NO:316) while the DD43-CR2 (SEQ ID NO:312) specific qPCR employed primer probe set DD43-F2 (SEQ ID NO:314)/DD43-T/DD43-R. The guide RNA/Cas9 DNA (SEQ ID NOs: 298, 300, 301, and 303) specific qPCR employed primer probe set Cas9-F (SEQ ID NO:317/Cas9-T(SEQ ID NO:318)/Cas-9-R(SEQ ID NO:319). The donor DNA (SEQ ID NOS: 299, and 302) specific qPCR employed primer probe set Sams-76F (SEQ ID NO:320)/FRT1I63-T (SEQ ID NO:321)/FRT1 I-41F (SEQ ID NO:322). The endogenous control probe HSP-T was labeled with VIC and the gene-specific probes DD20-T, DD43-T, Cas9-T, and FRT1I63-T were labeled with FAM for the simultaneous detection of both fluorescent probes (Applied Biosystems). PCR reaction data were captured and analyzed using the sequence detection software provided with the 7500 real time PCR system and the gene copy numbers were calculated using the relative quantification methodology (Applied Biosystems).

Since the wild type 93B86 genomic DNA with two alleles of the target site was used as the single copy calibrator, events without any change of the target site would be detected as one copy herein termed Wt-Homo (qPCR value >=0.7), events with one allele changed, which is no longer detectible by the target site-specific qPCR, would be detected as half copy herein termed NHEJ-Hemi (qPCR value between 0.1 and 0.7), while events with both alleles changed would be detected as null herein termed NHEJ-Null (qPCR value=<0.1). The wide range of the qPCR values suggested that most of the events contained mixed mutant and wild type sequences of the target site. High percentage of NHEJ-Hemi (ranging from 10.1 to 33.5%, Table 28) and NHEJ-Null (ranging from 32.3 to 46.4%, Table 21) were detected in all four experiments with combined NHEJ average frequencies of more than 60% (Table 28).

Both NHEJ-Hemi and NHEJ-Null were detected in the two experiments U6-9.1DD20CR1-Jack and U6-9.1DD43CR1-Jack repeated in "Jack" genotype though at lower frequencies (Table 29). The differences between NHEJ frequencies were likely caused by variations between transformation experiments.

The target region of NHEJ-Null events were amplified by regular PCR from the same genomic DNA samples using DD20-LB (SEQ ID NO: 323) and DD20-RB (SEQ ID NO: 326) primers specific respectively to DD20-HR1 and DD20-HR2 for DD20 target site specific HR1-HR2 PCR amplicon (FIG. 25 A-C; SEQ ID NO: 329), or DD43-LB (SEQ ID NO: 327) and DD43-RB (SEQ ID NO: 328) primers specific respectively to DD43-HR1 and DD43-HR2 for DD43 target site specific HR1-HR2 PCR amplicon (SEQ ID NO: 332). The PCR bands were cloned into pCR2.1 vector using a TOPO-TA cloning kit (Invitrogen) and multiple clones were sequenced to check for target site sequence changes as the results of NHEJ. Various small deletions at the Cas9 cleavage site, 3 bp upstream of the PAM, were revealed at all four tested target sites (FIG. 26 A-C). Small insertions were also detected in some sequences. Different mutated sequences were identified from some of the same events indicating the chimeric nature of these events. Some of the same mutated sequences were also identified from different events suggesting that the same mutations could have happened independently or some of the events could be clonal events. These sequence analysis confirmed the occurrence of NHEJ mediated by the guide RNA/Cas9 system at the specific Cas9 target sites.

TABLE 28

Target Site Mutations and Site Specific Gene Integration Induced by the Guide RNA/Cas9 system in elite soybean germplasm. Numbers indicate no. of events (numbers in parentheses are %). NA = not analyzed.

| Project | Total event | Wt-Homo (%) | NHEJ-Hemi (%) | NHEJ-Null (%) | Insertion Frequency (%) |
| --- | --- | --- | --- | --- | --- |
| U6-9.1DD20CR1 | 239 | 85 (35.6%) | 77 (32.2%) | 77 (32.2%) | 11 (4.6%) |
| U6-9.1DD20CR2 | 79 | 43 (54.4%) | 8 (10.1%) | 28 (35.4%) | NA |
| U6-9.1DD43CR1 | 263 | 53 (20.2%) | 88 (33.5%) | 122 (46.4%) | 10 (3.8%) |

TABLE 29

Target Site Mutations and Site Specific Gene Integration Induced by the Guide RNA/Cas9 system in non-elite soybean germplasm. Numbers indicate no. of events (numbers in parentheses are % of the total analyzed events).

| Project | Total event | Wt-Homo (%) | NHEJ-Hemi (%) | NHEJ-Null (%) | Insertion frequency (%) |
| --- | --- | --- | --- | --- | --- |
| U6-9.1DD20CR1-Jack | 149 | 99 (66.4%) | 34 (22.8%) | 16 (10.7%) | 0 (0%) |
| U6-9.1DD43CR1-Jack | 141 | 84 (59.6%) | 27 (19.1%) | 30 (21.3%) | 1 (0.7%) |

Example 21

Identification of Site-Specific Gene Integration Via Homologous Recombination Mediated by the Guide RNA/Cas9 System in Stably Transformed Soybean Site-specific gene integration via guide RNA/Cas9 system mediated DNA homologous recombination was determined by border-specific PCR analysis. The 5' end borders of DD20CR1 and DD20CR2 events were amplified as a 1204 bp DD20 HR1-SAMS PCR amplicon (SEQ ID NO: 330) by PCR with primers DD20-LB (SEQ ID NO: 323) and Sams-A1 (SEQ ID NO: 324) while the 3' borders of the same events were amplified as a 1459 bp DD20 NOS-HR2 PCR amplicon (SEQ ID NO: 331) with primers QC498A-S1 and DD20-RB (FIG. 25 A-C). Any events with both the 5' border and 3' border-specific bands amplified are considered as site-specific integration events through homologous recombination containing the transgene from the donor DNA fragment DD20HR1-SAMS:HPT-DD20HR2 or its circular form (FIG. 23). The 5' end borders of DD43CR1 and DD43CR2 events were amplified as a 1202 bp DD43 HR1-SAMS PCR amplicon (SEQ ID NO: 333) by PCR with primers DD43-LB and Sams-A1 while the 3' borders of the same events were amplified as a 1454 bp DD43 NOS-HR2 PCR amplicon (SEQ ID NO: 334) with primers QC498A-S1 (SEQ ID NO: 325) and DD43-RB (SEQ ID NO: 328). Any events with both the 5' border and 3' border-specific bands amplified are considered as site-specific integration events through homologous recombination containing the transgene from repair DNA fragment DD43HR1-SAMS:HPT-DD43HR2 or its circular form. Some of the border-specific PCR fragments were sequenced and were all confirmed to be recombined sequences as expected from homologous recombination. On average, gene integration through the guide RNA/Cas9 mediated homologous recombination occurred at approximately 4% of the total transgenic events (Insertion frequency, Table 28 and Table 29). One homologous recombination event was identified from experiment U6-9.1 DD43CR1-Jack repeated in "Jack" genotype (Table 29).

Example 22

The crRNA/tracrRNA/Cas Endonuclease System Cleaves Chromosomal DNA in Maize and Introduces Mutations by Imperfect Non-Homologous End-Joining To test whether the maize optimized crRNA/tracrRNA/Cas endonuclease system described in Example 1 could recognize, cleave, and mutate maize chromosomal DNA through imprecise non-homologous end-joining (NHEJ) repair pathways, three different genomic target sequences were targeted for cleavage (see Table 30) and examined by deep sequencing for the presence of NHEJ mutations.

TABLE 30

Maize genomic target sequences targeted by a crRNA/tracrRNA/Cas endonuclease system.

| Locus | Location | Cas RNA System Used | Target Site Designation | Maize Genomic Target Site Sequence | PAM Sequence | SEQ ID NO: |
|---|---|---|---|---|---|---|
| LIG | Chr. 2: 28.45cM | crRNA/ tracrRNA | LIGCas-1 | GTACCGTACGTGCCCCGGCGG | AGG | 16 |
| | | crRNA/ tracrRNA | LIGCas-2 | GGAATTGTACCGTACGTGCCC | CGG | 17 |
| | | crRNA/ tracrRNA | LIGCas-3 | GCGTACGCGTACGTGTG | AGG | 18 |

LIG = Liguleless 1 Gene Promoter

The maize optimized Cas9 endonuclease expression cassette, crRNA expression cassettes containing the specific maize variable targeting domains (SEQ ID NOs: 445-447) complementary to the antisense strand of the maize genomic target sequences listed in Table 30 and tracrRNA expression cassette (SEQ ID NO: 448) were co-delivered to 60-90 Hi-II immature maize embryos by particle-mediated delivery (see Example 5) in the presence of BBM and WUS2 genes (see Example 6). Hi-II maize embryos transformed with the Cas9 and long guide RNA expression cassettes targeting the LIGCas-3 genomic target site (SEQ ID NO: 18) for cleavage served as a positive control and embryos transformed with only the Cas9 expression cassette served as a negative control. After 7 days, the 20-30 most uniformly transformed embryos from each treatment were pooled and total genomic DNA was extracted. The region surrounding the intended target site was PCR amplified with Phusion® High Fidelity PCR Master Mix (New England Biolabs, M0531L) adding on the sequences necessary for amplicon-specific barcodes and Illumnia sequencing using "tailed" primers through two rounds of PCR. The primers used in the primary PCR reaction are shown in Table 31 and the primers used in the secondary PCR reaction were AATGATACGGCGACCACCGAGATCTACACTCTTTCCCTACACG (forward, SEQ ID NO: 53)

and

CAAGCAGAAGACGGCATA. (reverse, SEQ ID NO: 54)

TABLE 31

PCR primer sequences

| Target Site | Cas RNA System Used | Primer Orientation | Primary PCR Primer Sequence | SEQ ID NO: |
|---|---|---|---|---|
| LIGCas-1 | crRNA/tracrRNA | Forward | CTACACTCTTTCCCTACACGACGCTCTTCC GATCTTCCTCTGTAACGATTTACGCACCTG CTG | 36 |
| LIGCas-1 | crRNA/tracrRNA | Reverse | CAAGCAGAAGACGGCATACGAGCTCTTCC GATCTGCAAATGAGTAGCAGCGCACGTAT | 35 |
| LIGCas-2 | crRNA/tracrRNA | Forward | CTACACTCTTTCCCTACACGACGCTCTTCC GATCTGAAGCTGTAACGATTTACGCACCTG CTG | 449 |
| LIGCas-2 | crRNA/tracrRNA | Reverse | CAAGCAGAAGACGGCATACGAGCTCTTCC GATCTGCAAATGAGTAGCAGCGCACGTAT | 35 |
| LIGCas-3 | crRNA/tracrRNA | Forward | CTACACTCTTTCCCTACACGACGCTCTTCC GATCTAAGGCGCAAATGAGTAGCAGCGCAC | 37 |
| LIGCas-3 | crRNA/tracrRNA | Reverse | CAAGCAGAAGACGGCATACGAGCTCTTCC GATCTCACCTGCTGGGAATTGTACCGTA | 38 |
| LIGCas-3 | Long guide RNA | Forward | CTACACTCTTTCCCTACACGACGCTCTTCC GATCTTTCCCGCAAATGAGTAGCAGCGCAC | 450 |
| LIGCas-3 | Long guide RNA | Reverse | CAAGCAGAAGACGGCATACGAGCTCTTCC GATCTCACCTGCTGGGAATTGTACCGTA | 38 |

The resulting PCR amplifications were purified with a Qiagen PCR purification spin column, concentration measured with a Hoechst dye-based fluorometric assay, combined in an equimolar ratio, and single read 100 nucleotide-length deep sequencing was performed on Illumina's MiSeq Personal Sequencer with a 30-40% (v/v) spike of PhiX control v3 (Illumina, FC-110-3001) to off-set sequence bias. Only those reads with a ≥1 nucleotide indel arising within the 10 nucleotide window centered over the expected site of cleavage and not found in a similar level in the negative control were classified as NHEJ mutations. NHEJ mutant reads with the same mutation were counted and collapsed into a single read and the top 10 most prevalent mutations were visually confirmed as arising within the expected site of cleavage. The total numbers of visually confirmed NHEJ mutations were then used to calculate the % mutant reads based on the total number of reads of an appropriate length containing a perfect match to the barcode and forward primer.

The frequency of NHEJ mutations recovered by deep sequencing for the crRNA/tracrRNA/Cas endonuclease system targeting the three LIGCas targets (SEQ ID NOS: 16, 17, 18) compared to the long guide RNA/Cas endonuclease system targeting the same locus is shown in Table 32.

TABLE 32

Percent (%) mutant reads at maize Liguleless 1 target locus produced by crRNA/tracrRNA/Cas endonuclease system compared to the long guide RNA/Cas endonuclease system

| System | Total Number of Reads | Number of Mutant Reads | % Mutant Reads |
|---|---|---|---|
| Cas9 Only Control | 1,744,427 | 0 | 0.00% |
| LIGCas-3 long guide RNA | 1,596,955 | 35,300 | 2.21% |

TABLE 32-continued

Percent (%) mutant reads at maize Liguleless 1 target locus produced by crRNA/tracrRNA/Cas endonuclease system compared to the long guide RNA/Cas endonuclease system

| System | Total Number of Reads | Number of Mutant Reads | % Mutant Reads |
|---|---|---|---|
| LIGCas-1 crRNA/tracrRNA | 1,803,163 | 4,331 | 0.24% |
| LIGCas-2 crRNA/tracrRNA | 1,648,743 | 3,290 | 0.20% |
| LIGCas-3 crRNA/tracrRNA | 1,681,130 | 2,409 | 0.14% |

The ten most prevalent types of NHEJ mutations recovered based on the crRNA/tracrRNA/Cas endonuclease system are shown in FIG. 27A (for LIGCas-1 target site, corresponding to SEQ ID NOs:415-424), FIG. 27B (for LIGCas-2 target site corresponding to SEQ ID NOs: 425-434) and FIG. 27C (for LIGCas-3 target site corresponding to SEQ ID NOs:435-444). Approximately, 9-16 fold lower frequencies of NHEJ mutations were observed when using a crRNA/tracrRNA/Cas endonuclease system to introduce a double strand break at a maize genomic target site, relative to the long guide RNA/Cas endonuclease system control.

Taken together, our data indicate that the maize optimized crRNA/tracrRNA/Cas endonuclease system described herein cleaves maize chromosomal DNA and generates imperfect NHEJ mutations.

Example 23

Modifying the ARGOS8 Gene to Improve Drought Tolerance and Nitrogen Use Efficiency in Maize Plants ARGOS is a negative regulator for ethylene responses in plants (WO 2013/066805 A1, published 10 May 2013).

ARGOS proteins target the ethylene signal transduction pathway. When over-expressed in maize plants, ARGOS reduces plant sensitivity to ethylene and promotes organ growth, leading to increased drought tolerance (DRT) and improved nitrogen use efficiency (NUE) ((WO 2013/066805 A1, published 10 May 2013). To achieve optimal ethylene sensitivity, promoters have been tested for driving Zm-ARGOS8 over-expression in transgenic maize plants. Field trials showed that a maize promoter, Zm-GOS2 PRO:GOS2 INTRON (SEQ ID NO:460, U.S. Pat. No. 6,504,083 patent issued on Jan. 7, 2003; Zm-GOS2 is a maize homologous gene of rice GOS2. Rice GOS2 stands for Gene from Oryza Sativa 2), provided a favorable expression level and tissue coverage for Zm-ARGOS8 and the transgenic plants have a higher grain yield than non-transgenic controls under drought stress and low nitrogen conditions (WO 2013/066805 A1, published 10 May 2013). However, these transgenic plants contain two ARGOS8 genes, the endogenous gene and the transgene. ARGOS8 protein levels, therefore, are determined by these two genes. Because the endogenous ARGOS8 gene varies in sequence and the expression level among different inbred lines, the ARGOS8 protein level will be different when the transgene is integrated into different inbreds. Here we present a mutagenization (gene editing) method to modify the promoter region of the endogenous ARGOS8 gene to attain desired expression patterns and eliminate the need for a transgene.

The promoter Zm-GOS2 PRO:GOS2 INTRON (SEQ ID NO:460; U.S. Pat. No. 6,504,083 patent issued on Jan. 7, 2003) was inserted into the 5'-UTR of Zm-ARGOS8 (SEQ ID NO:462) by using a guideRNA/Cas9 system. The Zm-GOS2 PRO:GOS2 INTRON fragment also included a primer binding site (SEQ ID NO:459) at its 5' end to facilitate event screening with PCR. We also substituted the native promoter of Zm-ARGOS8 (SEQ ID NO:461) with Zm-GOS2 PRO::GOS2 INTRON (SEQ ID NO:460). Resulted maize lines carry a new ARGOS8 allele whose expression levels and tissue specificity will differ from the native form. We expect that these lines will recapitulate the phenotype of increased drought tolerance and improved NUE as observed in the Zm-GOS2 PRO:Zm-ARGOS8 transgenic plants (WO 2013/066805 A1, published 10 May 2013). These maize lines are different from those conventional transgenic events: (1) there is only one ARGOS8 gene in the genome; (2) this modified version of Zm-ARGOS8 resides at its native locus; (3) the ARGOS8 protein level and the tissue specificity of gene expression are entirely controlled by the edited allele. The DNA reagents used during the mutagenization, such as guideRNA, Cas9endonuclease, transformation selection marker and other DNA fragments are not required for function of the newly generated ARGOS8 allele and can be eliminated from the genome by segregation through standard breeding methods. Because the promoter Zm-GOS2 PRO:GOS2 INTRON was copied from maize GOS2 gene (SEQ ID NO:464) and inserted into the ARGOS8 locus through homologous recombination, this ARGOS8 allele is indistinguishable from natural mutant alleles.

A. Insertion of Zea mays-GOS2 PRO:GOS2 INTRON into Maize-ARGOS 8 Promoter

To insert Zm-GOS2 PRO:GOS2 INTRON into the 5'-UTR of maize ARGOS8 gene, a guideRNA construct, gRNA1, was made using maize U6 promoter and terminator as described herein. The 5'-end of the guide RNA contained a 19-bp variable targeting domain targeting the genomic target sequence 1 (CTS1; SEQ ID NO; 451) in the 5'-UTR of Zm-ARGOS8 (FIG. 28). A polynucleotide modification template containing the Zm-GOS2 PRO:GOS2 INTRON that was flanked by two genomic DNA fragments (HR1 and HR2, 370 and 430-bp in length, respectively) derived from the upstream and downstream region of the CTS1 (FIG. 28). The gRNA1 construct, the polynucleotide modification template, a Cas9 cassette and transformation selection marker phosphomannose isomerase (PMI) were introduced into maize immature embryo cells by using a particle bombardment method. PMI-resistant calli were screened with PCR for Zm-GOS2 PRO:GOS2 INTRON insertion (FIGS. 29A and 29B). Multiple callus events were identified and plants were regenerated. The insertion events were confirmed by amplifying the Zm-ARGOS8 region in T0 plants with PCR (FIG. 29C) and sequencing the PCR products.

B. Replacement of Zm-ARGOS 8 Promoter with Zm-GOS2 PRO:GOS2 INTRON Promoter (Promoter Swap).

To substitute (replace) the native promoter of Zm-ARGOS8 with Zm-GOS2 PRO:GOS2 INTRON, a guide RNA construct, gRNA3, was made for targeting the genomic target site CTS3 (SEQ ID NO:453), located 710-bp upstream of the Zm-ARGOS8 start codon (FIG. 30). Another guide RNA, gRNA2, was designed to target the genomic target site CTS2 (SEQ ID NO:452) located in the 5'-UTR of Zm-ARGOSO8 (FIG. 30). The polynucleotide modification template contained a 400-bp genomic DNA fragment derived from the upstream region of CTS3, Zm-GOS2 PRO:GOS2 INTRON and a 360-bp genomic DNA fragment derived from the downstream region of CTS2 (FIG. 30). The gRNA3 and gRNA2, the Cas9 cassette, the polynucleotide modification template and the PMI selection marker were used to transform immature embryo cells. Multiple promoter swap (promoter replacement) events were identified by PCR screening of the PMI-resistance calli (FIGS. 31A, 31B & 31C) and plants were regenerated. The swap events were confirmed by PCR analysis of the Zm-ARGOS8 region in T0 plants (FIG. 31D).

C. Deletion of Zm-ARGOS 8 Promoter

To delete the promoter of Zm-ARGOS8, we screened the PMI-resistance calli obtained from the above gRNA3/gRNA2 experiment to look for events that produce a 1.1-kb PCR product (FIG. 32A). Multiple deletion events were identified (FIG. 32B) and plants were regenerated. The deletion events were confirmed by amplifying the Zm-ARGOS8 region in T0 plants with PCR and sequencing of the PCR products.

Example 24

Gene Editing of the Soybean EPSPS1 Gene Using the Guide RNA/Cas Endonuclease System A. guideRNA/Cas9 Endonuclease Target Site Design on the Soybean EPSPS Genes.

Two guideRNA/Cas9 endonuclease target sites (soy EPSPS-CR1 and soy EPSPS-CR2) were identified in the Exon2 of the soybean EPSPS1 gene Glyma01g33660 (Table 33).

TABLE 33

Guide RNA/Cas9 endonuclease target sites on soybean EPSPS1 gene

| Name of gRNA-Cas9 endonuclease target site | Cas endonuclease target sequence (SEQ ID NO:) | Physical location |
|---|---|---|
| soy EPSPS-CR1 | 467 | Gm01: 45865337 ... 45865315 |
| soy EPSPS-CR2 | 468 | Gm01: 45865311 ... 45865333 |

B. Guide-RNA Expression Cassettes, Cas9 Endonuclease Expression Cassettes and Polynucleotide Modification Templates for Introduction of Specific Amino Acid Changes in the Soybean EPSPS1 Gene The soybean U6 small nuclear RNA promoter, GM-U6-13.1 (SEQ ID. NO: 469), was used to express guide RNAs to direct Cas9 nuclease to designated genomic target sites (Table 34). A soybean codon optimized Cas9 endonuclease (SEQ ID NO: 489) expression cassette and a guide RNA expression cassette were linked in a first plasmid that was co-delivered with a polynucleotide modification template. The polynucleotide modification template contained specific nucleotide changes that encoded for amino acid changes in the EPSPS1 polypeptide (Glyma01g33660), such as the T183I and P187S (TIPS) in the Exon2. Other amino acid changes in the EPSPS1 polypeptide can also be obtained using the guide RNA/Cas endonuclease system described herein. Specific amino acid modifications can be achieved by homologous recombination between the genomic DNA and the polynucleotide modification template facilitated by the guideRNA/Cas endonuclease system.

TABLE 34

Guide RNA/Cas9 expression cassettes and polynucleotide modification templates used in soybean stable transformation for the specific amino acid modifications of the EPSPS1 gene.

| Experiment | Guide RNA/Cas9 (plasmid name) | SEQ ID NO: | polynucleotide modification template | SEQ ID NO: |
|---|---|---|---|---|
| soy EPSPS-CR1 | U6-13.1:EPSPS CR1 + EF1A2:CAS9 (QC878) | 470 | RTW1013A | 472 |
| soy EPSPS-CR2 | U6-13.1:EPSPS CR2 + EF1A2:CAS9 (QC879) | 471 | RTW1012A | 473 |

C. Detection of Site-Specific Non-Homologous-End-Joining (NHEJ) Mediated by the Guide RNA/Cas9 System in Stably Transformed Soybean Genomic DNA was extracted from somatic embryo samples and analyzed by quantitative PCR using a 7500 real time PCR system (Applied Biosystems, Foster City, Calif.) with target site-specific primers and FAM-labeled fluorescence probe to check copy number changes of the double strand break target sites. The qPCR analysis was done in duplex reactions with a syringolide induced protein (SIP) as the endogenous controls and a wild type 93B86 genomic DNA sample that contains one copy of the target site with 2 alleles, as the single copy calibrator. The presence or absence of the guide RNA—Cas9 expression cassette in the transgenic events was also analyzed with the qPCR primer/probes for guideRNA/Cas9 (SEQ IDs: 477-479) and for PinII (SEQ ID: 480-482). The qPCR primers/probes are listed in Table 35.

TABLE 35

Primers/Probes used in qPCR analyses of transgenic soybean events.

| Target Site | Primer/Probe Name | Sequences | SEQ ID NOs: |
|---|---|---|---|
| EPSPS-CR1 & EPSPS-CR2 | Soy1-F1 | CCACTAGTAAGGAATCTAAAGATGAAATCA | 474 |
| | Soy1-R2 | CCTGCAGCAACCACAGCTGCTGTC | 475 |
| | Soy1-T1 (FAM-MGB) | CTGCAATGCGTCCTT | 476 |
| gRNA/CAS9 | Cas9-F | CCTTCTTCCACCGCCTTGA | 477 |
| | Cas9-R | TGGGTGTCTCTCGTGCTTTTT | 478 |
| | Cas9-T (FAM-MGB) | AATCATTCCTGGTGGAGGA | 479 |
| pINII | pINII-99F | TGATGCCCACATTATAGTGATTAGC | 480 |
| | pINII-13R | CATCTTCTGGATTGGCCAACTT | 481 |
| | pINII-69T (FAM-MGB) | ACTATGTGTGCATCCTT | 482 |
| SIP | SIP-130F | TTCAAGTTGGGCTTTTTCAGAAG | 483 |
| | SIP-198R | TCTCCTTGGTGCTCTCATCACA | 484 |
| | SIP-170T (VIC-MGB) | CTGCAGCAGAACCAA | 485 |

The endogenous control probe SIP-T was labeled with VIC and the gene-specific probes for all the target sites were labeled with FAM for the simultaneous detection of both fluorescent probes (Applied Biosystems). PCR reaction data were captured and analyzed using the sequence detection software provided with the 7500 real time PCR system and the gene copy numbers were calculated using the relative quantification methodology (Applied Biosystems).

Since the wild type 93B86 genomic DNA with two alleles of the double strand break target site was used as the single copy calibrator, events without any change of the target site would be detected as one copy herein termed Wt-Homo (qPCR value >=0.7), events with one allele changed, which is no longer detectible by the target site-specific qPCR, would be detected as half copy herein termed NHEJ-Hemi (qPCR value between 0.1 and 0.7), while events with both alleles changed would be detected as null herein termed NHEJ-Null (qPCR value=<0.1). As shown in Table 36, both guideRNA/Cas endonuclease systems targeting the soy EPSPS-CR1 and EPSPS-CR2 sites can introduce efficient Double Strand Break (DSB) efficiency at their designed target sites. Both NHEJ-Hemi and NHEJ-Null were detected in the 93B86 genotype. NHEJ (Non-Homologous-End-Joining) mutations mediated by the guide RNA/Cas9 system at the specific Cas9 target sites were confirmed by PCR/topo cloning/sequencing.

TABLE 36

Target Site Double Strand Break Rate Mutations Induced by the Guide RNA/Cas9 system on soybean EPSPS1 gene. Numbers indicate no. of events (numbers in parentheses are %).

| Project | Total event | Wt-Homo (%) | NHEJ-Hemi (%) | NHEJ-Null (%) |
|---|---|---|---|---|
| U6-13.1 EPSPS-CR1 | 168 | 63 (38%) | 66 (39%) | 39 (23%) |
| U6-13.1 EPSPS-CR2 | 111 | 50 (45%) | 21 (19%) | 40 (36%) |

D. Detection of the TIPS Mutation in the Soybean EPSPS Gene

In order to edit specific amino acids at the native EPSPS gene (such as those resulting in a TIPS modification), a polynucleotide modification template, such as RTW1013A or RTW1012A (Table 34), was co-delivered with the guideRNA/Cas9 expression cassettes into soybean cells.

The modification of the native EPSPS1 gene via guide RNA/Cas9 system mediated DNA homologous recombination was determined by specific PCR analysis. A specific PCR assay with primer pair WOL569 (SEQ ID NO: 486) and WOL876 (SEQ ID NO: 487) was used to detect perfect TIPS modification at the native EPSPS1 gene. A second primer pair WOL569 (SEQ ID NO: 486) and WOL570 (SEQ ID NO: 488) was used to amplify both TIPS modified EPSPS1 allele and WT (wild type)/NHEJ mutated allele. Topo cloning/sequencing was used to verify the sequences.

Example 25

Intron Replacement of Soybean Genes Using the guideRNA/Cas Endonuclease System

A. guideRNA/Cas9 Endonuclease Target Site Design.

Four guideRNA/Cas9 endonuclease target sites were identified in the soybean EPSPS1 gene Glyma01g33660 (Table 37). Two of the target sites (soy EPSPS-CR1 and soy EPSPS-CR2) were identified to target the Exon2 of the soybean EPSPS gene as described in Example 24. Another two target sites (soy EPSPS-CR4 and soy EPSPS-CR5) were designed near the 5' end of the intron1 of the soybean EPSPS gene.

TABLE 37

Guide RNA/Cas9 endonuclease target sites on soybean EPSPS1 gene.

| Name of gRNA-Cas9 endonuclease target site | Cas endonuclease target sequence (SEQ ID NO:) | Physical location |
|---|---|---|
| soy EPSPS-CR1 | 467 | Gm01: 45865337..45865315 |
| soy EPSPS-CR2 | 468 | Gm01: 45865311..45865333 |
| soy EPSPS-CR4 | 490 | Gm01: 45866302..45866280 |
| soy EPSPS-CR5 | 491 | Gm01: 45866295..45866274 |

B. Guide RNA/Cas9 Endonuclease Expression Cassettes and Polynucleotide Modification Templates Used in Soybean Stable Transformation for the Replacement of the Intron 1 of the Soybean EPSPS1 Gene with the Soybean Ubiquitin (UBQ) Intron 1

The soybean U6 small nuclear RNA promoter GM-U6-13.1 (SEQ ID. NO: 469) was used to express two guide RNAs (soy-EPSPS-CR1 and soy-EPSPS-CR4, or soy-EPSPS-CR1 and soy-EPSPS-CR5) to direct Cas9 endonuclease to designated genomic target sites (Table 38). One of the target sites (soy-EPSPS-CR1) was located in the exon2, as described in Example 24, and a second target site (soy-EPSPS-CR4 or soy-EPSPS-CR5) was located near the 5' end of intron1 of the native EPSPS1 gene. A soybean codon optimized Cas9 endonuclease expression cassette and a guide RNA expression cassette were linked in the expression plasmids QC878/RTW1199 (SEQ ID NO:470/492) or QC878/RTW1200 (SEQ ID NO:470/493) that was co-delivered with a polynucleotide modification template. The polynucleotide modification template, RTW1190A (SEQ ID NO:494), contained 532 bp intron1 of the soybean UBQ gene and the TIPS modified Exon2. Soybean EPSPS1 intron 1 replacement with the soybean UBQ intron1 can be achieved with the guide RNA/Cas system by homologous recombination between the genomic DNA and the polynucleotide modification template, resulting in enhancement of the native or modified soy EPSPS1 gene expression.

TABLE 38

Guide RNA/Cas9 endonuclease expression cassettes and polynucleotide modification templates used in soybean stable transformation for the replacement of the Intron1 of the soybean EPSPS1 gene with the soybean ubiquitin (UBQ) intron1

| Experiment | Guide RNA/Cas9 | SEQ ID NO: | poly-nucleotide modification template | SEQ ID NO: |
|---|---|---|---|---|
| soy EPSPS-CR1 and soy EPSPS-CR4 | U6-13.1:EPSPS CR1 + CR4 + EF1A2:CAS9 (QC878/RTW1199) | 470/492 | RTW1190A | 494 |
| soy EPSPS-CR1 and soy EPSPS-CR5 | U6-13.1:EPSPS CR1 + CR5 + EF1A2:CAS9 (QC878/RTW1200) | 470/493 | RTW1190A | 494 |

C. Detection of Site-Specific NHEJ Mediated by the Guide RNA/Cas9 System in Stably Transformed Soybean Site-specific NHEJ was detected as described in Example 24 C, using the qPCR primers/probes listed in Table 39.

TABLE 39

Primers/Probes used in qPCR analyses of transgenic soybean events.

| Target Site | Primer/Probe Name | Sequences | SEQ ID NOs: |
|---|---|---|---|
| EPSPS-CR1 & EPSPS-CR2 | Soy1-F1 | CCACTAGTAAGGAATCTAAAGATGAAATCA | 474 |
|  | Soy1-R2 | CCTGCAGCAACCACAGCTGCTGTC | 475 |
|  | Soy1-T1 (FAM-MGB) | CTGCAATGCGTCCTT | 476 |
| EPSPS-CR4 | Soy1-F3 | GTTTGTTTGTTGTTGGGTGTGGG | 495 |
|  | Soy1-R3 | GACATGATGCTTCATTTTCACAGAA | 496 |
|  | Soy-T2 (FAM-MGB) | TGTGTAGAGTGGATTTTG | 497 |
| EPSPS-CR5 | Soy1-F2 | TGTTGTTGGGTGTGGGAATAGG | 498 |
|  | Soy1-R3 | GACATGATGCTTCATTTTCACAGAA | 496 |
|  | Soy1-T2 (FAM-MGB) | TGTGTAGAGTGGATTTTG | 497 |
| gRNA/CAS9 | Cas9-F | CCTTCTTCCACCGCCTTGA | 477 |
|  | Cas9-R | TGGGTGTCTCTCGTGCTTTTT | 478 |
|  | Cas9-T (FAM-MGB) | AATCATTCCTGGTGGAGGA | 479 |
| pINII | pINII-99F | TGATGCCCACATTATAGTGATTAGC | 480 |
|  | pINII-13R | CATCTTCTGGATTGGCCAACTT | 481 |
|  | pINII-69T (FAM-MGB) | ACTATGTGTGCATCCTT | 482 |
| SIP | SIP-130F | TTCAAGTTGGGCTTTTTCAGAAG | 483 |
|  | SIP-198R | TCTCCTTGGTGCTCTCATCACA | 484 |
|  | SIP-170T (VIC-MGB) | CTGCAGCAGAACCAA | 485 |

D. Detection of the Replacement of the Soybean EPSPS 1 Intron 1 with the Soybean UBQ Intron 1 Using the Guide RNA/Cas9 Endonuclease System.

In order to replace the soybean EPSPS1 intron1 with the soybean UBQ intron1 at the native EPSPS1 gene, two guideRNA expression vectors were used as shown in Table 38. The QC878 vector (SEQ ID NO: 470) was targeting the exon2 and the RTW1199 (SEQ ID NO:492) or RTW1200 (SEQ ID NO:493) was targeting the 5' end of the intron1. The double cleavage of soybean EPSPS gene with the two guide RNA/Cas systems resulted in the removal of the native EPSPS1 intron1/partial Exon2 fragment. At the same time, a polynucleotide modification template RTW1190A (SEQ ID NO:494) was co-delivered into soybean cells and homologous recombination between the polynucleotide modification template and the genomic DNA resulted in the replacement of EPSPS1 intron1 with the soybean UBQ intronland the desired amino acid modifications in exon2 as evidenced by PCR analysis. PCR assays with primer WOL1001/WOL1002 pair (SEQ ID NO: 499 and 500) and WOL1003/WOL1004 pair (SEQ ID NO: 501 and 502) were used to detect the intron replacement events.

Example 26

Promoter Replacement (Promoter Swap) of Soybean Genes Using the guideRNA/Cas Endonuclease System A. guideRNA/Cas9 Endonuclease Target Site Design.

Four guideRNA/Cas9 endonuclease target sites were identified in the soybean EPSPS1 gene Glyma01g33660 (Table 40). Two of the target sites (soy EPSPS-CR1 and soy EPSPS-CR2) were identified to target the Exon2 of the soybean EPSPS gene as described in Example 24. The soy EPSPS-CR6 and soy EPSPS-CR7 were identified near the 5' end of the −798 bp of the native EPSPS promoter.

TABLE 40

Guide RNA/Cas9 endonuclease target sites on soybean EPSPS1 gene.

| Name of gRNA-Cas9 endonuclease target site | Cas endonuclease target sequence (SEQ ID NO:) | Physical location |
|---|---|---|
| soy EPSPS-CR1 | 467 | Gm01: 45865337..45865315 |
| soy EPSPS-CR2 | 468 | Gm01: 45865311..45865333 |
| soy EPSPS-CR6 | 503 | Gm01: 45867471..45867493 |
| soy EPSPS-CR7 | 504 | Gm01: 45867459..45867481 |

B. Guide RNA/Cas9 Endonuclease Expression Cassettes and Polynucleotide Modification Templates Used in Soybean Stable Transformation for the Replacement of the −798 bp Soybean EPSPS1 Promoter with the Soybean UBQ Promoter.

The soybean U6 small nuclear RNA promoter GM-U6-13.1 (SEQ ID. NO: 469) was used to express two guide RNAs (soyEPSPS-CR1 and soyEPSPS-CR6, or soyEPSPS-CR1 and soyEPSPS-CR7) to direct Cas9 nuclease to designated genomic target sites (Table 41). One of the target sites (soy-EPSPS-CR1) was located in the exon2 as described in Example 24 and a second target site (soy-EPSPS-CR6 or soy-EPSPS-CR7) was located near 5' end of the −798 bp of the native EPSPS1 promoter. A soybean codon optimized Cas9 endonuclease expression cassette and a guide RNA expression cassette were linked in the expression plasmids QC878/RTW1201 (SEQ ID NO:470/505) or QC878/RTW1202 (SEQ ID NO:470/506) that was co-delivered with a polynucleotide modification template, RTW1192A (SEQ ID NO:507). The polynucleotide modification template contained 1369 bp of the soybean UBQ gene promoter, 47 bp 5UTR and 532 bp UBQ intron1. Specific soybean EPSPS1 promoter replacement with the soybean UBQ promoter can be achieved with the guide RNA/Cas system by homologous recombination between the genomic DNA and the polynucleotide modification template, resulting enhancement of the native or modified soy EPSPS1 gene expression

TABLE 41

Guide RNA/Cas9 endonuclease expression cassettes and polynucleotide modification templates used in soybean stable transformation for the replacement of the −798 bp soybean EPSPS1 promoter with the soybean UBQ promoter

| Experiment | Guide RNA/Cas9 | SEQ ID NO: | polynucleotide modification template | SEQ ID NO: |
|---|---|---|---|---|
| soy EPSPS-CR1 and soy EPSPS-CR6 | U6-13.1:EPSPS CR1 + CR6 + EF1A2:CAS9 (QC878/RTW1201) | 470, 505 | RTW1192A | 507 |
| soy EPSPS-CR1 and soy EPSPS-CR7 | U6-13.1:EPSPS CR1 + CR7 + EF1A2:CAS9 (QC878/RTW1202) | 470, 506 | RTW1192A | 507 |

C. Detection of Site-Specific NHEJ Mediated by the Guide RNA/Cas9 System in Stably Transformed Soybean Site-specific NHEJ was detected as described in Example 24 C, using the qPCR primers/probes listed in Table 42.

TABLE 42

Primers/Probes used in qPCR analyses of transgenic soybean events

| Target Site | Primer/Probe Name | Sequences | SEQ ID NOs: |
|---|---|---|---|
| EPSPS-CR1 & EPSPS-CR12 | Soy1-F1 | CCACTAGTAAGGAATCTAAAGATGAAATCA | 474 |
| | Soy1-R2 | CCTGCAGCAACCACAGCTGCTGTC | 475 |
| | Soy1-T1 (FAM-MGB) | CTGCAATGCGTCCTT | 476 |
| EPSPS-CR6 & EPSPS-CR7 | Soy1-F4 | TCAATAATACTACTCTCTTAGACACCAAACAA | 508 |
| | Soy1-R4 | CAAGGAAAATGAATGATGGCTTT | 509 |
| | Soy1-T3 (FAM-MGB) | CCTTCCCAAACTATAATC | 510 |
| gRNA/CAS9 | Cas9-F | CCTTCTTCCACCGCCTTGA | 477 |
| | Cas9-R | TGGGTGTCTCTCGTGCTTTTT | 478 |
| | Cas9-T (FAM-MGB) | AATCATTCCTGGTGGAGGA | 479 |
| pINII | pINII-99F | TGATGCCCACATTATAGTGATTAGC | 480 |
| | pINII-13R | CATCTTCTGGATTGGCCAACTT | 481 |
| | pINII-69T (FAM-MGB) | ACTATGTGTGCATCCTT | 482 |
| SIP | SIP-130F | TTCAAGTTGGGCTTTTTCAGAAG | 483 |
| | SIP-198R | TCTCCTTGGTGCTCTCATCACA | 484 |
| | SIP-170T (VIC-MGB) | CTGCAGCAGAACCAA | 485 |

D. Detection of the Promoter Replacement of the Soybean EPSPS 1 Promoter with the Soybean UBQ Promoter Using the Guide RNA/Cas9 Endonuclease System.

In order to replace the soybean EPSPS1 promoter with the soybean UBQ promoter at the native EPSPS1 gene, two guideRNA expression vectors were used in each soybean transformation experiment as shown in Table 41. The QC878 (SEQ ID NO: 470) was targeting the exon2 and the RTW1201 (SEQ ID NO: 505) or RTW1202 (SEQ ID NO: 506) was targeting the 5′ end of the soybean −798 bp promoter. The double cleavage of the soybean EPSPS1 gene with the two guide RNA/Cas systems resulted in removal of the native EPSPS1 promoter/5′UTR-Exon1/Intron1/partial Exon2 fragment at the native EPSPS gene. At the same time, a polynucleotide modification template RTW1192A (SEQ ID NO: 507) was co-delivered into soybean cells. This RTW1192A DNA contained 1369 bp soybean UBQ promoter, its 47 bp 5-UTR and 532 bp UBQ intron1 in front of the EPSPS1 exon1-Intron1-modified Exon2. Homologous recombination between the polynucleotide modification template and the genomic DNA resulted in the replacement of EPSPS1 promoter/5′UTR with the soybean UBQ promoter/5′UTR/Intron1 and the desired amino acid modifications evidenced by PCR analysis. PCR assays with primer WOL1005/WOL1006 pair (SEQ ID NO: 511 and 512) and WOL1003/WOL1004 pair (SEQ ID NO: 501 and 502) were used to detect the promoter replacement events.

Example 27

Enhancer Element Deletions Using the guideRNA/Cas Endonuclease System

The guide RNA/Cas endonuclease system described herein can be used to allow for the deletion of a promoter element from either a transgenic (pre-existing, artificial) or endogenous gene. Promoter elements, such as enhancer elements, or often introduced in promoters driving gene expression cassettes in multiple copies (3×=3 copies of enhancer element, FIG. 33) for trait gene testing or to produce transgenic plants expressing specific trait. Enhancer elements can be, but are not limited to, a 35S enhancer element (Benfey et al, EMBO J, August 1989; 8(8): 2195-2202, SEQ ID NO:513). In some plants (events), the enhancer elements can cause an unwanted phenotype, a yield drag, or a change in expression pattern of the trait of interest that is not desired. For example, as shown in FIG. 33, a plant comprising multiple enhancer elements (3 copies, 3×) in its genomic DNA located between two trait cassettes (Trait A en Trait B) was characterized to show an unwanted phenotype. It is desired to remove the extra copies of the enhancer element while keeping the trait gene cassettes intact at their integrated genomic location. The guide RNA/Cas endonuclease system described herein can be used to removing the unwanted enhancing element from the plant genome. A guide RNA can be designed to contain a variable targeting region targeting a target site sequence of 12-30 bps adjacent to a NGG (PAM) in the enhancer. If a Cas endonuclease target site sequence is present in all copies of the enhancer elements (such as the three Cas endonuclease target sites 35S-CRTS1 (SEQ ID NO:514), 35S-CRTS2 (SEQ ID NO:515), 35S-CRTS3 (SEQ ID NO:516)), only one guide RNA is needed to guide the Cas endonuclease to the target sites and induce a double strand break in all the enhancer elements at once. The Cas endonuclease can make cleavage to remove one or multiple enhancers. The guideRNA/Cas endonuclease system can introduced by either *agrobacterium* or particle gun bombardment. Alternatively, two different guide RNAs (targeting two different genomic target sites) can be used to remove all 3× enhancer elements from the genome of an organism, in a manner similar to the removal of a (transgenic or endogenous) promoter described herein.

Example 28

Regulatory Sequence Modifications Using the Guide RNA/Cas Endonuclease System

A. Modification of Polyubiquitination Sites

There are defined ubiquitination sites on proteins to be degraded and they were found within the maize EPSPS protein by using dedicated computer programs (for example, the CKSAAP_UbSite (Ziding Zhang's Laboratory of Protein Bioinformatics College of Biological Sciences, China Agricultural University, 100193 Beijing, China). One of the selected polyubiquitination site within the maize EPSPS coding sequence is shown in FIG. 34A and its amino acid signature sequence is compared to the equivalent EPSPS sites from the other plants (FIG. 34A). The lysine amino acid (K) at position 90 (highly conserved in other plant species) was selected as a potential site of the EPSPS protein polyubiquitination. The polynucleotide modification template (referred to as EPSPS polynucleotide maize K90R template) used to edit the epsps locus is listed as SEQ ID NO: 517. This template allowed for editing the epsps locus to contain the lysine (K) to arginine (R) substitution at position 90 (K90R) and two additional TIPS substitutions at positions 102 and 106 (FIGS. 34B and 34C). Maize genomic DNA was edited using the guideRNA/Cas endonuclease system described herein and T0 plants were produced as described herein. The T0 plants that contained the nucleotide modifications, as specified by the information provided on the K90R template (FIG. 34C), were selected by the genotyping methods described herein. F1 EPSPS-K90R plants can be selected for elevated protein content due to a slower rate of the EPSPS protein degradation.

B. Editing Intron Elements to Introduce Intron Mediated Enhancer Elements (IMEs)

Transcriptional activity of the native EPSPS gene can be modulated by transcriptional enhancers positioned in the vicinity of other transcription controlling elements. Introns are known to contain enhancer elements affecting the overall rate of transcription from native promoters including the EPSPS promoter. For example, the first intron of the maize ubiquitin 5'UTR confers a high level of expression in monocot plants as specified in the WO 2011/156535 A1 patent application. An intron enhancing motif CATATCTG (FIG. 35 A), also referred to as a intron-mediated enhancer element, IME) was identified by proprietary analysis (WO2011/156535 A1, published on Dec. 15, 2011) and appropriate nucleotide sites at the 5' end of the EPSPS first intron were selected for editing in order to introduce the intron-mediated enhancer elements (IMEs) (FIG. 35B-35C). The polynucleotide modification template (referred to as EPSPS polynucleotide maize IME template) is listed as SEQ ID No: 518. The polynucleotide modification template allows for editing of the epsps locus to contain three IMEs (two on one strand of the DNA, one on the reverse strand) in the first EPSPS intron and the TIPS substitutions at positions 102 and 106. The genomic DNA of maize plants was edited using the guideRNA/Cas endonuclease system described herein. Maize plants containing the IME edited EPSPS coding sequence can be selected by genotyping the T0 plants and can be further evaluated for elevated EPSPS-TIPS protein content due to the enhanced transcription rate of the native EPSPS gene.

Example 29

Modifications of Splicing Sites and/or Introducing Alternate Splicing Sites Using the Guide RNA/Cas Endonuclease System In maize cells, the splicing process is affected by splicing sites at the exon-intron junction sites as illustrated in the EPSPS mRNA production (FIG. 36A-36B). FIG. 36A shows analysis of EPSPS amplified pre-mRNA (cDNA panel on left). Lane 14 in FIG. 36A shows amplification of the EPSPS pre-mRNA containing the $3^{rd}$ intron unspliced, resulting in a 804 bp diagnostic fragment indicative for an alternate splicing event. Lanes E3 and F8 show the EPSPS PCR amplified fragments resulting from regular spliced introns. Diagnostic fragments such as the 804 bp fragment of lane 14 are not amplified unless cDNA is synthesized (as is evident by the absence of bands in lanes E3, 14, and F8 comprising total RNA (shown in the total RNA panel on right of FIG. 36A). The canonical splice site in the maize EPSPS gene and genes from other species is AGGT, while other (alterative) variants of the splice sites may lead to the aberrant processing of pre-mRNA molecules. The EPSPS coding sequence contains a number of alternate splicing sites that may affect the overall efficiency of the pre-mRNA maturation process and as such may limit the EPSPS protein accumulation in maize cells.

In order to limit the occurrence of alternate splicing events during EPSPS gene expression, a guideRNA/Cas endonuclease system as described herein can be used to edit splicing sites. The splicing site at the junction of the second native EPSPS intron and the third exon is AGTT and can be edited in order to introduce the canonical AGGT splice site at this junction (FIG. 37). The T>G substitution does not affect the native EPSPS open reading frame and it does not change the EPSPS amino acid sequence. The polynucleotide modification template (referred to as EPSPS polynucleotide maize Tspliced template) is listed as SEQ ID NO: 519. This polynucleotide modification template allows for editing of the epsps locus to contain the canonical AGGT splice site at the $2^{nd}$ intron-$3^{rd}$ exon junction site and the TIPS substitutions at positions 102 and 106. Maize plants are edited using the procedures described herein. F1 EPSPS-Tspliced maize plants can be evaluated for increased protein content due to the enhanced production of functional EPSPS mRNA messages.

Example 30

Shortening Maturity Via Manipulation of Early Flowering Phenotype with ZmRap2.7 Down-Regulation Using the Guide RNA/Cas Endonuclease System Overall plant maturity can be shortened by modulating the flowering time phenotype of plants through modulation of a maize ZmRap2.7 gene. Shortening of plant maturity can be obtained by an early flowering phenotype.

RAP2.7 is an acronym for Related to APETALA 2.7. RAPL means RAP2.7 LIKE and RAP2.7 functions as an AP2-family transcription factor that suppresses floral transition (SEQ ID NOs:520 and 521). Transgenic phenotype upon silencing or knock-down of Rap2.7 resulted in early flowering, reduced plant height, but surprisingly developed normal ear and tassel as compared the wild-type plants (PCT/US14/26279 application, filed Mar. 13, 2014). The guide RNA/Cas endonuclease system described herein can be used to target and induce a double strand break at a Cas endonuclease target site located within the RAP2.7 gene. Plants comprising NHEJ within the RAP2.7 gene can be selected and evaluated for the presence of a shortened maturity phenotype.

Example 31

Modulating Expression of a Maize NPK1B Gene for Engineering Frost Tolerance in Maize Using a Guide RNA/Cas Endonuclease System

*Nicotiana* Protein Kinase1 (NPK1) is a mitogen activated protein kinase kinase kinase that is involved in cytokinesis regulation and oxidative stress signal transduction. The ZM-NPK1B (SEQ ID NO: 522 and SEQ ID NO: 523) which has about 70% amino acid similarity to rice NPKL3 has been tested for frost tolerance in maize seedlings and reproductive stages (PCT/US14/26279 application, filed Mar. 13, 2014). Transgenic seedlings and plants comprising a ZM-NPK1B driven by an inducible promoter Rab17, had significantly higher frost tolerance than control seedlings and control plants. The gene seemed inducted after cold acclimation and during −3° C. treatment period in most of the events but at low levels. (PCT/US14/26279 application, filed Mar. 13, 2014).

A guide RNA/Cas endonuclease system described herein can be used to replace the endogenous promoter of NPK1 gene, with a stress-inducible promoter such as the maize RAB17 promoter stages (SEQ ID NO: 524; PCT/US14/26279 application, filed Mar. 13, 2014), thus modulate NPK1B expression in a stress-responsive manner and provide frost tolerance to the modulated maize plants.

Example 32

Shortening Maturity Via Manipulation of Early Flowering Phenotype with FTM1 Expression Using a Guide RNA/Cas Endonuclease Systems Overall plant maturity can shortened by modulating the flowering time phenotype of plants through expressing a transgene. Such a phenotype modification can also be achieved with additional transgenes or through a breeding approach.

FTM1 stands for Floral Transition MADS 1 transcription factor (SEQ ID NOs: 525 and 526). It is a MADS Box transcriptional factor and induces floral transition. Upon expression of FTM1 under a constitutive promoter, transgenic plants exhibited early flowering and shortened maturity, but surprisingly ear and tassel developed normally as compared to the wild-type plants (PCT/US14/26279 application, filed Mar. 13, 2014).

FTM1-expressing maize plants demonstrated that by manipulating a floral transition gene, time to flowering can be reduced significantly, leading to a shortened maturity for the plant. As maturity can be generally described as time from seeding to harvest, a shorter maturity is desired for ensuring that a crop can finish in the northern continental dry climatic environment (PCT/US14/26279 application, filed Mar. 13, 2014).

A guide RNA/Cas endonuclease system described herein can be used to introduce enhancer elements such as the CaMV35S enhancers (Benfey et al, EMBO J, August 1989; 8(8): 2195-2202, SEQ ID NO:512), specifically targeted in front of the endogenous promoter of FTM1, in order to enhance the expression of FTM1 while preserving most of the tissue and temporal specificities of native expression, providing shortened maturity to the modulated plants.

Example 33

Inserting Inducible Responsive Elements in Plant Genomes

Inducible expression systems controlled by an external stimulus are desirable for functional analysis of cellular proteins as well as trait development as changes in the expression level of the gene of interest can lead to an accompanying phenotype modification. Ideally such a system would not only mediate an "on/off" status for gene expression but would also permit limited expression of a gene at a defined level.

The guide RNA/Cas endonuclease system described herein can be used to introduce components of repressor/operator/inducer systems to regulate gene expression of an organism. Repressor/operator/inducer systems and their components are well known I the art (US 2003/0186281 published Oct. 2, 2003; U.S. Pat. No. 6,271,348). For example, nut not limited to, components of the tetracycline (Tc) resistance system of *E. coli* have been found to function in eukaryotic cells and have been used to regulate gene expression (U.S. Pat. No. 6,271,348). Nucleotide sequences of tet operators of different classes are known in the art see for example: classA, calssB, classC, classD, classE TET operator sequences listed as SEQ ID NOs:11-15 of U.S. Pat. No. 6,271,348.

Components of a sulfonylurea-responsive repressor system (as described in U.S. Pat. No. 8,257,956, issued on Sep. 4, 2012) can also be introduced into plant genomes to generate a repressor/operator/inducer systems into said plant where polypeptides can specifically bind to an operator, wherein the specific binding is regulated by a sulfonylurea compound.

Example 34

Genome Deletion for Trait Locus Characterization

Trait mapping in plant breeding often results in the detection of chromosomal regions housing one or more genes controlling expression of a trait of interest. For quantitative traits, expression of a trait of interest is governed by multiple quantitative trait loci (QTL) of varying effect-size, complexity, and statistical significance across one or more chromosomes. A QTL or haplotype that is associated with suppression of kernel-row number in the maize ear can be found to be endemic in elite breeding germ plasm. The negative effect of this QTL for kernel row number can be fine-mapped to an acceptable resolution to desire selective elimination of this negative QTL segment within specific recipient germplasm. Two flanking cut sites for the guide polynucleotide/Cas endonuclease system are designed via haplotype, marker, and/or DNA sequence context at the targeted QTL region, and the two guide polynucleotide/Cas endonuclease systems are deployed simultaneously or sequentially to produce the desired end product of two independent double strand breaks (cuts) that liberate the intervening region from the chromosome. Individuals harboring the desired deletion event would result by the NHEJ repair of the two chromosomal ends and eliminating the intervening DNA region. Assays to identify these individuals is based on the presence of flanking DNA marker regions, but absence of intervening DNA markers. A proprietary haplotype for kernel-row-number is created that is not extant in the previously defined elite breeding germplasm pool.

An alternative approach would be to delete a region containing a fluorescent gene. Recovery of plants with, and without, fluorescence would give an approximate indication of the efficiency of the deletion process.

Example 35

Engineering Drought Tolerance and Nitrogen Use Efficiency into Maize Via Gene Silencing by Expressing an Inverted Repeat into an ACS6 Gene Using the Guide RNA/Cas Endonuclease System ACC (1-aminocyclopropane-1-carboxylic acid) synthase (ACS) genes encode enzymes that catalyze the rate limiting step in ethylene biosynthesis. A construct containing one of the maize ACS genes, ZM-ACS6, in an inverted repeat configuration, has been extensively tested for improved abiotic stress tolerance in maize (PCT/US2010/051358, filed Oct. 4, 2010; PCT/US2010/031008, filed Apr. 14, 2010). Multiple transgenic maize events containing a ZM-ACS6 RNAi sequence driven by a ubiquitin constitutive promoter had reduced ethylene emission, and a concomitant increase in grain yield relative to controls under both drought and low nitrogen field conditions (Plant Biotechnology Journal: 12 Mar. 2014, DOI: 10.1111/pbi.12172).

In an embodiment the insertion of the inverted gene fragment can result in the formation of an in-vivo created inverted repeat (hairpin) in a native (or modified) promoter of an ACS6 gene and/or in a native 5' end of the native ACS6 gene. The inverted gene fragment can further comprise an intron which can result in an enhanced silencing of the targeted ethylene biosynthetic gene.

Example 36

T0 Plants from the Multiplexed Guide RNA/Cas Experiment Carried High Frequency of Bi-Allelic Mutations and Demonstrated Proper Inheritance of Mutagenized Alleles in the T1 Population This example demonstrates the high efficiency of the guide RNA/Cas endonuclease system in generating maize plants with multiple mutagenized loci and their inheritance in the consecutive generation(s).

Mutated events generated in the multiplexed experiment described in Example 4 were used to regenerate T0 plants with mutations at 3 different target sites: MS26Cas-2 target site (SEQ ID NO: 14), LIGCas-3 target site (SEQ ID NO: 18) and MS45Cas-2 target site (SEQ ID NO: 20).

For further analysis, total genomic DNA was extracted from leaf tissue of individual T0 plants. Fragments spanning all 3 target sites were PCR amplified using primer pairs for the corresponding target sites, cloned into the pCR2.1-TOPO cloning vector (Invitrogen), and sequenced. Table 43 shows examples of mutations detected in four T0 plants resulting from imprecise NHEJ at all relevant loci when multiple guide RNA expression cassettes were simultaneously introduced either in duplex (see TS=Lig34/MS26) or triplex (see TS=Lig34/MS26/MS45), respectively.

TABLE 43

Examples of mutations at maize target loci produced by a multiplexed guide RNA/Cas system

| Target sites (TS) | T0 plant | qPCR data | Sequencing data | | |
|---|---|---|---|---|---|
| | | | Lig3/4 TS | Ms26 TS | Ms45 TS |
| Lig34/MS26 | 1 | NULL/NULL* | 1 bp ins/2 bp del + 1 bp ins | 1 bp ins/19 bp del | |
| | 2 | NULL/NULL | 1 bp ins/1 bp del | 1 bp ins/1 bp ins | |
| Lig34/MS26/ MS45 | 1 | NULL/NULL/ NULL | 1 bp ins/large del | 1 bp ins/1 bp del | 15 bp del/ large del |
| | 2 | INDEL**/NULL/ NULL | 1 bp ins/WT | 1 bp (T) ins/ 1 bp (C) ins | 1 bp ins/large del |

*NULL indicates that both alleles are mutated
**INDEL indicates mutation in one of the two alleles.
del = deletion,
ins = insertion,
bp = base pair All T0 plants were crossed with wild type maize plants to produce T1 seeds. T1 progeny plants (32 plants) of the second T0 plant from the triplex experiment (see Table 43, Lig34/MS26/MS45) were analyzed by sequencing to evaluate segregation frequencies of the mutated alleles. Our results demonstrated proper inheritance and expected (1:1) segregation of the mutated alleles as well as between mutated and wild type alleles at all three target sites.

The data clearly demonstrate that the guide RNA/maize optimized Cas endonuclease system described herein, can be used to simultaneously mutagenize multiple chromosomal loci and produce progeny plants containing the stably inherited multiple gene knock-outs.

Example 37

Guide RNA/Cas Endonuclease Mediated DNA Cleavage in Maize Chromosomal Loci can Stimulate Homologous Recombination Repair-Mediated Transgene Insertion and Resulting T1 Progeny Plants Demonstrated Proper Inheritance of the Modified Alleles Maize events generated in the experiment described in Example 5 were used to regenerate T0 plants. T0 plants were regenerated from 7 independent callus events with correct amplifications across both transgene genomic DNA junctions and analyzed. Leaf tissue was sampled, total genomic DNA extracted, and PCR amplification at both transgene genomic DNA junctions was carried out using the primer pairs (corresponding to SEQ ID NOs: 98-101). The resulting amplification products were sequenced for confirmation. Plants with confirmed junctions at both ends were further analyzed by Southern hybridization (FIG. 38) using two probes, genomic (outside HR1 region, SEQ ID: 533) and transgenic (within MoPAT gene, SEQ ID: 534). PCR, sequencing and Southern hybridization data demonstrated that plants regenerated from two of the 7 events (events 1 and 2) demonstrated perfect, clean, single copy transgene integration at the expected target site via homologous recombination. Plants regenerated from the remaining 5 events contained either additional, randomly integrated copies of the transgene (events 4, 5, and 6) or rearranged copies of the transgene integrated into the target site (events 3 and 7).

T0 plants from events 1 and 2 were crossed with wild type maize plants to produce T1 seeds. Ninety-six T1 plants from events 1 and 2 were analyzed by Southern hybridization (using the same probes as above) to evaluate segregation frequencies of the transgene locus. Southern results demonstrated proper inheritance and expected (1:1) segregation of the transgene and wild type loci.

The data clearly demonstrate that maize chromosomal loci cleaved with the maize optimized guide RNA/Cas system described herein can be used to stimulate HR repair pathways to site-specifically insert transgenes and produce progeny plants that have the inserted transgene stably inherited.

Example 38

Production of Maize Transgenic Lines with Pre-Integrated Cas9 for Transient Delivery of Guide RNA This example describes the rationale, production, and testing of maize transgenic lines with an integrated Cas9 gene under constitutive and temperature inducible promoters.

As demonstrated in Example 2, a high mutation frequency was observed when Cas9 endonuclease and guide RNA were delivered as DNA vectors by biolistic transformation to immature corn embryo cells. When Cas9 endonuclease was delivered as a DNA vector and guide RNA as RNA molecules, a reduced mutation frequency was observed (Table 44).

TABLE 44

Mutant reads at LigCas-3 target site produced by transiently delivered guide RNA.

| Target Site Examined for Mutations | Transient Delivery | Expression Cassette | Mutant Reads | Total Reads |
|---|---|---|---|---|
| LIGCas-3 | — | Cas9 | 24.2 | 1,599,492 |
| LIGCas-3 | — | Cas9/guide RNA | 44170 | 1,674,825 |
| LIGCas-3 | 35 ng guide RNA | Cas9 | 418 | 1,622,180 |
| LIGCas-3 | 70 ng guide RNA | Cas9 | 667 | 1,791,388 |
| LIGCas-3 | 140 ng guide RNA | Cas9 | 239 | 1,632,137 |

Increased efficiency (increased mutant reads) may occur when the Cas9 protein and guide RNA are present in the cell at the same time. To facilitate the presence of both Cas9 endonuclease and guide RNA in the same cell, a vector containing a constitutive and conditionally regulated Cas9 gene can be first delivered to plant cells to allow for stable integration into the plant genome to establish a plant line that contains only the Cas9 gene in the plant genome. Then, single or multiple guide RNAs can be delivered as either DNA or RNA, or combination, to the embryo cells of the plant line containing the genome-integrated version of the Cas9 gene.

Transgenic maize (genotype Hi-II) lines with an integrated Cas9 gene driven by either a constitutive (Ubi) or an inducible (CAS) promoter were generated via Agrobacterium-mediated transformation. Besides the Cas9 gene, the Agro vector also contained a visible marker (END2:Cyan) and a Red Fluorescent Protein sequence interrupted with a 318 bp long linker (H2B:RF-FP). The linker sequence was flanked with 370 bp long direct repeats to promote recombination and restoration of a functional RFP gene sequence upon double strand break within the linker.

Lines with single copies of the transgene were identified and used for further experiments. Two guide RNA constructs targeting 2 different sites (Table 45 in the linker sequence, were delivered into immature embryo cells via particle bombardment. Meganuclease variant LIG3-4 B65 with very high cutting activity previously used in similar experiments was used as the positive control.

TABLE 45

Target sites in the RF-FP linker for guideRNA/Cas endonuclease system.

| Locus | Guide RNA Used | Target Site Designation | Target Site Sequence | PAM Sequence | SEQ ID NO: |
|---|---|---|---|---|---|
| RF-FP linker | Long | RF-FPCas-1 | GCAGGTCTCACGACGGT | TGG | 535 |
| | Long | RF-FPCas-2 | GTAAAGTACGCGTACGTGTG | AGG | 536 |

After transformation, embryos with Cas9 gene under Ubiquitin promoter were incubated at 28° C. while embryos with Cas9 gene under temperature inducible CAS promoter were first incubated at 37° C. for 15-20 hours and then transferred to 28° C. Embryos were examined 3-5 days after bombardment under luminescent microscope. Expression and activity of the pre-integrated Cas9 protein was visually evaluated based on the number of embryo cells with RFP protein expression. In most lines, the guide RNA/Cas endonuclease system demonstrated similar or higher frequency of RFP repair than LIG3-4 B65 meganuclease indicating high level of Cas9 protein expression and activity in the generated transgenic lines.

This example describes the production of transgenic lines with a pre-integrated Cas9 gene that can be used in further experiments to evaluate efficiency of mutagenesis at a target site upon transient delivery of guide RNA in the form of RNA molecules.

Example 39
The Guide RNA/Cas Endonuclease System Delivers Double-Strand Breaks to the Maize ALS Locus and Facilitates Editing of the ALS Gene This example demonstrates that the guide RNA/Cas endonuclease system can be efficiently used to introduce specific changes into the nucleotide sequence of the maize ALS gene resulting in resistance to sulfonylurea class herbicides, specifically, chlorsulfuron.

Endogenous ALS protein is the target site of ALS inhibitor sulfonylurea class herbicides. Expression of the herbicide tolerant version of ALS protein in crops confers tolerance to this class of herbicides. The ALS protein contains N-terminal transit peptides, and the mature protein is formed following transport into the chloroplast and subsequent cleavage of the transit peptide. The mature protein starts at residue S41, resulting in a mature protein of 598 amino acids with a predicted molecular weight of 65 kDa (SEQ ID NO: 550).

TABLE 46

Deduced Amino Acid Sequence of the Full-Length ZM-ALS Protein (SEQ ID no: 550)

| | | | | |
|---|---|---|---|---|
| 1 | MATAAAASTA | LTGATTAAPK | ARRRAHLLAT | RRALAAPIRC | SAASPAMPMA |
| 51 | PPATPLRPWG | PTEPRKGADI | LVESLERCGV | RDVFAYPGGA | SMEIHQALTR |
| 101 | SPVIANHLFR | HEQGEAFAAS | GYARSSGRVG | VCIATSGPGA | TNLVSALADA |
| 151 | LLDSVPMVAI | TGQVPRRMIG | TDAFQETPIV | EVTRSITKHN | YLVLDVDDIP |
| 201 | RVVQEAFFLA | SSGRPGPVLV | DIPKDIQQQM | AVPVWDKPMS | LPGYIARLPK |
| 251 | PPATELLEQV | LRLVGESRRP | VLYVGGGCAA | SGEELRRFVE | LTGIPVTTTL |
| 301 | MGLGNFPSDD | PLSLRMLGMH | GTVYANYAVD | KADLLLALGV | RFDDRVTGKI |
| 351 | EAFASRAKIV | HVDIDPAEIG | KNKQPHVSIC | ADVKLALQGM | NALLEGSTSK |
| 401 | KSFDFGSWND | ELDQQKREFP | LGYKTSNEEI | QPQYAIQVLD | ELTKGEAIIG |
| 451 | TGVGQHQMWA | AQYYTYKRPR | QWLSSAGLGA | MGFGLPAAAG | ASVANPGVTV |
| 501 | VDIDGDGSFL | MNVQELAMIR | IENLPVKVFV | LNNQHLGMVV | QWEDRFYKAN |
| 551 | RAHTYLGNPE | NESEIYPDFV | TIAKGFNIPA | VRVTKKNEVR | AAIKKMLETP |
| 601 | GPYLLDIIVP | HQEHVLPMIP | SGGAFKDMIL | DGDGRTVY | |

Modification of a single amino acid residue (P165A or P165S, shown in bold) from the endogenous maize acetoacetate synthase protein provides resistance to herbicides in maize.

There are two ALS genes in maize, ALS1 and ALS2, located on chromosomes 5 and 4, respectively. As described in Example 2, guide RNA expressing constructs for 3 different target sites within the ALS genes were tested. Based on polymorphism between ALS1 and ALS2 nucleotide sequences, ALS1-specific and ALSCas-4 target site were identified and tested. ALSCas-1 guide RNA expressing construct targeting both ALS1 and ALS2 genes was used as control (Table 47)

TABLE 47

Maize ALS genomic target sites tested.

| Locus | Location | Guide RNA | Target Site Designation | Maize Genomic Target Site Sequence | PAM Sequence | SEQ ID NO: |
|---|---|---|---|---|---|---|
| ALS | Chr. 4: 107.73cM | Long | ALSCas-1 | GGTGCCAATCATGCGTCG | CGG | 22 |
| | | Long | ALSCas-4 | GCTGCTCGATTCCGTCCCA | TGG* | 537 |

TABLE 47-continued

Maize ALS genomic target sites tested.

| Locus | Guide Location | Target Site RNA Designation | Maize Genomic Target Site Sequence | PAM | SEQ ID NO: |
|---|---|---|---|---|---|
| and Chr. 5: 115.49cM | | | | | |

*Target site in the ALS1 gene; bolded nucleotides are different in the ALS2 gene.

The experiment was conducted and mutation frequency determined as described in Example 2 and results are shown in Table 48.

TABLE 48

Frequencies of NHEJ mutations at the two ALS target sites recovered by deep sequencing.

| TS | Total Reads | Mutant reads (ALS1) | Mutant reads (ALS2) |
|---|---|---|---|
| ALSCas-1 | 204,230 | 5072 (2.5%) | 2704 (1.3%) |
| ALSCas-4 | 120,766 | 3294 (2.7%) | 40 (0.03%) |

The results demonstrated that ALSCas-4 guide RNA/Cas9 system mutates the ALS1 gene with approximately 90 times higher efficiency than the ALS2 gene. Therefore, the ALS-Cas-4 target site and the corresponding guide RNA were selected for the ALS gene editing experiment.

To produce edited events, the ALS polynucleotide modification repair template was co-delivered using particle bombardment as a plasmid with an 804 bp long homologous region (SEQ ID NO: 538) or as a single-stranded 127 bp DNA fragment (SEQ ID NO: 539), the maize optimized Cas9 endonuclease expression vector described in Example 1, the guide RNA expression cassette (targeting ALSCas-4 site), a moPAT-DsRed fusion as selectable and visible markers, and developmental genes (ODP-2 and WUS). Approximately 1000 Hi-II immature embryos were bombarded with each of the two repair templates described above. Forty days after bombardment, 600 young callus events (300 for each repair template) were collected and transferred to the media with bialaphos selection. The embryos with remaining events were transferred to the media with 100 ppm of chlorsulfuron for selection. A month later, events that continued growing under chlorsulfuron selection were collected and used for analysis.

A small amount of callus tissue from each selected event was used for total DNA extraction. A pair of genomic primers outside the repair/donor DNA fragment (SEQ ID NO:540 and SEQ ID NO:541) was used to amplify an endogenous fragment of the ALS1 locus containing the ALSCas4 target sequence. The PCR amplification products were gel purified, cloned into the pCR2.1 TOPO cloning vector (Invitrogen) and sequenced. A total of 6 events demonstrated the presence of the specifically edited ALS1 allele as well as either a wild type or a mutagenized second allele.

These data indicate that a guide RNA/Cas system can be successfully used to create edited ALS allele in maize. The data further demonstrates that the guide RNA/maize optimized Cas endonuclease system described herein, can be used to produce progeny plants containing gene edits that are stably inherited.

Example 40

Gene Editing of the Soybean ALS1 Gene and Use as a Transformation Selectable Marker for Soybean Transformation with the Guide RNA/Cas Endonuclease System A. guideRNA/Cas9 Endonuclease Target Site Design on the Soybean ALS1 Gene.

There are four ALS genes in soybean (Glyma04g37270, Glyma06g17790, Glyma13g31470 and Glyma15g07860). Two guideRNA/Cas9 endonuclease target sites (soy ALS1-CR1 and soy ALS1-CR2) were designed near the Proline 178 of the soybean ALS1 gene Glyma04g37270 (Table 49).

TABLE 49

Guide RNA/Cas9 endonuclease target sites on soybean ALS1 gene

| Name of gRNA-Cas9 endonuclease target site | Cas endonuclease target sequence (SEQ ID NO:) | Physical location |
|---|---|---|
| soy ALS1-CR1 | 542 | Gm04: 43645633..43645612 |
| soy ALS1-CR2 | 543 | Gm04: 43645594..43645615 |

B. Guide-RNA Expression Cassettes, Cas9 Endonuclease Expression Cassettes, Polynucleotide Modification Templates for Introduction of Specific Amino Acid Changes and Use the P178S Modified ALS1 Allele as a Soybean Transformation Selectable Marker The soybean U6 small nuclear RNA promoter, GM-U6-13.1 (SEQ ID. NO: 469), was used to express guide RNAs to direct Cas9 nuclease to designated genomic target sites (Table 50). A soybean codon optimized Cas9 endonuclease (SEQ ID NO:489) expression cassette and a guide RNA expression cassette were linked in a first plasmid that was co-delivered with a polynucleotide modification template. The polynucleotide modification template contained specific nucleotide changes that encoded for amino acid changes in the soy ALS1 polypeptide (Glyma04g37270), such as the P178S. Other amino acid changes in the ALS1 polypeptide can also be obtained using the guide RNA/Cas endonuclease system described herein. Specific amino acid modifications can be achieved by homologous recombination between the genomic DNA and the polynucleotide modification template facilitated by the guideRNA/Cas endonuclease system.

TABLE 50

Guide RNA/Cas9 expression cassettes and polynucleotide modification templates used in soybean stable transformation for the specific amino acid modifications of the soy ALS1 gene.

| Experiment | Guide RNA/Cas9 (plasmid name) | SEQ ID NO: | polynucleotide modification template | SEQ ID NO: |
|---|---|---|---|---|
| soy ALS1-CR1 | U6-13.1:ALS1-CR1 + EF1A2:CAS9 (QC880) | 544 | RTW1026A | 546 |
| soy ALS-CR2 | U6-13.1:ALS1-CR2 + EF1A2:CAS9 (QC881) | 545 | RTW1026A | 546 |

C. Detection of the P178S Mutation in the Soybean ALS1 Gene in the Event Selected by Chlorsulfuron In order to edit specific amino acids at the native ALS1 gene (such as the P178S modification), a polynucleotide modification template such as RTW1026A (Table 50), was co-delivered with the guideRNA/Cas9 expression cassettes into soybean cells. Chlorsulfuron (100 ppb) was used to select the P178S ALS1 gene editing events in soybean transformation process.

The modification of the native ALS1 gene via guide RNA/Cas9 system mediated DNA homologous recombination was determined by specific PCR analysis. A specific PCR assay with primer pair WOL900 (SEQ ID NO: 547) and WOL578 (SEQ ID NO: 548) was used to detect perfect P178S modification at the native ALS1 gene. A second primer pair WOL573 (SEQ ID NO: 549) and WOL578 (SEQ ID NO: 548) was used to amplify both a P178S modified Soy ALS1 allele and a NHEJ mutated allele. A chlorsulfuron tolerant event (MSE3772-18) was generated from the soy ALS1-CR2 experiment. The event contained a perfect P178S modified allele and a $2^{nd}$ allele with a 5 bp deletion at the soyALS1-CR2 cleavage site. Topo cloning/sequencing was used to verify the sequences. Our results demonstrated one P178S modified ALS1 allele is sufficient to provide Chlorsulfuron selection in soybean transformation process.

Example 41

Soybean FAD2-1 Gene Knockout in Combination with P178S ALS1 Modification as a Selectable Marker Using the guideRNA/Cas Endonuclease System This example describes a method for gene modification in a plant genome using the guide RNA/Cas system without the insertion of an exogenous selectable marker into said plant genome. Instead, an herbicide resistance trait is generated by editing a first gene located in a plant genome while simultaneously knocking out a second gene located at a different locus than the first gene. This is accomplished by using two guides in combination with the Cas endonuclease as described below.

A. guideRNA/Cas9 Endonuclease Target Site Design on the Soybean FAD2-1 Genes.

There are two FAD2-1 genes in soybean (FAD2-1A for Glyma10g42470 and FAD2-1B for Glyma20g24530). Two guideRNA/Cas9 endonuclease target sites (soy FAD2-1-CR1 and soy FAD2-1-CR2) were designed to target both FAD2-1 genes for each gRNA (Table 51).

TABLE 51

Guide RNA/Cas9 endonuclease target sites on soybean FAD2-1 gene

| Name of gRNA-Cas9 endonuclease target site | Cas endonuclease target sequence (SEQ ID NO:) | Physical location |
|---|---|---|
| soy FAD2-1-CR1 | 551 | Gm10: 49417140..49417118<br>Gm20: 34178367..34178345 |
| soy FAD2-1-CR2 | 552 | Gm10: 49417140..49417161<br>Gm20: 34178367..34178388 |

B. Guide-RNA Expression Cassettes, Cas9 Endonuclease Expression Cassettes and Knockout of the Soybean FAD2-1 Genes with P178S ALS1 Gene Editing as the Transformation Selectable Marker.

The soybean U6 small nuclear RNA promoter, GM-U6-13.1 (SEQ ID. NO: 469), was used to express guide RNAs to direct Cas9 nuclease to designated genomic target sites (Table 52). A soybean codon optimized Cas9 endonuclease (SEQ ID NO: 489) expression cassette and a guide RNA expression cassette for the ALS1 gene were linked in a first plasmid (QC881) that was co-delivered with an ALS1 polynucleotide modification template (RTW1026A). With a second gRNA plasmid (RTW1211 or RTW1212) targeting the FAD2-1 genes simultaneously, the FAD2-1 knockout events can be identified in the chlorsulfuron tolerant events by qPCR and PCR assays.

TABLE 52

Guide RNA/Cas9 expression cassettes and polynucleotide modification templates used in soybean stable transformation for the specific amino acid modifications of the soy ALS1 gene and FAD2-1 knock-out.

| Experiment | Guide RNA/Cas9 (plasmid name) | SEQ ID NO: | polynucleotide modification template | SEQ ID NO: |
|---|---|---|---|---|
| soy ALS1-CR2 | QC881 | 545 | RTW1026A | 546 |
| soy FAD2-1-CR1 | RTW1211 | 553 | | |
| soy ALS-CR2 | QC881 | 545 | RTW1026A | 546 |
| soy FAD2-1 CR2 | RTW1212 | 554 | | |

Example 42

Soybean EPSPS1 Gene Editing in Combination with P178S ALS1 Modification as a Selectable Marker Using the Guide RNA/Cas Endonuclease System This example describes a method for gene modification in a plant genome using the guide RNA/Cas system without the insertion of an exogenous selectable marker into said plant genome. Instead, an herbicide resistance trait is generated by editing a first gene located in a plant genome while simultaneously inserting a polynucleotide of interest located at a different locus in the plant genome. This is accomplished by using two guides in combination with the Cas endonuclease as described below.

The EPSPS gene editing as described in Example 24, 25 and 26 can also be carried out in combination with the P178S ALS1 modification by using multiple gRNAs targeting both the soybean EPSPS gene and soy ALS1 gene. The soybean EPSPS1 gene editing events can be identified in the chlorsulfuron tolerant events.

Example 43

Targeted Gene Integration in Combination with P178S ALS1 Modification as a Selectable Marker Using the Guide RNA/Cas Endonuclease System This example describes a method for gene modification in a plant genome using the guide RNA/Cas system without the insertion of an exogenous selectable marker into said plant genome. Instead, an herbicide resistance trait is generated by editing a first gene located in a plant genome while simultaneously editing a second gene located at a different locus in the plant genome. This is accomplished by using two guides in combination with the Cas endonuclease as described below.

The targeted gene integration in soybean as described in Example 19, 20 and 21 can also be carried out in combination with the P178S ALS1 modification by using multiple gRNAs targeting both the intended gene integration sites and soy ALS1 gene. The perfect gene integration events can be identified in the chlorsulfuron tolerant events.

---

That which is claimed:

1. A method for producing a second generation of soybean plant that comprises herbicide resistance, the method comprising:
   (a) stably integrating a polynucleotide encoding a Cas endonuclease within a genome of a first soybean plant cell,
   (b) introducing a first guide polynucleotide, a polynucleotide modification template, and a second guide polynucleotide into the first soybean plant cell;
   wherein said first guide polynucleotide and Cas endonuclease are capable of forming a first complex that enables the Cas endonuclease to introduce a double strand break at a first target site, located in or near a endogenous enolpyruvylshikimate-3-phosphate synthase (EPSPS) gene, in the genome of said first soybean plant cell;
   wherein said second guide polynucleotide and Cas endonuclease are capable of forming a second complex that enables the Cas endonuclease to introduce a double strand break at a second target site in the genome of said first soybean plant cell;
   wherein said polynucleotide modification template causes a deletion of the native promoter of the endogenous enolpyruvylshikimate-3-phosphate synthase (EPSPS) gene with the insertion of a heterologous promoter and at least one nucleotide alteration when compared to the endogenous enolpyruvylshikimate-3-phosphate synthase (EPSPS) gene, and; wherein said at least one nucleotide alteration encodes for an amino acid change in the endogenous enolpyruvylshikimate-3-phosphate synthase (EPSPS) gene,
   (c) producing a genetic modification within said endogenous enolpyruvylshikimate-3-phosphate synthase (EPSPS) of the first soybean plant cell genome without introducing an exogenous selectable marker into the first or second target site of said first soybean plant cell genome, wherein the first soybean plant cell comprises a modified endogenous enolpyruvylshikimate-3-phosphate synthase (EPSPS) gene that confers herbicide resistance,
   (d) generating a first generation soybean plant from the first soybean plant cell,
   (e) crossing the first generation soybean plant with a second soybean plant to produce a second generation soybean plant; wherein the second generation of soybean plant comprises in its genome a modification of a gene corresponding to said endogenous enolpyruvylshikimate-3-phosphate synthase (EPSPS) gene and a modification at a site corresponding to the second target site; wherein said modification of a gene corresponding to said endogenous enolpyruvylshikimate-3-phosphate synthase (EPSPS) gene confers herbicide resistance to the second generation of soybean plant.

2. The method of claim 1, wherein the first target site and the second target site are located at two different genomic loci.

3. The method of claim 1, wherein the Cas endonuclease is a Cas9 endonuclease.

4. The method of claim 1, further comprising selecting at least one soybean plant cell that has resistance to a glyphosate herbicide and comprises a modification of said second target site, wherein said modification includes at least one deletion, insertion or substitution of one or more nucleotides in said second target site of the soybean plant genome.

5. The method of claim 4, wherein said modification of said second target site includes at least one deletion, insertion, or substitution of one or more nucleotides in a Fatty Acid Desaturase 2-1 (FAD2-1) gene.

6. The method of claim 5, further comprising producing a soybean plant from said soybean plant cell, wherein said soybean plant has resistance to said glyphosate herbicide and has a high oleic phenotype due to the at least one deletion, insertion, or substitution of one or more nucleotides in said Fatty Acid Desaturase 2-1 (FAD2-1) gene.

* * * * *